United States Patent
Shelton, IV et al.

(10) Patent No.: US 9,839,420 B2
(45) Date of Patent: *Dec. 12, 2017

(54) TISSUE THICKNESS COMPENSATOR COMPRISING AT LEAST ONE MEDICAMENT

(75) Inventors: Frederick E. Shelton, IV, Hillsboro, OH (US); Katherine J. Schmid, Cincinnati, OH (US); Charles J. Scheib, Loveland, OH (US); Taylor W. Aronhalt, Loveland, OH (US); Matthew M. Lang, Mason, OH (US); Steven G. Hall, Cincinnati, OH (US); Chester O. Baxter, III, Loveland, OH (US)

(73) Assignee: Ethicon LLC, Los Frailes Industrial Park, Guaynabo, PR (US)

(*) Notice: Subject to any disclaimer, the term of this patent is extended or adjusted under 35 U.S.C. 154(b) by 1145 days.

This patent is subject to a terminal disclaimer.

(21) Appl. No.: 13/433,136

(22) Filed: Mar. 28, 2012

(65) Prior Publication Data

US 2012/0241492 A1    Sep. 27, 2012

Related U.S. Application Data

(63) Continuation-in-part of application No. 13/097,891, filed on Apr. 29, 2011, now Pat. No. 8,864,009.
(Continued)

(51) Int. Cl.
*A61B 17/04* (2006.01)
*A61B 17/10* (2006.01)
(Continued)

(52) U.S. Cl.
CPC ...... *A61B 17/068* (2013.01); *A61B 17/00491* (2013.01); *A61B 17/0643* (2013.01);
(Continued)

(58) Field of Classification Search
CPC .......... A61B 17/068; A61B 17/07207; A61B 17/105; A61B 2017/07271; A61B 17/072;
(Continued)

(56) References Cited

U.S. PATENT DOCUMENTS 66,052 A    6/1867   Smith
662,587 A   11/1900  Blake
(Continued)

FOREIGN PATENT DOCUMENTS

AU    2008207624 A1    3/2009
AU    2010214687 A1    9/2010
(Continued)

OTHER PUBLICATIONS

International Preliminary Report on Patentability for PCT/US2013/046513, dated Dec. 31, 2014 (9 pages).
(Continued)

*Primary Examiner* — Robert Long

(57) ABSTRACT

A stapling assembly comprising a tissue thickness compensator is disclosed. The tissue thickness compensator comprises a body portion comprising a porous material and a plurality of cavities defined in the body portion, wherein the cavities are aligned with forming surfaces of an anvil such that fasteners of a fastener cartridge are configured to at least one of the cavities when the fasteners are ejected from the fastener cartridge or capture the cavities and compress the cavities within the tissue thickness compensator when the fasteners are ejected from the fastener cartridge and formed by forming surfaces of the anvil. The stapling assembly further comprises at least one medicament positioned within each cavity prior to firing the stapler, wherein the medicament is different than the porous material.

2 Claims, 147 Drawing Sheets

Related U.S. Application Data which is a continuation-in-part of application No. 12/894,377, filed on Sep. 30, 2010, now Pat. No. 8,393,514.

(51) Int. Cl.

| | |
|---|---|
| *A61B 17/068* | (2006.01) |
| *A61B 17/072* | (2006.01) |
| *A61L 17/00* | (2006.01) |
| *A61B 17/064* | (2006.01) |
| *A61B 17/115* | (2006.01) |
| *A61B 17/00* | (2006.01) |
| *A61B 17/29* | (2006.01) |
| *A61B 17/32* | (2006.01) |
| *A61B 90/00* | (2016.01) |

(52) U.S. Cl.
CPC ...... *A61B 17/072* (2013.01); *A61B 17/07207* (2013.01); *A61B 17/07292* (2013.01); *A61B 17/1155* (2013.01); *A61L 17/005* (2013.01); *A61B 17/0644* (2013.01); *A61B 17/2909* (2013.01); *A61B 2017/00004* (2013.01); *A61B 2017/0053* (2013.01); *A61B 2017/00477* (2013.01); *A61B 2017/00526* (2013.01); *A61B 2017/00561* (2013.01); *A61B 2017/00818* (2013.01); *A61B 2017/00862* (2013.01); *A61B 2017/00884* (2013.01); *A61B 2017/00889* (2013.01); *A61B 2017/00893* (2013.01); *A61B 2017/00898* (2013.01); *A61B 2017/00942* (2013.01); *A61B 2017/00951* (2013.01); *A61B 2017/07228* (2013.01); *A61B 2017/07235* (2013.01); *A61B 2017/07242* (2013.01); *A61B 2017/07264* (2013.01); *A61B 2017/07271* (2013.01); *A61B 2017/07278* (2013.01); *A61B 2017/07285* (2013.01); *A61B 2017/2908* (2013.01); *A61B 2017/2919* (2013.01); *A61B 2017/2923* (2013.01); *A61B 2017/2927* (2013.01); *A61B 2017/2933* (2013.01); *A61B 2017/2936* (2013.01); *A61B 2017/2946* (2013.01); *A61B 2017/320052* (2013.01); *A61B 2090/0811* (2016.02); *A61L 2300/102* (2013.01); *A61L 2300/232* (2013.01); *A61L 2300/45* (2013.01); *F04C 2270/0421* (2013.01); *Y10T 29/49826* (2015.01)

(58) Field of Classification Search
CPC A61B 2017/07278; A61B 2017/07285; A61B 2017/320052; A61B 17/32; A61B 2018/1455; A61B 17/320092; A61B 17/3203
USPC .............................................. 227/175.1–182.1
See application file for complete search history.

(56) References Cited

U.S. PATENT DOCUMENTS

| | | | |
|---|---|---|---|
| 670,748 | A | 3/1901 | Weddeler |
| 951,393 | A | 3/1910 | Hahn |
| 1,306,107 | A | 6/1919 | Elliott |
| 1,314,601 | A | 9/1919 | McCaskey |
| 1,677,337 | A | 7/1928 | Grove |
| 2,037,727 | A | 4/1936 | La Chapelle |
| 2,132,295 | A | 10/1938 | Hawkins |
| 2,161,632 | A | 6/1939 | Nattenheinner |
| 2,211,117 | A | 8/1940 | Hess |
| 2,214,870 | A | 9/1940 | West |
| 2,441,096 | A | 5/1948 | Happe |
| 2,526,902 | A | 10/1950 | Rublee |
| 2,674,149 | A | 4/1954 | Benson |
| 2,804,848 | A | 9/1957 | O'Farrell et al. |
| 2,808,482 | A | 10/1957 | Zanichkowsky et al. |
| 2,853,074 | A | 9/1958 | Olson |
| 2,959,974 | A | 11/1960 | Emrick |
| 3,032,769 | A | 5/1962 | Palmer |
| 3,075,062 | A | 1/1963 | Iaccarino |
| 3,078,465 | A | 2/1963 | Bobrov |
| 3,079,606 | A | 3/1963 | Bobrov et al. |
| 3,166,072 | A | 1/1965 | Sullivan, Jr. |
| 3,196,869 | A | 7/1965 | Scholl |
| 3,266,494 | A | 8/1966 | Brownrigg et al. |
| 3,269,630 | A | 8/1966 | Fleischer |
| 3,275,211 | A | 9/1966 | Hirsch et al. |
| 3,317,103 | A | 5/1967 | Cullen et al. |
| 3,317,105 | A | 5/1967 | Astafjev et al. |
| 3,357,296 | A | 12/1967 | Lefever |
| 3,490,675 | A | 1/1970 | Green et al. |
| 3,494,533 | A | 2/1970 | Green et al. |
| 3,499,591 | A | 3/1970 | Green |
| 3,551,987 | A | 1/1971 | Wilkinson |
| 3,568,675 | A | 3/1971 | Harvey |
| 3,572,159 | A | 3/1971 | Tschanz |
| 3,598,943 | A | 8/1971 | Barrett |
| 3,608,549 | A | 9/1971 | Merrill |
| 3,643,851 | A | 2/1972 | Green et al. |
| 3,662,939 | A | 5/1972 | Bryan |
| 3,709,221 | A | 1/1973 | Riely |
| 3,717,294 | A | 2/1973 | Green |
| 3,734,207 | A | 5/1973 | Fishbein |
| 3,740,994 | A | 6/1973 | DeCarlo, Jr. |
| 3,744,495 | A | 7/1973 | Johnson |
| 3,746,002 | A | 7/1973 | Haller |
| 3,751,902 | A | 8/1973 | Kingsbury et al. |
| 3,819,100 | A | 6/1974 | Noiles et al. |
| 3,821,919 | A | 7/1974 | Knohl |
| 3,841,474 | A | 10/1974 | Maier |
| 3,851,196 | A | 11/1974 | Hinds |
| 3,885,491 | A | 5/1975 | Curtis |
| 3,892,228 | A | 7/1975 | Mitsui |
| 3,894,174 | A * | 7/1975 | Cartun .................. B21F 45/24 174/159 |
| 3,940,844 | A * | 3/1976 | Colby .................. B21D 53/46 29/235 |
| 3,955,581 | A | 5/1976 | Spasiano et al. |
| RE28,932 | E | 8/1976 | Noiles et al. |
| 3,981,051 | A | 9/1976 | Brumlik |
| 4,054,108 | A | 10/1977 | Gill |
| 4,060,089 | A | 11/1977 | Noiles |
| 4,106,446 | A | 8/1978 | Yamada et al. |
| 4,111,206 | A | 9/1978 | Vishnevsky et al. |
| 4,129,059 | A | 12/1978 | Van Eck |
| 4,169,990 | A | 10/1979 | Lerdman |
| 4,198,734 | A | 4/1980 | Brumlik |
| 4,198,982 | A | 4/1980 | Fortner et al. |
| 4,207,898 | A | 6/1980 | Becht |
| 4,213,562 | A | 7/1980 | Garrett et al. |
| 4,226,242 | A | 10/1980 | Jarvik |
| 4,244,372 | A | 1/1981 | Kapitanov et al. |
| 4,250,436 | A | 2/1981 | Weissman |
| 4,261,244 | A | 4/1981 | Becht et al. |
| 4,272,002 | A | 6/1981 | Moshofsky |
| 4,272,662 | A | 6/1981 | Simpson |
| 4,274,304 | A | 6/1981 | Curtiss |
| 4,275,813 | A | 6/1981 | Noiles |
| 4,289,133 | A | 9/1981 | Rothfuss |
| 4,305,539 | A | 12/1981 | Korolkov et al. |
| 4,312,685 | A | 1/1982 | Riedl |
| 4,317,451 | A | 3/1982 | Cerwin et al. |
| 4,321,002 | A | 3/1982 | Froehlich |
| 4,328,839 | A | 5/1982 | Lyons et al. |
| 4,331,277 | A | 5/1982 | Green |
| 4,340,331 | A | 7/1982 | Savino |
| 4,347,450 | A | 8/1982 | Colligan |
| 4,349,028 | A | 9/1982 | Green |
| 4,353,371 | A | 10/1982 | Cosman |
| 4,379,457 | A | 4/1983 | Gravener et al. |
| 4,380,312 | A | 4/1983 | Landrus |
| 4,382,326 | A | 5/1983 | Rabuse |

(56) References Cited

U.S. PATENT DOCUMENTS

| | | |
|---|---|---|
| 4,383,634 A | 5/1983 | Green |
| 4,393,728 A | 7/1983 | Larson et al. |
| 4,396,139 A | 8/1983 | Hall et al. |
| 4,397,311 A | 8/1983 | Kanshin et al. |
| 4,402,445 A | 9/1983 | Green |
| 4,408,692 A | 10/1983 | Sigel et al. |
| 4,409,057 A | 10/1983 | Molenda et al. |
| 4,415,112 A | 11/1983 | Green |
| 4,416,276 A | 11/1983 | Newton et al. |
| 4,428,376 A | 1/1984 | Mericle |
| 4,429,695 A | 2/1984 | Green |
| 4,434,796 A | 3/1984 | Karapetian et al. |
| 4,438,659 A | 3/1984 | Desplats |
| 4,442,964 A | 4/1984 | Becht |
| 4,451,743 A | 5/1984 | Suzuki et al. |
| 4,454,887 A | 6/1984 | Krüger |
| 4,467,805 A | 8/1984 | Fukuda |
| 4,473,077 A | 9/1984 | Noiles et al. |
| 4,475,679 A | 10/1984 | Fleury, Jr. |
| 4,485,816 A | 12/1984 | Krumme |
| 4,486,928 A | 12/1984 | Tucker et al. |
| 4,488,523 A | 12/1984 | Shichman |
| 4,489,875 A | 12/1984 | Crawford et al. |
| 4,500,024 A | 2/1985 | DiGiovanni et al. |
| 4,505,272 A | 3/1985 | Utyamyshev et al. |
| 4,505,273 A | 3/1985 | Braun et al. |
| 4,505,414 A | 3/1985 | Filipi |
| 4,506,671 A | 3/1985 | Green |
| 4,520,817 A | 6/1985 | Green |
| 4,522,327 A | 6/1985 | Korthoff et al. |
| 4,526,174 A | 7/1985 | Froehlich |
| 4,527,724 A | 7/1985 | Chow et al. |
| 4,530,453 A | 7/1985 | Green |
| 4,531,522 A | 7/1985 | Bedi et al. |
| 4,532,927 A | 8/1985 | Miksza, Jr. |
| 4,548,202 A | 10/1985 | Duncan |
| 4,565,109 A | 1/1986 | Tsay |
| 4,565,189 A | 1/1986 | Mabuchi |
| 4,566,620 A | 1/1986 | Green et al. |
| 4,571,213 A | 2/1986 | Ishimoto |
| 4,573,468 A | 3/1986 | Conta et al. |
| 4,573,469 A | 3/1986 | Golden et al. |
| 4,573,622 A | 3/1986 | Green et al. |
| 4,576,167 A | 3/1986 | Noiles |
| 4,580,712 A | 4/1986 | Green |
| 4,585,153 A | 4/1986 | Failla et al. |
| 4,589,416 A | 5/1986 | Green |
| 4,591,085 A | 5/1986 | Di Giovanni |
| 4,597,753 A | 7/1986 | Turley |
| 4,600,037 A | 7/1986 | Hatten |
| 4,604,786 A | 8/1986 | Howie, Jr. |
| 4,605,001 A | 8/1986 | Rothfuss et al. |
| 4,605,004 A | 8/1986 | Di Giovanni et al. |
| 4,606,343 A | 8/1986 | Conta et al. |
| 4,607,638 A | 8/1986 | Crainich |
| 4,608,981 A | 9/1986 | Rothfuss et al. |
| 4,610,250 A | 9/1986 | Green |
| 4,610,383 A | 9/1986 | Rothfuss et al. |
| 4,619,262 A | 10/1986 | Taylor |
| 4,619,391 A | 10/1986 | Sharkany et al. |
| 4,628,459 A | 12/1986 | Shinohara et al. |
| 4,629,107 A | 12/1986 | Fedotov et al. |
| 4,632,290 A | 12/1986 | Green et al. |
| 4,633,874 A | 1/1987 | Chow et al. |
| 4,634,419 A | 1/1987 | Kreizman et al. |
| 4,641,076 A | 2/1987 | Linden |
| 4,643,731 A | 2/1987 | Eckenhoff |
| 4,646,722 A | 3/1987 | Silverstein et al. |
| 4,655,222 A | 4/1987 | Florez et al. |
| 4,662,555 A | 5/1987 | Thornton |
| 4,663,874 A | 5/1987 | Sano et al. |
| 4,664,305 A | 5/1987 | Blake, III et al. |
| 4,665,916 A | 5/1987 | Green |
| 4,667,674 A | 5/1987 | Korthoff et al. |
| 4,669,647 A | 6/1987 | Storace |
| 4,671,445 A | 6/1987 | Barker et al. |
| 4,676,245 A | 6/1987 | Fukuda |
| 4,684,051 A | 8/1987 | Akopov et al. |
| 4,693,248 A | 9/1987 | Failla |
| 4,700,703 A | 10/1987 | Resnick et al. |
| 4,708,141 A | 11/1987 | Inoue et al. |
| 4,709,120 A | 11/1987 | Pearson |
| 4,715,520 A | 12/1987 | Roehr, Jr. et al. |
| 4,719,917 A | 1/1988 | Barrows et al. |
| 4,727,308 A | 2/1988 | Huljak et al. |
| 4,728,020 A | 3/1988 | Green et al. |
| 4,728,876 A | 3/1988 | Mongeon et al. |
| 4,729,260 A | 3/1988 | Dudden |
| 4,730,726 A | 3/1988 | Holzwarth |
| 4,741,336 A | 5/1988 | Failla et al. |
| 4,743,214 A | 5/1988 | Tai-Cheng |
| 4,747,820 A | 5/1988 | Hornlein et al. |
| 4,750,902 A | 6/1988 | Wuchinich et al. |
| 4,752,024 A | 6/1988 | Green et al. |
| 4,754,909 A | 7/1988 | Barker et al. |
| 4,767,044 A | 8/1988 | Green |
| 4,773,420 A | 9/1988 | Green |
| 4,777,780 A | 10/1988 | Holzwarth |
| 4,787,387 A | 11/1988 | Burbank, III et al. |
| 4,790,225 A | 12/1988 | Moody et al. |
| 4,805,617 A | 2/1989 | Bedi et al. |
| 4,805,823 A | 2/1989 | Rothfuss |
| 4,809,695 A | 3/1989 | Gwathmey et al. |
| 4,817,847 A | 4/1989 | Redtenbacher et al. |
| 4,819,853 A | 4/1989 | Green |
| 4,821,939 A | 4/1989 | Green |
| 4,827,911 A | 5/1989 | Broadwin et al. |
| 4,830,855 A | 5/1989 | Stewart |
| 4,834,720 A | 5/1989 | Blinkhorn |
| 4,844,068 A | 7/1989 | Arata et al. |
| 4,848,637 A | 7/1989 | Pruitt |
| 4,865,030 A | 9/1989 | Polyak |
| 4,869,414 A | 9/1989 | Green et al. |
| 4,869,415 A | 9/1989 | Fox |
| 4,873,977 A | 10/1989 | Avant et al. |
| 4,880,015 A | 11/1989 | Nierman |
| 4,890,613 A | 1/1990 | Golden et al. |
| 4,892,244 A | 1/1990 | Fox et al. |
| 4,893,622 A | 1/1990 | Green et al. |
| 4,896,678 A | 1/1990 | Ogawa |
| 4,900,303 A | 2/1990 | Lemelson |
| 4,903,697 A | 2/1990 | Resnick et al. |
| 4,915,100 A | 4/1990 | Green |
| 4,930,503 A | 6/1990 | Pruitt |
| 4,930,674 A | 6/1990 | Barak |
| 4,931,047 A | 6/1990 | Broadwin et al. |
| 4,932,960 A | 6/1990 | Green et al. |
| 4,938,408 A | 7/1990 | Bedi et al. |
| 4,941,623 A | 7/1990 | Pruitt |
| 4,944,443 A | 7/1990 | Oddsen et al. |
| 4,955,959 A | 9/1990 | Tompkins et al. |
| 4,965,709 A | 10/1990 | Ngo |
| 4,973,274 A | 11/1990 | Hirukawa |
| 4,978,049 A | 12/1990 | Green |
| 4,978,333 A | 12/1990 | Broadwin et al. |
| 4,986,808 A | 1/1991 | Broadwin et al. |
| 4,988,334 A | 1/1991 | Hornlein et al. |
| 5,002,543 A | 3/1991 | Bradshaw et al. |
| 5,002,553 A | 3/1991 | Shiber |
| 5,009,661 A | 4/1991 | Michelson |
| 5,014,899 A | 5/1991 | Presty et al. |
| 5,015,227 A | 5/1991 | Broadwin et al. |
| 5,018,515 A | 5/1991 | Gilman |
| 5,024,671 A | 6/1991 | Tu et al. |
| 5,027,834 A | 7/1991 | Pruitt |
| 5,031,814 A | 7/1991 | Tompkins et al. |
| 5,038,109 A | 8/1991 | Goble et al. |
| 5,040,715 A | 8/1991 | Green et al. |
| 5,042,707 A | 8/1991 | Taheri |
| 5,061,269 A | 10/1991 | Muller |
| 5,062,563 A | 11/1991 | Green et al. |
| 5,065,929 A | 11/1991 | Schulze et al. |
| 5,071,052 A | 12/1991 | Rodak et al. |
| 5,071,430 A | 12/1991 | de Salis et al. |

(56) References Cited

U.S. PATENT DOCUMENTS

| | | |
|---|---|---|
| 5,074,454 A | 12/1991 | Peters |
| 5,079,006 A | 1/1992 | Urquhart |
| 5,080,556 A | 1/1992 | Carreno |
| 5,083,695 A | 1/1992 | Foslien et al. |
| 5,084,057 A | 1/1992 | Green et al. |
| 5,088,979 A | 2/1992 | Filipi et al. |
| 5,088,997 A | 2/1992 | Delahuerga et al. |
| 5,094,247 A | 3/1992 | Hernandez et al. |
| 5,100,420 A | 3/1992 | Green et al. |
| 5,104,025 A | 4/1992 | Main et al. |
| 5,104,397 A | 4/1992 | Vasconcelos et al. |
| 5,106,008 A | 4/1992 | Tompkins et al. |
| 5,111,987 A | 5/1992 | Moeinzadeh et al. |
| 5,116,349 A | 5/1992 | Aranyi |
| 5,122,156 A | 6/1992 | Granger et al. |
| 5,129,570 A | 7/1992 | Schulze et al. |
| 5,137,198 A | 8/1992 | Nobis et al. |
| 5,139,513 A | 8/1992 | Segato |
| 5,141,144 A | 8/1992 | Foslien et al. |
| 5,142,932 A | 9/1992 | Moya et al. |
| 5,155,941 A | 10/1992 | Takahashi et al. |
| 5,156,315 A | 10/1992 | Green et al. |
| 5,156,609 A | 10/1992 | Nakao et al. |
| 5,156,614 A | 10/1992 | Green et al. |
| 5,158,567 A | 10/1992 | Green |
| D330,699 S | 11/1992 | Gill |
| 5,163,598 A | 11/1992 | Peters et al. |
| 5,171,247 A | 12/1992 | Hughett et al. |
| 5,171,249 A | 12/1992 | Stefanchik et al. |
| 5,171,253 A | 12/1992 | Klieman et al. |
| 5,188,111 A | 2/1993 | Yates et al. |
| 5,190,517 A | 3/1993 | Zieve et al. |
| 5,192,288 A | 3/1993 | Thompson et al. |
| 5,195,968 A | 3/1993 | Lundquist et al. |
| 5,197,648 A | 3/1993 | Gingold |
| 5,197,649 A | 3/1993 | Bessler et al. |
| 5,200,280 A | 4/1993 | Karasa |
| 5,205,459 A | 4/1993 | Brinkerhoff et al. |
| 5,207,697 A | 5/1993 | Carusillo et al. |
| 5,209,747 A | 5/1993 | Knoepfler |
| 5,211,649 A | 5/1993 | Kohler et al. |
| 5,211,655 A | 5/1993 | Hasson |
| 5,217,457 A | 6/1993 | Delahuerga et al. |
| 5,217,478 A | 6/1993 | Rexroth |
| 5,219,111 A | 6/1993 | Bilotti et al. |
| 5,221,036 A | 6/1993 | Takase |
| 5,221,281 A | 6/1993 | Klicek |
| 5,222,963 A | 6/1993 | Brinkerhoff et al. |
| 5,222,975 A | 6/1993 | Crainich |
| 5,222,976 A | 6/1993 | Yoon |
| 5,223,675 A | 6/1993 | Taft |
| 5,234,447 A | 8/1993 | Kaster et al. |
| 5,236,440 A | 8/1993 | Hlavacek |
| 5,239,981 A | 8/1993 | Anapliotis |
| 5,240,163 A | 8/1993 | Stein et al. |
| 5,242,457 A | 9/1993 | Akopov et al. |
| 5,244,462 A | 9/1993 | Delahuerga et al. |
| 5,246,156 A | 9/1993 | Rothfuss et al. |
| 5,246,443 A | 9/1993 | Mai |
| 5,253,793 A | 10/1993 | Green et al. |
| 5,258,009 A | 11/1993 | Conners |
| 5,258,012 A | 11/1993 | Luscombe et al. |
| 5,259,366 A | 11/1993 | Reydel et al. |
| 5,259,835 A * | 11/1993 | Clark ............... A61F 13/02 |
| | | 602/48 |
| 5,260,637 A | 11/1993 | Pizzi |
| 5,263,629 A | 11/1993 | Trumbull et al. |
| 5,263,973 A | 11/1993 | Cook |
| 5,264,218 A | 11/1993 | Rogozinski |
| 5,268,622 A | 12/1993 | Philipp |
| 5,271,543 A | 12/1993 | Grant et al. |
| 5,271,544 A | 12/1993 | Fox et al. |
| RE34,519 E | 1/1994 | Fox et al. |
| 5,275,323 A | 1/1994 | Schulze et al. |
| 5,275,608 A | 1/1994 | Forman et al. |
| 5,279,416 A | 1/1994 | Malec et al. |
| 5,281,216 A | 1/1994 | Klicek |
| 5,282,806 A | 2/1994 | Haber et al. |
| 5,282,829 A | 2/1994 | Hermes |
| 5,284,128 A | 2/1994 | Hart |
| 5,285,945 A | 2/1994 | Brinkerhoff et al. |
| 5,289,963 A | 3/1994 | McGarry et al. |
| 5,290,271 A | 3/1994 | Jernberg |
| 5,292,053 A | 3/1994 | Bilotti et al. |
| 5,297,714 A | 3/1994 | Kramer |
| 5,304,204 A | 4/1994 | Bregen |
| 5,307,976 A | 5/1994 | Olson et al. |
| 5,309,927 A | 5/1994 | Welch |
| 5,312,023 A | 5/1994 | Green et al. |
| 5,312,024 A | 5/1994 | Grant et al. |
| 5,312,329 A | 5/1994 | Beaty et al. |
| 5,314,424 A | 5/1994 | Nicholas |
| 5,314,445 A | 5/1994 | Heidmueller née Degwitz et al. |
| 5,318,221 A | 6/1994 | Green et al. |
| 5,330,487 A | 7/1994 | Thornton et al. |
| 5,330,502 A | 7/1994 | Hassler et al. |
| 5,332,142 A | 7/1994 | Robinson et al. |
| 5,333,422 A | 8/1994 | Warren et al. |
| 5,333,772 A | 8/1994 | Rothfuss et al. |
| 5,334,183 A | 8/1994 | Wuchinich |
| 5,336,232 A | 8/1994 | Green et al. |
| 5,339,799 A | 8/1994 | Kami et al. |
| 5,341,724 A | 8/1994 | Vatel |
| 5,341,810 A | 8/1994 | Dardel |
| 5,342,381 A | 8/1994 | Tidemand |
| 5,342,395 A | 8/1994 | Jarrett et al. |
| 5,342,396 A | 8/1994 | Cook |
| 5,344,060 A | 9/1994 | Gravener et al. |
| 5,344,454 A | 9/1994 | Clarke et al. |
| 5,346,504 A | 9/1994 | Ortiz et al. |
| 5,348,259 A | 9/1994 | Blanco et al. |
| 5,350,388 A | 9/1994 | Epstein |
| 5,350,391 A | 9/1994 | Iacovelli |
| 5,350,400 A | 9/1994 | Esposito et al. |
| 5,352,229 A | 10/1994 | Goble et al. |
| 5,352,235 A | 10/1994 | Koros et al. |
| 5,352,238 A | 10/1994 | Green et al. |
| 5,354,303 A | 10/1994 | Spaeth et al. |
| 5,356,006 A | 10/1994 | Alpern et al. |
| 5,358,506 A | 10/1994 | Green et al. |
| 5,358,510 A | 10/1994 | Luscombe et al. |
| 5,359,231 A | 10/1994 | Flowers et al. |
| D352,780 S | 11/1994 | Glaeser et al. |
| 5,360,428 A | 11/1994 | Hutchinson, Jr. |
| 5,364,001 A | 11/1994 | Bryan |
| 5,364,003 A | 11/1994 | Williamson, IV |
| 5,366,133 A | 11/1994 | Geiste |
| 5,366,134 A | 11/1994 | Green et al. |
| 5,366,479 A | 11/1994 | McGarry et al. |
| 5,368,015 A | 11/1994 | Wilk |
| 5,368,592 A | 11/1994 | Stern et al. |
| 5,370,645 A | 12/1994 | Klicek et al. |
| 5,372,596 A | 12/1994 | Klicek et al. |
| 5,372,602 A | 12/1994 | Burke |
| 5,374,277 A | 12/1994 | Hassler |
| 5,376,095 A | 12/1994 | Ortiz |
| 5,379,933 A | 1/1995 | Green et al. |
| 5,381,782 A | 1/1995 | DeLaRama et al. |
| 5,382,247 A | 1/1995 | Cimino et al. |
| 5,383,880 A | 1/1995 | Hooven |
| 5,383,881 A | 1/1995 | Green et al. |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,389,104 A | 2/1995 | Hahnen et al. |
| 5,391,180 A | 2/1995 | Tovey et al. |
| 5,392,979 A | 2/1995 | Green et al. |
| 5,395,030 A | 3/1995 | Kuramoto et al. |
| 5,395,033 A | 3/1995 | Byrne et al. |
| 5,395,034 A | 3/1995 | Allen et al. |
| 5,395,312 A | 3/1995 | Desai |
| 5,395,384 A | 3/1995 | Duthoit |
| 5,397,046 A | 3/1995 | Savage et al. |
| 5,397,324 A | 3/1995 | Carroll et al. |

(56) References Cited

U.S. PATENT DOCUMENTS

| | | |
|---|---|---|
| 5,403,312 A | 4/1995 | Yates et al. |
| 5,405,072 A | 4/1995 | Zlock et al. |
| 5,405,073 A | 4/1995 | Porter |
| 5,405,344 A | 4/1995 | Williamson et al. |
| 5,405,360 A | 4/1995 | Tovey |
| 5,407,293 A | 4/1995 | Crainich |
| 5,409,498 A | 4/1995 | Braddock et al. |
| 5,411,508 A | 5/1995 | Bessler et al. |
| 5,413,267 A | 5/1995 | Solyntjes et al. |
| 5,413,268 A | 5/1995 | Green et al. |
| 5,413,272 A | 5/1995 | Green et al. |
| 5,413,573 A | 5/1995 | Koivukangas |
| 5,415,334 A | 5/1995 | Williamson, IV et al. |
| 5,415,335 A | 5/1995 | Knodell, Jr. |
| 5,417,203 A | 5/1995 | Tovey et al. |
| 5,417,361 A | 5/1995 | Williamson, IV |
| 5,421,829 A | 6/1995 | Olichney et al. |
| 5,422,567 A | 6/1995 | Matsunaga |
| 5,423,471 A | 6/1995 | Mastri et al. |
| 5,423,809 A | 6/1995 | Klicek |
| 5,425,745 A | 6/1995 | Green et al. |
| 5,431,322 A | 7/1995 | Green et al. |
| 5,431,654 A | 7/1995 | Nic |
| 5,431,668 A | 7/1995 | Burbank, III et al. |
| 5,433,721 A | 7/1995 | Hooven et al. |
| 5,437,681 A | 8/1995 | Meade et al. |
| 5,438,302 A | 8/1995 | Goble |
| 5,439,155 A | 8/1995 | Viola |
| 5,439,156 A | 8/1995 | Grant et al. |
| 5,439,479 A | 8/1995 | Schichman et al. |
| 5,441,191 A | 8/1995 | Linden |
| 5,441,193 A | 8/1995 | Gravener |
| 5,441,483 A | 8/1995 | Avitall |
| 5,441,494 A | 8/1995 | Ortiz |
| 5,444,113 A | 8/1995 | Sinclair et al. |
| 5,445,155 A | 8/1995 | Sieben |
| 5,445,304 A | 8/1995 | Plyley et al. |
| 5,445,644 A | 8/1995 | Pietrafitta et al. |
| 5,447,417 A | 9/1995 | Kuhl et al. |
| 5,447,513 A | 9/1995 | Davison et al. |
| 5,449,355 A | 9/1995 | Rhum et al. |
| 5,449,365 A | 9/1995 | Green et al. |
| 5,449,370 A | 9/1995 | Vaitekunas |
| 5,452,836 A | 9/1995 | Huitema et al. |
| 5,452,837 A | 9/1995 | Williamson, IV et al. |
| 5,454,378 A | 10/1995 | Palmer et al. |
| 5,454,827 A | 10/1995 | Aust et al. |
| 5,456,401 A | 10/1995 | Green et al. |
| 5,458,579 A | 10/1995 | Chodorow et al. |
| 5,462,215 A | 10/1995 | Viola et al. |
| 5,464,013 A | 11/1995 | Lemelson |
| 5,464,144 A | 11/1995 | Guy et al. |
| 5,464,300 A | 11/1995 | Crainich |
| 5,465,894 A | 11/1995 | Clark et al. |
| 5,465,895 A | 11/1995 | Knodel et al. |
| 5,465,896 A | 11/1995 | Allen et al. |
| 5,466,020 A | 11/1995 | Page et al. |
| 5,467,911 A | 11/1995 | Tsuruta et al. |
| 5,468,253 A | 11/1995 | Bezwada et al. |
| 5,470,006 A | 11/1995 | Rodak |
| 5,470,007 A | 11/1995 | Plyley et al. |
| 5,470,009 A | 11/1995 | Rodak |
| 5,470,010 A | 11/1995 | Rothfuss et al. |
| 5,472,132 A | 12/1995 | Savage et al. |
| 5,472,442 A | 12/1995 | Klicek |
| 5,473,204 A | 12/1995 | Temple |
| 5,474,057 A | 12/1995 | Makower et al. |
| 5,474,566 A | 12/1995 | Alesi et al. |
| 5,476,206 A | 12/1995 | Green et al. |
| 5,476,479 A | 12/1995 | Green et al. |
| 5,478,003 A | 12/1995 | Green et al. |
| 5,478,354 A | 12/1995 | Tovey et al. |
| 5,480,089 A | 1/1996 | Blewett |
| 5,480,409 A | 1/1996 | Riza |
| 5,482,197 A | 1/1996 | Green et al. |
| 5,484,095 A | 1/1996 | Green et al. |
| 5,484,398 A | 1/1996 | Stoddard |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,489,256 A | 2/1996 | Adair |
| 5,496,312 A | 3/1996 | Klicek |
| 5,496,317 A | 3/1996 | Goble et al. |
| 5,497,933 A | 3/1996 | DeFonzo et al. |
| 5,503,320 A | 4/1996 | Webster et al. |
| 5,503,635 A | 4/1996 | Sauer et al. |
| 5,503,638 A | 4/1996 | Cooper et al. |
| 5,505,363 A | 4/1996 | Green et al. |
| 5,507,426 A | 4/1996 | Young et al. |
| 5,509,596 A | 4/1996 | Green et al. |
| 5,509,916 A | 4/1996 | Taylor |
| 5,511,564 A | 4/1996 | Wilk |
| 5,514,129 A | 5/1996 | Smith |
| 5,514,157 A | 5/1996 | Nicholas et al. |
| 5,518,163 A | 5/1996 | Hooven |
| 5,518,164 A | 5/1996 | Hooven |
| 5,520,678 A | 5/1996 | Heckele et al. |
| 5,520,700 A | 5/1996 | Beyar et al. |
| 5,522,817 A | 6/1996 | Sander et al. |
| 5,527,320 A | 6/1996 | Carruthers et al. |
| 5,529,235 A | 6/1996 | Boiarski et al. |
| D372,086 S | 7/1996 | Grasso et al. |
| 5,531,305 A | 7/1996 | Roberts et al. |
| 5,531,744 A | 7/1996 | Nardella et al. |
| 5,533,521 A | 7/1996 | Granger |
| 5,533,581 A | 7/1996 | Barth et al. |
| 5,533,661 A | 7/1996 | Main et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,541,376 A | 7/1996 | Ladtkow et al. |
| 5,542,594 A | 8/1996 | McKean et al. |
| 5,542,949 A | 8/1996 | Yoon |
| 5,543,119 A | 8/1996 | Sutter et al. |
| 5,547,117 A | 8/1996 | Hamblin et al. |
| 5,549,621 A | 8/1996 | Bessler et al. |
| 5,549,628 A | 8/1996 | Cooper et al. |
| 5,549,637 A | 8/1996 | Crainich |
| 5,551,622 A | 9/1996 | Yoon |
| 5,553,675 A | 9/1996 | Pitzen et al. |
| 5,553,765 A | 9/1996 | Knodel et al. |
| 5,554,148 A | 9/1996 | Aebischer et al. |
| 5,554,169 A | 9/1996 | Green et al. |
| 5,556,416 A | 9/1996 | Clark et al. |
| 5,558,665 A | 9/1996 | Kieturakis |
| 5,558,671 A | 9/1996 | Yates |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,690 A | 10/1996 | Green et al. |
| 5,562,701 A | 10/1996 | Huitema et al. |
| 5,562,702 A | 10/1996 | Huitema et al. |
| 5,564,615 A | 10/1996 | Bishop et al. |
| 5,569,161 A | 10/1996 | Ebling et al. |
| 5,569,270 A | 10/1996 | Weng |
| 5,569,284 A | 10/1996 | Young et al. |
| 5,571,090 A | 11/1996 | Sherts |
| 5,571,100 A | 11/1996 | Goble et al. |
| 5,571,116 A | 11/1996 | Bolanos et al. |
| 5,571,285 A | 11/1996 | Chow et al. |
| 5,573,543 A | 11/1996 | Akopov et al. |
| 5,574,431 A | 11/1996 | McKeown et al. |
| 5,575,054 A | 11/1996 | Klinzing et al. |
| 5,575,789 A | 11/1996 | Bell et al. |
| 5,575,799 A | 11/1996 | Bolanos et al. |
| 5,575,803 A | 11/1996 | Cooper et al. |
| 5,575,805 A | 11/1996 | Li |
| 5,577,654 A | 11/1996 | Bishop |

(56) References Cited

U.S. PATENT DOCUMENTS

| | | |
|---|---|---|
| 5,579,978 A | 12/1996 | Green et al. |
| 5,580,067 A | 12/1996 | Hamblin et al. |
| 5,582,611 A | 12/1996 | Tsuruta et al. |
| 5,582,617 A | 12/1996 | Klieman et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,591,170 A | 1/1997 | Spievack et al. |
| 5,591,187 A | 1/1997 | Dekel |
| 5,597,107 A | 1/1997 | Knodel et al. |
| 5,599,151 A | 2/1997 | Daum et al. |
| 5,599,344 A | 2/1997 | Paterson |
| 5,599,350 A | 2/1997 | Schulze et al. |
| 5,599,852 A | 2/1997 | Scopelianos et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,607,433 A | 3/1997 | Polla et al. |
| 5,607,450 A | 3/1997 | Zvenyatsky et al. |
| 5,609,285 A | 3/1997 | Grant et al. |
| 5,609,601 A | 3/1997 | Kolesa et al. |
| 5,611,709 A | 3/1997 | McAnulty |
| 5,613,966 A | 3/1997 | Makower et al. |
| 5,615,820 A | 4/1997 | Viola |
| 5,618,294 A | 4/1997 | Aust et al. |
| 5,618,303 A | 4/1997 | Marlow et al. |
| 5,618,307 A | 4/1997 | Donlon et al. |
| 5,619,992 A | 4/1997 | Guthrie et al. |
| 5,620,289 A | 4/1997 | Curry |
| 5,620,452 A | 4/1997 | Yoon |
| 5,624,398 A | 4/1997 | Smith et al. |
| 5,624,452 A | 4/1997 | Yates |
| 5,626,587 A | 5/1997 | Bishop et al. |
| 5,626,595 A | 5/1997 | Sklar et al. |
| 5,628,446 A | 5/1997 | Geiste et al. |
| 5,628,743 A | 5/1997 | Cimino |
| 5,628,745 A | 5/1997 | Bek |
| 5,630,539 A | 5/1997 | Plyley et al. |
| 5,630,540 A | 5/1997 | Blewett |
| 5,630,541 A | 5/1997 | Williamson, IV et al. |
| 5,630,782 A | 5/1997 | Adair |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,643,291 A | 7/1997 | Pier et al. |
| 5,645,209 A | 7/1997 | Green et al. |
| 5,647,526 A | 7/1997 | Green et al. |
| 5,647,869 A | 7/1997 | Goble et al. |
| 5,649,937 A | 7/1997 | Bito et al. |
| 5,649,956 A | 7/1997 | Jensen et al. |
| 5,651,491 A | 7/1997 | Heaton et al. |
| 5,653,373 A | 8/1997 | Green et al. |
| 5,653,374 A | 8/1997 | Young et al. |
| 5,653,677 A | 8/1997 | Okada et al. |
| 5,653,721 A | 8/1997 | Knodel et al. |
| 5,655,698 A | 8/1997 | Yoon |
| 5,657,921 A | 8/1997 | Young et al. |
| 5,658,281 A | 8/1997 | Heard |
| 5,658,300 A | 8/1997 | Bito et al. |
| 5,658,307 A | 8/1997 | Exconde |
| 5,662,258 A | 9/1997 | Knodel et al. |
| 5,662,260 A | 9/1997 | Yoon |
| 5,662,662 A | 9/1997 | Bishop et al. |
| 5,665,085 A | 9/1997 | Nardella |
| 5,667,517 A | 9/1997 | Hooven |
| 5,667,526 A | 9/1997 | Levin |
| 5,667,527 A | 9/1997 | Cook |
| 5,669,544 A | 9/1997 | Schulze et al. |
| 5,669,904 A | 9/1997 | Platt, Jr. et al. |
| 5,669,907 A | 9/1997 | Platt, Jr. et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,674,286 A | 10/1997 | D'Alessio et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,683,349 A | 11/1997 | Makower et al. |
| 5,685,474 A | 11/1997 | Seeber |
| 5,686,090 A | 11/1997 | Schilder et al. |
| 5,688,270 A | 11/1997 | Yates et al. |
| 5,690,269 A | 11/1997 | Bolanos et al. |
| 5,692,668 A | 12/1997 | Schulze et al. |
| 5,693,020 A | 12/1997 | Rauh |
| 5,693,042 A | 12/1997 | Boiarski et al. |
| 5,693,051 A | 12/1997 | Schulze et al. |
| 5,695,494 A | 12/1997 | Becker |
| 5,695,502 A | 12/1997 | Pier et al. |
| 5,695,504 A | 12/1997 | Gifford, III et al. |
| 5,695,524 A | 12/1997 | Kelley et al. |
| 5,697,543 A | 12/1997 | Burdorff |
| 5,697,943 A | 12/1997 | Sauer et al. |
| 5,700,270 A | 12/1997 | Peyser et al. |
| 5,702,387 A | 12/1997 | Arts et al. |
| 5,702,408 A | 12/1997 | Wales et al. |
| 5,702,409 A | 12/1997 | Rayburn et al. |
| 5,704,087 A | 1/1998 | Strub |
| 5,704,534 A | 1/1998 | Huitema et al. |
| 5,706,997 A | 1/1998 | Green et al. |
| 5,706,998 A | 1/1998 | Plyley et al. |
| 5,707,392 A | 1/1998 | Kortenbach |
| 5,709,334 A | 1/1998 | Sorrentino et al. |
| 5,709,680 A | 1/1998 | Yates et al. |
| 5,709,706 A | 1/1998 | Kienzle et al. |
| 5,711,472 A | 1/1998 | Bryan |
| 5,713,128 A | 2/1998 | Schrenk et al. |
| 5,713,505 A | 2/1998 | Huitema |
| 5,713,895 A | 2/1998 | Lontine et al. |
| 5,713,896 A | 2/1998 | Nardella |
| 5,713,920 A | 2/1998 | Bezwada et al. |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,718,548 A | 2/1998 | Cotellessa |
| 5,720,744 A | 2/1998 | Eggleston et al. |
| D393,067 S | 3/1998 | Geary et al. |
| 5,725,536 A | 3/1998 | Oberlin et al. |
| 5,725,554 A | 3/1998 | Simon et al. |
| 5,728,110 A | 3/1998 | Vidal et al. |
| 5,728,121 A | 3/1998 | Bimbo et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,733,308 A | 3/1998 | Daugherty et al. |
| 5,735,445 A | 4/1998 | Vidal et al. |
| 5,735,848 A | 4/1998 | Yates et al. |
| 5,735,874 A | 4/1998 | Measamer et al. |
| 5,738,474 A | 4/1998 | Blewett |
| 5,738,648 A | 4/1998 | Lands et al. |
| 5,743,456 A | 4/1998 | Jones et al. |
| 5,747,953 A | 5/1998 | Philipp |
| 5,749,889 A | 5/1998 | Bacich et al. |
| 5,749,893 A | 5/1998 | Vidal et al. |
| 5,752,644 A | 5/1998 | Bolanos et al. |
| 5,752,965 A | 5/1998 | Francis et al. |
| 5,755,717 A | 5/1998 | Yates et al. |
| 5,758,814 A | 6/1998 | Gallagher et al. |
| 5,762,255 A | 6/1998 | Chrisman et al. |
| 5,762,256 A | 6/1998 | Mastri et al. |
| 5,766,188 A | 6/1998 | Igaki |
| 5,766,205 A | 6/1998 | Zvenyatsky et al. |

(56) References Cited

U.S. PATENT DOCUMENTS

| | | |
|---|---|---|
| 5,769,892 A | 6/1998 | Kingwell |
| 5,772,379 A | 6/1998 | Evensen |
| 5,772,578 A | 6/1998 | Heimberger et al. |
| 5,772,659 A | 6/1998 | Becker et al. |
| 5,776,130 A | 7/1998 | Buysse et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,782,749 A | 7/1998 | Riza |
| 5,782,859 A | 7/1998 | Nicholas et al. |
| 5,784,934 A | 7/1998 | Izumisawa |
| 5,785,232 A | 7/1998 | Vidal et al. |
| 5,785,647 A | 7/1998 | Tompkins et al. |
| 5,787,897 A | 8/1998 | Kieturakis |
| 5,792,135 A | 8/1998 | Madhani et al. |
| 5,792,165 A | 8/1998 | Klieman et al. |
| 5,794,834 A | 8/1998 | Hamblin et al. |
| 5,796,188 A | 8/1998 | Bays |
| 5,797,536 A | 8/1998 | Smith et al. |
| 5,797,537 A | 8/1998 | Oberlin et al. |
| 5,797,538 A | 8/1998 | Heaton et al. |
| 5,797,906 A | 8/1998 | Rhum et al. |
| 5,797,959 A | 8/1998 | Castro et al. |
| 5,799,857 A | 9/1998 | Robertson et al. |
| 5,800,379 A | 9/1998 | Edwards |
| 5,800,423 A | 9/1998 | Jensen |
| 5,806,676 A | 9/1998 | Wasgien |
| 5,807,376 A | 9/1998 | Viola et al. |
| 5,807,378 A | 9/1998 | Jensen et al. |
| 5,807,393 A | 9/1998 | Williamson, IV et al. |
| 5,809,441 A | 9/1998 | McKee |
| 5,810,721 A | 9/1998 | Mueller et al. |
| 5,810,811 A | 9/1998 | Yates et al. |
| 5,810,846 A | 9/1998 | Virnich et al. |
| 5,810,855 A | 9/1998 | Rayburn et al. |
| 5,813,813 A | 9/1998 | Daum et al. |
| 5,814,055 A | 9/1998 | Knodel et al. |
| 5,814,057 A * | 9/1998 | Oi et al. ............ 606/151 |
| 5,816,471 A | 10/1998 | Plyley et al. |
| 5,817,084 A | 10/1998 | Jensen |
| 5,817,091 A | 10/1998 | Nardella et al. |
| 5,817,093 A | 10/1998 | Williamson, IV et al. |
| 5,817,109 A | 10/1998 | McGarry et al. |
| 5,817,119 A | 10/1998 | Klieman et al. |
| 5,820,009 A | 10/1998 | Melling et al. |
| 5,823,066 A | 10/1998 | Huitema et al. |
| 5,826,776 A | 10/1998 | Schulze et al. |
| 5,827,271 A | 10/1998 | Buysse et al. |
| 5,827,298 A | 10/1998 | Hart et al. |
| 5,829,662 A | 11/1998 | Allen et al. |
| 5,833,690 A | 11/1998 | Yates et al. |
| 5,833,695 A | 11/1998 | Yoon |
| 5,833,696 A | 11/1998 | Whitfield et al. |
| 5,836,503 A | 11/1998 | Ehrenfels et al. |
| 5,836,960 A | 11/1998 | Kolesa et al. |
| 5,839,639 A | 11/1998 | Sauer et al. |
| 5,843,021 A | 12/1998 | Edwards et al. |
| 5,843,096 A | 12/1998 | Igaki et al. |
| 5,843,122 A | 12/1998 | Riza |
| 5,843,132 A | 12/1998 | Ilvento |
| 5,846,254 A | 12/1998 | Schulze et al. |
| 5,849,011 A | 12/1998 | Jones et al. |
| 5,849,023 A | 12/1998 | Mericle |
| 5,855,311 A | 1/1999 | Hamblin et al. |
| 5,855,583 A | 1/1999 | Wang et al. |
| 5,860,581 A | 1/1999 | Robertson et al. |
| 5,860,975 A | 1/1999 | Goble et al. |
| 5,865,361 A | 2/1999 | Milliman et al. |
| 5,868,760 A | 2/1999 | McGuckin, Jr. |
| 5,871,135 A | 2/1999 | Williamson IV et al. |
| 5,873,885 A | 2/1999 | Weidenbenner |
| 5,876,401 A | 3/1999 | Schulze et al. |
| 5,878,193 A | 3/1999 | Wang et al. |
| 5,878,937 A | 3/1999 | Green et al. |
| 5,878,938 A | 3/1999 | Bittner et al. |
| 5,891,160 A | 4/1999 | Williamson, IV et al. |
| 5,893,506 A | 4/1999 | Powell |
| 5,893,835 A | 4/1999 | Witt et al. |
| 5,894,979 A | 4/1999 | Powell |
| 5,897,552 A | 4/1999 | Edwards et al. |
| 5,897,562 A | 4/1999 | Bolanos et al. |
| 5,899,914 A | 5/1999 | Zirps et al. |
| 5,901,895 A | 5/1999 | Heaton et al. |
| 5,902,312 A | 5/1999 | Frater et al. |
| 5,904,693 A | 5/1999 | Dicesare et al. |
| 5,906,625 A | 5/1999 | Bito et al. |
| 5,908,402 A | 6/1999 | Blythe |
| 5,908,427 A | 6/1999 | McKean et al. |
| 5,911,353 A | 6/1999 | Bolanos et al. |
| 5,915,616 A | 6/1999 | Viola et al. |
| 5,916,225 A | 6/1999 | Kugel |
| 5,918,791 A | 7/1999 | Sorrentino et al. |
| 5,919,198 A | 7/1999 | Graves, Jr. et al. |
| 5,921,956 A | 7/1999 | Grinberg et al. |
| 5,928,256 A | 7/1999 | Riza |
| 5,931,847 A | 8/1999 | Bittner et al. |
| 5,931,853 A | 8/1999 | McEwen et al. |
| 5,937,951 A | 8/1999 | Izuchukwu et al. |
| 5,938,667 A | 8/1999 | Peyser et al. |
| 5,941,442 A | 8/1999 | Geiste et al. |
| 5,944,172 A | 8/1999 | Hannula |
| 5,944,715 A | 8/1999 | Goble et al. |
| 5,947,984 A | 9/1999 | Whipple |
| 5,948,030 A | 9/1999 | Miller et al. |
| 5,951,552 A | 9/1999 | Long et al. |
| 5,951,574 A | 9/1999 | Stefanchik et al. |
| 5,951,581 A | 9/1999 | Saadat et al. |
| 5,954,259 A | 9/1999 | Viola et al. |
| 5,964,774 A | 10/1999 | McKean et al. |
| 5,971,916 A | 10/1999 | Koren |
| 5,973,221 A | 10/1999 | Collyer et al. |
| 5,984,949 A | 11/1999 | Levin |
| 5,988,479 A | 11/1999 | Palmer |
| 5,997,528 A | 12/1999 | Bisch et al. |
| 5,997,552 A | 12/1999 | Person et al. |
| 6,003,517 A | 12/1999 | Sheffield et al. |
| 6,004,319 A | 12/1999 | Goble et al. |
| 6,010,054 A | 1/2000 | Johnson et al. |
| 6,010,513 A | 1/2000 | Törmälä et al. |
| 6,012,494 A | 1/2000 | Balazs |
| 6,013,076 A | 1/2000 | Goble et al. |
| 6,015,406 A | 1/2000 | Goble et al. |
| 6,017,322 A | 1/2000 | Snoke et al. |
| 6,017,354 A | 1/2000 | Culp et al. |
| 6,017,356 A | 1/2000 | Frederick et al. |
| 6,022,352 A | 2/2000 | Vandewalle |
| 6,024,741 A | 2/2000 | Williamson, IV et al. |
| 6,024,748 A | 2/2000 | Manzo et al. |
| 6,027,501 A | 2/2000 | Goble et al. |
| 6,032,849 A | 3/2000 | Mastri et al. |
| 6,033,378 A | 3/2000 | Lundquist et al. |
| 6,033,399 A | 3/2000 | Gines |
| 6,033,427 A | 3/2000 | Lee |
| 6,037,724 A | 3/2000 | Buss et al. |
| 6,039,733 A | 3/2000 | Buysse et al. |
| 6,039,734 A | 3/2000 | Goble |
| 6,042,601 A | 3/2000 | Smith |
| 6,045,560 A * | 4/2000 | McKean ........ A61B 17/07207 227/180.1 |
| 6,047,861 A | 4/2000 | Vidal et al. |
| 6,050,472 A | 4/2000 | Shibata |
| 6,050,990 A | 4/2000 | Tankovich et al. |
| 6,050,996 A | 4/2000 | Schmaltz et al. |
| 6,053,390 A | 4/2000 | Green et al. |
| 6,053,922 A | 4/2000 | Krause et al. |
| RE36,720 E | 5/2000 | Green et al. |
| 6,056,735 A | 5/2000 | Okada et al. |
| 6,056,746 A | 5/2000 | Goble et al. |
| 6,062,360 A | 5/2000 | Shields |
| 6,063,097 A | 5/2000 | Oi et al. |
| 6,063,098 A | 5/2000 | Houser et al. |
| 6,065,919 A | 5/2000 | Peck |

(56) References Cited

U.S. PATENT DOCUMENTS

| | | | |
|---|---|---|---|
| 6,066,132 A | 5/2000 | Chen et al. | |
| 6,068,627 A | 5/2000 | Orszulak et al. | |
| 6,071,233 A | 6/2000 | Ishikawa et al. | |
| 6,074,386 A | 6/2000 | Goble et al. | |
| 6,074,401 A | 6/2000 | Gardiner et al. | |
| 6,077,286 A | 6/2000 | Cuschieri et al. | |
| 6,079,606 A | 6/2000 | Milliman et al. | |
| 6,082,577 A | 7/2000 | Coates et al. | |
| 6,083,191 A | 7/2000 | Rose | |
| 6,083,234 A | 7/2000 | Nicholas et al. | |
| 6,083,242 A | 7/2000 | Cook | |
| 6,086,544 A | 7/2000 | Hibner et al. | |
| 6,086,600 A | 7/2000 | Kortenbach | |
| 6,090,106 A | 7/2000 | Goble et al. | |
| 6,093,186 A | 7/2000 | Goble | |
| 6,099,537 A | 8/2000 | Sugai et al. | |
| 6,099,551 A | 8/2000 | Gabbay | |
| 6,102,271 A | 8/2000 | Longo et al. | |
| 6,109,500 A | 8/2000 | Alli et al. | |
| 6,110,187 A * | 8/2000 | Donlon | A61B 17/11 128/898 |
| 6,117,148 A | 9/2000 | Ravo et al. | |
| 6,117,158 A | 9/2000 | Measamer et al. | |
| 6,119,913 A | 9/2000 | Adams et al. | |
| 6,120,433 A | 9/2000 | Mizuno et al. | |
| 6,123,241 A | 9/2000 | Walter et al. | |
| H1904 H | 10/2000 | Yates et al. | |
| 6,126,058 A | 10/2000 | Adams et al. | |
| 6,126,670 A | 10/2000 | Walker et al. | |
| 6,131,789 A | 10/2000 | Schulze et al. | |
| 6,131,790 A | 10/2000 | Piraka | |
| 6,132,368 A | 10/2000 | Cooper | |
| 6,139,546 A | 10/2000 | Koenig et al. | |
| 6,149,660 A | 11/2000 | Laufer et al. | |
| 6,152,935 A | 11/2000 | Kammerer et al. | |
| 6,155,473 A | 12/2000 | Tompkins et al. | |
| 6,156,056 A | 12/2000 | Kearns et al. | |
| 6,159,146 A | 12/2000 | El Gazayerli | |
| 6,159,200 A | 12/2000 | Verdura et al. | |
| 6,159,224 A | 12/2000 | Yoon | |
| 6,162,208 A | 12/2000 | Hipps | |
| 6,165,175 A | 12/2000 | Wampler et al. | |
| 6,165,184 A | 12/2000 | Verdura et al. | |
| 6,165,188 A | 12/2000 | Saadat et al. | |
| 6,168,605 B1 | 1/2001 | Measamer et al. | |
| 6,171,316 B1 | 1/2001 | Kovac et al. | |
| 6,171,330 B1 | 1/2001 | Benchetrit | |
| 6,174,308 B1 | 1/2001 | Goble et al. | |
| 6,174,309 B1 | 1/2001 | Wrublewski et al. | |
| 6,179,195 B1 | 1/2001 | Adams et al. | |
| 6,179,776 B1 | 1/2001 | Adams et al. | |
| 6,181,105 B1 | 1/2001 | Cutolo et al. | |
| 6,182,673 B1 | 2/2001 | Kindermann et al. | |
| 6,187,003 B1 | 2/2001 | Buysse et al. | |
| 6,190,386 B1 | 2/2001 | Rydell | |
| 6,193,129 B1 | 2/2001 | Bittner et al. | |
| 6,197,042 B1 | 3/2001 | Ginn et al. | |
| 6,200,330 B1 | 3/2001 | Benderev et al. | |
| 6,202,914 B1 | 3/2001 | Geiste et al. | |
| 6,206,897 B1 | 3/2001 | Jamiolkowski et al. | |
| 6,210,403 B1 | 4/2001 | Klicek | |
| 6,213,999 B1 | 4/2001 | Platt, Jr. et al. | |
| 6,214,028 B1 | 4/2001 | Yoon et al. | |
| 6,220,368 B1 | 4/2001 | Ark et al. | |
| 6,223,100 B1 | 4/2001 | Green | |
| 6,223,835 B1 | 5/2001 | Habedank et al. | |
| 6,224,617 B1 | 5/2001 | Saadat et al. | |
| 6,228,081 B1 | 5/2001 | Goble | |
| 6,228,083 B1 | 5/2001 | Lands et al. | |
| 6,228,084 B1 | 5/2001 | Kirwan, Jr. | |
| 6,231,565 B1 | 5/2001 | Tovey et al. | |
| 6,234,178 B1 | 5/2001 | Goble et al. | |
| 6,241,139 B1 | 6/2001 | Milliman et al. | |
| 6,241,140 B1 | 6/2001 | Adams et al. | |
| 6,241,723 B1 | 6/2001 | Heim et al. | |
| 6,245,084 B1 | 6/2001 | Mark et al. | |
| 6,248,116 B1 * | 6/2001 | Chevillon | A61B 17/064 128/898 |
| 6,248,117 B1 | 6/2001 | Blatter | |
| 6,249,076 B1 | 6/2001 | Madden et al. | |
| 6,250,532 B1 | 6/2001 | Green et al. | |
| 6,258,107 B1 | 7/2001 | Balázs et al. | |
| 6,261,286 B1 | 7/2001 | Goble et al. | |
| 6,264,086 B1 | 7/2001 | McGuckin, Jr. | |
| 6,264,087 B1 | 7/2001 | Whitman | |
| 6,270,508 B1 | 8/2001 | Klieman et al. | |
| 6,273,876 B1 | 8/2001 | Klima et al. | |
| 6,273,897 B1 | 8/2001 | Dalessandro et al. | |
| 6,277,114 B1 | 8/2001 | Bullivant et al. | |
| 6,293,942 B1 | 9/2001 | Goble et al. | |
| 6,296,640 B1 | 10/2001 | Wampler et al. | |
| 6,302,311 B1 | 10/2001 | Adams et al. | |
| 6,305,891 B1 | 10/2001 | Burlingame | |
| 6,306,134 B1 | 10/2001 | Goble et al. | |
| 6,306,149 B1 | 10/2001 | Meade | |
| 6,309,403 B1 | 10/2001 | Minor et al. | |
| 6,315,184 B1 | 11/2001 | Whitman | |
| 6,320,123 B1 | 11/2001 | Reimers | |
| 6,322,494 B1 | 11/2001 | Bullivant et al. | |
| 6,324,339 B1 | 11/2001 | Hudson et al. | |
| 6,325,799 B1 | 12/2001 | Goble | |
| 6,325,810 B1 | 12/2001 | Hamilton et al. | |
| 6,330,965 B1 | 12/2001 | Milliman et al. | |
| 6,331,181 B1 | 12/2001 | Tierney et al. | |
| 6,331,761 B1 | 12/2001 | Kumar et al. | |
| 6,333,029 B1 | 12/2001 | Vyakarnam et al. | |
| 6,334,860 B1 | 1/2002 | Dorn | |
| 6,334,861 B1 | 1/2002 | Chandler et al. | |
| 6,336,926 B1 | 1/2002 | Goble | |
| 6,338,737 B1 | 1/2002 | Toledano | |
| 6,343,731 B1 | 2/2002 | Adams et al. | |
| 6,346,077 B1 | 2/2002 | Taylor et al. | |
| 6,352,503 B1 | 3/2002 | Matsui et al. | |
| 6,352,532 B1 | 3/2002 | Kramer et al. | |
| 6,355,699 B1 | 3/2002 | Vyakarnam et al. | |
| 6,358,224 B1 | 3/2002 | Tims et al. | |
| 6,364,877 B1 | 4/2002 | Goble et al. | |
| 6,364,888 B1 | 4/2002 | Niemeyer et al. | |
| 6,370,981 B2 | 4/2002 | Watarai | |
| 6,373,152 B1 | 4/2002 | Wang et al. | |
| 6,383,201 B1 | 5/2002 | Dong | |
| 6,387,113 B1 | 5/2002 | Hawkins et al. | |
| 6,387,114 B2 | 5/2002 | Adams | |
| 6,391,038 B2 | 5/2002 | Vargas et al. | |
| 6,398,781 B1 | 6/2002 | Goble et al. | |
| 6,398,797 B2 | 6/2002 | Bombard et al. | |
| 6,402,766 B2 | 6/2002 | Bowman et al. | |
| 6,406,440 B1 | 6/2002 | Stefanchik | |
| 6,406,472 B1 | 6/2002 | Jensen | |
| 6,409,724 B1 | 6/2002 | Penny et al. | |
| H2037 H | 7/2002 | Yates et al. | |
| 6,413,274 B1 | 7/2002 | Pedros | |
| 6,416,486 B1 | 7/2002 | Wampler | |
| 6,416,509 B1 | 7/2002 | Goble et al. | |
| 6,419,695 B1 | 7/2002 | Gabbay | |
| RE37,814 E | 8/2002 | Allgeyer | |
| 6,428,070 B1 | 8/2002 | Takanashi et al. | |
| 6,429,611 B1 | 8/2002 | Li | |
| 6,436,097 B1 | 8/2002 | Nardella | |
| 6,436,107 B1 | 8/2002 | Wang et al. | |
| 6,436,110 B2 | 8/2002 | Bowman et al. | |
| 6,436,122 B1 | 8/2002 | Frank et al. | |
| 6,439,439 B1 | 8/2002 | Rickard et al. | |
| 6,439,446 B1 | 8/2002 | Perry et al. | |
| 6,440,146 B2 | 8/2002 | Nicholas et al. | |
| 6,443,973 B1 | 9/2002 | Whitman | |
| 6,447,518 B1 | 9/2002 | Krause et al. | |
| 6,450,391 B1 | 9/2002 | Kayan et al. | |
| 6,450,989 B2 | 9/2002 | Dubrul et al. | |
| 6,454,781 B1 | 9/2002 | Witt et al. | |
| 6,468,275 B1 | 10/2002 | Wampler et al. | |
| 6,471,106 B1 | 10/2002 | Reining | |
| 6,478,210 B2 | 11/2002 | Adams et al. | |
| 6,482,200 B2 | 11/2002 | Shippert | |

(56) References Cited

U.S. PATENT DOCUMENTS

| | | |
|---|---|---|
| 6,485,490 B2 | 11/2002 | Wampler et al. |
| 6,485,667 B1 | 11/2002 | Tan |
| 6,488,196 B1 | 12/2002 | Fenton, Jr. |
| 6,488,197 B1 | 12/2002 | Whitman |
| 6,491,201 B1 | 12/2002 | Whitman |
| 6,491,690 B1 | 12/2002 | Goble et al. |
| 6,491,701 B2 | 12/2002 | Tierney et al. |
| 6,492,785 B1 | 12/2002 | Kasten et al. |
| 6,494,896 B1 | 12/2002 | D'Alessio et al. |
| 6,500,176 B1 | 12/2002 | Truckai et al. |
| 6,500,194 B2 | 12/2002 | Benderev et al. |
| 6,503,257 B2 | 1/2003 | Grant et al. |
| 6,503,259 B2 | 1/2003 | Huxel et al. |
| 6,505,768 B2 | 1/2003 | Whitman |
| 6,510,854 B2 | 1/2003 | Goble |
| 6,511,468 B1 | 1/2003 | Cragg et al. |
| 6,517,528 B1 | 2/2003 | Pantages et al. |
| 6,517,535 B2 | 2/2003 | Edwards |
| 6,517,565 B1 | 2/2003 | Whitman et al. |
| 6,517,566 B1 | 2/2003 | Hovland et al. |
| 6,522,101 B2 | 2/2003 | Malackowski |
| 6,527,785 B2 | 3/2003 | Sancoff et al. |
| 6,533,157 B1 | 3/2003 | Whitman |
| 6,533,784 B2 | 3/2003 | Truckai et al. |
| 6,535,764 B2 | 3/2003 | Imran et al. |
| 6,543,456 B1 | 4/2003 | Freeman |
| 6,545,384 B1 | 4/2003 | Pelrine et al. |
| 6,547,786 B1 | 4/2003 | Goble |
| 6,550,546 B2 | 4/2003 | Thurler et al. |
| 6,551,333 B2 | 4/2003 | Kuhns et al. |
| 6,554,861 B2 | 4/2003 | Knox et al. |
| 6,558,379 B1 | 5/2003 | Batchelor et al. |
| 6,565,560 B1 | 5/2003 | Goble et al. |
| 6,569,085 B2 | 5/2003 | Kortenbach et al. |
| 6,569,171 B2 | 5/2003 | DeGuillebon et al. |
| 6,578,751 B2 | 6/2003 | Hartwick |
| 6,582,427 B1 | 6/2003 | Goble et al. |
| 6,582,441 B1 | 6/2003 | He et al. |
| 6,583,533 B2 | 6/2003 | Pelrine et al. |
| 6,585,144 B2 | 7/2003 | Adams et al. |
| 6,588,643 B2 | 7/2003 | Bolduc et al. |
| 6,589,164 B1 | 7/2003 | Flaherty |
| 6,592,538 B1 | 7/2003 | Hotchkiss et al. |
| 6,592,597 B2 | 7/2003 | Grant et al. |
| 6,596,296 B1 | 7/2003 | Nelson et al. |
| 6,596,304 B1 | 7/2003 | Bayon et al. |
| 6,596,432 B2 | 7/2003 | Kawakami et al. |
| D478,665 S | 8/2003 | Isaacs et al. |
| D478,986 S | 8/2003 | Johnston et al. |
| 6,601,749 B2 | 8/2003 | Sullivan et al. |
| 6,602,252 B2 | 8/2003 | Mollenauer |
| 6,602,262 B2 | 8/2003 | Griego et al. |
| 6,605,078 B2 | 8/2003 | Adams |
| 6,605,669 B2 | 8/2003 | Awokola et al. |
| 6,607,475 B2 | 8/2003 | Doyle et al. |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,626,834 B2 | 9/2003 | Dunne et al. |
| 6,629,630 B2 | 10/2003 | Adams |
| 6,629,974 B2 | 10/2003 | Penny et al. |
| 6,629,988 B2 | 10/2003 | Weadock |
| 6,636,412 B2 | 10/2003 | Smith |
| 6,638,108 B2 | 10/2003 | Tachi |
| 6,638,285 B2 | 10/2003 | Gabbay |
| 6,638,297 B1 | 10/2003 | Huitema |
| RE38,335 E | 11/2003 | Aust et al. |
| 6,641,528 B2 | 11/2003 | Torii |
| 6,644,532 B2 | 11/2003 | Green et al. |
| 6,645,201 B1 | 11/2003 | Utley et al. |
| 6,646,307 B1 | 11/2003 | Yu et al. |
| 6,648,816 B2 | 11/2003 | Irion et al. |
| 6,652,595 B1 | 11/2003 | Nicolo |
| D484,243 S | 12/2003 | Ryan et al. |
| D484,595 S | 12/2003 | Ryan et al. |
| D484,596 S | 12/2003 | Ryan et al. |
| 6,656,177 B2 | 12/2003 | Truckai et al. |
| 6,656,193 B2 | 12/2003 | Grant et al. |
| 6,663,641 B1 | 12/2003 | Kovac et al. |
| 6,666,854 B1 | 12/2003 | Lange |
| 6,666,875 B1 | 12/2003 | Sakurai et al. |
| 6,667,825 B2 | 12/2003 | Lu et al. |
| 6,669,073 B2 | 12/2003 | Milliman et al. |
| 6,671,185 B2 | 12/2003 | Duval |
| D484,977 S | 1/2004 | Ryan et al. |
| 6,676,660 B2 | 1/2004 | Wampler et al. |
| 6,679,269 B2 | 1/2004 | Swanson |
| 6,679,410 B2 | 1/2004 | Würsch et al. |
| 6,681,978 B2 | 1/2004 | Geiste et al. |
| 6,681,979 B2 | 1/2004 | Whitman |
| 6,682,527 B2 | 1/2004 | Strul |
| 6,682,528 B2 | 1/2004 | Frazier et al. |
| 6,685,727 B2 | 2/2004 | Fisher et al. |
| 6,689,153 B1 | 2/2004 | Skiba |
| 6,692,507 B2 | 2/2004 | Pugsley et al. |
| 6,695,198 B2 | 2/2004 | Adams et al. |
| 6,695,199 B2 | 2/2004 | Whitman |
| 6,698,643 B2 | 3/2004 | Whitman |
| 6,699,235 B2 | 3/2004 | Wallace et al. |
| 6,704,210 B1 | 3/2004 | Myers |
| 6,705,503 B1 | 3/2004 | Pedicini et al. |
| 6,709,445 B2 | 3/2004 | Boebel et al. |
| 6,712,773 B1 | 3/2004 | Viola |
| 6,716,223 B2 | 4/2004 | Leopold et al. |
| 6,716,232 B1 | 4/2004 | Vidal et al. |
| 6,716,233 B1 | 4/2004 | Whitman |
| 6,722,552 B2 | 4/2004 | Fenton, Jr. |
| 6,723,087 B2 | 4/2004 | O'Neill et al. |
| 6,723,091 B2 | 4/2004 | Goble et al. |
| 6,726,697 B2 | 4/2004 | Nicholas et al. |
| 6,729,119 B2 | 5/2004 | Schnipke et al. |
| 6,736,825 B2 | 5/2004 | Blatter et al. |
| 6,736,854 B2 | 5/2004 | Vadurro et al. |
| 6,740,030 B2 | 5/2004 | Martone et al. |
| 6,747,121 B2 | 6/2004 | Gogolewski |
| 6,749,560 B1 | 6/2004 | Konstorum et al. |
| 6,752,768 B2 | 6/2004 | Burdorff et al. |
| 6,752,816 B2 | 6/2004 | Culp et al. |
| 6,755,195 B1 | 6/2004 | Lemke et al. |
| 6,755,338 B2 | 6/2004 | Hahnen et al. |
| 6,758,846 B2 | 7/2004 | Goble et al. |
| 6,761,685 B2 | 7/2004 | Adams et al. |
| 6,762,339 B1 | 7/2004 | Klun et al. |
| 6,767,352 B2 | 7/2004 | Field et al. |
| 6,767,356 B2 | 7/2004 | Kanner et al. |
| 6,769,590 B2 | 8/2004 | Vresh et al. |
| 6,769,594 B2 | 8/2004 | Orban, III |
| 6,770,072 B1 | 8/2004 | Truckai et al. |
| 6,773,409 B2 | 8/2004 | Truckai et al. |
| 6,773,438 B1 | 8/2004 | Knodel et al. |
| 6,777,838 B2 | 8/2004 | Miekka et al. |
| 6,780,151 B2 | 8/2004 | Grabover et al. |
| 6,780,180 B1 | 8/2004 | Goble et al. |
| 6,783,524 B2 | 8/2004 | Anderson et al. |
| 6,786,382 B1 | 9/2004 | Hoffman |
| 6,786,864 B2 | 9/2004 | Matsuura et al. |
| 6,786,896 B1 | 9/2004 | Madhani et al. |
| 6,790,173 B2 | 9/2004 | Saadat et al. |
| 6,793,652 B1 | 9/2004 | Whitman et al. |
| 6,793,661 B2 | 9/2004 | Hamilton et al. |
| 6,793,663 B2 | 9/2004 | Kneifel et al. |
| 6,802,843 B2 | 10/2004 | Truckai et al. |
| 6,805,273 B2 | 10/2004 | Bilotti et al. |
| 6,806,808 B1 | 10/2004 | Watters et al. |
| 6,808,525 B2 | 10/2004 | Latterell et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,818,018 B1 | 11/2004 | Sawhney |
| 6,820,791 B2 | 11/2004 | Adams |
| 6,821,273 B2 | 11/2004 | Mollenauer |
| 6,821,284 B2 | 11/2004 | Sturtz et al. |
| 6,827,246 B2 | 12/2004 | Sullivan et al. |

(56) References Cited

U.S. PATENT DOCUMENTS

| | | |
|---|---|---|
| 6,827,712 B2 | 12/2004 | Tovey et al. |
| 6,827,725 B2 | 12/2004 | Batchelor et al. |
| 6,828,902 B2 | 12/2004 | Casden |
| 6,830,174 B2 | 12/2004 | Hillstead et al. |
| 6,831,629 B2 | 12/2004 | Nishino et al. |
| 6,832,998 B2 | 12/2004 | Goble |
| 6,834,001 B2 | 12/2004 | Myono |
| 6,835,199 B2 | 12/2004 | McGuckin, Jr. et al. |
| 6,835,336 B2 | 12/2004 | Watt |
| 6,837,846 B2 | 1/2005 | Jaffe et al. |
| 6,838,493 B2 | 1/2005 | Williams et al. |
| 6,840,423 B2 | 1/2005 | Adams et al. |
| 6,843,403 B2 | 1/2005 | Whitman |
| 6,843,789 B2 | 1/2005 | Goble |
| 6,843,793 B2 | 1/2005 | Brock et al. |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,850,817 B1 | 2/2005 | Green |
| 6,858,005 B2 | 2/2005 | Ohline et al. |
| RE38,708 E | 3/2005 | Bolanos et al. |
| 6,861,142 B1 | 3/2005 | Wilkie et al. |
| 6,863,694 B1 | 3/2005 | Boyce et al. |
| 6,866,178 B2 | 3/2005 | Adams et al. |
| 6,866,671 B2 | 3/2005 | Tierney et al. |
| 6,867,248 B1 | 3/2005 | Martin et al. |
| 6,869,435 B2 | 3/2005 | Blake, III |
| 6,872,214 B2 | 3/2005 | Sonnenschein et al. |
| 6,874,669 B2 | 4/2005 | Adams et al. |
| 6,877,647 B2 | 4/2005 | Green et al. |
| 6,878,106 B1 | 4/2005 | Herrmann |
| 6,889,116 B2 | 5/2005 | Jinno |
| 6,893,435 B2 | 5/2005 | Goble |
| 6,905,057 B2 | 6/2005 | Swayze et al. |
| 6,905,497 B2 | 6/2005 | Truckai et al. |
| 6,908,472 B2 | 6/2005 | Wiener et al. |
| 6,911,033 B2 | 6/2005 | de Guillebon et al. |
| 6,913,579 B2 | 7/2005 | Truckai et al. |
| 6,913,608 B2 | 7/2005 | Liddicoat et al. |
| 6,913,613 B2 | 7/2005 | Schwarz et al. |
| 6,921,397 B2 | 7/2005 | Corcoran et al. |
| 6,921,412 B1 | 7/2005 | Black et al. |
| 6,923,803 B2 | 8/2005 | Goble |
| 6,926,716 B2 | 8/2005 | Baker et al. |
| 6,929,641 B2 | 8/2005 | Goble et al. |
| 6,929,644 B2 | 8/2005 | Truckai et al. |
| 6,931,830 B2 | 8/2005 | Liao |
| 6,932,218 B2 | 8/2005 | Kosann et al. |
| 6,932,810 B2 | 8/2005 | Ryan |
| 6,936,042 B2 | 8/2005 | Wallace et al. |
| 6,939,358 B2 | 9/2005 | Palacios et al. |
| 6,942,662 B2 | 9/2005 | Goble et al. |
| 6,945,444 B2 | 9/2005 | Gresham et al. |
| 6,945,981 B2 | 9/2005 | Donofrio et al. |
| 6,953,138 B1 | 10/2005 | Dworak et al. |
| 6,953,139 B2 | 10/2005 | Milliman et al. |
| 6,958,035 B2 | 10/2005 | Friedman et al. |
| 6,959,851 B2 | 11/2005 | Heinrich |
| 6,959,852 B2 | 11/2005 | Shelton, IV et al. |
| 6,960,107 B1 | 11/2005 | Schaub et al. |
| 6,960,163 B2 | 11/2005 | Ewers et al. |
| 6,960,220 B2 | 11/2005 | Marino et al. |
| 6,964,363 B2 | 11/2005 | Wales et al. |
| 6,966,907 B2 | 11/2005 | Goble |
| 6,966,909 B2 | 11/2005 | Marshall et al. |
| 6,971,988 B2 | 12/2005 | Orban, III |
| 6,972,199 B2 | 12/2005 | Lebouitz et al. |
| 6,974,462 B2 | 12/2005 | Sater |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,981,978 B2 | 1/2006 | Gannoe |
| 6,984,203 B2 | 1/2006 | Tartaglia et al. |
| 6,984,231 B2 | 1/2006 | Goble et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,990,796 B2 | 1/2006 | Schnipke et al. |
| 6,994,708 B2 | 2/2006 | Manzo |
| 6,995,729 B2 | 2/2006 | Govari et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,001,380 B2 | 2/2006 | Goble |
| 7,001,408 B2 | 2/2006 | Knodel et al. |
| 7,008,435 B2 | 3/2006 | Cummins |
| 7,009,039 B2 | 3/2006 | Yayon et al. |
| 7,011,657 B2 | 3/2006 | Truckai et al. |
| 7,018,357 B2 | 3/2006 | Emmons |
| 7,018,390 B2 | 3/2006 | Turovskiy et al. |
| 7,025,743 B2 | 4/2006 | Mann et al. |
| 7,029,435 B2 | 4/2006 | Nakao |
| 7,032,798 B2 | 4/2006 | Whitman et al. |
| 7,032,799 B2 | 4/2006 | Viola et al. |
| 7,033,356 B2 | 4/2006 | Latterell et al. |
| 7,036,680 B1 | 5/2006 | Flannery |
| 7,037,344 B2 | 5/2006 | Kagan et al. |
| 7,041,102 B2 | 5/2006 | Truckai et al. |
| 7,041,868 B2 | 5/2006 | Greene et al. |
| 7,043,852 B2 | 5/2006 | Hayashida et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,048,745 B2 | 5/2006 | Tierney et al. |
| 7,052,494 B2 | 5/2006 | Goble et al. |
| 7,055,730 B2 | 6/2006 | Ehrenfels et al. |
| 7,055,731 B2 | 6/2006 | Shelton, IV et al. |
| 7,056,284 B2 | 6/2006 | Martone et al. |
| 7,056,330 B2 | 6/2006 | Gayton |
| 7,059,331 B2 | 6/2006 | Adams et al. |
| 7,059,508 B2 | 6/2006 | Shelton, IV et al. |
| 7,063,712 B2 | 6/2006 | Vargas et al. |
| 7,066,879 B2 | 6/2006 | Fowler et al. |
| 7,066,944 B2 | 6/2006 | Laufer et al. |
| 7,067,038 B2 | 6/2006 | Trokhan et al. |
| 7,070,083 B2 | 7/2006 | Jankowski |
| 7,070,559 B2 | 7/2006 | Adams et al. |
| 7,070,597 B2 | 7/2006 | Truckai et al. |
| 7,071,287 B2 | 7/2006 | Rhine et al. |
| 7,075,770 B1 | 7/2006 | Smith |
| 7,077,856 B2 | 7/2006 | Whitman |
| 7,080,769 B2 | 7/2006 | Vresh et al. |
| 7,081,114 B2 | 7/2006 | Rashidi |
| 7,083,073 B2 | 8/2006 | Yoshie et al. |
| 7,083,075 B2 | 8/2006 | Swayze et al. |
| 7,083,571 B2 | 8/2006 | Wang et al. |
| 7,083,615 B2 | 8/2006 | Peterson et al. |
| 7,083,619 B2 | 8/2006 | Truckai et al. |
| 7,083,620 B2 | 8/2006 | Jahns et al. |
| 7,087,054 B2 | 8/2006 | Truckai et al. |
| 7,087,071 B2 | 8/2006 | Nicholas et al. |
| 7,090,637 B2 | 8/2006 | Danitz et al. |
| 7,090,673 B2 | 8/2006 | Dycus et al. |
| 7,090,683 B2 | 8/2006 | Brock et al. |
| 7,090,684 B2 | 8/2006 | McGuckin, Jr. et al. |
| 7,094,202 B2 | 8/2006 | Nobis et al. |
| 7,094,247 B2 | 8/2006 | Monassevitch et al. |
| 7,097,089 B2 | 8/2006 | Marczyk |
| 7,097,644 B2 | 8/2006 | Long |
| 7,097,650 B2 | 8/2006 | Weller et al. |
| 7,098,794 B2 | 8/2006 | Lindsay et al. |
| 7,104,741 B2 | 9/2006 | Krohn |
| 7,108,695 B2 | 9/2006 | Witt et al. |
| 7,108,701 B2 | 9/2006 | Evens et al. |
| 7,108,709 B2 | 9/2006 | Cummins |
| 7,111,769 B2 | 9/2006 | Wales et al. |
| 7,112,214 B2 | 9/2006 | Peterson et al. |
| RE39,358 E | 10/2006 | Goble |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |

(56) References Cited

U.S. PATENT DOCUMENTS

| | | |
|---|---|---|
| 7,125,409 B2 | 10/2006 | Truckai et al. |
| 7,126,303 B2 | 10/2006 | Farritor et al. |
| 7,128,253 B2 | 10/2006 | Mastri et al. |
| 7,128,254 B2 | 10/2006 | Shelton, IV et al. |
| 7,128,748 B2 | 10/2006 | Mooradian et al. |
| 7,131,445 B2 | 11/2006 | Amoah |
| 7,133,601 B2 | 11/2006 | Phillips et al. |
| 7,134,587 B2 | 11/2006 | Schwemberger et al. |
| 7,137,981 B2 | 11/2006 | Long |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,147,139 B2 | 12/2006 | Schwemberger et al. |
| 7,147,140 B2 | 12/2006 | Wukusick et al. |
| 7,147,637 B2 | 12/2006 | Goble |
| 7,147,650 B2 | 12/2006 | Lee |
| 7,150,748 B2 | 12/2006 | Ebbutt et al. |
| 7,153,300 B2 | 12/2006 | Goble |
| 7,156,863 B2 | 1/2007 | Sonnenschein et al. |
| 7,159,750 B2 | 1/2007 | Racenet et al. |
| 7,160,299 B2 | 1/2007 | Baily |
| 7,161,036 B2 | 1/2007 | Oikawa et al. |
| 7,168,604 B2 | 1/2007 | Milliman et al. |
| 7,172,104 B2 | 2/2007 | Scirica et al. |
| 7,179,223 B2 | 2/2007 | Motoki et al. |
| 7,179,267 B2 | 2/2007 | Nolan et al. |
| 7,182,239 B1 | 2/2007 | Myers |
| 7,182,763 B2 | 2/2007 | Nardella |
| 7,183,737 B2 | 2/2007 | Kitagawa |
| 7,188,758 B2 | 3/2007 | Viola et al. |
| 7,189,207 B2 | 3/2007 | Viola |
| 7,195,627 B2 | 3/2007 | Amoah et al. |
| 7,199,537 B2 | 4/2007 | Okamura et al. |
| 7,204,835 B2 | 4/2007 | Latterell et al. |
| 7,207,233 B2 | 4/2007 | Wadge |
| 7,207,471 B2 | 4/2007 | Heinrich et al. |
| 7,207,472 B2 | 4/2007 | Wukusick et al. |
| 7,207,556 B2 | 4/2007 | Saitoh et al. |
| 7,208,005 B2 | 4/2007 | Frecker et al. |
| 7,210,609 B2 | 5/2007 | Leiboff et |
| 7,211,081 B2 | 5/2007 | Goble |
| 7,211,084 B2 | 5/2007 | Goble et a |
| 7,213,736 B2 | 5/2007 | Wales et al. |
| 7,214,224 B2 | 5/2007 | Goble |
| 7,217,285 B2 | 5/2007 | Vargas et al. |
| 7,220,260 B2 | 5/2007 | Fleming et al. |
| 7,220,272 B2 | 5/2007 | Weadock |
| 7,225,963 B2 | 6/2007 | Scirica |
| 7,225,964 B2 | 6/2007 | Mastri et al. |
| 7,234,624 B2 | 6/2007 | Gresham et al. |
| 7,235,089 B1 | 6/2007 | McGuckin, Jr. |
| 7,235,302 B2 | 6/2007 | Jing et al. |
| 7,237,708 B1 | 7/2007 | Guy et al. |
| 7,238,195 B2 | 7/2007 | Viola |
| 7,241,288 B2 | 7/2007 | Braun |
| 7,246,734 B2 | 7/2007 | Shelton, IV |
| 7,247,161 B2 | 7/2007 | Johnston et al. |
| 7,252,660 B2 | 8/2007 | Kunz |
| 7,255,696 B2 | 8/2007 | Goble et al. |
| 7,256,695 B2 | 8/2007 | Hamel et al. |
| 7,258,262 B2 | 8/2007 | Mastri et al. |
| 7,258,546 B2 | 8/2007 | Beier et al. |
| 7,260,431 B2 | 8/2007 | Libbus et al. |
| 7,265,374 B2 | 9/2007 | Lee et al. |
| 7,267,679 B2 | 9/2007 | McGuckin, Jr. et al. |
| 7,273,483 B2 | 9/2007 | Wiener et al. |
| 7,278,562 B2 | 10/2007 | Mastri et al. |
| 7,278,563 B1 | 10/2007 | Green |
| 7,278,949 B2 | 10/2007 | Bader |
| 7,278,994 B2 | 10/2007 | Goble |
| 7,282,048 B2 | 10/2007 | Goble et al. |
| 7,287,682 B1 | 10/2007 | Ezzat et al. |
| 7,293,685 B2 | 11/2007 | Ehrenfels et al. |
| 7,295,907 B2 | 11/2007 | Lu et al. |
| 7,296,722 B2 | 11/2007 | Ivanko |
| 7,296,724 B2 | 11/2007 | Green et al. |
| 7,297,149 B2 | 11/2007 | Vitali et al. |
| 7,300,450 B2 | 11/2007 | Vleugels et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,303,502 B2 | 12/2007 | Thompson |
| 7,303,556 B2 | 12/2007 | Metzger |
| 7,308,998 B2 | 12/2007 | Mastri et al. |
| 7,322,975 B2 | 1/2008 | Goble et al. |
| 7,322,994 B2 | 1/2008 | Nicholas et al. |
| 7,324,572 B2 | 1/2008 | Chang |
| 7,326,203 B2 | 2/2008 | Papineau et al. |
| 7,326,213 B2 | 2/2008 | Benderev et al. |
| 7,328,828 B2 | 2/2008 | Ortiz et al. |
| 7,328,829 B2 | 2/2008 | Arad et al. |
| 7,330,004 B2 | 2/2008 | DeJonge et al. |
| 7,331,340 B2 | 2/2008 | Barney |
| 7,334,717 B2 | 2/2008 | Rethy et al. |
| 7,334,718 B2 | 2/2008 | McAlister et al. |
| 7,335,199 B2 | 2/2008 | Goble et al. |
| 7,336,048 B2 | 2/2008 | Lohr |
| 7,336,184 B2 | 2/2008 | Smith et al. |
| 7,338,513 B2 | 3/2008 | Lee et al. |
| 7,341,591 B2 | 3/2008 | Grinberg |
| 7,343,920 B2 | 3/2008 | Toby et al. |
| 7,344,532 B2 | 3/2008 | Goble et al. |
| 7,348,763 B1 | 3/2008 | Reinhart et al. |
| RE40,237 E | 4/2008 | Bilotti et al. |
| 7,351,258 B2 | 4/2008 | Ricotta et al. |
| 7,354,447 B2 | 4/2008 | Shelton, IV et al. |
| 7,354,502 B2 | 4/2008 | Polat et al. |
| 7,357,287 B2 | 4/2008 | Shelton, IV et al. |
| 7,357,806 B2 | 4/2008 | Rivera et al. |
| 7,361,195 B2 | 4/2008 | Schwartz et al. |
| 7,364,060 B2 | 4/2008 | Milliman |
| 7,364,061 B2 | 4/2008 | Swayze et al. |
| 7,377,918 B2 | 5/2008 | Amoah |
| 7,377,928 B2 | 5/2008 | Zubik et al. |
| 7,380,695 B2 | 6/2008 | Doll et al. |
| 7,380,696 B2 | 6/2008 | Shelton, IV et al. |
| 7,386,730 B2 | 6/2008 | Uchikubo |
| 7,388,217 B2 | 6/2008 | Buschbeck et al. |
| 7,391,173 B2 | 6/2008 | Schena |
| 7,396,356 B2 | 7/2008 | Mollenauer |
| 7,397,364 B2 | 7/2008 | Govari |
| 7,398,907 B2 | 7/2008 | Racenet et al. |
| 7,398,908 B2 | 7/2008 | Holsten et al. |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,404,822 B2 | 7/2008 | Viart et al. |
| 7,407,074 B2 | 8/2008 | Ortiz et al. |
| 7,407,075 B2 | 8/2008 | Holsten et al. |
| 7,407,076 B2 | 8/2008 | Racenet et al. |
| 7,407,077 B2 | 8/2008 | Ortiz et al. |
| 7,407,078 B2 | 8/2008 | Shelton, IV et al. |
| 7,410,086 B2 | 8/2008 | Ortiz et al. |
| 7,413,563 B2 | 8/2008 | Corcoran et al. |
| 7,416,101 B2 | 8/2008 | Shelton, IV et al. |
| 7,418,078 B2 | 8/2008 | Blanz et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,427,607 B2 | 9/2008 | Suzuki |
| 7,431,188 B1 | 10/2008 | Marczyk |
| 7,431,189 B2 | 10/2008 | Shelton, IV et al. |
| 7,431,694 B2 | 10/2008 | Stefanchik et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |

(56) References Cited

U.S. PATENT DOCUMENTS

| | | |
|---|---|---|
| 7,438,209 B1 | 10/2008 | Hess et al. |
| 7,438,718 B2 | 10/2008 | Milliman et al. |
| 7,439,354 B2 | 10/2008 | Lenges et al. |
| 7,441,684 B2 | 10/2008 | Shelton, IV et al. |
| 7,441,685 B1 | 10/2008 | Boudreaux |
| 7,442,201 B2 | 10/2008 | Pugsley et al. |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,455,682 B2 | 11/2008 | Viola |
| 7,461,767 B2 | 12/2008 | Viola et al. |
| 7,462,187 B2 | 12/2008 | Johnston et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,467,849 B2 | 12/2008 | Silverbrook et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,253 B2 | 1/2009 | Dycus et al. |
| 7,473,263 B2 | 1/2009 | Johnston et al. |
| 7,479,608 B2 | 1/2009 | Smith |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,485,133 B2 | 2/2009 | Cannon et al. |
| 7,485,142 B2 | 2/2009 | Milo |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,494,499 B2 | 2/2009 | Nagase et al. |
| 7,500,979 B2 | 3/2009 | Hueil et al. |
| 7,501,198 B2 | 3/2009 | Barlev et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,507,202 B2 | 3/2009 | Schoellhorn |
| 7,510,107 B2 | 3/2009 | Timm et al. |
| 7,510,566 B2 | 3/2009 | Jacobs et al. |
| 7,513,408 B2 | 4/2009 | Shelton, IV et al. |
| 7,517,356 B2 | 4/2009 | Heinrich |
| 7,524,320 B2 | 4/2009 | Tierney et al. |
| 7,530,984 B2 | 5/2009 | Sonnenschein et al. |
| 7,530,985 B2 | 5/2009 | Takemoto et al. |
| 7,534,259 B2 | 5/2009 | Lashinski et al. |
| 7,546,939 B2 | 6/2009 | Adams et al. |
| 7,546,940 B2 | 6/2009 | Milliman et al. |
| 7,547,312 B2 * | 6/2009 | Bauman et al. ............... 606/151 |
| 7,549,563 B2 | 6/2009 | Mather et al. |
| 7,549,564 B2 | 6/2009 | Boudreaux |
| 7,549,998 B2 | 6/2009 | Braun |
| 7,552,854 B2 | 6/2009 | Wixey et al. |
| 7,556,185 B2 | 7/2009 | Viola |
| 7,556,186 B2 | 7/2009 | Milliman |
| 7,556,647 B2 | 7/2009 | Drews et al. |
| 7,559,449 B2 | 7/2009 | Viola |
| 7,559,450 B2 | 7/2009 | Wales et al. |
| 7,559,452 B2 | 7/2009 | Wales et al. |
| 7,559,937 B2 | 7/2009 | de la Torre et al. |
| 7,563,862 B2 | 7/2009 | Sieg et al. |
| 7,565,993 B2 | 7/2009 | Milliman et al. |
| 7,566,300 B2 | 7/2009 | Devierre et al. |
| 7,567,045 B2 | 7/2009 | Fristedt |
| 7,568,603 B2 | 8/2009 | Shelton, IV et al. |
| 7,568,604 B2 | 8/2009 | Ehrenfels et al. |
| 7,568,619 B2 | 8/2009 | Todd et al. |
| 7,575,144 B2 | 8/2009 | Ortiz et al. |
| 7,588,174 B2 | 9/2009 | Holsten et al. |
| 7,588,175 B2 | 9/2009 | Timm et al. |
| 7,588,176 B2 | 9/2009 | Timm et al. |
| 7,588,177 B2 | 9/2009 | Racenet |
| 7,591,783 B2 | 9/2009 | Boulais et al. |
| 7,597,229 B2 | 10/2009 | Boudreaux et al. |
| 7,597,230 B2 | 10/2009 | Racenet et al. |
| 7,600,663 B2 | 10/2009 | Green |
| 7,604,150 B2 | 10/2009 | Boudreaux |
| 7,604,151 B2 | 10/2009 | Hess et al. |
| 7,607,557 B2 | 10/2009 | Shelton, IV et al. |
| 7,611,038 B2 | 11/2009 | Racenet et al. |
| 7,611,474 B2 | 11/2009 | Hibner et al. |
| 7,615,003 B2 | 11/2009 | Stefanchik et al. |
| 7,615,067 B2 | 11/2009 | Lee et al. |
| 7,617,961 B2 | 11/2009 | Viola |
| 7,624,902 B2 | 12/2009 | Marczyk et al. |
| 7,624,903 B2 | 12/2009 | Green et al. |
| 7,625,370 B2 | 12/2009 | Hart et al. |
| 7,631,793 B2 | 12/2009 | Rethy et al. |
| 7,631,794 B2 | 12/2009 | Rethy et al. |
| 7,635,074 B2 | 12/2009 | Olson et al. |
| 7,637,409 B2 | 12/2009 | Marczyk |
| 7,638,958 B2 | 12/2009 | Philipp et al. |
| 7,641,091 B2 | 1/2010 | Olson et al. |
| 7,641,092 B2 | 1/2010 | Kruszynski et al. |
| 7,641,093 B2 | 1/2010 | Doll et al. |
| 7,641,095 B2 | 1/2010 | Viola |
| 7,644,783 B2 | 1/2010 | Roberts et al. |
| 7,644,848 B2 | 1/2010 | Swayze et al. |
| 7,645,230 B2 | 1/2010 | Mikkaichi et al. |
| 7,648,519 B2 | 1/2010 | Lee et al. |
| 7,651,017 B2 | 1/2010 | Ortiz et al. |
| 7,651,498 B2 | 1/2010 | Shifrin et al. |
| 7,654,431 B2 | 2/2010 | Hueil et al. |
| 7,655,288 B2 | 2/2010 | Bauman et al. |
| 7,656,131 B2 | 2/2010 | Embrey et al. |
| 7,658,311 B2 | 2/2010 | Boudreaux |
| 7,658,312 B2 | 2/2010 | Vidal et al. |
| 7,659,219 B2 | 2/2010 | Biran et al. |
| 7,662,161 B2 | 2/2010 | Briganti et al. |
| 7,665,646 B2 | 2/2010 | Prommersberger |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,670,334 B2 | 3/2010 | Hueil et al. |
| 7,673,780 B2 | 3/2010 | Shelton, IV et al. |
| 7,673,781 B2 | 3/2010 | Swayze et al. |
| 7,673,782 B2 | 3/2010 | Hess et al. |
| 7,673,783 B2 | 3/2010 | Morgan et al. |
| 7,674,253 B2 | 3/2010 | Fisher et al. |
| 7,674,255 B2 | 3/2010 | Braun |
| 7,674,263 B2 | 3/2010 | Ryan |
| 7,682,307 B2 | 3/2010 | Danitz et al. |
| 7,686,201 B2 | 3/2010 | Csiky |
| 7,686,826 B2 | 3/2010 | Lee et al. |
| 7,688,028 B2 | 3/2010 | Phillips et al. |
| 7,691,098 B2 | 4/2010 | Wallace et al. |
| 7,691,106 B2 | 4/2010 | Schenberger et al. |
| 7,694,865 B2 | 4/2010 | Scirica |
| 7,695,485 B2 | 4/2010 | Whitman et al. |
| 7,699,204 B2 | 4/2010 | Viola |
| 7,699,835 B2 | 4/2010 | Lee et al. |
| 7,699,844 B2 | 4/2010 | Utley et al. |
| 7,699,846 B2 | 4/2010 | Ryan |
| 7,699,856 B2 | 4/2010 | Van Wyk et al. |
| 7,699,859 B2 | 4/2010 | Bombard et al. |
| 7,699,860 B2 | 4/2010 | Huitema et al. |
| 7,703,653 B2 | 4/2010 | Shah et al. |
| 7,708,180 B2 * | 5/2010 | Murray et al. ............. 227/175.1 |
| 7,708,181 B2 | 5/2010 | Cole et al. |
| 7,708,758 B2 | 5/2010 | Lee et al. |
| 7,714,239 B2 | 5/2010 | Smith |
| 7,717,312 B2 | 5/2010 | Beetel |
| 7,717,313 B2 | 5/2010 | Criscuolo et al. |
| 7,717,846 B2 | 5/2010 | Zirps et al. |
| 7,718,180 B2 | 5/2010 | Karp |
| 7,718,556 B2 | 5/2010 | Matsuda et al. |
| 7,721,930 B2 | 5/2010 | McKenna et al. |
| 7,721,931 B2 | 5/2010 | Shelton, IV et al. |
| 7,721,933 B2 | 5/2010 | Ehrenfels et al. |
| 7,721,934 B2 | 5/2010 | Shelton, IV et al. |
| 7,721,936 B2 | 5/2010 | Shalton, IV et al. |
| 7,722,607 B2 | 5/2010 | Dumbauld et al. |

(56) References Cited

U.S. PATENT DOCUMENTS

| | | | |
|---|---|---|---|
| 7,722,610 B2 | 5/2010 | Viola et al. |
| 7,726,537 B2 | 6/2010 | Olson et al. |
| 7,726,538 B2 | 6/2010 | Holsten et al. |
| 7,726,539 B2 | 6/2010 | Holsten et al. |
| 7,727,954 B2 | 6/2010 | McKay |
| 7,731,072 B2 | 6/2010 | Timm et al. |
| 7,731,073 B2 | 6/2010 | Wixey et al. |
| 7,731,724 B2 | 6/2010 | Huitema et al. |
| 7,735,703 B2 | 6/2010 | Morgan et al. |
| 7,736,374 B2 | 6/2010 | Vaughan et al. |
| 7,738,971 B2 | 6/2010 | Swayze et al. |
| 7,740,159 B2 | 6/2010 | Shelton, IV et al. |
| 7,743,960 B2 | 6/2010 | Whitman et al. |
| 7,744,624 B2 | 6/2010 | Bettuchi |
| 7,744,627 B2 | 6/2010 | Orban, III et al. |
| 7,744,628 B2 | 6/2010 | Viola |
| 7,748,587 B2 | 7/2010 | Haramiishi et al. |
| 7,749,204 B2 | 7/2010 | Dhanaraj et al. |
| 7,751,870 B2 | 7/2010 | Whitman |
| 7,753,245 B2 | 7/2010 | Boudreaux et al. |
| 7,753,904 B2 | 7/2010 | Shelton, IV et al. |
| 7,758,612 B2 | 7/2010 | Shipp |
| 7,766,209 B2 | 8/2010 | Baxter, III et al. |
| 7,766,210 B2 | 8/2010 | Shelton, IV et al. |
| 7,766,821 B2 | 8/2010 | Brunnen et al. |
| 7,766,894 B2 | 8/2010 | Weitzner et al. |
| 7,770,773 B2 | 8/2010 | Whitman et al. |
| 7,770,774 B2 | 8/2010 | Mastri et al. |
| 7,770,775 B2 | 8/2010 | Shelton, IV et al. |
| 7,770,776 B2 | 8/2010 | Chen et al. |
| 7,771,396 B2 | 8/2010 | Stefanchik et al. |
| 7,772,720 B2 | 8/2010 | McGee et al. |
| 7,776,060 B2 | 8/2010 | Mooradian et al. |
| 7,778,004 B2 | 8/2010 | Nerheim et al. |
| 7,780,054 B2 | 8/2010 | Wales |
| 7,780,055 B2 | 8/2010 | Scirica et al. |
| 7,780,663 B2 | 8/2010 | Yates et al. |
| 7,780,685 B2 | 8/2010 | Hunt et al. |
| 7,784,662 B2 | 8/2010 | Wales et al. |
| 7,784,663 B2 | 8/2010 | Shelton, IV |
| 7,789,875 B2 | 9/2010 | Brock et al. |
| 7,789,883 B2 | 9/2010 | Takashino et al. |
| 7,789,889 B2 | 9/2010 | Zubik et al. |
| 7,793,812 B2 | 9/2010 | Moore et al. |
| 7,794,475 B2 | 9/2010 | Hess et al. |
| 7,798,386 B2 | 9/2010 | Schall et al. |
| 7,799,039 B2 | 9/2010 | Shelton, IV et al. |
| 7,799,044 B2 | 9/2010 | Johnston et al. |
| 7,799,965 B2 | 9/2010 | Patel et al. |
| 7,803,151 B2 | 9/2010 | Whitman |
| 7,806,891 B2 | 10/2010 | Nowlin et al. |
| 7,810,690 B2 | 10/2010 | Bilotti et al. |
| 7,810,691 B2 | 10/2010 | Boyden et al. |
| 7,810,692 B2 | 10/2010 | Hall et al. |
| 7,810,693 B2 | 10/2010 | Broehl et al. |
| 7,815,092 B2 | 10/2010 | Whitman et al. |
| 7,815,565 B2 | 10/2010 | Stefanchik et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,819,886 B2 | 10/2010 | Whitfield et al. |
| 7,823,592 B2 | 11/2010 | Bettuchi et al. |
| 7,824,401 B2 | 11/2010 | Manzo et al. |
| 7,824,426 B2 | 11/2010 | Racenet et al. |
| 7,828,189 B2 | 11/2010 | Holsten et al. |
| 7,828,794 B2 | 11/2010 | Sartor |
| 7,828,808 B2 | 11/2010 | Hinman et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,833,234 B2 | 11/2010 | Bailly et al. |
| 7,836,400 B2 | 11/2010 | May et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,837,694 B2 | 11/2010 | Tethrake et al. |
| 7,841,503 B2 | 11/2010 | Sonnenschein et al. |
| 7,842,025 B2 | 11/2010 | Coleman et al. |
| 7,842,028 B2 | 11/2010 | Lee |
| 7,845,533 B2 | 12/2010 | Marczyk et al. |
| 7,845,534 B2 | 12/2010 | Viola et al. |
| 7,845,535 B2 | 12/2010 | Scircia |
| 7,845,536 B2 | 12/2010 | Viola et al. |
| 7,845,537 B2 | 12/2010 | Shelton, IV et al. |
| 7,846,149 B2 | 12/2010 | Jankowski |
| 7,850,642 B2 | 12/2010 | Moll et al. |
| 7,850,982 B2 | 12/2010 | Stopek et al. |
| 7,854,736 B2 | 12/2010 | Ryan |
| 7,857,183 B2 | 12/2010 | Shelton, IV |
| 7,857,185 B2 | 12/2010 | Swayze et al. |
| 7,857,186 B2 | 12/2010 | Baxter, III et al. |
| 7,857,813 B2 | 12/2010 | Schmitz et al. |
| 7,861,906 B2 | 1/2011 | Doll et al. |
| 7,862,579 B2 | 1/2011 | Ortiz et al. |
| 7,866,525 B2 | 1/2011 | Scirica |
| 7,866,527 B2 | 1/2011 | Hall et al. |
| 7,866,528 B2 | 1/2011 | Olson et al. |
| 7,870,989 B2 | 1/2011 | Viola et al. |
| 7,871,418 B2 | 1/2011 | Thompson et al. |
| 7,879,070 B2 | 2/2011 | Ortiz et al. |
| 7,883,465 B2 | 2/2011 | Donofrio et al. |
| 7,886,951 B2 | 2/2011 | Hessler |
| 7,886,952 B2 | 2/2011 | Scirica et al. |
| 7,887,530 B2 | 2/2011 | Zemlok et al. |
| 7,887,535 B2 | 2/2011 | Lands et al. |
| 7,891,531 B1 | 2/2011 | Ward |
| 7,891,532 B2 | 2/2011 | Mastri et al. |
| 7,893,586 B2 | 2/2011 | West et al. |
| 7,896,214 B2 | 3/2011 | Farascioni |
| 7,896,215 B2 | 3/2011 | Adams et al. |
| 7,896,877 B2 | 3/2011 | Hall et al. |
| 7,900,805 B2 | 3/2011 | Shelton, IV et al. |
| 7,905,380 B2 | 3/2011 | Shelton, IV et al. |
| 7,905,381 B2 | 3/2011 | Baxter, III et al. |
| 7,905,889 B2 | 3/2011 | Catanese, III et al. |
| 7,905,902 B2 | 3/2011 | Huitema et al. |
| 7,909,191 B2 | 3/2011 | Baker et al. |
| 7,909,220 B2 | 3/2011 | Viola |
| 7,909,221 B2 | 3/2011 | Viola et al. |
| 7,913,891 B2 | 3/2011 | Doll et al. |
| 7,913,893 B2 | 3/2011 | Mastri et al. |
| 7,914,543 B2 | 3/2011 | Roth et al. |
| 7,914,551 B2 | 3/2011 | Ortiz et al. |
| 7,918,376 B1 | 4/2011 | Knodel et al. |
| 7,918,377 B2 | 4/2011 | Measamer et al. |
| 7,918,848 B2 | 4/2011 | Lau et al. |
| 7,922,061 B2 | 4/2011 | Shelton, IV et al. |
| 7,922,063 B2 | 4/2011 | Zemlok et al. |
| 7,922,743 B2 * | 4/2011 | Heinrich ......... A61B 17/00491 227/178.1 |
| 7,926,691 B2 | 4/2011 | Viola et al. |
| 7,927,328 B2 | 4/2011 | Orszulak et al. |
| 7,928,281 B2 | 4/2011 | Augustine |
| 7,931,660 B2 | 4/2011 | Aranyi et al. |
| 7,931,695 B2 | 4/2011 | Ringeisen |
| 7,934,630 B2 | 5/2011 | Shelton, IV et al. |
| 7,934,631 B2 | 5/2011 | Balbierz et al. |
| 7,935,773 B2 | 5/2011 | Hadba et al. |
| 7,938,307 B2 | 5/2011 | Bettuchi |
| 7,941,865 B2 | 5/2011 | Seman, Jr. et al. |
| 7,942,303 B2 | 5/2011 | Shah |
| 7,942,890 B2 | 5/2011 | D'Agostino et al. |
| 7,944,175 B2 | 5/2011 | Mori et al. |
| 7,950,560 B2 | 5/2011 | Zemlok et al. |
| 7,950,561 B2 | 5/2011 | Aranyi |
| 7,951,071 B2 | 5/2011 | Whitman et al. |
| 7,951,166 B2 | 5/2011 | Orban et al. |
| 7,954,682 B2 | 6/2011 | Giordano et al. |
| 7,954,684 B2 | 6/2011 | Boudreaux |
| 7,954,686 B2 | 6/2011 | Baxter, III et al. |
| 7,954,687 B2 | 6/2011 | Zemlok et al. |
| 7,955,257 B2 | 6/2011 | Frasier et al. |

(56) References Cited

U.S. PATENT DOCUMENTS

| | | | |
|---|---|---|---|
| 7,955,380 B2* | 6/2011 | Chu | A61B 17/0401 623/1.11 |
| 7,959,050 B2 | 6/2011 | Smith et al. | |
| 7,959,051 B2 | 6/2011 | Smith et al. | |
| 7,959,052 B2 | 6/2011 | Sonnenschein et al. | |
| 7,963,432 B2 | 6/2011 | Knodel et al. | |
| 7,963,433 B2 | 6/2011 | Whitman et al. | |
| 7,963,963 B2 | 6/2011 | Francischelli et al. | |
| 7,963,964 B2 | 6/2011 | Santilli et al. | |
| 7,966,799 B2 | 6/2011 | Morgan et al. | |
| 7,967,180 B2 | 6/2011 | Scirica | |
| 7,967,181 B2 | 6/2011 | Viola et al. | |
| 7,967,839 B2 | 6/2011 | Flock et al. | |
| 7,972,298 B2 | 7/2011 | Wallace et al. | |
| 7,980,443 B2 | 7/2011 | Scheib et al. | |
| 7,988,026 B2 | 8/2011 | Knodel et al. | |
| 7,988,027 B2* | 8/2011 | Olson | A61B 17/07207 227/175.1 |
| 7,988,028 B2 | 8/2011 | Farascioni et al. | |
| 7,992,757 B2 | 8/2011 | Wheeler et al. | |
| 7,997,469 B2 | 8/2011 | Olson et al. | |
| 8,002,696 B2 | 8/2011 | Suzuki | |
| 8,002,784 B2 | 8/2011 | Jinno et al. | |
| 8,002,785 B2 | 8/2011 | Weiss et al. | |
| 8,002,795 B2 | 8/2011 | Beetel | |
| 8,006,365 B2 | 8/2011 | Levin et al. | |
| 8,006,885 B2 | 8/2011 | Marczyk | |
| 8,006,889 B2 | 8/2011 | Adams et al. | |
| 8,011,550 B2 | 9/2011 | Aranyi et al. | |
| 8,011,551 B2 | 9/2011 | Marczyk et al. | |
| 8,011,553 B2 | 9/2011 | Mastri et al. | |
| 8,011,555 B2 | 9/2011 | Tarinelli et al. | |
| 8,016,176 B2 | 9/2011 | Kasvikis et al. | |
| 8,016,177 B2 | 9/2011 | Bettuchi et al. | |
| 8,016,178 B2 | 9/2011 | Olson et al. | |
| 8,016,855 B2 | 9/2011 | Whitman et al. | |
| 8,016,858 B2 | 9/2011 | Whitman | |
| 8,016,881 B2 | 9/2011 | Furst | |
| 8,020,742 B2 | 9/2011 | Marczyk | |
| 8,020,743 B2 | 9/2011 | Shelton, IV | |
| 8,021,375 B2 | 9/2011 | Aldrich et al. | |
| 8,025,199 B2 | 9/2011 | Whitman et al. | |
| 8,028,883 B2 | 10/2011 | Stopek | |
| 8,028,884 B2 | 10/2011 | Sniffin et al. | |
| 8,028,885 B2 | 10/2011 | Smith et al. | |
| 8,034,077 B2 | 10/2011 | Smith et al. | |
| 8,034,363 B2 | 10/2011 | Li et al. | |
| 8,037,591 B2 | 10/2011 | Spivey et al. | |
| 8,038,045 B2 | 10/2011 | Bettuchi et al. | |
| 8,038,046 B2 | 10/2011 | Smith et al. | |
| 8,038,686 B2 | 10/2011 | Huitema et al. | |
| 8,043,207 B2 | 10/2011 | Adams | |
| 8,043,328 B2 | 10/2011 | Hahnen et al. | |
| 8,047,236 B2 | 11/2011 | Perry | |
| 8,056,787 B2 | 11/2011 | Boudreaux et al. | |
| 8,056,788 B2 | 11/2011 | Mastri et al. | |
| 8,057,508 B2 | 11/2011 | Shelton, IV | |
| 8,061,576 B2 | 11/2011 | Cappola | |
| 8,062,330 B2 | 11/2011 | Prommersberger et al. | |
| 8,066,167 B2 | 11/2011 | Measamer et al. | |
| 8,066,168 B2 | 11/2011 | Vidal et al. | |
| D650,074 S | 12/2011 | Hunt et al. | |
| 8,070,743 B2 | 12/2011 | Kagan et al. | |
| 8,075,571 B2 | 12/2011 | Vitali et al. | |
| 8,083,118 B2 | 12/2011 | Milliman et al. | |
| 8,083,119 B2 | 12/2011 | Prommersberger | |
| 8,083,120 B2 | 12/2011 | Shelton, IV et al. | |
| 8,084,001 B2 | 12/2011 | Burns et al. | |
| 8,091,756 B2 | 1/2012 | Viola | |
| 8,092,443 B2 | 1/2012 | Bischoff | |
| 8,092,932 B2 | 1/2012 | Phillips et al. | |
| 8,096,458 B2 | 1/2012 | Hessler | |
| 8,097,017 B2 | 1/2012 | Viola | |
| 8,100,310 B2 | 1/2012 | Zemlok | |
| 8,100,872 B2 | 1/2012 | Patel | |
| 8,105,350 B2 | 1/2012 | Lee et al. | |
| 8,108,072 B2 | 1/2012 | Zhao et al. | |
| 8,109,426 B2 | 2/2012 | Milliman et al. | |
| 8,110,208 B1 | 2/2012 | Hen | |
| 8,113,405 B2 | 2/2012 | Milliman | |
| 8,113,410 B2 | 2/2012 | Hall et al. | |
| 8,114,100 B2 | 2/2012 | Smith et al. | |
| 8,123,103 B2 | 2/2012 | Milliman | |
| 8,123,766 B2* | 2/2012 | Bauman et al. | 606/151 |
| 8,123,767 B2 | 2/2012 | Bauman et al. | |
| 8,127,975 B2 | 3/2012 | Olson et al. | |
| 8,127,976 B2 | 3/2012 | Scirica et al. | |
| 8,128,624 B2 | 3/2012 | Couture et al. | |
| 8,128,645 B2 | 3/2012 | Sonnenschein et al. | |
| 8,132,703 B2 | 3/2012 | Milliman et al. | |
| 8,132,706 B2 | 3/2012 | Marczyk et al. | |
| 8,136,712 B2 | 3/2012 | Zingman | |
| 8,136,713 B2 | 3/2012 | Hathaway et al. | |
| 8,140,417 B2 | 3/2012 | Shibata | |
| 8,141,762 B2 | 3/2012 | Bedi et al. | |
| 8,141,763 B2 | 3/2012 | Milliman | |
| 8,146,790 B2 | 4/2012 | Milliman | |
| 8,152,041 B2 | 4/2012 | Kostrzewski | |
| 8,157,145 B2 | 4/2012 | Shelton, IV et al. | |
| 8,157,148 B2 | 4/2012 | Scirica | |
| 8,157,151 B2 | 4/2012 | Ingmanson et al. | |
| 8,157,152 B2 | 4/2012 | Holsten et al. | |
| 8,157,153 B2 | 4/2012 | Shelton, IV et al. | |
| 8,157,793 B2 | 4/2012 | Omori et al. | |
| 8,161,977 B2 | 4/2012 | Shelton, IV et al. | |
| 8,162,138 B2 | 4/2012 | Bettenhausen et al. | |
| 8,162,197 B2 | 4/2012 | Mastri et al. | |
| 8,167,185 B2 | 5/2012 | Shelton, IV et al. | |
| 8,167,895 B2 | 5/2012 | D'Agostino et al. | |
| 8,167,898 B1 | 5/2012 | Schaller et al. | |
| 8,172,120 B2 | 5/2012 | Boyden et al. | |
| 8,172,122 B2 | 5/2012 | Kasvikis et al. | |
| 8,172,124 B2 | 5/2012 | Shelton, IV et al. | |
| 8,177,797 B2 | 5/2012 | Shimoji et al. | |
| 8,180,458 B2 | 5/2012 | Kane et al. | |
| 8,181,840 B2 | 5/2012 | Milliman | |
| 8,186,555 B2 | 5/2012 | Shelton, IV et al. | |
| 8,186,560 B2 | 5/2012 | Hess et al. | |
| 8,191,752 B2 | 6/2012 | Scirica | |
| 8,192,460 B2 | 6/2012 | Orban, III et al. | |
| 8,196,795 B2 | 6/2012 | Moore et al. | |
| 8,196,796 B2 | 6/2012 | Shelton, IV et al. | |
| 8,201,720 B2 | 6/2012 | Hessler | |
| 8,201,721 B2 | 6/2012 | Zemlok et al. | |
| 8,205,779 B2 | 6/2012 | Ma et al. | |
| 8,205,780 B2 | 6/2012 | Sorrentino et al. | |
| 8,205,781 B2 | 6/2012 | Baxter, III et al. | |
| 8,210,411 B2 | 7/2012 | Yates et al. | |
| 8,210,414 B2 | 7/2012 | Bettuchi et al. | |
| 8,210,415 B2 | 7/2012 | Ward | |
| 8,210,416 B2 | 7/2012 | Milliman et al. | |
| 8,211,125 B2 | 7/2012 | Spivey | |
| 8,214,019 B2 | 7/2012 | Govari et al. | |
| 8,215,531 B2 | 7/2012 | Shelton, IV et al. | |
| 8,215,533 B2 | 7/2012 | Viola et al. | |
| 8,220,468 B2 | 7/2012 | Cooper et al. | |
| 8,220,688 B2 | 7/2012 | Laurent et al. | |
| 8,220,690 B2 | 7/2012 | Hess et al. | |
| 8,221,424 B2 | 7/2012 | Cha | |
| 8,225,799 B2 | 7/2012 | Bettuchi | |
| 8,226,715 B2 | 7/2012 | Hwang et al. | |
| 8,231,040 B2 | 7/2012 | Zemlok et al. | |
| 8,231,041 B2 | 7/2012 | Marczyk et al. | |
| 8,231,042 B2 | 7/2012 | Hessler et al. | |
| 8,231,043 B2 | 7/2012 | Tarinelli et al. | |
| 8,236,010 B2 | 8/2012 | Ortiz et al. | |
| 8,241,271 B2 | 8/2012 | Millman et al. | |
| 8,241,308 B2 | 8/2012 | Kortenbach et al. | |
| 8,241,322 B2 | 8/2012 | Whitman et al. | |
| 8,245,898 B2 | 8/2012 | Smith et al. | |
| 8,245,899 B2 | 8/2012 | Swensgard et al. | |
| 8,245,900 B2 | 8/2012 | Scirica | |
| 8,245,901 B2 | 8/2012 | Stopek | |
| 8,246,637 B2 | 8/2012 | Viola et al. | |

(56) References Cited

U.S. PATENT DOCUMENTS

| | | | |
|---|---|---|---|
| 8,256,654 B2 | 9/2012 | Bettuchi et al. |
| 8,256,655 B2 | 9/2012 | Sniffin et al. |
| 8,257,251 B2 | 9/2012 | Shelton, IV et al. |
| 8,257,356 B2 | 9/2012 | Bleich et al. |
| 8,257,391 B2 | 9/2012 | Orban, III et al. |
| 8,267,300 B2 | 9/2012 | Boudreaux |
| 8,267,924 B2 | 9/2012 | Zemlok et al. |
| 8,267,946 B2 | 9/2012 | Whitfield et al. |
| 8,267,951 B2 | 9/2012 | Whayne et al. |
| 8,269,121 B2 | 9/2012 | Smith |
| 8,272,553 B2 | 9/2012 | Mastri et al. |
| 8,272,554 B2 | 9/2012 | Whitman et al. |
| 8,276,801 B2 | 10/2012 | Zemlok et al. |
| 8,276,802 B2 | 10/2012 | Kostrzewski |
| 8,281,973 B2 | 10/2012 | Wenchell et al. |
| 8,281,974 B2 | 10/2012 | Hessler et al. |
| 8,282,654 B2 * | 10/2012 | Ferrari ............... A61B 17/122 606/139 |
| 8,286,845 B2 | 10/2012 | Perry et al. |
| 8,287,561 B2 | 10/2012 | Nunez et al. |
| 8,292,151 B2 | 10/2012 | Viola |
| 8,292,155 B2 | 10/2012 | Shelton, IV et al. |
| 8,292,157 B2 | 10/2012 | Smith et al. |
| 8,292,888 B2 | 10/2012 | Whitman |
| 8,298,677 B2 | 10/2012 | Wiesner et al. |
| 8,302,323 B2 | 11/2012 | Fortier et al. |
| 8,308,040 B2 | 11/2012 | Huang et al. |
| 8,308,042 B2 | 11/2012 | Aranyi |
| 8,308,046 B2 | 11/2012 | Prommersberger |
| 8,308,659 B2 | 11/2012 | Scheibe et al. |
| 8,313,496 B2 | 11/2012 | Sauer et al. |
| 8,313,509 B2 | 11/2012 | Kostrzewski |
| 8,317,070 B2 | 11/2012 | Hueil et al. |
| 8,317,071 B1 | 11/2012 | Knodel |
| 8,317,074 B2 | 11/2012 | Ortiz et al. |
| 8,317,790 B2 | 11/2012 | Bell et al. |
| 8,319,002 B2 | 11/2012 | Daniels et al. |
| 8,322,455 B2 | 12/2012 | Shelton, IV et al. |
| 8,322,589 B2 | 12/2012 | Boudreaux |
| 8,323,789 B2 | 12/2012 | Rozhin et al. |
| 8,328,062 B2 | 12/2012 | Viola |
| 8,328,063 B2 | 12/2012 | Milliman et al. |
| 8,328,064 B2 | 12/2012 | Racenet et al. |
| 8,328,802 B2 | 12/2012 | Deville et al. |
| 8,328,823 B2 | 12/2012 | Aranyi et al. |
| 8,333,313 B2 | 12/2012 | Boudreaux et al. |
| 8,333,764 B2 | 12/2012 | Francischelli et al. |
| 8,336,753 B2 | 12/2012 | Olson et al. |
| 8,336,754 B2 | 12/2012 | Cappola et al. |
| 8,348,123 B2 | 1/2013 | Scirica et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,348,972 B2 | 1/2013 | Soltz et al. |
| 8,353,437 B2 | 1/2013 | Boudreaux |
| 8,353,438 B2 | 1/2013 | Baxter, III et al. |
| 8,353,439 B2 | 1/2013 | Baxter, III et al. |
| 8,357,144 B2 | 1/2013 | Whitman et al. |
| 8,360,296 B2 | 1/2013 | Zingman |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,973 B1 | 2/2013 | White et al. |
| 8,365,976 B2 | 2/2013 | Hess et al. |
| 8,366,559 B2 | 2/2013 | Papenfuss et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,372,094 B2 | 2/2013 | Bettuchi et al. |
| 8,376,865 B2 | 2/2013 | Forster et al. |
| 8,377,044 B2 | 2/2013 | Coe et al. |
| 8,393,513 B2 | 3/2013 | Jankowski |
| 8,393,514 B2 | 3/2013 | Shelton, IV et al. |
| 8,397,971 B2 | 3/2013 | Yates et al. |
| 8,398,673 B2 | 3/2013 | Hinchliffe et al. |
| 8,403,138 B2 | 3/2013 | Weisshaupt et al. |
| 8,403,198 B2 | 3/2013 | Sorrentino et al. |
| 8,403,945 B2 | 3/2013 | Whitfield et al. |
| 8,408,439 B2 | 4/2013 | Huang et al. |
| 8,408,442 B2 | 4/2013 | Racenet et al. |
| 8,409,079 B2 | 4/2013 | Okamoto et al. |
| 8,409,174 B2 | 4/2013 | Omori |
| 8,409,222 B2 | 4/2013 | Whitfield et al. |
| 8,413,870 B2 | 4/2013 | Pastorelli et al. |
| 8,413,871 B2 | 4/2013 | Racenet et al. |
| 8,413,872 B2 | 4/2013 | Patel |
| 8,414,577 B2 | 4/2013 | Boudreaux et al. |
| 8,418,909 B2 | 4/2013 | Kostrzewski |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,424,741 B2 | 4/2013 | Mcguckin, Jr. et al. |
| 8,425,600 B2 | 4/2013 | Maxwell |
| 8,430,292 B2 | 4/2013 | Patel et al. |
| 8,430,898 B2 | 4/2013 | Wiener et al. |
| 8,439,246 B1 | 5/2013 | Knodel |
| 8,444,036 B2 | 5/2013 | Shelton, IV |
| 8,444,549 B2 | 5/2013 | Viola et al. |
| 8,453,904 B2 | 6/2013 | Eskaros et al. |
| 8,453,907 B2 | 6/2013 | Laurent et al. |
| 8,453,908 B2 | 6/2013 | Bedi et al. |
| 8,453,912 B2 | 6/2013 | Mastri et al. |
| 8,453,914 B2 | 6/2013 | Laurent et al. |
| 8,454,628 B2 | 6/2013 | Smith et al. |
| 8,457,757 B2 | 6/2013 | Cauller et al. |
| 8,459,520 B2 | 6/2013 | Giordano et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,464,924 B2 | 6/2013 | Gresham et al. |
| 8,464,925 B2 * | 6/2013 | Hull et al. ............... 227/179.1 |
| 8,474,677 B2 | 7/2013 | Woodard, Jr. et al. |
| 8,475,453 B2 | 7/2013 | Marczyk et al. |
| 8,475,474 B2 | 7/2013 | Bombard et al. |
| 8,479,969 B2 | 7/2013 | Shelton, IV |
| 8,485,412 B2 | 7/2013 | Shelton, IV et al. |
| 8,485,413 B2 | 7/2013 | Scheib et al. |
| 8,490,853 B2 | 7/2013 | Criscuolo et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,500,762 B2 | 8/2013 | Sholev et al. |
| 8,506,557 B2 | 8/2013 | Zemlok et al. |
| 8,512,359 B2 | 8/2013 | Whitman et al. |
| 8,517,239 B2 | 8/2013 | Scheib et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,881 B2 | 9/2013 | Cabiri et al. |
| 8,529,588 B2 | 9/2013 | Ahlberg et al. |
| 8,529,600 B2 | 9/2013 | Woodard, Jr. et al. |
| 8,529,819 B2 | 9/2013 | Ostapoff et al. |
| 8,534,528 B2 | 9/2013 | Shelton, IV |
| 8,535,304 B2 | 9/2013 | Sklar et al. |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,133 B2 | 9/2013 | Bedi et al. |
| 8,540,733 B2 | 9/2013 | Whitman et al. |
| 8,556,151 B2 | 10/2013 | Viola |
| 8,556,918 B2 | 10/2013 | Bauman et al. |
| 8,561,870 B2 | 10/2013 | Baxter, III et al. |
| 8,561,873 B2 | 10/2013 | Ingmanson et al. |
| 8,567,656 B2 | 10/2013 | Shelton, IV et al. |
| 8,573,461 B2 | 11/2013 | Shelton, IV et al. |
| 8,573,465 B2 | 11/2013 | Shelton, IV |
| 8,579,176 B2 | 11/2013 | Smith et al. |
| 8,579,937 B2 | 11/2013 | Gresham |
| 8,584,919 B2 | 11/2013 | Hueil et al. |
| 8,585,721 B2 | 11/2013 | Kirsch |
| 8,590,762 B2 | 11/2013 | Hess et al. |
| 8,602,287 B2 | 12/2013 | Yates et al. |

(56) References Cited

U.S. PATENT DOCUMENTS

| | | |
|---|---|---|
| 8,602,288 B2 | 12/2013 | Shelton, IV et al. |
| 8,603,135 B2 | 12/2013 | Mueller |
| 8,608,044 B2 | 12/2013 | Hueil et al. |
| 8,608,045 B2 | 12/2013 | Smith et al. |
| 8,608,046 B2 | 12/2013 | Laurent et al. |
| 8,608,745 B2 | 12/2013 | Guzman et al. |
| 8,613,383 B2 | 12/2013 | Beckman et al. |
| 8,616,431 B2 | 12/2013 | Timm et al. |
| 8,622,274 B2 | 1/2014 | Yates et al. |
| 8,622,275 B2 | 1/2014 | Baxter, III et al. |
| 8,631,987 B2 | 1/2014 | Shelton, IV et al. |
| 8,632,462 B2 | 1/2014 | Yoo et al. |
| 8,632,525 B2 | 1/2014 | Kerr et al. |
| 8,632,535 B2 | 1/2014 | Shelton, IV et al. |
| 8,632,563 B2 | 1/2014 | Nagase et al. |
| 8,636,187 B2 | 1/2014 | Hueil et al. |
| 8,636,736 B2 | 1/2014 | Yates et al. |
| 8,646,674 B2 * | 2/2014 | Schulte ............ A61B 17/00491 227/179.1 |
| 8,647,258 B2 | 2/2014 | Aranyi et al. |
| 8,652,120 B2 | 2/2014 | Giordano et al. |
| 8,652,151 B2 | 2/2014 | Lehman et al. |
| 8,657,174 B2 | 2/2014 | Yates et al. |
| 8,657,178 B2 | 2/2014 | Hueil et al. |
| 8,662,370 B2 | 3/2014 | Takei |
| 8,668,129 B2 | 3/2014 | Olson |
| 8,668,130 B2 | 3/2014 | Hess et al. |
| 8,672,206 B2 | 3/2014 | Aranyi et al. |
| 8,672,207 B2 | 3/2014 | Shelton, IV et al. |
| 8,672,208 B2 | 3/2014 | Hess et al. |
| 8,678,263 B2 | 3/2014 | Viola |
| 8,679,093 B2 | 3/2014 | Farra |
| 8,679,137 B2 | 3/2014 | Bauman et al. |
| 8,679,454 B2 | 3/2014 | Guire et al. |
| 8,684,250 B2 | 4/2014 | Bettuchi et al. |
| 8,684,253 B2 | 4/2014 | Giordano et al. |
| 8,685,020 B2 | 4/2014 | Weizman et al. |
| 8,695,866 B2 | 4/2014 | Leimbach et al. |
| 8,696,665 B2 | 4/2014 | Hunt et al. |
| 8,701,958 B2 | 4/2014 | Shelton, IV et al. |
| 8,701,959 B2 | 4/2014 | Shah |
| 8,708,213 B2 | 4/2014 | Shelton, IV et al. |
| 8,715,256 B2 | 5/2014 | Greener |
| 8,720,766 B2 | 5/2014 | Hess et al. |
| 8,721,666 B2 | 5/2014 | Schroeder et al. |
| 8,727,197 B2 | 5/2014 | Hess et al. |
| 8,733,613 B2 | 5/2014 | Huitema et al. |
| 8,734,478 B2 | 5/2014 | Widenhouse et al. |
| 8,746,529 B2 | 6/2014 | Shelton, IV et al. |
| 8,746,530 B2 | 6/2014 | Giordano et al. |
| 8,747,238 B2 | 6/2014 | Shelton, IV et al. |
| 8,752,747 B2 | 6/2014 | Shelton, IV et al. |
| 8,752,749 B2 | 6/2014 | Moore et al. |
| 8,758,235 B2 | 6/2014 | Jaworek |
| 8,758,391 B2 | 6/2014 | Swayze et al. |
| 8,758,438 B2 | 6/2014 | Boyce et al. |
| 8,763,875 B2 | 7/2014 | Morgan et al. |
| 8,763,879 B2 | 7/2014 | Shelton, IV et al. |
| 8,783,541 B2 | 7/2014 | Shelton, IV et al. |
| 8,783,543 B2 | 7/2014 | Shelton, IV et al. |
| 8,784,404 B2 | 7/2014 | Doyle et al. |
| 8,789,739 B2 | 7/2014 | Swensgard |
| 8,789,740 B2 | 7/2014 | Baxter, III et al. |
| 8,790,684 B2 | 7/2014 | Dave et al. |
| 8,794,496 B2 | 8/2014 | Scirica |
| 8,794,497 B2 | 8/2014 | Zingman |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,820,603 B2 | 9/2014 | Shelton, IV et al. |
| 8,820,605 B2 | 9/2014 | Shelton, IV |
| 8,827,133 B2 | 9/2014 | Shelton, IV et al. |
| 8,827,903 B2 | 9/2014 | Shelton, IV et al. |
| 8,833,632 B2 | 9/2014 | Swensgard |
| 8,840,603 B2 | 9/2014 | Shelton, IV et al. |
| 8,844,789 B2 | 9/2014 | Shelton, IV et al. |
| 8,851,354 B2 | 10/2014 | Swensgard et al. |
| 8,857,693 B2 | 10/2014 | Schuckmann et al. |
| 8,858,571 B2 | 10/2014 | Shelton, IV et al. |
| 8,858,590 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,946 B2 | 11/2014 | Boudreaux et al. |
| 8,899,465 B2 | 12/2014 | Shelton, IV et al. |
| 8,899,466 B2 | 12/2014 | Baxter, III et al. |
| 8,911,426 B2 | 12/2014 | Coppeta et al. |
| 8,911,471 B2 | 12/2014 | Spivey et al. |
| 8,925,788 B2 | 1/2015 | Hess et al. |
| 8,926,598 B2 | 1/2015 | Mollere et al. |
| 8,931,682 B2 | 1/2015 | Timm et al. |
| 8,936,614 B2 | 1/2015 | Allen, IV |
| 8,960,520 B2 | 2/2015 | McCuen |
| 8,973,803 B2 | 3/2015 | Hall et al. |
| 8,973,804 B2 | 3/2015 | Hess et al. |
| 8,978,955 B2 | 3/2015 | Aronhalt et al. |
| 9,005,243 B2 * | 4/2015 | Stopek ............ A61B 17/07207 227/175.1 |
| 9,084,602 B2 | 7/2015 | Glieman |
| 9,358,005 B2 | 6/2016 | Shelton, IV et al. |
| 2001/0025183 A1 | 9/2001 | Shahidi |
| 2001/0044637 A1 | 11/2001 | Jacobs et al. |
| 2002/0022836 A1 | 2/2002 | Goble et al. |
| 2002/0029032 A1 * | 3/2002 | Arkin ..................... A61B 17/00 606/1 |
| 2002/0029036 A1 | 3/2002 | Goble et al. |
| 2002/0095175 A1 | 7/2002 | Brock et al. |
| 2002/0103494 A1 | 8/2002 | Pacey |
| 2002/0117534 A1 | 8/2002 | Green et al. |
| 2002/0127265 A1 | 9/2002 | Bowman et al. |
| 2002/0134811 A1 | 9/2002 | Napier et al. |
| 2002/0165541 A1 | 11/2002 | Whitman |
| 2002/0165559 A1 * | 11/2002 | Grant ................ A61B 17/07207 606/139 |
| 2002/0193808 A1 | 12/2002 | Belef et al. |
| 2003/0023316 A1 | 1/2003 | Brown et al. |
| 2003/0078647 A1 | 4/2003 | Vallana et al. |
| 2003/0084983 A1 | 5/2003 | Rangachari et al. |
| 2003/0093103 A1 | 5/2003 | Malackowski et al. |
| 2003/0096158 A1 | 5/2003 | Takano et al. |
| 2003/0105478 A1 | 6/2003 | Whitman et al. |
| 2003/0130677 A1 | 7/2003 | Whitman et al. |
| 2003/0139741 A1 | 7/2003 | Goble et al. |
| 2003/0153908 A1 | 8/2003 | Goble et al. |
| 2003/0153968 A1 * | 8/2003 | Geis .......................... A61F 2/07 623/1.11 |
| 2003/0163085 A1 | 8/2003 | Tanner et al. |
| 2003/0181900 A1 | 9/2003 | Long |
| 2003/0195387 A1 | 10/2003 | Kortenbach et al. |
| 2003/0205029 A1 | 11/2003 | Chapolini et al. |
| 2003/0216732 A1 | 11/2003 | Truckai et al. |
| 2003/0220660 A1 | 11/2003 | Kortenbach et al. |
| 2003/0236505 A1 | 12/2003 | Bonadio et al. |
| 2004/0002726 A1 | 1/2004 | Nunez et al. |
| 2004/0006335 A1 | 1/2004 | Garrison |
| 2004/0006340 A1 | 1/2004 | Latterell et al. |
| 2004/0006372 A1 | 1/2004 | Racenet et al. |
| 2004/0006861 A1 | 1/2004 | Haytayan |
| 2004/0030333 A1 | 2/2004 | Goble |
| 2004/0030379 A1 * | 2/2004 | Hamm .................. A61K 31/335 623/1.15 |
| 2004/0034357 A1 * | 2/2004 | Beane ..................... A61L 31/16 606/232 |
| 2004/0034369 A1 | 2/2004 | Sauer et al. |
| 2004/0044364 A1 | 3/2004 | DeVries et al. |
| 2004/0068161 A1 | 4/2004 | Couvillon, Jr. |
| 2004/0068224 A1 | 4/2004 | Couvillon, Jr. et al. |
| 2004/0068307 A1 | 4/2004 | Goble |
| 2004/0070369 A1 | 4/2004 | Sakakibara |
| 2004/0073222 A1 | 4/2004 | Koseki |
| 2004/0078037 A1 | 4/2004 | Batchelor et al. |
| 2004/0093024 A1 | 5/2004 | Lousararian et al. |
| 2004/0094597 A1 | 5/2004 | Whitman et al. |
| 2004/0097987 A1 | 5/2004 | Pugsley et al. |

(56) References Cited

U.S. PATENT DOCUMENTS

| | | |
|---|---|---|
| 2004/0098040 A1 | 5/2004 | Taniguchi et al. |
| 2004/0101822 A1 | 5/2004 | Wiesner et al. |
| 2004/0102783 A1 | 5/2004 | Sutterlin, III et al. |
| 2004/0108357 A1 | 6/2004 | Milliman et al. |
| 2004/0110439 A1 | 6/2004 | Chaikof et al. |
| 2004/0111081 A1 | 6/2004 | Whitman et al. |
| 2004/0115022 A1 | 6/2004 | Albertson et al. |
| 2004/0116952 A1 | 6/2004 | Sakurai et al. |
| 2004/0147909 A1 | 7/2004 | Johnston et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0181219 A1 | 9/2004 | Goble et al. |
| 2004/0186470 A1 | 9/2004 | Goble et al. |
| 2004/0193189 A1 | 9/2004 | Kortenbach et al. |
| 2004/0199181 A1 | 10/2004 | Knodel et al. |
| 2004/0222268 A1 | 11/2004 | Bilotti et al. |
| 2004/0225186 A1 | 11/2004 | Horne, Jr. et al. |
| 2004/0230214 A1 | 11/2004 | Donofrio et al. |
| 2004/0232201 A1 | 11/2004 | Wenchell et al. |
| 2004/0236352 A1 | 11/2004 | Wang et al. |
| 2004/0243147 A1 | 12/2004 | Lipow |
| 2004/0243151 A1 | 12/2004 | Demmy et al. |
| 2004/0243163 A1 | 12/2004 | Casiano et al. |
| 2004/0243176 A1 | 12/2004 | Hahnen et al. |
| 2004/0247415 A1 | 12/2004 | Mangone, Jr. |
| 2004/0254566 A1 | 12/2004 | Plicchi et al. |
| 2004/0254608 A1 | 12/2004 | Huitema et al. |
| 2004/0260315 A1 | 12/2004 | Dell et al. |
| 2004/0267310 A1 | 12/2004 | Racenet et al. |
| 2005/0010213 A1 | 1/2005 | Stad et al. |
| 2005/0032511 A1 | 2/2005 | Malone et al. |
| 2005/0033357 A1 | 2/2005 | Braun |
| 2005/0054946 A1 | 3/2005 | Krzyzanowski |
| 2005/0059997 A1 | 3/2005 | Bauman et al. |
| 2005/0070929 A1 | 3/2005 | Dalessandro et al. |
| 2005/0075561 A1 | 4/2005 | Golden |
| 2005/0080454 A1 | 4/2005 | Drews et al. |
| 2005/0085693 A1 | 4/2005 | Belson et al. |
| 2005/0090817 A1 | 4/2005 | Phan |
| 2005/0096683 A1 | 5/2005 | Ellins et al. |
| 2005/0103819 A1 | 5/2005 | Racenet et al. |
| 2005/0107814 A1 | 5/2005 | Johnston et al. |
| 2005/0107824 A1 | 5/2005 | Hillstead et al. |
| 2005/0113820 A1 | 5/2005 | Goble et al. |
| 2005/0119525 A1 | 6/2005 | Takemoto |
| 2005/0119669 A1 | 6/2005 | Demmy |
| 2005/0124855 A1 | 6/2005 | Jaffe et al. |
| 2005/0125009 A1 | 6/2005 | Perry et al. |
| 2005/0125897 A1 | 6/2005 | Wyslucha et al. |
| 2005/0131173 A1 | 6/2005 | McDaniel et al. |
| 2005/0131211 A1 | 6/2005 | Bayley et al. |
| 2005/0131390 A1 | 6/2005 | Heinrich et al. |
| 2005/0131436 A1 | 6/2005 | Johnston et al. |
| 2005/0131437 A1 | 6/2005 | Johnston et al. |
| 2005/0131457 A1 | 6/2005 | Douglas et al. |
| 2005/0137454 A1 | 6/2005 | Saadat et al. |
| 2005/0137455 A1 | 6/2005 | Ewers et al. |
| 2005/0143759 A1 | 6/2005 | Kelly |
| 2005/0143769 A1 | 6/2005 | White et al. |
| 2005/0145675 A1 | 7/2005 | Hartwick et al. |
| 2005/0154258 A1 | 7/2005 | Tartaglia et al. |
| 2005/0154406 A1 | 7/2005 | Bombard et al. |
| 2005/0165419 A1 | 7/2005 | Sauer et al. |
| 2005/0165435 A1 | 7/2005 | Johnston et al. |
| 2005/0169974 A1 | 8/2005 | Tenerz et al. |
| 2005/0171522 A1 | 8/2005 | Christopherson |
| 2005/0177181 A1 | 8/2005 | Kagan et al. |
| 2005/0182298 A1 | 8/2005 | Ikeda et al. |
| 2005/0187545 A1 | 8/2005 | Hooven et al. |
| 2005/0187572 A1 | 8/2005 | Johnston et al. |
| 2005/0187576 A1 | 8/2005 | Whitman et al. |
| 2005/0189397 A1 | 9/2005 | Jankowski |
| 2005/0192609 A1 | 9/2005 | Whitman et al. |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0228224 A1 | 10/2005 | Okada et al. |
| 2005/0240178 A1 | 10/2005 | Morley et al. |
| 2005/0245965 A1 | 11/2005 | Orban, III et al. |
| 2005/0251128 A1 | 11/2005 | Amoah |
| 2005/0256452 A1 | 11/2005 | DeMarchi et al. |
| 2005/0256522 A1 | 11/2005 | Francischelli et al. |
| 2005/0261676 A1 | 11/2005 | Hall et al. |
| 2005/0261677 A1 | 11/2005 | Hall et al. |
| 2005/0263563 A1 | 12/2005 | Racenet et al. |
| 2005/0267325 A1* | 12/2005 | Bouchier et al. ............... 600/37 |
| 2005/0267455 A1 | 12/2005 | Eggers et al. |
| 2005/0274768 A1 | 12/2005 | Cummins et al. |
| 2005/0283188 A1 | 12/2005 | Loshakove et al. |
| 2006/0004407 A1 | 1/2006 | Hiles et al. |
| 2006/0008787 A1 | 1/2006 | Hayman et al. |
| 2006/0011699 A1 | 1/2006 | Olson et al. |
| 2006/0015009 A1 | 1/2006 | Jaffe et al. |
| 2006/0020247 A1 | 1/2006 | Kagan et al. |
| 2006/0020258 A1 | 1/2006 | Strauss et al. |
| 2006/0020336 A1 | 1/2006 | Liddicoat |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0041188 A1 | 2/2006 | Dirusso et al. |
| 2006/0047275 A1 | 3/2006 | Goble |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0064086 A1 | 3/2006 | Odom |
| 2006/0079115 A1 | 4/2006 | Aranyi et al. |
| 2006/0079735 A1 | 4/2006 | Martone et al. |
| 2006/0085030 A1* | 4/2006 | Bettuchi ............... A61B 17/072 606/214 |
| 2006/0085031 A1 | 4/2006 | Bettuchi |
| 2006/0085033 A1 | 4/2006 | Criscuolo et al. |
| 2006/0085034 A1* | 4/2006 | Bettuchi ............... A61B 17/115 606/219 |
| 2006/0086032 A1 | 4/2006 | Valencic et al. |
| 2006/0087746 A1 | 4/2006 | Lipow |
| 2006/0089535 A1 | 4/2006 | Raz et al. |
| 2006/0100643 A1 | 5/2006 | Laufer et al. |
| 2006/0108393 A1* | 5/2006 | Heinrich ............ A61B 17/00491 227/179.1 |
| 2006/0111711 A1 | 5/2006 | Goble |
| 2006/0111723 A1 | 5/2006 | Chapolini et al. |
| 2006/0122636 A1 | 6/2006 | Bailly et al. |
| 2006/0135992 A1* | 6/2006 | Bettuchi ............... A61B 17/072 606/219 |
| 2006/0142772 A1 | 6/2006 | Ralph et al. |
| 2006/0149163 A1 | 7/2006 | Hibner et al. |
| 2006/0161185 A1 | 7/2006 | Saadat et al. |
| 2006/0167471 A1 | 7/2006 | Phillips |
| 2006/0173470 A1 | 8/2006 | Oray et al. |
| 2006/0178556 A1 | 8/2006 | Hasser et al. |
| 2006/0180634 A1 | 8/2006 | Shelton, IV et al. |
| 2006/0185682 A1 | 8/2006 | Marczyk |
| 2006/0200123 A1 | 9/2006 | Ryan |
| 2006/0201989 A1 | 9/2006 | Ojeda |
| 2006/0212069 A1 | 9/2006 | Shelton, IV |
| 2006/0217729 A1 | 9/2006 | Eskridge et al. |
| 2006/0226196 A1 | 10/2006 | Hueil et al. |
| 2006/0235368 A1 | 10/2006 | Oz |
| 2006/0235469 A1 | 10/2006 | Viola |
| 2006/0241655 A1 | 10/2006 | Viola |
| 2006/0241692 A1 | 10/2006 | McGuckin, Jr. et al. |
| 2006/0244460 A1 | 11/2006 | Weaver |
| 2006/0252993 A1 | 11/2006 | Freed et al. |
| 2006/0253069 A1 | 11/2006 | Li et al. |
| 2006/0258904 A1 | 11/2006 | Stefanchik et al. |
| 2006/0258910 A1 | 11/2006 | Stefanchik et al. |
| 2006/0259073 A1 | 11/2006 | Miyamoto et al. |
| 2006/0264927 A1 | 11/2006 | Ryan |
| 2006/0264929 A1 | 11/2006 | Goble et al. |
| 2006/0271042 A1 | 11/2006 | Latterell et al. |
| 2006/0271102 A1 | 11/2006 | Bosshard et al. |

(56) References Cited

U.S. PATENT DOCUMENTS

| | | | |
|---|---|---|---|
| 2006/0271104 A1* | 11/2006 | Viola | A61B 17/00491 606/214 |
| 2006/0278680 A1 | 12/2006 | Viola et al. | |
| 2006/0278681 A1 | 12/2006 | Viola et al. | |
| 2006/0284730 A1 | 12/2006 | Schmid et al. | |
| 2006/0287576 A1 | 12/2006 | Tsuji et al. | |
| 2006/0289602 A1 | 12/2006 | Wales et al. | |
| 2006/0291981 A1* | 12/2006 | Viola | A61B 17/0644 411/457 |
| 2007/0010702 A1* | 1/2007 | Wang | A61F 2/82 600/8 |
| 2007/0010838 A1 | 1/2007 | Shelton, IV et al. | |
| 2007/0023476 A1 | 2/2007 | Whitman et al. | |
| 2007/0023477 A1 | 2/2007 | Whitman et al. | |
| 2007/0026039 A1 | 2/2007 | Drumheller et al. | |
| 2007/0026040 A1 | 2/2007 | Crawley et al. | |
| 2007/0027468 A1 | 2/2007 | Wales et al. | |
| 2007/0027472 A1 | 2/2007 | Hiles et al. | |
| 2007/0027551 A1 | 2/2007 | Farnsworth et al. | |
| 2007/0034668 A1 | 2/2007 | Holsten et al. | |
| 2007/0049966 A1 | 3/2007 | Bonadio et al. | |
| 2007/0051375 A1 | 3/2007 | Milliman | |
| 2007/0055219 A1 | 3/2007 | Whitman et al. | |
| 2007/0066981 A1 | 3/2007 | Meagher | |
| 2007/0070574 A1 | 3/2007 | Nerheim et al. | |
| 2007/0073341 A1 | 3/2007 | Smith | |
| 2007/0078484 A1 | 4/2007 | Talarico et al. | |
| 2007/0083193 A1 | 4/2007 | Werneth et al. | |
| 2007/0084897 A1 | 4/2007 | Shelton, IV et al. | |
| 2007/0093869 A1 | 4/2007 | Bloom et al. | |
| 2007/0102472 A1 | 5/2007 | Shelton, IV | |
| 2007/0106113 A1 | 5/2007 | Ravo | |
| 2007/0106317 A1 | 5/2007 | Shelton, IV et al. | |
| 2007/0118175 A1 | 5/2007 | Butler et al. | |
| 2007/0129605 A1 | 6/2007 | Schaaf | |
| 2007/0135686 A1 | 6/2007 | Pruitt, Jr. et al. | |
| 2007/0135803 A1 | 6/2007 | Belson | |
| 2007/0155010 A1 | 7/2007 | Farnsworth et al. | |
| 2007/0158358 A1 | 7/2007 | Mason, II et al. | |
| 2007/0170225 A1 | 7/2007 | Shelton, IV et al. | |
| 2007/0173687 A1 | 7/2007 | Shima et al. | |
| 2007/0173806 A1 | 7/2007 | Orszulak et al. | |
| 2007/0173813 A1 | 7/2007 | Odom | |
| 2007/0175950 A1 | 8/2007 | Shelton, IV et al. | |
| 2007/0175951 A1 | 8/2007 | Shelton, IV et al. | |
| 2007/0175955 A1 | 8/2007 | Shelton, IV et al. | |
| 2007/0179528 A1 | 8/2007 | Soltz et al. | |
| 2007/0181632 A1 | 8/2007 | Milliman | |
| 2007/0190110 A1 | 8/2007 | Pameijer et al. | |
| 2007/0194079 A1 | 8/2007 | Hueil et al. | |
| 2007/0194082 A1 | 8/2007 | Morgan et al. | |
| 2007/0198039 A1 | 8/2007 | Jones et al. | |
| 2007/0203510 A1 | 8/2007 | Bettuchi | |
| 2007/0219571 A1 | 9/2007 | Balbierz et al. | |
| 2007/0221700 A1 | 9/2007 | Ortiz et al. | |
| 2007/0225562 A1 | 9/2007 | Spivey et al. | |
| 2007/0233163 A1 | 10/2007 | Bombard et al. | |
| 2007/0239028 A1 | 10/2007 | Houser et al. | |
| 2007/0243227 A1 | 10/2007 | Gertner | |
| 2007/0244471 A1 | 10/2007 | Malackowski | |
| 2007/0246505 A1 | 10/2007 | Pace-Floridia et al. | |
| 2007/0249999 A1 | 10/2007 | Sklar et al. | |
| 2007/0255273 A1* | 11/2007 | Fernandez | A61B 18/14 606/41 |
| 2007/0260278 A1 | 11/2007 | Wheeler et al. | |
| 2007/0270784 A1 | 11/2007 | Smith et al. | |
| 2007/0270884 A1 | 11/2007 | Smith et al. | |
| 2007/0275035 A1 | 11/2007 | Herman et al. | |
| 2007/0276409 A1 | 11/2007 | Ortiz et al. | |
| 2007/0279011 A1 | 12/2007 | Jones et al. | |
| 2007/0286892 A1 | 12/2007 | Herzberg et al. | |
| 2007/0287993 A1 | 12/2007 | Hinman et al. | |
| 2007/0288044 A1 | 12/2007 | Jinno et al. | |
| 2007/0299427 A1 | 12/2007 | Yeung et al. | |
| 2008/0015598 A1 | 1/2008 | Prommersberger | |
| 2008/0029570 A1 | 2/2008 | Shelton et al. | |
| 2008/0029573 A1 | 2/2008 | Shelton et al. | |
| 2008/0029574 A1 | 2/2008 | Shelton et al. | |
| 2008/0029575 A1 | 2/2008 | Shelton et al. | |
| 2008/0030170 A1 | 2/2008 | Dacquay et al. | |
| 2008/0035701 A1 | 2/2008 | Racenet et al. | |
| 2008/0041916 A1 | 2/2008 | Milliman et al. | |
| 2008/0041917 A1 | 2/2008 | Racenet et al. | |
| 2008/0078800 A1* | 4/2008 | Hess | A61B 17/0644 227/175.1 |
| 2008/0078802 A1 | 4/2008 | Hess et al. | |
| 2008/0082114 A1 | 4/2008 | McKenna et al. | |
| 2008/0082124 A1* | 4/2008 | Hess | A61B 17/064 606/219 |
| 2008/0082125 A1 | 4/2008 | Murray et al. | |
| 2008/0082126 A1 | 4/2008 | Murray et al. | |
| 2008/0083808 A1 | 4/2008 | Scirica | |
| 2008/0083813 A1 | 4/2008 | Zemlok et al. | |
| 2008/0085296 A1 | 4/2008 | Powell et al. | |
| 2008/0086078 A1 | 4/2008 | Powell et al. | |
| 2008/0114315 A1 | 5/2008 | Voegele et al. | |
| 2008/0114385 A1 | 5/2008 | Byrum et al. | |
| 2008/0128469 A1 | 6/2008 | Dalessandro et al. | |
| 2008/0129253 A1 | 6/2008 | Shiue et al. | |
| 2008/0140115 A1 | 6/2008 | Stopek | |
| 2008/0154299 A1 | 6/2008 | Linvneh | |
| 2008/0169328 A1 | 7/2008 | Shelton | |
| 2008/0169332 A1 | 7/2008 | Shelton et al. | |
| 2008/0169333 A1 | 7/2008 | Shelton et al. | |
| 2008/0172087 A1 | 7/2008 | Fuchs et al. | |
| 2008/0172088 A1 | 7/2008 | Smith et al. | |
| 2008/0183193 A1 | 7/2008 | Omori et al. | |
| 2008/0185419 A1 | 8/2008 | Smith et al. | |
| 2008/0190989 A1 | 8/2008 | Crews et al. | |
| 2008/0197167 A1 | 8/2008 | Viola et al. | |
| 2008/0200762 A1 | 8/2008 | Stokes et al. | |
| 2008/0200835 A1 | 8/2008 | Monson et al. | |
| 2008/0200933 A1 | 8/2008 | Bakos et al. | |
| 2008/0200949 A1 | 8/2008 | Hiles et al. | |
| 2008/0228029 A1 | 9/2008 | Mikkaichi et al. | |
| 2008/0245841 A1 | 10/2008 | Smith et al. | |
| 2008/0251568 A1 | 10/2008 | Zemlok et al. | |
| 2008/0251569 A1 | 10/2008 | Smith et al. | |
| 2008/0255413 A1 | 10/2008 | Zemlok et al. | |
| 2008/0255607 A1 | 10/2008 | Zemlok | |
| 2008/0262654 A1 | 10/2008 | Omori et al. | |
| 2008/0283570 A1 | 11/2008 | Boyden et al. | |
| 2008/0287944 A1 | 11/2008 | Pearson et al. | |
| 2008/0290134 A1 | 11/2008 | Bettuchi et al. | |
| 2008/0294179 A1 | 11/2008 | Balbierz et al. | |
| 2008/0296346 A1 | 12/2008 | Shelton, IV et al. | |
| 2008/0297287 A1 | 12/2008 | Shachar et al. | |
| 2008/0308602 A1 | 12/2008 | Timm et al. | |
| 2008/0308603 A1 | 12/2008 | Shelton, IV et al. | |
| 2008/0308608 A1 | 12/2008 | Prommersberger | |
| 2008/0314960 A1* | 12/2008 | Marczyk | A61B 17/07207 227/178.1 |
| 2008/0315829 A1 | 12/2008 | Jones et al. | |
| 2009/0001121 A1 | 1/2009 | Hess et al. | |
| 2009/0001122 A1 | 1/2009 | Prommersberger et al. | |
| 2009/0001130 A1 | 1/2009 | Hess et al. | |
| 2009/0004455 A1 | 1/2009 | Gravagna et al. | |
| 2009/0005807 A1 | 1/2009 | Hess et al. | |
| 2009/0005809 A1 | 1/2009 | Hess et al. | |
| 2009/0012534 A1 | 1/2009 | Madhani et al. | |
| 2009/0018553 A1 | 1/2009 | McLean et al. | |
| 2009/0020958 A1 | 1/2009 | Soul | |
| 2009/0047329 A1 | 2/2009 | Stucky et al. | |
| 2009/0048589 A1 | 2/2009 | Takashino et al. | |
| 2009/0048612 A1 | 2/2009 | Farritor et al. | |
| 2009/0054908 A1 | 2/2009 | Zand et al. | |
| 2009/0076506 A1 | 3/2009 | Baker | |
| 2009/0078736 A1 | 3/2009 | Van Lue | |
| 2009/0082789 A1 | 3/2009 | Milliman et al. | |
| 2009/0088774 A1 | 4/2009 | Swarup et al. | |
| 2009/0090763 A1 | 4/2009 | Zemlok et al. | |
| 2009/0092651 A1 | 4/2009 | Shah et al. | |
| 2009/0093728 A1 | 4/2009 | Hyde et al. | |
| 2009/0099579 A1 | 4/2009 | Nentwick et al. | |

(56) References Cited

U.S. PATENT DOCUMENTS

| | | |
|---|---|---|
| 2009/0099876 A1 | 4/2009 | Whitman |
| 2009/0108048 A1 | 4/2009 | Zemlok et al. |
| 2009/0112229 A1 | 4/2009 | Omori et al. |
| 2009/0114701 A1 | 5/2009 | Zemlok et al. |
| 2009/0119011 A1 | 5/2009 | Kondo et al. |
| 2009/0120994 A1* | 5/2009 | Murray et al. ............ 227/180.1 |
| 2009/0143805 A1 | 6/2009 | Palmer et al. |
| 2009/0143855 A1 | 6/2009 | Weber et al. |
| 2009/0149871 A9 | 6/2009 | Kagan et al. |
| 2009/0157067 A1 | 6/2009 | Kane et al. |
| 2009/0157087 A1 | 6/2009 | Wei et al. |
| 2009/0171147 A1 | 7/2009 | Lee et al. |
| 2009/0177226 A1 | 7/2009 | Reinprecht et al. |
| 2009/0188964 A1 | 7/2009 | Orlov |
| 2009/0196903 A1* | 8/2009 | Kliman ................ A61F 9/0017 424/423 |
| 2009/0198272 A1 | 8/2009 | Kerver et al. |
| 2009/0204108 A1 | 8/2009 | Steffen |
| 2009/0206125 A1* | 8/2009 | Huitema .......... A61B 17/07207 227/175.1 |
| 2009/0206126 A1 | 8/2009 | Huitema et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0206139 A1 | 8/2009 | Hall et al. |
| 2009/0206141 A1 | 8/2009 | Huitema et al. |
| 2009/0206142 A1* | 8/2009 | Huitema .......... A61B 17/07207 227/176.1 |
| 2009/0213685 A1 | 8/2009 | Mak et al. |
| 2009/0218384 A1* | 9/2009 | Aranyi ............ A61B 17/07207 227/176.1 |
| 2009/0242610 A1 | 10/2009 | Shelton, IV et al. |
| 2009/0247901 A1 | 10/2009 | Zimmer |
| 2009/0255974 A1 | 10/2009 | Viola |
| 2009/0255975 A1 | 10/2009 | Zemlok et al. |
| 2009/0255976 A1 | 10/2009 | Marczyk et al. |
| 2009/0255977 A1 | 10/2009 | Zemlok |
| 2009/0255978 A1 | 10/2009 | Viola et al. |
| 2009/0270895 A1 | 10/2009 | Churchill et al. |
| 2009/0277949 A1 | 11/2009 | Viola et al. |
| 2009/0287300 A1* | 11/2009 | Dave et al. ................. 623/1.42 |
| 2009/0292283 A1 | 11/2009 | Odom |
| 2009/0308907 A1 | 12/2009 | Nalagatla et al. |
| 2010/0010511 A1 | 1/2010 | Harris et al. |
| 2010/0012704 A1 | 1/2010 | Tarinelli Racenet et al. |
| 2010/0016888 A1 | 1/2010 | Calabrese et al. |
| 2010/0023024 A1 | 1/2010 | Zeiner et al. |
| 2010/0036370 A1 | 2/2010 | Mirel et al. |
| 2010/0049084 A1 | 2/2010 | Nock et al. |
| 2010/0057087 A1 | 3/2010 | Cha |
| 2010/0057107 A1 | 3/2010 | Sorrentino et al. |
| 2010/0069942 A1 | 3/2010 | Shelton, IV |
| 2010/0072254 A1 | 3/2010 | Aranyi et al. |
| 2010/0076475 A1 | 3/2010 | Yates et al. |
| 2010/0076483 A1 | 3/2010 | Imuta |
| 2010/0076489 A1 | 3/2010 | Stopek et al. |
| 2010/0087840 A1 | 4/2010 | Ebersole et al. |
| 2010/0094289 A1 | 4/2010 | Taylor et al. |
| 2010/0096431 A1 | 4/2010 | Smith et al. |
| 2010/0100124 A1 | 4/2010 | Calabrese et al. |
| 2010/0108740 A1 | 5/2010 | Pastorelli et al. |
| 2010/0108741 A1 | 5/2010 | Hessler et al. |
| 2010/0127039 A1* | 5/2010 | Hessler ................ A61B 17/115 227/175.1 |
| 2010/0133317 A1 | 6/2010 | Shelton, IV et al. |
| 2010/0145146 A1 | 6/2010 | Melder |
| 2010/0147921 A1 | 6/2010 | Olson |
| 2010/0147922 A1 | 6/2010 | Olson |
| 2010/0147923 A1 | 6/2010 | D'Agostino et al. |
| 2010/0163598 A1 | 7/2010 | Belzer |
| 2010/0179022 A1 | 7/2010 | Shirokoshi |
| 2010/0179540 A1 | 7/2010 | Marczyk et al. |
| 2010/0186219 A1 | 7/2010 | Smith |
| 2010/0193566 A1 | 8/2010 | Scheib et al. |
| 2010/0200637 A1 | 8/2010 | Beetel |
| 2010/0204717 A1 | 8/2010 | Knodel |
| 2010/0222901 A1 | 9/2010 | Swayze et al. |
| 2010/0230465 A1 | 9/2010 | Smith et al. |
| 2010/0243707 A1 | 9/2010 | Olson et al. |
| 2010/0243708 A1 | 9/2010 | Aranyi et al. |
| 2010/0249519 A1 | 9/2010 | Park et al. |
| 2010/0258611 A1 | 10/2010 | Smith et al. |
| 2010/0267662 A1 | 10/2010 | Fielder et al. |
| 2010/0268030 A1 | 10/2010 | Viola et al. |
| 2010/0274160 A1 | 10/2010 | Yachi et al. |
| 2010/0276471 A1 | 11/2010 | Whitman |
| 2010/0292540 A1 | 11/2010 | Hess et al. |
| 2010/0294827 A1 | 11/2010 | Boyden et al. |
| 2010/0298636 A1 | 11/2010 | Castro et al. |
| 2010/0305552 A1 | 12/2010 | Shelton, IV et al. |
| 2010/0312261 A1 | 12/2010 | Suzuki et al. |
| 2010/0320252 A1 | 12/2010 | Viola et al. |
| 2010/0331856 A1 | 12/2010 | Carlson et al. |
| 2010/0331880 A1 | 12/2010 | Stopek |
| 2011/0003528 A1 | 1/2011 | Lam |
| 2011/0006101 A1 | 1/2011 | Hall et al. |
| 2011/0011916 A1 | 1/2011 | Levine |
| 2011/0017799 A1 | 1/2011 | Whitman et al. |
| 2011/0017801 A1 | 1/2011 | Zemlok et al. |
| 2011/0022032 A1 | 1/2011 | Zemlok et al. |
| 2011/0024477 A1 | 2/2011 | Hall |
| 2011/0024478 A1 | 2/2011 | Shelton, IV |
| 2011/0024479 A1 | 2/2011 | Swensgard et al. |
| 2011/0034918 A1 | 2/2011 | Reschke |
| 2011/0036887 A1 | 2/2011 | Zemlok et al. |
| 2011/0036890 A1 | 2/2011 | Ma |
| 2011/0036891 A1 | 2/2011 | Zemlok et al. |
| 2011/0045047 A1 | 2/2011 | Bennett et al. |
| 2011/0060363 A1 | 3/2011 | Hess et al. |
| 2011/0066243 A1* | 3/2011 | Rivin .................... A61F 2/3872 623/14.12 |
| 2011/0084112 A1 | 4/2011 | Kostrzewski |
| 2011/0087279 A1 | 4/2011 | Shah et al. |
| 2011/0095068 A1 | 4/2011 | Patel |
| 2011/0101065 A1 | 5/2011 | Milliman |
| 2011/0112513 A1* | 5/2011 | Hester et al. ................. 604/514 |
| 2011/0114697 A1 | 5/2011 | Baxter, III et al. |
| 2011/0118754 A1 | 5/2011 | Dachs, II et al. |
| 2011/0118778 A1 | 5/2011 | Burbank |
| 2011/0125176 A1 | 5/2011 | Yates et al. |
| 2011/0125177 A1 | 5/2011 | Yates et al. |
| 2011/0144430 A1 | 6/2011 | Spivey et al. |
| 2011/0144640 A1 | 6/2011 | Heinrich et al. |
| 2011/0147433 A1 | 6/2011 | Shelton, IV et al. |
| 2011/0155786 A1 | 6/2011 | Shelton, IV |
| 2011/0155787 A1 | 6/2011 | Baxter, III et al. |
| 2011/0163146 A1 | 7/2011 | Ortiz et al. |
| 2011/0174099 A1 | 7/2011 | Ross et al. |
| 2011/0174861 A1 | 7/2011 | Shelton, IV et al. |
| 2011/0178536 A1 | 7/2011 | Kostrzewski |
| 2011/0184459 A1 | 7/2011 | Malkowski et al. |
| 2011/0192882 A1 | 8/2011 | Hess et al. |
| 2011/0210156 A1 | 9/2011 | Smith et al. |
| 2011/0253765 A1 | 10/2011 | Nicholas et al. |
| 2011/0264119 A1 | 10/2011 | Bayon et al. |
| 2011/0275901 A1 | 11/2011 | Shelton, IV |
| 2011/0276083 A1 | 11/2011 | Shelton, IV et al. |
| 2011/0278343 A1 | 11/2011 | Knodel et al. |
| 2011/0278346 A1* | 11/2011 | Hull ................ A61B 17/00491 227/180.1 |
| 2011/0282446 A1 | 11/2011 | Schulte et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290856 A1 | 12/2011 | Shelton, IV et al. |
| 2011/0293690 A1 | 12/2011 | Griffin et al. |
| 2011/0295242 A1 | 12/2011 | Spivey et al. |
| 2011/0295269 A1 | 12/2011 | Swensgard et al. |
| 2011/0295295 A1 | 12/2011 | Shelton, IV et al. |
| 2011/0315413 A1 | 12/2011 | Fisher et al. |
| 2011/0315740 A1* | 12/2011 | Stopek ................ A61B 17/072 227/176.1 |
| 2012/0004636 A1 | 1/2012 | Lo |

(56) References Cited

U.S. PATENT DOCUMENTS

| | | |
|---|---|---|
| 2012/0018326 A1 | 1/2012 | Racenet et al. |
| 2012/0022523 A1 | 1/2012 | Smith et al. |
| 2012/0022630 A1 | 1/2012 | Wübbeling |
| 2012/0029272 A1 | 2/2012 | Shelton, IV et al. |
| 2012/0046692 A1 | 2/2012 | Smith et al. |
| 2012/0071711 A1 | 3/2012 | Shelton, IV et al. |
| 2012/0074200 A1 | 3/2012 | Schmid et al. |
| 2012/0074201 A1 | 3/2012 | Baxter, III et al. |
| 2012/0080332 A1 | 4/2012 | Shelton, IV et al. |
| 2012/0080335 A1 | 4/2012 | Shelton, IV et al. |
| 2012/0080336 A1 | 4/2012 | Shelton, IV et al. |
| 2012/0080337 A1 | 4/2012 | Shelton, IV et al. |
| 2012/0080338 A1 | 4/2012 | Shelton, IV et al. |
| 2012/0080339 A1 | 4/2012 | Shelton, IV et al. |
| 2012/0080340 A1 | 4/2012 | Shelton, IV et al. |
| 2012/0080344 A1 | 4/2012 | Shelton, IV |
| 2012/0080345 A1 | 4/2012 | Morgan et al. |
| 2012/0080475 A1 | 4/2012 | Smith et al. |
| 2012/0080478 A1 | 4/2012 | Morgan et al. |
| 2012/0080479 A1 | 4/2012 | Shelton, IV |
| 2012/0080480 A1 | 4/2012 | Woodard, Jr. et al. |
| 2012/0080481 A1 | 4/2012 | Widenhouse et al. |
| 2012/0080482 A1 | 4/2012 | Schall et al. |
| 2012/0080483 A1 | 4/2012 | Riestenberg et al. |
| 2012/0080484 A1 | 4/2012 | Morgan et al. |
| 2012/0080485 A1 | 4/2012 | Woodard, Jr. et al. |
| 2012/0080486 A1 | 4/2012 | Woodard, Jr. et al. |
| 2012/0080488 A1 | 4/2012 | Shelton, IV et al. |
| 2012/0080489 A1 | 4/2012 | Shelton, IV et al. |
| 2012/0080490 A1 | 4/2012 | Shelton, IV et al. |
| 2012/0080491 A1 | 4/2012 | Shelton, IV et al. |
| 2012/0080493 A1 | 4/2012 | Shelton, IV et al. |
| 2012/0080496 A1 | 4/2012 | Schall et al. |
| 2012/0080498 A1 | 4/2012 | Shelton, IV et al. |
| 2012/0080499 A1 | 4/2012 | Schall et al. |
| 2012/0080500 A1 | 4/2012 | Morgan et al. |
| 2012/0080501 A1 | 4/2012 | Morgan et al. |
| 2012/0080502 A1 | 4/2012 | Morgan et al. |
| 2012/0080503 A1 | 4/2012 | Woodard, Jr. et al. |
| 2012/0083833 A1 | 4/2012 | Shelton, IV et al. |
| 2012/0083834 A1 | 4/2012 | Shelton, IV et al. |
| 2012/0083835 A1 | 4/2012 | Shelton, IV et al. |
| 2012/0083836 A1 | 4/2012 | Shelton, IV et al. |
| 2012/0089131 A1 | 4/2012 | Zemlok et al. |
| 2012/0125792 A1* | 5/2012 | Cassivi ........................ 206/205 |
| 2012/0138658 A1 | 6/2012 | Ullrich et al. |
| 2012/0150192 A1 | 6/2012 | Dachs, II et al. |
| 2012/0160721 A1 | 6/2012 | Shelton, IV et al. |
| 2012/0175398 A1 | 7/2012 | Sandborn et al. |
| 2012/0187179 A1 | 7/2012 | Gleiman |
| 2012/0199632 A1 | 8/2012 | Spivey et al. |
| 2012/0209289 A1 | 8/2012 | Duque et al. |
| 2012/0223123 A1 | 9/2012 | Baxter, III et al. |
| 2012/0234890 A1 | 9/2012 | Aronhalt et al. |
| 2012/0234892 A1 | 9/2012 | Aronhalt et al. |
| 2012/0234895 A1 | 9/2012 | O'Connor et al. |
| 2012/0234897 A1 | 9/2012 | Shelton, IV et al. |
| 2012/0234898 A1 | 9/2012 | Shelton, IV et al. |
| 2012/0234899 A1 | 9/2012 | Scheib et al. |
| 2012/0238823 A1 | 9/2012 | Hagerty et al. |
| 2012/0238824 A1 | 9/2012 | Widenhouse et al. |
| 2012/0239010 A1 | 9/2012 | Shelton, IV et al. |
| 2012/0241491 A1 | 9/2012 | Aldridge et al. |
| 2012/0241493 A1 | 9/2012 | Baxter, III et al. |
| 2012/0241496 A1 | 9/2012 | Mandakolathur Vasudevan et al. |
| 2012/0241497 A1* | 9/2012 | Mandakolathur Vasudevan ........................ A61B 17/00491 227/176.1 |
| 2012/0241498 A1 | 9/2012 | Gonzalez et al. |
| 2012/0241499 A1 | 9/2012 | Baxter, III et al. |
| 2012/0241500 A1 | 9/2012 | Timmer et al. |
| 2012/0241501 A1 | 9/2012 | Swayze et al. |
| 2012/0241502 A1 | 9/2012 | Aldridge et al. |
| 2012/0241503 A1 | 9/2012 | Baxter, III et al. |
| 2012/0241505 A1 | 9/2012 | Alexander, III et al. |
| 2012/0248169 A1 | 10/2012 | Widenhouse et al. |
| 2012/0253298 A1 | 10/2012 | Henderson et al. |
| 2012/0253329 A1 | 10/2012 | Zemlok et al. |
| 2012/0265176 A1 | 10/2012 | Braun |
| 2012/0273550 A1 | 11/2012 | Scirica |
| 2012/0283707 A1 | 11/2012 | Giordano et al. |
| 2012/0283748 A1 | 11/2012 | Ortiz et al. |
| 2012/0289979 A1 | 11/2012 | Eskaros et al. |
| 2012/0292367 A1 | 11/2012 | Morgan et al. |
| 2012/0296333 A1 | 11/2012 | Twomey |
| 2012/0298719 A1 | 11/2012 | Shelton, IV et al. |
| 2012/0298722 A1 | 11/2012 | Hess et al. |
| 2012/0310255 A1 | 12/2012 | Brisson et al. |
| 2012/0310256 A1 | 12/2012 | Brisson |
| 2012/0312860 A1 | 12/2012 | Ming et al. |
| 2012/0318842 A1 | 12/2012 | Anim et al. |
| 2012/0318843 A1 | 12/2012 | Henderson et al. |
| 2012/0318844 A1 | 12/2012 | Shelton, IV et al. |
| 2012/0325892 A1 | 12/2012 | Kostrzewski |
| 2013/0012983 A1 | 1/2013 | Kleyman |
| 2013/0018361 A1 | 1/2013 | Bryant |
| 2013/0020375 A1 | 1/2013 | Shelton, IV et al. |
| 2013/0020376 A1 | 1/2013 | Shelton, IV et al. |
| 2013/0023861 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037596 A1 | 2/2013 | Bear et al. |
| 2013/0048697 A1 | 2/2013 | Shelton, IV et al. |
| 2013/0056518 A1 | 3/2013 | Swensgard |
| 2013/0056521 A1 | 3/2013 | Swensgard |
| 2013/0062391 A1 | 3/2013 | Boudreaux et al. |
| 2013/0075446 A1* | 3/2013 | Wang et al. ................ 227/176.1 |
| 2013/0075448 A1 | 3/2013 | Schmid et al. |
| 2013/0075449 A1 | 3/2013 | Schmid et al. |
| 2013/0075450 A1 | 3/2013 | Schmid et al. |
| 2013/0079814 A1 | 3/2013 | Hess et al. |
| 2013/0087597 A1 | 4/2013 | Shelton, IV et al. |
| 2013/0087599 A1 | 4/2013 | Krumanaker et al. |
| 2013/0087602 A1 | 4/2013 | Olson et al. |
| 2013/0098970 A1 | 4/2013 | Racenet et al. |
| 2013/0103024 A1 | 4/2013 | Monson et al. |
| 2013/0116668 A1 | 5/2013 | Shelton, IV et al. |
| 2013/0116669 A1 | 5/2013 | Shelton, IV et al. |
| 2013/0119108 A1 | 5/2013 | Altman et al. |
| 2013/0123822 A1 | 5/2013 | Wellman et al. |
| 2013/0126581 A1 | 5/2013 | Yates et al. |
| 2013/0126582 A1 | 5/2013 | Shelton, IV et al. |
| 2013/0146641 A1 | 6/2013 | Shelton, IV et al. |
| 2013/0146642 A1 | 6/2013 | Shelton, IV et al. |
| 2013/0146643 A1 | 6/2013 | Schmid et al. |
| 2013/0150832 A1 | 6/2013 | Belson et al. |
| 2013/0153633 A1 | 6/2013 | Casasanta, Jr. et al. |
| 2013/0153634 A1 | 6/2013 | Carter et al. |
| 2013/0153636 A1 | 6/2013 | Shelton, IV et al. |
| 2013/0153638 A1 | 6/2013 | Carter et al. |
| 2013/0153641 A1 | 6/2013 | Shelton, IV et al. |
| 2013/0161374 A1 | 6/2013 | Swayze et al. |
| 2013/0161375 A1 | 6/2013 | Huitema et al. |
| 2013/0168431 A1 | 7/2013 | Zemlok et al. |
| 2013/0168435 A1 | 7/2013 | Huang et al. |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0181033 A1 | 7/2013 | Shelton, IV et al. |
| 2013/0181034 A1 | 7/2013 | Shelton, IV et al. |
| 2013/0184718 A1 | 7/2013 | Smith et al. |
| 2013/0184719 A1 | 7/2013 | Shelton, IV et al. |
| 2013/0186932 A1 | 7/2013 | Shelton, IV et al. |
| 2013/0186933 A1 | 7/2013 | Shelton, IV et al. |
| 2013/0186934 A1 | 7/2013 | Shelton, IV et al. |
| 2013/0186936 A1 | 7/2013 | Shelton, IV |
| 2013/0190733 A1 | 7/2013 | Giordano et al. |
| 2013/0190757 A1 | 7/2013 | Yates et al. |
| 2013/0193188 A1 | 8/2013 | Shelton, IV et al. |
| 2013/0193189 A1 | 8/2013 | Swensgard et al. |
| 2013/0197556 A1 | 8/2013 | Shelton, IV et al. |
| 2013/0200132 A1 | 8/2013 | Moore et al. |
| 2013/0206814 A1 | 8/2013 | Morgan et al. |

(56) References Cited

U.S. PATENT DOCUMENTS

| | | |
|---|---|---|
| 2013/0214025 A1 | 8/2013 | Zemlok et al. |
| 2013/0214030 A1 | 8/2013 | Aronhalt et al. |
| 2013/0221063 A1 | 8/2013 | Aronhalt et al. |
| 2013/0221064 A1 | 8/2013 | Aronhalt et al. |
| 2013/0221065 A1 | 8/2013 | Aronhalt et al. |
| 2013/0233906 A1 | 9/2013 | Hess et al. |
| 2013/0248576 A1 | 9/2013 | Laurent et al. |
| 2013/0248577 A1 | 9/2013 | Leimbach et al. |
| 2013/0256365 A1 | 10/2013 | Shelton, IV et al. |
| 2013/0256366 A1 | 10/2013 | Shelton, IV et al. |
| 2013/0256367 A1 | 10/2013 | Scheib et al. |
| 2013/0256368 A1 | 10/2013 | Timm et al. |
| 2013/0256369 A1 | 10/2013 | Schmid et al. |
| 2013/0256371 A1 | 10/2013 | Shelton, IV et al. |
| 2013/0256372 A1 | 10/2013 | Baxter, III et al. |
| 2013/0256373 A1 | 10/2013 | Schmid et al. |
| 2013/0256374 A1 | 10/2013 | Shelton, IV et al. |
| 2013/0256375 A1 | 10/2013 | Shelton, IV et al. |
| 2013/0256376 A1 | 10/2013 | Barton et al. |
| 2013/0256377 A1 | 10/2013 | Schmid et al. |
| 2013/0256378 A1 | 10/2013 | Schmid et al. |
| 2013/0256379 A1 | 10/2013 | Schmid et al. |
| 2013/0256380 A1 | 10/2013 | Schmid et al. |
| 2013/0256382 A1 | 10/2013 | Swayze et al. |
| 2013/0256383 A1 | 10/2013 | Aronhalt et al. |
| 2013/0261648 A1 | 10/2013 | Laurent et al. |
| 2013/0270322 A1 | 10/2013 | Scheib et al. |
| 2013/0277412 A1 | 10/2013 | Gresham et al. |
| 2013/0310873 A1 | 11/2013 | Stopek et al. |
| 2013/0313303 A1 | 11/2013 | Shelton, IV et al. |
| 2013/0313304 A1 | 11/2013 | Shelton, IV et al. |
| 2013/0313306 A1 | 11/2013 | Shelton, IV et al. |
| 2013/0324981 A1 | 12/2013 | Smith et al. |
| 2013/0324982 A1 | 12/2013 | Smith et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2013/0341374 A1 | 12/2013 | Shelton, IV et al. |
| 2014/0000411 A1 | 1/2014 | Shelton, IV et al. |
| 2014/0001231 A1 | 1/2014 | Shelton, IV et al. |
| 2014/0001234 A1 | 1/2014 | Shelton, IV et al. |
| 2014/0001235 A1 | 1/2014 | Shelton, IV |
| 2014/0001236 A1 | 1/2014 | Shelton, IV et al. |
| 2014/0001237 A1 | 1/2014 | Shelton, IV et al. |
| 2014/0001238 A1 | 1/2014 | Shelton, IV et al. |
| 2014/0001239 A1 | 1/2014 | Shelton, IV et al. |
| 2014/0001240 A1 | 1/2014 | Shelton, IV et al. |
| 2014/0005640 A1 | 1/2014 | Shelton, IV et al. |
| 2014/0005653 A1 | 1/2014 | Shelton, IV et al. |
| 2014/0005661 A1 | 1/2014 | Shelton, IV et al. |
| 2014/0005662 A1 | 1/2014 | Shelton, IV |
| 2014/0005676 A1 | 1/2014 | Shelton, IV et al. |
| 2014/0005678 A1 | 1/2014 | Shelton, IV et al. |
| 2014/0005679 A1 | 1/2014 | Shelton, IV et al. |
| 2014/0005680 A1 | 1/2014 | Shelton, IV et al. |
| 2014/0005693 A1 | 1/2014 | Shelton, IV et al. |
| 2014/0005694 A1 | 1/2014 | Shelton, IV et al. |
| 2014/0005695 A1 | 1/2014 | Shelton, IV |
| 2014/0005702 A1 | 1/2014 | Timm et al. |
| 2014/0005703 A1 | 1/2014 | Stulen et al. |
| 2014/0005708 A1 | 1/2014 | Shelton, IV |
| 2014/0005718 A1 | 1/2014 | Shelton, IV et al. |
| 2014/0008414 A1 | 1/2014 | Shelton, IV et al. |
| 2014/0014705 A1 | 1/2014 | Baxter, III |
| 2014/0015782 A1 | 1/2014 | Kim et al. |
| 2014/0042205 A1 | 2/2014 | Baxter, III et al. |
| 2014/0048582 A1 | 2/2014 | Shelton, IV et al. |
| 2014/0061279 A1 | 3/2014 | Laurent et al. |
| 2014/0097227 A1 | 4/2014 | Aronhalt et al. |
| 2014/0107640 A1 | 4/2014 | Yates et al. |
| 2014/0128850 A1 | 5/2014 | Kerr et al. |
| 2014/0138423 A1* | 5/2014 | Whitfield ......... A61B 17/07292 227/176.1 |
| 2014/0151431 A1 | 6/2014 | Hodgkinson et al. |
| 2014/0151433 A1 | 6/2014 | Shelton, IV et al. |
| 2014/0151434 A1 | 6/2014 | Shelton, IV et al. |
| 2014/0166722 A1 | 6/2014 | Hess et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0171966 A1 | 6/2014 | Giordano et al. |
| 2014/0175152 A1 | 6/2014 | Hess et al. |
| 2014/0175154 A1 | 6/2014 | Shelton, IV et al. |
| 2014/0175155 A1 | 6/2014 | Shelton, IV et al. |
| 2014/0191014 A1 | 7/2014 | Shelton, IV |
| 2014/0191015 A1 | 7/2014 | Shelton, IV |
| 2014/0205637 A1 | 7/2014 | Widenhouse et al. |
| 2014/0207166 A1 | 7/2014 | Shelton, IV et al. |
| 2014/0224686 A1 | 8/2014 | Aronhalt et al. |
| 2014/0224857 A1 | 8/2014 | Schmid |
| 2014/0236184 A1 | 8/2014 | Leimbach et al. |
| 2014/0239036 A1 | 8/2014 | Zerkle et al. |
| 2014/0243865 A1 | 8/2014 | Swayze et al. |
| 2014/0246471 A1 | 9/2014 | Jaworek et al. |
| 2014/0246472 A1 | 9/2014 | Kimsey et al. |
| 2014/0246473 A1 | 9/2014 | Auld |
| 2014/0246474 A1 | 9/2014 | Hall et al. |
| 2014/0246475 A1 | 9/2014 | Hall et al. |
| 2014/0246476 A1 | 9/2014 | Hall et al. |
| 2014/0246477 A1 | 9/2014 | Koch, Jr. et al. |
| 2014/0246478 A1 | 9/2014 | Baber et al. |
| 2014/0246479 A1 | 9/2014 | Baber et al. |
| 2014/0249557 A1 | 9/2014 | Koch, Jr. et al. |
| 2014/0252066 A1 | 9/2014 | Shelton, IV et al. |
| 2014/0252067 A1 | 9/2014 | Moore et al. |
| 2014/0252068 A1 | 9/2014 | Shelton, Iv et al. |
| 2014/0252069 A1 | 9/2014 | Moore et al. |
| 2014/0252071 A1 | 9/2014 | Moore et al. |
| 2014/0259591 A1 | 9/2014 | Shelton, IV et al. |
| 2014/0263537 A1 | 9/2014 | Leimbach et al. |
| 2014/0263538 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263551 A1 | 9/2014 | Hall et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263571 A1 | 9/2014 | Morgan et al. |
| 2014/0263572 A1 | 9/2014 | Shelton, IV et al. |
| 2014/0277017 A1 | 9/2014 | Leimbach et al. |
| 2014/0284371 A1 | 9/2014 | Morgan et al. |
| 2014/0284373 A1 | 9/2014 | Shelton, IV et al. |
| 2014/0291378 A1 | 10/2014 | Shelton, IV et al. |
| 2014/0291379 A1 | 10/2014 | Schellin et al. |
| 2014/0291380 A1 | 10/2014 | Weaner et al. |
| 2014/0291381 A1 | 10/2014 | Weaner et al. |
| 2014/0291382 A1 | 10/2014 | Lloyd et al. |
| 2014/0291383 A1 | 10/2014 | Spivey et al. |
| 2014/0296873 A1 | 10/2014 | Morgan et al. |
| 2014/0296874 A1 | 10/2014 | Morgan et al. |
| 2014/0299648 A1 | 10/2014 | Shelton, IV et al. |
| 2014/0299649 A1 | 10/2014 | Shelton, IV et al. |
| 2014/0303645 A1 | 10/2014 | Morgan et al. |
| 2014/0303646 A1 | 10/2014 | Morgan et al. |
| 2014/0305986 A1 | 10/2014 | Hall et al. |
| 2014/0305987 A1 | 10/2014 | Parihar et al. |
| 2014/0305988 A1 | 10/2014 | Boudreaux et al. |
| 2014/0305989 A1 | 10/2014 | Parihar et al. |
| 2014/0305990 A1 | 10/2014 | Shelton, IV et al. |
| 2014/0305991 A1 | 10/2014 | Parihar et al. |
| 2014/0305992 A1 | 10/2014 | Kimsey et al. |
| 2014/0305993 A1 | 10/2014 | Timm et al. |

(56) References Cited

U.S. PATENT DOCUMENTS

| | | |
|---|---|---|
| 2014/0305994 A1 | 10/2014 | Parihar et al. |
| 2014/0305995 A1 | 10/2014 | Shelton, IV et al. |
| 2014/0309665 A1 | 10/2014 | Parihar et al. |
| 2014/0309666 A1 | 10/2014 | Shelton, IV et al. |
| 2014/0326777 A1 | 11/2014 | Zingman |
| 2014/0330161 A1 | 11/2014 | Swayze et al. |
| 2014/0339286 A1 | 11/2014 | Motooka et al. |
| 2014/0352463 A1 | 12/2014 | Parihar |
| 2014/0353358 A1 | 12/2014 | Shelton, IV et al. |
| 2014/0353359 A1 | 12/2014 | Hall et al. |
| 2014/0367447 A1 | 12/2014 | Woodard, Jr. et al. |
| 2015/0008248 A1 | 1/2015 | Giordano et al. |
| 2015/0034696 A1 | 2/2015 | Shelton, IV et al. |
| 2015/0038986 A1 | 2/2015 | Swensgard et al. |
| 2015/0041518 A1 | 2/2015 | Shelton, IV et al. |
| 2015/0053737 A1 | 2/2015 | Leimbach et al. |
| 2015/0053738 A1 | 2/2015 | Morgan et al. |
| 2015/0053739 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060518 A1 | 3/2015 | Shelton, IV et al. |
| 2015/0060519 A1 | 3/2015 | Shelton, IV et al. |
| 2015/0060520 A1 | 3/2015 | Shelton, IV et al. |
| 2015/0060521 A1 | 3/2015 | Weisenburgh, II et al. |
| 2015/0076207 A1 | 3/2015 | Boudreaux et al. |
| 2015/0076208 A1 | 3/2015 | Shelton, IV |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083780 A1 | 3/2015 | Shelton, IV et al. |
| 2015/0282809 A1 | 10/2015 | Shelton, IV et al. |
| 2015/0282810 A1 | 10/2015 | Shelton, IV et al. |
| 2015/0297218 A1 | 10/2015 | Shelton, IV et al. |
| 2015/0305745 A1 | 10/2015 | Baxter, III et al. |
| 2015/0313591 A1 | 11/2015 | Baxter, III et al. |
| 2015/0313594 A1 | 11/2015 | Shelton, IV et al. |
| 2015/0335329 A1 | 11/2015 | Shelton, IV et al. |
| 2015/0342607 A1 | 12/2015 | Shelton, IV et al. |
| 2016/0000430 A1 | 1/2016 | Ming et al. |
| 2016/0074040 A1 | 3/2016 | Widenhouse et al. |
| 2016/0174974 A1 | 6/2016 | Schmid et al. |
| 2016/0199063 A1 | 7/2016 | Mandakolathur Vasudevan et al. |
| 2016/0220254 A1 | 8/2016 | Baxter, III et al. |
| 2016/0287249 A1 | 10/2016 | Alexander, III et al. |
| 2016/0287254 A1 | 10/2016 | Baxter, III et al. |

FOREIGN PATENT DOCUMENTS

| | | |
|---|---|---|
| AU | 2012200178 B2 | 7/2013 |
| CA | 2458946 A1 | 3/2003 |
| CA | 2512960 A1 | 1/2006 |
| CA | 2514274 A1 | 1/2006 |
| CA | 2639177 A1 | 2/2009 |
| CN | 2488482 Y | 5/2002 |
| CN | 1523725 A | 8/2004 |
| CN | 1634601 A | 7/2005 |
| CN | 1726874 A | 2/2006 |
| CN | 1726878 A | 2/2006 |
| CN | 1868411 A | 11/2006 |
| CN | 1915180 A | 2/2007 |
| CN | 1960679 A | 5/2007 |
| CN | 101011286 A | 8/2007 |
| CN | 101095621 A | 1/2008 |
| CN | 101224124 A | 7/2008 |
| CN | 101507620 A | 8/2009 |
| CN | 101541251 A | 9/2009 |
| CN | 101626731 A | 1/2010 |
| CN | 101675898 A | 3/2010 |
| CN | 101868203 A | 10/2010 |
| CN | 101912285 A | 12/2010 |
| CN | 101934098 A | 5/2011 |
| CN | 102038531 A | 5/2011 |
| CN | 101336835 B | 9/2011 |
| CN | 101310680 B | 4/2012 |
| CN | 101023879 B | 3/2013 |
| CN | 101332110 B | 7/2013 |
| DE | 273689 C | 5/1914 |
| DE | 1775926 A | 1/1972 |
| DE | 3036217 A1 | 4/1982 |
| DE | 3212828 A1 | 11/1982 |
| DE | 3210466 A1 | 9/1983 |
| DE | 3709067 A1 | 9/1988 |
| DE | 9412228 U | 9/1994 |
| DE | 19509116 A1 | 9/1996 |
| DE | 19851291 A1 | 1/2000 |
| DE | 19924311 A1 | 11/2000 |
| DE | 69328576 T2 | 1/2001 |
| DE | 20016423 U1 | 2/2001 |
| DE | 10052679 A1 | 5/2001 |
| DE | 20112837 U1 | 10/2001 |
| DE | 20121753 U1 | 4/2003 |
| DE | 10314072 A1 | 10/2004 |
| DE | 202007003114 U1 | 6/2007 |
| EP | 0000756 A1 | 2/1979 |
| EP | 0122046 A1 | 10/1984 |
| EP | 0070230 B1 | 10/1985 |
| EP | 0156774 A2 | 10/1985 |
| EP | 0387980 B1 | 10/1985 |
| EP | 0033548 B1 | 5/1986 |
| EP | 0077262 B1 | 8/1986 |
| EP | 0129442 B1 | 11/1987 |
| EP | 0276104 A2 | 7/1988 |
| EP | 0178940 B1 | 1/1991 |
| EP | 0178941 B1 | 1/1991 |
| EP | 0169044 B1 | 6/1991 |
| EP | 0248844 B1 | 1/1993 |
| EP | 0539762 A1 | 5/1993 |
| EP | 0545029 A1 | 6/1993 |
| EP | 0277959 B1 | 10/1993 |
| EP | 0591946 A1 | 10/1993 |
| EP | 0233940 B1 | 11/1993 |
| EP | 0261230 B1 | 11/1993 |
| EP | 0639349 A2 | 2/1994 |
| EP | 0324636 B1 | 3/1994 |
| EP | 0593920 A1 | 4/1994 |
| EP | 0594148 A1 | 4/1994 |
| EP | 0427949 B1 | 6/1994 |
| EP | 0523174 B1 | 6/1994 |
| EP | 0600182 A2 | 6/1994 |
| EP | 0310431 B1 | 11/1994 |
| EP | 0375302 B1 | 11/1994 |
| EP | 0376562 B1 | 11/1994 |
| EP | 0630612 A1 | 12/1994 |
| EP | 0634144 A1 | 1/1995 |
| EP | 0646356 A2 | 4/1995 |
| EP | 0646357 A1 | 4/1995 |
| EP | 0505036 B1 | 5/1995 |
| EP | 0653189 A2 | 5/1995 |
| EP | 0669104 A1 | 8/1995 |
| EP | 0511470 B1 | 10/1995 |
| EP | 0674876 A2 | 10/1995 |
| EP | 0679367 A2 | 11/1995 |
| EP | 0392547 B1 | 12/1995 |
| EP | 0685204 A1 | 12/1995 |
| EP | 0364216 B1 | 1/1996 |
| EP | 0699418 A1 | 3/1996 |
| EP | 0702937 A1 | 3/1996 |
| EP | 0705571 A1 | 4/1996 |
| EP | 0711611 A2 | 5/1996 |
| EP | 0484677 B2 | 6/1996 |
| EP | 0541987 B1 | 7/1996 |
| EP | 0667119 B1 | 7/1996 |
| EP | 0737446 A1 | 10/1996 |
| EP | 0748614 A1 | 12/1996 |
| EP | 0710618 B1 | 3/1997 |
| EP | 0770355 A1 | 5/1997 |

(56) References Cited

FOREIGN PATENT DOCUMENTS

| | | |
|---|---|---|
| EP | 0503662 B1 | 6/1997 |
| EP | 0447121 B1 | 7/1997 |
| EP | 0621009 B1 | 7/1997 |
| EP | 0625077 B1 | 7/1997 |
| EP | 0633749 B1 | 8/1997 |
| EP | 0710090 B1 | 8/1997 |
| EP | 0578425 B1 | 9/1997 |
| EP | 0625335 B1 | 11/1997 |
| EP | 0552423 B1 | 1/1998 |
| EP | 0592244 B1 | 1/1998 |
| EP | 0648476 B1 | 1/1998 |
| EP | 0649290 B1 | 3/1998 |
| EP | 0598618 B1 | 9/1998 |
| EP | 0676173 B1 | 9/1998 |
| EP | 0678007 B1 | 9/1998 |
| EP | 0869104 A1 | 10/1998 |
| EP | 0603472 B1 | 11/1998 |
| EP | 0605351 B1 | 11/1998 |
| EP | 0878169 A1 | 11/1998 |
| EP | 0879742 A1 | 11/1998 |
| EP | 0695144 B1 | 12/1998 |
| EP | 0722296 B1 | 12/1998 |
| EP | 0760230 B1 | 2/1999 |
| EP | 0623316 B1 | 3/1999 |
| EP | 0650701 B1 | 3/1999 |
| EP | 0537572 B1 | 6/1999 |
| EP | 0923907 A1 | 6/1999 |
| EP | 0640317 A1 | 9/1999 |
| EP | 0843906 B1 | 3/2000 |
| EP | 0552050 B1 | 5/2000 |
| EP | 0833592 B1 | 5/2000 |
| EP | 0832605 BI | 6/2000 |
| EP | 0830094 B1 | 9/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1058177 A1 | 12/2000 |
| EP | 1080694 A1 | 3/2001 |
| EP | 1090592 A1 | 4/2001 |
| EP | 1095627 A1 | 5/2001 |
| EP | 1256318 B1 | 5/2001 |
| EP | 0806914 B1 | 9/2001 |
| EP | 0768840 B1 | 12/2001 |
| EP | 0908152 B1 | 1/2002 |
| EP | 0872213 B1 | 5/2002 |
| EP | 0862386 B1 | 6/2002 |
| EP | 0949886 B1 | 9/2002 |
| EP | 1238634 A2 | 9/2002 |
| EP | 0858295 B1 | 12/2002 |
| EP | 0656188 B1 | 1/2003 |
| EP | 0717960 BI | 2/2003 |
| EP | 1284120 A1 | 2/2003 |
| EP | 1287788 A1 | 3/2003 |
| EP | 0717966 B1 | 4/2003 |
| EP | 0869742 B1 | 5/2003 |
| EP | 0829235 B1 | 6/2003 |
| EP | 0887046 B1 | 7/2003 |
| EP | 0852480 B1 | 8/2003 |
| EP | 0891154 B1 | 9/2003 |
| EP | 0813843 B1 | 10/2003 |
| EP | 0873089 B1 | 10/2003 |
| EP | 0856326 B1 | 11/2003 |
| EP | 1374788 A1 | 1/2004 |
| EP | 0741996 B1 | 2/2004 |
| EP | 0814712 B1 | 2/2004 |
| EP | 1402837 A1 | 3/2004 |
| EP | 0705570 B1 | 4/2004 |
| EP | 0959784 B1 | 4/2004 |
| EP | 1407719 A2 | 4/2004 |
| EP | 1086713 B1 | 5/2004 |
| EP | 0996378 B1 | 6/2004 |
| EP | 1426012 A1 | 6/2004 |
| EP | 0833593 B2 | 7/2004 |
| EP | 1442694 A1 | 8/2004 |
| EP | 0888749 B1 | 9/2004 |
| EP | 0959786 B1 | 9/2004 |
| EP | 1459695 A1 | 9/2004 |
| EP | 1254636 B1 | 10/2004 |
| EP | 1473819 A1 | 11/2004 |
| EP | 1477119 A1 | 11/2004 |
| EP | 1479345 A1 | 11/2004 |
| EP | 1479347 A1 | 11/2004 |
| EP | 1479348 A1 | 11/2004 |
| EP | 0754437 B2 | 12/2004 |
| EP | 1025807 B1 | 12/2004 |
| EP | 1001710 B1 | 1/2005 |
| EP | 1520521 A1 | 4/2005 |
| EP | 1520522 A1 | 4/2005 |
| EP | 1520523 A1 | 4/2005 |
| EP | 1520525 A1 | 4/2005 |
| EP | 1522264 A1 | 4/2005 |
| EP | 1523942 A2 | 4/2005 |
| EP | 1550408 A1 | 7/2005 |
| EP | 1557129 A1 | 7/2005 |
| EP | 1064883 B1 | 8/2005 |
| EP | 1067876 B1 | 8/2005 |
| EP | 0870473 B1 | 9/2005 |
| EP | 1157666 B1 | 9/2005 |
| EP | 0880338 B1 | 10/2005 |
| EP | 1158917 B1 | 11/2005 |
| EP | 1344498 B1 | 11/2005 |
| EP | 0906764 B1 | 12/2005 |
| EP | 1330989 B1 | 12/2005 |
| EP | 0771176 B2 | 1/2006 |
| EP | 1621138 A2 | 2/2006 |
| EP | 1621139 A2 | 2/2006 |
| EP | 1621141 A2 | 2/2006 |
| EP | 1621145 A2 | 2/2006 |
| EP | 1621151 A2 | 2/2006 |
| EP | 1034746 B1 | 3/2006 |
| EP | 1201196 B1 | 3/2006 |
| EP | 1632191 A2 | 3/2006 |
| EP | 1647231 A1 | 4/2006 |
| EP | 1065981 B1 | 5/2006 |
| EP | 1082944 B1 | 5/2006 |
| EP | 1230899 B1 | 5/2006 |
| EP | 1652481 A2 | 5/2006 |
| EP | 1382303 B1 | 6/2006 |
| EP | 1253866 B1 | 7/2006 |
| EP | 1032318 B1 | 8/2006 |
| EP | 1045672 B1 | 8/2006 |
| EP | 1617768 B1 | 8/2006 |
| EP | 1693015 A2 | 8/2006 |
| EP | 1400214 B1 | 9/2006 |
| EP | 1702567 A2 | 9/2006 |
| EP | 1129665 B1 | 11/2006 |
| EP | 1400206 B1 | 11/2006 |
| EP | 1721568 A1 | 11/2006 |
| EP | 1256317 B1 | 12/2006 |
| EP | 1285633 B1 | 12/2006 |
| EP | 1728473 A1 | 12/2006 |
| EP | 1728475 A2 | 12/2006 |
| EP | 1736105 A1 | 12/2006 |
| EP | 1011494 B1 | 1/2007 |
| EP | 1479346 B1 | 1/2007 |
| EP | 1484024 B1 | 1/2007 |
| EP | 1749485 A1 | 2/2007 |
| EP | 1754445 A2 | 2/2007 |
| EP | 1759812 A1 | 3/2007 |
| EP | 1767157 A1 | 3/2007 |
| EP | 1767163 A1 | 3/2007 |
| EP | 1769756 A1 | 4/2007 |
| EP | 1769758 A1 | 4/2007 |
| EP | 1581128 B1 | 5/2007 |
| EP | 1780825 A1 | 5/2007 |
| EP | 1785097 A2 | 5/2007 |
| EP | 1790293 A2 | 5/2007 |
| EP | 1790294 A1 | 5/2007 |
| EP | 1563793 B1 | 6/2007 |

(56) References Cited

FOREIGN PATENT DOCUMENTS

| | | | |
|---|---|---|---|
| EP | 1791473 | A2 | 6/2007 |
| EP | 1800610 | A1 | 6/2007 |
| EP | 1300117 | B1 | 8/2007 |
| EP | 1813199 | A1 | 8/2007 |
| EP | 1813200 | A2 | 8/2007 |
| EP | 1813201 | A1 | 8/2007 |
| EP | 1813202 | A1 | 8/2007 |
| EP | 1813203 | A2 | 8/2007 |
| EP | 1813207 | A1 | 8/2007 |
| EP | 1813209 | A1 | 8/2007 |
| EP | 1330991 | B1 | 9/2007 |
| EP | 1806103 | B1 | 9/2007 |
| EP | 1837041 | A1 | 9/2007 |
| EP | 0922435 | B1 | 10/2007 |
| EP | 1487359 | B1 | 10/2007 |
| EP | 1599146 | B1 | 10/2007 |
| EP | 1839596 | A1 | 10/2007 |
| EP | 2110083 | A2 | 10/2007 |
| EP | 1679096 | B1 | 11/2007 |
| EP | 1857057 | A2 | 11/2007 |
| EP | 1402821 | B1 | 12/2007 |
| EP | 1872727 | A1 | 1/2008 |
| EP | 1550410 | B1 | 2/2008 |
| EP | 1671593 | B1 | 2/2008 |
| EP | 1897502 | A1 | 3/2008 |
| EP | 1611856 | B1 | 4/2008 |
| EP | 1908417 | A2 | 4/2008 |
| EP | 1330201 | B1 | 6/2008 |
| EP | 1702568 | B1 | 7/2008 |
| EP | 1943955 | A2 | 7/2008 |
| EP | 1943957 | A2 | 7/2008 |
| EP | 1943959 | A1 | 7/2008 |
| EP | 1943962 | A2 | 7/2008 |
| EP | 1943964 | A1 | 7/2008 |
| EP | 1943976 | A2 | 7/2008 |
| EP | 1593337 | B1 | 8/2008 |
| EP | 1970014 | A1 | 9/2008 |
| EP | 1980213 | A2 | 10/2008 |
| EP | 1759645 | B1 | 11/2008 |
| EP | 1987780 | A2 | 11/2008 |
| EP | 1990014 | A2 | 11/2008 |
| EP | 1552795 | B1 | 12/2008 |
| EP | 1693008 | B1 | 12/2008 |
| EP | 1759640 | B1 | 12/2008 |
| EP | 1997439 | A2 | 12/2008 |
| EP | 2000102 | A2 | 12/2008 |
| EP | 2005894 | A2 | 12/2008 |
| EP | 2005901 | A1 | 12/2008 |
| EP | 2008595 | A2 * | 12/2008 ........... A61B 17/072 |
| EP | 1736104 | B1 | 3/2009 |
| EP | 1749486 | B1 | 3/2009 |
| EP | 1782743 | B1 | 3/2009 |
| EP | 2039302 | A2 | 3/2009 |
| EP | 2039308 | A2 | 3/2009 |
| EP | 2039316 | A2 | 3/2009 |
| EP | 1721576 | B1 | 4/2009 |
| EP | 1733686 | B1 | 4/2009 |
| EP | 2044890 | A1 | 4/2009 |
| EP | 2055243 | A2 | 5/2009 |
| EP | 1550409 | B1 | 6/2009 |
| EP | 1550413 | B1 | 6/2009 |
| EP | 1719461 | B1 | 6/2009 |
| EP | 1834594 | B1 | 6/2009 |
| EP | 1709911 | B1 | 7/2009 |
| EP | 2077093 | A2 | 7/2009 |
| EP | 1745748 | B1 | 8/2009 |
| EP | 2090231 | A1 | 8/2009 |
| EP | 2090237 | A1 * | 8/2009 ........... A61B 17/072 |
| EP | 2090241 | A1 | 8/2009 |
| EP | 2090244 | A2 | 8/2009 |
| EP | 2090245 | A1 | 8/2009 |
| EP | 2090254 | A1 | 8/2009 |
| EP | 2090256 | A2 | 8/2009 |
| EP | 2095777 | A2 | 9/2009 |
| EP | 2098170 | A2 | 9/2009 |
| EP | 2110082 | A1 | 10/2009 |
| EP | 2110084 | A2 | 10/2009 |
| EP | 2111803 | A2 | 10/2009 |
| EP | 1762190 | B8 | 11/2009 |
| EP | 1813208 | B1 | 11/2009 |
| EP | 1908426 | B1 | 11/2009 |
| EP | 2116195 | A1 | 11/2009 |
| EP | 2116197 | A2 | 11/2009 |
| EP | 1607050 | B1 | 12/2009 |
| EP | 1815804 | B1 | 12/2009 |
| EP | 1875870 | B1 | 12/2009 |
| EP | 1878395 | B1 | 1/2010 |
| EP | 2151204 | A1 | 2/2010 |
| EP | 1813211 | B1 | 3/2010 |
| EP | 2165656 | A2 | 3/2010 |
| EP | 2165660 | A2 | 3/2010 |
| EP | 1566150 | B1 | 4/2010 |
| EP | 1813206 | B1 | 4/2010 |
| EP | 1769754 | B1 | 6/2010 |
| EP | 1854416 | B1 | 6/2010 |
| EP | 1911408 | B1 | 6/2010 |
| EP | 2198787 | A1 | 6/2010 |
| EP | 2214610 | A1 | 8/2010 |
| EP | 1647286 | B1 | 9/2010 |
| EP | 1825821 | B1 | 9/2010 |
| EP | 1535565 | B1 | 10/2010 |
| EP | 1702570 | B1 | 10/2010 |
| EP | 1785098 | B1 | 10/2010 |
| EP | 2005896 | B1 | 10/2010 |
| EP | 2030578 | B1 | 11/2010 |
| EP | 2036505 | B1 | 11/2010 |
| EP | 2245993 | A2 | 11/2010 |
| EP | 1627605 | B1 | 12/2010 |
| EP | 2027811 | B1 | 12/2010 |
| EP | 2130498 | B1 | 12/2010 |
| EP | 2258282 | A2 | 12/2010 |
| EP | 2263568 | A2 | 12/2010 |
| EP | 1994890 | B1 | 1/2011 |
| EP | 2005900 | B1 | 1/2011 |
| EP | 2286738 | A2 | 2/2011 |
| EP | 1494595 | B1 | 3/2011 |
| EP | 1690502 | B1 | 3/2011 |
| EP | 2292153 | A1 | 3/2011 |
| EP | 1769755 | B1 | 4/2011 |
| EP | 2090240 | B1 | 4/2011 |
| EP | 2305135 | A1 | 4/2011 |
| EP | 2314254 | A2 | 4/2011 |
| EP | 2316345 | A1 | 5/2011 |
| EP | 2316366 | A2 | 5/2011 |
| EP | 1813205 | B1 | 6/2011 |
| EP | 2090243 | B1 | 6/2011 |
| EP | 2329773 | A1 | 6/2011 |
| EP | 2090239 | B1 | 7/2011 |
| EP | 2340771 | A2 | 7/2011 |
| EP | 2353545 | A1 | 8/2011 |
| EP | 2361562 | A1 | 8/2011 |
| EP | 1836986 | B1 | 11/2011 |
| EP | 1908414 | B1 | 11/2011 |
| EP | 2153781 | B1 | 11/2011 |
| EP | 2389928 | A2 | 11/2011 |
| EP | 1847225 | B1 | 12/2011 |
| EP | 2399538 | A2 | 12/2011 |
| EP | 1785102 | B1 | 1/2012 |
| EP | 2090253 | B1 | 3/2012 |
| EP | 2430986 | A2 | 3/2012 |
| EP | 2446834 | A1 | 5/2012 |
| EP | 2455007 | A2 | 5/2012 |
| EP | 2457519 | A1 | 5/2012 |
| EP | 2462880 | A2 | 6/2012 |
| EP | 1813204 | B1 | 7/2012 |
| EP | 2189121 | B1 | 7/2012 |
| EP | 2005895 | B1 | 8/2012 |
| EP | 2090248 | B1 | 8/2012 |
| EP | 2481359 | A1 | 8/2012 |
| EP | 1935351 | B1 | 9/2012 |
| EP | 2497431 | A1 | 9/2012 |
| EP | 1616549 | B1 | 10/2012 |
| EP | 2030579 | B1 | 10/2012 |
| EP | 2090252 | B1 | 10/2012 |

(56) References Cited

FOREIGN PATENT DOCUMENTS

| | | |
|---|---|---|
| EP | 2517637 A1 | 10/2012 |
| EP | 2517638 A1 | 10/2012 |
| EP | 2517642 A2 | 10/2012 |
| EP | 2517645 A2 | 10/2012 |
| EP | 2517649 A2 | 10/2012 |
| EP | 2517651 A2 | 10/2012 |
| EP | 1884206 B1 | 3/2013 |
| EP | 2090238 BI | 4/2013 |
| EP | 1982657 B1 | 7/2013 |
| EP | 2090234 B1 | 9/2013 |
| EP | 2633830 A1 | 9/2013 |
| EP | 2644124 A1 | 10/2013 |
| EP | 2644209 A2 | 10/2013 |
| EP | 2649948 A1 | 10/2013 |
| EP | 2700367 A1 | 2/2014 |
| EP | 1772105 B1 | 5/2014 |
| EP | 2446835 B1 | 1/2015 |
| EP | 2131750 B1 | 5/2016 |
| ES | 2396594 T3 | 2/2013 |
| FR | 459743 A | 11/1913 |
| FR | 999646 A | 2/1952 |
| FR | 1112936 A | 3/1956 |
| FR | 2598905 A1 | 11/1987 |
| FR | 2765794 A | 1/1999 |
| FR | 2815842 A | 10/2000 |
| GB | 939929 A | 10/1963 |
| GB | 1210522 A | 10/1970 |
| GB | 1217159 A | 12/1970 |
| GB | 1339394 A | 12/1973 |
| GB | 2024012 A | 1/1980 |
| GB | 2109241 A | 6/1983 |
| GB | 2272159 A | 5/1994 |
| GB | 2284242 A | 5/1995 |
| GB | 2286435 A | 8/1995 |
| GB | 2336214 A | 10/1999 |
| GB | 2425903 A | 11/2006 |
| GR | 93100110 A | 11/1993 |
| JP | 50-33988 U | 4/1975 |
| JP | S 58500053 A | 1/1983 |
| JP | S 59-174920 A | 3/1984 |
| JP | 60-100955 A | 6/1985 |
| JP | 61-98249 A | 5/1986 |
| JP | S 61502036 A | 9/1986 |
| JP | S 63-59764 A | 3/1988 |
| JP | S 63-147449 A | 6/1988 |
| JP | 63-203149 A | 8/1988 |
| JP | H 02-279149 A | 11/1990 |
| JP | 3-12126 A | 1/1991 |
| JP | H 05-084252 A | 4/1993 |
| JP | 5-212039 A | 8/1993 |
| JP | 6007357 A | 1/1994 |
| JP | H 6-30945 A | 2/1994 |
| JP | H 06-54857 A | 3/1994 |
| JP | H 06-26812 U | 4/1994 |
| JP | H 6-121798 A | 5/1994 |
| JP | H 06-197901 A | 7/1994 |
| JP | H 06-237937 A | 8/1994 |
| JP | 7-31623 A | 2/1995 |
| JP | 7051273 A | 2/1995 |
| JP | 7-124166 A | 5/1995 |
| JP | H 7-163574 A | 6/1995 |
| JP | 07-171163 | 7/1995 |
| JP | 7-255735 A | 10/1995 |
| JP | H 7-285089 A | 10/1995 |
| JP | 8-33642 A | 2/1996 |
| JP | 8033641 A | 2/1996 |
| JP | 8-164141 A | 6/1996 |
| JP | H 08-182684 A | 7/1996 |
| JP | H 08-507708 A | 8/1996 |
| JP | 8229050 A | 9/1996 |
| JP | H 09-501081 A | 2/1997 |
| JP | H 09-501577 A | 2/1997 |
| JP | H 09-164144 A | 6/1997 |
| JP | H 10-118090 A | 5/1998 |
| JP | 10-512469 A | 12/1998 |
| JP | 2000-14632 | 1/2000 |
| JP | 2000033071 A | 2/2000 |
| JP | 2000-112002 A | 4/2000 |
| JP | 2000-166932 A | 6/2000 |
| JP | 2000171730 A | 6/2000 |
| JP | 2000287987 A | 10/2000 |
| JP | 2000325303 A | 11/2000 |
| JP | 2001-037763 A | 2/2001 |
| JP | 2001-046384 A | 2/2001 |
| JP | 2001-87272 A | 4/2001 |
| JP | 2001-514541 A | 9/2001 |
| JP | 2001-276091 A | 10/2001 |
| JP | 2001-517473 A | 10/2001 |
| JP | 2001286477 A | 10/2001 |
| JP | 2002-51974 A | 2/2002 |
| JP | 2002-085415 A | 3/2002 |
| JP | 2002143078 A | 5/2002 |
| JP | 2002-528161 A | 9/2002 |
| JP | 2002-542186 A | 12/2002 |
| JP | 2002369820 A | 12/2002 |
| JP | 2003-500153 A | 1/2003 |
| JP | 2003-504104 A | 2/2003 |
| JP | 2003-135473 A | 5/2003 |
| JP | 2003-148903 A | 5/2003 |
| JP | 2003-164066 | 6/2003 |
| JP | 2003-521301 A | 7/2003 |
| JP | 2004-162035 A | 6/2004 |
| JP | 2004-229976 A | 8/2004 |
| JP | 2004-524076 A | 8/2004 |
| JP | 2004-531280 A | 10/2004 |
| JP | 2004-532084 A | 10/2004 |
| JP | 2004-532676 A | 10/2004 |
| JP | 2004-329624 A | 11/2004 |
| JP | 2004-337617 A | 12/2004 |
| JP | 2004-344663 | 12/2004 |
| JP | 2005-028147 A | 2/2005 |
| JP | 2005-28148 A | 2/2005 |
| JP | 2005-028149 A | 2/2005 |
| JP | 2005-505309 A | 2/2005 |
| JP | 2005505322 T | 2/2005 |
| JP | 2005-103280 A | 4/2005 |
| JP | 2005-103281 A | 4/2005 |
| JP | 2005-511131 A | 4/2005 |
| JP | 2005103293 A | 4/2005 |
| JP | 2005131163 A | 5/2005 |
| JP | 2005131164 A | 5/2005 |
| JP | 2005131173 A | 5/2005 |
| JP | 2005131211 A | 5/2005 |
| JP | 2005131212 A | 5/2005 |
| JP | 2005-137919 A | 6/2005 |
| JP | 2005-144183 A | 6/2005 |
| JP | 2005-516714 A | 6/2005 |
| JP | 2005137423 A | 6/2005 |
| JP | 2005152416 A | 6/2005 |
| JP | 2005-187954 A | 7/2005 |
| JP | 2005-521109 A | 7/2005 |
| JP | 2005-523105 A | 8/2005 |
| JP | 4461008 B2 | 8/2005 |
| JP | 2005524474 A | 8/2005 |
| JP | 2005-296412 A | 10/2005 |
| JP | 2005-529675 A | 10/2005 |
| JP | 2005-328882 A | 12/2005 |
| JP | 2005-335432 A | 12/2005 |
| JP | 2005-342267 A | 12/2005 |
| JP | 2006-034975 A | 2/2006 |
| JP | 2006-34977 A | 2/2006 |
| JP | 2006-034978 A | 2/2006 |
| JP | 2006-034980 A | 2/2006 |
| JP | 2006-506106 A | 2/2006 |
| JP | 2006-510879 A | 3/2006 |
| JP | 2006-187649 A | 7/2006 |
| JP | 2006-218297 A | 8/2006 |
| JP | 2006-223872 A | 8/2006 |
| JP | 2006-281405 A | 10/2006 |
| JP | 2006-334417 A | 12/2006 |
| JP | 2006-346445 A | 12/2006 |
| JP | 2007-61628 A | 3/2007 |
| JP | 2007-098130 A | 4/2007 |
| JP | 2007-105481 A | 4/2007 |

(56) References Cited

FOREIGN PATENT DOCUMENTS

| | | |
|---|---|---|
| JP | 3906843 B2 | 4/2007 |
| JP | 2007-117725 A | 5/2007 |
| JP | 2007-130471 A | 5/2007 |
| JP | 2007-222615 A | 6/2007 |
| JP | 2007-203047 A | 8/2007 |
| JP | 2007-203051 A | 8/2007 |
| JP | 2007-203057 A | 8/2007 |
| JP | 2007-524435 A | 8/2007 |
| JP | 2007-229448 A | 9/2007 |
| JP | 2007-526026 A | 9/2007 |
| JP | 4001860 B2 | 10/2007 |
| JP | 2007-325922 A | 12/2007 |
| JP | 2008-68073 A | 3/2008 |
| JP | 2008-510515 A | 4/2008 |
| JP | 2008-516669 A | 5/2008 |
| JP | 2008-206967 A | 9/2008 |
| JP | 2008-212637 A | 9/2008 |
| JP | 2008-212638 A | 9/2008 |
| JP | 2008-259860 A | 10/2008 |
| JP | 2008-264535 A | 11/2008 |
| JP | 2008-283459 A | 11/2008 |
| JP | 2008-307393 A | 12/2008 |
| JP | 2009-000531 A | 1/2009 |
| JP | 2009-006137 A | 1/2009 |
| JP | 2009-502351 A | 1/2009 |
| JP | 2009-506799 A | 2/2009 |
| JP | 2009-072595 A | 4/2009 |
| JP | 2009-72599 A | 4/2009 |
| JP | 2009-090113 A | 4/2009 |
| JP | 2009-106752 A | 5/2009 |
| JP | 2009-189836 A | 8/2009 |
| JP | 2009-189838 A | 8/2009 |
| JP | 2009-189847 A | 8/2009 |
| JP | 2009-201998 A | 9/2009 |
| JP | 2009-536082 A | 10/2009 |
| JP | 2009-261944 A | 11/2009 |
| JP | 2009-539420 A | 11/2009 |
| JP | 2010-504808 A | 2/2010 |
| JP | 2010-069307 A | 4/2010 |
| JP | 2010-098844 A | 4/2010 |
| JP | 2010-142636 A | 7/2010 |
| JP | 4549018 B2 | 9/2010 |
| JP | 2010-279690 A | 12/2010 |
| JP | 2011-005260 A | 1/2011 |
| JP | 2011-504391 A | 2/2011 |
| JP | 2011-072797 A | 4/2011 |
| JP | 2011-078763 A | 4/2011 |
| JP | 4783373 B2 | 7/2011 |
| JP | 2011-251156 A | 12/2011 |
| JP | 2012-040398 A | 3/2012 |
| JP | 5140421 B2 | 2/2013 |
| JP | 5162595 B2 | 3/2013 |
| JP | 2013-128791 A | 7/2013 |
| JP | 5333899 B2 | 11/2013 |
| RU | 2008830 C1 | 3/1994 |
| RU | 2052979 C1 | 1/1996 |
| RU | 2098025 C1 | 12/1997 |
| RU | 2141279 C1 | 11/1999 |
| RU | 2144791 C1 | 1/2000 |
| RU | 2181566 C2 | 4/2002 |
| RU | 2187249 C2 | 8/2002 |
| RU | 2189091 C2 | 9/2002 |
| RU | 32984 U1 | 10/2003 |
| RU | 2225170 C2 | 3/2004 |
| RU | 42750 U1 | 12/2004 |
| RU | 61114 U1 | 2/2007 |
| SU | 189517 A | 1/1967 |
| SU | 328636 A | 9/1972 |
| SU | 674747 A1 | 7/1979 |
| SU | 886900 A1 | 12/1981 |
| SU | 1009439 A | 4/1983 |
| SU | 1022703 A1 | 6/1983 |
| SU | 1333319 A2 | 8/1987 |
| SU | 1377053 A1 | 2/1988 |
| SU | 1509051 A1 | 9/1989 |
| SU | 1561964 A1 | 5/1990 |
| SU | 1708312 A1 | 1/1992 |
| SU | 1722476 A1 | 3/1992 |
| SU | 1752361 A1 | 8/1992 |
| SU | 1814161 A1 | 5/1993 |
| WO | WO 82/02824 A1 | 9/1982 |
| WO | WO 86/02254 A1 | 4/1986 |
| WO | WO 91/15157 A1 | 10/1991 |
| WO | WO 92/20295 A1 | 11/1992 |
| WO | WO 92/21300 A1 | 12/1992 |
| WO | WO 93/08755 A1 | 5/1993 |
| WO | WO 93/13718 A1 | 7/1993 |
| WO | WO 93/14690 A1 | 8/1993 |
| WO | WO 93/15648 A1 | 8/1993 |
| WO | WO 93/15850 A1 | 8/1993 |
| WO | WO 93/19681 A1 | 10/1993 |
| WO | WO 94/00060 A1 | 1/1994 |
| WO | WO 94/11057 A1 | 5/1994 |
| WO | WO 94/12108 A1 | 6/1994 |
| WO | WO 94/18893 A1 | 9/1994 |
| WO | WO 94/20030 A1 | 9/1994 |
| WO | WO 94/22378 A1 | 10/1994 |
| WO | WO 94/23659 A1 | 10/1994 |
| WO | WO 94/24943 A1 | 11/1994 |
| WO | WO 94/24947 A1 | 11/1994 |
| WO | WO 95/02369 A1 | 1/1995 |
| WO | WO 95/03743 A1 | 2/1995 |
| WO | WO 95/06817 A1 | 3/1995 |
| WO | WO 95/09576 A1 | 4/1995 |
| WO | WO 95/09577 A1 | 4/1995 |
| WO | WO 95/14436 A1 | 6/1995 |
| WO | WO 95/17855 A1 | 7/1995 |
| WO | WO 95/18383 A1 | 7/1995 |
| WO | WO 95/18572 A1 | 7/1995 |
| WO | WO 95/19739 A1 | 7/1995 |
| WO | WO 95/20360 A1 | 8/1995 |
| WO | WO 95/23557 A1 | 9/1995 |
| WO | WO 95/24865 A1 | 9/1995 |
| WO | WO 95/25471 A3 | 9/1995 |
| WO | WO 95/26562 A1 | 10/1995 |
| WO | WO 95/29639 A1 | 11/1995 |
| WO | WO 96/04858 A1 | 2/1996 |
| WO | WO 96/18344 A2 | 6/1996 |
| WO | WO 96/19151 A1 | 6/1996 |
| WO | WO 96/19152 A1 | 6/1996 |
| WO | WO 96/20652 A1 | 7/1996 |
| WO | WO 96/21119 A1 | 7/1996 |
| WO | WO 96/22055 A1 | 7/1996 |
| WO | WO 96/23448 A1 | 8/1996 |
| WO | WO 96/24301 A1 | 8/1996 |
| WO | WO 96/27337 A1 | 9/1996 |
| WO | WO 96/31155 A1 | 10/1996 |
| WO | WO 96/35464 A1 | 11/1996 |
| WO | WO 96/39085 A1 | 12/1996 |
| WO | WO 96/39086 A1 | 12/1996 |
| WO | WO 96/39087 A1 | 12/1996 |
| WO | WO 96/39088 A1 | 12/1996 |
| WO | WO 96/39089 A1 | 12/1996 |
| WO | WO 97/00646 A1 | 1/1997 |
| WO | WO 97/00647 A1 | 1/1997 |
| WO | WO 97/01989 A1 | 1/1997 |
| WO | WO 97/06582 A1 | 2/1997 |
| WO | WO 97/10763 A1 | 3/1997 |
| WO | WO 97/10764 A1 | 3/1997 |
| WO | WO 97/11648 A2 | 4/1997 |
| WO | WO 97/11649 A1 | 4/1997 |
| WO | WO 97/15237 A1 | 5/1997 |
| WO | WO 97/24073 A1 | 7/1997 |
| WO | WO 97/24993 A1 | 7/1997 |
| WO | WO 97/30644 A1 | 8/1997 |
| WO | WO 97/34533 A1 | 9/1997 |
| WO | WO 97/37598 A1 | 10/1997 |
| WO | WO 97/39688 A2 | 10/1997 |
| WO | WO 98/01080 A1 | 1/1998 |
| WO | WO 98/17180 A1 | 4/1998 |
| WO | WO 98/27880 A1 | 7/1998 |
| WO | WO 98/30153 A1 | 7/1998 |
| WO | WO 98/47436 A1 | 10/1998 |
| WO | WO 98/58589 A1 | 12/1998 |

(56) References Cited

FOREIGN PATENT DOCUMENTS

| | | |
|---|---|---|
| WO | WO 99/03407 A1 | 1/1999 |
| WO | WO 99/03408 A1 | 1/1999 |
| WO | WO 99/03409 A1 | 1/1999 |
| WO | WO 99/12483 A1 | 3/1999 |
| WO | WO 99/12487 A1 | 3/1999 |
| WO | WO 99/12488 A1 | 3/1999 |
| WO | WO 99/15086 A1 | 4/1999 |
| WO | WO 99/15091 A1 | 4/1999 |
| WO | WO 99/23933 A2 | 5/1999 |
| WO | WO 99/23959 A1 | 5/1999 |
| WO | WO 99/25261 A1 | 5/1999 |
| WO | WO 99/29244 A1 | 6/1999 |
| WO | WO 99/34744 A1 | 7/1999 |
| WO | WO 99/45849 A1 | 9/1999 |
| WO | WO 99/48430 A1 | 9/1999 |
| WO | WO 99/51158 A1 | 10/1999 |
| WO | WO 00/24322 A1 | 5/2000 |
| WO | WO 00/24330 A1 | 5/2000 |
| WO | WO 00/41638 A1 | 7/2000 |
| WO | WO 00/48506 A1 | 8/2000 |
| WO | WO 00/53112 A2 | 9/2000 |
| WO | WO 00/54653 A1 | 9/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/03587 A1 | 1/2001 |
| WO | WO 01/05702 A1 | 1/2001 |
| WO | WO 01/10482 A1 | 2/2001 |
| WO | WO 01/35845 A1 | 5/2001 |
| WO | WO 01/54594 A1 | 8/2001 |
| WO | WO 01/58371 A1 | 8/2001 |
| WO | WO 01/62158 A2 | 8/2001 |
| WO | WO 01/62161 A1 | 8/2001 |
| WO | WO 01/62162 A1 | 8/2001 |
| WO | WO 01/62164 A2 | 8/2001 |
| WO | WO 01/62169 A2 | 8/2001 |
| WO | WO 01/78605 A2 | 10/2001 |
| WO | WO 01/80757 A2 | 11/2001 |
| WO | WO 01/91646 A1 | 12/2001 |
| WO | WO 02/00121 A1 | 1/2002 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/19932 A1 | 3/2002 |
| WO | WO 02/26143 A1 | 4/2002 |
| WO | WO 02/30297 A2 | 4/2002 |
| WO | WO 02/32322 A2 | 4/2002 |
| WO | WO 02/36028 A1 | 5/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/085218 A2 | 10/2002 |
| WO | WO 02/087586 A1 | 11/2002 |
| WO | WO 02/098302 A1 | 12/2002 |
| WO | WO 03/000138 A2 | 1/2003 |
| WO | WO 03/001329 A2 | 1/2003 |
| WO | WO 03/001986 A2 | 1/2003 |
| WO | WO 03/013363 A1 | 2/2003 |
| WO | WO 03/013372 A2 | 2/2003 |
| WO | WO 03/015604 A2 | 2/2003 |
| WO | WO 03/020106 A2 | 3/2003 |
| WO | WO 03/020139 A2 | 3/2003 |
| WO | WO 03/024339 A1 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/055402 A1 | 7/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/079911 A1 | 10/2003 |
| WO | WO 03/082126 A1 | 10/2003 |
| WO | WO 03/086206 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/011037 A2 | 2/2004 |
| WO | WO 2004/019769 A1 | 3/2004 |
| WO | WO 2004/019803 A1 | 3/2004 |
| WO | WO 2004/021868 A2 | 3/2004 |
| WO | WO 2004/028585 A2 | 4/2004 |
| WO | WO 2004/030554 A1 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/032783 A1 | 4/2004 |
| WO | WO 2004/034875 A2 | 4/2004 |
| WO | WO 2004/047626 A1 | 6/2004 |
| WO | WO 2004/047653 A2 | 6/2004 |
| WO | WO 2004/049956 A2 | 6/2004 |
| WO | WO 2004/052426 A2 | 6/2004 |
| WO | WO 2004/056276 A1 | 7/2004 |
| WO | WO 2004/056277 A1 | 7/2004 |
| WO | WO 2004/062516 A1 | 7/2004 |
| WO | WO 2004/064600 A2 | 8/2004 |
| WO | WO 2004/078050 A2 | 9/2004 |
| WO | WO 2004/078051 A2 | 9/2004 |
| WO | WO 2004/078236 A2 | 9/2004 |
| WO | WO 2004/086987 A1 | 10/2004 |
| WO | WO 2004/096015 A2 | 11/2004 |
| WO | WO 2004/096057 A2 | 11/2004 |
| WO | WO 2004/103157 A2 | 12/2004 |
| WO | WO 2004/105593 A1 | 12/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/042041 A1 | 5/2005 |
| WO | WO 2005/044078 A2 | 5/2005 |
| WO | WO 2005/055846 A1 | 6/2005 |
| WO | WO 2005/072634 A2 | 8/2005 |
| WO | WO 2005/078892 A1 | 8/2005 |
| WO | WO 2005/079675 A2 | 9/2005 |
| WO | WO 2005/096954 A2 | 10/2005 |
| WO | WO 2005/112806 A2 | 12/2005 |
| WO | WO 2005/112808 A1 | 12/2005 |
| WO | WO 2005/115251 A1 | 12/2005 |
| WO | WO 2005/115253 A2 | 12/2005 |
| WO | WO 2005/117735 A1 | 12/2005 |
| WO | WO 2005/122936 A1 | 12/2005 |
| WO | WO 2006/023486 A1 | 3/2006 |
| WO | WO 2006/023578 A2 | 3/2006 |
| WO | WO 2006/027014 A1 | 3/2006 |
| WO | WO 2006/028314 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/085389 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A2 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/089603 A2 | 8/2007 |

(56) References Cited

FOREIGN PATENT DOCUMENTS

| WO | WO 2007/098220 A2 | 8/2007 |
|---|---|---|
| WO | WO 2007/121579 A1 | 11/2007 |
| WO | WO 2007/131110 A2 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2007/145825 A2 | 12/2007 |
| WO | WO 2007/146987 A2 | 12/2007 |
| WO | WO 2007/147439 A1 | 12/2007 |
| WO | WO 2008/020964 A2 | 2/2008 |
| WO | WO 2008/021969 A2 | 2/2008 |
| WO | WO 2008/039249 A1 | 4/2008 |
| WO | WO 2008/039270 A1 | 4/2008 |
| WO | WO 2008/045383 A2 | 4/2008 |
| WO | WO 2008/057281 A2 | 5/2008 |
| WO | WO 2008/070763 A1 | 6/2008 |
| WO | WO 2008/089404 A2 | 7/2008 |
| WO | WO 2008/101080 A1 | 8/2008 |
| WO | WO 2008/101228 A2 | 8/2008 |
| WO | WO 2008/103797 A2 | 8/2008 |
| WO | WO 2008/109123 A2 | 9/2008 |
| WO | WO 2008/109125 A1 | 9/2008 |
| WO | WO 2008/124748 A1 | 10/2008 |
| WO | WO 2009/022614 A1 | 2/2009 |
| WO | WO 2009/023851 A1 | 2/2009 |
| WO | WO 2009/033057 A2 | 3/2009 |
| WO | WO 2009/039506 A1 | 3/2009 |
| WO | WO 2009/046394 A1 | 4/2009 |
| WO | WO 2009/066105 A1 | 5/2009 |
| WO | WO 2009/067649 A2 | 5/2009 |
| WO | WO 2009/091497 A2 | 7/2009 |
| WO | WO 2009/137761 A2 | 11/2009 |
| WO | WO 2009/143092 A1 | 11/2009 |
| WO | WO 2009/143331 A1 | 11/2009 |
| WO | WO 2009/150650 A2 | 12/2009 |
| WO | WO 2010/028332 A2 | 3/2010 |
| WO | WO 2010/030434 A1 | 3/2010 |
| WO | WO 2010/050771 A2 | 5/2010 |
| WO | WO 2010/054404 A1 | 5/2010 |
| WO | WO 2010/063795 A1 | 6/2010 |
| WO | WO 2010/098871 A2 | 9/2010 |
| WO | WO 2011/008672 A2 | 1/2011 |
| WO | WO 2011/044343 A2 | 4/2011 |
| WO | WO 2011/060311 A2 | 5/2011 |
| WO | WO 2012/006306 A2 | 1/2012 |
| WO | WO 2012/021671 A1 | 2/2012 |
| WO | WO 2012/040438 A1 | 3/2012 |
| WO | WO 2012/044551 A1 | 4/2012 |
| WO | WO 2012/044554 A1 | 4/2012 |
| WO | WO 2012/044606 A2 | 4/2012 |
| WO | WO 2012/044820 A1 | 4/2012 |
| WO | WO 2012/044844 A2 | 4/2012 |
| WO | WO 2012/044853 A1 | 4/2012 |
| WO | WO 2012/058213 A2 | 5/2012 |
| WO | WO 2012/068156 A2 | 5/2012 |
| WO | WO 2012/148667 A2 | 11/2012 |
| WO | WO 2012/148703 A2 | 11/2012 |
| WO | WO 2013/043707 A2 | 3/2013 |
| WO | WO 2013/043717 A1 | 3/2013 |

OTHER PUBLICATIONS

International Preliminary Report on Patentability for PCT/US2013/046500, dated Dec. 31, 2014 (9 pages).
International Preliminary Report on Patentability for PCT/US2013/034019, dated Oct. 1, 2014 (11 pages).
International Preliminary Report on Patentability for PCT/US2013/034021, dated Oct. 1, 2014 (6 pages).
International Preliminary Report on Patentability for PCT/US2013/034004, dated Oct. 1, 2014 (9 pages).
International Preliminary Report on Patentability for PCT/US2013/034011, dated Oct. 1, 2014 (7 pages).
International Preliminary Report on Patentability for PCT/US2013/034008, dated Oct. 1, 2014 (8 pages).
International Preliminary Report on Patentability for PCT/US2013/034002, dated Oct. 1, 2014 (8 pages).
International Preliminary Report on Patentability for PCT/US2013/033999, dated Oct. 1, 2014 (16 pages).
International Preliminary Report on Patentability for PCT/US2013/033997, dated Oct. 1, 2014 (8 pages).
International Preliminary Report on Patentability for PCT/US2013/046525, dated Dec. 31, 2014 (9 pages).
International Preliminary Report on Patentability for PCT/US2013/046516, dated Dec. 31, 2014 (9 pages).
International Preliminary Report on Patentability for PCT/US2013/034048, dated Oct. 1, 2014 (13 pages).
International Preliminary Report on Patentability for PCT/US2013/034040, dated Oct. 1, 2014 (9 pages).
International Preliminary Report on Patentability for PCT/US2013/034025, dated Oct. 1, 2014 (9 pages).
European Search Report for Application No. 13161480.2, dated Jan. 9, 2015 (7 pages).
European Search Report for Application No. 14154558.2, dated Sep. 4, 2014 (9 pages).
International Preliminary Report on Patentability for PCT/US2013/034031, dated Oct. 1, 2014 (8 pages).
International Search Report, Application No. PCT/US2014/014815, dated May 12, 2014 (5 pages).
International Preliminary Report on Patentability, Application No. PCT/US2014/014815, dated Aug. 11, 2015 (7 pages).
International Search Report for PCT/US2013/046513, dated Nov. 6, 2013 (6 pages).
International Search Report for PCT/US2013/046500, dated Nov. 6, 2013 (6 pages).
International Search Report for PCT/US2013/034019, dated Nov. 19, 2013 (9 pages).
Written Opinion for PCT/US2013/034019, dated Nov. 19, 2013 (10 pages).
International Search Report for PCT/US2013/034021, dated Jul. 31, 2013 (4 pages).
Written Opinion for PCT/US2013/034004, dated Jul. 26, 2013 (8 pages).
International Search Report for PCT/US2013/034004, dated Jul. 26, 2013 (4 pages).
International Search Report for PCT/US2013/034011, dated Sep. 5, 2013 (6 pages).
International Search Report for PCT/US2013/034008, dated Dec. 6, 2013 (6 pages).
Written Opinion for PCT/US2013/034008, dated Dec. 6, 2013 (6 pages).
International Search Report for PCT/US2013/034002, dated Sep. 27, 2013 (7 pages).
International Search Report for PCT/US2013/033999, dated Sep. 20, 2013 (10 pages).
Written Opinion for PCT/US2013/033999, dated Sep. 20, 2013 (15 pages).
International Search Report for PCT/US2013/033997, dated Sep. 20, 2013 (8 pages).
Written Opinion for PCT/US2013/033997, dated Sep. 20, 2013 (8 pages).
International Search Report for PCT/US2013/046525, dated Nov. 6, 2013 (6 pages).
Written Opinion for PCT/US2013/046525, dated Nov. 6, 2013 (8 pages).
International Search Report for PCT/US2013/046516, dated Nov. 6, 2013 (6 pages).
Written Opinion for PCT/US2013/046516, dated Nov. 6, 2013 (8 pages).
International Search Report for PCT/US2013/034048, dated Jan. 14, 2014 (10 pages).
Written Opinion for PCT/US2013/034048, dated Jan. 14, 2014 (12 pages).
International Search Report for PCT/US2013/034040, dated Sep. 17, 2013 (7 pages).
International Search Report for PCT/US2013/034025, dated Dec. 3, 2013 (9 pages).

(56) References Cited

OTHER PUBLICATIONS

Written Opinion for PCT/US2013/034025, dated Dec. 3, 2013 (8 pages).
International Search Report for PCT/US2012/032976, dated Oct. 17, 2013 (7 pages).
International Preliminary Report on Patentability for PCT/US2012/032976, dated Oct. 29, 2013 (9 pages).
International Preliminary Report on Patentability for PCT/US2011/053542, dated Apr. 2, 2013 (8 pages).
European Search Report for 13161459.6, dated Nov. 28, 2013 (15 pages).
Matsuda, "Thermodynamics of Formation of Porous Polymeric Membrane from Solutions," Polymer Journal, vol. 23, No. 5, pp. 435-444 (1991).
Young, "Microcellular foams via phase separation," Journal of Vacuum Science & Technology A 4(3), (May/Jun. 1986).
U.S. Appl. No. 14/540,731, filed Nov. 13, 2014.
U.S. Appl. No. 14/540,779, filed Nov. 13, 2014.
U.S. Appl. No. 14/540,807, filed Nov. 13, 2014.
U.S. Appl. No. 14/549,098, filed Nov. 20, 2014.
U.S. Appl. No. 14/549,219, filed Nov. 20, 2014.
U.S. Appl. No. 14/518,652, filed Oct. 20, 2014.
U.S. Appl. No. 14/578,909, filed Dec. 22, 2014.
Disclosed Anonymously, "Motor-Driven Surgical Stapler Improvements," Research Disclosure Database No. 526041, Published: Feb. 2008.
C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.
B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
The Sodem Aseptic Battery Transfer Kit, Sodem Systems, (2000), 3 pages.
"Biomedical Coatings," Fort Wayne Metals, Research Products Corporation, obtained online at www.fwmetals.com on Jun. 21, 2010 (1 page).
Van Meer et al., "A Disposable Plastic Compact Wrist for Smart Minimally Invasive Surgical Tools," LAAS/CNRS (Aug. 2005).
Breedveld et al., "A New, Easily Miniaturized Sterrable Endoscope," IEEE Engineering in Medicine and Biology Magazine (Nov./Dec. 2005).
D. Tuite, Ed., "Get the Lowdown on Ultracapacitors," Nov. 15, 2007; [online] URL:http://electronicdesign.com/Articles/Print.cfm?ArticleID=17465, accessed Jan. 15, 2008 (5 pages).
Datasheet for Panasonic TK Relays Ultra Low Profile 2 A Polarized Relay, Copyright Matsushita Electric Works, Ltd. (Known of at least as early as Aug. 17, 2010), 5 pages.
Covidien Brochure, "Endo GIA™ Reloads with Tri-Staple™ Technology," (2010), 1 page.
Covidien Brochure, "Endo GIA™ Reloads with Tri-Staple™ Technology and Endo GIA™ Ultra Universal Staplers," (2010), 2 pages.
Covidien Brochure, "Endo GIA™ Black Reload with Tri-Staple™ Technology," (2012), 2 pages.
Covidien Brochure, "Endo GIA™ Curved Tip Reload with Tri-Staple™ Technology," (2012), 2 pages.
Covidien Brochure, "Endo GIA™ Reloads with Tri-Staple™ Technology," (2010), 2 pages.
Covidien Brochure, "Endo GIA™ Ultra Universal Stapler," (2010), 2 pages.
Chen et al., "Elastomeric Biomaterials for Tissue Engineering," Progress in Polymer Science 38 (2013), pp. 584-671.
Pitt et al., "Attachment of Hyaluronan to Metallic Surfaces," J. Biomed. Mater. Res. 68A: pp. 95-106, 2004.
Schellhannmer et al., "Poly-Lactic-Acid for Coating of Endovascular Stents: Preliminary Results in Canine Experimental Av-Fistulae," Mat.-wiss. u. Werkstofftech., 32, pp. 193-199 (2001).
Solorio et al., "Gelatin Microspheres Crosslinked with Genipin for Local Delivery of Growth Factors," J. Tissue Eng. Regen. Med. (2010), 4(7): pp. 514-523.
U.S. Appl. No. 14/498,070, filed Sep. 26, 2014.
U.S. Appl. No. 14/498,087, filed Sep. 26, 2014.
U.S. Appl. No. 14/498,105, filed Sep. 26, 2014.
U.S. Appl. No. 14/498,107, filed Sep. 26, 2014.
U.S. Appl. No. 14/498,121, filed Sep. 26, 2014.
U.S. Appl. No. 14/498,145, filed Sep. 26, 2014.
U.S. Appl. No. 14/318,996, filed Jun. 30, 2014.
U.S. Appl. No. 14/319,006, filed Jun. 30, 2014.
U.S. Appl. No. 14/319,014, filed Jun. 30, 2014.
U.S. Appl. No. 14/318,991, filed Jun. 30, 2014.
U.S. Appl. No. 14/319,004, filed Jun. 30, 2014.
U.S. Appl. No. 14/319,008, filed Jun. 30, 2014.
U.S. Appl. No. 14/318,997, filed Jun. 30, 2014.
U.S. Appl. No. 14/319,002, filed Jun. 30, 2014.
U.S. Appl. No. 14/319,013, filed Jun. 30, 2014.
U.S. Appl. No. 14/319,016, filed Jun. 30, 2014.
U.S. Appl. No. 14/138,481, filed Dec. 23, 2013.
U.S. Appl. No. 14/559,172, filed Dec. 3, 2014.
U.S. Appl. No. 14/559,188, filed Dec. 3, 2014.
U.S. Appl. No. 14/559,224, filed Dec. 3, 2014.
U.S. Appl. No. 14/559,251, filed Dec. 3, 2014.
U.S. Appl. No. 14/595,645, filed Jan. 13, 2015.
U.S. Appl. No. 12/031,573, filed Feb. 14, 2008.
U.S. Appl. No. 14/187,383, filed Feb. 24, 2014.
U.S. Appl. No. 14/187,386, filed Feb. 24, 2014.
U.S. Appl. No. 14/187,390, filed Feb. 24, 2014.
U.S. Appl. No. 14/187,385, filed Feb. 24, 2014.
U.S. Appl. No. 14/187,384, filed Feb. 24, 2014.
U.S. Appl. No. 14/187,389, filed Feb. 24, 2014.
U.S. Appl. No. 14/226,142, filed Mar. 26, 2014.
U.S. Appl. No. 14/226,106, filed Mar. 26, 2014.
U.S. Appl. No. 14/226,099, filed Mar. 26, 2014.
U.S. Appl. No. 14/226,094, filed Mar. 26, 2014.
U.S. Appl. No. 14/226,117, filed Mar. 26, 2014.
U.S. Appl. No. 14/226,075, filed Mar. 26, 2014.
U.S. Appl. No. 14/226,093, filed Mar. 26, 2014.
U.S. Appl. No. 14/226,116, filed Mar. 26, 2014.
U.S. Appl. No. 14/226,071, filed Mar. 26, 2014.
U.S. Appl. No. 14/226,097, filed Mar. 26, 2014.
U.S. Appl. No. 14/226,126, filed Mar. 26, 2014.
U.S. Appl. No. 14/226,133, filed Mar. 26, 2014.
U.S. Appl. No. 14/226,081, filed Mar. 26, 2014.
U.S. Appl. No. 14/226,076, filed Mar. 26, 2014.
U.S. Appl. No. 14/226,111, filed Mar. 26, 2014.
U.S. Appl. No. 14/226,125, filed Mar. 26, 2014.
ASTM procedure 02240-00, "Standard Test Method for Rubber Property-Durometer Hardness," (Published Aug. 2000).
ASTM procedure D2240-05, "Standard Test Method for Rubber Property-Durometer Hardness," (Published Apr. 2010).
Miyata et al., "Biomolecule-Sensitive Hydrogels," Advanced Drug Delivery Reviews, 54 (2002) pp. 79-98.
Jeong et al., "Thermosensitive Sol-Gel Reversible Hydrogels," Advanced Drug Delivery Reviews, 54 (2002) pp. 37-51.
Byrne et al., "Molecular Imprinting Within Hydrogels," Advanced Drug Delivery Reviews, 54 (2002) pp. 149-161.
Qiu et al., "Environment-Sensitive Hydrogels for Drug Delivery," Advanced Drug Delivery Reviews, 53 (2001) pp. 321-339.
Hoffman, "Hydrogels for Biomedical Applications," Advanced Drug Delivery Reviews, 43 (2002) pp. 3-12.
Hoffman, "Hydrogels for Biomedical Applications," Advanced Drug Delivery Reviews, 54 (2002) pp. 3-12.
Peppas, "Physiologically Responsive Hydrogels," Journal of Bioactive and Compatible Polymers, vol. 6 (Jul. 1991) pp. 241-246.
Ebara, "Carbohydrate-Derived Hydrogels and Microgels," Engineered Carbohydrate-Based Materials for Biomedical Applications: Polymers, Surfaes, Dendrimers, Nanoparticles, and Hydrogels, Edited by Ravin Narain, 2011, pp. 337-345.

(56) References Cited

OTHER PUBLICATIONS

Peppas, Editor "Hydrogels in Medicine and Pharmacy," vol. I, Fundamentals, CRC Press, 1986.
"U.S. Appl. No. 13/763,054, filed Feb. 8, 2013".
International Search Report for PCT/US2011/053542, dated Jan. 18, 2012 (6 pages).
Written Opinion for PCT/US2011/053542, dated Jan. 18, 2012 (8 pages).
Partial European Search Report for 13161457.0, dated Jul. 31, 2013 (6 pages).
European Search Report for 13161481.0, dated Jul. 30, 2013 (9 pages).
European Search Report for 13161485.1, dated Jul. 26, 2013 (7 pages).
European Search Report for 1316397.8, dated Jul. 29, 2013 (5 pages).
Partial European Search Report for 13161459.6, dated Aug. 1, 2013 (11 pages).
Partial European Search Report for 13161352.3, dated Jul. 29, 2013 (9 pages).
European Search Report for 13161352.3, dated Nov. 18, 2013 (12 pages).
European Search Report for 13161457.0, dated Nov. 18, 2013 (10 pages).
European Search Report for 12166178.9, dated Oct. 17, 2013 (8 pages).
European Search Report for 13161472.9, dated Sep. 23, 2013 (5 pages).
European Search Report for 13161450.5, dated Sep. 25, 2013 (8 pages).
European Search Report for 13161431.5, dated Sep. 30, 2013 (7 pages).
European Search Report for 13161438.0, dated Sep. 5, 2013 (8 pages).

\* cited by examiner

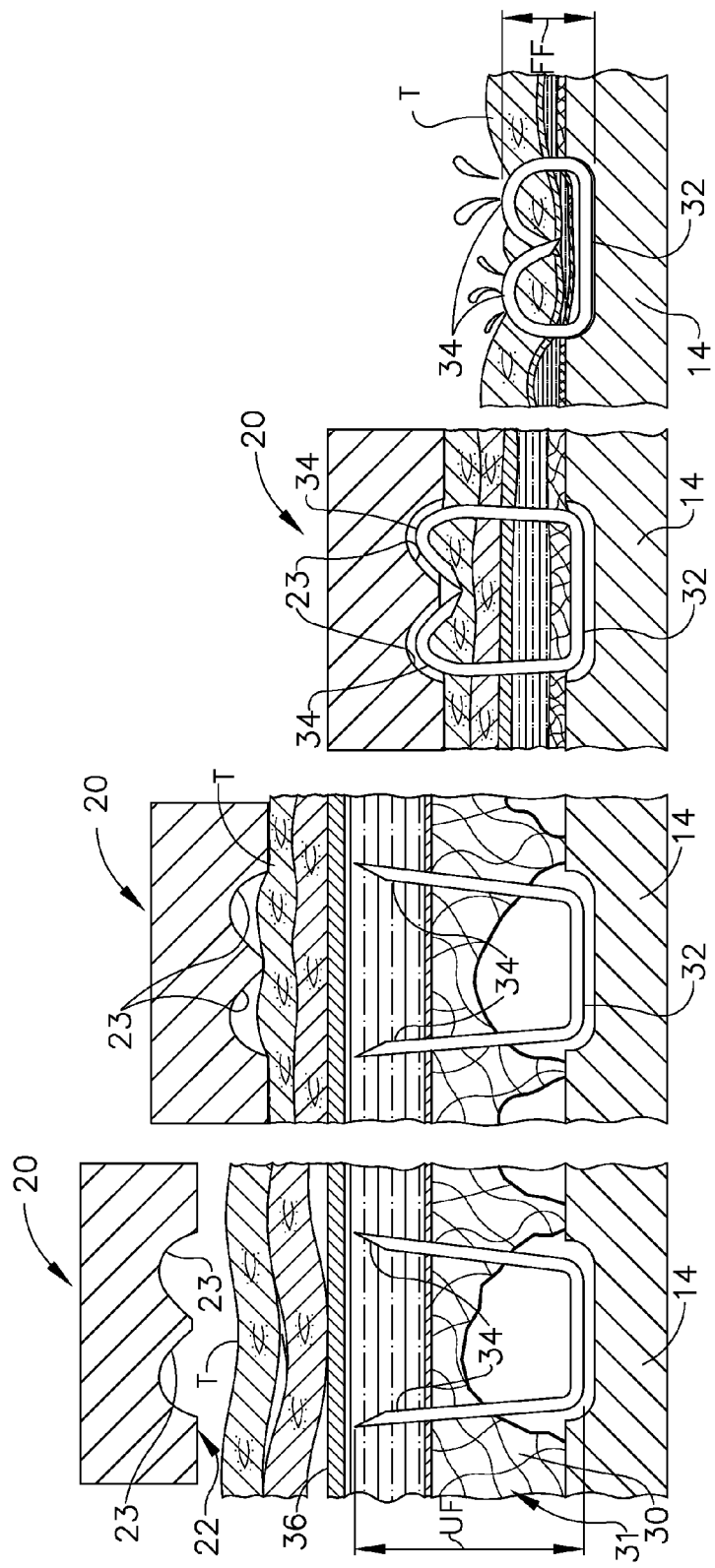

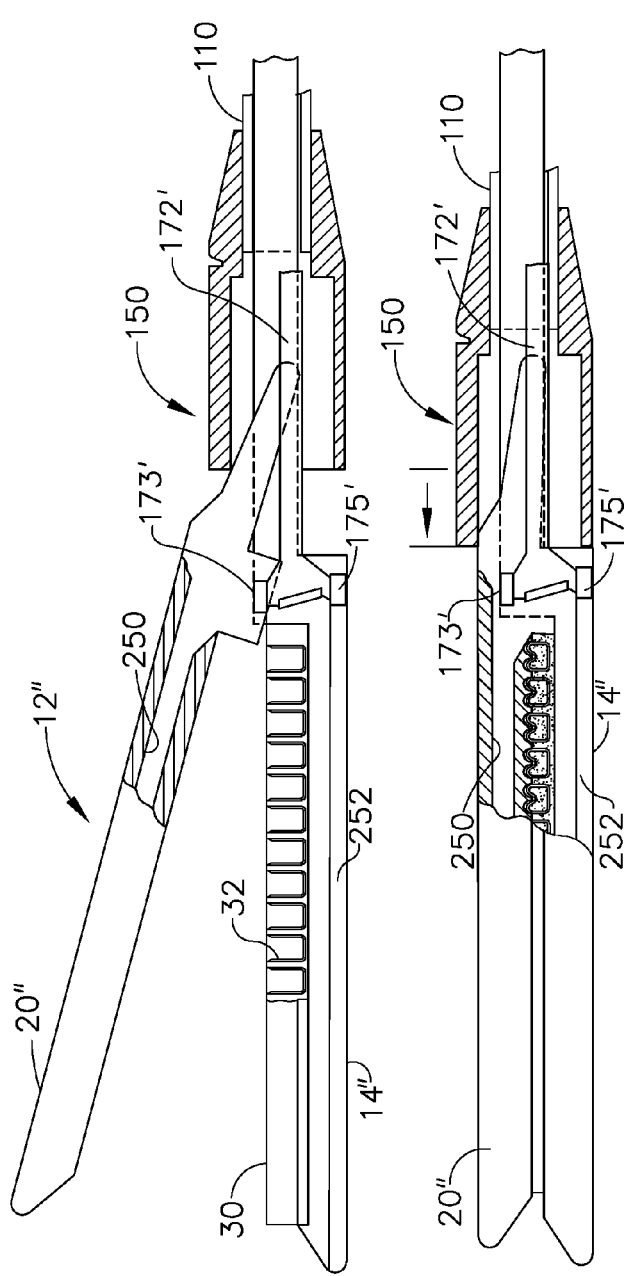
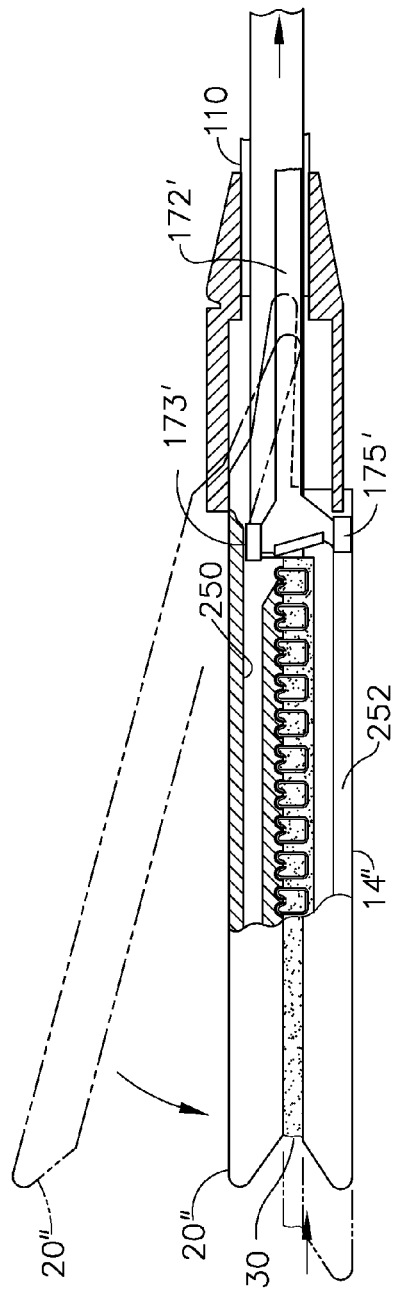
FIG. 2
FIG. 3
FIG. 4

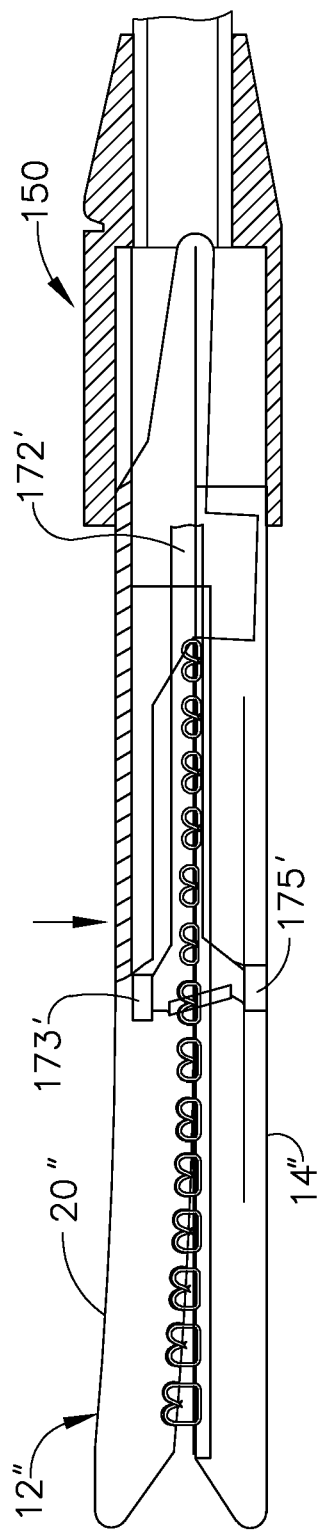

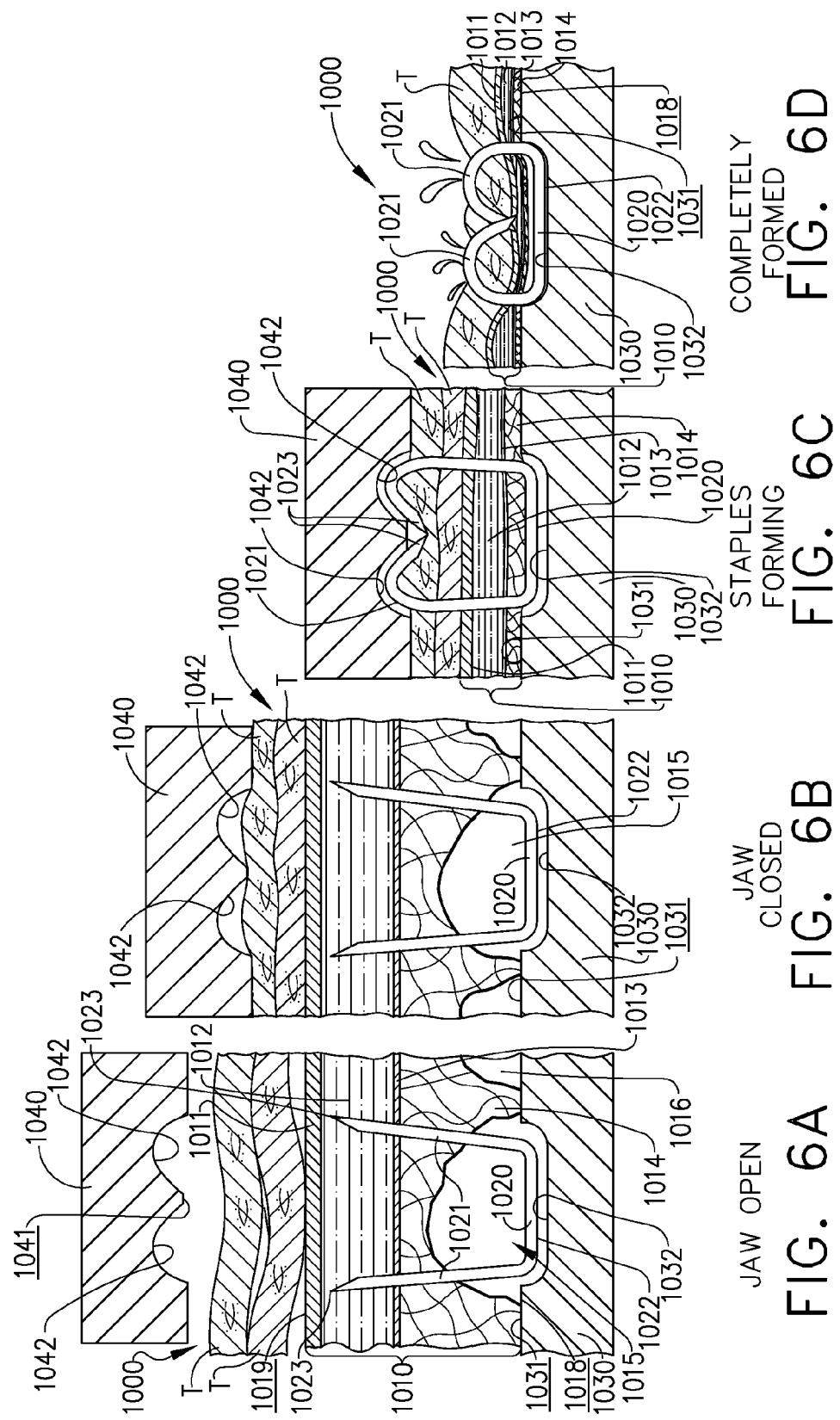

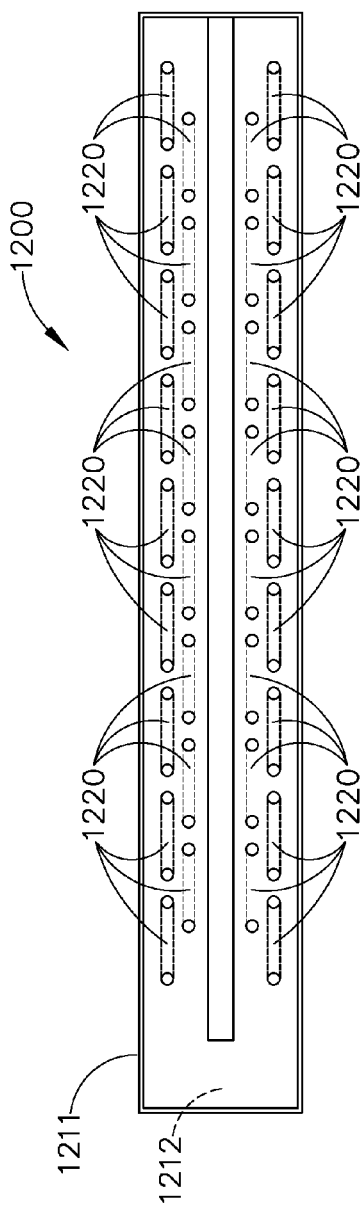
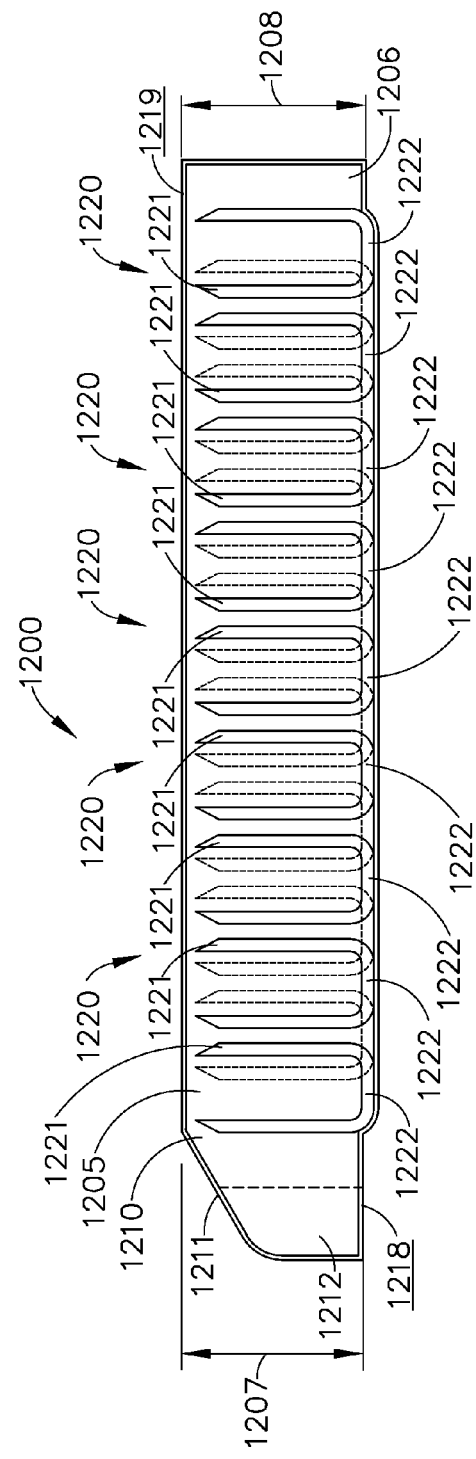
FIG. 8
FIG. 9

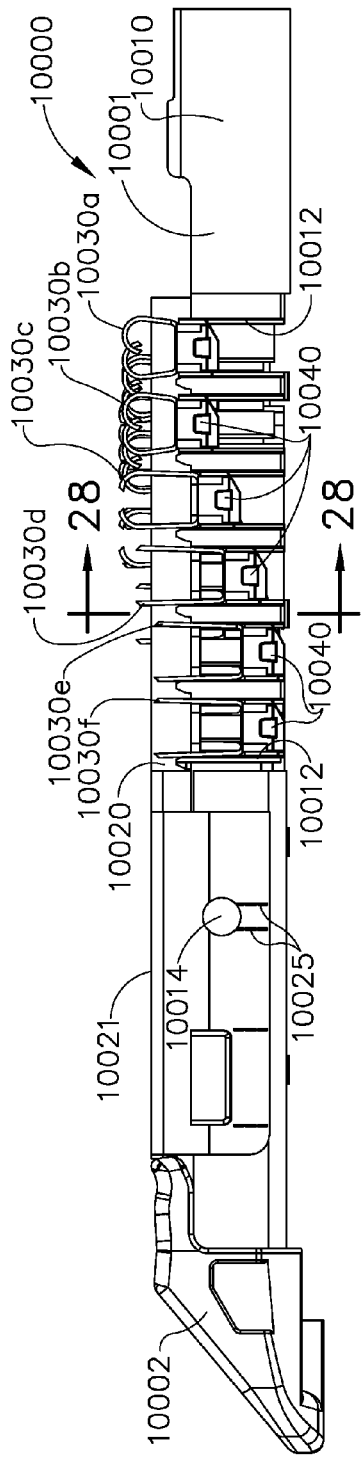
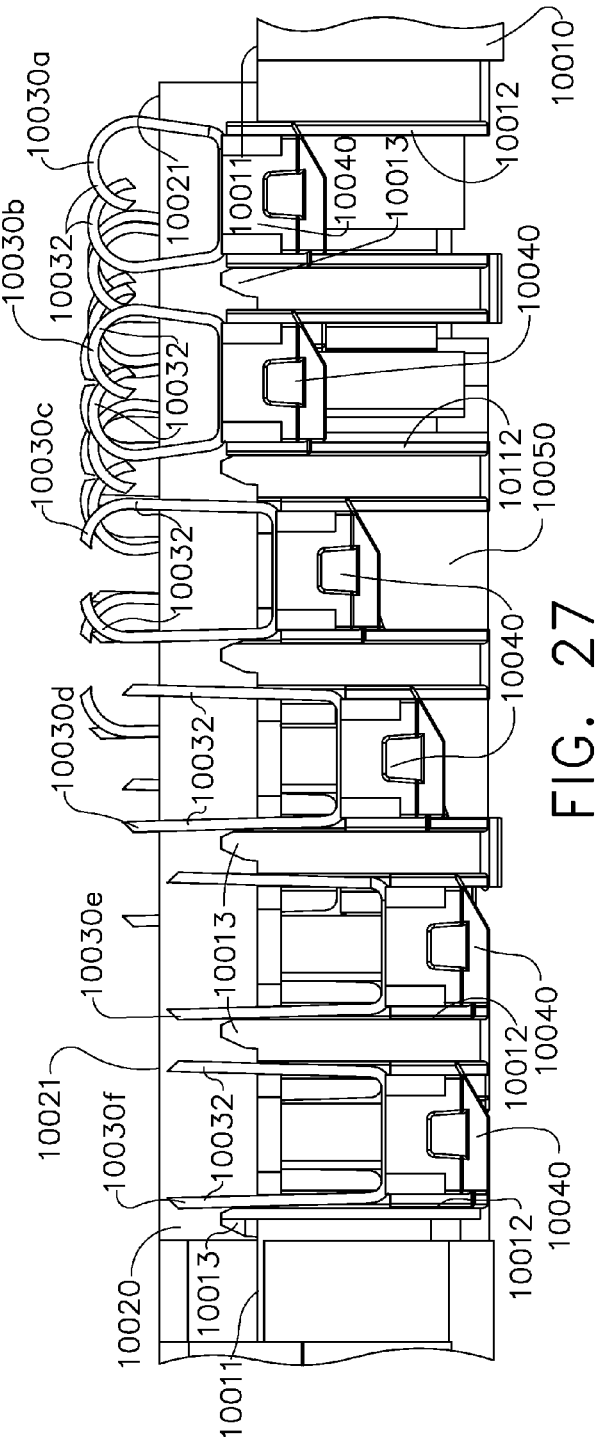
FIG. 26
FIG. 27

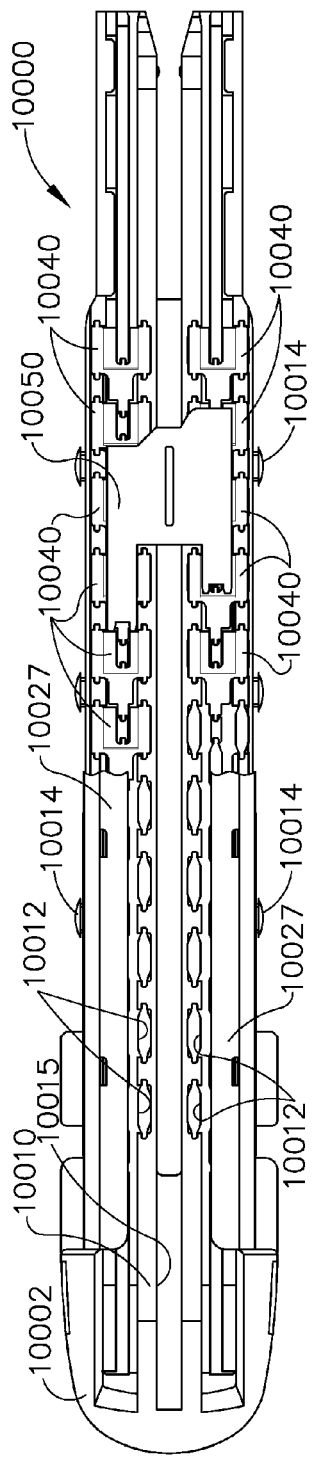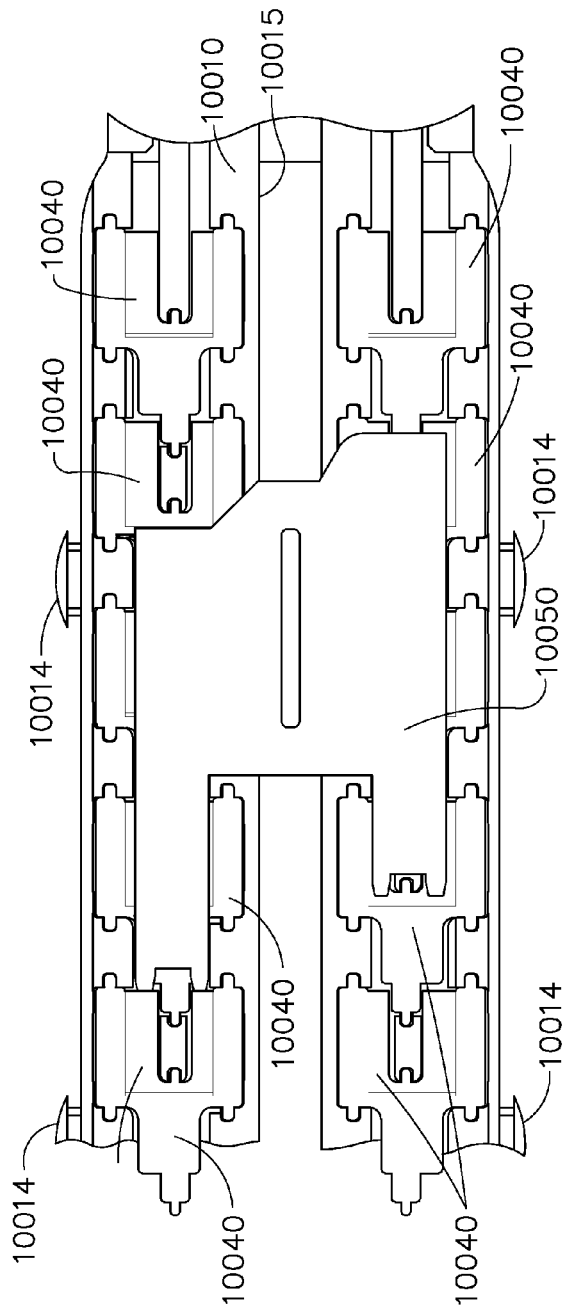

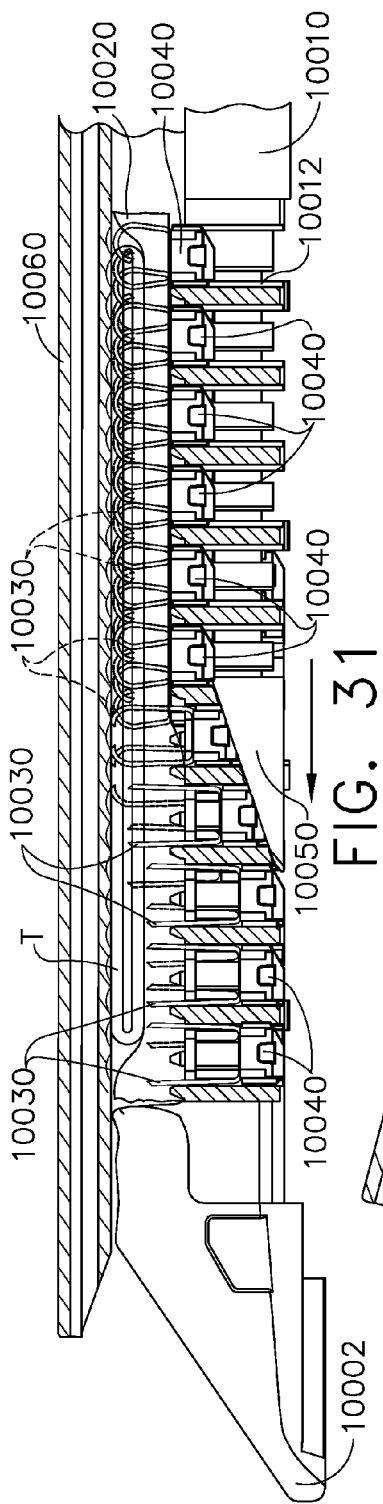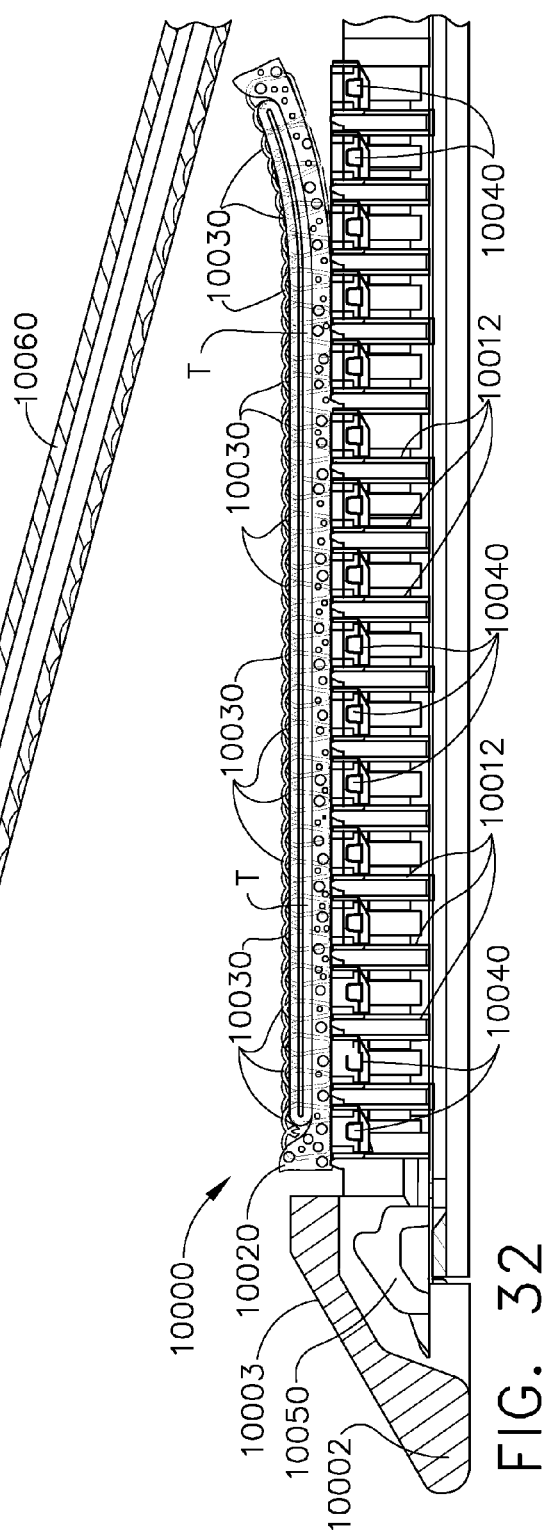

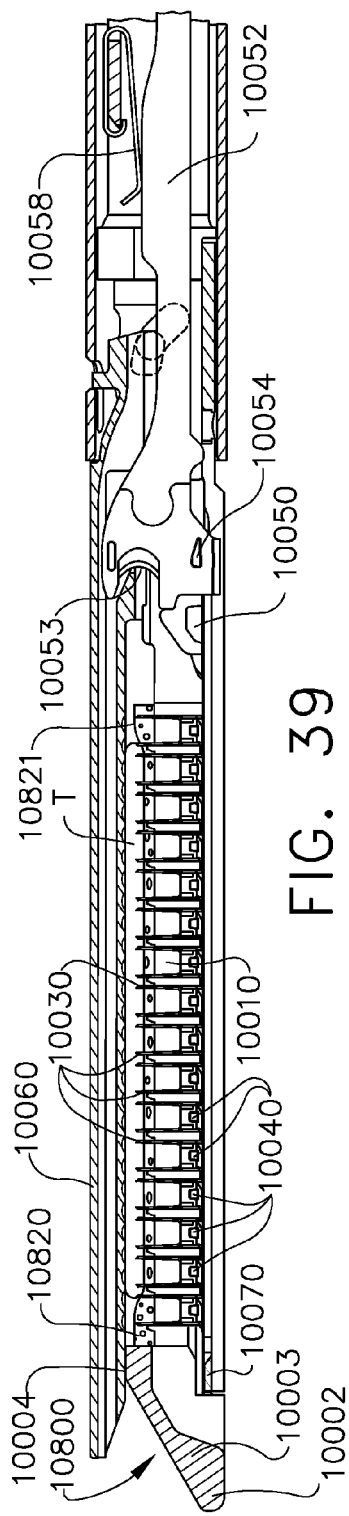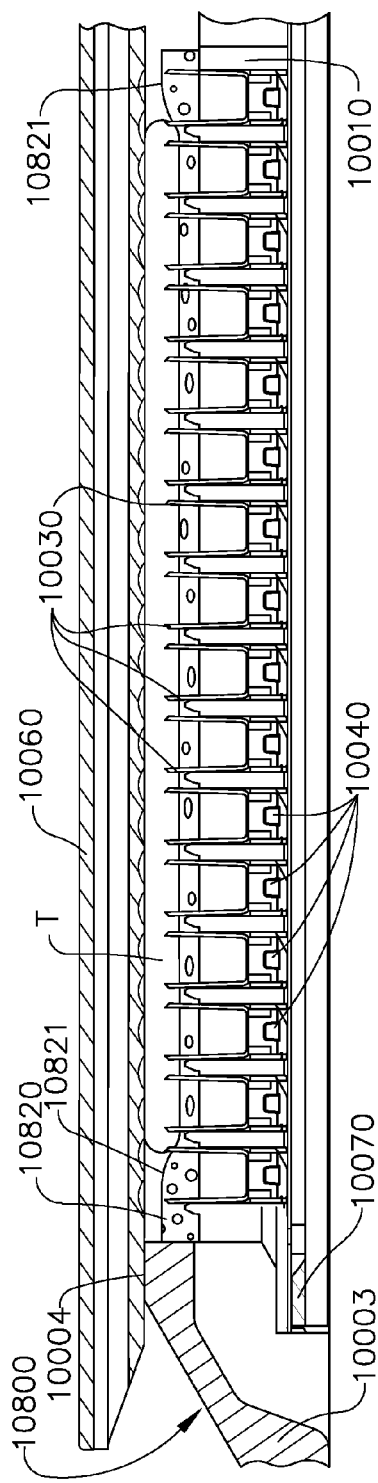

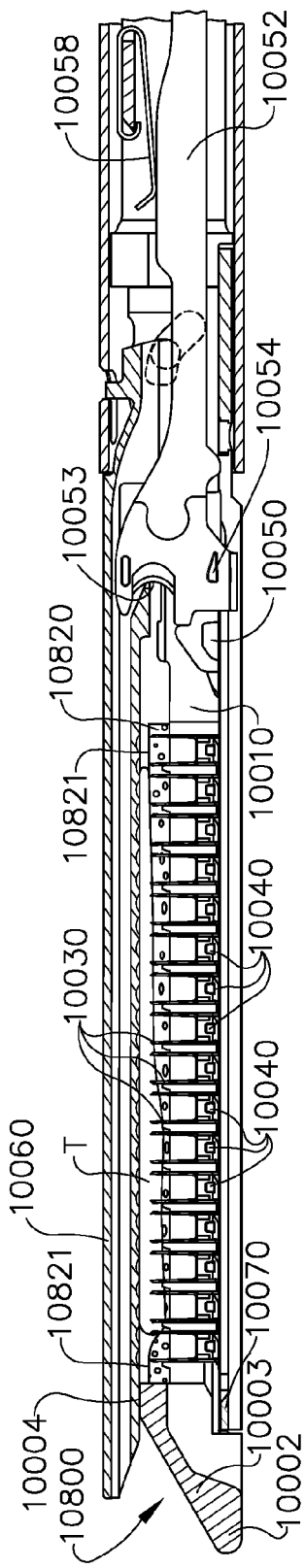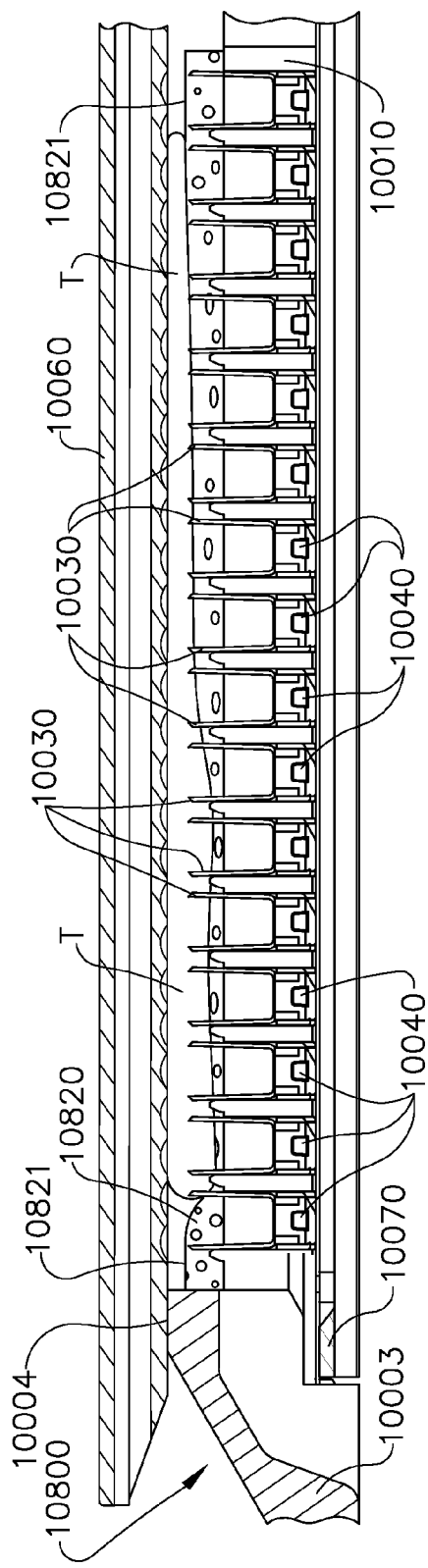

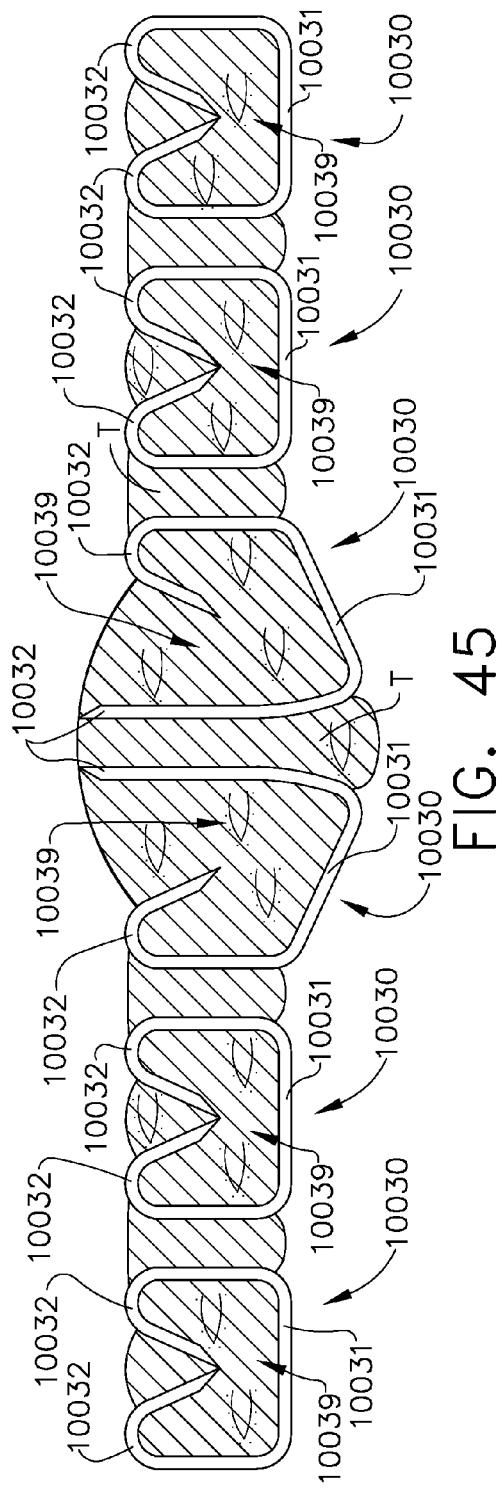
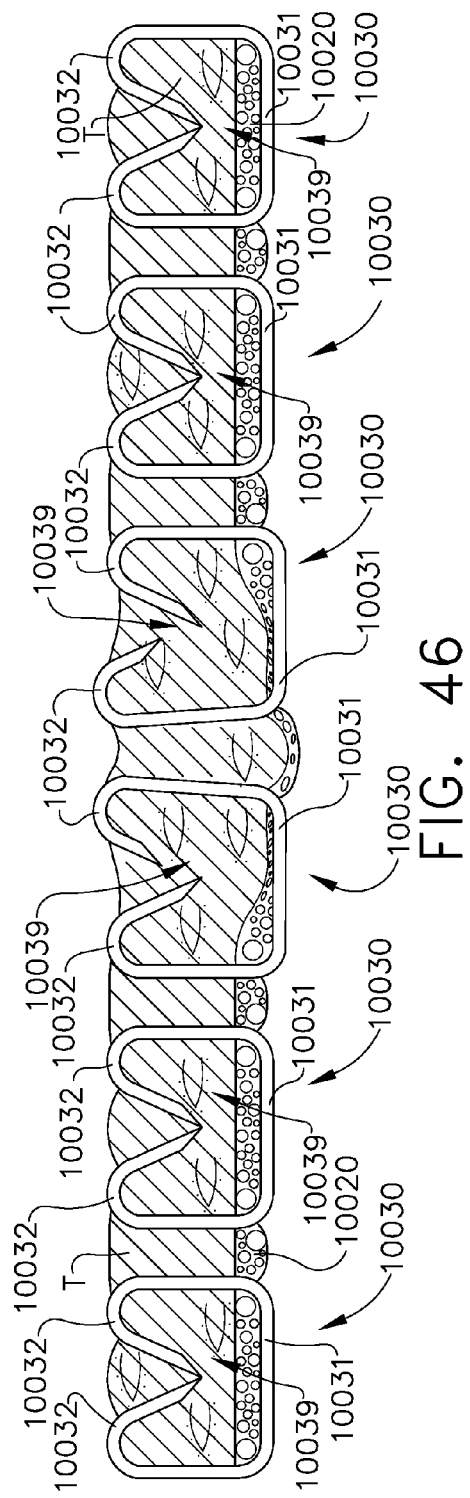
FIG. 45
FIG. 46

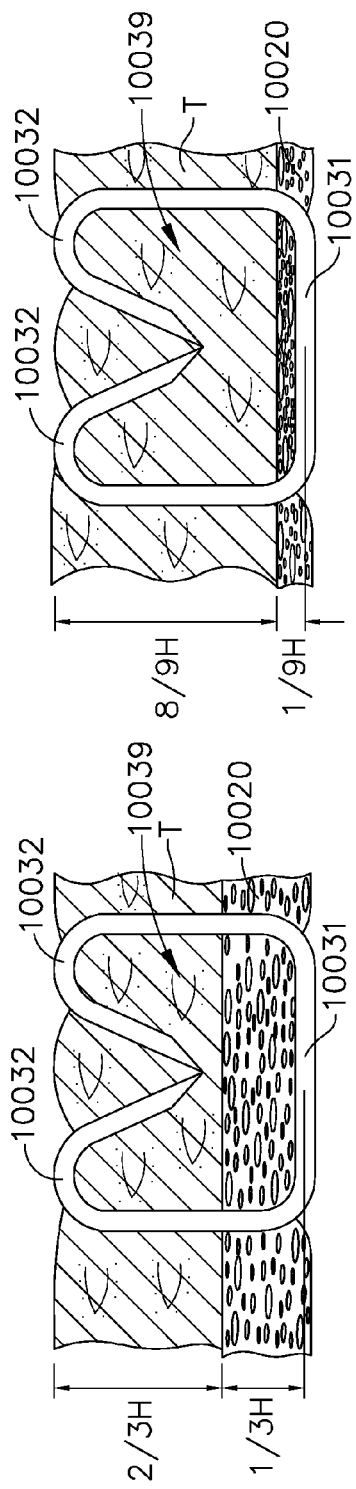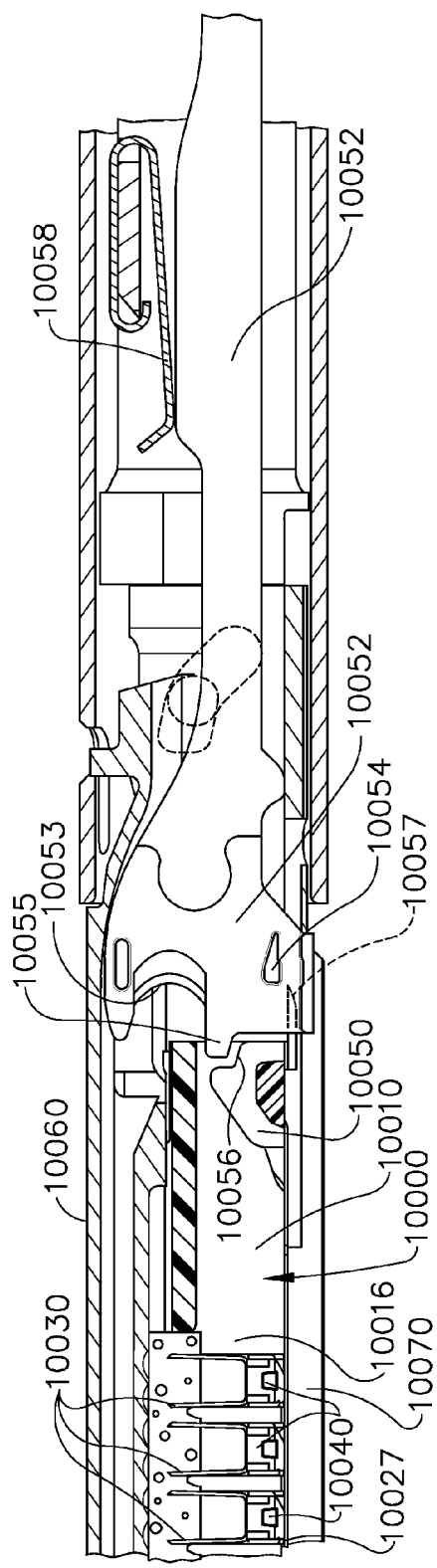

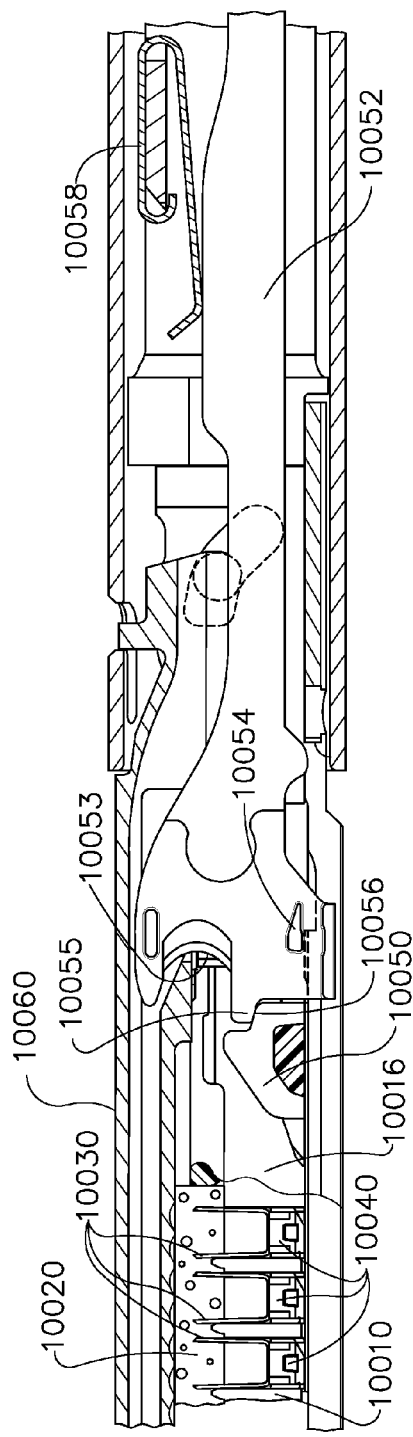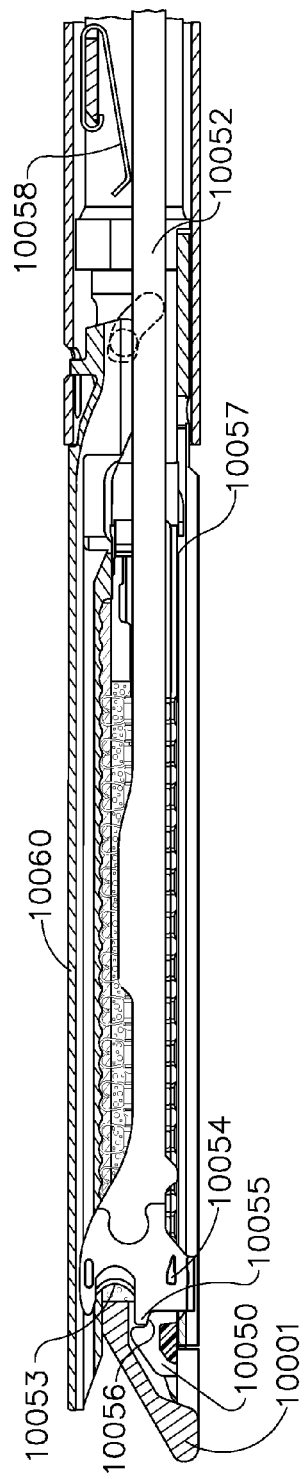

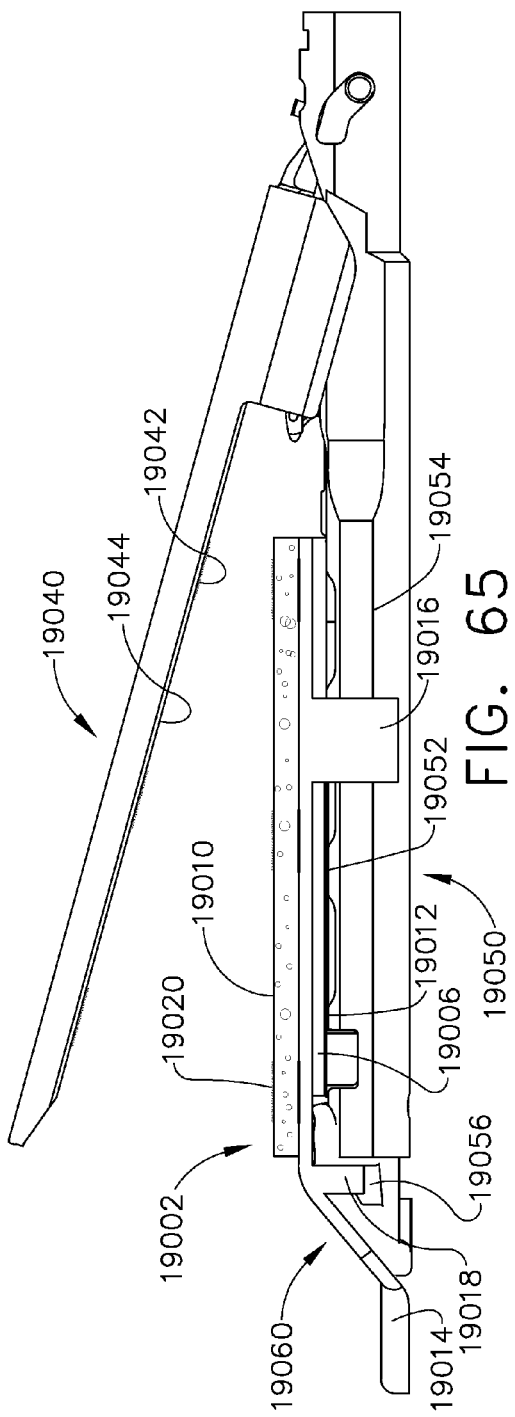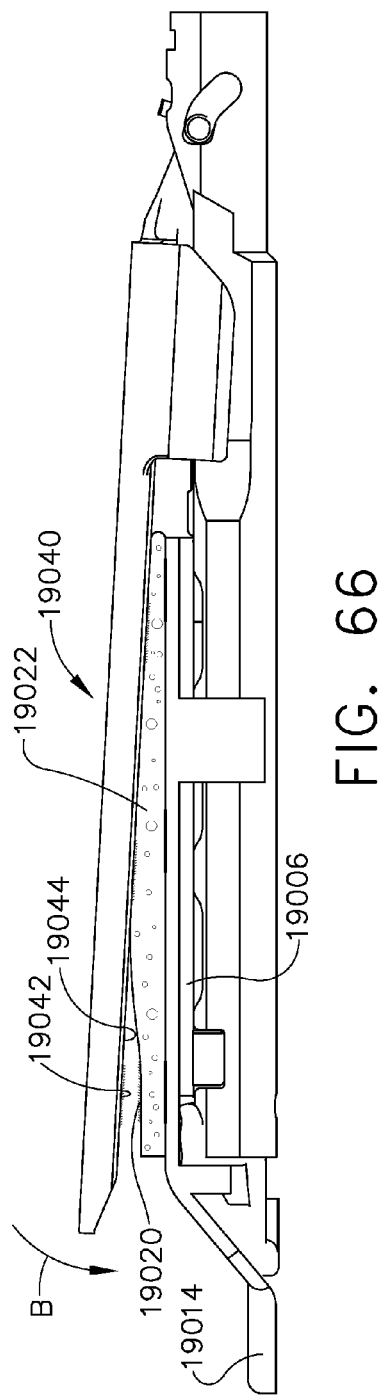

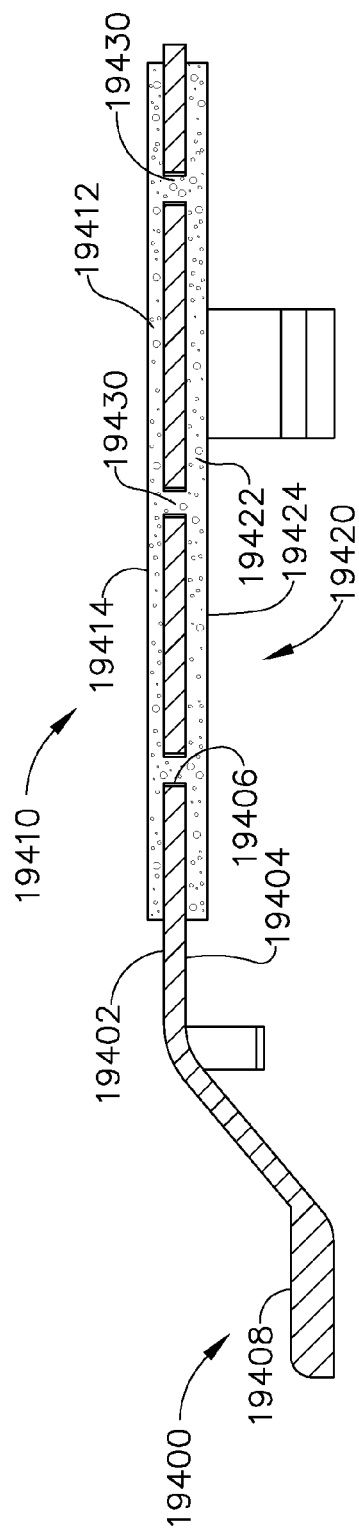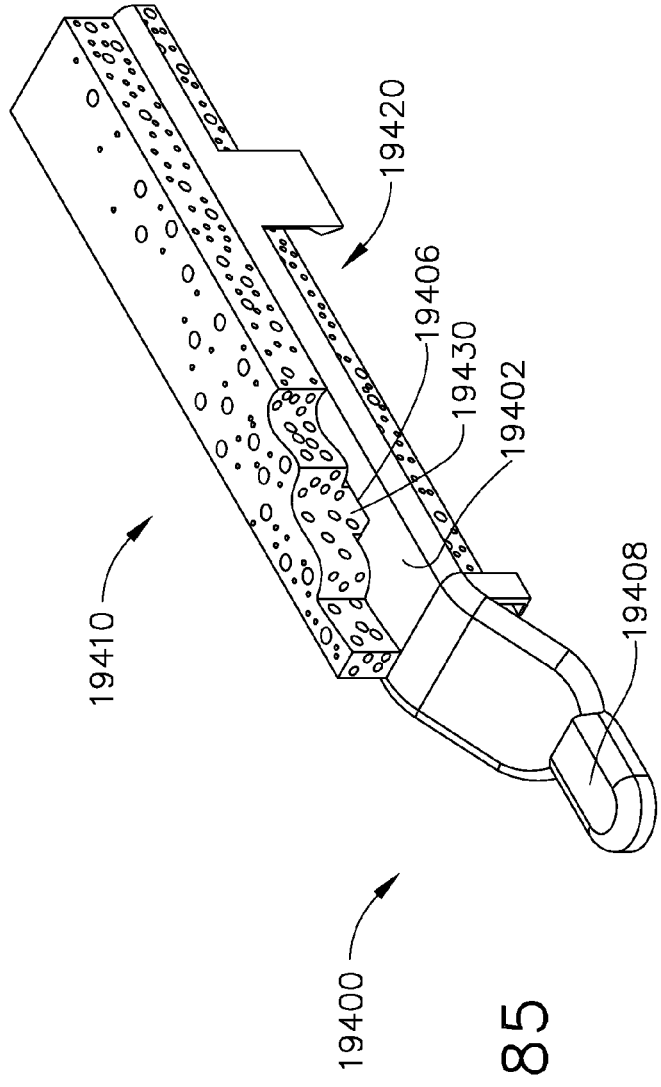
FIG. 84
FIG. 85

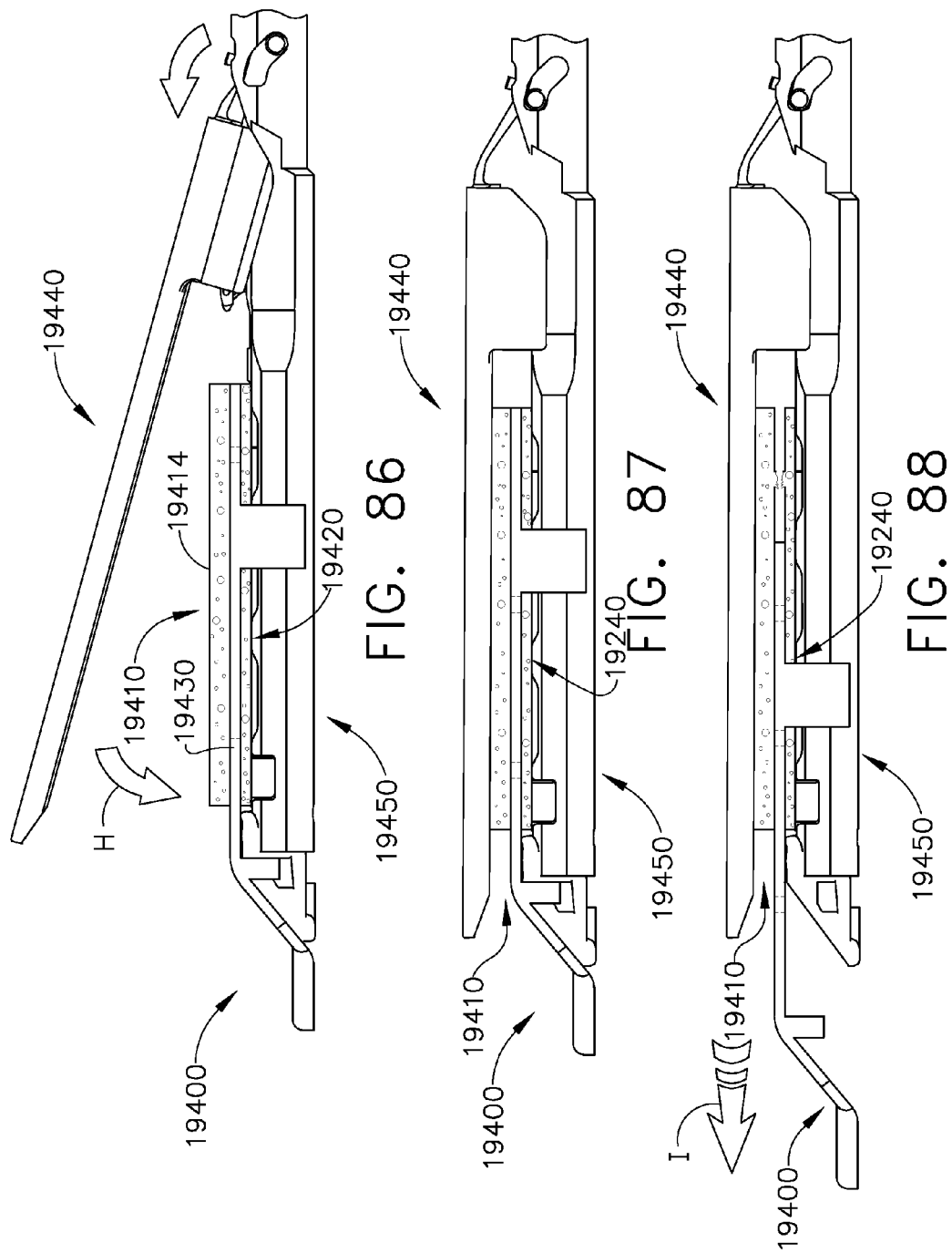

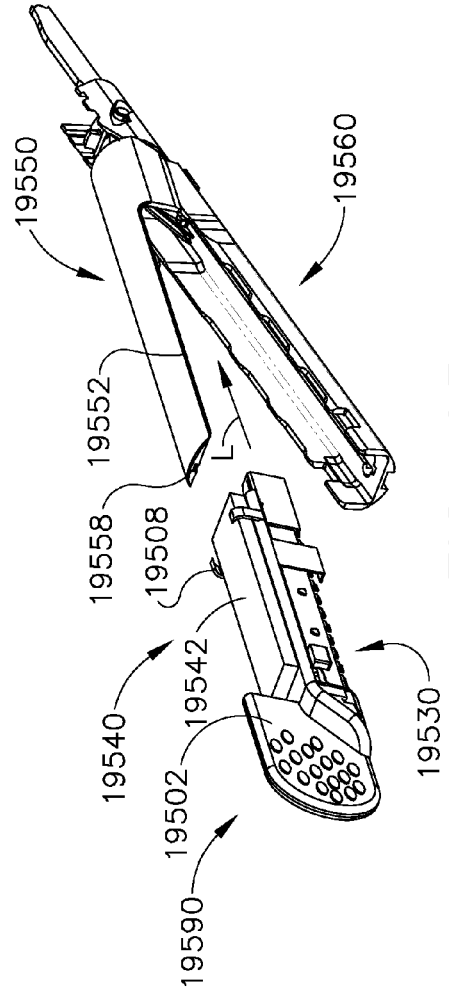
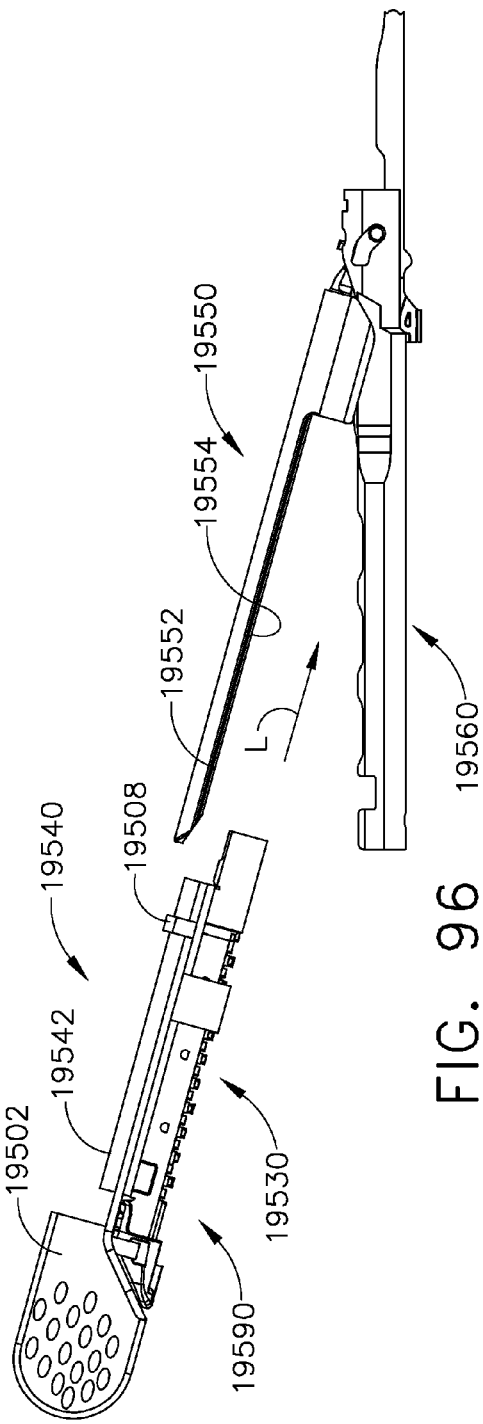
FIG. 95
FIG. 96

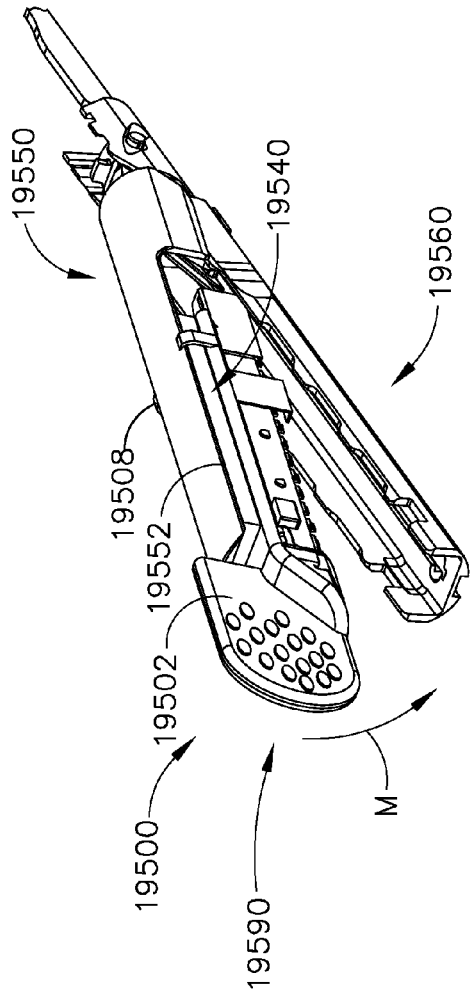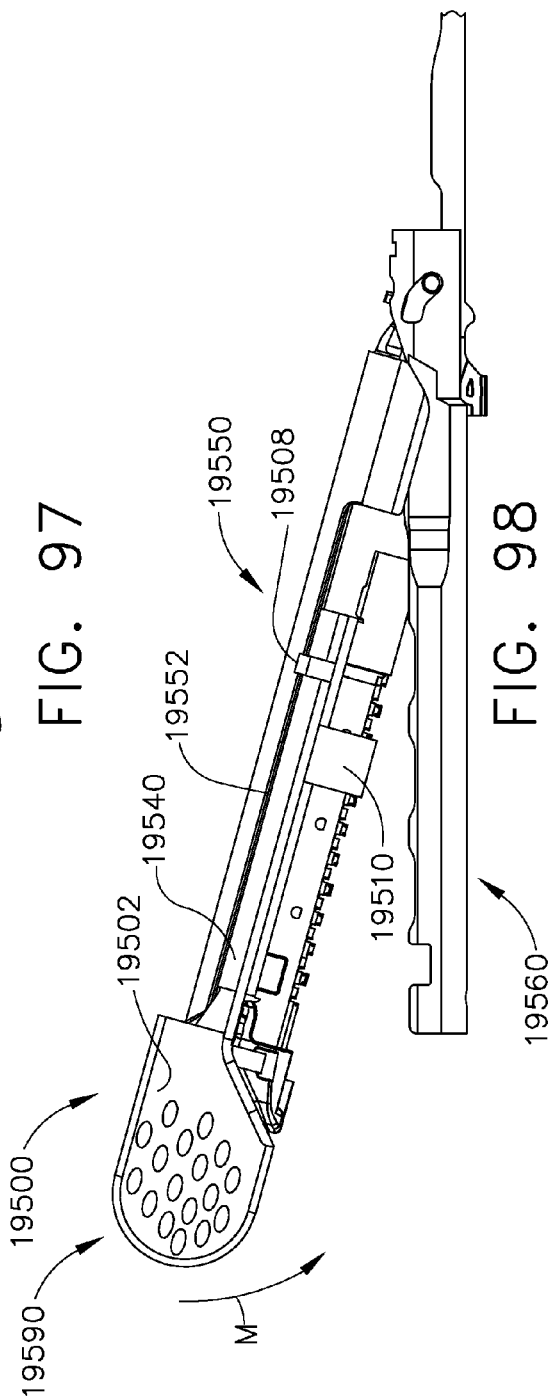

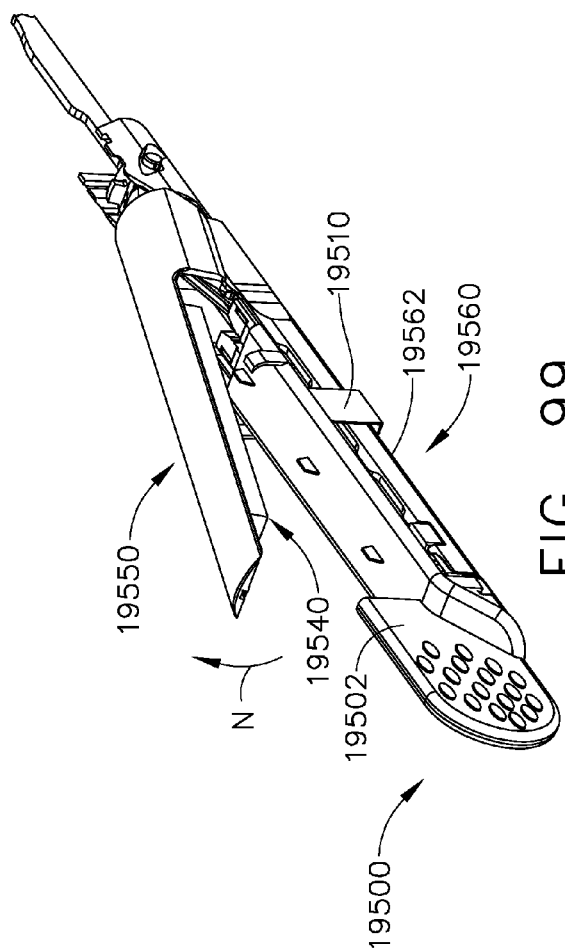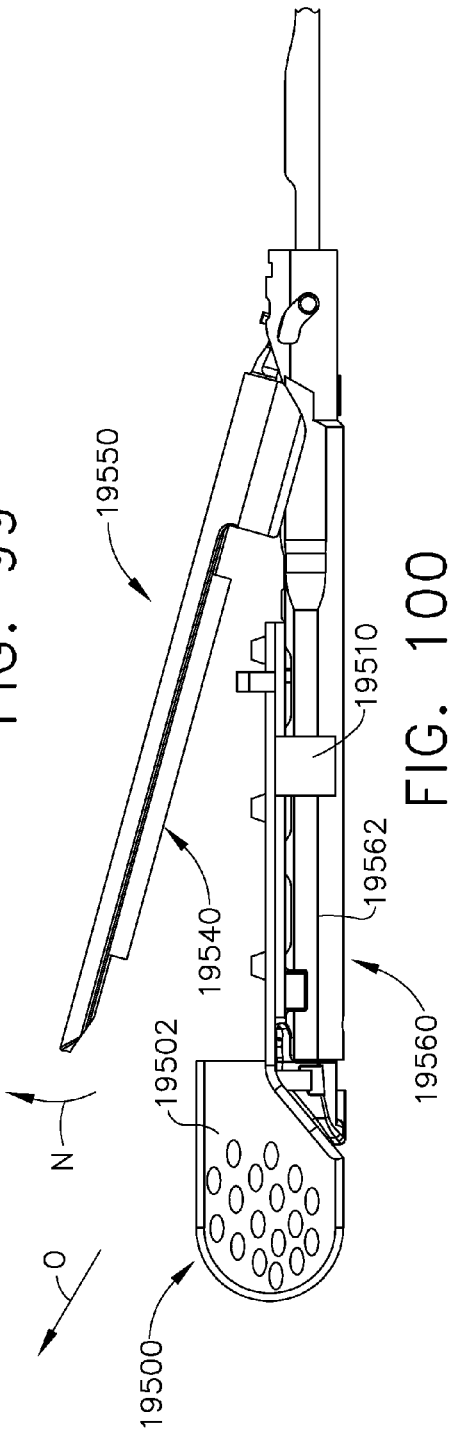

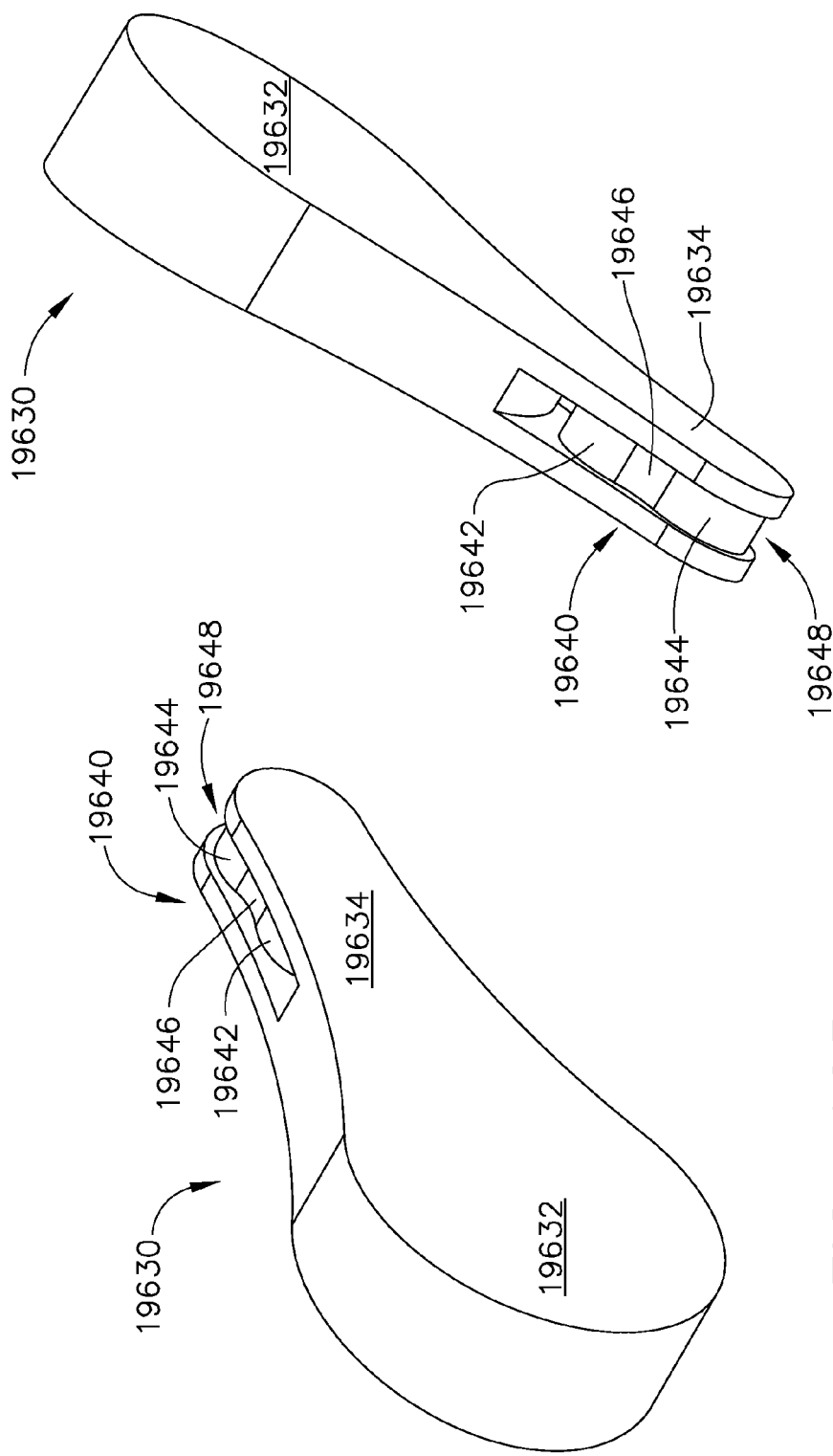

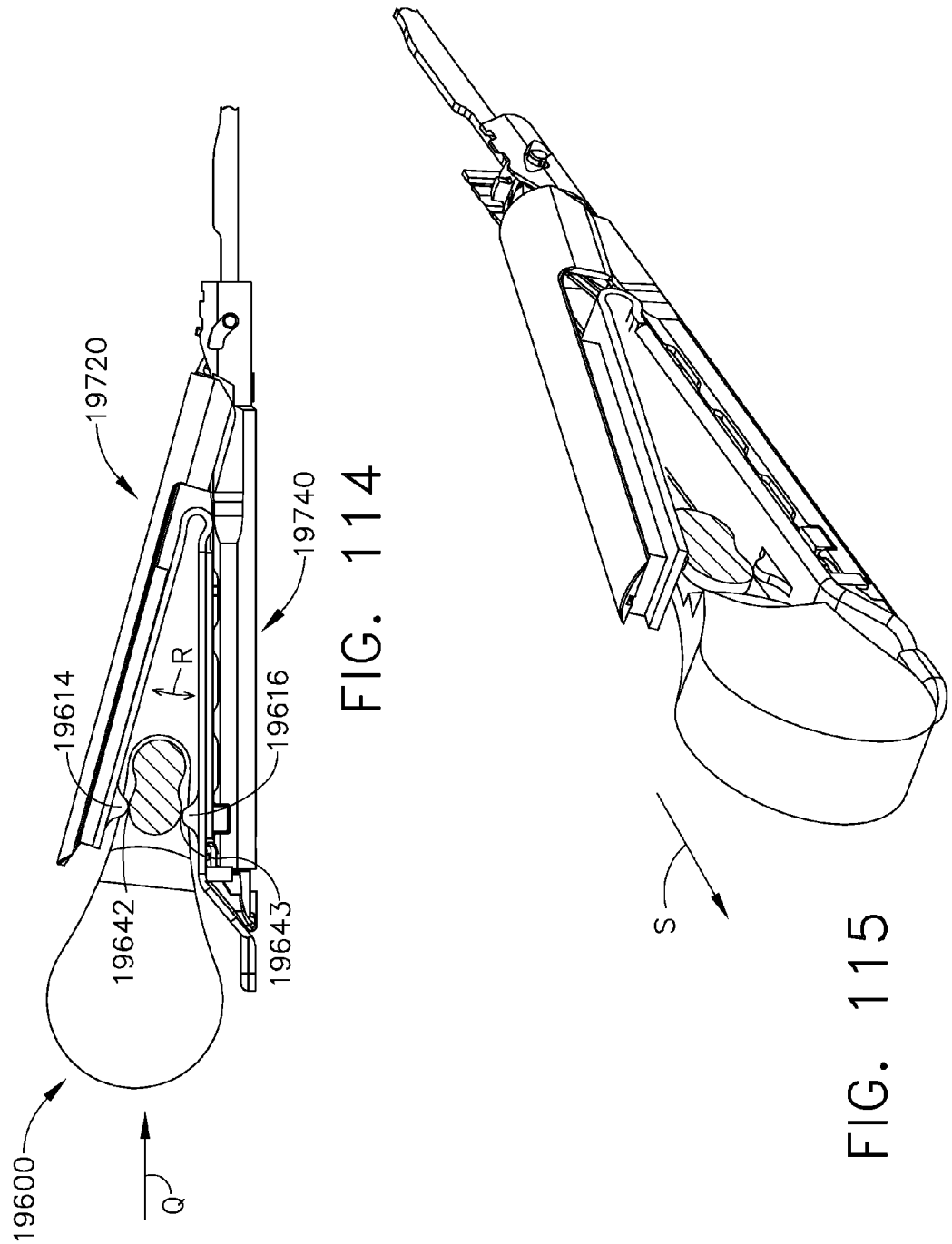

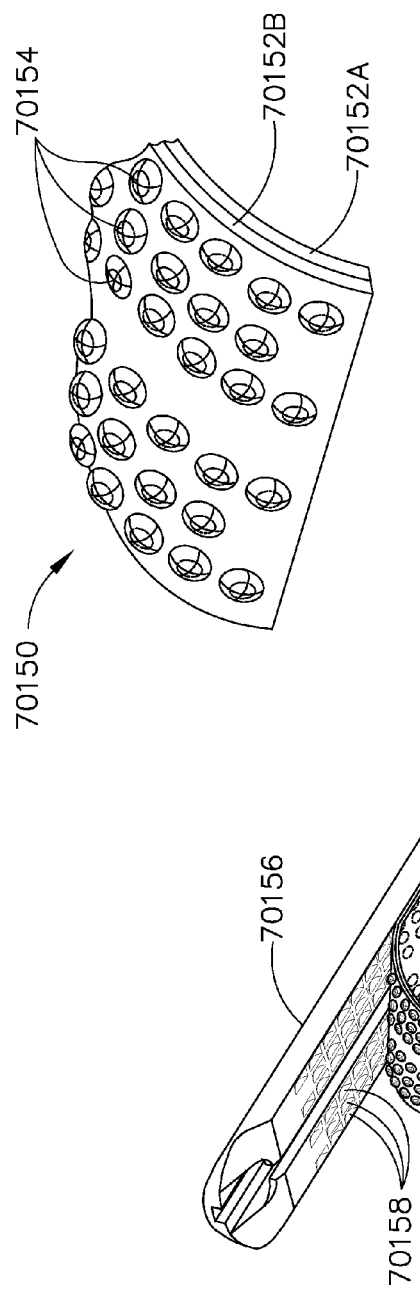
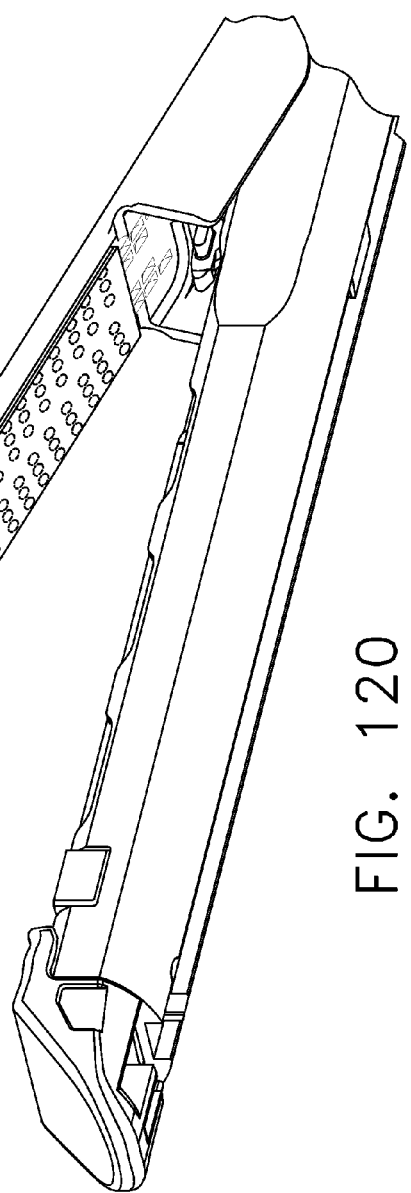
FIG. 120A
FIG. 120

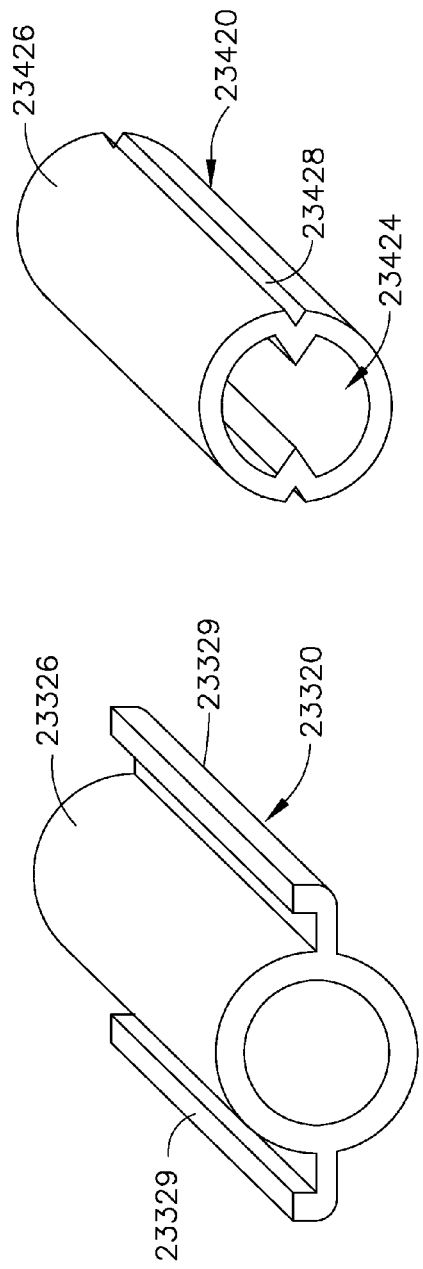
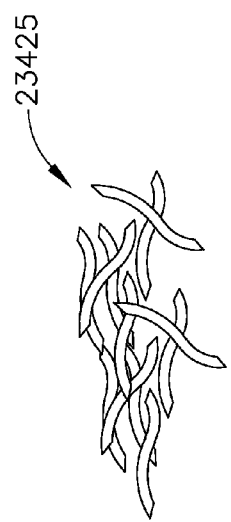
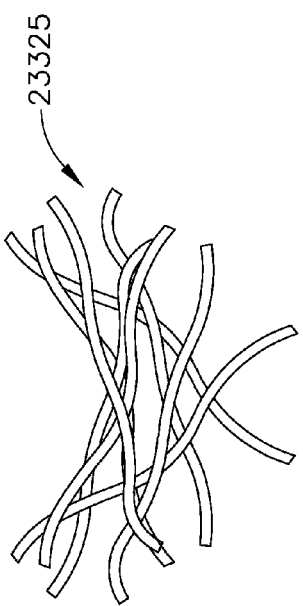
FIG. 144
FIG. 146
FIG. 143
FIG. 145

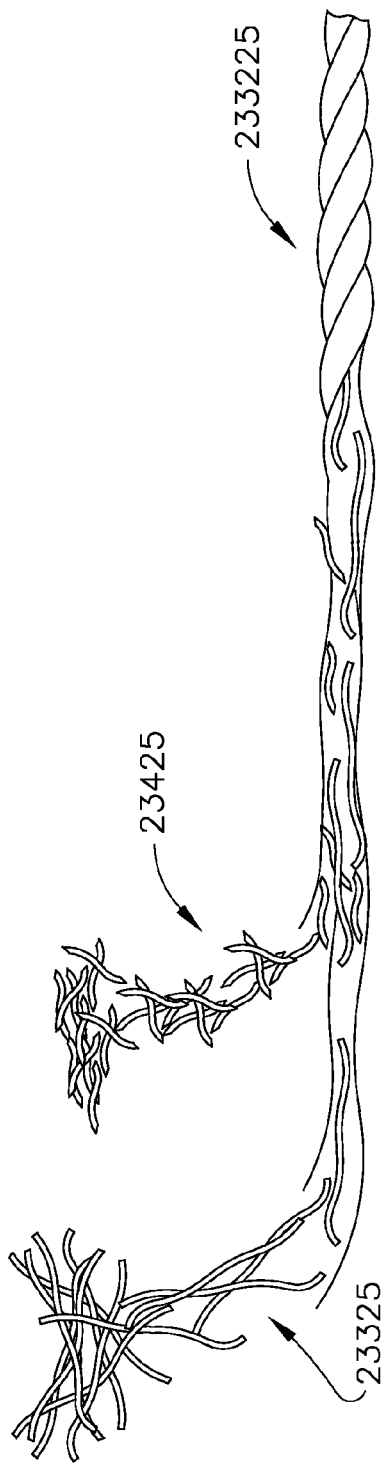
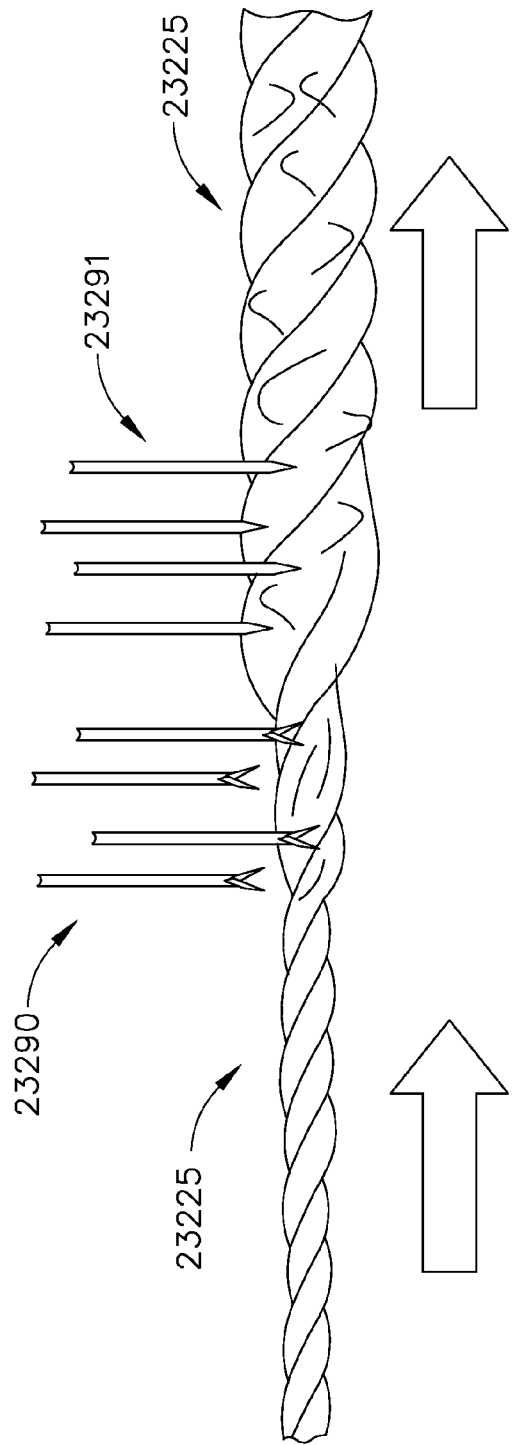

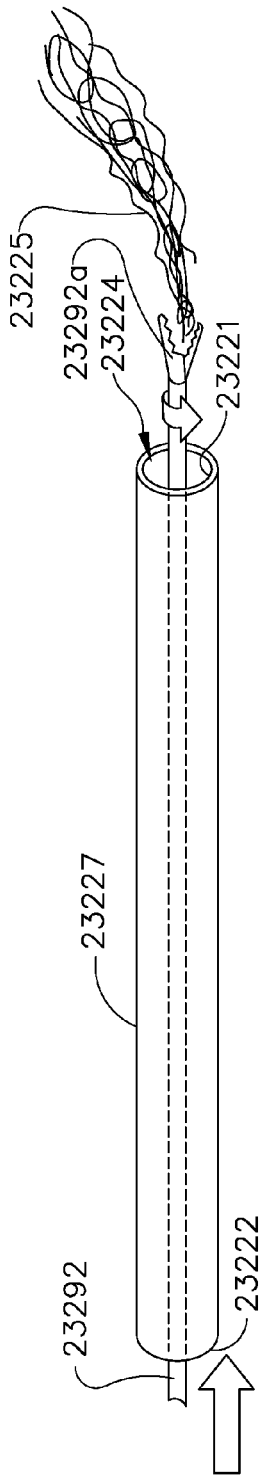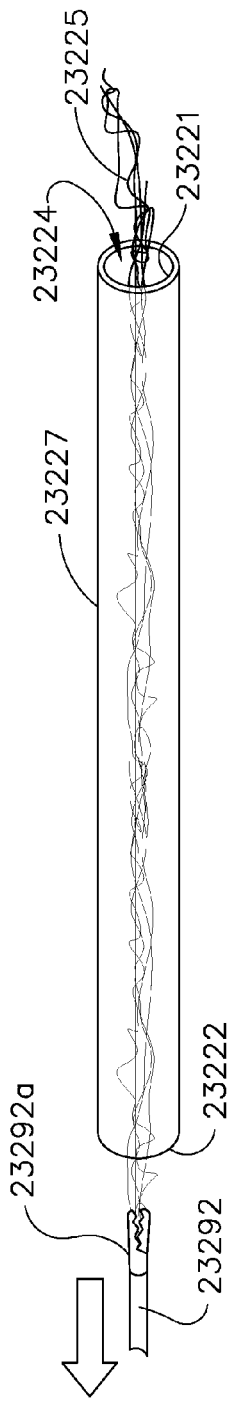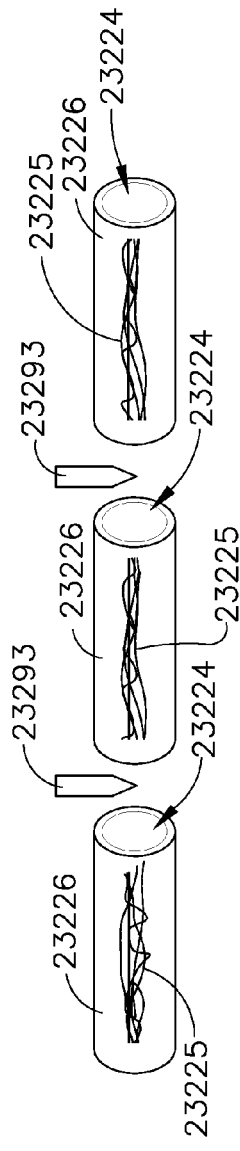

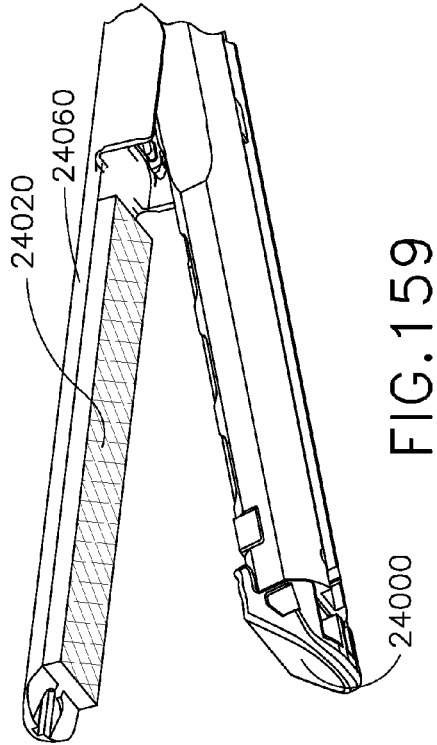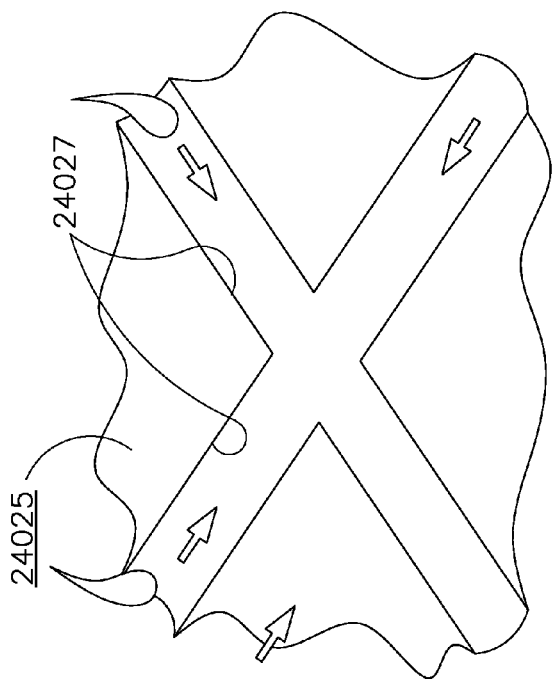

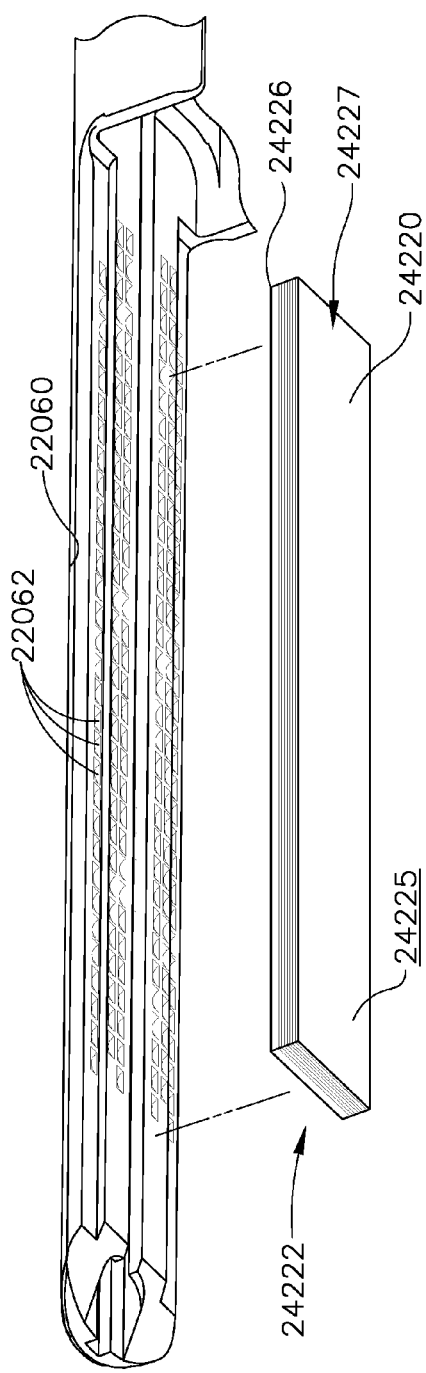
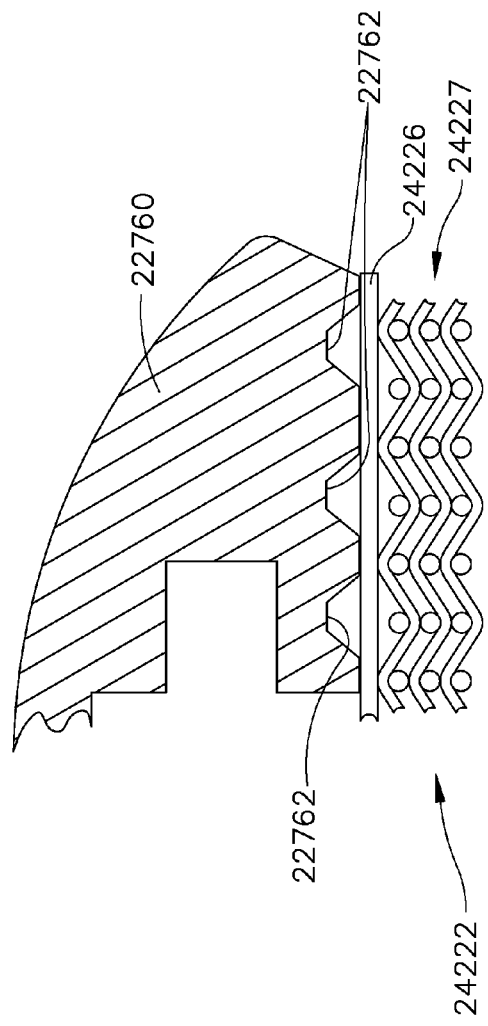

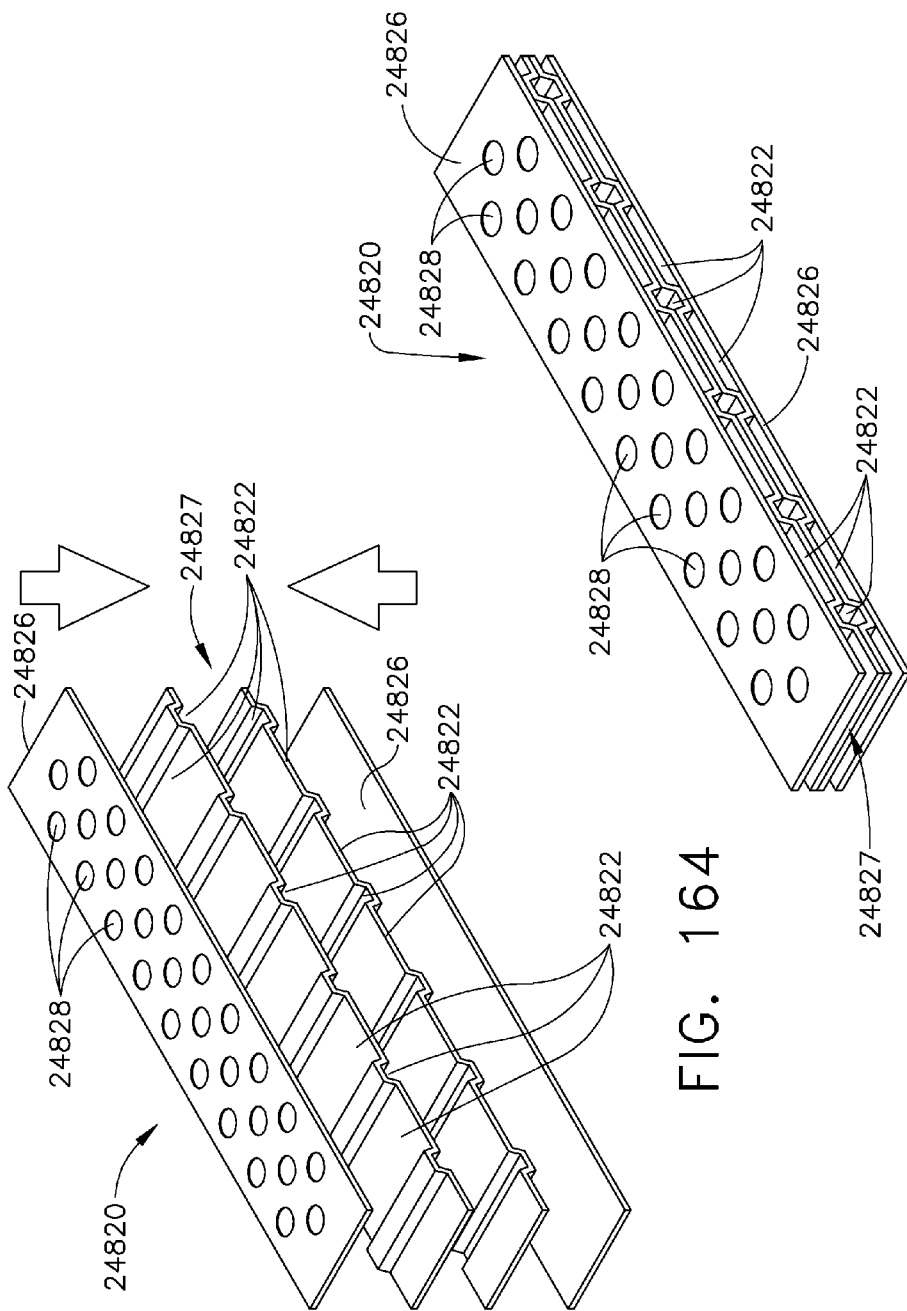

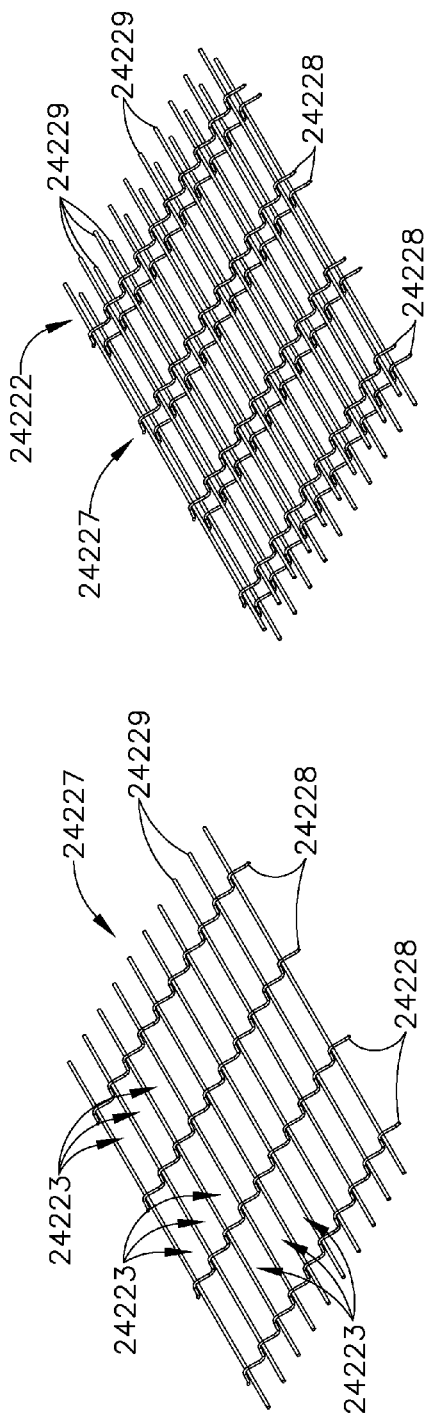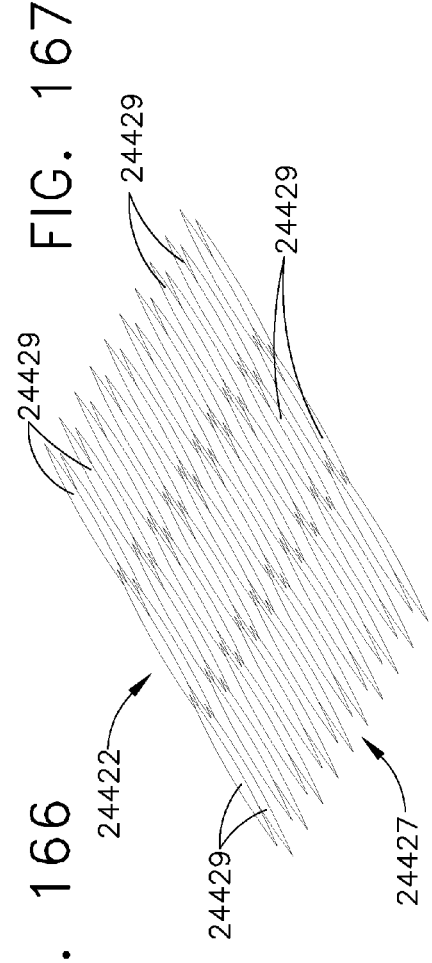
FIG. 167
FIG. 168
FIG. 166

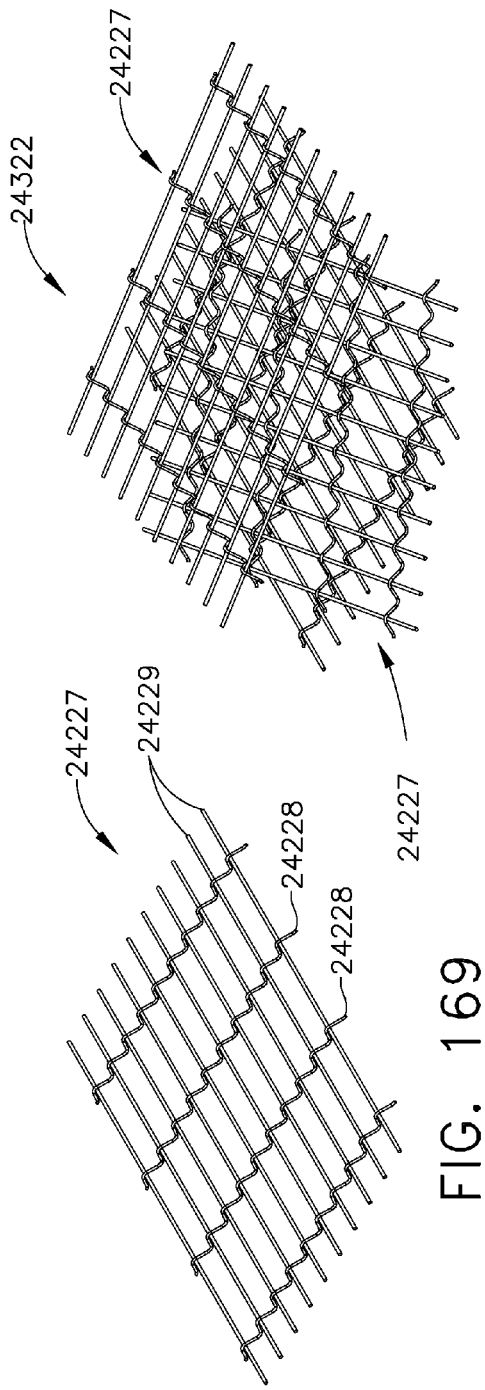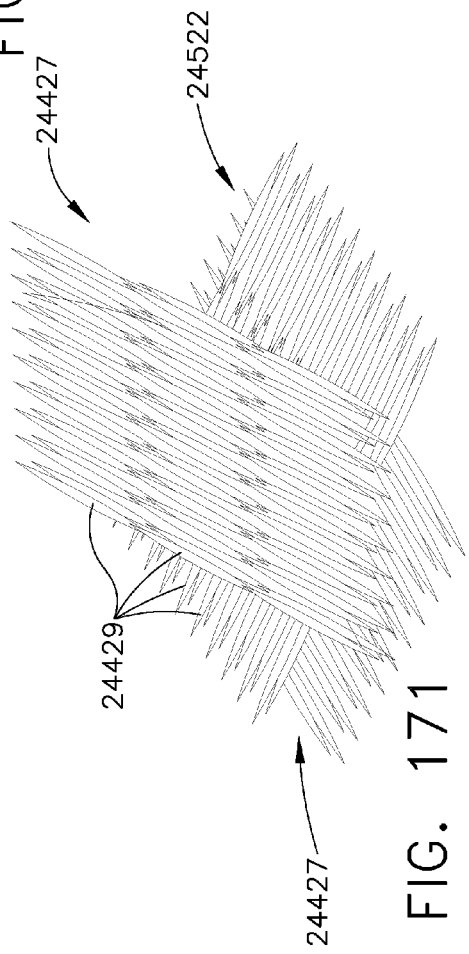
FIG. 169
FIG. 170
FIG. 171

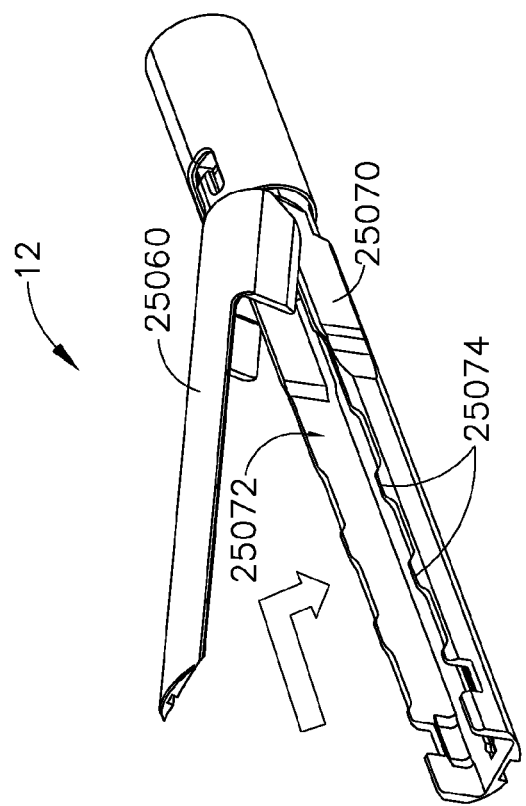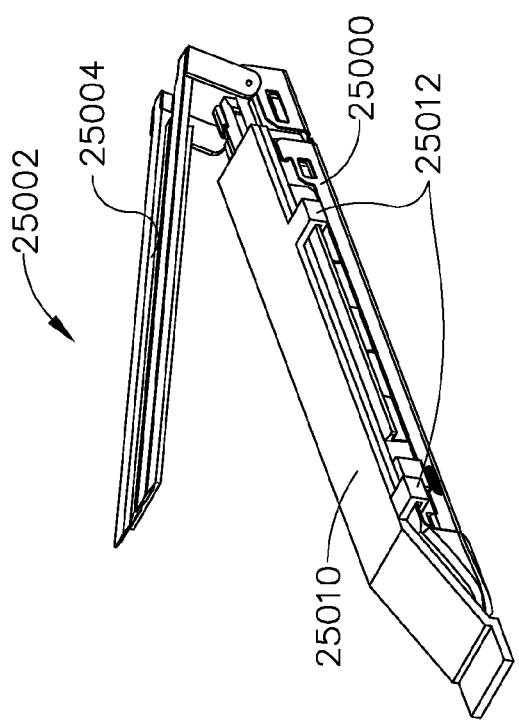
FIG. 172

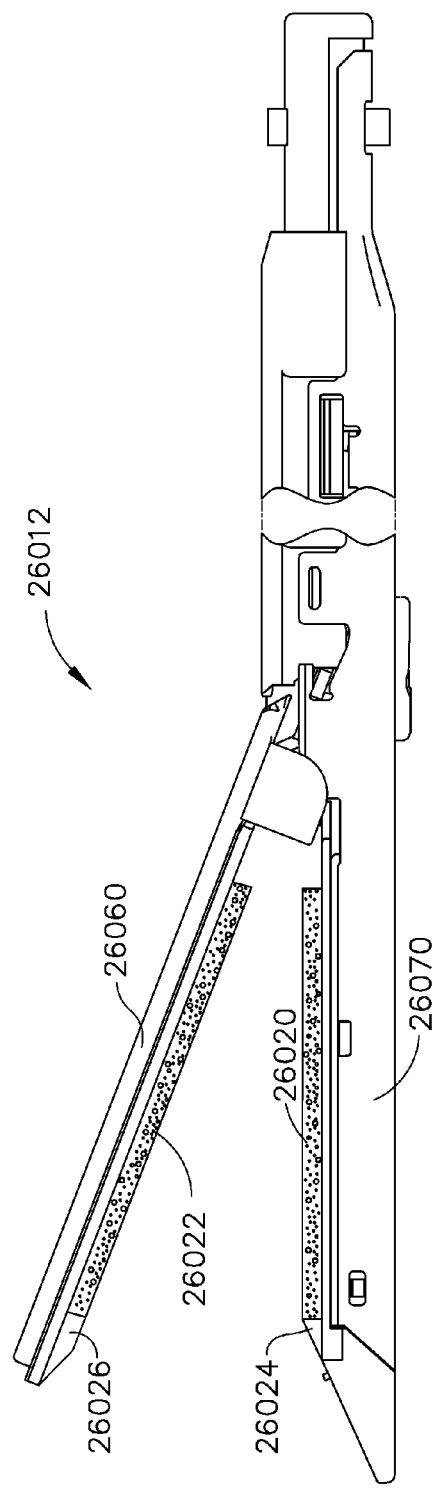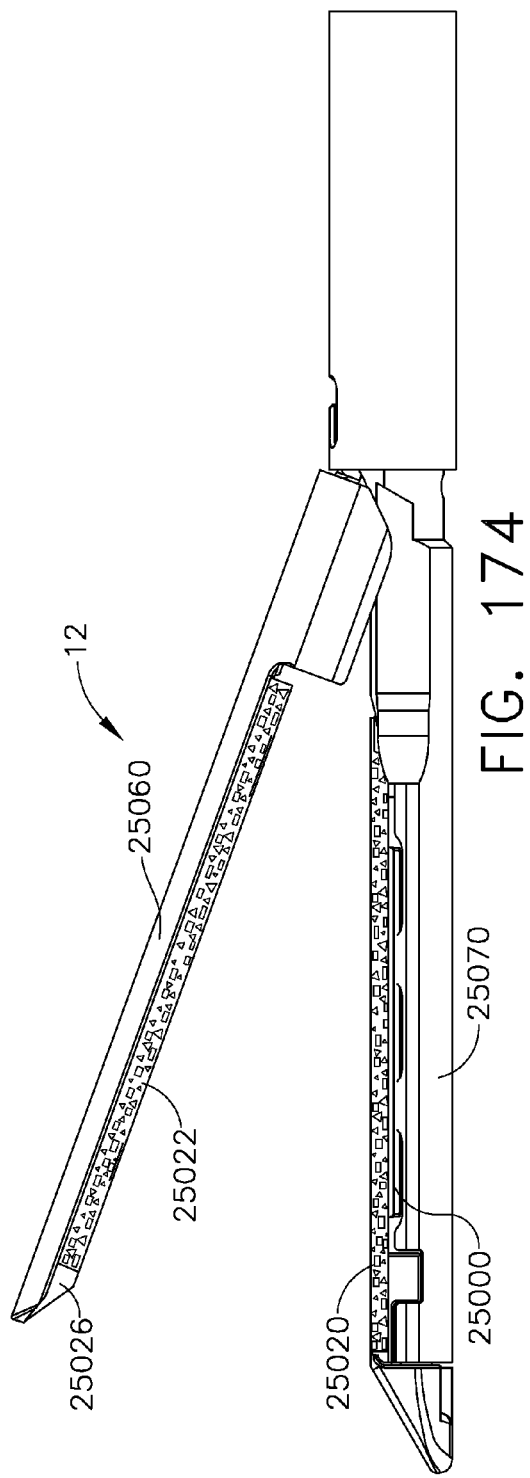

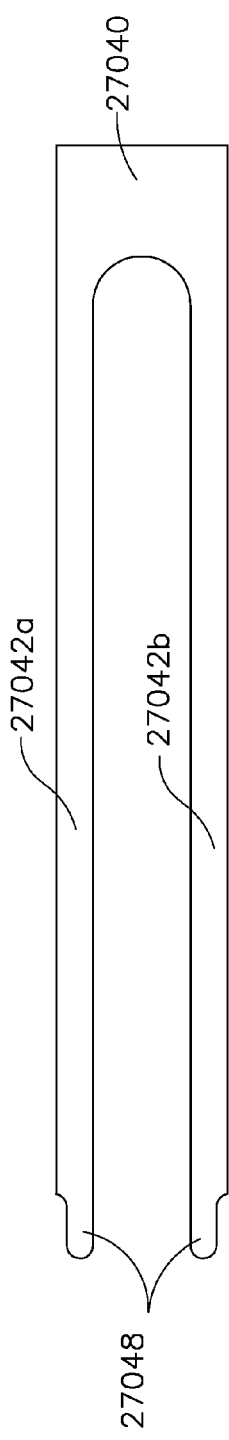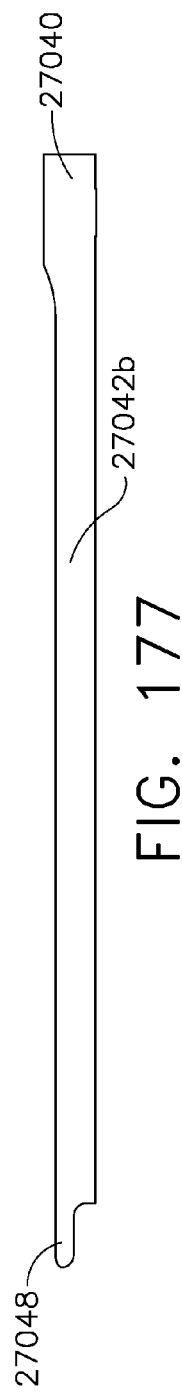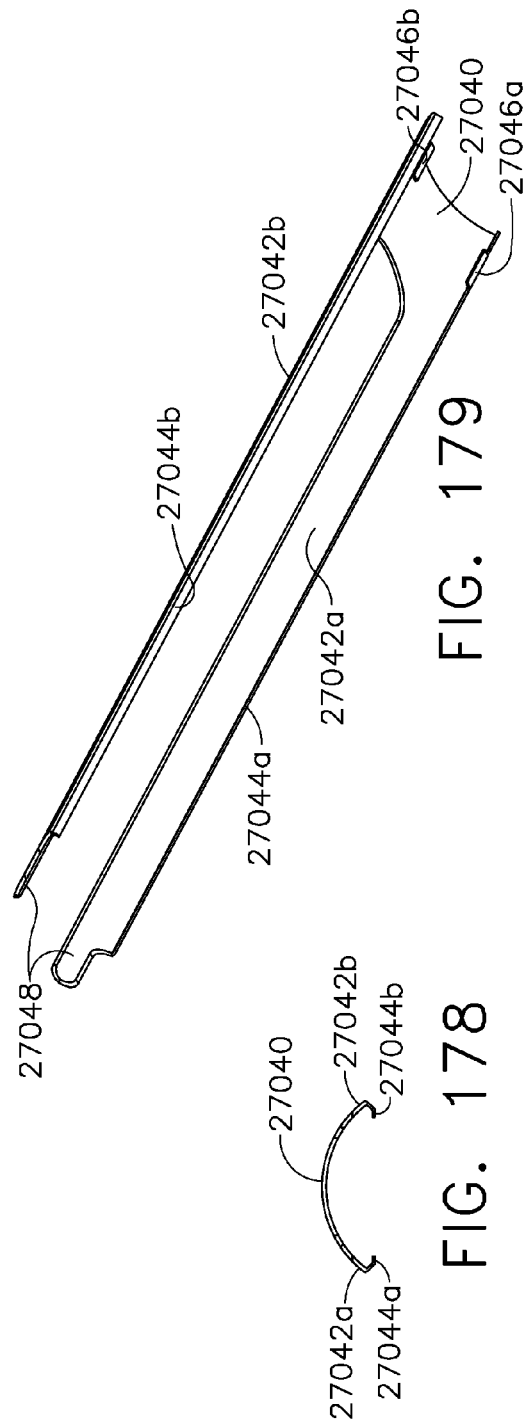

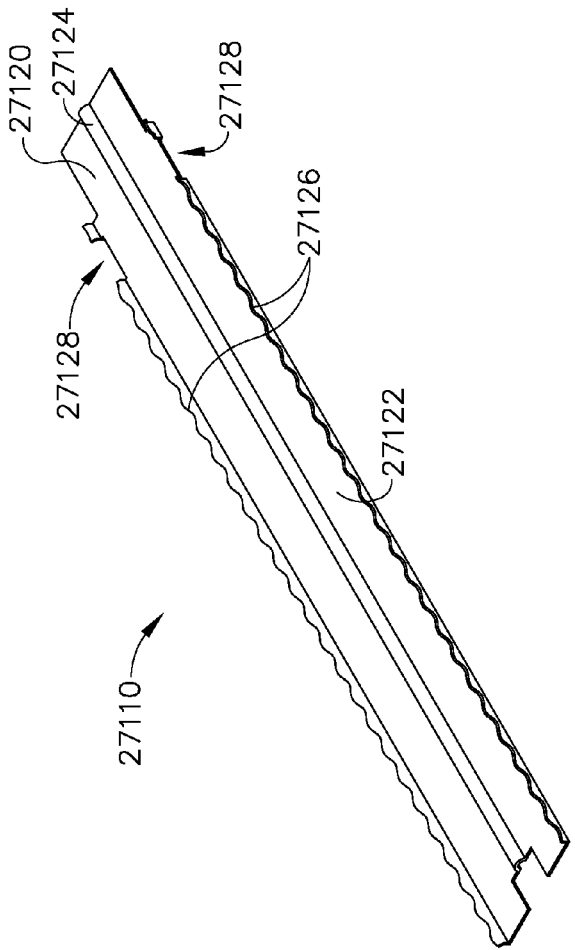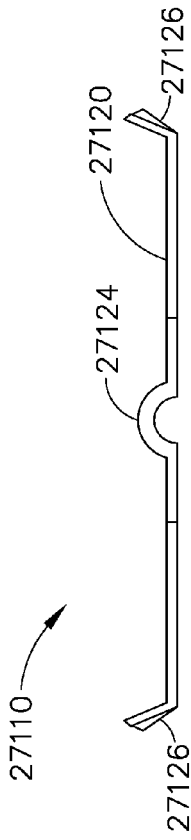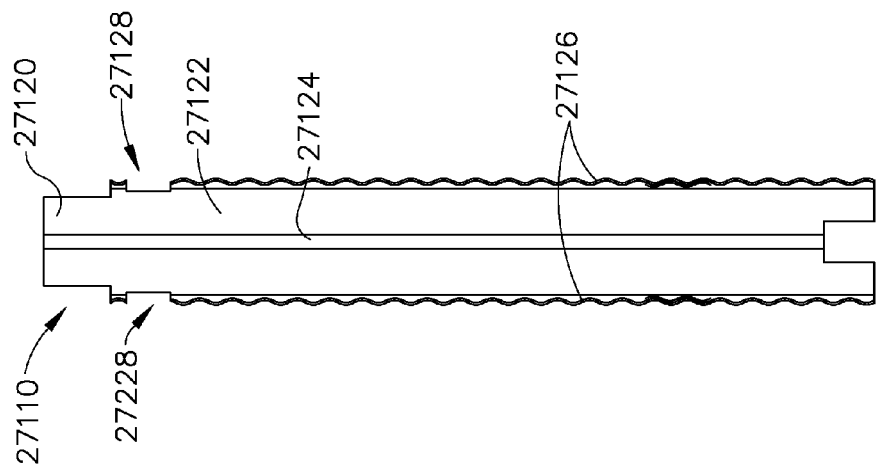

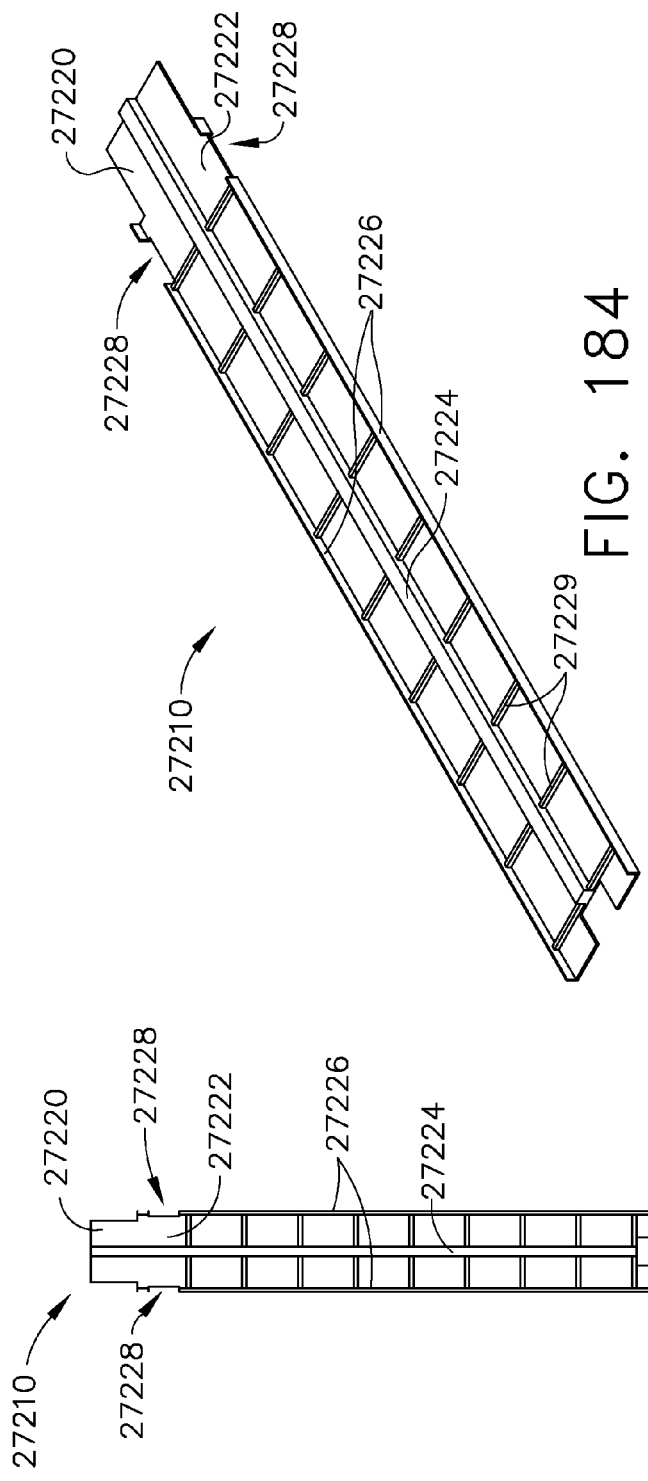
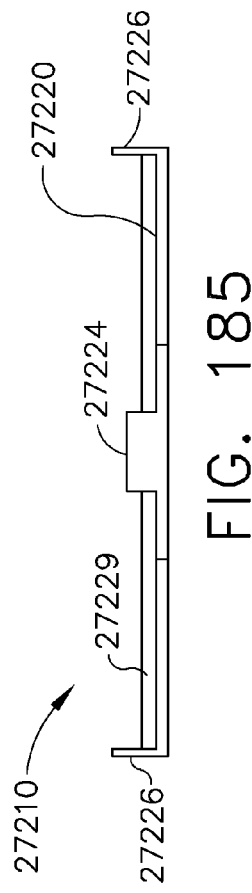
FIG. 184
FIG. 185
FIG. 183

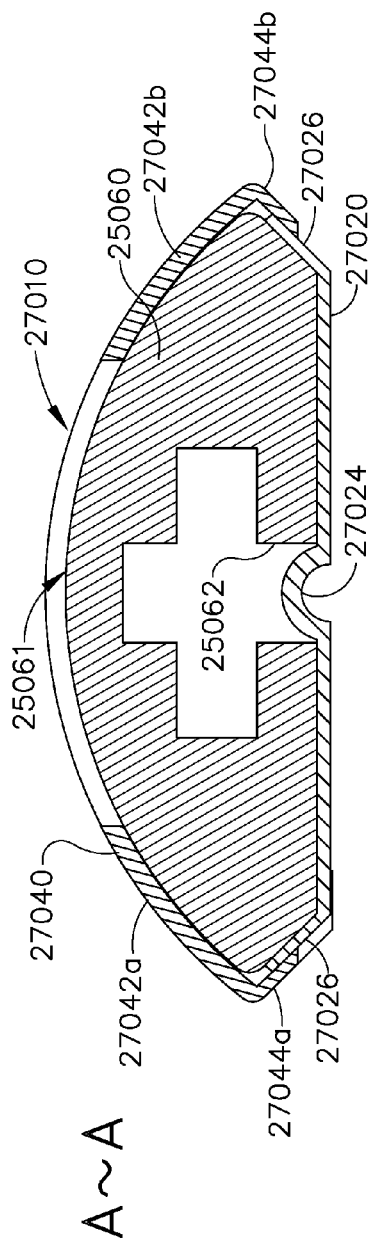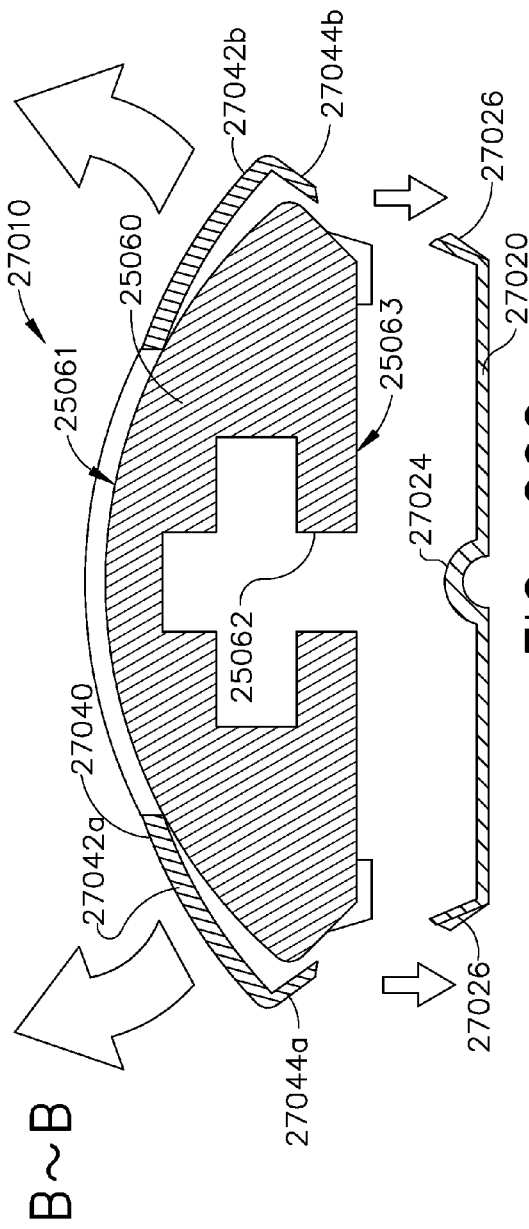

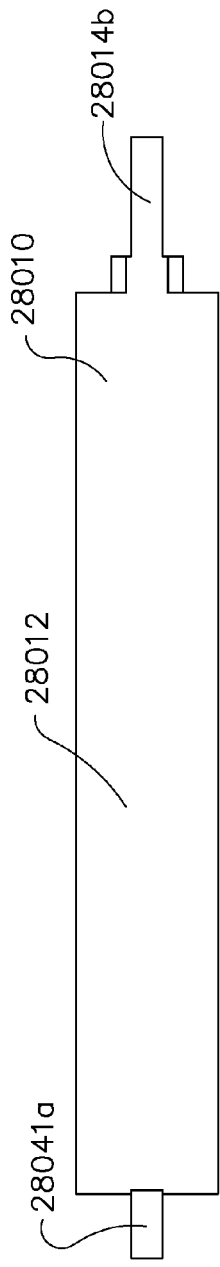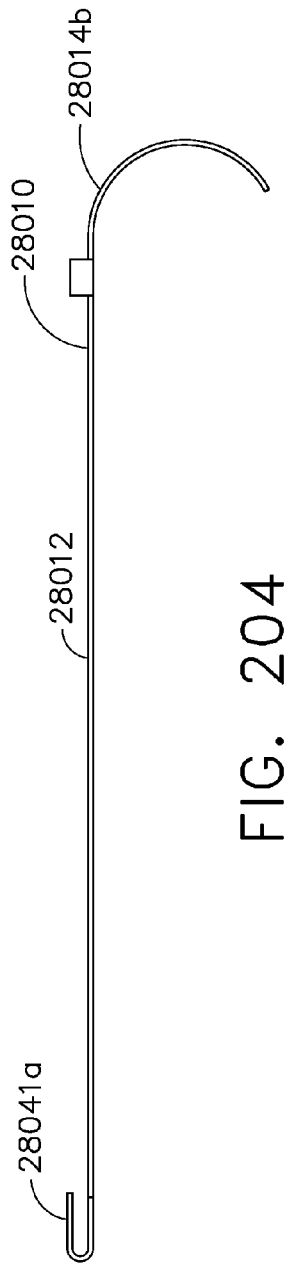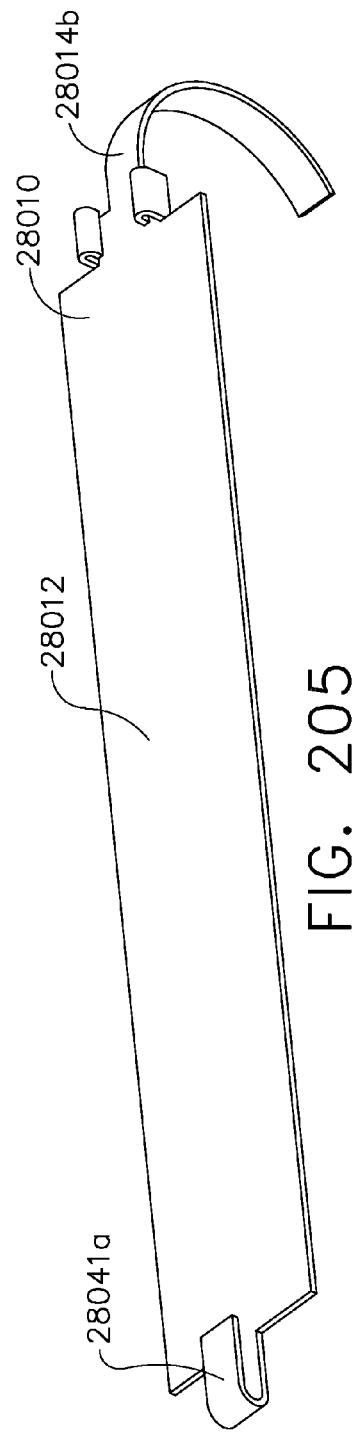

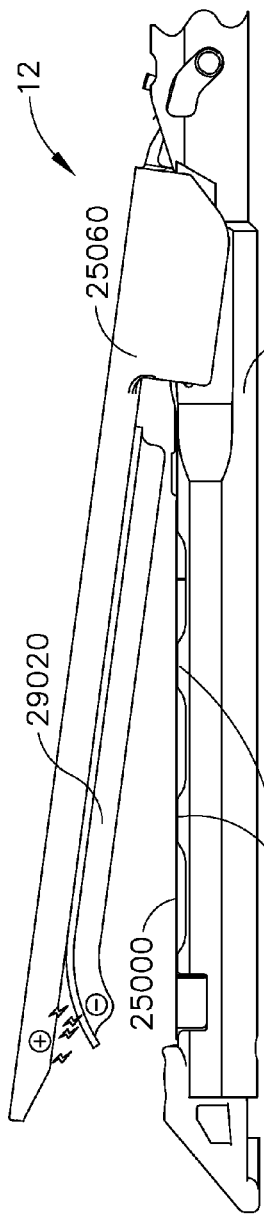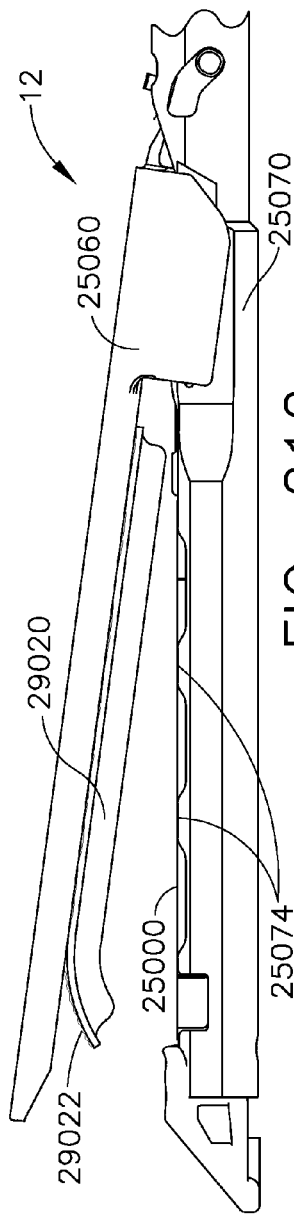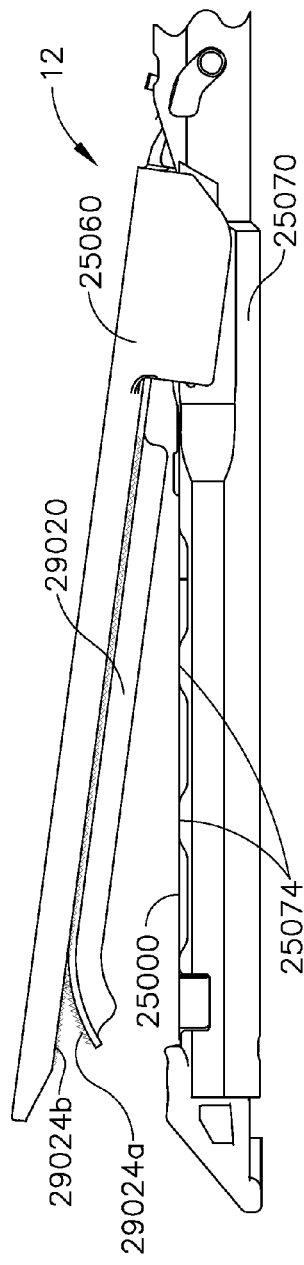

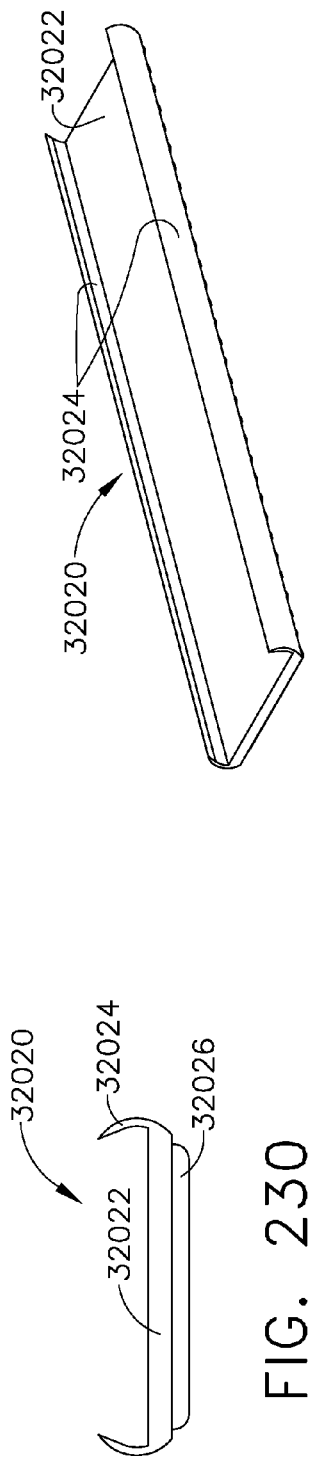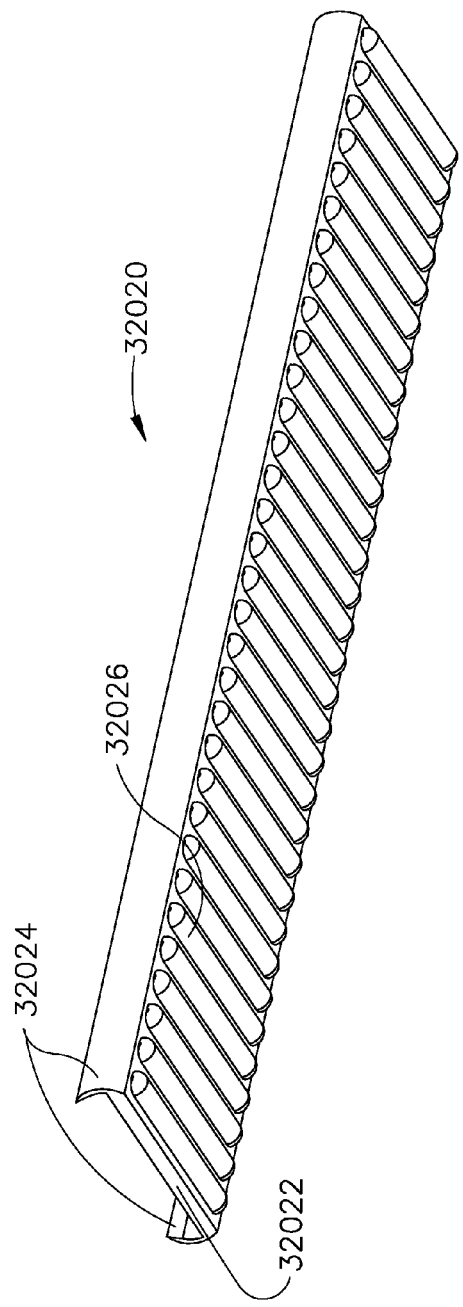
FIG. 230
FIG. 231
FIG. 232

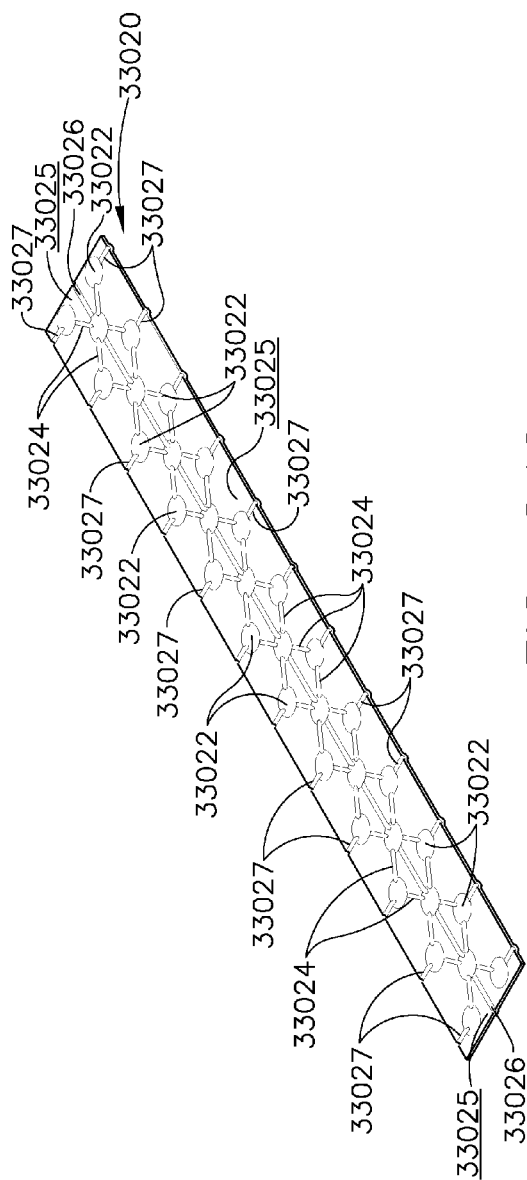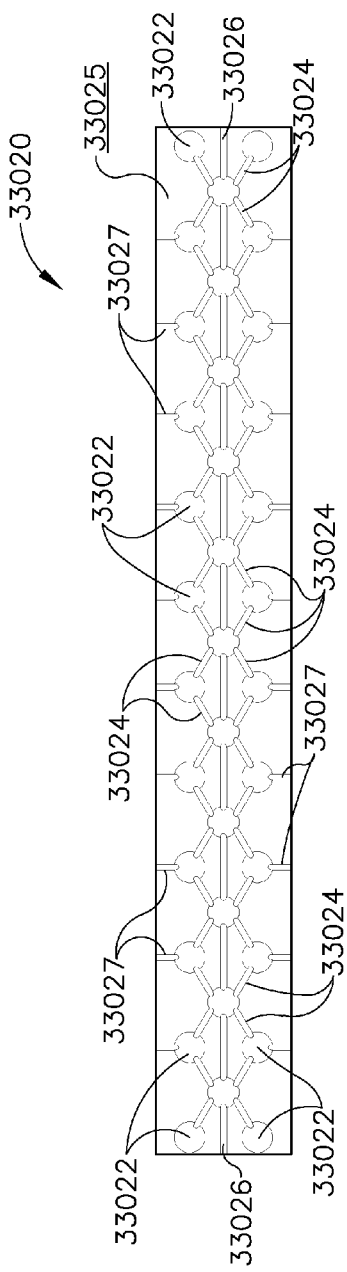
FIG. 240
FIG. 241

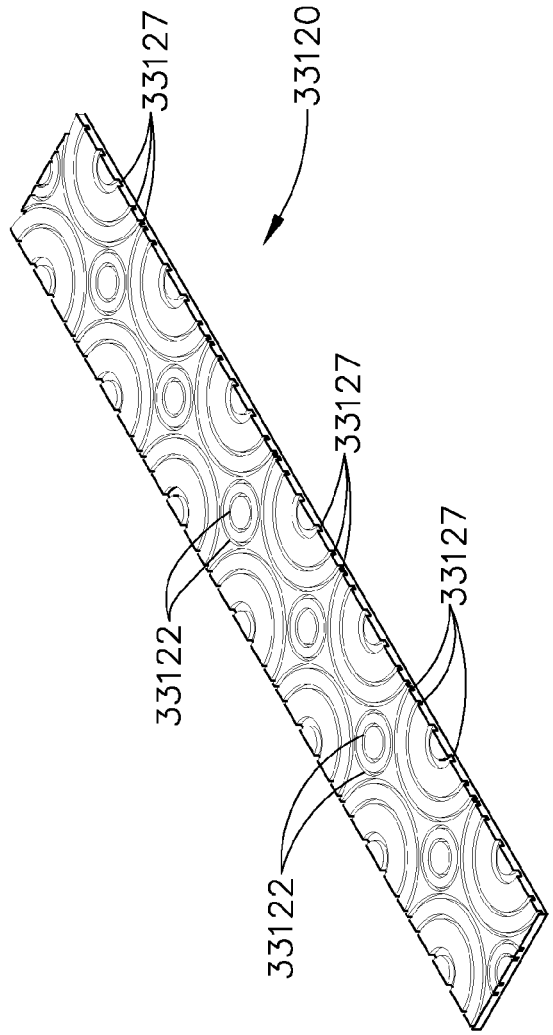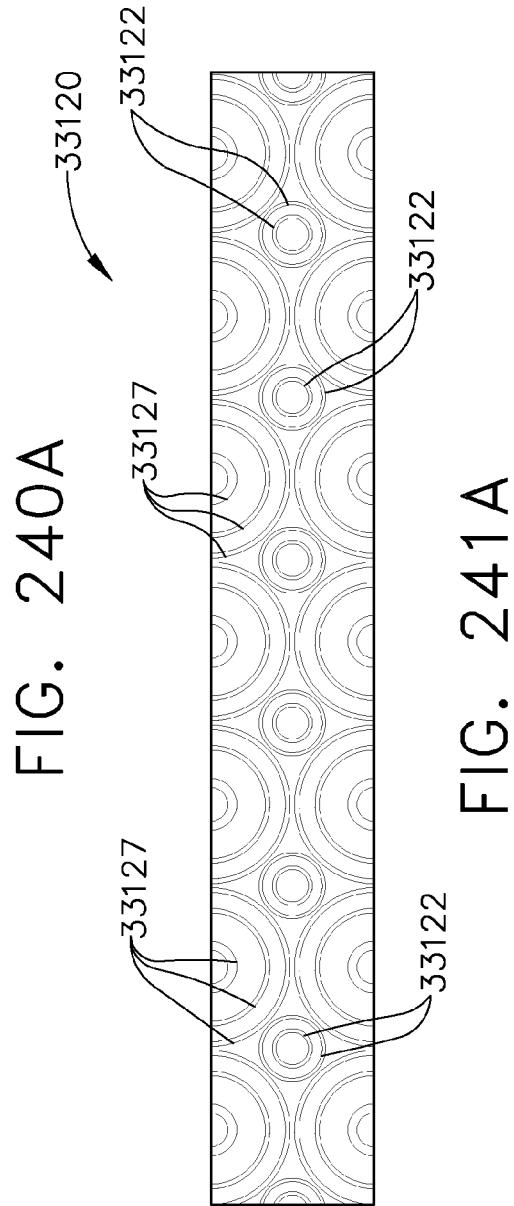

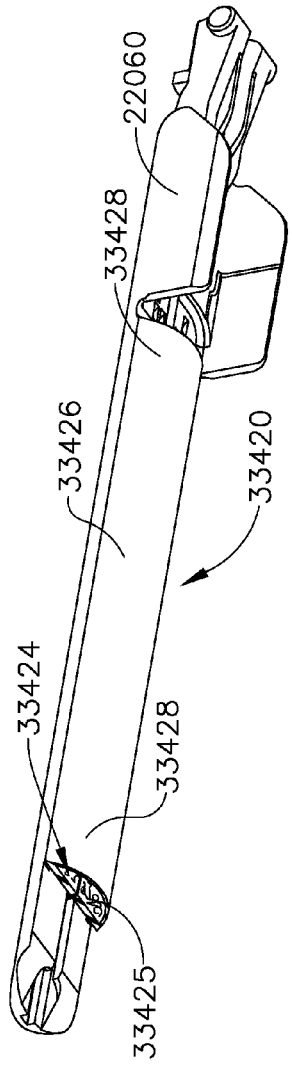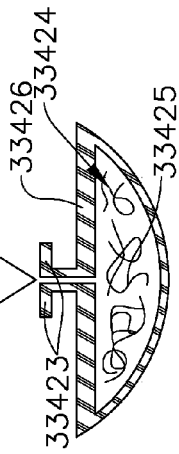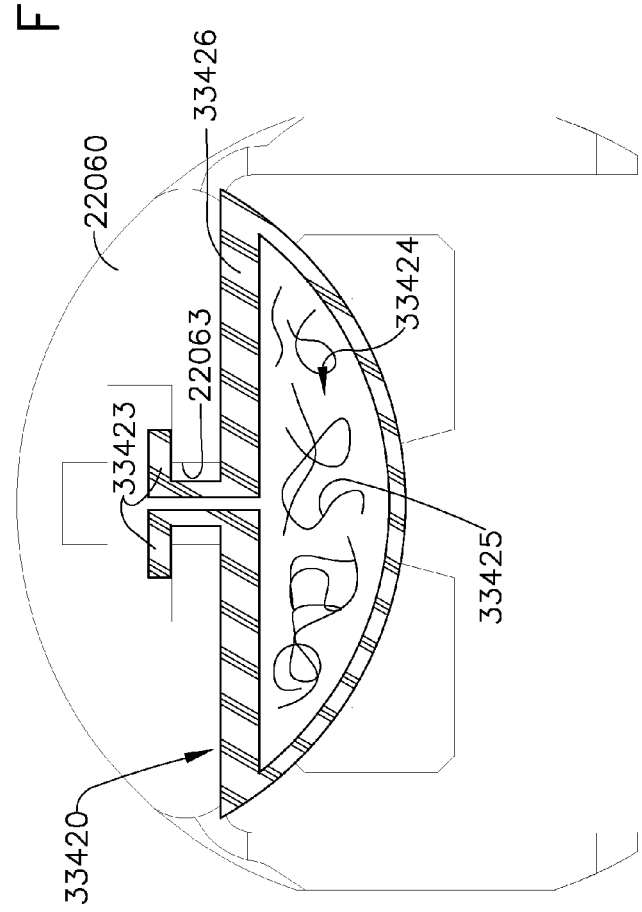

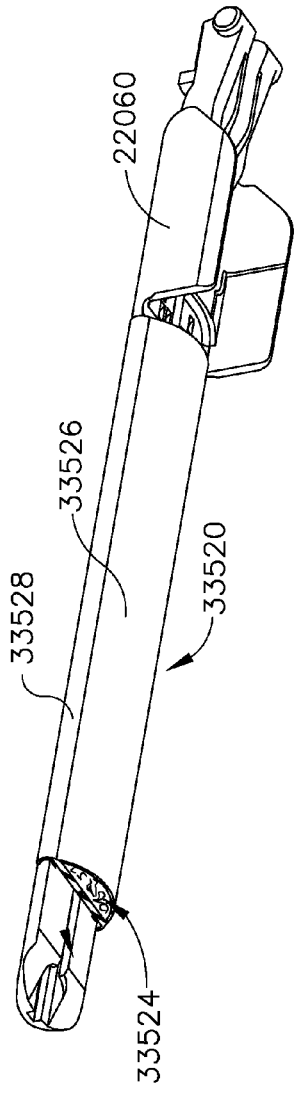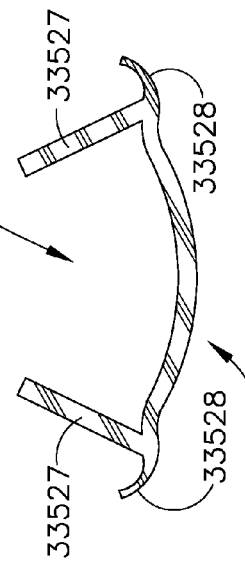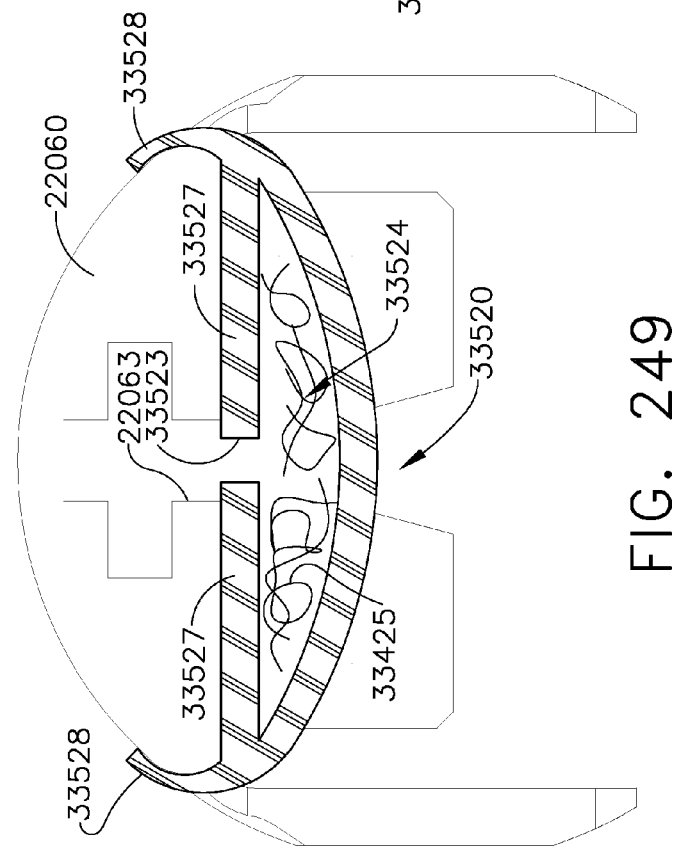

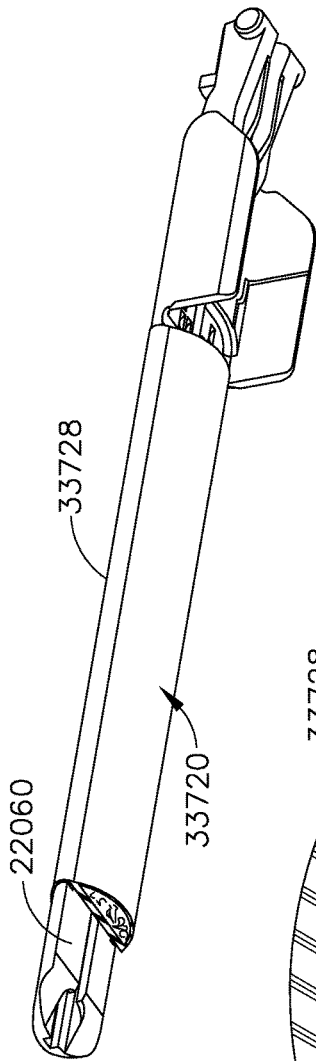
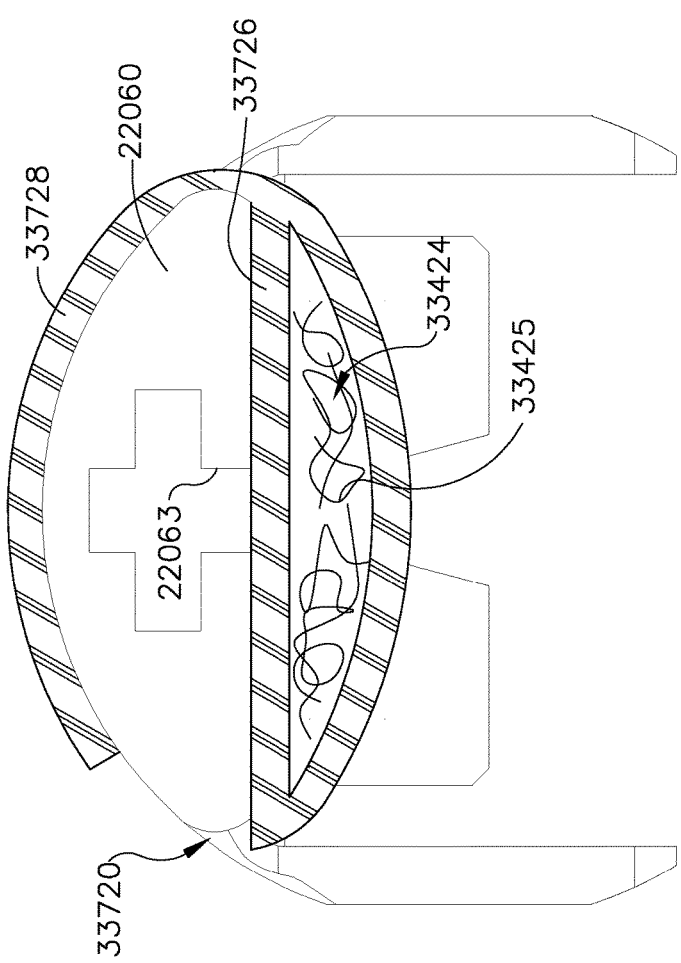
FIG. 253
FIG. 254

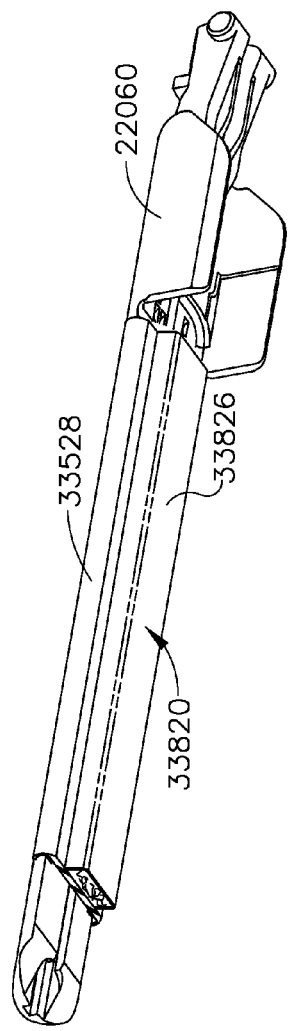
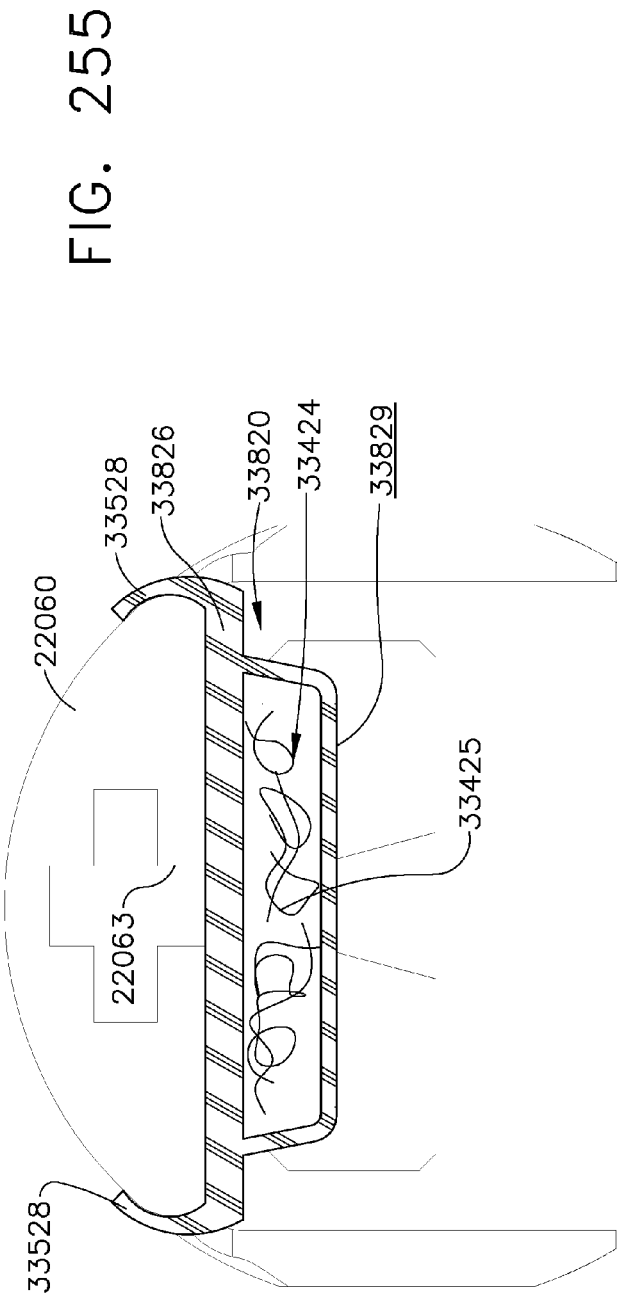
FIG. 255
FIG. 256

TISSUE THICKNESS COMPENSATOR COMPRISING AT LEAST ONE MEDICAMENT

CROSS REFERENCE TO RELATED APPLICATIONS

This non-provisional patent application is a continuation-in-part application claiming priority under 35 U.S.C. §120 to U.S. patent application Ser. No. 13/097,891, entitled "Tissue Thickness Compensator For A Surgical Stapler Comprising An Adjustable Anvil, filed on Apr. 29, 2011, which issued on Oct. 21, 2014 as U.S. Pat. No. 8,864,009, which is a continuation-in-part application under 35 U.S.C. §120 to U.S. patent application Ser. No. 12/894,377, entitled "Selectively Orientable Implantable Fastener Cartridge", filed on Sep. 30, 2010, which issued on Mar. 12, 2013 as U.S. Pat. No. 8,393,514, the entire disclosures of which are hereby incorporated by reference herein.

BACKGROUND

The present invention relates to surgical instruments and, in various embodiments, to surgical cutting and stapling instruments and staple cartridges therefor that are designed to cut and staple tissue.

BRIEF DESCRIPTION OF THE DRAWINGS

The features and advantages of this invention, and the manner of attaining them, will become more apparent and the invention itself will be better understood by reference to the following description of embodiments of the invention taken in conjunction with the accompanying drawings, wherein:

FIGS. 1B-1E illustrate portions of an end effector clamping and stapling tissue with an implantable staple cartridge;

FIG. 2 is a partial cross-sectional side view of another end effector coupled to a portion of a surgical instrument with the end effector supporting a surgical staple cartridge and with the anvil thereof in an open position;

FIG. 3 is another partial cross-sectional side view of the end effector of FIG. 2 in a closed position;

FIG. 4 is another partial cross-sectional side view of the end effector of FIGS. 2 and 3 as the knife bar is starting to advance through the end effector;

FIG. 5 is another partial cross-sectional side view of the end effector of FIGS. 2-4 with the knife bar partially advanced therethrough;

FIGS. 6A-6D diagram the deformation of a surgical staple positioned within a collapsible staple cartridge body in accordance with at least one embodiment;

FIG. 8 is a top view of a staple cartridge in accordance with at least one embodiment comprising staples embedded in a collapsible staple cartridge body;

FIG. 9 is an elevational view of the staple cartridge of FIG. 8;

FIG. 26 is an elevational view of the staple cartridge of FIG. 25;

FIG. 27 is a detail elevational view of the staple cartridge of FIG. 25;

FIG. 29 is a bottom view of the staple cartridge of FIG. 25;

FIG. 30 is a detail bottom view of the staple cartridge of FIG. 25;

FIG. 31 is a longitudinal cross-sectional view of an anvil in a closed position and a staple cartridge comprising a rigid support portion and a compressible tissue thickness compensator illustrated with staples being moved from an unfired position to a fired position during a first sequence;

FIG. 32 is another cross-sectional view of the anvil and the staple cartridge of FIG. 31 illustrating the anvil in an open position after the firing sequence has been completed;

FIG. 39 is an elevational view of an anvil in a closed position and a staple cartridge comprising a rigid support portion and a compressible tissue thickness compensator illustrating the staples in an unfired position illustrating thicker tissue positioned between the anvil and the staple cartridge;

FIG. 40 is a detail view of the anvil and staple cartridge of FIG. 39;

FIG. 41 is an elevational view of the anvil and staple cartridge of FIG. 39 illustrating tissue having different thicknesses positioned between the anvil and the staple cartridge;

FIG. 42 is a detail view of the anvil and staple cartridge of FIG. 39 as illustrated in FIG. 41;

FIG. 45 is a diagram illustrating a circumstance wherein one or more staples have been improperly formed;

FIG. 46 is a diagram illustrating a tissue thickness compensator which could compensate for improperly formed staples;

FIG. 54 is a diagram illustrating tissue having another intermediate thickness and a tissue thickness compensator captured within a staple;

FIG. 55 is a diagram illustrating thick tissue and a tissue thickness compensator captured within a staple;

FIG. 56 is a partial cross-sectional view of an end effector of a surgical stapling instrument illustrating a firing bar and staple-firing sled in a retracted, unfired position;

FIG. 57 is another partial cross-sectional view of the end effector of FIG. 56 illustrating the firing bar and the staple-firing sled in a partially advanced position;

FIG. 58 is a cross-sectional view of the end effector of FIG. 56 illustrating the firing bar in a fully advanced, or fired, position;

FIG. 65 is a side view of the retainer assembly shown in FIG. 61 engaged with the staple cartridge of FIG. 64;

FIG. 66 is a side view of the retainer assembly shown in FIG. 61 engaged with the staple cartridge and the anvil of FIG. 64 illustrating the anvil in a closed position;

FIG. 84 is a side cross-sectional view of a retainer assembly comprising a retainer, tissue thickness compensators mounted on first and second surfaces of the retainer, and connectors passing through holes in the retainer in accordance with at least one embodiment;

FIG. 85 is a perspective view of the retainer assembly of FIG. 84 illustrated with a portion of a tissue thickness compensator removed for the purposes of illustration;

FIG. 86 is a side view of the retainer assembly of FIG. 84 engaged with a surgical stapler comprising an anvil illustrated in an open position;

FIG. 87 is a side view of the retainer assembly of FIG. 84 and the anvil of FIG. 86 illustrated in a closed position;

FIG. 88 is a side view of the retainer assembly of FIG. 84 illustrating the retainer being removed from between the tissue thickness compensators of the retainer assembly;

FIG. 95 illustrates the retainer assembly and staple cartridge of FIG. 94 engaging an anvil of an end effector of a surgical stapler;

FIG. 96 illustrates the retainer assembly and staple cartridge of FIG. 94 engaging the anvil of the end effector of the surgical stapler of FIG. 95;

FIG. 97 illustrates the retainer assembly and staple cartridge of FIG. 94 engaged on the anvil of the surgical stapler of FIG. 95;

FIG. 98 illustrates the retainer assembly and staple cartridge of FIG. 94 engaged on the anvil of the surgical stapler of FIG. 95 and the anvil being moved into a closed position;

FIG. 99 illustrates the anvil of the surgical stapler of FIG. 95 in an open position with the tissue thickness compensator attached thereto and the retainer engaged with the staple cartridge channel of the surgical stapler;

FIG. 100 illustrates the retainer of FIG. 94 engaged with the staple cartridge channel of the surgical stapler of FIG. 95 and the anvil in an open position;

FIG. 105 is a rear perspective view of an embodiment of an insertion tool configured for use with the retainer of FIG. 103;

FIG. 106 is a top perspective view of the insertion tool of FIG. 105;

FIG. 113 illustrates the retainer assembly of FIG. 110 being inserted into a surgical instrument comprising an anvil and a staple cartridge channel, wherein a portion of the insertion tool is removed for the purposes of illustration;

FIG. 114 illustrates the insertion tool of FIG. 105 being moved relative to the retainer to engage the staple cartridge in the staple cartridge channel and to engage the tissue thickness compensator with the anvil, wherein a portion of the insertion tool is removed for the purposes of illustration;

FIG. 115 illustrates the insertion tool of FIG. 105 being moved relative to the retainer to disengage the retainer from the tissue thickness compensator and from the staple cartridge, wherein a portion of the insertion tool is removed for the purposes of illustration;

FIG. 116 is a cross-sectional view of a tissue thickness compensator attached to an anvil of a surgical stapling instrument in accordance with at least one embodiment;

FIG. 117 is a diagram illustrating deformed staples at least partially capturing the tissue thickness compensator of FIG. 116 therein;

FIG. 118 is a cross-sectional view of an end effector of a surgical stapling instrument including a staple cartridge comprising a first tissue thickness compensator and an anvil comprising a second tissue thickness compensator in accordance with at least one embodiment;

FIG. 119 is a cross-sectional view of the end effector of FIG. 118 illustrating staples from the staple cartridge moved from an unfired position to a fired position;

FIG. 120 is a perspective view of a tissue thickness compensator attached to an anvil of an end effector wherein the tissue thickness compensator comprises a plurality of capsules in accordance with at least one embodiment;

FIG. 120A is a partial perspective view of the tissue thickness compensator of FIG. 120;

FIG. 121 is a cross-sectional view of staples being moved from an unfired position to a fired position to puncture the capsules of the tissue thickness compensator of FIG. 120;

FIG. 122 is an exploded view of an anvil and a tissue thickness compensator in accordance with at least one embodiment;

FIG. 123 is a cross-sectional view of an anvil comprising a plurality of staple forming pockets and a tissue thickness compensator comprising a plurality of capsules aligned with the forming pockets in accordance with at least one embodiment;

Figure 123:
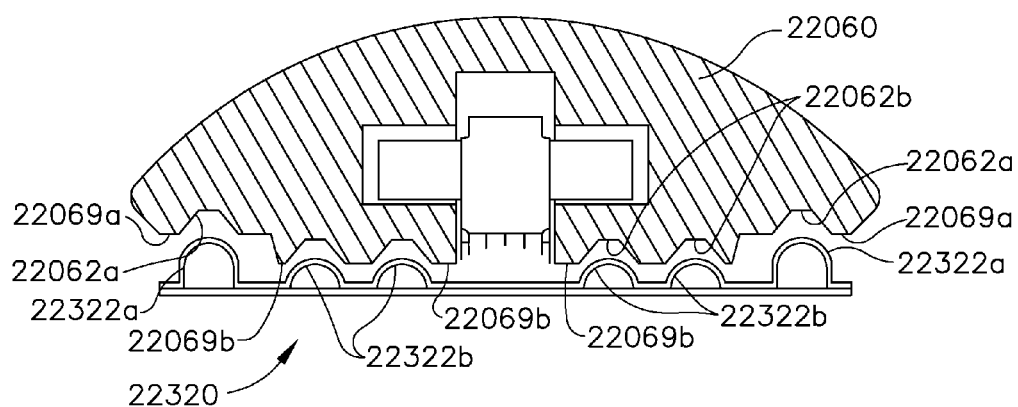
Figure 124:
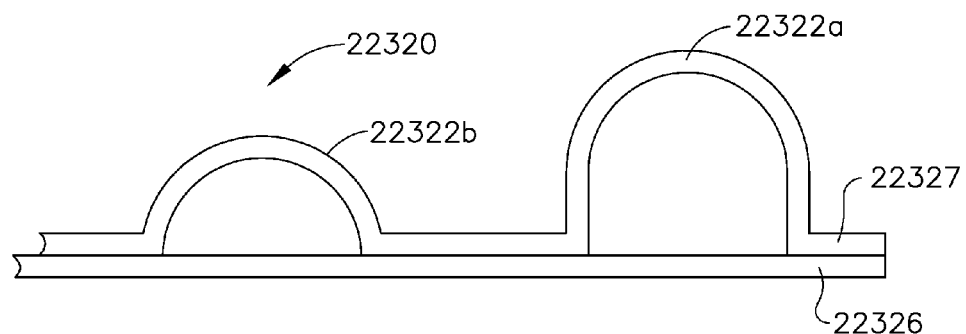
Figure 125:
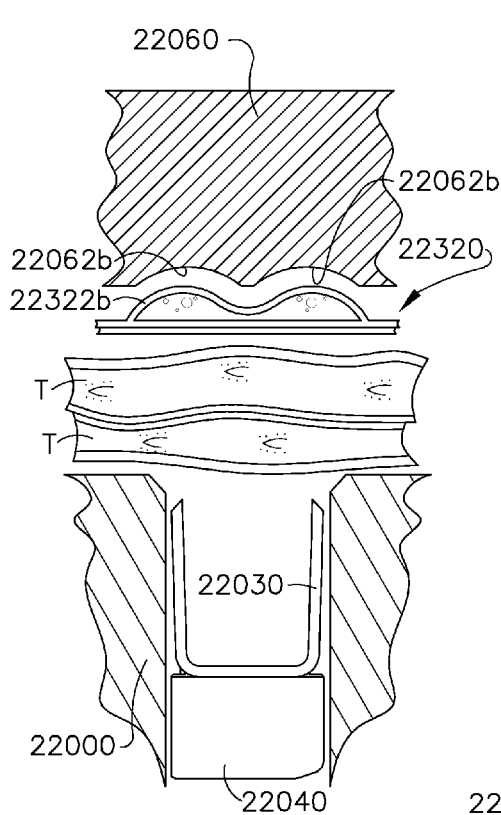
Figure 126:
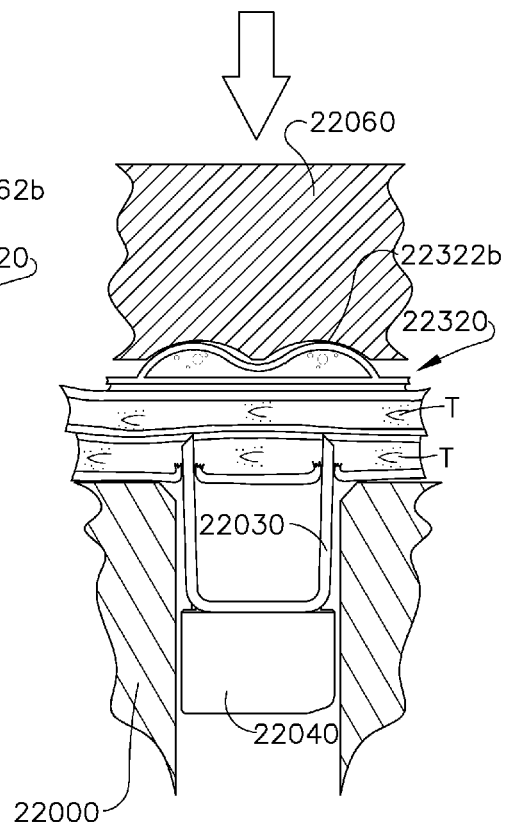
Figure 127:
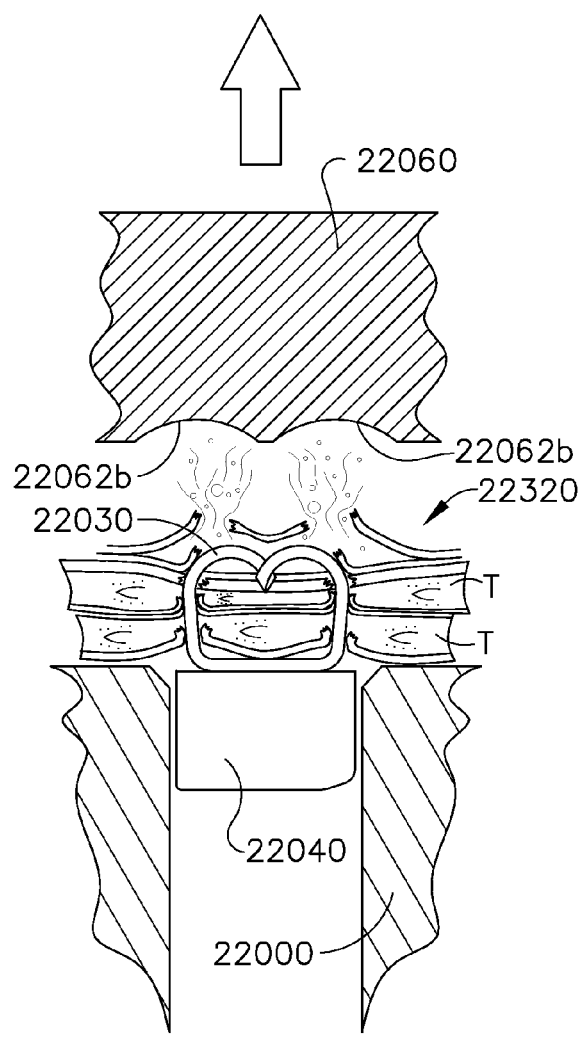
Figure 128:
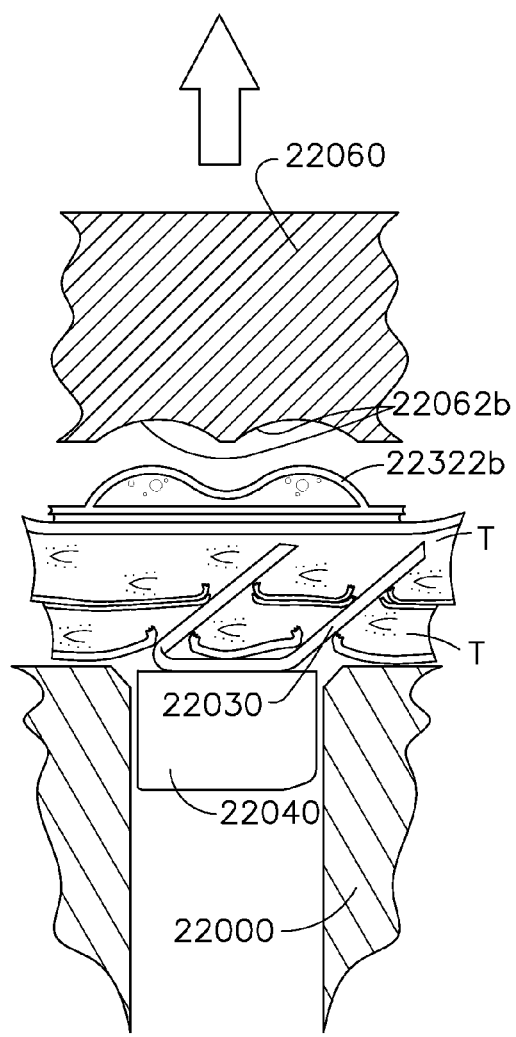
Figure 129:
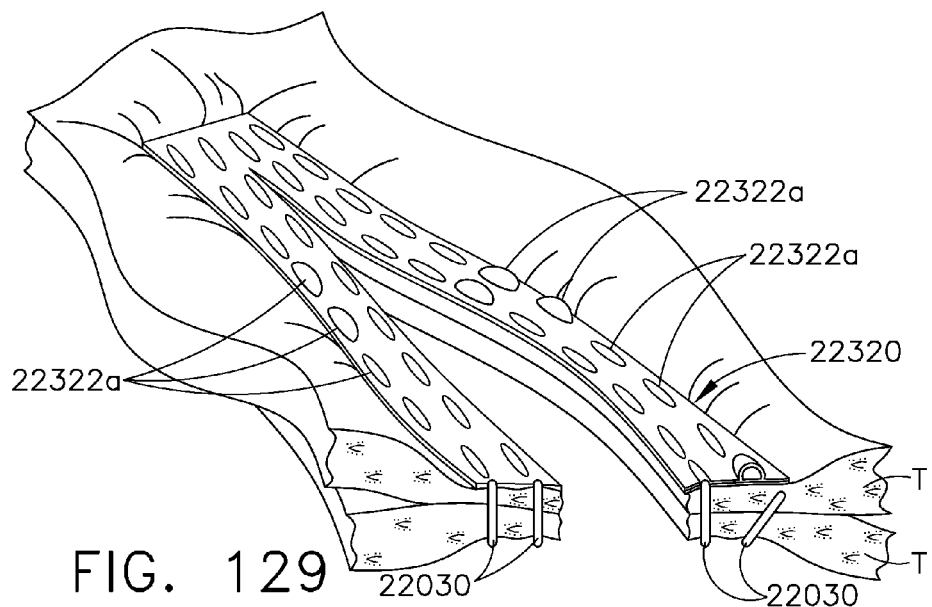
Figure 130:
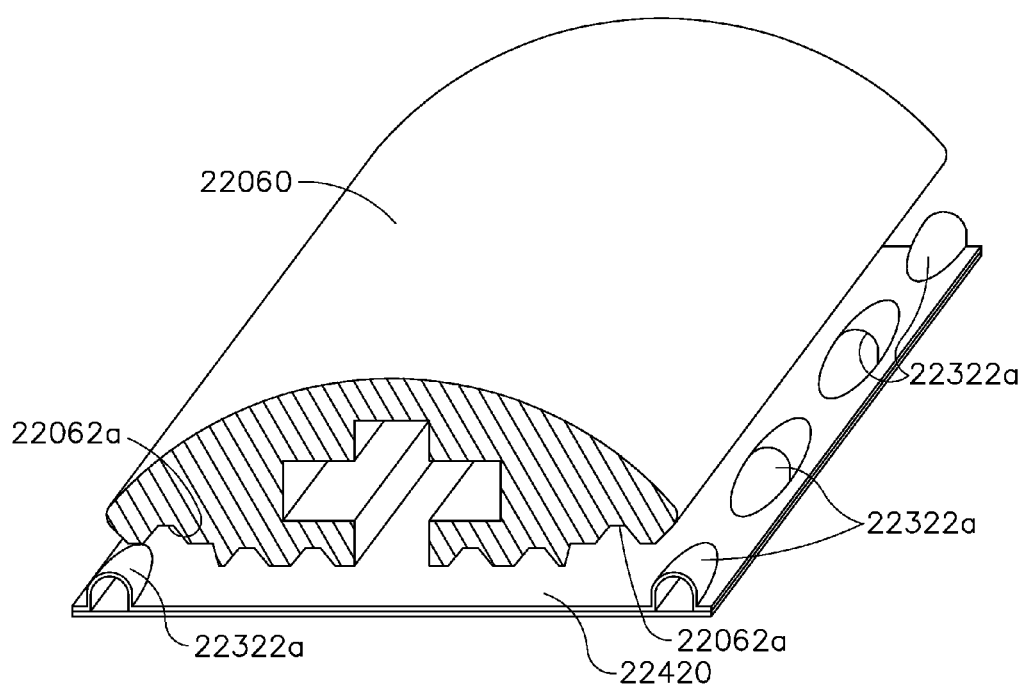
Figure 131:
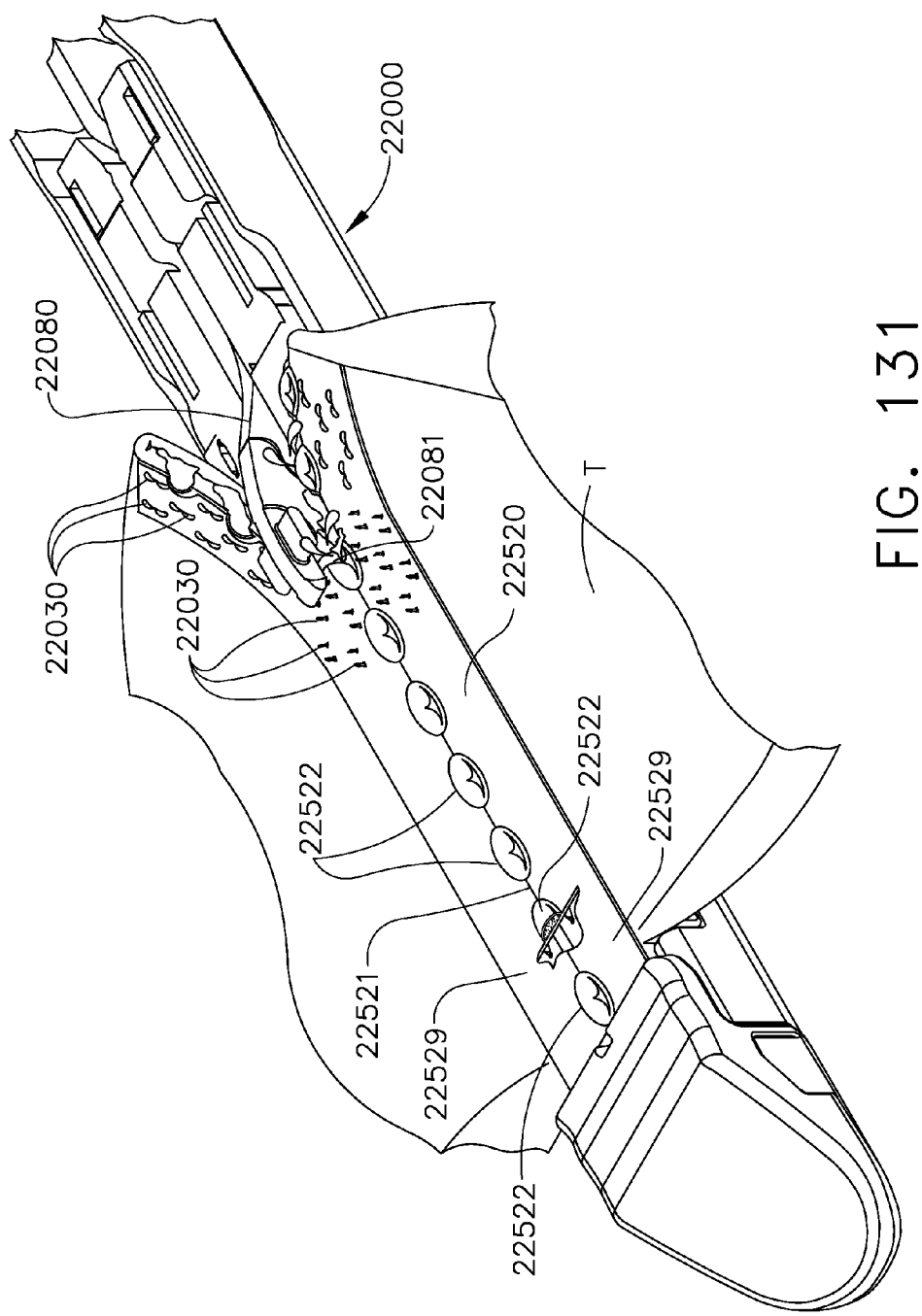
Figure 132:
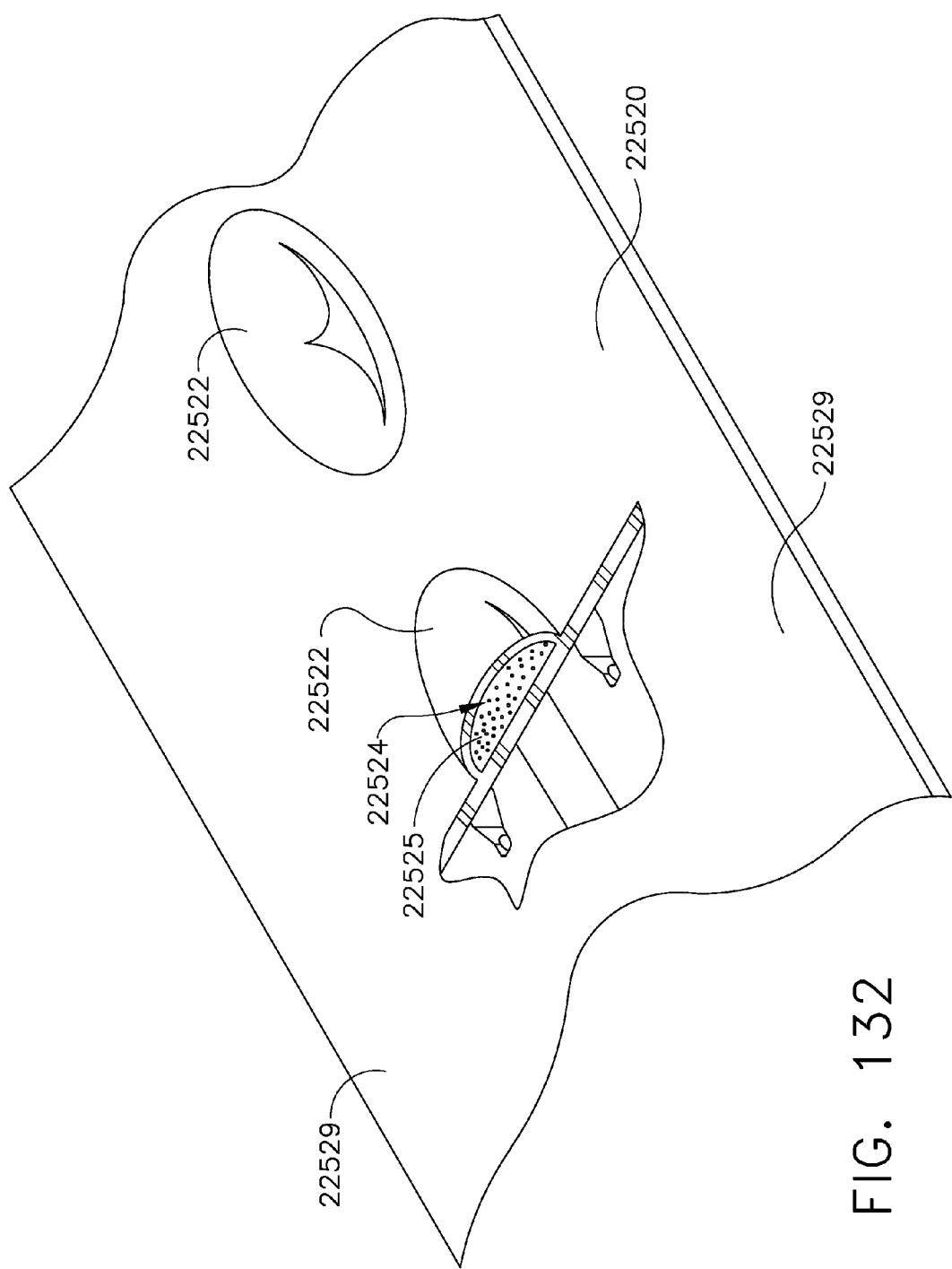
Figure 133:
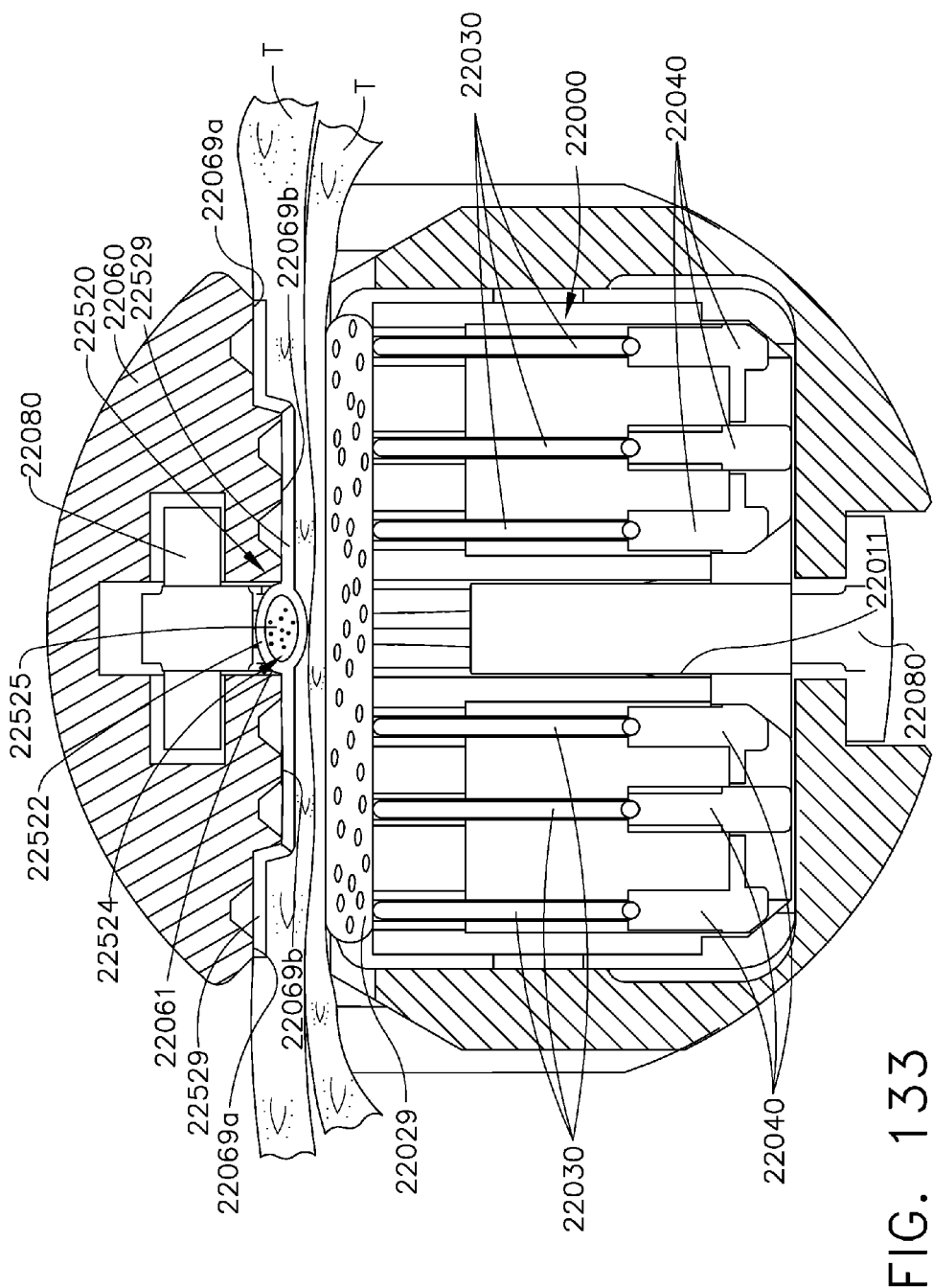
Figure 134:
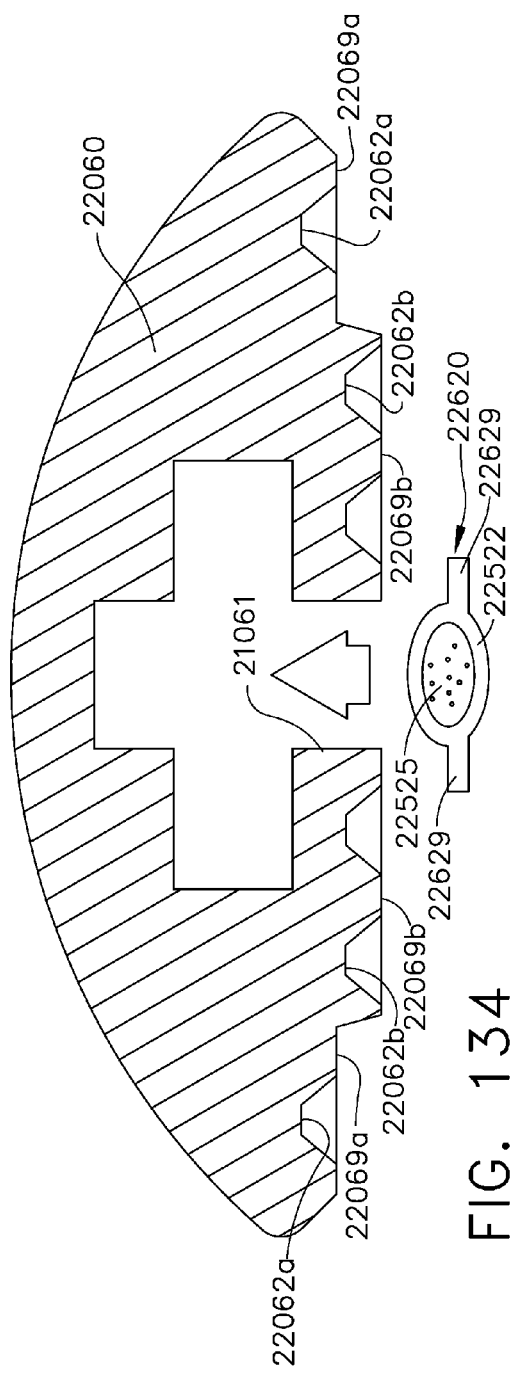
Figure 135:
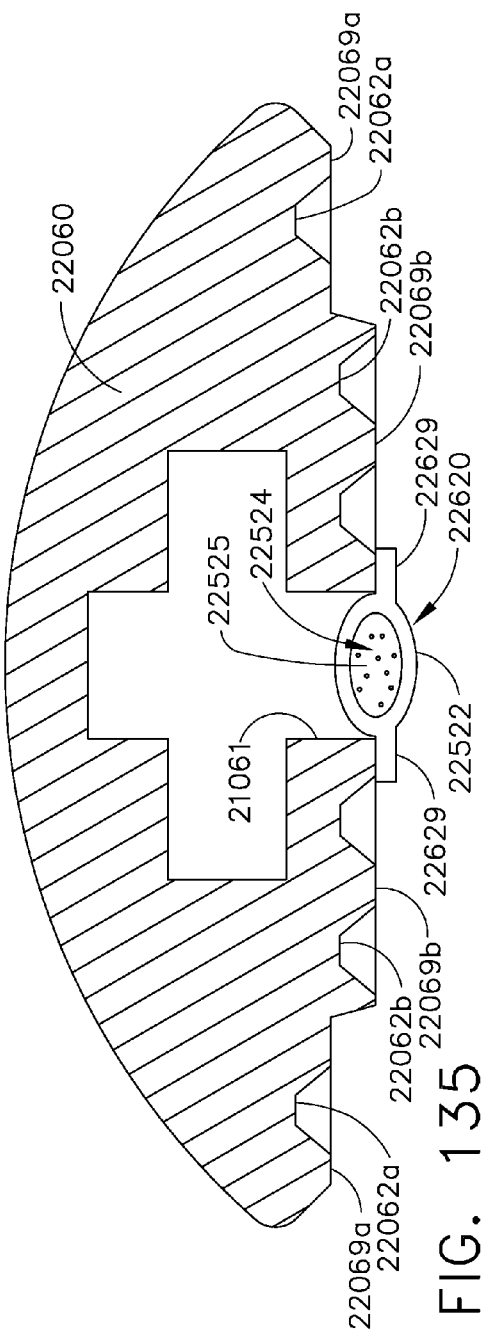
Figure 136:
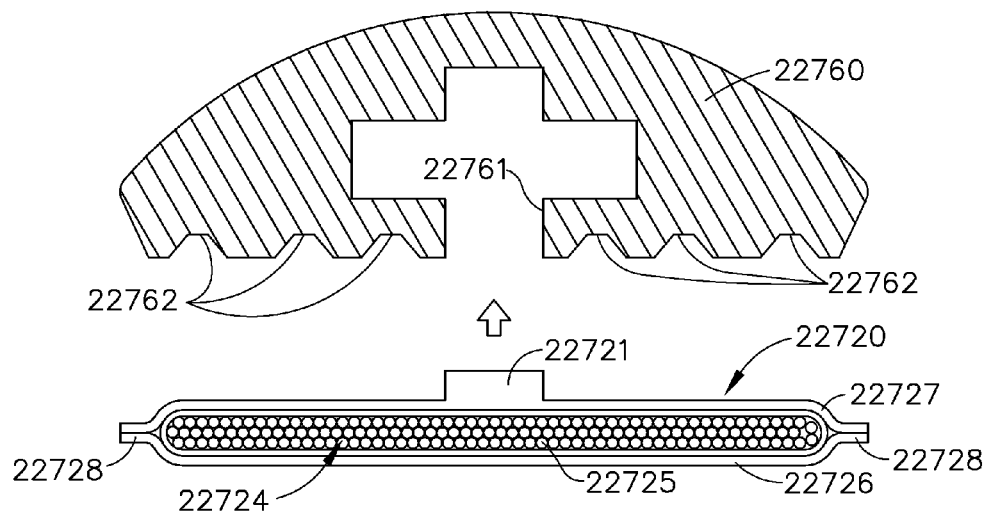
Figure 137:
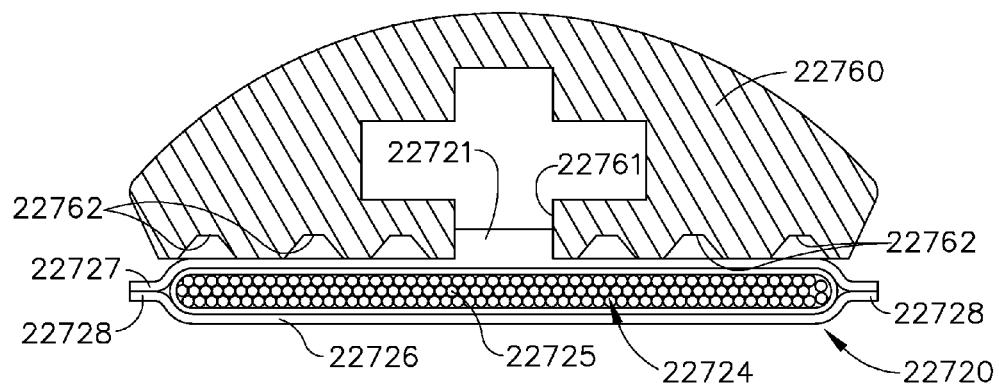
Figure 138:
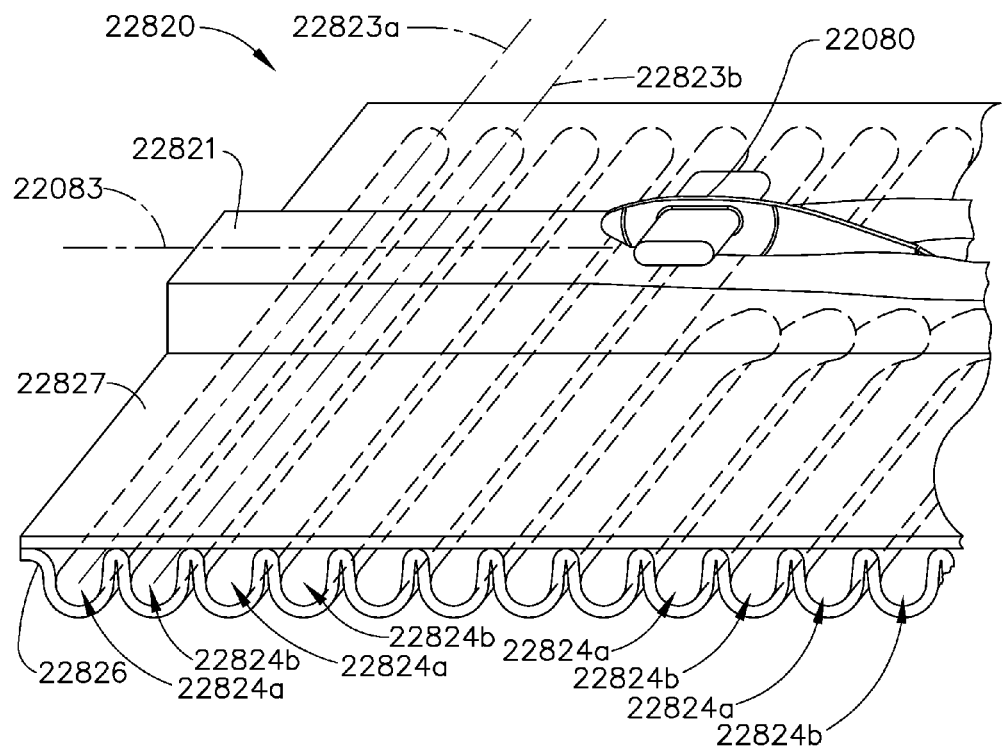
Figure 139:
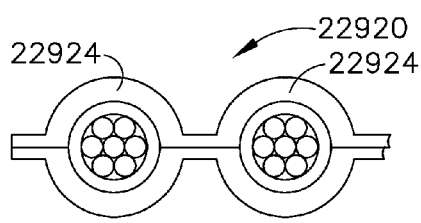
Figure 140:
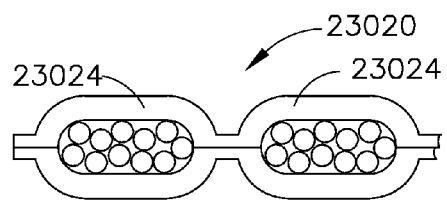
Figure 141:
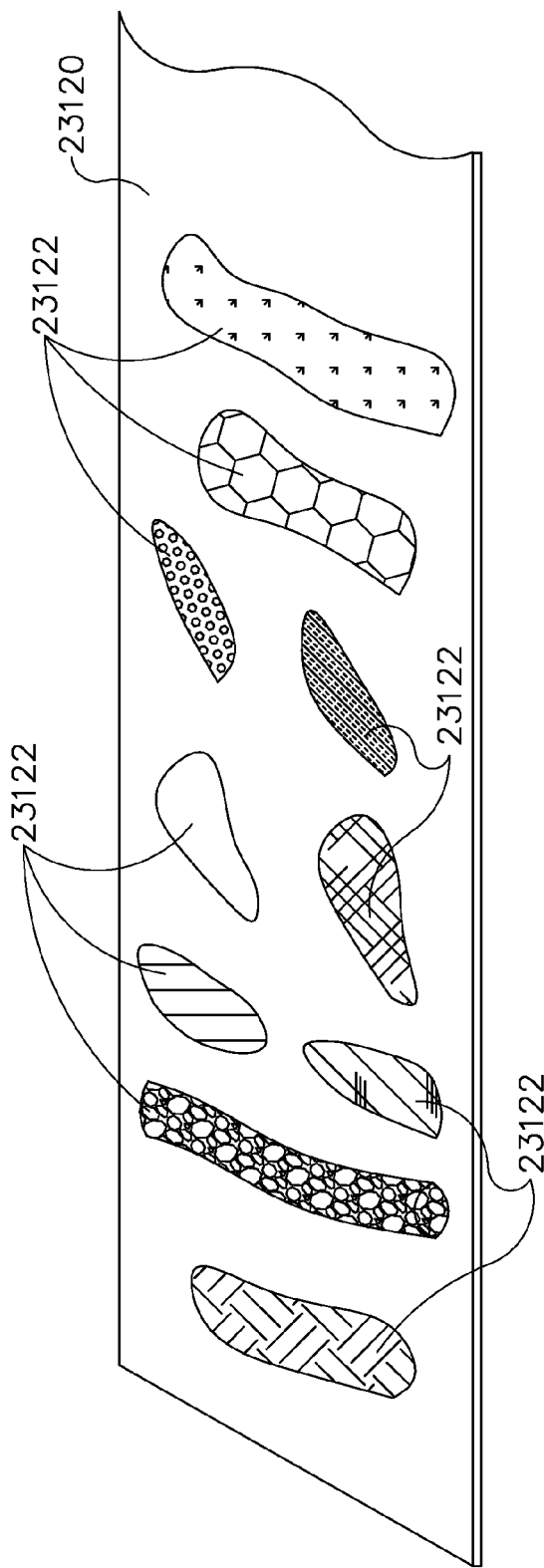
Figure 142:
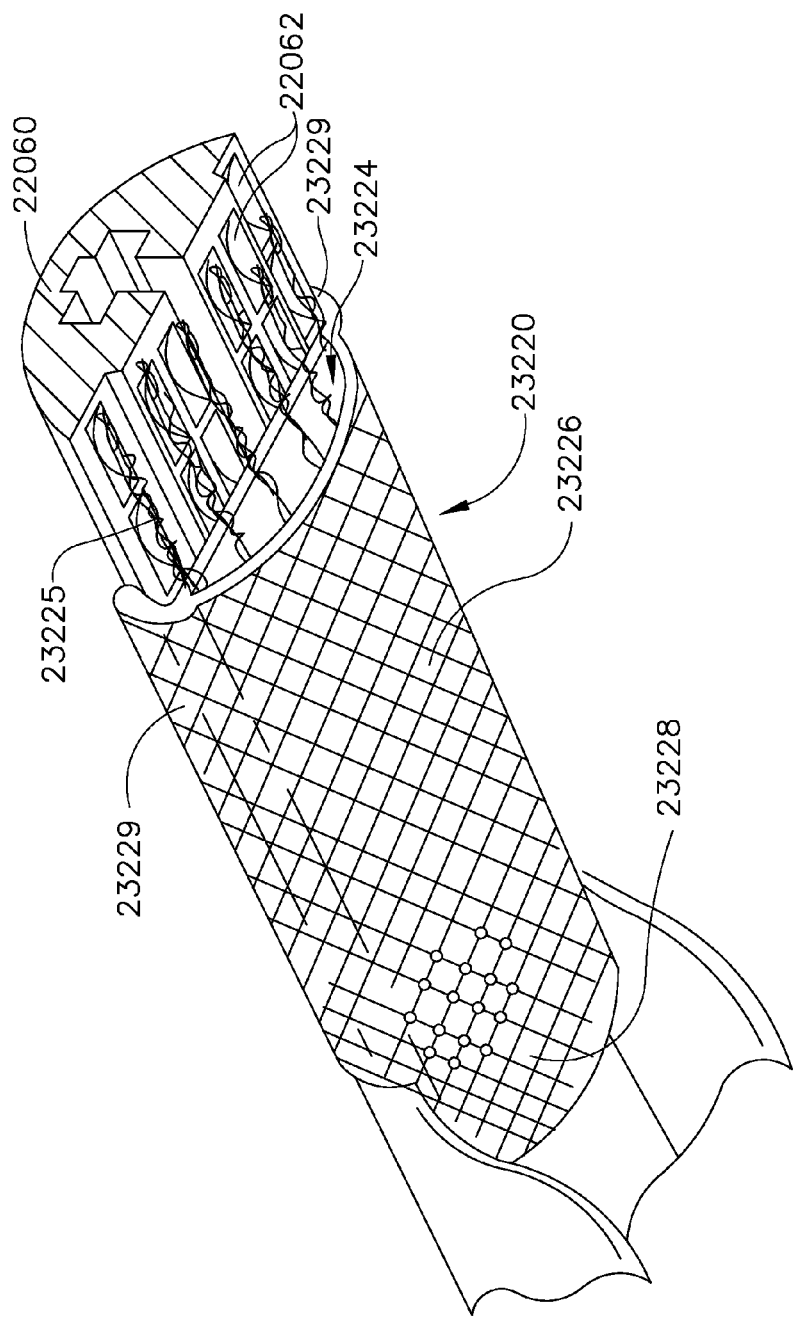
Figure 152:
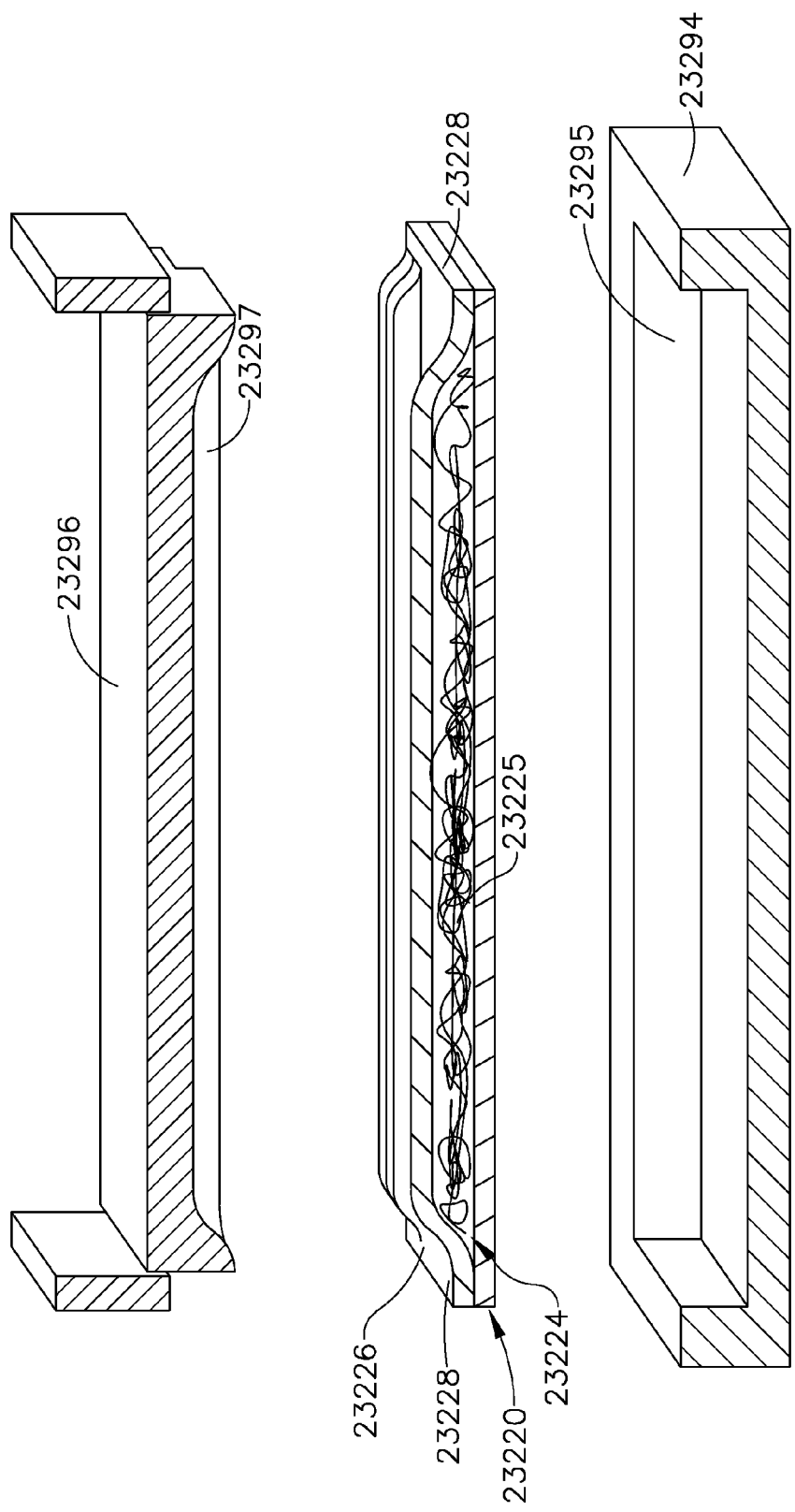
Figure 153:
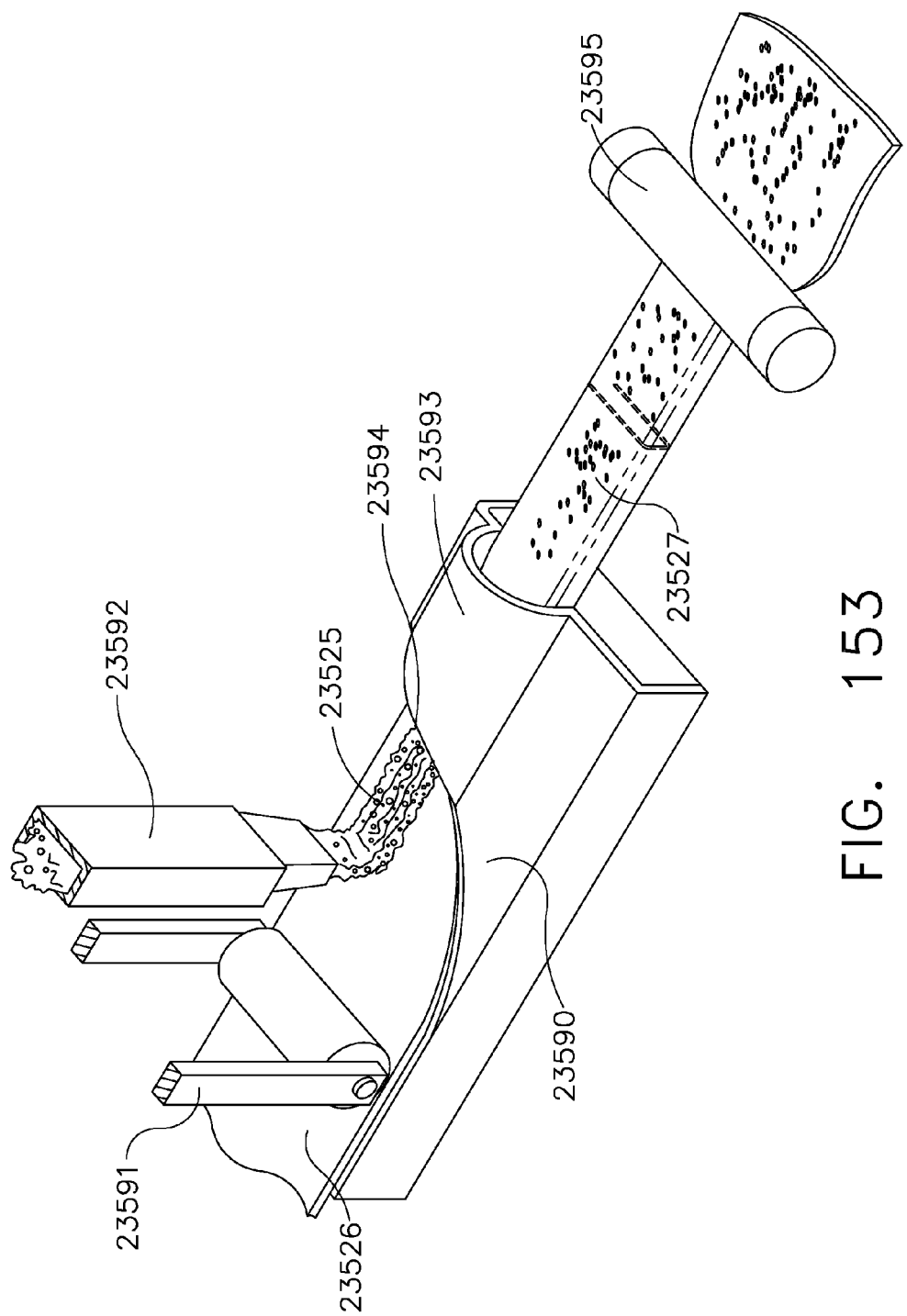
Figure 154:
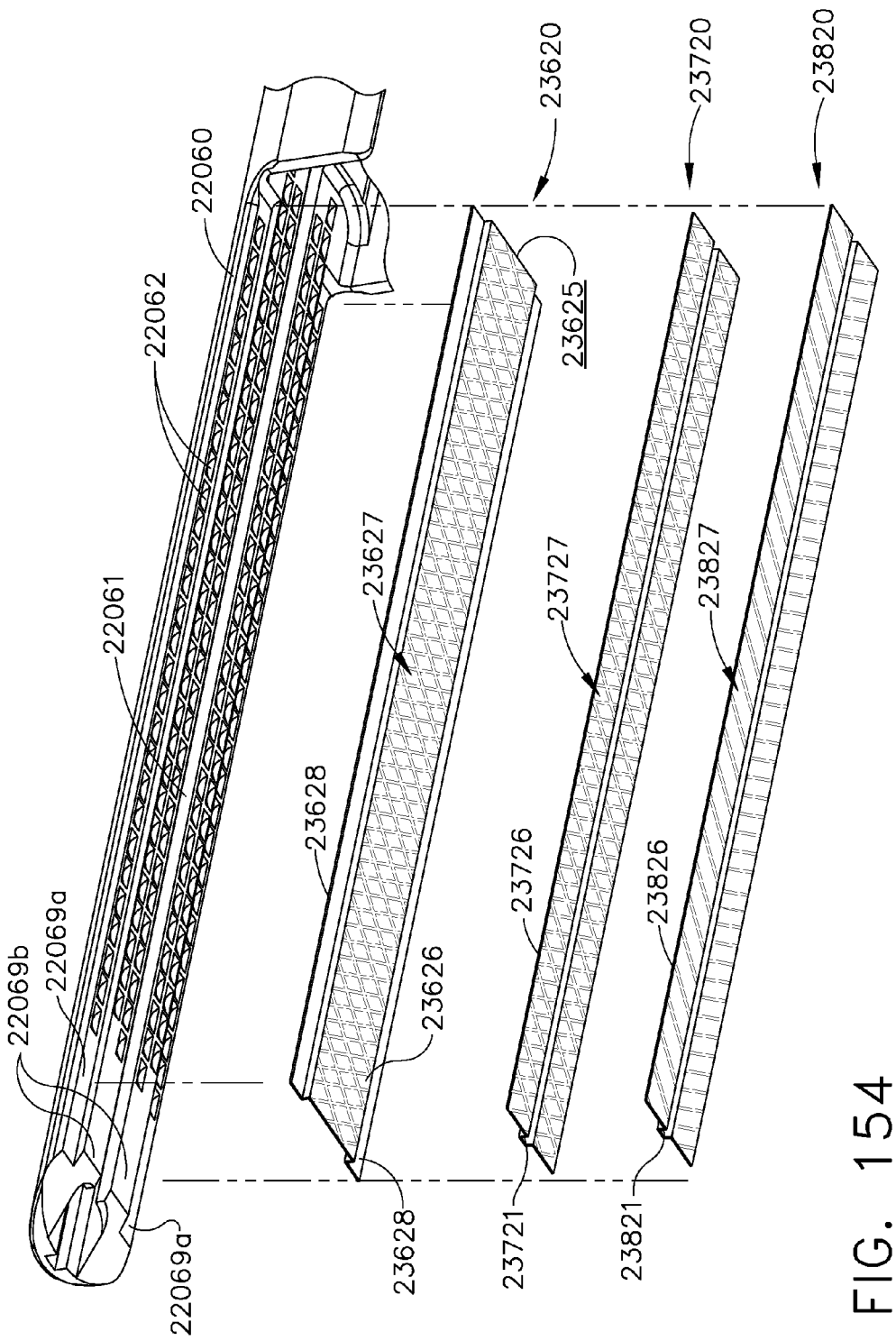
Figure 155:
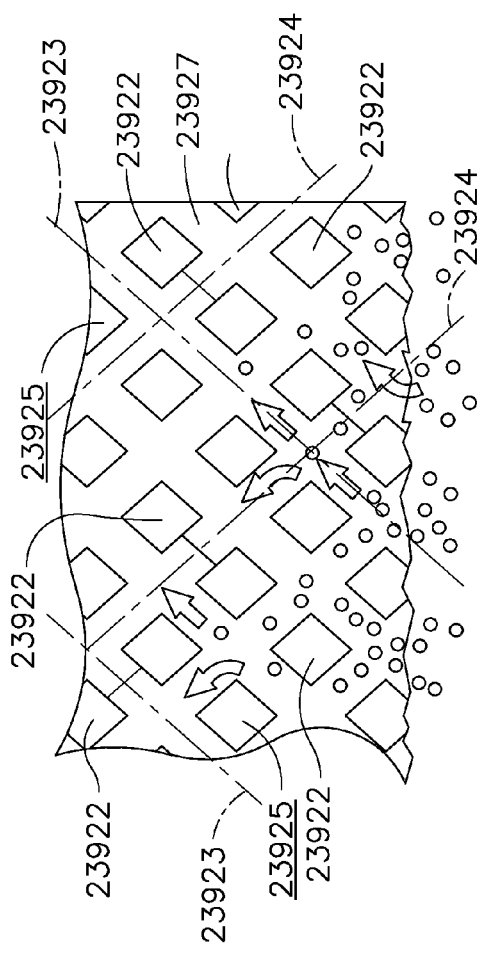
Figure 156:
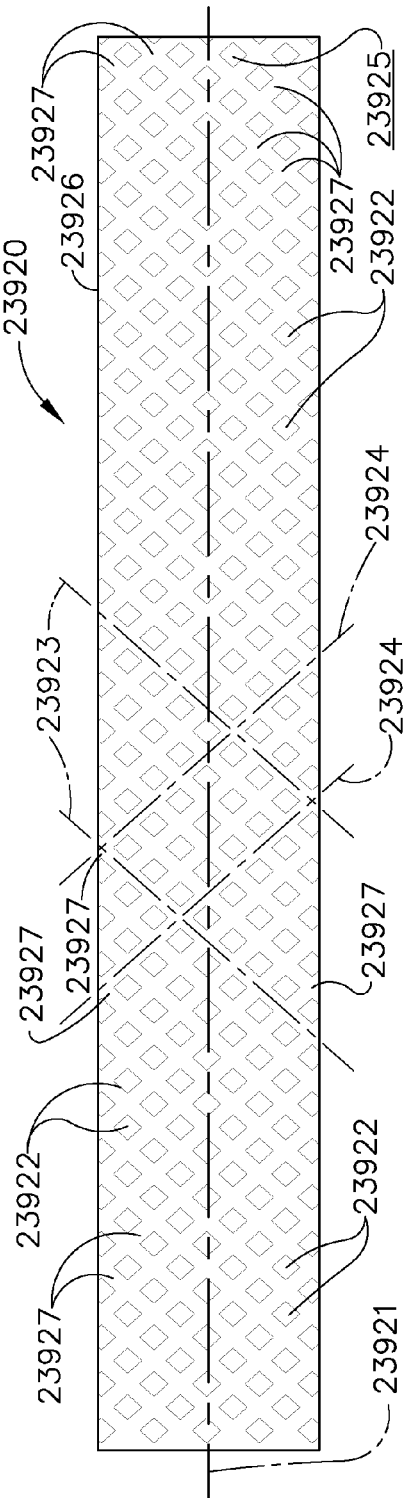
Figure 157:
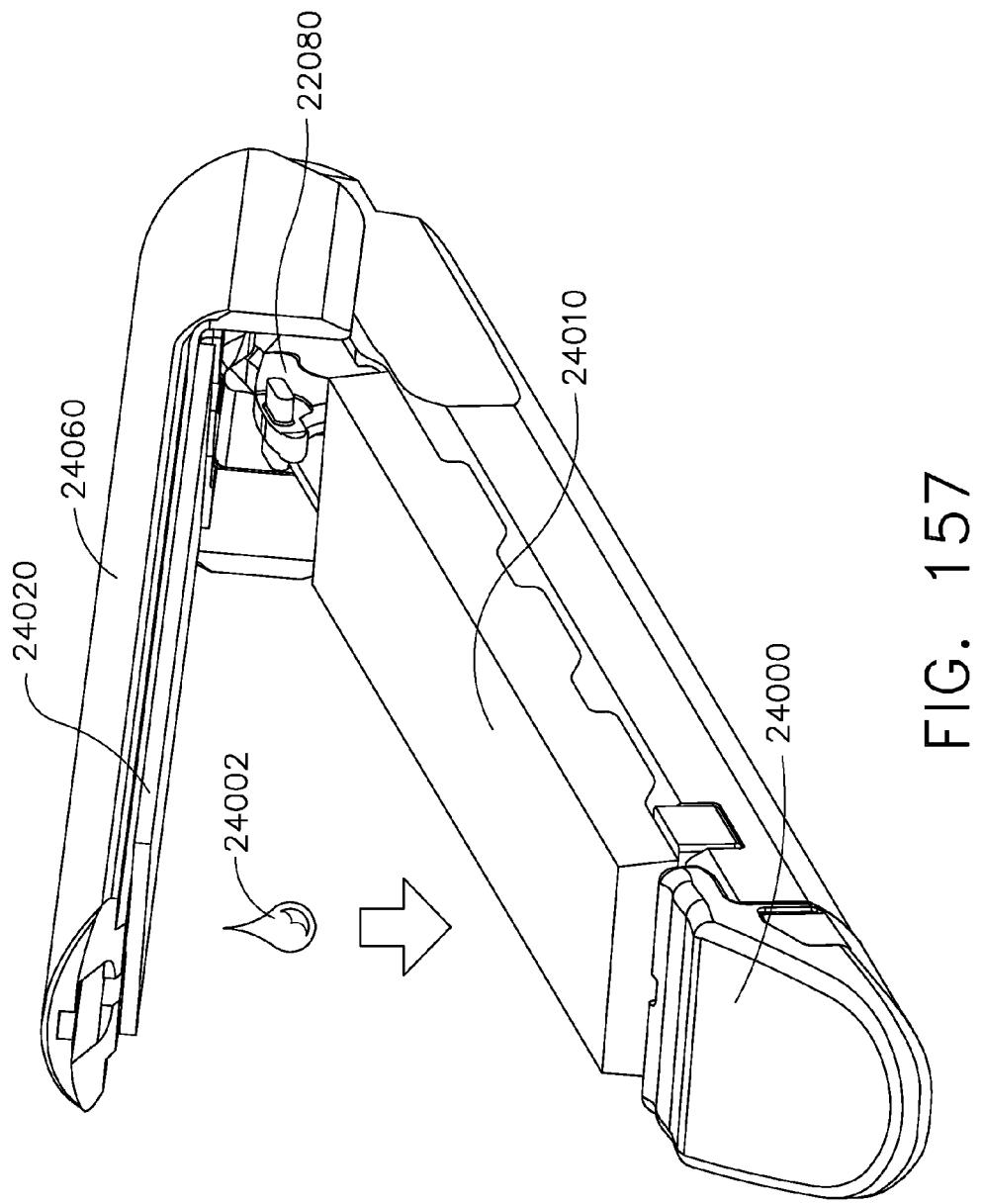
Figure 158:
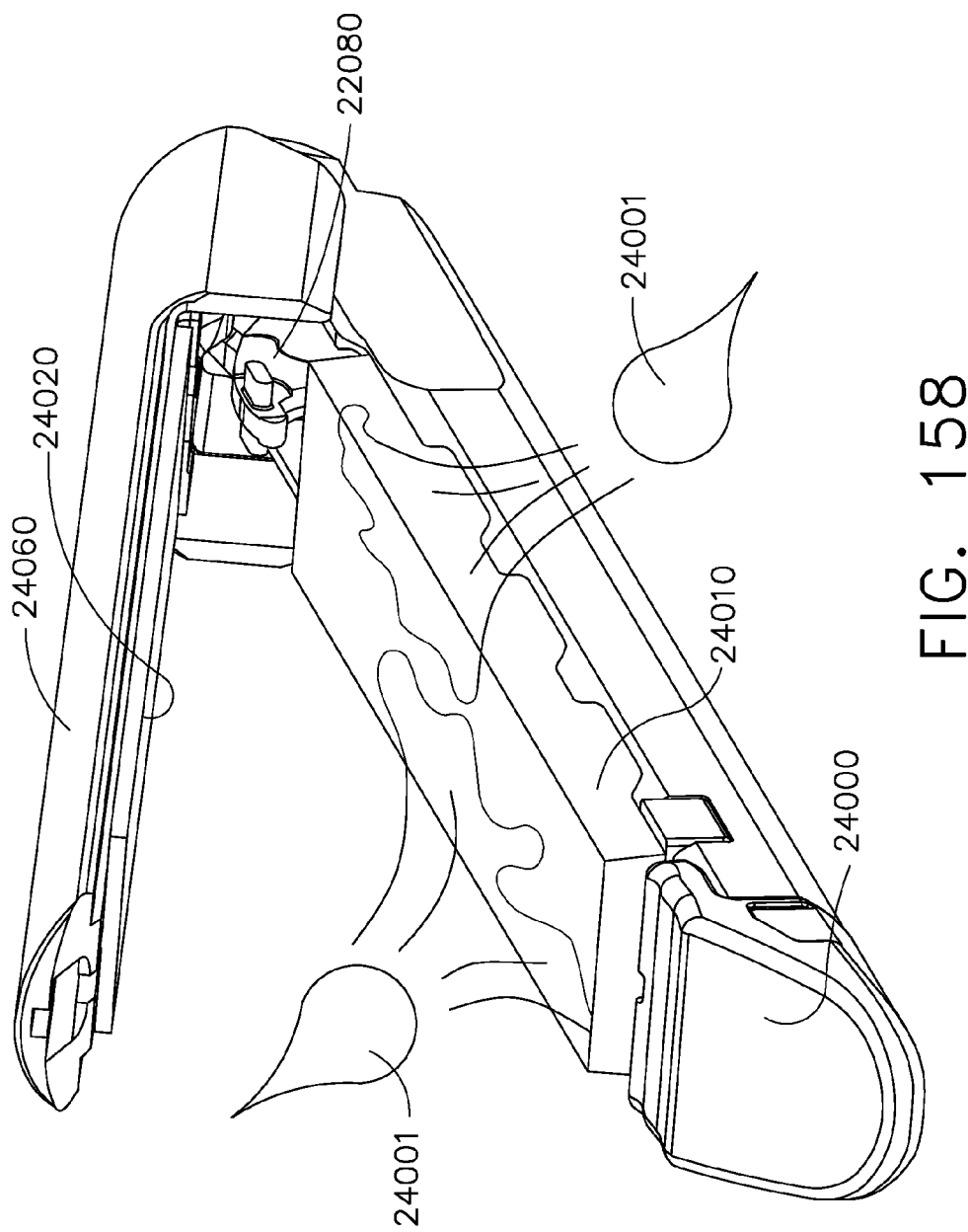
Figure 161:
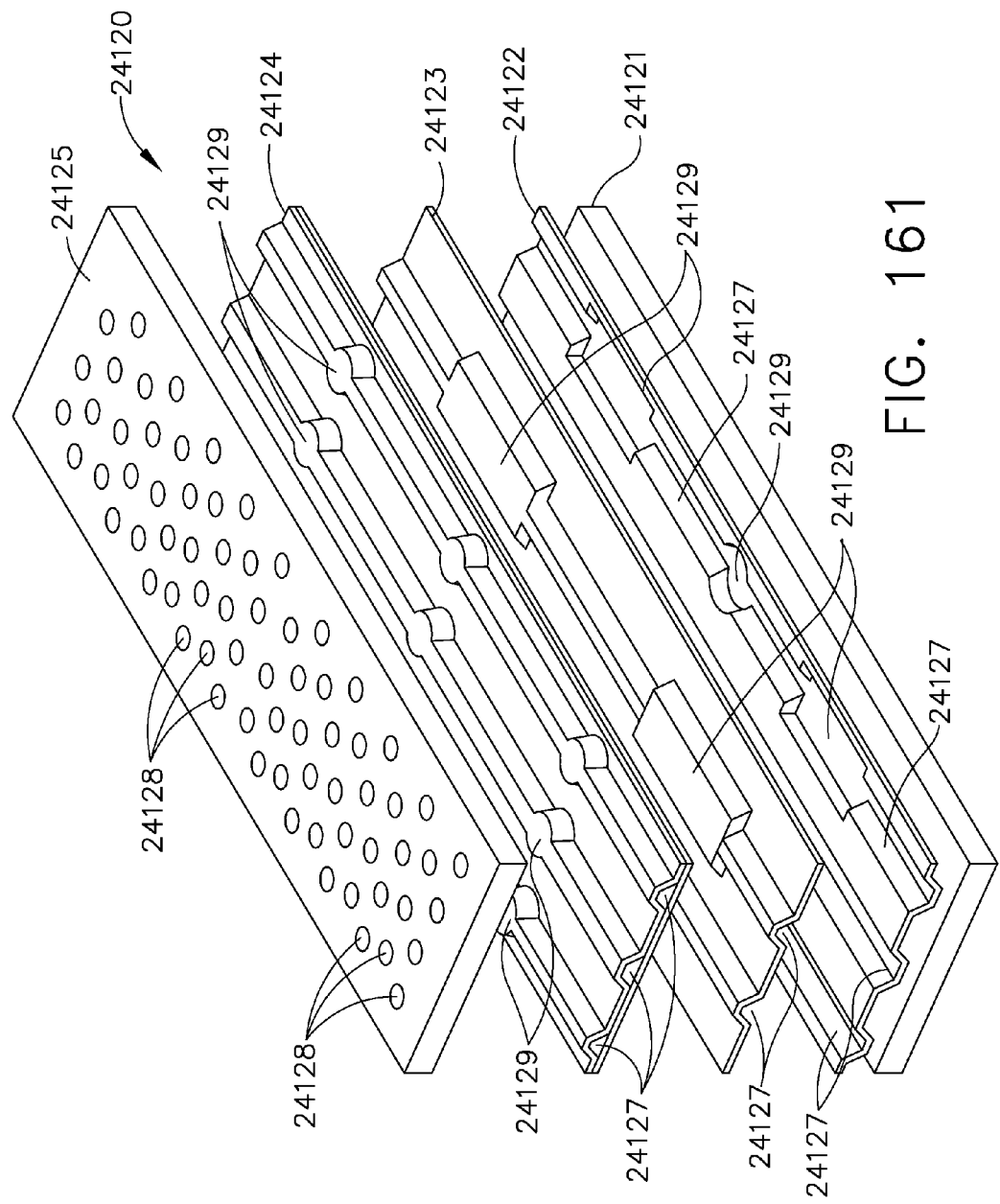
Figure 175:
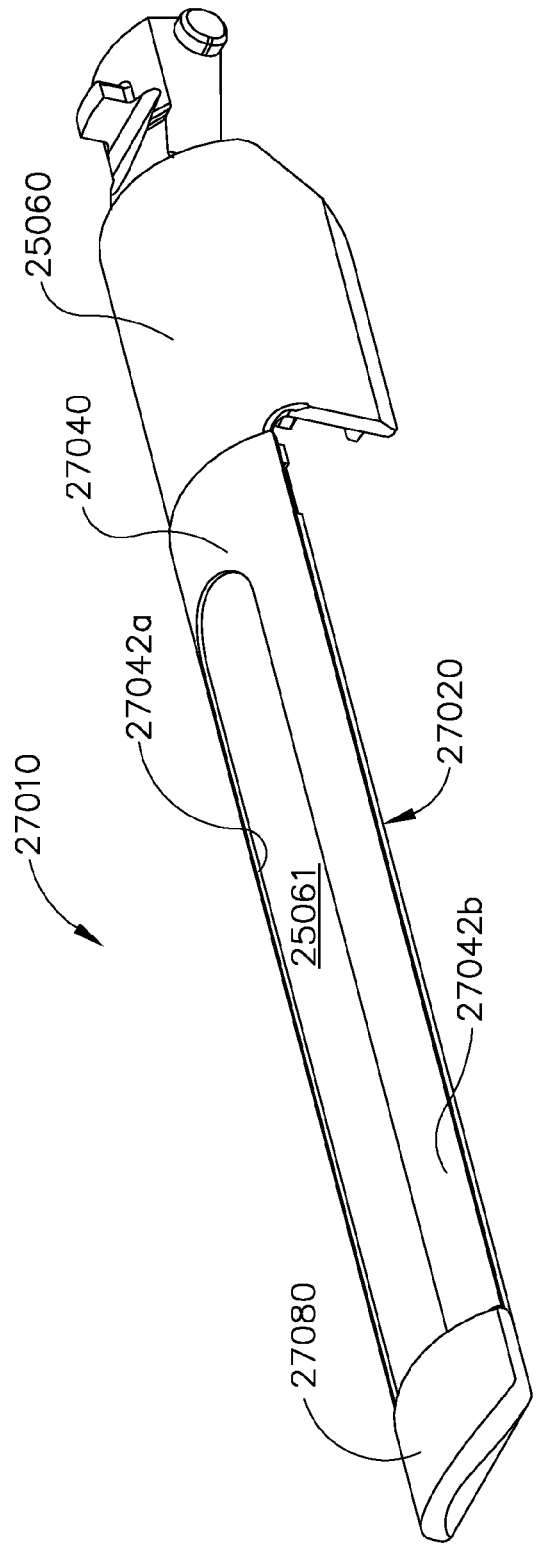
Figure 188:
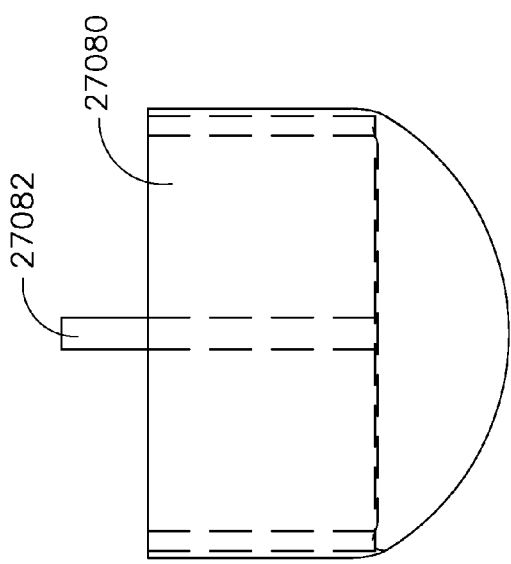
Figure 189:
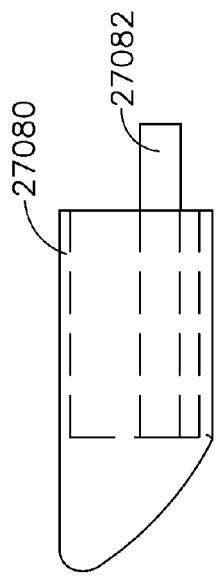
Figure 186:
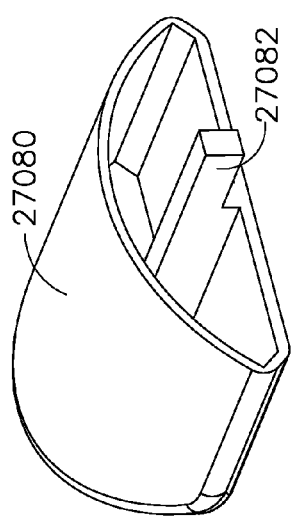
Figure 187:
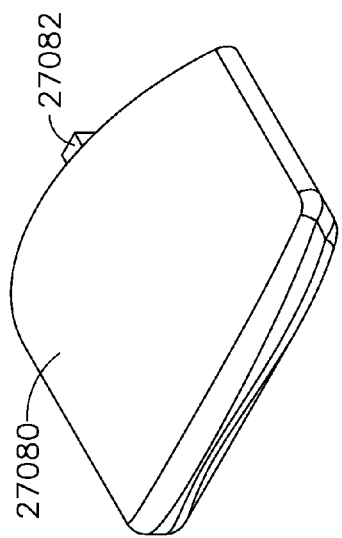
Figure 190:
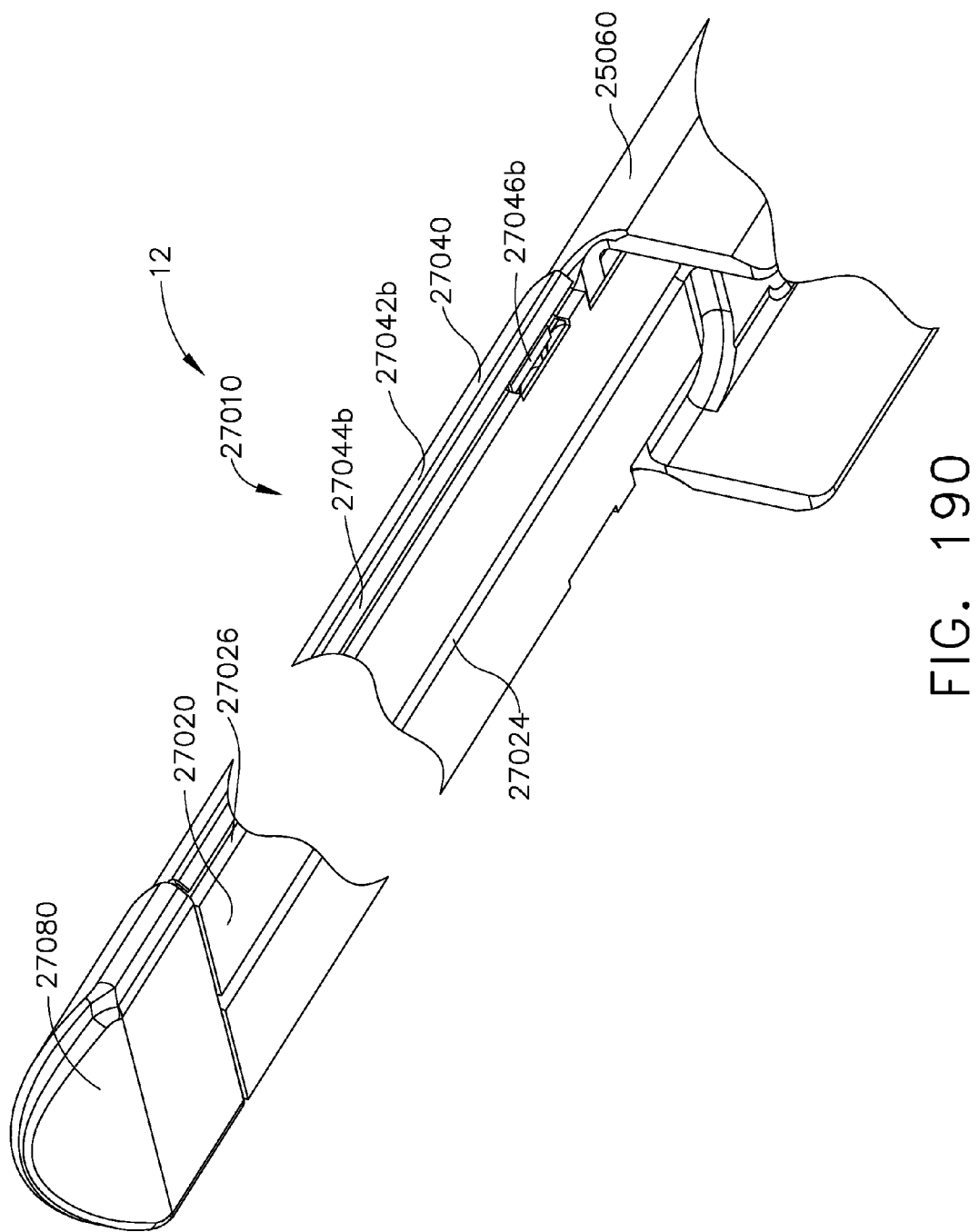
Figure 191:
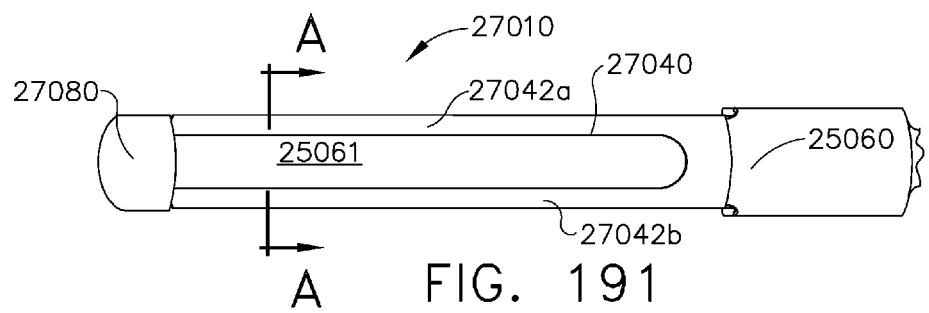
Figure 192:
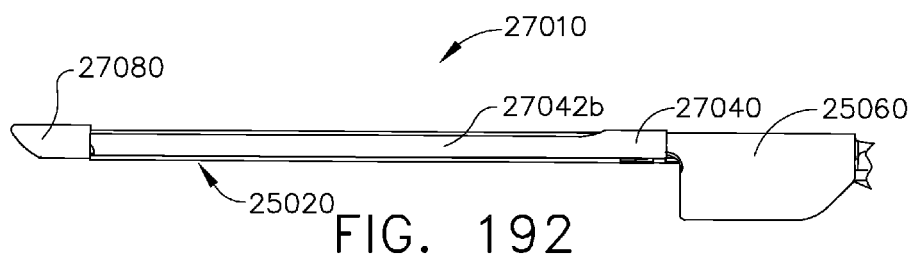
Figure 193:
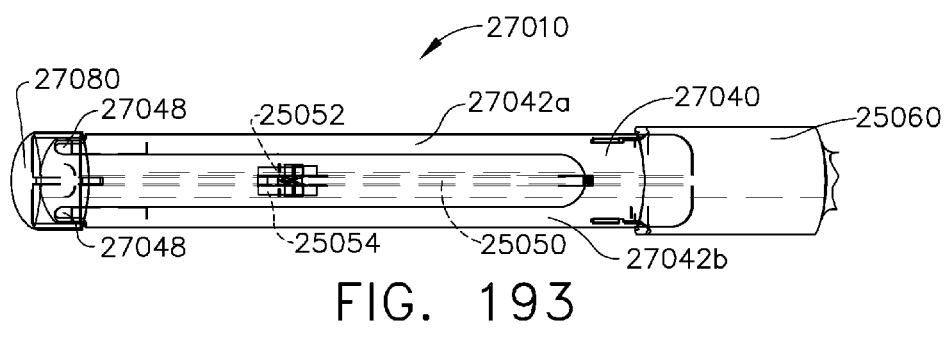
Figure 194:
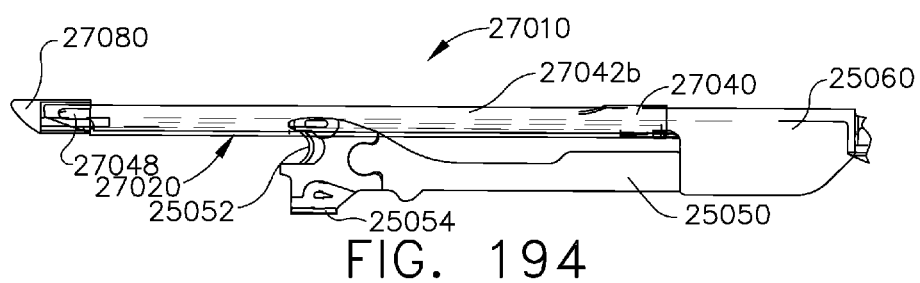
Figure 195:
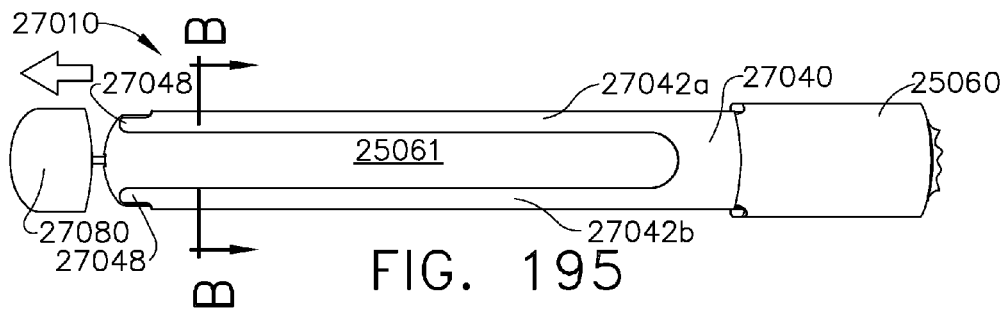
Figure 196:
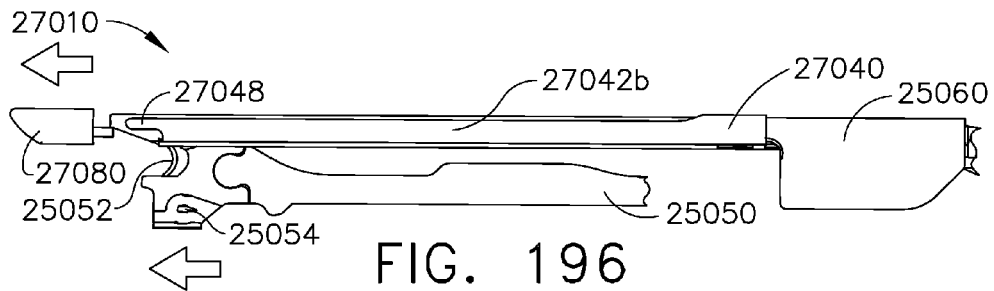
Figure 197:
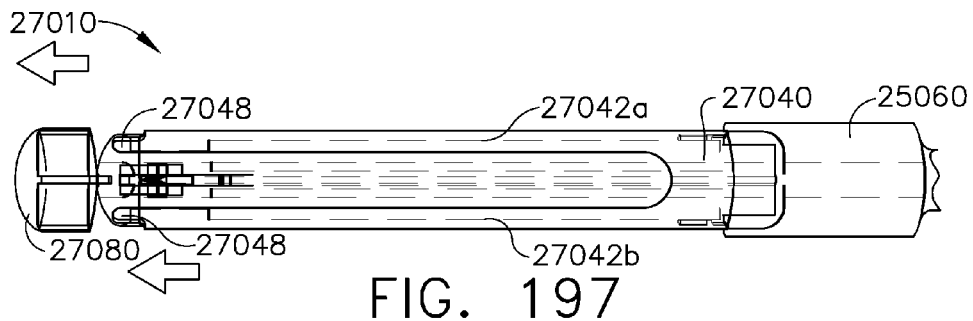
Figure 198:
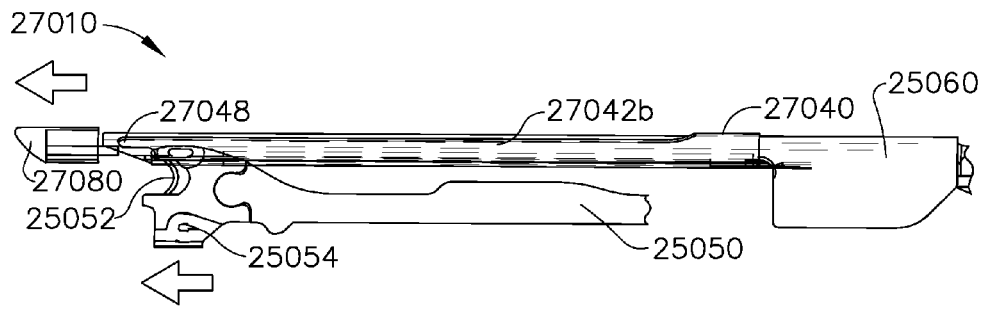
Figure 199:
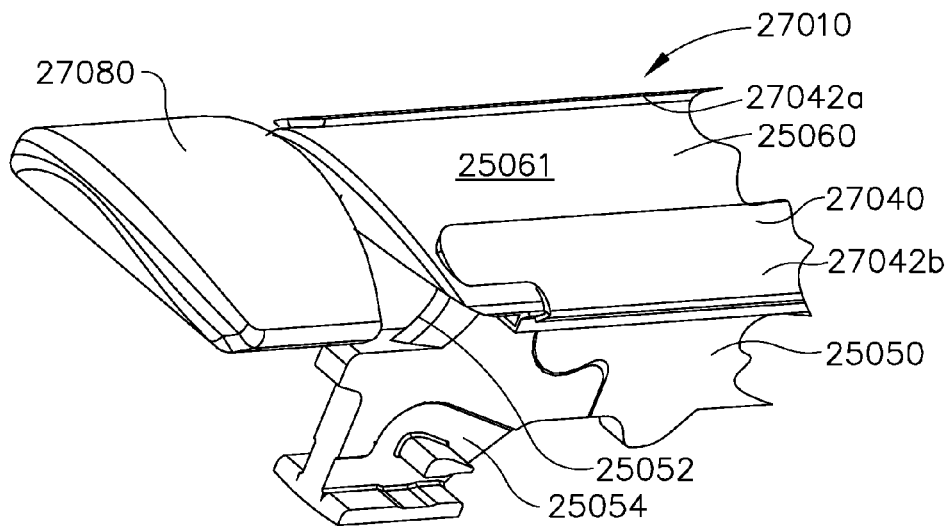
Figure 200:
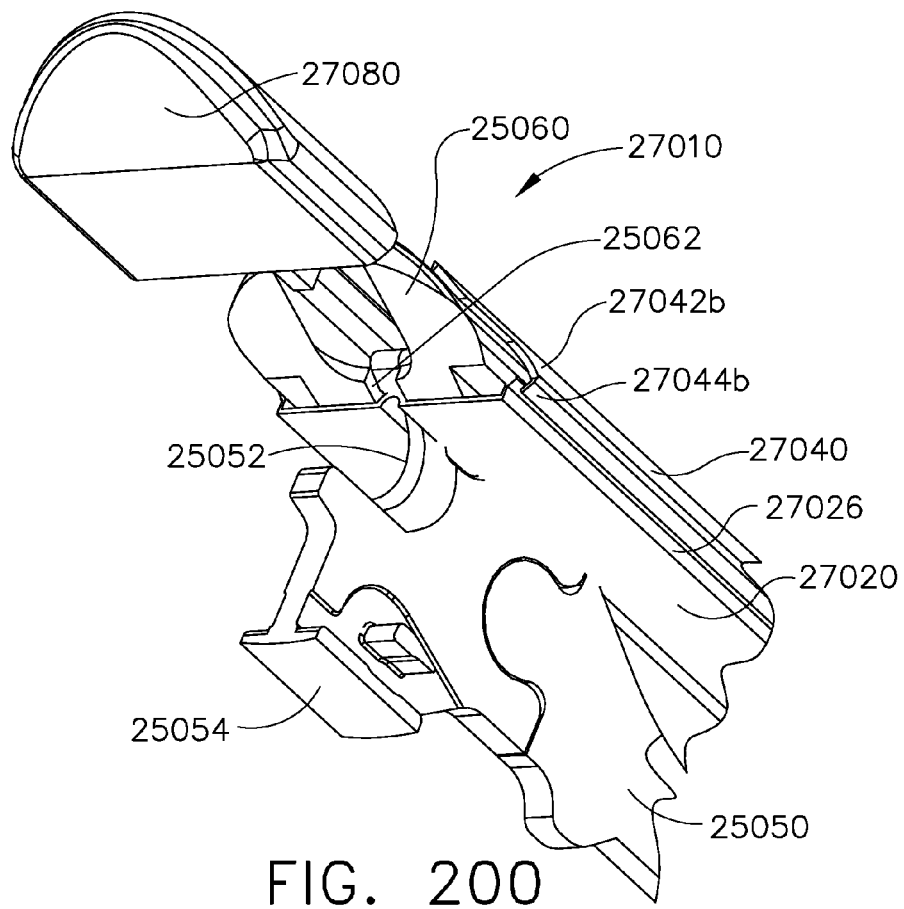
Figure 206:
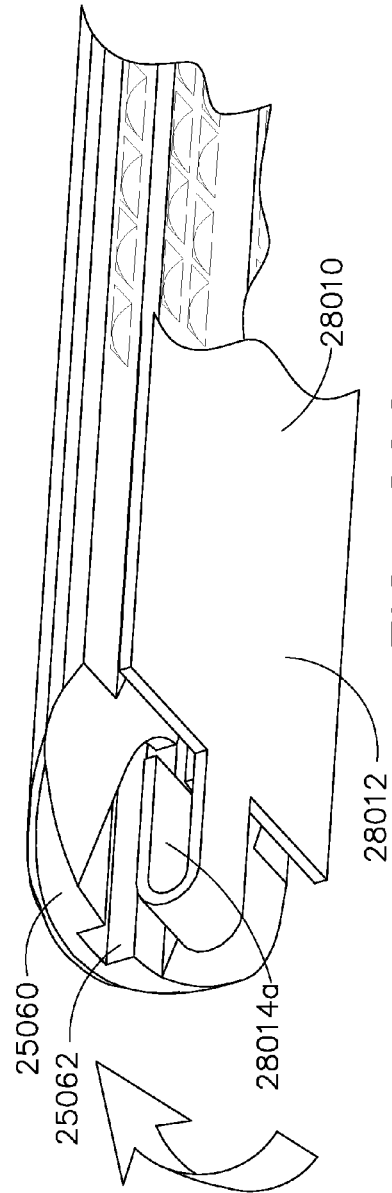
Figure 207:
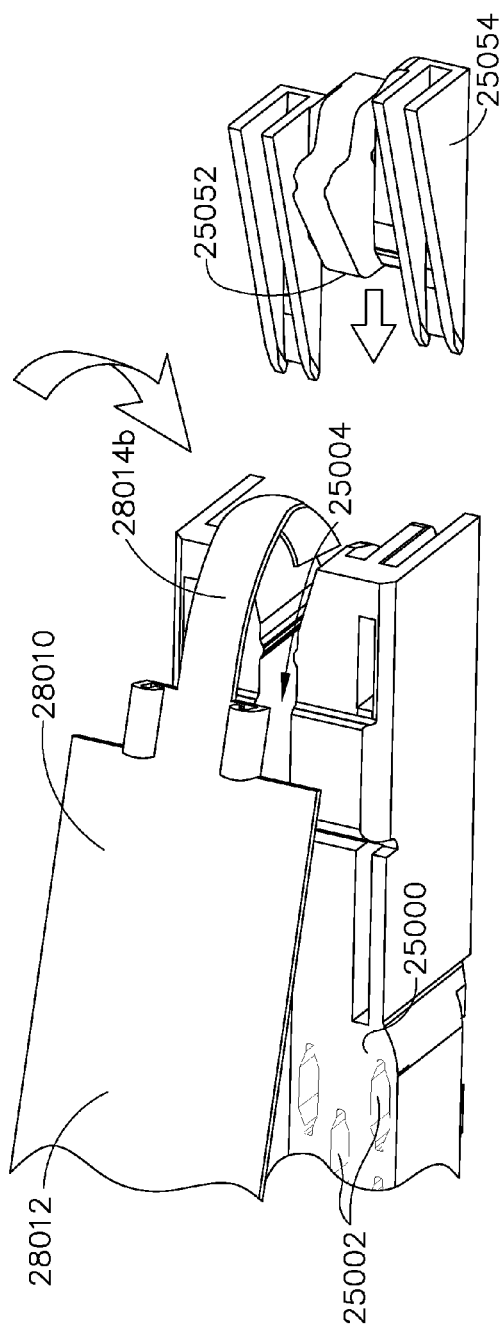
Figure 208:
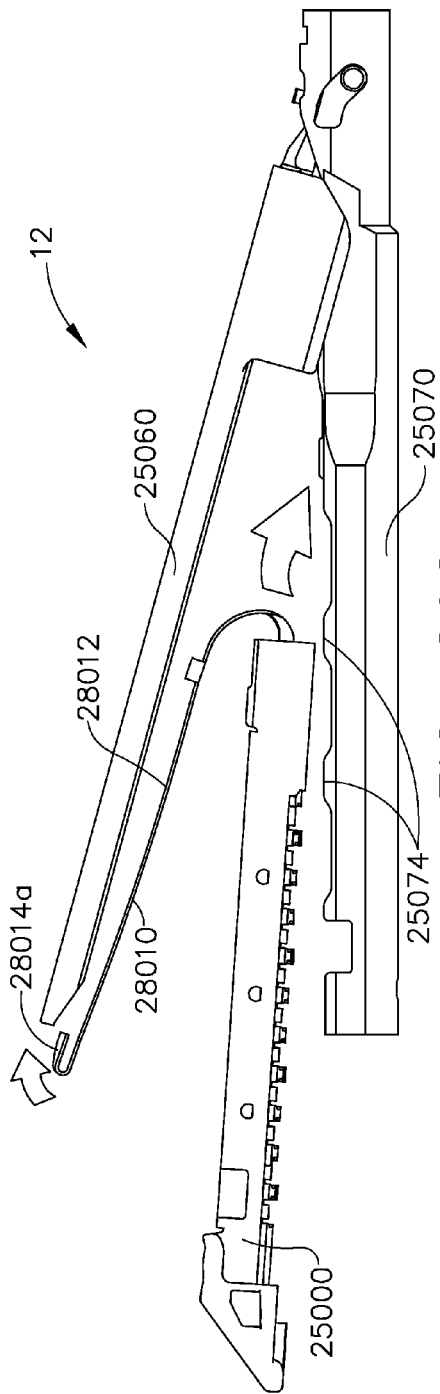
Figure 209:
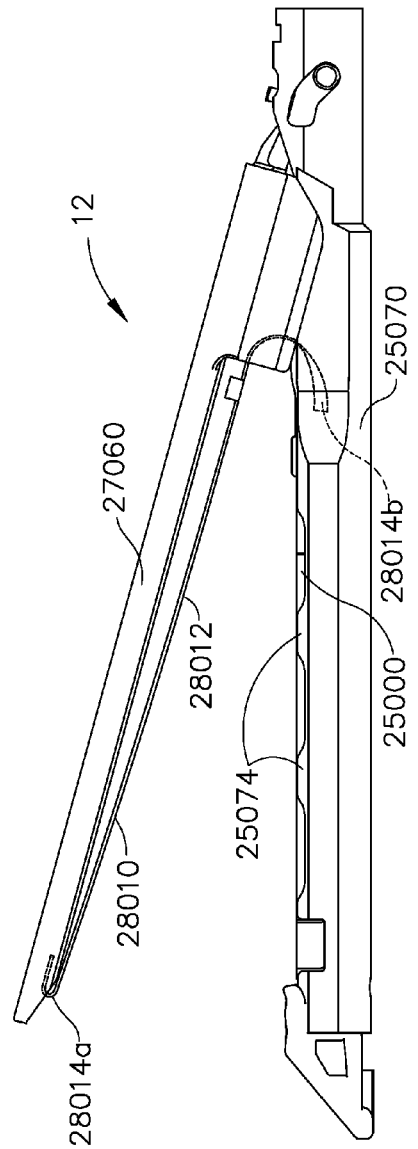
Figure 210:
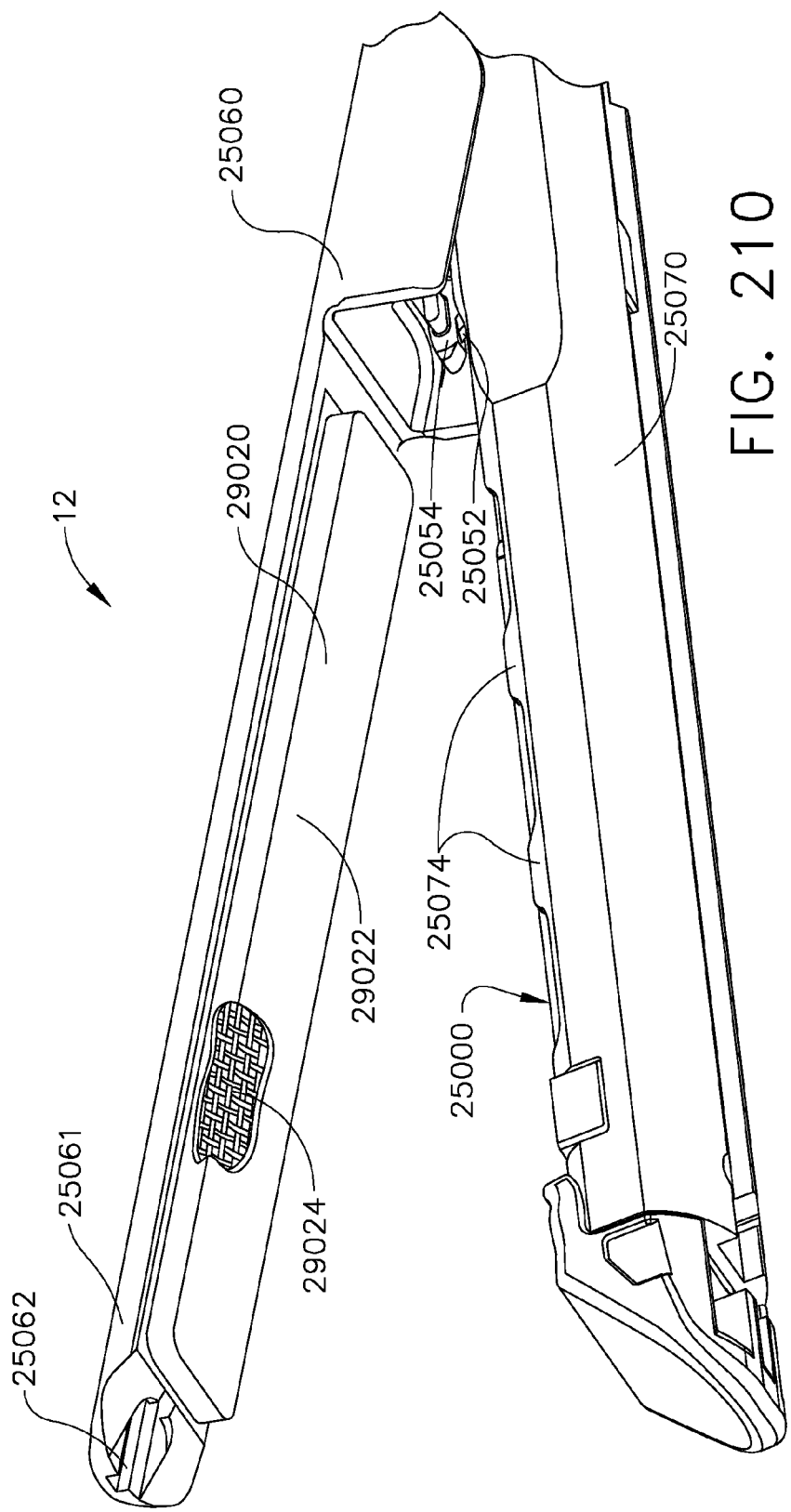
Figure 214:
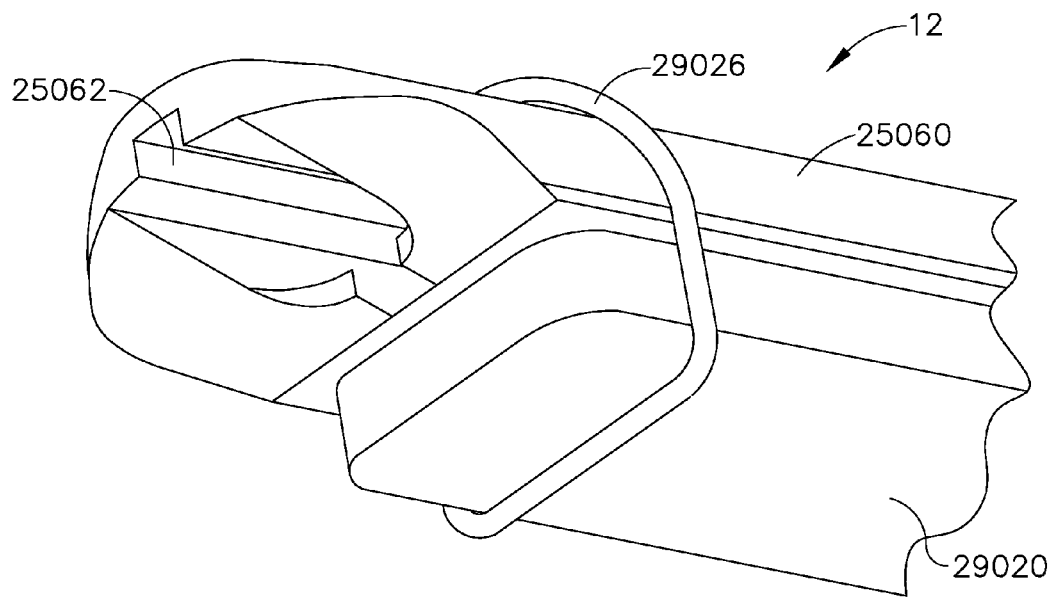
Figure 215:
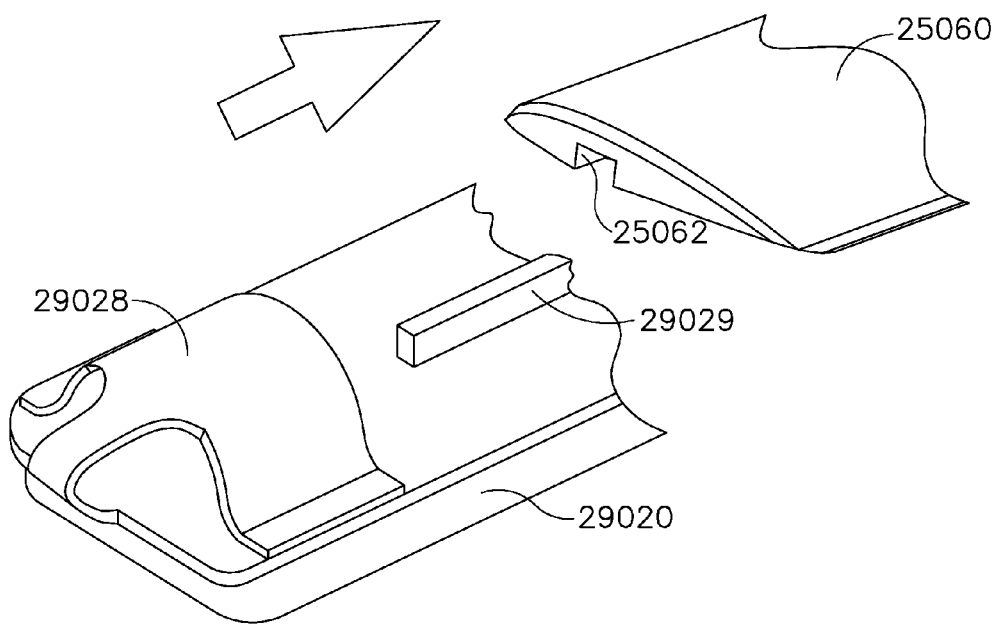
Figure 216:
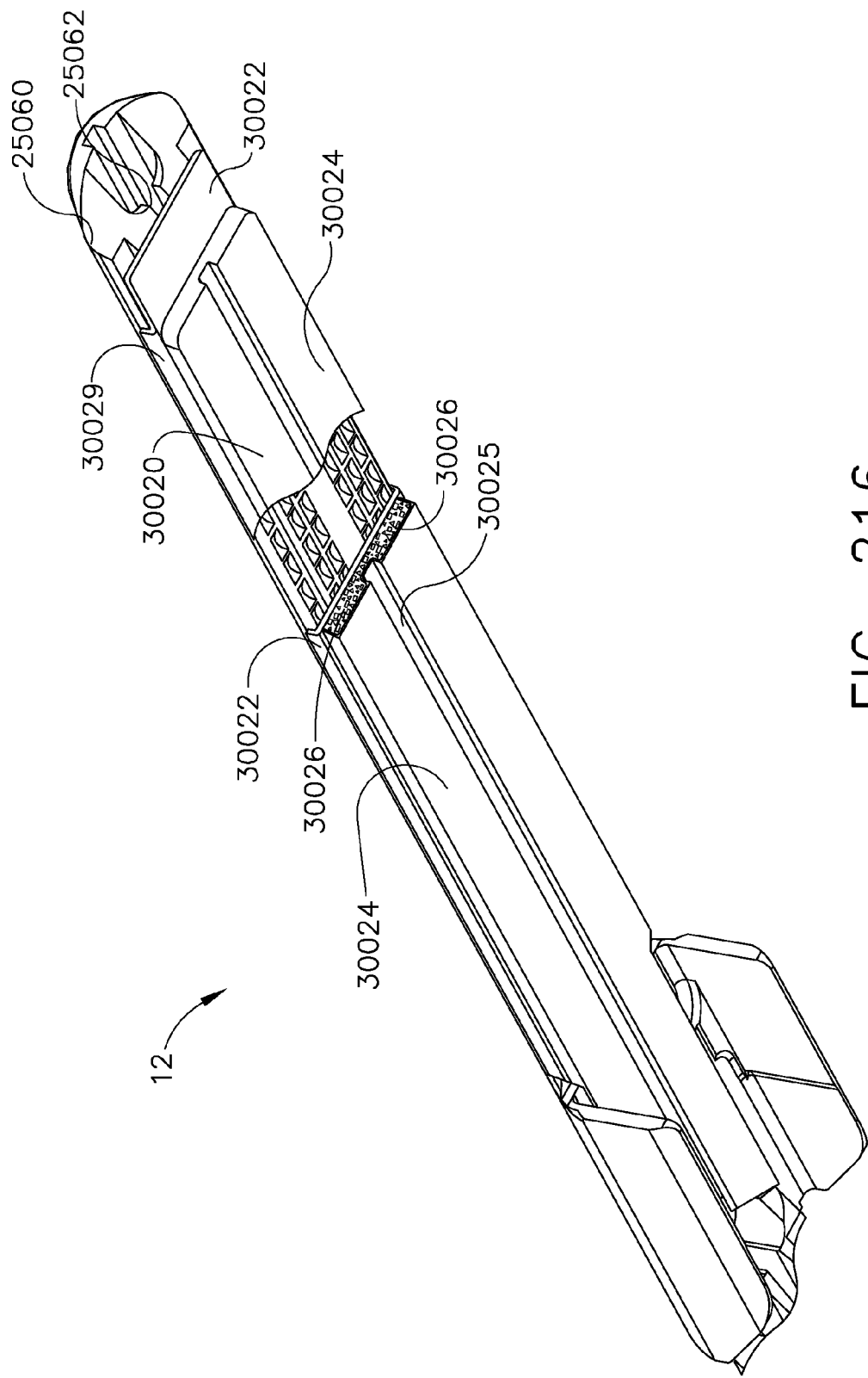
Figure 217:
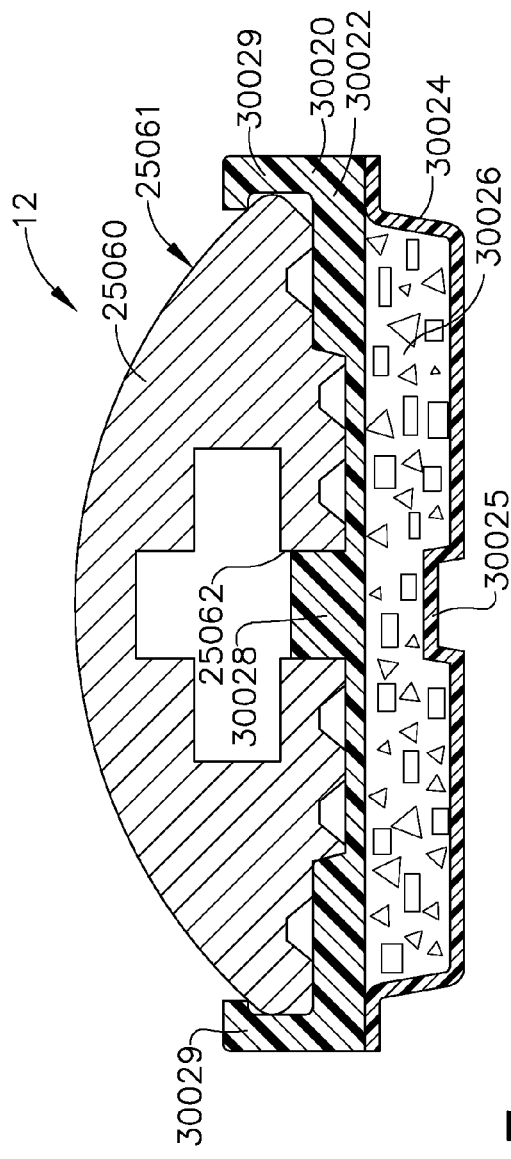
Figure 218:
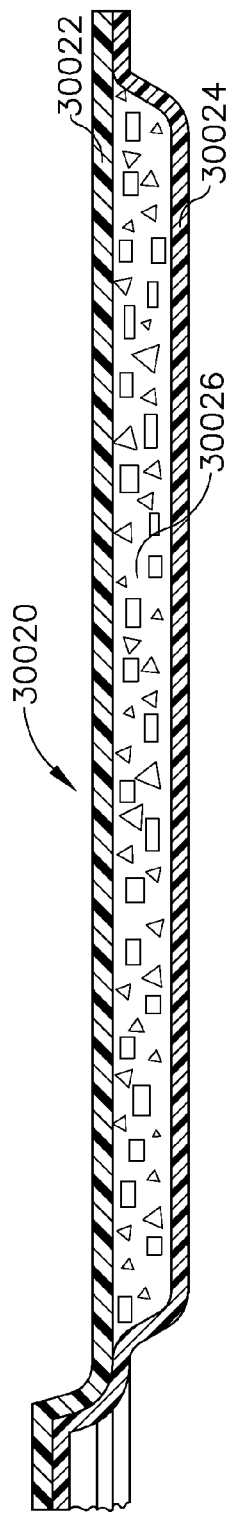
Figure 219:
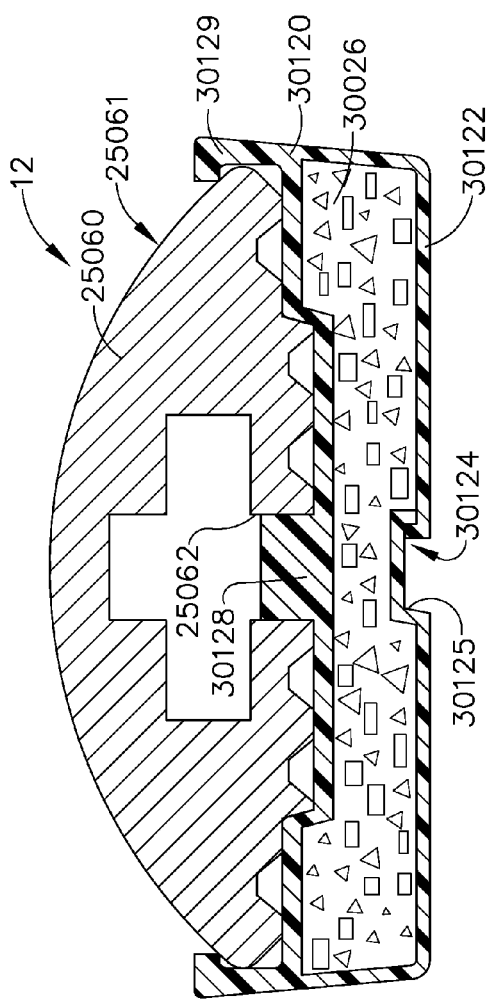
Figure 220:
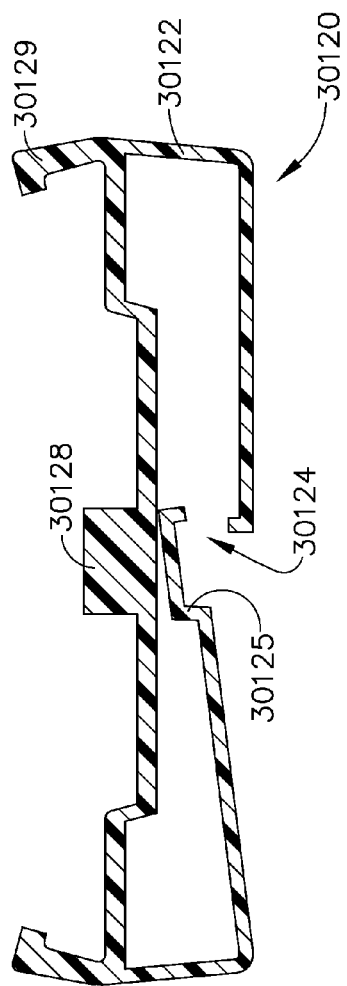
Figure 221:
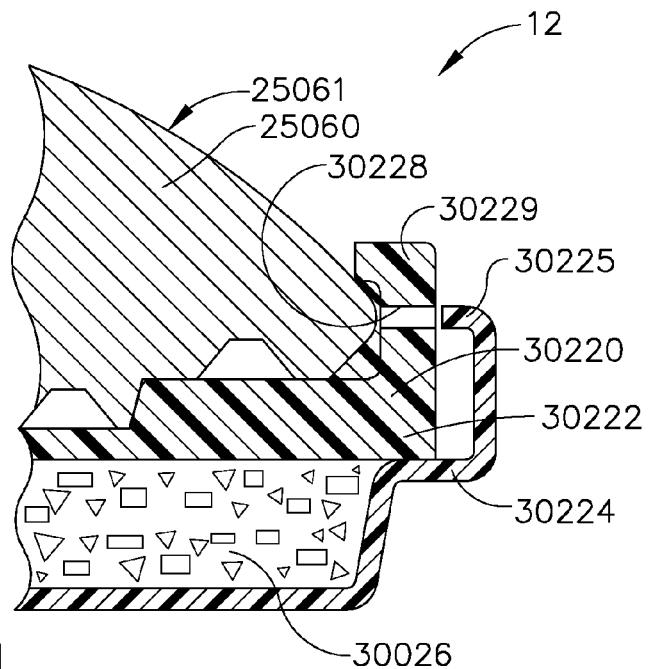
Figure 222:
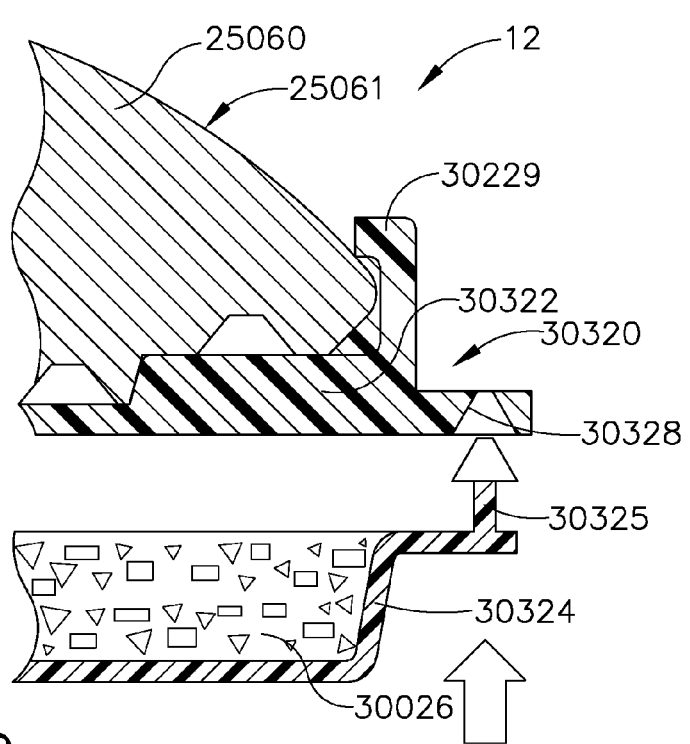
Figure 223:
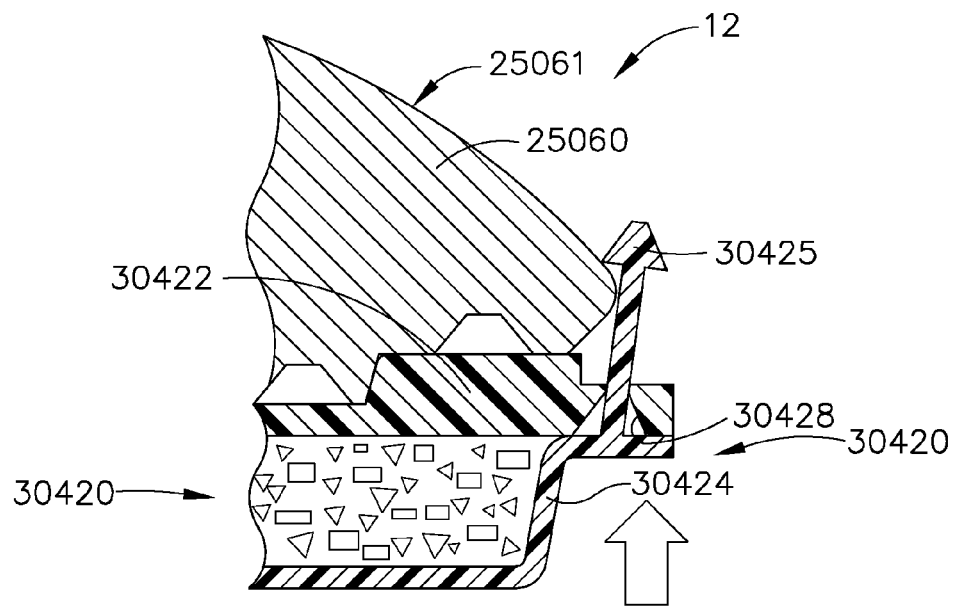
Figure 224:
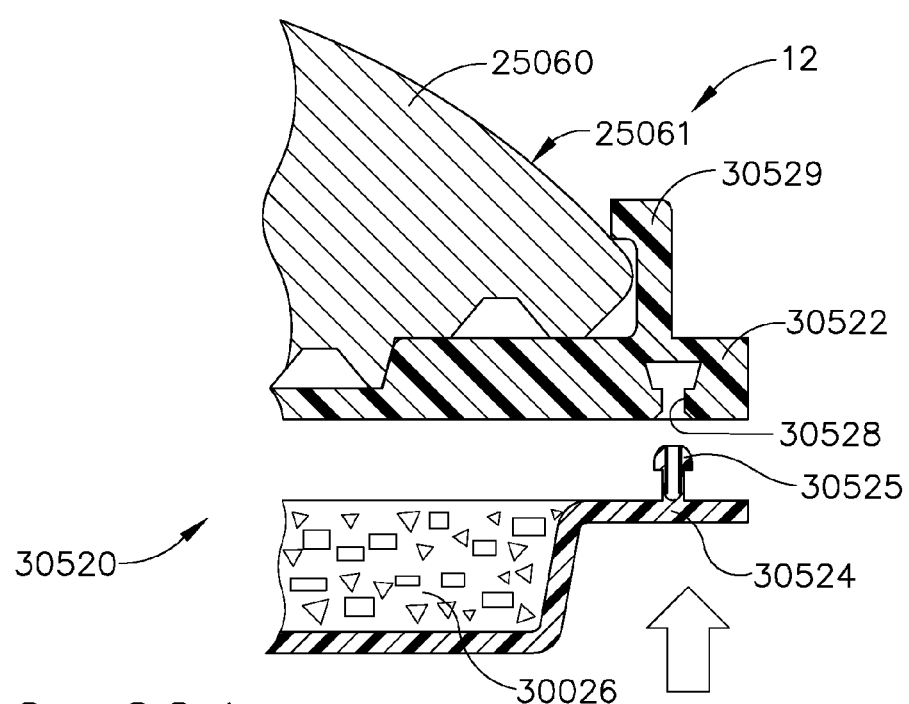
Figure 225:
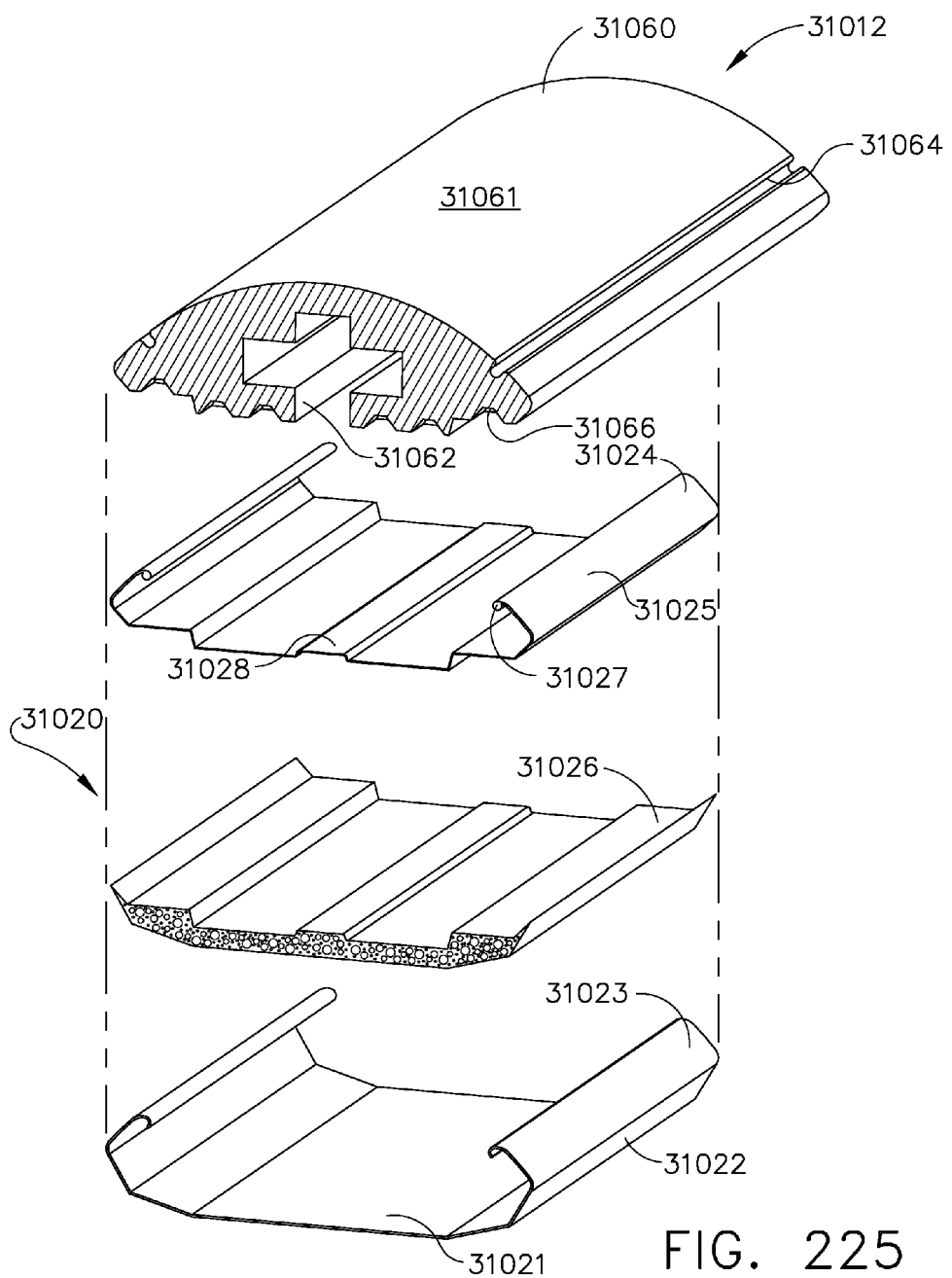
Figure 226:
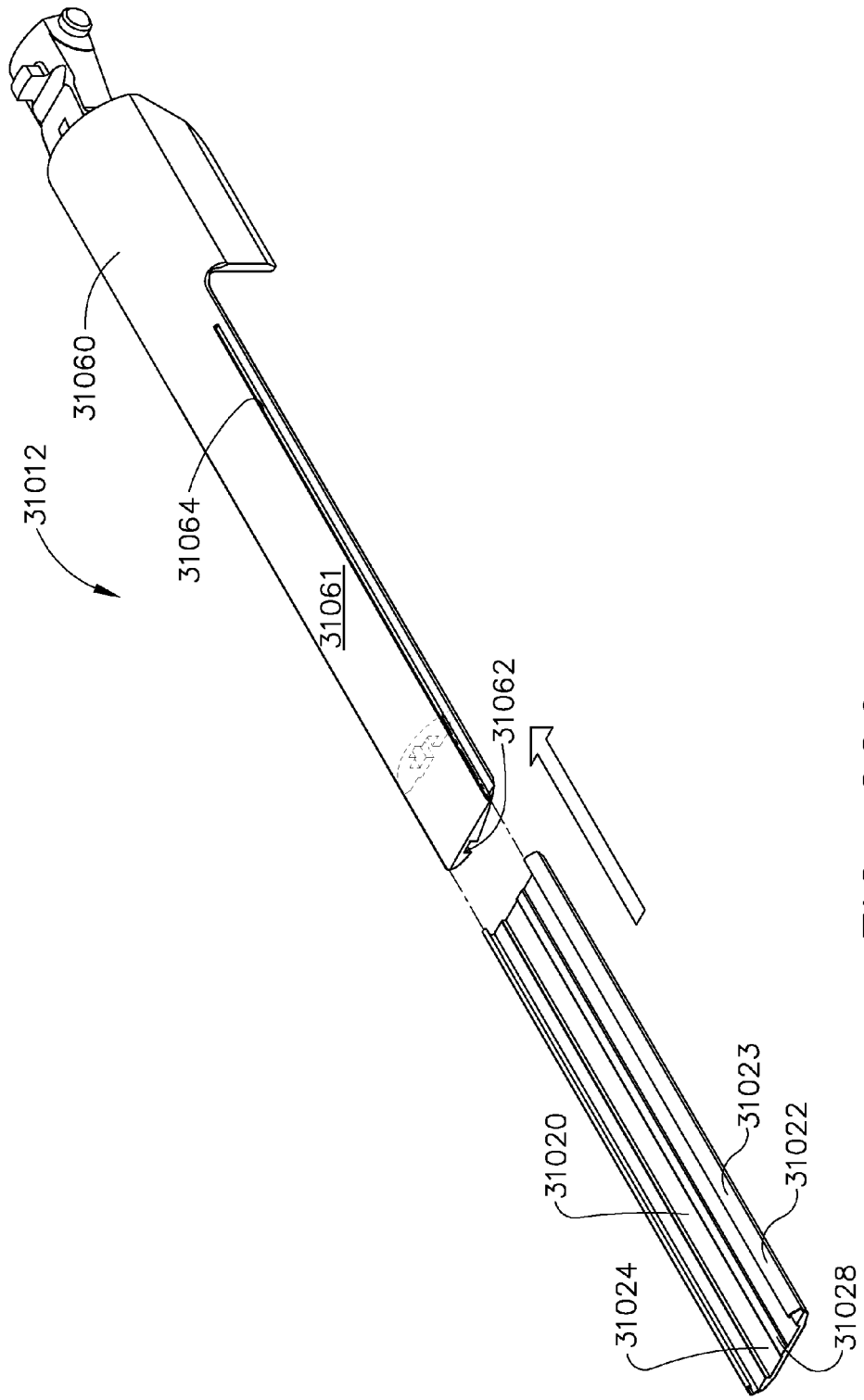
Figure 227:
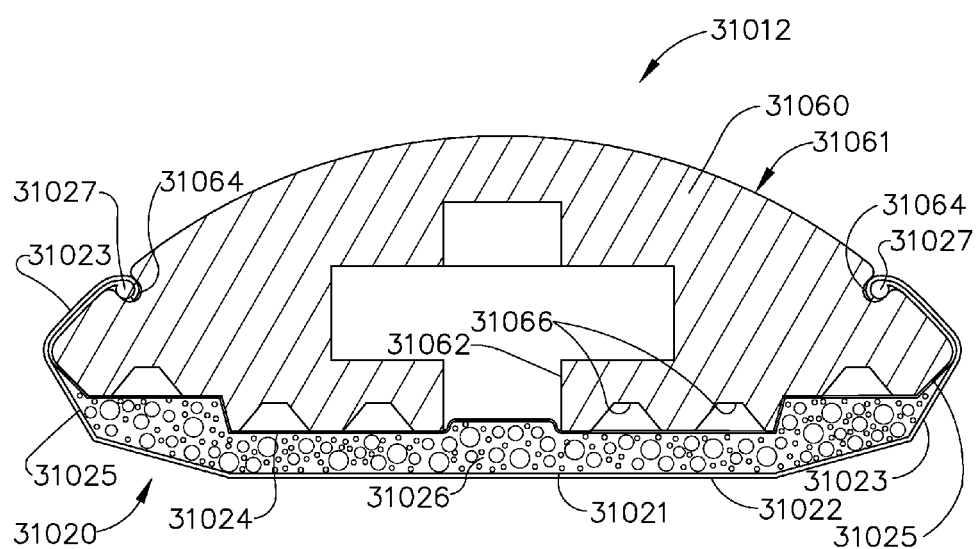
Figure 228:
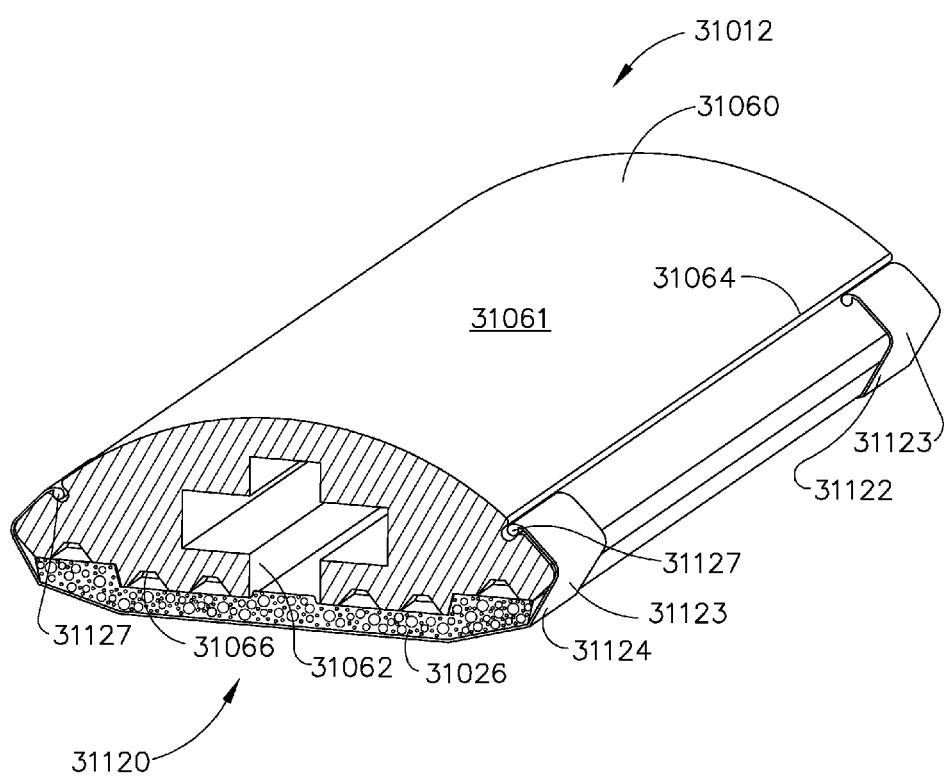
Figure 229:
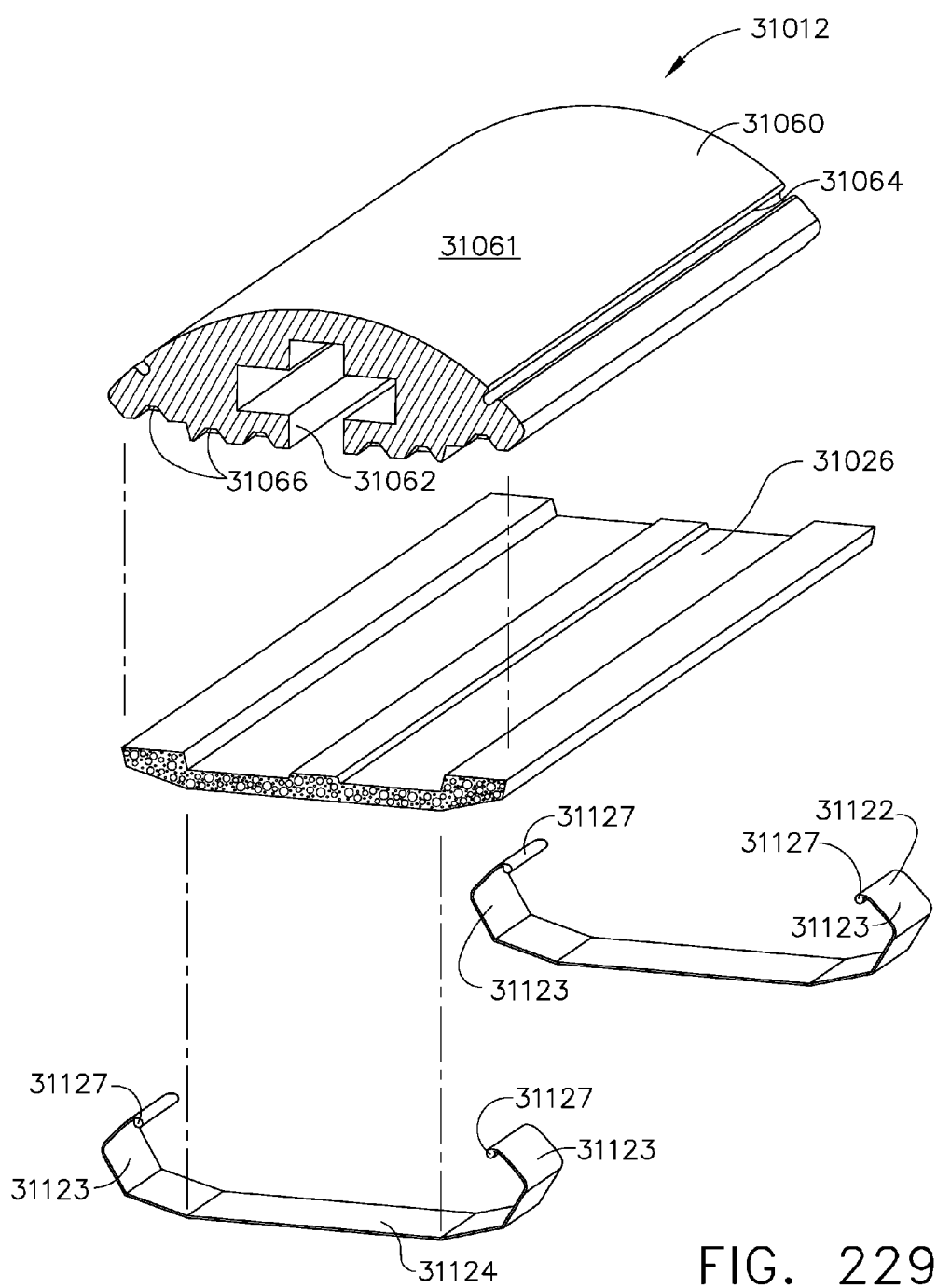
Figure 233:
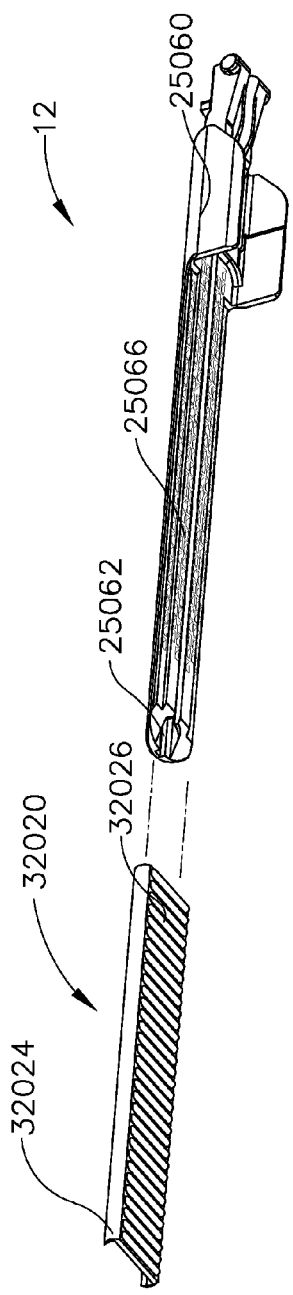
Figure 234:
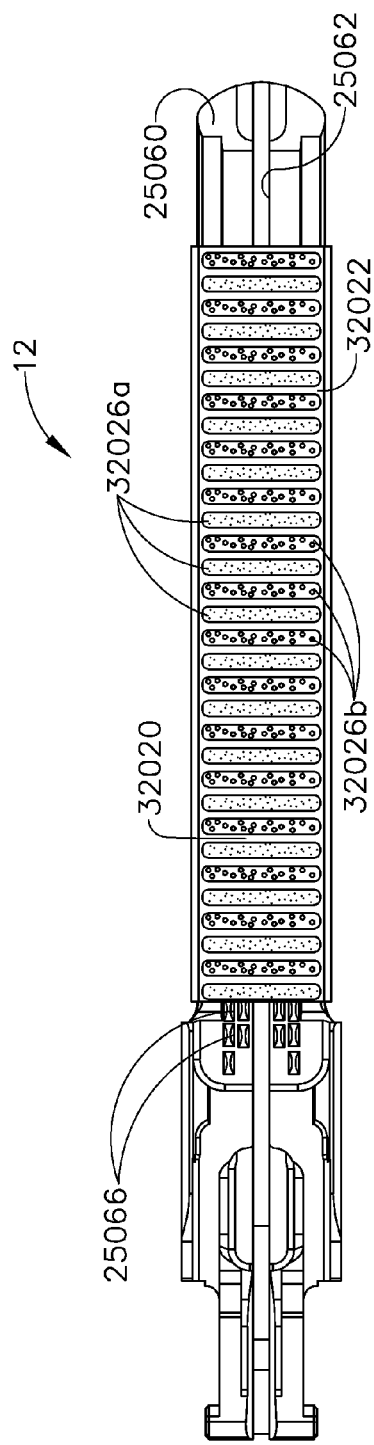
Figure 235:
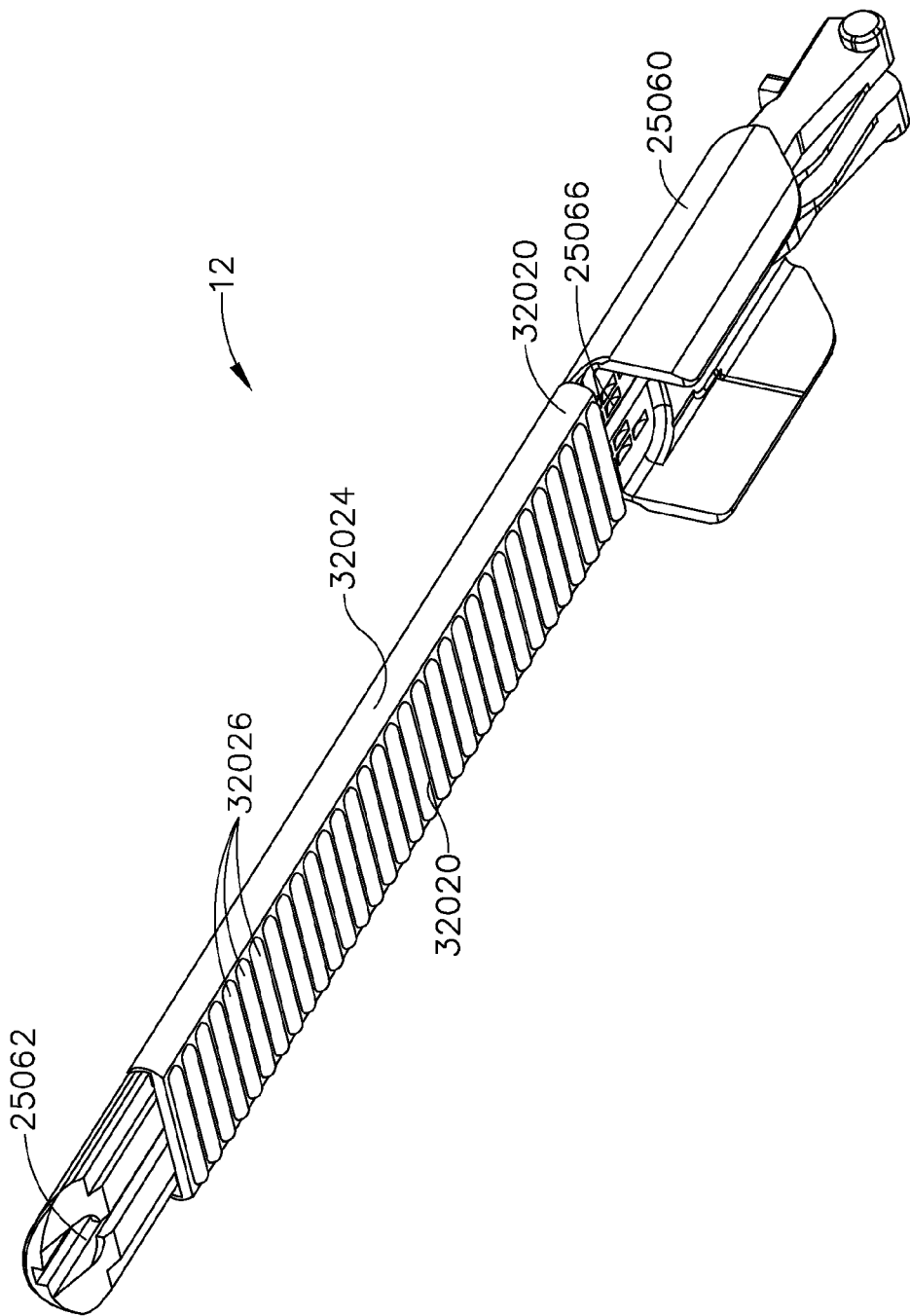
Figure 236:
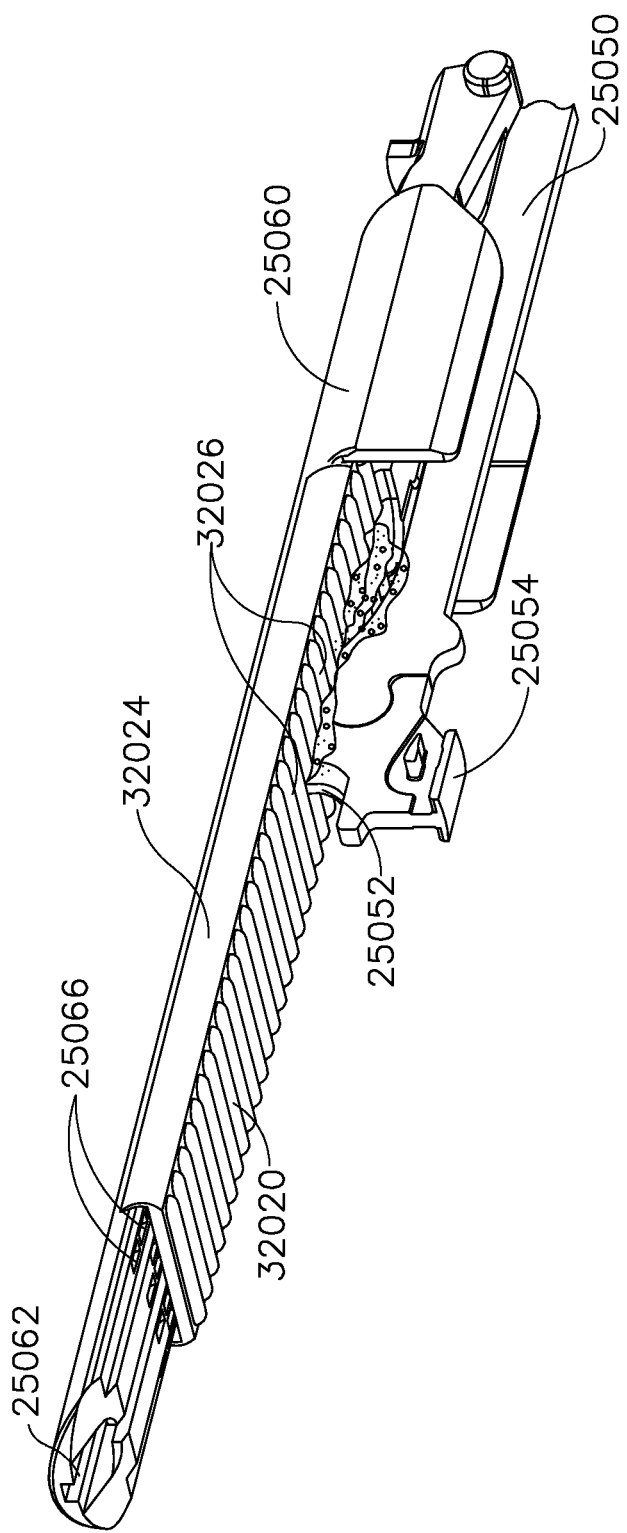
Figure 237:
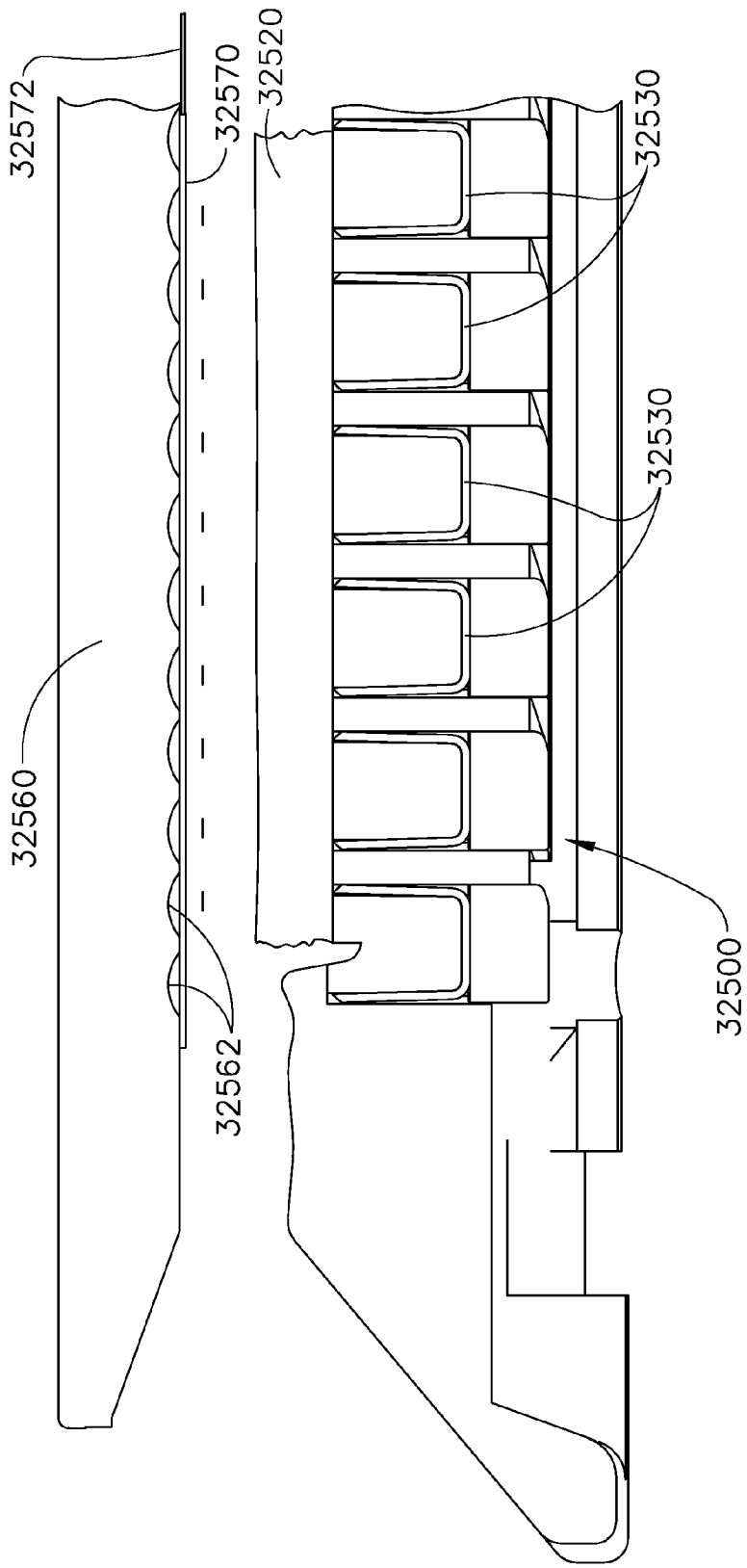
Figure 238:
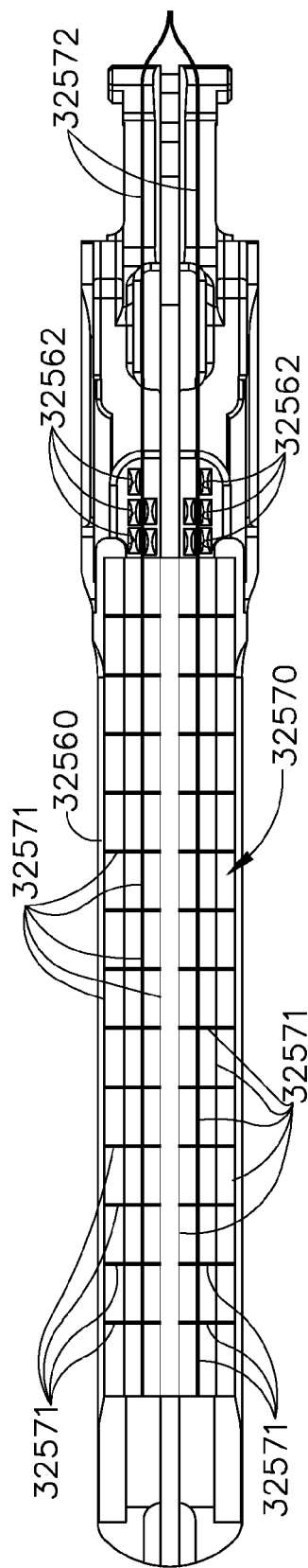
Figure 239:
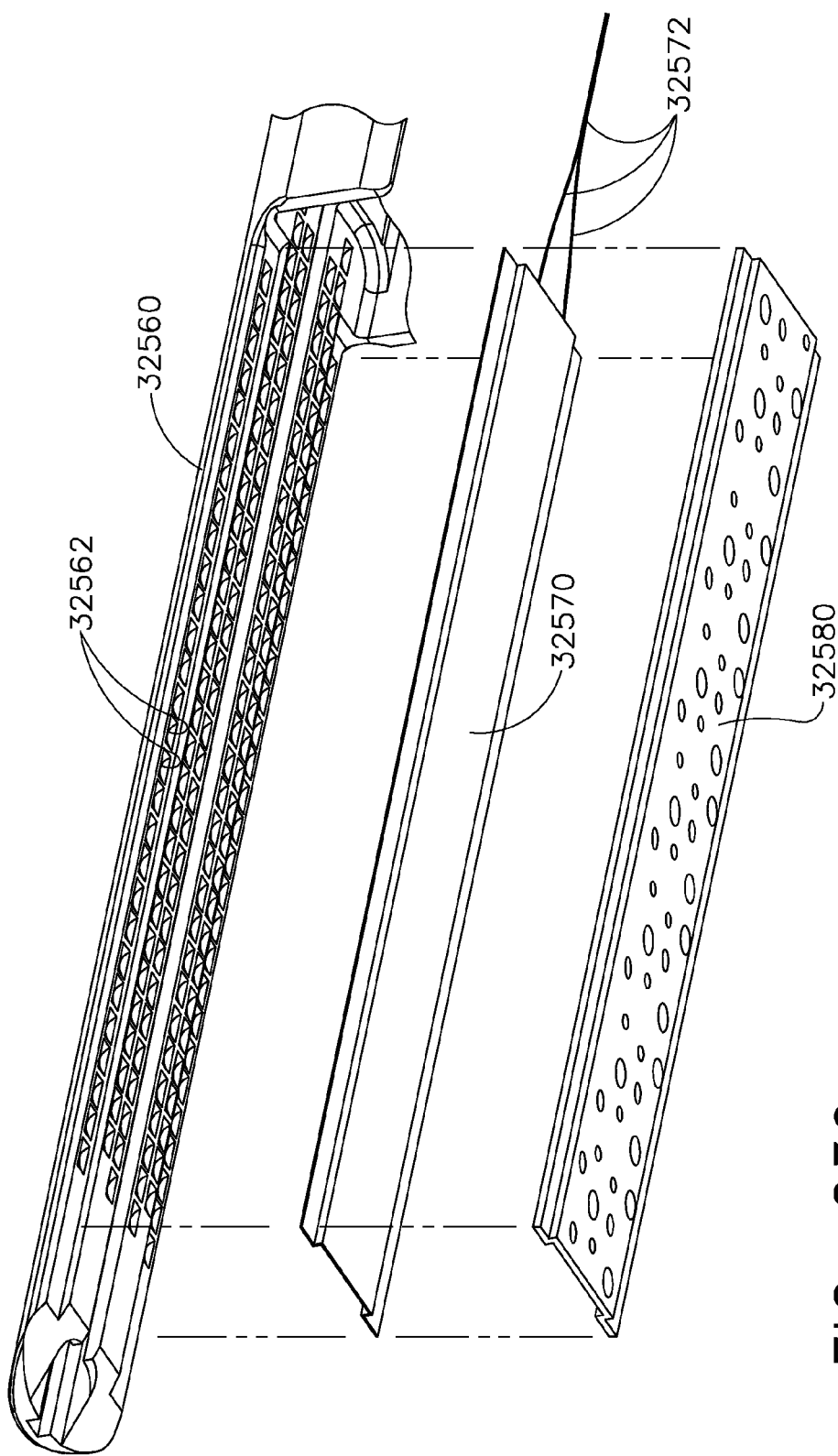
Figure 242:
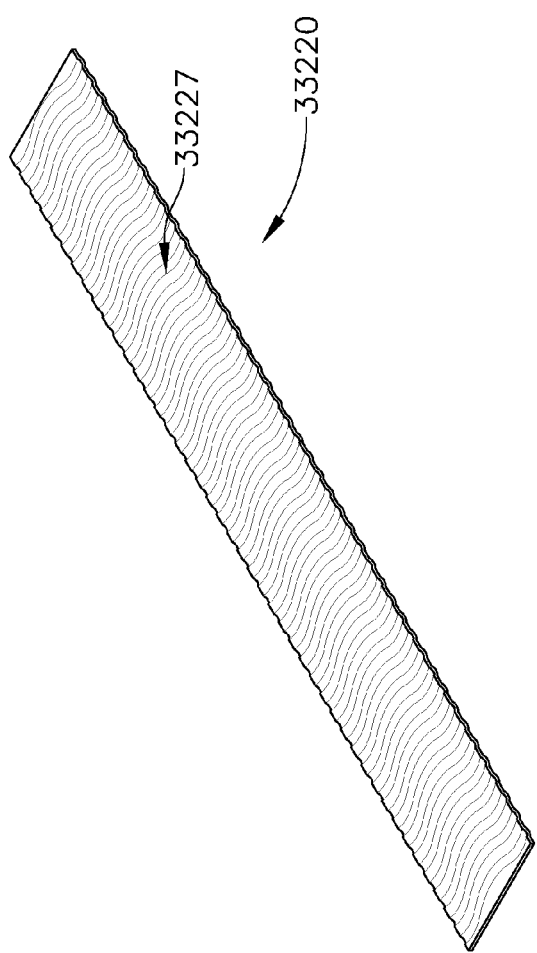
Figure 243:
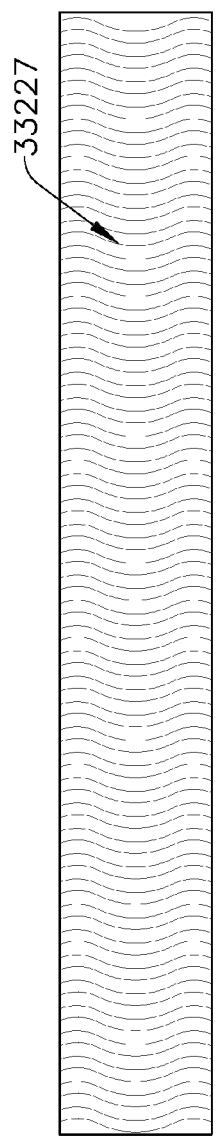
Figure 244:
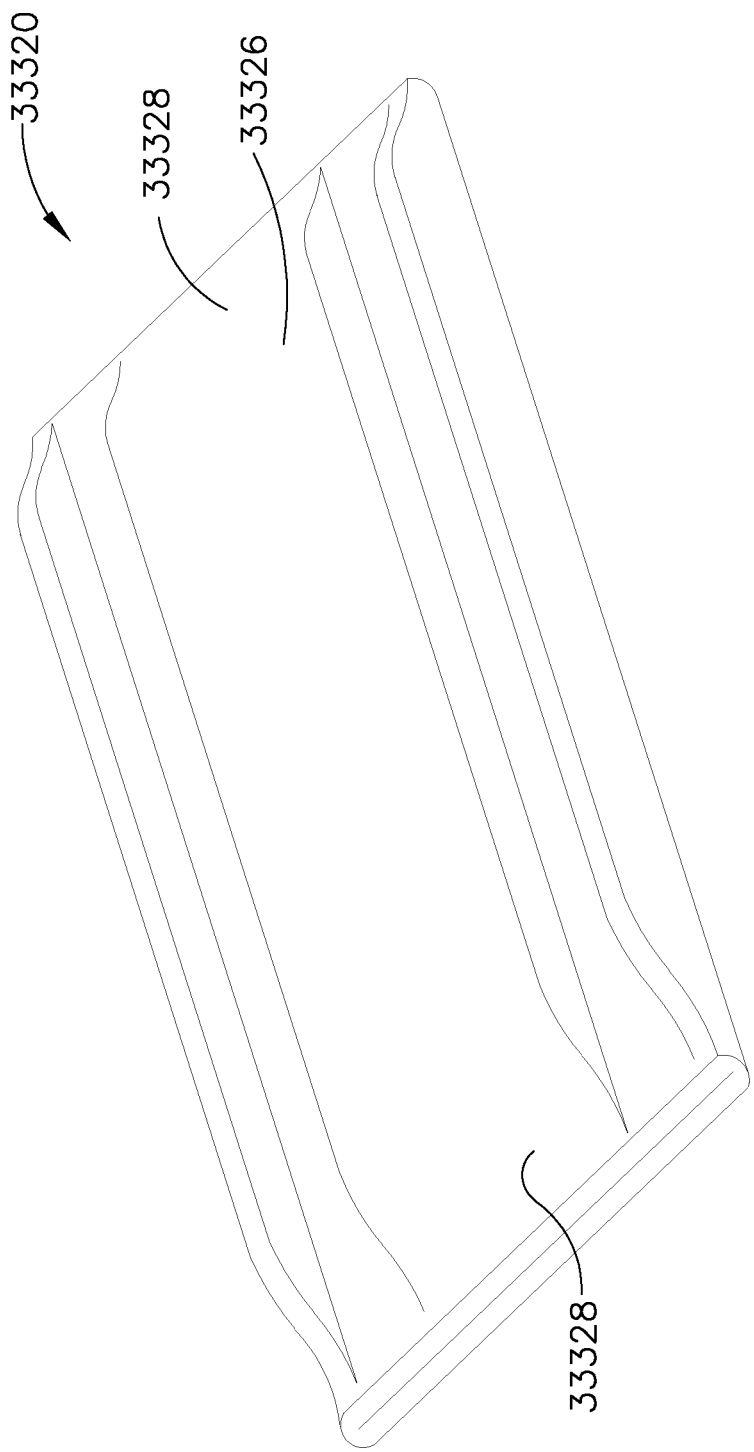
Figure 251:
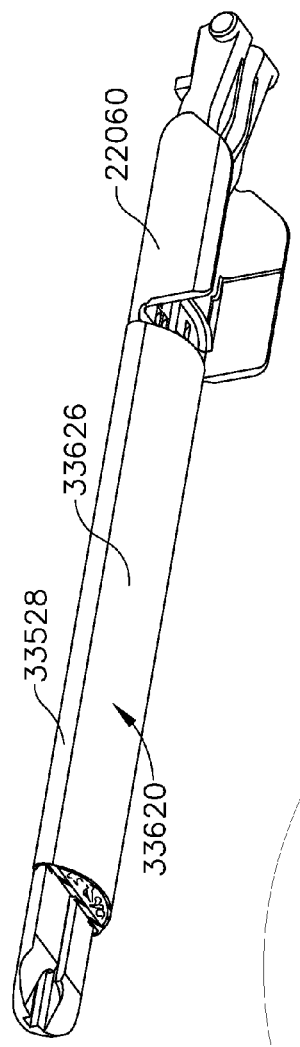
Figure 252:
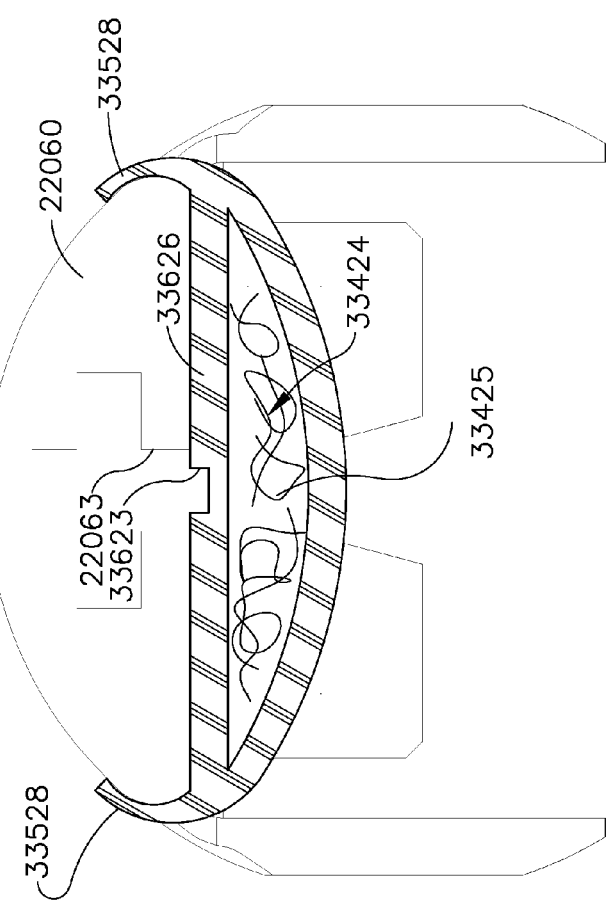
Figure 257:
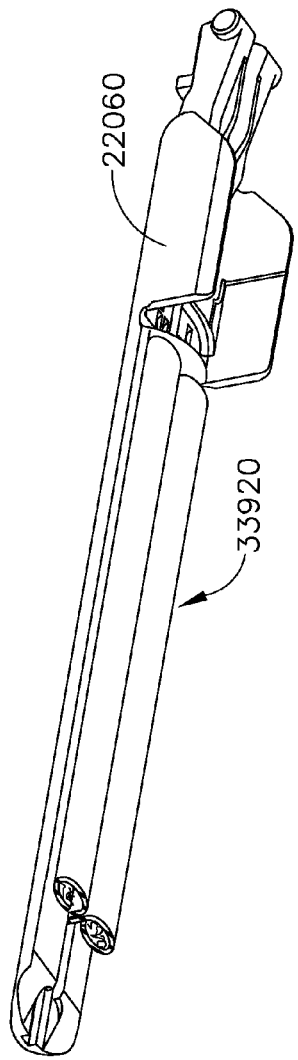
Figure 258:
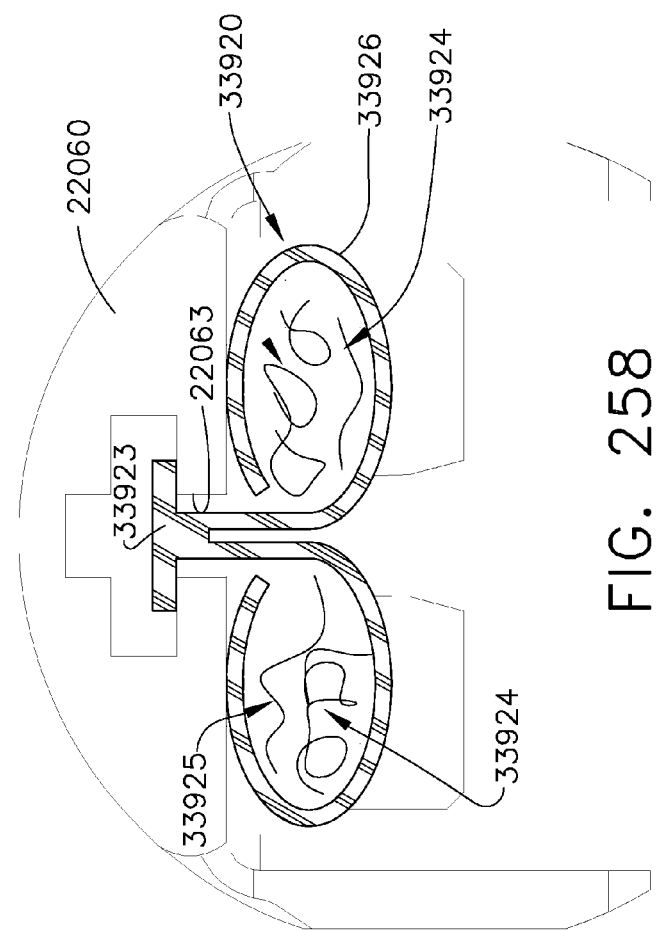

FIG. 124 is a detail view of the capsules of the tissue thickness compensator of FIG. 123;

FIG. 125 is a diagram illustrating the anvil and the tissue thickness compensator of FIG. 123 positioned relative to tissue which is to be stapled by staples from a staple cartridge positioned on the opposite side of the tissue;

FIG. 126 is a diagram illustrating the anvil of FIG. 123 moved toward the staple cartridge of FIG. 125 and staples partially fired from the staple cartridge;

FIG. 127 is a diagram illustrating the staples of FIG. 126 in a fully-fired configuration and the capsules of the tissue thickness compensator of FIG. 123 in a ruptured state;

FIG. 128 is a diagram illustrating a staple of FIG. 126 in a misfired condition;

FIG. 129 is a diagram illustrating the staples of FIG. 126 in a fully-fired configuration and the tissue thickness compensator of FIG. 123 in at least partially transected condition;

FIG. 130 is a cross-sectional perspective view of an alternative embodiment of a tissue thickness compensator in accordance with at least one embodiment;

FIG. 131 is a perspective view of an alternative embodiment of a tissue thickness compensator comprising a plurality of capsules aligned with a cutting member of a surgical stapling instrument;

FIG. 132 is a detail view of the capsules of FIG. 131;

FIG. 133 is a cross-sectional view of the tissue thickness compensator of FIG. 131 comprising a plurality of capsules aligned with a knife slot of an anvil of a surgical stapling instrument;

FIGS. 134 and 135 illustrate an alternative embodiment of a tissue thickness compensator being attached to an anvil;

FIG. 136 is a cross-sectional exploded view of an anvil and a compensator in accordance with at least one embodiment;

FIG. 137 illustrates the compensator of FIG. 136 attached to the anvil;

FIG. 138 is a partial perspective view of a tissue thickness compensator and a cutting member incising the tissue thickness compensator in accordance with at least one embodiment;

FIG. 139 is a partial cross-sectional view of an alternative embodiment of a tissue thickness compensator in accordance with at least one embodiment;

FIG. 140 is a partial cross-sectional view of another alternative embodiment of a tissue thickness compensator in accordance with at least one embodiment;

FIG. 141 is an illustration depicting a tissue thickness compensator comprising a plurality of irregular and/or asymmetrical cavities in accordance with various embodiments;

FIG. 142 is a partial cut-away view of a tissue thickness compensator attached to an anvil of a surgical stapling instrument in accordance with at least one embodiment;

FIG. 143 is a perspective view of a seamless extruded casing, or outer tube, of a tissue thickness compensator in accordance with at least one embodiment;

FIG. 144 is a perspective view of another seamless extruded casing, or outer tube, of a tissue thickness compensator in accordance with at least one embodiment;

FIG. 145 is a perspective view of oxidized regenerated cellulose fibers;

FIG. 146 is a perspective view of oxidized regenerated cellulose fibers which are shorter than the fibers of FIG. 145;

FIG. 147 is a diagram illustrating the fibers of FIG. 145 being woven into a strand utilizing the fibers of FIG. 146;

FIG. 148 depicts the strand of FIG. 147 being fluffed and at least partially cut;

FIG. 149 depicts a grasper inserted through a casing, or outer tube, of a tissue thickness compensator and positioned to grasp the strand of FIG. 147;

FIG. 150 illustrates the grasper of FIG. 149 being withdrawn from the casing and the strand of FIG. 147 being pulled through the casing;

FIG. 151 illustrates the casing and the strand of FIG. 150 being segmented;

FIG. 152 illustrates the ends of the casing being heat-welded and/or sealed;

FIG. 153 illustrates a process for creating a tissue thickness compensator without lateral seams;

FIG. 154 illustrates an anvil of a surgical stapling instrument and a plurality of compensators which can be selectively attached to the anvil, wherein each of the compensators comprises an array of capillary channels;

FIG. 155 is a plan view of a compensator configured to be attached to an anvil;

FIG. 156 is a detail view of a portion of the compensator of FIG. 155;

FIG. 157 is a perspective view of an end effector of a surgical stapling instrument;

FIG. 158 is another perspective view of the end effector of FIG. 157 illustrating a fluid being placed on a tissue thickness compensator of the end effector;

FIG. 159 is another perspective view of the end effector of FIG. 159 illustrating a compensator attached to an anvil of the end effector;

FIG. 160 is a detail view of an array of capillary channels on the compensator of FIG. 159;

FIG. 161 is an exploded view of a compensator comprising a plurality of layers in accordance with at least one embodiment;

FIG. 162 is an exploded view of a compensator and an anvil of a surgical stapling instrument in accordance with at least one embodiment;

FIG. 163 is a partial cross-sectional view of the compensator and the anvil of FIG. 162;

FIG. 164 is an exploded view of a compensator comprising a cellular ingrowth matrix in accordance with at least one embodiment;

FIG. 165 is a perspective view of the compensator of FIG. 164;

FIG. 166 is a perspective view of a fibrous layer of material for a compensator;

FIG. 167 is a perspective view of a plurality of fibrous layers stacked on one another in accordance with at least one embodiment;

FIG. 168 is a perspective view of another plurality of fibrous layers stacked on one another in accordance with at least one embodiment;

FIG. 169 is a perspective view of a fibrous layer of material for a compensator;

FIG. 170 is a perspective view of a plurality of fibrous layers stacked on one another wherein the fibers are arranged in different directions in accordance with at least one embodiment;

FIG. 171 is a perspective view of another plurality of fibrous layers stacked on one another in accordance with at least one embodiment;

FIG. 172 is a perspective view of an end effector insert and an end effector of a surgical instrument in accordance with at least one embodiment;

FIG. 173 is an elevational view of a tissue thickness compensator positioned in an end effector of a surgical instrument in accordance with at least one embodiment;

FIG. 174 is an elevational view of a tissue thickness compensator positioned in the end effector of the surgical instrument in accordance with at least one embodiment;

FIG. 175 is a perspective view of a sleeve positioned on an anvil for the end effector of the surgical instrument in accordance with at least one embodiment;

FIG. 176 is a plan view of a pronged portion of the sleeve of FIG. 175;

FIG. 177 is an elevational view of the pronged portion of the sleeve of FIG. 175;

FIG. 178 is an end view of the pronged portion of the sleeve of FIG. 175;

FIG. 179 is a perspective view of the pronged portion of the sleeve of FIG. 175;

FIG. 180 is a plan view of a tissue compensator of a sleeve in accordance with at least one embodiment;

FIG. 181 is a perspective view of the tissue compensator of FIG. 180;

FIG. 182 is an elevational view of the tissue compensator of FIG. 180;

FIG. 183 is a plan view of a tissue compensator of a sleeve in accordance with at least one embodiment;

FIG. 184 is a perspective view of the tissue compensator of FIG. 183;

FIG. 185 is an elevational view of the tissue compensator of FIG. 183;

FIG. 186 is a perspective view of a nose of the sleeve of FIG. 175;

FIG. 187 is another perspective view of the nose of FIG. 186;

FIG. 188 is a plan view of the nose of FIG. 186 depicting the inner geometry in phantom lines;

FIG. 189 is an elevational view of the nose of FIG. 186 depicting the inner geometry in phantom lines;

FIG. 190 is another perspective view of the sleeve of FIG. 175 positioned on the anvil;

FIG. 191 is a plan view of the sleeve of FIG. 175 positioned on the anvil;

FIG. 192 is an elevational view of the sleeve of FIG. 175 positioned on the anvil;

FIG. 193 is a plan view of the sleeve of FIG. 175 positioned on the anvil depicting a translating firing bar shown in phantom lines;

FIG. 194 is an elevational view of the sleeve of FIG. 175 positioned on the anvil depicting a translating firing bar shown in phantom lines;

FIG. 195 is a plan view of the sleeve of FIG. 175 positioned on the anvil depicting the release of the nose from the sleeve;

FIG. 196 is an elevational view of the sleeve of FIG. 175 positioned on the anvil depicting the release of the nose from the sleeve;

FIG. 197 is a plan view of the sleeve of FIG. 175 positioned on the anvil depicting the firing bar in phantom lines and the release of the nose from the sleeve;

FIG. 198 is an elevational view of the sleeve of FIG. 175 positioned on the anvil depicting the firing bar in phantom lines and the release of the nose from the sleeve;

FIG. 199 is a partial perspective view of the sleeve, the anvil, and the firing bar of FIG. 197;

FIG. 200 is another partial perspective view of the sleeve, the anvil, and the firing bar of FIG. 197;

FIG. 201 is an elevational cross-sectional view of the sleeve and the anvil of FIG. 175;

FIG. 202 is an elevational cross-sectional view of the anvil of FIG. 175 depicting the release of the tissue compensator from the sleeve;

FIG. 203 is a plan view of an end effector insert in accordance with at least one embodiment;

FIG. 204 is an elevational view of the end effector insert of FIG. 203;

FIG. 205 is a perspective view of the end effector insert of FIG. 205;

FIG. 206 is a partial perspective view of the end effector insert of FIG. 203 depicting the end effector insert engaging the anvil of the end effector of a surgical instrument;

FIG. 207 is a partial perspective view of the end effector insert of FIG. 203 depicting the end effector insert engaging the staple cartridge of the end effector of a surgical instrument;

FIG. 208 is an elevational view of the end effector insert of FIG. 203 depicting the end effector insert engaging the end effector of a surgical instrument;

FIG. 209 is an elevational view of the end effector insert of FIG. 203 positioned in the end effector of a surgical instrument;

FIG. 210 is a perspective view of a tissue thickness compensator positioned in the end effector of a surgical instrument in accordance with at least one embodiment illustrated with a portion of the tissue thickness compensator cut away;

FIG. 211 is a perspective view of the tissue thickness compensator of FIG. 210 secured to the anvil of the end effector by a static charge;

FIG. 212 is a perspective view of the tissue thickness compensator of FIG. 210 secured to the anvil of the end effector by suction elements;

FIG. 213 is a perspective view of the tissue thickness compensator of FIG. 210 secured to the anvil of the end effector by hook and loop fasteners;

FIG. 214 is a partial perspective view of the tissue thickness compensator of FIG. 210 secured to the anvil of the end effector by a band;

FIG. 215 is a partial perspective view of the tissue thickness compensator of FIG. 210 secured to the anvil of the end effector by a sock at the distal end of the tissue thickness compensator;

FIG. 216 is a perspective partial cross-sectional view of a tissue thickness compensator secured to the anvil of the end effector of a surgical instrument in accordance with at least one embodiment;

FIG. 217 is an elevational cross-sectional view of the tissue thickness compensator of FIG. 216;

FIG. 218 is another elevational cross-sectional view of the tissue thickness compensator of FIG. 216;

FIG. 219 is an elevational cross-sectional view of a tissue thickness compensator secured to the anvil of the end effector of a surgical instrument depicting a latch in a closed position in accordance with at least one embodiment;

FIG. 220 is an elevational cross-sectional view the tissue thickness compensator of FIG. 219 depicting the latch in the open position;

FIG. 221 is an elevational cross-sectional view of a tissue thickness compensator secured to the anvil of the end effector of a surgical instrument in accordance with at least one embodiment;

FIG. 222 is an elevational cross-sectional view of a tissue thickness compensator secured to the anvil of the end effector of a surgical instrument in accordance with at least one embodiment;

FIG. 223 is an elevational cross-sectional view of a tissue thickness compensator secured to the anvil of the end effector of a surgical instrument in accordance with at least one embodiment;

FIG. 224 is an elevational cross-sectional view of a tissue thickness compensator secured to the anvil of the end effector of the surgical instrument in accordance with at least one embodiment;

FIG. 225 is a perspective cross-sectional exploded view of a tissue thickness compensator secured to an anvil of an end effector of the surgical instrument in accordance with at least one embodiment;

FIG. 226 is a perspective view of the tissue thickness compensator of FIG. 225 depicting movement of the tissue thickness compensator towards the anvil;

FIG. 227 is an elevational cross-sectional view of the tissue thickness compensator of FIG. 225 engaged with the anvil;

FIG. 228 is a perspective cross-sectional view of a tissue thickness compensator secured to the anvil of the end effector of a surgical instrument in accordance with at least one embodiment;

FIG. 229 is a perspective cross-sectional exploded view of the tissue thickness compensator and the anvil of FIG. 228;

FIG. 230 is an elevational view of a tissue thickness compensator in accordance with at least one embodiment;

FIG. 231 is a perspective view of the tissue thickness compensator of FIG. 230;

FIG. 232 is another perspective of the tissue thickness compensator of FIG. 230;

FIG. 233 is a perspective view of the tissue thickness compensator of FIG. 230 depicting movement of the tissue thickness compensator towards the anvil of the end effector of a surgical instrument;

FIG. 234 is a plan cross-sectional view of the tissue thickness compensator of FIG. 230 positioned on the anvil;

FIG. 235 is a perspective view of the tissue thickness compensator of FIG. 230 positioned on the anvil;

FIG. 236 is a perspective view of the tissue thickness compensator of FIG. 230 positioned on the anvil illustrating a cutting element severing the tissue thickness compensator;

FIG. 237 is a cross-sectional elevational view of an end effector of a surgical stapling instrument comprising an anvil and a chargeable layer in accordance with at least one embodiment;

FIG. 238 is a bottom view of the anvil and the chargeable layer of FIG. 237;

FIG. 239 is an exploded view of the anvil and the chargeable layer of FIG. 237 and a tissue thickness compensator releasably attachable to the chargeable layer;

FIG. 240 is a perspective view of a tissue thickness compensator in accordance with at least one embodiment;

FIG. 241 is a plan view of the tissue thickness compensator of FIG. 240;

FIG. 240A is a perspective view of a tissue thickness compensator in accordance with at least one alternative embodiment;

FIG. 241A is a plan view of the tissue thickness compensator of FIG. 240A;

FIG. 242 is a perspective view of a tissue thickness compensator in accordance with at least one alternative embodiment;

FIG. 243 is a plan view of the tissue thickness compensator of FIG. 242;

FIG. 244 is a perspective view of a tissue thickness compensator in accordance with at least one embodiment;

FIG. 245 is a perspective view of a tissue thickness compensator attached to an anvil in accordance with at least one embodiment;

FIG. 246 is a cross-sectional view of the anvil and the tissue thickness compensator of FIG. 245;

FIG. 247 is a cross-sectional view of the tissue thickness compensator of FIG. 245;

FIG. 248 is a perspective view of a tissue thickness compensator attached to an anvil in accordance with at least one alternative embodiment;

FIG. 249 is a cross-sectional view of the anvil and the tissue thickness compensator of FIG. 248;

FIG. 250 is a cross-sectional view of the tissue thickness compensator of FIG. 248 in an open configuration;

FIG. 251 is a perspective view of a tissue thickness compensator attached to an anvil in accordance with at least one alternative embodiment;

FIG. 252 is a cross-sectional view of the anvil and the tissue thickness compensator of FIG. 251;

FIG. 253 is a perspective view of a tissue thickness compensator attached to an anvil in accordance with at least one alternative embodiment;

FIG. 254 is a cross-sectional view of the anvil and the tissue thickness compensator of FIG. 253;

FIG. 255 is a perspective view of a tissue thickness compensator attached to an anvil in accordance with at least one alternative embodiment;

FIG. 256 is a cross-sectional view of the anvil and the tissue thickness compensator of FIG. 255;

FIG. 257 is a perspective view of a tissue thickness compensator attached to an anvil in accordance with at least one alternative embodiment; and FIG. 258 is a cross-sectional view of the anvil and the tissue thickness compensator of FIG. 257.

Corresponding reference characters indicate corresponding parts throughout the several views. The exemplifications set out herein illustrate certain embodiments of the invention, in one form, and such exemplifications are not to be construed as limiting the scope of the invention in any manner.

DETAILED DESCRIPTION

The Applicant of the present application also owns the U.S. Patent Applications identified below which are each herein incorporated by reference in their respective entirety:

U.S. patent application Ser. No. 12/894,311, entitled SURGICAL INSTRUMENTS WITH RECONFIGURABLE SHAFT SEGMENTS, now U.S. Patent Application Publication No. 2012/0080496;

U.S. patent application Ser. No. 12/894,340, entitled SURGICAL STAPLE CARTRIDGES SUPPORTING NON-LINEARLY ARRANGED STAPLES AND SURGICAL STAPLING INSTRUMENTS WITH COMMON STAPLE-FORMING POCKETS, now U.S. Patent Application Publication No. 2012/0080482;

U.S. patent application Ser. No. 12/894,327, entitled JAW CLOSURE ARRANGEMENTS FOR SURGICAL INSTRUMENTS, now U.S. Patent Application Publication No. 2012/0080499;

U.S. patent application Ser. No. 12/894,351, entitled SURGICAL CUTTING AND FASTENING INSTRUMENTS WITH SEPARATE AND DISTINCT FASTENER DEPLOYMENT AND TISSUE CUTTING SYSTEMS, now U.S. Patent Application Publication No. 2012/0080502;

U.S. patent application Ser. No. 12/894,338, entitled IMPLANTABLE FASTENER CARTRIDGE HAVING A NON-UNIFORM ARRANGEMENT, now U.S. Patent Application Publication No. 2012/0080481;

U.S. patent application Ser. No. 12/894,369, entitled IMPLANTABLE FASTENER CARTRIDGE COMPRISING A SUPPORT RETAINER, now U.S. Patent Application Publication No. 2012/0080344;

U.S. patent application Ser. No. 12/894,312, entitled IMPLANTABLE FASTENER CARTRIDGE COMPRISING MULTIPLE LAYERS, now U.S. Patent Application Publication No. 2012/0080479;

U.S. patent application Ser. No. 12/894,377, entitled SELECTIVELY ORIENTABLE IMPLANTABLE FASTENER CARTRIDGE, now U.S. Pat. No. 8,393,514;

U.S. patent application Ser. No. 12/894,339, entitled SURGICAL STAPLING INSTRUMENT WITH COMPACT ARTICULATION CONTROL ARRANGEMENT, now U.S. Patent Application Publication No. 2012/0080500;

U.S. patent application Ser. No. 12/894,360, entitled SURGICAL STAPLING INSTRUMENT WITH A VARIABLE STAPLE FORMING SYSTEM, now U.S. Patent Application Publication No. 2012/0080484;

U.S. patent application Ser. No. 12/894,322, entitled SURGICAL STAPLING INSTRUMENT WITH INTERCHANGEABLE STAPLE CARTRIDGE ARRANGEMENTS, now U.S. Patent Application Publication No. 2012/0080501;

U.S. patent application Ser. No. 12/894,350, entitled SURGICAL STAPLE CARTRIDGES WITH DETACHABLE SUPPORT STRUCTURES AND SURGICAL STAPLING INSTRUMENTS WITH SYSTEMS FOR PREVENTING ACTUATION MOTIONS WHEN A CARTRIDGE IS NOT PRESENT, now U.S. Patent Application No. 2012/0080478;

U.S. patent application Ser. No. 12/894,383, entitled IMPLANTABLE FASTENER CARTRIDGE COMPRISING BIOABSORBABLE LAYERS, now U.S. Patent Application No. 2012/0080345;

U.S. patent application Ser. No. 12/894,389, entitled COMPRESSIBLE FASTENER CARTRIDGE, now U.S. Patent Application Publication No. 2012/0080335;

U.S. patent application Ser. No. 12/894,345, entitled FASTENERS SUPPORTED BY A FASTENER CARTRIDGE SUPPORT, now U.S. Patent Application Publication No. 2012/0080483;

U.S. patent application Ser. No. 12/894,306, entitled COLLAPSIBLE FASTENER CARTRIDGE, now U.S. Patent Application Publication No. 2012/0080332;

U.S. patent application Ser. No. 12/894,318, entitled FASTENER SYSTEM COMPRISING A PLURALITY OF CONNECTED RETENTION MATRIX ELEMENTS, now U.S. Patent Application Publication No. 2012/0080480;

U.S. patent application Ser. No. 12/894,330, entitled FASTENER SYSTEM COMPRISING A RETENTION MATRIX AND AN ALIGNMENT MATRIX, now U.S. Patent Application Publication No. 2012/0080503;

U.S. patent application Ser. No. 12/894,361, entitled FASTENER SYSTEM COMPRISING A RETENTION MATRIX, now U.S. Pat. No. 8,529,600;

U.S. patent application Ser. No. 12/894,367, entitled FASTENING INSTRUMENT FOR DEPLOYING A FASTENER SYSTEM COMPRISING A RETENTION MATRIX, now U.S. Patent Application Publication No. 2012/0080485;

U.S. patent application Ser. No. 12/894,388, entitled FASTENER SYSTEM COMPRISING A RETENTION MATRIX AND A COVER, now U.S. Pat. No. 8,474,677;

U.S. patent application Ser. No. 12/894,376, entitled FASTENER SYSTEM COMPRISING A PLURALITY OF FASTENER CARTRIDGES, now U.S. Patent Application Publication No. 2012/0080486;

U.S. patent application Ser. No. 13/097,865, entitled SURGICAL STAPLER ANVIL COMPRISING A PLURALITY OF FORMING POCKETS, now U.S. Patent Application Publication No. 2012/0080488;

U.S. patent application Ser. No. 13/097,936, entitled TISSUE THICKNESS COMPENSATOR FOR A SURGICAL STAPLER, now U.S. Patent Application Publication No. 2012/0080339;

U.S. patent application Ser. No. 13/097,954, entitled STAPLE CARTRIDGE COMPRISING A VARIABLE THICKNESS COMPRESSIBLE PORTION, now U.S. Patent Application Publication No. 2012/0080340;

U.S. patent application Ser. No. 13/097,856, entitled STAPLE CARTRIDGE COMPRISING STAPLES POSITIONED WITHIN A COMPRESSIBLE PORTION THEREOF, now U.S. Patent Application Publication No. 2012/0080336;

U.S. patent application Ser. No. 13/097,928, entitled TISSUE THICKNESS COMPENSATOR COMPRISING DETACHABLE PORTIONS, now U.S. Patent Application Publication No. 2012/0080490;

U.S. patent application Ser. No. 13/097,891, entitled TISSUE THICKNESS COMPENSATOR FOR A SURGICAL STAPLER COMPRISING AN ADJUSTABLE ANVIL, now U.S. Patent Application Publication No. 2012/0080489;

U.S. patent application Ser. No. 13/097,948, entitled STAPLE CARTRIDGE COMPRISING AN ADJUSTABLE DISTAL PORTION, now U.S. Patent Application Publication No. 2012/0083836;

U.S. patent application Ser. No. 13/097,907, entitled COMPRESSIBLE STAPLE CARTRIDGE ASSEMBLY, now U.S. Patent Application Publication No. 2012/0080338;

U.S. patent application Ser. No. 13/097,861, entitled TISSUE THICKNESS COMPENSATOR COMPRISING PORTIONS HAVING DIFFERENT PROPERTIES, U.S. Patent Application Publication No. 2012/0080337;

U.S. patent application Ser. No. 13/097,869, entitled STAPLE CARTRIDGE LOADING ASSEMBLY, now U.S. Patent Application Publication No. 2012/0160721;

U.S. patent application Ser. No. 13/097,917, entitled COMPRESSIBLE STAPLE CARTRIDGE COMPRISING ALIGNMENT MEMBERS, now U.S. Patent Application No. 2012/0083834;

U.S. patent application Ser. No. 13/097,873, entitled STAPLE CARTRIDGE COMPRISING A RELEASABLE PORTION, now U.S. Patent Application Publication No. 2012/0083833;

U.S. patent application Ser. No. 13/097,938, entitled STAPLE CARTRIDGE COMPRISING COMPRESSIBLE DISTORTION RESISTANT COMPONENTS, now U.S. Patent Application Publication No. 2012/0080491;

U.S. patent application Ser. No. 13/097,924, entitled STAPLE CARTRIDGE COMPRISING A TISSUE THICKNESS COMPENSATOR, now U.S. Patent Application Publication No. 2012/0083835;

U.S. patent application Ser. No. 13/242,029, entitled SURGICAL STAPLER WITH FLOATING ANVIL, now U.S. Patent Application Publication No. 2012/0080493;

U.S. patent application Ser. No. 13/242,066, entitled CURVED END EFFECTOR FOR A STAPLING INSTRUMENT, now U.S. Patent Application Publication No. 2012/0080498;

U.S. patent application Ser. No. 13/242,086, entitled STAPLE CARTRIDGE INCLUDING COLLAPSIBLE DECK, now U.S. Patent Application Publication No. 2013/0075450;

U.S. patent application Ser. No. 13/241,912, entitled STAPLE CARTRIDGE INCLUDING COLLAPSIBLE DECK ARRANGEMENT, now U.S. Patent Application Publication No. 2013/0075448;

U.S. patent application Ser. No. 13/241,922, entitled SURGICAL STAPLER WITH STATIONARY STAPLE DRIVERS, now U.S. Patent Application Publication No. 2013/0075449;

U.S. patent application Ser. No. 13/241,637, entitled SURGICAL INSTRUMENT WITH TRIGGER ASSEMBLY FOR GENERATING MULTIPLE ACTUATION MOTIONS, now U.S. Patent Application Publication No. 2012/0074201; and U.S. patent application Ser. No. 13/241,629, entitled SURGICAL INSTRUMENT WITH SELECTIVELY ARTICULATABLE END EFFECTOR, now U.S. Patent Application Publication No. 2012/0074200.

The Applicant of the present application also owns the U.S. Patent Applications identified below which were filed on even date herewith and which are each herein incorporated by reference in their respective entirety:

U.S. application Ser. No. 13/433,096, entitled TISSUE THICKNESS COMPENSATOR COMPRISING A PLURALITY OF CAPSULES, now U.S. Patent Application Publication No. 2012/0241496;

U.S. application Ser. No. 13/433,103, entitled TISSUE THICKNESS COMPENSATOR COMPRISING A PLURALITY OF LAYERS, now U.S. Patent Application Publication No. 2012/0241498;

U.S. application Ser. No. 13/433,098, entitled EXPANDABLE TISSUE THICKNESS COMPENSATOR, now U.S. Patent Application Publication No. 2012/0241491;

U.S. application Ser. No. 13/433,102, entitled TISSUE THICKNESS COMPENSATOR COMPRISING A RESERVOIR, now U.S. Patent Application Publication No. 2012/0241497;

U.S. application Ser. No. 13/433,114, entitled RETAINER ASSEMBLY INCLUDING A TISSUE THICKNESS COMPENSATOR, now U.S. Patent Application Publication No. 2012/0241499;

U.S. application Ser. No. 13/433,141, entitled TISSUE THICKNESS COMPENSATOR COMPRISING CONTROLLED RELEASE AND EXPANSION, now U.S. Patent Application Publication No. 2012/0241493;

U.S. application Ser. No. 13/433,144, entitled TISSUE THICKNESS COMPENSATOR COMPRISING FIBERS TO PRODUCE A RESILIENT LOAD, now U.S. Patent Application Publication Serial No. 2012/0241500;

U.S. application Ser. No. 13/433,148, entitled TISSUE THICKNESS COMPENSATOR COMPRISING STRUCTURE TO PRODUCE A RESILIENT LOAD, now U.S. Patent Application Publication Serial No. 2012/0241501;

U.S. application Ser. No. 13/433,155, entitled TISSUE THICKNESS COMPENSATOR COMPRISING RESILIENT MEMBERS, now U.S. Patent Application Publication No. 2012/0241502;

U.S. application Ser. No. 13/433,163, entitled METHODS FOR FORMING TISSUE THICKNESS COMPENSATOR ARRANGEMENTS FOR SURGICAL STAPLERS, now U.S. Patent Application Publication No. 2012/0248169;

U.S. application Ser. No. 13/433,167, entitled TISSUE THICKNESS COMPENSATORS, now U.S. Patent Application Publication No. 2012/0241503;

U.S. application Ser. No. 13/433,175, entitled LAYERED TISSUE THICKNESS COMPENSATOR, now U.S. Patent Application Publication No. 2012/0253298;

U.S. application Ser. No. 13/433,179, entitled TISSUE THICKNESS COMPENSATORS FOR CIRCULAR SURGICAL STAPLERS, now U.S. Patent Application Publication No. 2012/0241505;

U.S. application Ser. No. 13/433,115, entitled TISSUE THICKNESS COMPENSATOR COMPRISING CAPSULES DEFINING A LOW PRESSURE ENVIRONMENT, now U.S. Patent Application Publication No. 2013/0256372;

U.S. application Ser. No. 13/433,118, entitled TISSUE THICKNESS COMPENSATOR COMPRISED OF A PLURALITY OF MATERIALS, now U.S. Patent Application Publication No. 2013/0256365;

U.S. application Ser. No. 13/433,135, entitled MOVABLE MEMBER FOR USE WITH A TISSUE THICKNESS COMPENSATOR, U.S. Patent Application Publication No. 2013/0256382;

U.S. application Ser. No. 13/433,129, entitled TISSUE THICKNESS COMPENSATOR COMPRISING A PLURALITY OF MEDICAMENTS, now U.S. Patent Application Publication No. 2013/0256367;

U.S. application Ser. No. 13/433,140, entitled TISSUE THICKNESS COMPENSATOR AND METHOD FOR MAKING THE SAME, now U.S. Patent Application Publication No. 2013/0256368;

U.S. application Ser. No. 13/433,147, entitled TISSUE THICKNESS COMPENSATOR COMPRISING CHANNELS, now U.S. Patent Application Publication No. 2013/0256369;

U.S. application Ser. No. 13/433,126, entitled TISSUE THICKNESS COMPENSATOR COMPRISING TISSUE INGROWTH FEATURES, now U.S. Patent Application Publication No. 2013/0256366; and U.S. application Ser. No. 13/433,132, entitled DEVICES AND METHODS FOR ATTACHING TISSUE THICKNESS COMPENSATING MATERIALS TO SURGICAL STAPLING INSTRUMENTS, now U.S. Patent Application Publication No. 2013/0256373.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment", or "in an embodiment", or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the present invention.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the person of ordinary skill in the art will readily appreciate that the various methods and devices disclosed herein can be used in numerous surgical procedures and applications including, for example, in connection with open surgical procedures. As the present Detailed Description proceeds, those of ordinary skill in the art will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongated shaft of a surgical instrument can be advanced.

Figure 1:
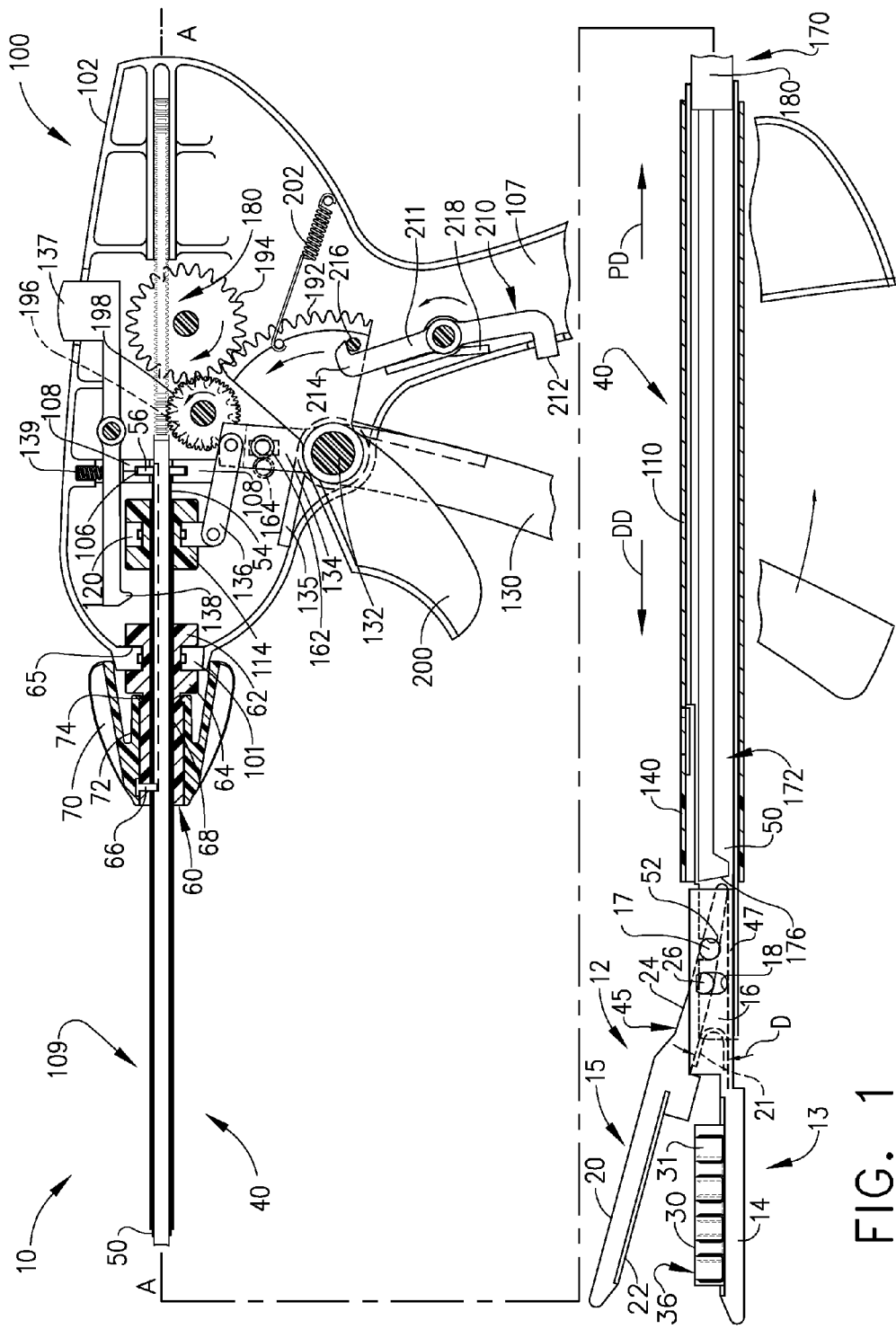
FIG. 1 is a cross-sectional view of a surgical instrument embodiment.

Turning to the Drawings wherein like numerals denote like components throughout the several views, FIG. 1 depicts a surgical instrument 10 that is capable of practicing several unique benefits. The surgical stapling instrument 10 is designed to manipulate and/or actuate various forms and sizes of end effectors 12 that are operably attached thereto. In the embodiment depicted in FIGS. 1-1E, for example, the end effector 12 includes an elongated channel 14 that forms a lower jaw 13 of the end effector 12. The elongated channel 14 is configured to support an "implantable" staple cartridge 30 and also movably support an anvil 20 that functions as an upper jaw 15 of the end effector 12.

In various embodiments, the elongated channel 14 may be fabricated from, for example, 300 & 400 Series, 17-4 & 17-7 stainless steel, titanium, etc. and be formed with spaced side walls 16. The anvil 20 may be fabricated from, for example, 300 & 400 Series, 17-4 & 17-7 stainless steel, titanium, etc. and have a staple forming undersurface, generally labeled as 22 that has a plurality of staple forming pockets 23 formed therein. See FIGS. 1B-1E. In addition, the anvil 20 has a bifurcated ramp assembly 24 that protrudes proximally therefrom. An anvil pin 26 protrudes from each lateral side of the ramp assembly 24 to be received within a corresponding slot or opening 18 in the side walls 16 of the elongated channel 14 to facilitate its movable or pivotable attachment thereto.

Figure 1A:
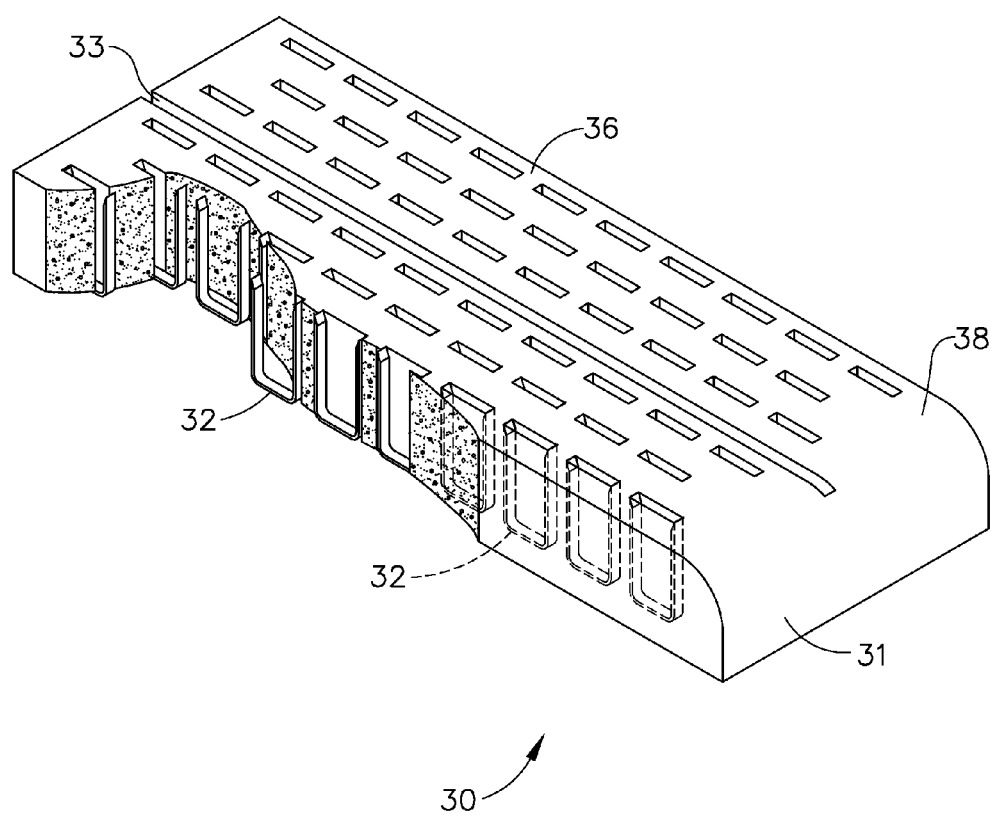
FIG. 1A is a perspective view of one embodiment of an implantable staple cartridge.

Various forms of implantable staple cartridges may be employed with the various embodiments of the surgical instruments disclosed herein. Specific staple cartridge configurations and constructions will be discussed in further detail below. However, in the embodiment depicted in FIG. 1A, an implantable staple cartridge 30 is shown. In at least one embodiment, the staple cartridge 30 has a body portion 31 that consists of a compressible hemostat material such as, for example, oxidized regenerated cellulose ("ORC") or a bioabsorbable foam in which lines of unformed metal staples 32 are supported. In at least some embodiments, in order to prevent the staple from being affected and the hemostat material from being activated during the introduction and positioning process, the entire cartridge may be coated or wrapped in a biodegradable film 38 such as a polydioxanon film sold under the trademark PDS® or with a Polyglycerol sebacate (PGS) film or other biodegradable films formed from PGA (Polyglycolic acid, marketed under the trade mark Vicryl), PCL (Polycaprolactone), PLA or PLLA (Polylactic acid), PHA (polyhydroxyalkanoate), PGCL (poliglecaprone 25, sold under the trademark Monocryl) or a composite of PGA, PCL, PLA, PDS that would be impermeable until ruptured. The body 31 of staple cartridge 30 is sized to be removably supported within the elongated channel 14 as shown such that each staple 32 therein is aligned with corresponding staple forming pockets 23 in the anvil when the anvil 20 is driven into forming contact with the staple cartridge 30.

In use, once the end effector 12 has been positioned adjacent the target tissue, the end effector 12 is manipulated to capture or clamp the target tissue between an upper face 36 of the staple cartridge 30 and the staple forming surface 22 of the anvil 20. The staples 32 are formed by moving the anvil 20 in a path that is substantially parallel to the elongated channel 14 to bring the staple forming surface 22 and, more particularly, the staple forming pockets 23 therein into substantially simultaneous contact with the upper face 36 of the staple cartridge 30. As the anvil 20 continues to move into the staple cartridge 30, the legs 34 of the staples 32 contact a corresponding staple forming pocket 23 in anvil 20 which serves to bend the staple legs 34 over to form the staples 32 into a "B shape". Further movement of the anvil 20 toward the elongated channel 14 will further compress and form the staples 32 to a desired final formed height "FF".

The above-described staple forming process is generally depicted in FIGS. 1B-1E. For example, FIG. 1B illustrates the end effector 12 with target tissue "T" between the anvil 20 and the upper face 36 of the implantable staple cartridge 30. FIG. 1C illustrates the initial clamping position of the anvil 20 wherein the anvil has 20 been closed onto the target tissue "T" to clamp the target tissue "T" between the anvil 20 and the upper face 36 of the staple cartridge 30. FIG. 1D illustrates the initial staple formation wherein the anvil 20 has started to compress the staple cartridge 30 such that the legs 34 of the staples 32 are starting to be formed by the staple forming pockets 23 in the anvil 20. FIG. 1E illustrates the staple 32 in its final formed condition through the target tissue "T" with the anvil 20 removed for clarity purposes.

Once the staples 32 have been formed and fastened to the target tissue "T", the surgeon will move the anvil 20 to the open position to enable the cartridge body 31 and the staples 32 to remain affixed to the target tissue while the end effector 12 is being withdrawn from the patient. The end effector 12 forms all of the staples simultaneously as the two jaws 13, 15 are clamped together. The remaining "crushed" body materials 31 act as both a hemostat (the ORC) and a staple line reinforcement (PGA, PDS or any of the other film compositions mentioned above 38). Also, since the staples 32 never have to leave the cartridge body 31 during forming, the likelihood of the staples 32 being malformed during forming is minimized. As used herein the term "implantable" means that, in addition to the staples, the cartridge body materials that support the staples will also remain in the patient and may eventually be absorbed by the patient's body. Such implantable staple cartridges are distinguishable from prior cartridge arrangements that remain positioned within the end effector in their entirety after they have been fired.

In various implementations, the end effector 12 is configured to be coupled to an elongated shaft assembly 40 that protrudes from a handle assembly 100. The end effector 12 (when closed) and the elongated shaft assembly 40 may have similar cross-sectional shapes and be sized to operably pass through a trocar tube or working channel in another form of access instrument. As used herein, the term "operably pass" means that the end effector and at least a portion of the elongated shaft assembly may be inserted through or passed through the channel or tube opening and can be manipulated therein as needed to complete the surgical stapling procedure. In some embodiments, when in a closed position, the jaws 13 and 15 of the end effector 12 may provide the end effector with a roughly circular cross-sectional shape that facilitates its passage through a circular passage/opening. However, the end effectors of various embodiments of the present invention, as well as the elongated shaft assembly embodiments, could conceivably be provided with other cross-sectional shapes that could otherwise pass through access passages and openings that have non-circular cross-sectional shapes. Thus, an overall size of a cross-section of a closed end effector will be related to the size of the passage or opening through which it is intended to pass. Thus, one end effector for example, may be referred to as a "5 mm" end effector which means it can operably pass through an opening that is at least approximately 5 mm in diameter.

In various embodiments, the elongated shaft assembly 40 may have an outer diameter that is substantially the same as the outer diameter of the end effector 12 when in a closed position. For example, a 5 mm end effector may be coupled to an elongated shaft assembly 40 that has 5 mm cross-sectional diameter. However, as the present Detailed Description proceeds, it will become apparent that various embodiments of the present may be effectively used in connection with different sizes of end effectors. For example, a 10 mm end effector may be attached to an elongated shaft that has a 5 mm cross-sectional diameter. Conversely, for those applications wherein a 10 mm or larger access opening or passage is provided, the elongated shaft assembly 40 may have a 10 mm (or larger) cross-sectional diameter, but may also be able to actuate a 5 mm or 10 mm end effector. Accordingly, the outer shaft 40 may have an outer diameter that is the same as or is different from the outer diameter of a closed end effector 12 attached thereto.

As depicted, the elongated shaft assembly 40 extends distally from the handle assembly 100 in a generally straight line to define a longitudinal axis A-A. In various embodiments, for example, the elongated shaft assembly 40 may be approximately 9-16 inches (229-406 mm) long. However, the elongated shaft assembly 40 may be provided in other lengths and, in other embodiments, may have joints therein or be otherwise configured to facilitate articulation of the end effector 12 relative to other portions of the shaft or handle assembly as will be discussed in further detail below. In various embodiments, the elongated shaft assembly 40 includes a spine member 50 that extends from the handle assembly 100 to the end effector 12. The proximal end of the elongated channel 14 of the end effector 12 has a pair of retention trunnions 17 protruding therefrom that are sized to be received within corresponding trunnion openings or cradles 52 that are provided in a distal end of the spine member 50 to enable the end effector 12 to be removably coupled the elongated shaft assembly 40. The spine member 50 may be fabricated from, for example, 6061 or 7075 aluminum, stainless steel, titanium, etc.

In various embodiments, the handle assembly 100 comprises a pistol grip-type housing that may be fabricated in two or more pieces for assembly purposes. For example, the handle assembly 100 as shown comprises a right hand case member 102 and a left hand case member (not illustrated) that are molded or otherwise fabricated from a polymer or plastic material and are designed to mate together. Such case members may be attached together by snap features, pegs and sockets molded or otherwise formed therein and/or by adhesive, screws, etc. The spine member 50 has a proximal end 54 that has a flange 56 formed thereon. The flange 56 is configured to be rotatably supported within a groove 106 formed by mating ribs 108 that protrude inwardly from each of the case members 102, 104. Such arrangement facilitates the attachment of the spine member 50 to the handle assembly 100 while enabling the spine member 50 to be rotated relative to the handle assembly 100 about the longitudinal axis A-A in a 360° path.

As can be further seen in FIG. 1, the spine member 50 passes through and is supported by a mounting bushing 60 that is rotatably affixed to the handle assembly 100. The mounting bushing 60 has a proximal flange 62 and a distal flange 64 that define a rotational groove 65 that is configured to rotatably receive a nose portion 101 of the handle assembly 100 therebetween. Such arrangement enables the mounting bushing 60 to rotate about longitudinal axis A-A relative to the handle assembly 100. The spine member 50 is non-rotatably pinned to the mounting bushing 60 by a spine pin 66. In addition, a rotation knob 70 is attached to the mounting bushing 60. In one embodiment, for example, the rotation knob 70 has a hollow mounting flange portion 72 that is sized to receive a portion of the mounting bushing 60 therein. In various embodiments, the rotation knob 70 may be fabricated from, for example, glass or carbon filled Nylon, polycarbonate, Ultem®, etc. and is affixed to the mounting bushing 60 by the spine pin 66 as well. In addition, an inwardly protruding retention flange 74 is formed on the mounting flange portion 72 and is configured to extend into a radial groove 68 formed in the mounting bushing 60. Thus, the surgeon may rotate the spine member 50 (and the end effector 12 attached thereto) about longitudinal axis A-A in a 360° path by grasping the rotation knob 70 and rotating it relative to the handle assembly 100.

In various embodiments, the anvil 20 is retained in an open position by an anvil spring 21 and/or another biasing arrangement. The anvil 20 is selectively movable from the open position to various closed or clamping and firing positions by a firing system, generally designated as 109. The firing system 109 includes a "firing member" 110 which, in various embodiments, comprises a hollow firing tube 110. The hollow firing tube 110 is axially movable on the spine member 50 and thus forms the outer portion of the elongated shaft assembly 40. The firing tube 110 may be fabricated from a polymer or other suitable material and have a proximal end that is attached to a firing yoke 114 of the firing system 109. In various embodiments for example, the firing yoke 114 may be over-molded to the proximal end of the firing tube 110. However, other fastener arrangements may be employed.

As can be seen in FIG. 1, the firing yoke 114 may be rotatably supported within a support collar 120 that is configured to move axially within the handle assembly 100. In various embodiments, the support collar 120 has a pair of laterally extending fins that are sized to be slidably received within fin slots formed in the right and left hand case members. Thus, the support collar 120 may slide axially within the handle housing 100 while enabling the firing yoke 114 and firing tube 110 to rotate relative thereto about the longitudinal axis A-A. In various embodiments, a longitudinal slot is provided through the firing tube 110 to enable the spine pin 66 to extend therethrough into the spine member 50 while facilitating the axial travel of the firing tube 110 on the spine member 50.

The firing system 109 further comprises a firing trigger 130 which serves to control the axial travel of the firing tube 110 on the spine member 50. See FIG. 1. Such axial movement in the distal direction of the firing tube 110 into firing interaction with the anvil 20 is referred to herein as "firing motion". As can be seen in FIG. 1, the firing trigger 130 is movably or pivotally coupled to the handle assembly 100 by a pivot pin 132. A torsion spring 135 is employed to bias the firing trigger 130 away from the pistol grip portion 107 of the handle assembly 100 to an un-actuated "open" or starting position. As can be seen in FIG. 1, the firing trigger 130 has an upper portion 134 that is movably attached to (pinned) firing links 136 that are movably attached to (pinned) the support collar 120. Thus, movement of the firing trigger 130 from the starting position (FIG. 1) toward an ending position adjacent the pistol grip portion 107 of the handle assembly 100 will cause the firing yoke 114 and the firing tube 110 to move in the distal direction "DD". Movement of the firing trigger 130 away from the pistol grip portion 107 of the handle assembly 100 (under the bias of the torsion spring 135) will cause the firing yoke 114 and firing tube 110 to move in the proximal direction "PD" on the spine member 50.

Various embodiments of the present invention may be employed with different sizes and configurations of implantable staple cartridges. For example, the surgical instrument 10, when used in connection with a first firing adapter 140, may be used with a 5 mm end effector 12 that is approximately 20 mm long (or in other lengths) which supports an implantable staple cartridge 30. Such end effector size may be particularly well-suited, for example, to complete relatively fine dissection and vascular transactions. However, as will be discussed in further detail below, the surgical instrument 10 may also be employed, for example, in connection with other sizes of end effectors and staple cartridges by replacing the first firing adapter 140 with a second firing adapter. In still other embodiments, the elongated shaft assembly 40 may configured to be attached to only one form or size of end effector.

One method of removably coupling the end effector 12 to the spine member 50 will now be explained. The coupling process is commenced by inserting the retention trunnions 17 on the elongated channel 14 into the trunnion cradles 52 in the spine member 50. Thereafter, the surgeon advances the firing trigger 130 toward the pistol grip 107 of the housing assembly 100 to distally advance the firing tube 110 and the first firing adapter 140 over a proximal end portion 47 of the elongated channel 14 to thereby retain the trunnions 17 in their respective cradles 52. Such position of the first firing adapter 140 over the trunnions 17 is referred to herein as the "coupled position". Various embodiments of the present invention may also have an end effector locking assembly for locking the firing trigger 130 in position after an end effector 12 has been attached to the spine member 50.

More specifically, one embodiment of the end effector locking assembly 160 includes a retention pin 162 that is movably supported in the upper portion 134 of the firing trigger 130. As discussed above, the firing tube 110 must initially be advanced distally to the coupled position wherein the first firing adapter 140 retains the retention trunnions 17 of the end effector 12 in the trunnion cradles 52 in the spine member 50. The surgeon advances the firing adapter 140 distally to the coupled position by pulling the firing trigger 130 from the starting position toward the pistol grip 107. As the firing trigger 130 is initially actuated, the retention pin 162 is moved distally until the firing tube 110 has advanced the first firing adapter 140 to the coupled position at which point the retention pin 162 is biased into a locking cavity 164 formed in the case member. In various embodiments, when the retention pin 162 enters into the locking cavity 164, the pin 162 may make an audible "click" or other sound, as well as provide a tactile indication to the surgeon that the end effector 12 has been "locked" onto the spine member 50. In addition, the surgeon cannot inadvertently continue to actuate the firing trigger 130 to start to form staples 32 in the end effector 12 without intentionally biasing the retention pin 162 out of the locking cavity 164. Similarly, if the surgeon releases the firing trigger 130 when in the coupled position, it is retained in that position by the retention pin 162 to prevent the firing trigger 130 from returning to the starting position and thereby releasing the end effector 12 from the spine member 50.

Various embodiments of the present invention may further include a firing system lock button 137 that is pivotally attached to the handle assembly 100. In one form, the firing system lock button 137 has a latch 138 formed on a distal end thereof that is oriented to engage the firing yoke 114 when the firing release button is in a first latching position. As can be seen in FIG. 1, a latch spring 139 serves to bias the firing system lock button 137 to the first latching position. In various circumstances, the latch 138 serves to engage the firing yoke 114 at a point where the position of the firing yoke 114 on the spine member 50 corresponds to a point wherein the first firing adapter 140 is about to distally advance up the clamping ramp 28 on the anvil 20. It will be understood that, as the first firing adapter 140 advances axially up the clamping ramp 28, the anvil 20 will move in a path such that its staple forming surface portion 22 is substantially parallel to the upper face 36 of the staple cartridge 30.

After the end effector 12 has been coupled to the spine member 50, the staple forming process is commenced by first depressing the firing system lock button 137 to enable the firing yoke 114 to be further moved distally on the spine member 50 and ultimately compress the anvil 20 into the staple cartridge 30. After depressing the firing system lock button 137, the surgeon continues to actuate the firing trigger 130 towards the pistol grip 107 thereby driving the first staple collar 140 up the corresponding staple forming ramp 29 to force the anvil 20 into forming contact with the staples 32 in the staple cartridge 30. The firing system lock button 137 prevents the inadvertent forming of the staples 32 until the surgeon is ready to start that process. In this embodiment, the surgeon must depress the firing system lock button 137 before the firing trigger 130 may be further actuated to begin the staple forming process.

The surgical instrument 10 may be solely used as a tissue stapling device if so desired. However, various embodiments of the present invention may also include a tissue cutting system, generally designated as 170. In at least one form, the tissue cutting system 170 comprises a knife member 172 that may be selectively advanced from an un-actuated position adjacent the proximal end of the end effector 12 to an actuated position by actuating a knife advancement trigger 200. The knife member 172 is movably supported within the spine member 50 and is attached or otherwise protrudes from a knife rod 180. The knife member 172 may be fabricated from, for example, 420 or 440 stainless steel with a hardness of greater than 38HRC (Rockwell Hardness C-scale) and have a tissue cutting edge 176 formed on the distal end 174 thereof and be configured to slidably extend through a slot in the anvil 20 and a centrally disposed slot 33 in the staple cartridge 30 to cut through tissue that is clamped in the end effector 12. In various embodiments, the knife rod 180 extends through the spine member 50 and has a proximal end portion which drivingly interfaces with a knife transmission that is operably attached to the knife advance trigger 200. In various embodiments, the knife advance trigger 200 is attached to pivot pin 132 such that it may be pivoted or otherwise actuated without actuating the firing trigger 130. In various embodiments, a first knife gear 192 is also attached to the pivot pin 132 such that actuation of the knife advance trigger 200 also pivots the first knife gear 192. A firing return spring 202 is attached between the first knife gear 192 and the handle housing 100 to bias the knife advancement trigger 200 to a starting or un-actuated position.

Various embodiments of the knife transmission also include a second knife gear 194 that is rotatably supported on a second gear spindle and in meshing engagement with the first knife gear 192. The second knife gear 194 is in meshing engagement with a third knife gear 196 that is supported on a third gear spindle. Also supported on the third gear spindle 195 is a fourth knife gear 198. The fourth knife gear 198 is adapted to drivingly engage a series of annular gear teeth or rings on a proximal end of the knife rod 180. Thus, such arrangement enables the fourth knife gear 198 to axially drive the knife rod 180 in the distal direction "DD" or proximal direction "PD" while enabling the firing rod 180 to rotate about longitudinal axis A-A with respect to the fourth knife gear 198. Accordingly, the surgeon may axially advance the firing rod 180 and ultimately the knife member 172 distally by pulling the knife advancement trigger 200 towards the pistol grip 107 of the handle assembly 100.

Various embodiments of the present invention further include a knife lockout system 210 that prevents the advancement of the knife member 172 unless the firing trigger 130 has been pulled to the fully fired position. Such feature will therefore prevent the activation of the knife advancement system 170 unless the staples have first been fired or formed into the tissue. As can be seen in FIG. 1, various implementations of the knife lockout system 210 comprise a knife lockout bar 211 that is pivotally supported within the pistol grip portion 107 of the handle assembly 100. The knife lockout bar 211 has an activation end 212 that is adapted to be engaged by the firing trigger 130 when the firing trigger 130 is in the fully fired position. In addition, the knife lockout bar 211 has a retaining hook 214 on its other end that is adapted to hookingly engage a latch rod 216 on the first cut gear 192. A knife lock spring 218 is employed to bias the knife lockout bar 211 to a "locked" position wherein the retaining hook 214 is retained in engagement with the latch rod 216 to thereby prevent actuation of the knife advancement trigger 200 unless the firing trigger 130 is in the fully fired position.

After the staples have been "fired" (formed) into the target tissue, the surgeon may depress the firing trigger release button 167 to enable the firing trigger 130 to return to the starting position under the bias of the torsion spring 135 which enables the anvil 20 to be biased to an open position under the bias of spring 21. When in the open position, the surgeon may withdraw the end effector 12 leaving the implantable staple cartridge 30 and staples 32 behind. In applications wherein the end effector was inserted through a passage, working channel, etc. the surgeon will return the anvil 20 to the closed position by activating the firing trigger 130 to enable the end effector 12 to be withdrawn out through the passage or working channel. If, however, the surgeon desires to cut the target tissue after firing the staples, the surgeon activates the knife advancement trigger 200 in the above-described manner to drive the knife bar 172 through the target tissue to the end of the end effector. Thereafter, the surgeon may release the knife advancement trigger 200 to enable the firing return spring 202 to cause the firing transmission to return the knife bar 172 to the starting (un-actuated) position. Once the knife bar 172 has been returned to the starting position, the surgeon may open the end effector jaws 13, 15 to release the implantable cartridge 30 within the patient and then withdraw the end effector 12 from the patient. Thus, such surgical instruments facilitate the use of small implantable staple cartridges that may be inserted through relatively smaller working channels and passages, while providing the surgeon with the option to fire the staples without cutting tissue or if desired to also cut tissue after the staples have been fired.

Various unique and novel embodiments of the present invention employ a compressible staple cartridge that supports staples in a substantially stationary position for forming contact by the anvil. In various embodiments, the anvil is driven into the unformed staples wherein, in at least one such embodiment, the degree of staple formation attained is dependent upon how far the anvil is driven into the staples. Such an arrangement provides the surgeon with the ability to adjust the amount of forming or firing pressure applied to the staples and thereby alter the final formed height of the staples. In other various embodiments of the present invention, surgical stapling arrangements can employ staple driving elements which can lift the staples toward the anvil. Such embodiments are described in greater detail further below.

In various embodiments, with regard to the embodiments described in detail above, the amount of firing motion that is applied to the movable anvil is dependent upon the degree of actuation of the firing trigger. For example, if the surgeon desires to attain only partially formed staples, then the firing trigger is only partially depressed inward towards the pistol grip 107. To attain more staple formation, the surgeon simply compresses the firing trigger further which results in the anvil being further driven into forming contact with the staples. As used herein, the term "forming contact" means that the staple forming surface or staple forming pockets have contacted the ends of the staple legs and have started to form or bend the legs over into a formed position. The degree of staple formation refers to how far the staple legs have been folded over and ultimately relates to the forming height of the staple as referenced above. Those of ordinary skill in the art will further understand that, because the anvil 20 moves in a substantially parallel relationship with respect to the staple cartridge as the firing motions are applied thereto, the staples are formed substantially simultaneously with substantially the same formed heights.

FIGS. 2 and 3 illustrate an alternative end effector 12" that is similar to the end effector 12' described above, except with the following differences that are configured to accommodate a knife bar 172'. The knife bar 172' is coupled to or protrudes from a knife rod 180 and is otherwise operated in the above described manner with respect to the knife bar 172. However, in this embodiment, the knife bar 172' is long enough to traverse the entire length of the end effector 12" and therefore, a separate distal knife member is not employed in the end effector 12". The knife bar 172' has an upper transverse member 173' and a lower transverse member 175' formed thereon. The upper transverse member 173' is oriented to slidably transverse a corresponding elongated slot 250 in anvil 20" and the lower transverse member 175' is oriented to traverse an elongated slot 252 in the elongated channel 14" of the end effector 12". A disengagement slot (not shown) is also provide din the anvil 20" such that when the knife bar 172' has been driven to an ending position with thin end effector 12", the upper transverse member 173' drops through the corresponding slot to enable the anvil 20" to move to the open position to disengage the stapled and cut tissue. The anvil 20" may be otherwise identical to anvil 20 described above and the elongated channel 14" may be otherwise identical to elongated channel 14 described above.

In these embodiments, the anvil 20" is biased to a fully open position (FIG. 2) by a spring or other opening arrangement (not shown). The anvil 20" is moved between the open and fully clamped positions by the axial travel of the firing adapter 150 in the manner described above. Once the firing adapter 150 has been advanced to the fully clamped position (FIG. 3), the surgeon may then advance the knife bar 172" distally in the manner described above. If the surgeon desires to use the end effector as a grasping device to manipulate tissue, the firing adapter may be moved proximally to allow the anvil 20" to move away from the elongated channel 14" as represented in FIG. 4 in broken lines. In this embodiment, as the knife bar 172" moves distally, the upper transverse member 173' and the lower transverse member 175' draw the anvil 20" and elongated channel 14" together to achieve the desired staple formation as the knife bar 172" is advanced distally through the end effector 12". See FIG. 5. Thus, in this embodiment, staple formation occurs simultaneously with tissue cutting, but the staples themselves may be sequentially formed as the knife bar 172" is driven distally.

The unique and novel features of the various surgical staple cartridges and the surgical instruments of the present invention enable the staples in those cartridges to be arranged in one or more linear or non-linear lines. A plurality of such staple lines may be provided on each side of an elongated slot that is centrally disposed within the staple cartridge for receiving the tissue cutting member therethrough. In one arrangement, for example, the staples in one line may be substantially parallel with the staples in adjacent line(s) of staples, but offset therefrom. In still other embodiments, one or more lines of staples may be non-linear in nature. That is, the base of at least one staple in a line of staples may extend along an axis that is substantially transverse to the bases of other staples in the same staple line. For example, the lines of staples on each side of the elongated slot may have a zigzag appearance.

In various embodiments, a staple cartridge can comprise a cartridge body and a plurality of staples stored within the cartridge body. In use, the staple cartridge can be introduced into a surgical site and positioned on a side of the tissue being treated. In addition, a staple-forming anvil can be positioned on the opposite side of the tissue. In various embodiments, the anvil can be carried by a first jaw and the staple cartridge can be carried by a second jaw, wherein the first jaw and/or the second jaw can be moved toward the other. Once the staple cartridge and the anvil have been positioned relative to the tissue, the staples can be ejected from the staple cartridge body such that the staples can pierce the tissue and contact the staple-forming anvil. Once the staples have been deployed from the staple cartridge body, the staple cartridge body can then be removed from the surgical site. In various embodiments disclosed herein, a staple cartridge, or at least a portion of a staple cartridge, can be implanted with the staples. In at least one such embodiment, as described in greater detail further below, a staple cartridge can comprise a cartridge body which can be compressed, crushed, and/or collapsed by the anvil when the anvil is moved from an open position into a closed position. When the cartridge body is compressed, crushed, and/or collapsed, the staples positioned within the cartridge body can be deformed by the anvil. Alternatively, the jaw supporting the staple cartridge can be moved toward the anvil into a closed position. In either event, in various embodiments, the staples can be deformed while they are at least partially positioned within the cartridge body. In certain embodiments, the staples may not be ejected from the staple cartridge while, in some embodiments, the staples can be ejected from the staple cartridge along with a portion of the cartridge body.

Referring now to FIGS. 6A-6D, a compressible staple cartridge, such as staple cartridge 1000, for example, can comprise a compressible, implantable cartridge body 1010 and, in addition, a plurality of staples 1020 positioned in the compressible cartridge body 1010, although only one staple 1020 is depicted in FIGS. 6A-6D. FIG. 6A illustrates the staple cartridge 1000 supported by a staple cartridge support, or staple cartridge channel, 1030, wherein the staple cartridge 1000 is illustrated in an uncompressed condition. In such an uncompressed condition, the anvil 1040 may or may not be in contact with the tissue T. In use, the anvil 1040 can be moved from an open position into contact with the tissue T as illustrated in FIG. 6B and position the tissue T against the cartridge body 1010. Even though the anvil 1040 can position the tissue T against a tissue-contacting surface 1019 of staple cartridge body 1010, referring again to FIG. 6B, the staple cartridge body 1010 may be subjected to little, if any, compressive force or pressure at such point and the staples 1020 may remain in an unformed, or unfired, condition. As illustrated in FIGS. 6A and 6B, the staple cartridge body 1010 can comprise one or more layers and the staple legs 1021 of staples 1020 can extend upwardly through these layers. In various embodiments, the cartridge body 1010 can comprise a first layer 1011, a second layer 1012, a third layer 1013, wherein the second layer 1012 can be positioned intermediate the first layer 1011 and the third layer 1013, and a fourth layer 1014, wherein the third layer 1013 can be positioned intermediate the second layer 1012 and the fourth layer 1014. In at least one embodiment, the bases 1022 of the staples 1020 can be positioned within cavities 1015 in the fourth layer 1014 and the staple legs 1021 can extend upwardly from the bases 1022 and through the fourth layer 1014, the third layer 1013, and the second layer 1012, for example. In various embodiments, each deformable leg 1021 can comprise a tip, such as sharp tip 1023, for example, which can be positioned in the second layer 1012, for example, when the staple cartridge 1000 is in an uncompressed condition. In at least one such embodiment, the tips 1023 may not extend into and/or through the first layer 1011, wherein, in at least one embodiment, the tips 1023 may not protrude through the tissue-contacting surface 1019 when the staple cartridge 1000 is in an uncompressed condition. In certain other embodiments, the sharp tips 1023 may be positioned in the third layer 1013, and/or any other suitable layer, when the staple cartridge is in an uncompressed condition. In various alternative embodiments, a cartridge body of a staple cartridge may have any suitable number of layers such as less than four layers or more than four layers, for example.

In various embodiments, as described in greater detail below, the first layer 1011 can be comprised of a buttress material and/or plastic material, such as polydioxanone (PDS) and/or polyglycolic acid (PGA), for example, and the second layer 1012 can be comprised of a bioabsorbable foam material and/or a compressible haemostatic material, such as oxidized regenerated cellulose (ORC), for example. In various embodiments, one or more of the first layer 1011, the second layer 1012, the third layer 1013, and the fourth layer 1014 may hold the staples 1020 within the staple cartridge body 1010 and, in addition, maintain the staples 1020 in alignment with one another. In various embodiments, the third layer 1013 can be comprised of a buttress material, or a fairly incompressible or inelastic material, which can be configured to hold the staple legs 1021 of the staples 1020 in position relative to one another. Furthermore, the second layer 1012 and the fourth layer 1014, which are positioned on opposite sides of the third layer 1013, can stabilize, or reduce the movement of, the staples 1020 even though the second layer 1012 and the fourth layer 1014 can be comprised of a compressible foam or elastic material. In certain embodiments, the staple tips 1023 of the staple legs 1021 can be at least partially embedded in the first layer 1011. In at least one such embodiment, the first layer 1011 and the third layer 1013 can be configured to co-operatively and firmly hold the staple legs 1021 in position. In at least one embodiment, the first layer 1011 and the third layer 1013 can each be comprised of a sheet of bioabsorbable plastic, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example, and the second layer 1012 and the fourth layer 1014 can each be comprised of at least one haemostatic material or agent.

Although the first layer 1011 can be compressible, the second layer 1012 can be substantially more compressible than the first layer 1011. For example, the second layer 1012 can be about twice as compressible, about three times as compressible, about four times as compressible, about five times as compressible, and/or about ten times as compressible, for example, as the first layer 1011. Stated another way, the second layer 1012 may compress about two times, about three times, about four times, about five times, and/or about ten times as much as first layer 1011, for a given force. In certain embodiments, the second layer 1012 can be between about twice as compressible and about ten times as compressible, for example, as the first layer 1011. In at least one embodiment, the second layer 1012 can comprise a plurality of air voids defined therein, wherein the amount and/or size of the air voids in the second layer 1012 can be controlled in order to provide a desired compressibility of the second layer 1012. Similar to the above, although the third layer 1013 can be compressible, the fourth layer 1014 can be substantially more compressible than the third layer 1013. For example, the fourth layer 1014 can be about twice as compressible, about three times as compressible, about four times as compressible, about five times as compressible, and/or about ten times as compressible, for example, as the third layer 1013. Stated another way, the fourth layer 1014 may compress about two times, about three times, about four times, about five times, and/or about ten times as much as third layer 1013, for a given force. In certain embodiments, the fourth layer 1014 can be between about twice as compressible and about ten times as compressible, for example, as the third layer 1013. In at least one embodiment, the fourth layer 1014 can comprise a plurality of air voids defined therein, wherein the amount and/or size of the air voids in the fourth layer 1014 can be controlled in order to provide a desired compressibility of the fourth layer 1014. In various circumstances, the compressibility of a cartridge body, or cartridge body layer, can be expressed in terms of a compression rate, i.e., a distance in which a layer is compressed for a given amount of force. For example, a layer having a high compression rate will compress a larger distance for a given amount of compressive force applied to the layer as compared to a layer having a lower compression rate. This being said, the second layer 1012 can have a higher compression rate than the first layer 1011 and, similarly, the fourth layer 1014 can have a higher compression rate than the third layer 1013. In various embodiments, the second layer 1012 and the fourth layer 1014 can be comprised of the same material and can comprise the same compression rate. In various embodiments, the second layer 1012 and the fourth layer 1014 can be comprised of materials having different compression rates. Similarly, the first layer 1011 and the third layer 1013 can be comprised of the same material and can comprise the same compression rate. In certain embodiments, the first layer 1011 and the third layer 1013 can be comprised of materials having different compression rates.

As the anvil 1040 is moved toward its closed position, the anvil 1040 can contact tissue T and apply a compressive force to the tissue T and the staple cartridge 1000, as illustrated in FIG. 6C. In such circumstances, the anvil 1040 can push the top surface, or tissue-contacting surface 1019, of the cartridge body 1010 downwardly toward the staple cartridge support 1030. In various embodiments, the staple cartridge support 1030 can comprise a cartridge support surface 1031 which can be configured to support the staple cartridge 1000 as the staple cartridge 1000 is compressed between the cartridge support surface 1031 and the tissue-contacting surface 1041 of anvil 1040. Owing to the pressure applied by the anvil 1040, the cartridge body 1010 can be compressed and the anvil 1040 can come into contact with the staples 1020. More particularly, in various embodiments, the compression of the cartridge body 1010 and the downward movement of the tissue-contacting surface 1019 can cause the tips 1023 of the staple legs 1021 to pierce the first layer 1011 of cartridge body 1010, pierce the tissue T, and enter into forming pockets 1042 in the anvil 1040. As the cartridge body 1010 is further compressed by the anvil 1040, the tips 1023 can contact the walls defining the forming pockets 1042 and, as a result, the legs 1021 can be deformed or curled inwardly, for example, as illustrated in FIG. 6C. As the staple legs 1021 are being deformed, as also illustrated in FIG. 6C, the bases 1022 of the staples 1020 can be in contact with or supported by the staple cartridge support 1030. In various embodiments, as described in greater detail below, the staple cartridge support 1030 can comprise a plurality of support features, such as staple support grooves, slots, or troughs 1032, for example, which can be configured to support the staples 1020, or at least the bases 1022 of the staples 1020, as the staples 1020 are being deformed. As also illustrated in FIG. 6C, the cavities 1015 in the fourth layer 1014 can collapse as a result of the compressive force applied to the staple cartridge body 1010. In addition to the cavities 1015, the staple cartridge body 1010 can further comprise one or more voids, such as voids 1016, for example, which may or may not comprise a portion of a staple positioned therein, that can be configured to allow the cartridge body 1010 to collapse. In various embodiments, the cavities 1015 and/or the voids 1016 can be configured to collapse such that the walls defining the cavities and/or walls deflect downwardly and contact the cartridge support surface 1031 and/or contact a layer of the cartridge body 1010 positioned underneath the cavities and/or voids.

Upon comparing FIG. 6B and FIG. 6C, it is evident that the second layer 1012 and the fourth layer 1014 have been substantially compressed by the compressive pressure applied by the anvil 1040. It may also be noted that the first layer 1011 and the third layer 1013 have been compressed as well. As the anvil 1040 is moved into its closed position, the anvil 1040 may continue to further compress the cartridge body 1010 by pushing the tissue-contacting surface 1019 downwardly toward the staple cartridge support 1030. As the cartridge body 1010 is further compressed, the anvil 1040 can deform the staples 1020 into their completely-formed shape as illustrated in FIG. 6D. Referring to FIG. 6D, the legs 1021 of each staple 1020 can be deformed downwardly toward the base 1022 of each staple 1020 in order to capture at least a portion of the tissue T, the first layer 1011, the second layer 1012, the third layer 1013, and the fourth layer 1014 between the deformable legs 1021 and the base 1022. Upon comparing FIGS. 6C and 6D, it is further evident that the second layer 1012 and the fourth layer 1014 have been further substantially compressed by the compressive pressure applied by the anvil 1040. It may also be noted upon comparing FIGS. 6C and 6D that the first layer 1011 and the third layer 1013 have been further compressed as well. After the staples 1020 have been completely, or at least sufficiently, formed, the anvil 1040 can be lifted away from the tissue T and the staple cartridge support 1030 can be moved away, and/or detached from, the staple cartridge 1000. As depicted in FIG. 6D, and as a result of the above, the cartridge body 1010 can be implanted with the staples 1020. In various circumstances, the implanted cartridge body 1010 can support the tissue along the staple line. In some circumstances, a haemostatic agent, and/or any other suitable therapeutic medicament, contained within the implanted cartridge body 1010 can treat the tissue over time. A haemostatic agent, as mentioned above, can reduce the bleeding of the stapled and/or incised tissue while a bonding agent or tissue adhesive can provide strength to the tissue over time. The implanted cartridge body 1010 can be comprised of materials such as ORC (oxidized regenerated cellulose), extracellular proteins such as collagen, polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain circumstances, the cartridge body 1010 can comprise an antibiotic and/or anti-microbial material, such as colloidal silver and/or triclosan, for example, which can reduce the possibility of infection in the surgical site.

In various embodiments, the layers of the cartridge body 1010 can be connected to one another. In at least one embodiment, the second layer 1012 can be adhered to the first layer 1011, the third layer 1013 can be adhered to the second layer 1012, and the fourth layer 1014 can be adhered to the third layer 1013 utilizing at least one adhesive, such as fibrin and/or protein hydrogel, for example. In certain embodiments, although not illustrated, the layers of the cartridge body 1010 can be connected together by interlocking mechanical features. In at least one such embodiment, the first layer 1011 and the second layer 1012 can each comprise corresponding interlocking features, such as a tongue and groove arrangement and/or a dovetail joint arrangement, for example. Similarly, the second layer 1012 and the third layer 1013 can each comprise corresponding interlocking features while the third layer 1013 and the fourth layer 1014 can each comprise corresponding interlocking features. In certain embodiments, although not illustrated, the staple cartridge 1000 can comprise one or more rivets, for example, which can extend through one or more layers of the cartridge body 1010. In at least one such embodiment, each rivet can comprise a first end, or head, positioned adjacent to the first layer 1011 and a second head positioned adjacent to the fourth layer 1014 which can be either assembled to or formed by a second end of the rivet. Owing to the compressible nature of the cartridge body 1010, in at least one embodiment, the rivets can compress the cartridge body 1010 such that the heads of the rivets can be recessed relative to the tissue-contacting surface 1019 and/or the bottom surface 1018 of the cartridge body 1010, for example. In at least one such embodiment, the rivets can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In certain embodiments, the layers of the cartridge body 1010 may not be connected to one another other than by the staples 1020 contained therein. In at least one such embodiment, the frictional engagement between the staple legs 1021 and the cartridge body 1010, for example, can hold the layers of the cartridge body 1010 together and, once the staples have been formed, the layers can be captured within the staples 1020. In certain embodiments, at least a portion of the staple legs 1021 can comprise a roughened surface or rough coating which can increase the friction forces between the staples 1020 and the cartridge body 1010.

As described above, a surgical instrument can comprise a first jaw including the staple cartridge support 1030 and a second jaw including the anvil 1040. In various embodiments, as described in greater detail further below, the staple cartridge 1000 can comprise one or more retention features which can be configured to engage the staple cartridge support 1030 and, as a result, releasably retain the staple cartridge 1000 to the staple cartridge support 1030. In certain embodiments, the staple cartridge 1000 can be adhered to the staple cartridge support 1030 by at least one adhesive, such as fibrin and/or protein hydrogel, for example. In use, in at least one circumstance, especially in laparoscopic and/or endoscopic surgery, the second jaw can be moved into a closed position opposite the first jaw, for example, such that the first and second jaws can be inserted through a trocar into a surgical site. In at least one such embodiment, the trocar can define an approximately 5 mm aperture, or cannula, through which the first and second jaws can be inserted. In certain embodiments, the second jaw can be moved into a partially-closed position intermediate the open position and the closed position which can allow the first and second jaws to be inserted through the trocar without deforming the staples 1020 contained in the staple cartridge body 1010. In at least one such embodiment, the anvil 1040 may not apply a compressive force to the staple cartridge body 1010 when the second jaw is in its partially-closed intermediate position while, in certain other embodiments, the anvil 1040 can compress the staple cartridge body 1010 when the second jaw is in its partially-closed intermediate position. Even though the anvil 1040 can compress the staple cartridge body 1010 when it is in such an intermediate position, the anvil 1040 may not sufficiently compress the staple cartridge body 1010 such that the anvil 1040 comes into contact with the staples 1020 and/or such that the staples 1020 are deformed by the anvil 1040. Once the first and second jaws have been inserted through the trocar into the surgical site, the second jaw can be opened once again and the anvil 1040 and the staple cartridge 1000 can be positioned relative to the targeted tissue as described above.

Figure 7A:
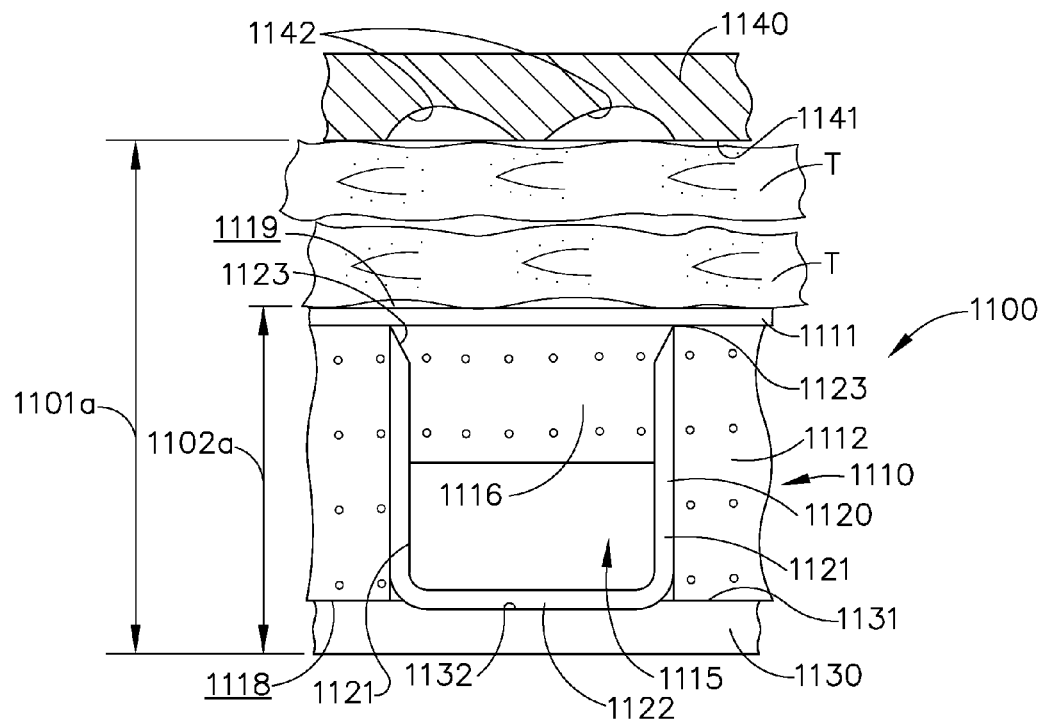
FIG. 7A is a diagram illustrating a staple positioned in a crushable staple cartridge body.
Figure 7B:
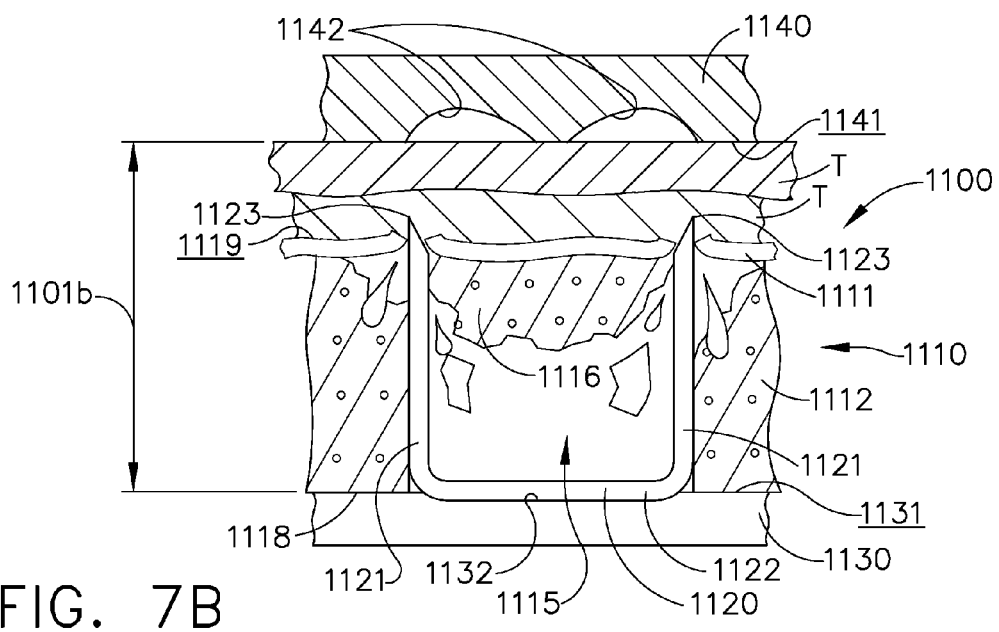
FIG. 7B is a diagram illustrating the crushable staple cartridge body of FIG. 7A being crushed by an anvil.
Figure 7C:
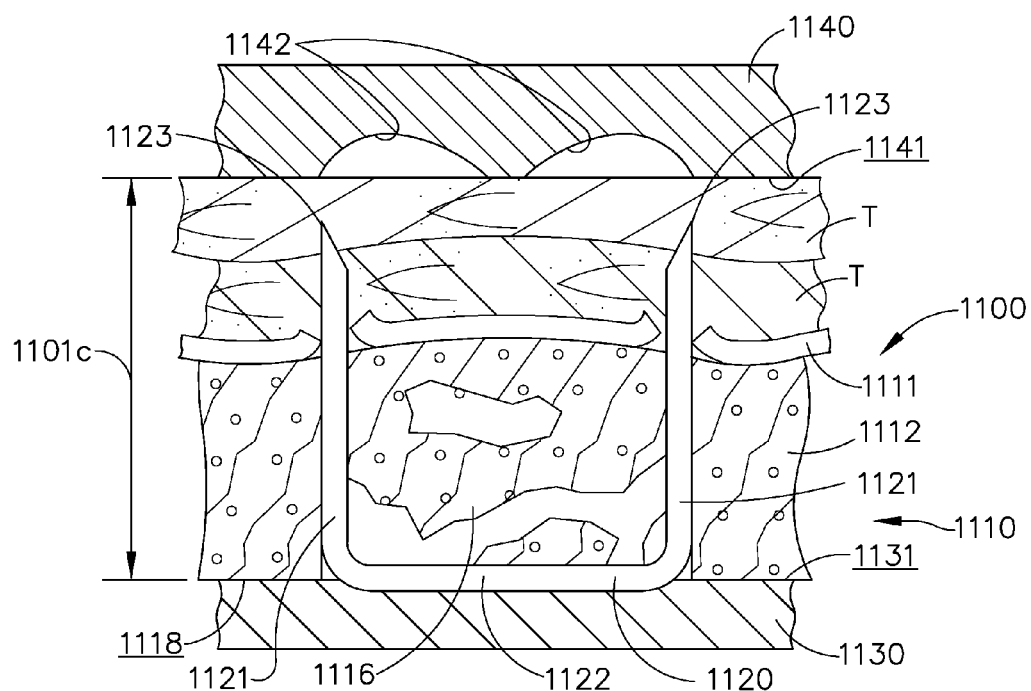
FIG. 7C is a diagram illustrating the crushable staple cartridge body of FIG. 7A being further crushed by the anvil.

In various embodiments, referring now to FIGS. 7A-7D, an end effector of a surgical stapler can comprise an implantable staple cartridge 1100 positioned intermediate an anvil 1140 and a staple cartridge support 1130. Similar to the above, the anvil 1140 can comprise a tissue-contacting surface 1141, the staple cartridge 1100 can comprise a tissue-contacting surface 1119, and the staple cartridge support 1130 can comprise a support surface 1131 which can be configured to support the staple cartridge 1100. Referring to FIG. 7A, the anvil 1140 can be utilized to position the tissue T against the tissue contacting surface 1119 of staple cartridge 1100 without deforming the staple cartridge 1100 and, when the anvil 1140 is in such a position, the tissue-contacting surface 1141 can be positioned a distance 1101a away from the staple cartridge support surface 1131 and the tissue-contacting surface 1119 can be positioned a distance 1102a away from the staple cartridge support surface 1131. Thereafter, as the anvil 1140 is moved toward the staple cartridge support 1130, referring now to FIG. 7B, the anvil 1140 can push the top surface, or tissue-contacting surface 1119, of staple cartridge 1100 downwardly and compress the first layer 1111 and the second layer 1112 of cartridge body 1110. As the layers 1111 and 1112 are compressed, referring again to FIG. 7B, the second layer 1112 can be crushed and the legs 1121 of staples 1120 can pierce the first layer 1111 and enter into the tissue T. In at least one such embodiment, the staples 1120 can be at least partially positioned within staple cavities, or voids, 1115 in the second layer 1112 and, when the second layer 1112 is compressed, the staple cavities 1115 can collapse and, as a result, allow the second layer 1112 to collapse around the staples 1120. In various embodiments, the second layer 1112 can comprise cover portions 1116 which can extend over the staple cavities 1115 and enclose, or at least partially enclose, the staple cavities 1115. FIG. 7B illustrates the cover portions 1116 being crushed downwardly into the staple cavities 1115. In certain embodiments, the second layer 1112 can comprise one or more weakened portions which can facilitate the collapse of the second layer 1112. In various embodiments, such weakened portions can comprise score marks, perforations, and/or thin cross-sections, for example, which can facilitate a controlled collapse of the cartridge body 1110. In at least one embodiment, the first layer 1111 can comprise one or more weakened portions which can facilitate the penetration of the staple legs 1121 through the first layer 1111. In various embodiments, such weakened portions can comprise score marks, perforations, and/or thin cross-sections, for example, which can be aligned, or at least substantially aligned, with the staple legs 1121.

Figure 7D:
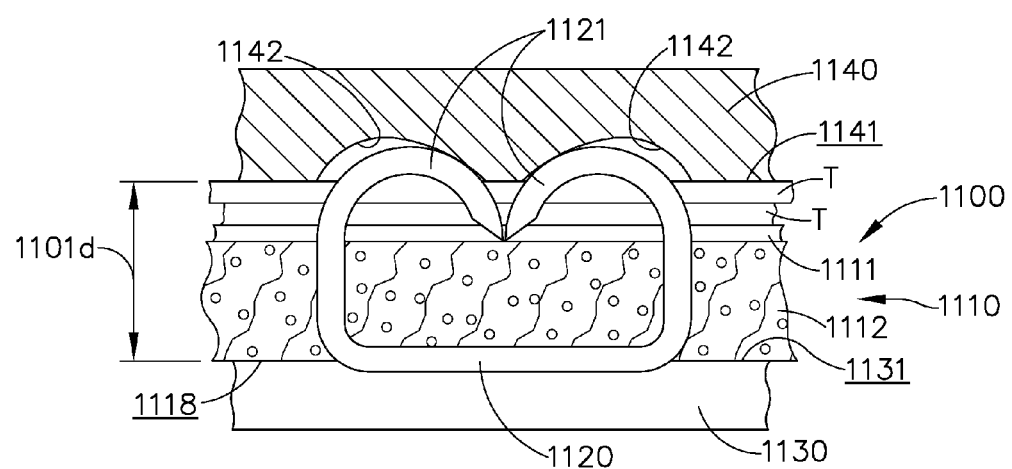
FIG. 7D is a diagram illustrating the staple of FIG. 7A in a fully formed configuration and the crushable staple cartridge of FIG. 7A in a fully crushed condition.

When the anvil 1140 is in a partially closed, unfired position, referring again to FIG. 7A, the anvil 1140 can be positioned a distance 1101a away from the cartridge support surface 1131 such that a gap is defined therebetween. This gap can be filled by the staple cartridge 1100, having a staple cartridge height 1102a, and the tissue T. As the anvil 1140 is moved downwardly to compress the staple cartridge 1100, referring again to FIG. 7B, the distance between the tissue contacting surface 1141 and the cartridge support surface 1131 can be defined by a distance 1101b which is shorter than the distance 1101a. In various circumstances, the gap between the tissue-contacting surface 1141 of anvil 1140 and the cartridge support surface 1131, defined by distance 1101b, may be larger than the original, undeformed staple cartridge height 1102a. As the anvil 1140 is moved closer to the cartridge support surface 1131, referring now to FIG. 7C, the second layer 1112 can continue to collapse and the distance between the staple legs 1121 and the forming pockets 1142 can decrease. Similarly, the distance between the tissue-contacting surface 1141 and the cartridge support surface 1131 can decrease to a distance 1101c which, in various embodiments, may be greater than, equal to, or less than the original, undeformed cartridge height 1102a. Referring now to FIG. 7D, the anvil 1140 can be moved into a final, fired position in which the staples 1120 have been fully formed, or at least formed to a desired height. In such a position, the tissue-contacting surface 1141 of anvil 1140 can be a distance 1101d away from the cartridge support surface 1131, wherein the distance 1101d can be shorter than the original, undeformed cartridge height 1102a. As also illustrated in FIG. 7D, the staple cavities 1115 may be fully, or at least substantially, collapsed and the staples 1120 may be completely, or at least substantially, surrounded by the collapsed second layer 1112. In various circumstances, the anvil 1140 can be thereafter moved away from the staple cartridge 1100. Once the anvil 1140 has been disengaged from the staple cartridge 1100, the cartridge body 1110 can at least partially re-expand in various locations, i.e., locations intermediate adjacent staples 1120, for example. In at least one embodiment, the crushed cartridge body 1110 may not resiliently re-expand. In various embodiments, the formed staples 1120 and, in addition, the cartridge body 1110 positioned intermediate adjacent staples 1120 may apply pressure, or compressive forces, to the tissue T which may provide various therapeutic benefits.

As discussed above, referring again to the embodiment illustrated in FIG. 7A, each staple 1120 can comprise staple legs 1121 extending therefrom. Although staples 1120 are depicted as comprising two staple legs 1121, various staples can be utilized which can comprise one staple leg or, alternatively, more than two staple legs, such as three staple legs or four staple legs, for example. As illustrated in FIG. 7A, each staple leg 1121 can be embedded in the second layer 1112 of the cartridge body 1110 such that the staples 1120 are secured within the second layer 1112. In various embodiments, the staples 1120 can be inserted into the staple cavities 1115 in cartridge body 1110 such that the tips 1123 of the staple legs 1121 enter into the cavities 1115 before the bases 1122. After the tips 1123 have been inserted into the cavities 1115, in various embodiments, the tips 1123 can be pressed into the cover portions 1116 and incise the second layer 1112. In various embodiments, the staples 1120 can be seated to a sufficient depth within the second layer 1112 such that the staples 1120 do not move, or at least substantially move, relative to the second layer 1112. In certain embodiments, the staples 1120 can be seated to a sufficient depth within the second layer 1112 such that the bases 1122 are positioned or embedded within the staple cavities 1115. In various other embodiments, the bases 1122 may not be positioned or embedded within the second layer 1112. In certain embodiments, referring again to FIG. 7A, the bases 1122 may extend below the bottom surface 1118 of the cartridge body 1110. In certain embodiments, the bases 1122 can rest on, or can be directly positioned against, the cartridge support surface 1130. In various embodiments, the cartridge support surface 1130 can comprise support features extending therefrom and/or defined therein wherein, in at least one such embodiment, the bases 1122 of the staples 1120 may be positioned within and supported by one or more support grooves, slots, or troughs, 1132, for example, in the staple cartridge support 1130, as described in greater detail further below.

In various embodiments, referring now to FIGS. 8 and 9, a staple cartridge, such as staple cartridge 1200, for example, can comprise a compressible, implantable cartridge body 1210 comprising an outer layer 1211 and an inner layer 1212. Similar to the above, the staple cartridge 1200 can comprise a plurality of staples 1220 positioned within the cartridge body 1210. In various embodiments, each staple 1220 can comprise a base 1222 and one or more staple legs 1221 extending therefrom. In at least one such embodiment, the staple legs 1221 can be inserted into the inner layer 1212 and seated to a depth in which the bases 1222 of the staples 1220 abut and/or are positioned adjacent to the bottom surface 1218 of the inner layer 1212, for example. In the embodiment depicted in FIGS. 8 and 9, the inner layer 1212 does not comprise staple cavities configured to receive a portion of the staples 1220 while, in other embodiments, the inner layer 1212 can comprise such staple cavities. In various embodiments, further to the above, the inner layer 1212 can be comprised of a compressible material, such as bioabsorbable foam and/or oxidized regenerated cellulose (ORC), for example, which can be configured to allow the cartridge body 1210 to collapse when a compressive load is applied thereto. In various embodiments, the inner layer 1212 can be comprised of a lyophilized foam comprising polylactic acid (PLA) and/or polyglycolic acid (PGA), for example. The ORC may be commercially available under the trade name Surgicel and can comprise a loose woven fabric (like a surgical sponge), loose fibers (like a cotton ball), and/or a foam. In at least one embodiment, the inner layer 1212 can be comprised of a material including medicaments, such as freeze-dried thrombin and/or fibrin, for example, contained therein and/or coated thereon which can be water-activated and/or activated by fluids within the patient's body, for example. In at least one such embodiment, the freeze-dried thrombin and/or fibrin can be held on a Vicryl (PGA) matrix, for example. In certain circumstances, however, the activatable medicaments can be unintentionally activated when the staple cartridge 1200 is inserted into a surgical site within the patient, for example. In various embodiments, referring again to FIGS. 8 and 9, the outer layer 1211 can be comprised of a water impermeable, or at least substantially water impermeable, material such that liquids do not come into contact with, or at least substantially contact, the inner layer 1212 until after the cartridge body 1210 has been compressed and the staple legs have penetrated the outer layer 1211 and/or after the outer layer 1211 has been incised in some fashion. In various embodiments, the outer layer 1211 can be comprised of a buttress material and/or plastic material, such as polydioxanone (PDS) and/or polyglycolic acid (PGA), for example. In certain embodiments, the outer layer 1211 can comprise a wrap which surrounds the inner layer 1212 and the staples 1220. More particularly, in at least one embodiment, the staples 1220 can be inserted into the inner layer 1212 and the outer layer 1211 can be wrapped around the sub-assembly comprising the inner layer 1212 and the staples 1220 and then sealed.

Figure 10:
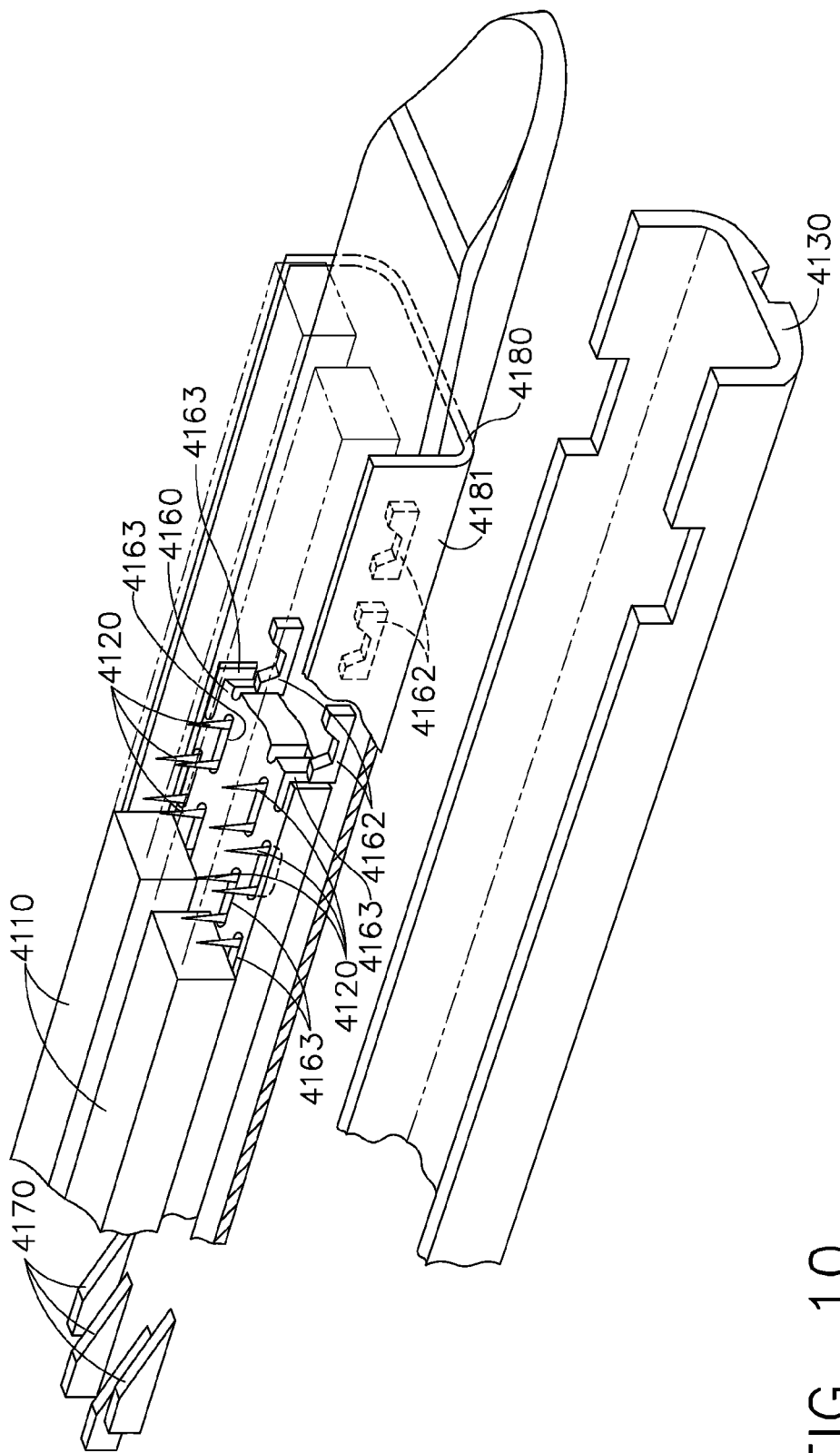
FIG. 10 is an exploded perspective view of an alternative embodiment of a compressible staple cartridge comprising staples therein and a system for driving the staples against an anvil.
Figure 10A:
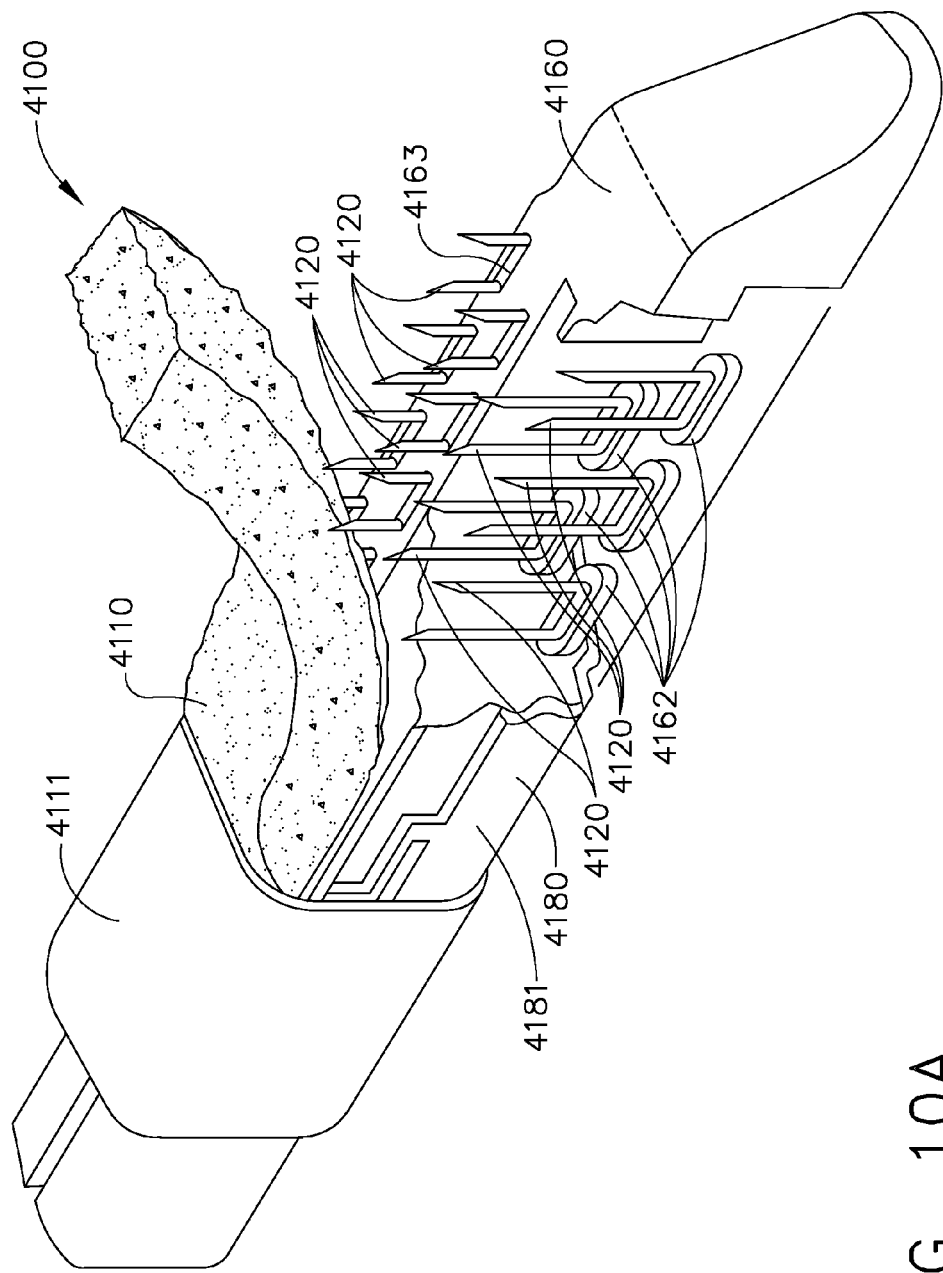
FIG. 10A is a partial cut-away view of an alternative embodiment of the staple cartridge of FIG. 10.
Figure 11:
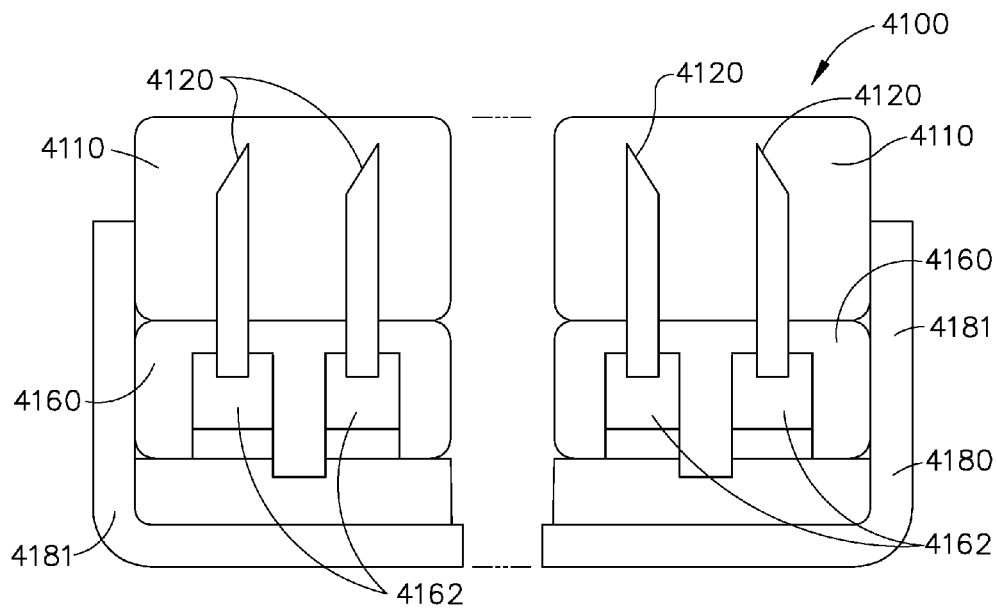
FIG. 11 is a cross-sectional view of the staple cartridge of FIG. 10.
Figure 12:
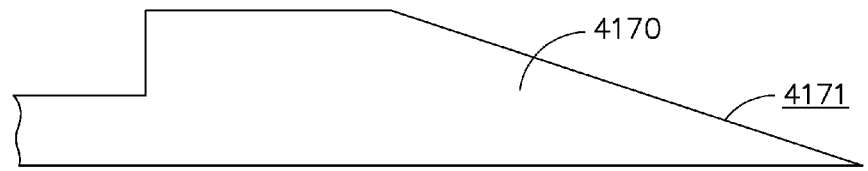
FIG. 12 is an elevational view of a sled configured to traverse the staple cartridge of FIG. 10 and move the staples to toward the anvil.

In various embodiments described herein, the staples of a staple cartridge can be fully formed by an anvil when the anvil is moved into a closed position. In various other embodiments, referring now to FIGS. 10-13, the staples of a staple cartridge, such as staple cartridge 4100, for example, can be deformed by an anvil when the anvil is moved into a closed position and, in addition, by a staple driver system which moves the staples toward the closed anvil. The staple cartridge 4100 can comprise a compressible cartridge body 4110 which can be comprised of a foam material, for example, and a plurality of staples 4120 at least partially positioned within the compressible cartridge body 4110. In various embodiments, the staple driver system can comprise a driver holder 4160, a plurality of staple drivers 4162 positioned within the driver holder 4160, and a staple cartridge pan 4180 which can be configured to retain the staple drivers 4162 in the driver holder 4160. In at least one such embodiment, the staple drivers 4162 can be positioned within one or more slots 4163 in the driver holder 4160 wherein the sidewalls of the slots 4163 can assist in guiding the staple drivers 4162 upwardly toward the anvil. In various embodiments, the staples 4120 can be supported within the slots 4163 by the staple drivers 4162 wherein, in at least one embodiment, the staples 4120 can be entirely positioned in the slots 4163 when the staples 4120 and the staple drivers 4162 are in their unfired positions. In certain other embodiments, at least a portion of the staples 4120 can extend upwardly through the open ends 4161 of slots 4163 when the staples 4120 and staple drivers 4162 are in their unfired positions. In at least one such embodiment, referring primarily now to FIG. 11, the bases of the staples 4120 can be positioned within the driver holder 4160 and the tips of the staples 4120 can be embedded within the compressible cartridge body 4110. In certain embodiments, approximately one-third of the height of the staples 4120 can be positioned within the driver holder 4160 and approximately two-thirds of the height of the staples 4120 can be positioned within the cartridge body 4110. In at least one embodiment, referring to FIG. 10A, the staple cartridge 4100 can further comprise a water impermeable wrap or membrane 4111 surrounding the cartridge body 4110 and the driver holder 4160, for example.

Figure 13:
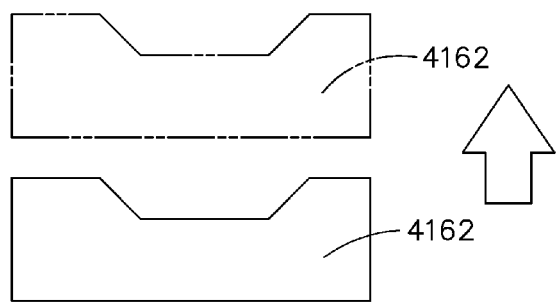
FIG. 13 is a diagram of a staple driver which can be lifted toward the anvil by the sled of FIG. 12.

In use, the staple cartridge 4100 can be positioned within a staple cartridge channel, for example, and the anvil can be moved toward the staple cartridge 4100 into a closed position. In various embodiments, the anvil can contact and compress the compressible cartridge body 4110 when the anvil is moved into its closed position. In certain embodiments, the anvil may not contact the staples 4120 when the anvil is in its closed position. In certain other embodiments, the anvil may contact the legs of the staples 4120 and at least partially deform the staples 4120 when the anvil is moved into its closed position. In either event, the staple cartridge 4100 can further comprise one or more sleds 4170 which can be advanced longitudinally within the staple cartridge 4100 such that the sleds 4170 can sequentially engage the staple drivers 4162 and move the staple drivers 4162 and the staples 4120 toward the anvil. In various embodiments, the sleds 4170 can slide between the staple cartridge pan 4180 and the staple drivers 4162. In embodiments where the closure of the anvil has started the forming process of the staples 4120, the upward movement of the staples 4120 toward the anvil can complete the forming process and deform the staples 4120 to their fully formed, or at least desired, height. In embodiments where the closure of the anvil has not deformed the staples 4120, the upward movement of the staples 4120 toward the anvil can initiate and complete the forming process and deform the staples 4120 to their fully formed, or at least desired, height. In various embodiments, the sleds 4170 can be advanced from a proximal end of the staple cartridge 4100 to a distal end of the staple cartridge 4100 such that the staples 4120 positioned in the proximal end of the staple cartridge 4100 are fully formed before the staples 4120 positioned in the distal end of the staple cartridge 4100 are fully formed. In at least one embodiment, referring to FIG. 12, the sleds 4170 can each comprise at least one angled or inclined surface 4711 which can be configured to slide underneath the staple drivers 4162 and lift the staple drivers 4162 as illustrated in FIG. 13.

In various embodiments, further to the above, the staples 4120 can be formed in order to capture at least a portion of the tissue T and at least a portion of the compressible cartridge body 4110 of the staple cartridge 4100 therein. After the staples 4120 have been formed, the anvil and the staple cartridge channel 4130 of the surgical stapler can be moved away from the implanted staple cartridge 4100. In various circumstances, the cartridge pan 4180 can be fixedly engaged with the staple cartridge channel 4130 wherein, as a result, the cartridge pan 4180 can become detached from the compressible cartridge body 4110 as the staple cartridge channel 4130 is pulled away from the implanted cartridge body 4110. In various embodiments, referring again to FIG. 10, the cartridge pan 4180 can comprise opposing side walls 4181 between which the cartridge body 4110 can be removably positioned. In at least one such embodiment, the compressible cartridge body 4110 can be compressed between the side walls 4181 such that the cartridge body 4110 can be removably retained therebetween during use and releasably disengaged from the cartridge pan 4180 as the cartridge pan 4180 is pulled away. In at least one such embodiment, the driver holder 4160 can be connected to the cartridge pan 4180 such that the driver holder 4160, the drivers 4162, and/or the sleds 4170 can remain in the cartridge pan 4180 when the cartridge pan 4180 is removed from the surgical site. In certain other embodiments, the drivers 4162 can be ejected from the driver holder 4160 and left within the surgical site. In at least one such embodiment, the drivers 4162 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the drivers 4162 can be attached to the staples 4120 such that the drivers 4162 are deployed with the staples 4120. In at least one such embodiment, each driver 4162 can comprise a trough configured to receive the bases of the staples 4120, for example, wherein, in at least one embodiment, the troughs can be configured to receive the staple bases in a press-fit and/or snap-fit manner.

In certain embodiments, further to the above, the driver holder 4160 and/or the sleds 4170 can be ejected from the cartridge pan 4180. In at least one such embodiment, the sleds 4170 can slide between the cartridge pan 4180 and the driver holder 4160 such that, as the sleds 4170 are advanced in order to drive the staple drivers 4162 and staples 4120 upwardly, the sleds 4170 can move the driver holder 4160 upwardly out of the cartridge pan 4180 as well. In at least one such embodiment, the driver holder 4160 and/or the sleds 4170 can be comprised of a bioabsorbable material, such as polyglycolic acid (PGA) which is marketed under the trade name Vicryl, polylactic acid (PLA or PLLA), polydioxanone (PDS), polyhydroxyalkanoate (PHA), poliglecaprone 25 (PGCL) which is marketed under the trade name Monocryl, polycaprolactone (PCL), and/or a composite of PGA, PLA, PDS, PHA, PGCL and/or PCL, for example. In various embodiments, the sleds 4170 can be integrally formed and/or attached to a drive bar, or cutting member, which pushes the sleds 4170 through the staple cartridge 4100. In such embodiments, the sleds 4170 may not be ejected from the cartridge pan 4180 and may remain with the surgical stapler while, in other embodiments in which the sleds 4170 are not attached to the drive bar, the sleds 4170 may be left in the surgical site. In any event, further to the above, the compressibility of the cartridge body 4110 can allow thicker staple cartridges to be used within an end effector of a surgical stapler as the cartridge body 4110 can compress, or shrink, when the anvil of the stapler is closed. In certain embodiments, as a result of the staples being at least partially deformed upon the closure of the anvil, taller staples, such as staples having an approximately 0.18" staple height, for example, could be used, wherein approximately 0.12" of the staple height can be positioned within the compressible layer 4110 and wherein the compressible layer 4110 can have an uncompressed height of approximately 0.14", for example.

In many embodiments described herein, a staple cartridge can comprise a plurality of staples therein. In various embodiments, such staples can be comprised of a metal wire deformed into a substantially U-shaped configuration having two staple legs. Other embodiments are envisioned in which staples can comprise different configurations such as two or more wires that have been joined together having three or more staple legs. In various embodiments, the wire, or wires, used to form the staples can comprise a round, or at least substantially round, cross-section. In at least one embodiment, the staple wires can comprise any other suitable cross-section, such as square and/or rectangular cross-sections, for example. In certain embodiments, the staples can be comprised of plastic wires. In at least one embodiment, the staples can be comprised of plastic-coated metal wires. In various embodiments, a cartridge can comprise any suitable type of fastener in addition to or in lieu of staples. In at least one such embodiment, such a fastener can comprise pivotable arms which are folded when engaged by an anvil. In certain embodiments, two-part fasteners could be utilized. In at least one such embodiment, a staple cartridge can comprise a plurality of first fastener portions and an anvil can comprise a plurality of second fastener portions which are connected to the first fastener portions when the anvil is compressed against the staple cartridge. In certain embodiments, as described above, a sled or driver can be advanced within a staple cartridge in order to complete the forming process of the staples. In certain embodiments, a sled or driver can be advanced within an anvil in order to move one or more forming members downwardly into engagement with the opposing staple cartridge and the staples, or fasteners, positioned therein.

In various embodiments described herein, a staple cartridge can comprise four rows of staples stored therein. In at least one embodiment, the four staple rows can be arranged in two inner staple rows and two outer staple rows. In at least one such embodiment, an inner staple row and an outer staple row can be positioned on a first side of a cutting member, or knife, slot within the staple cartridge and, similarly, an inner staple row and an outer staple row can be positioned on a second side of the cutting member, or knife, slot. In certain embodiments, a staple cartridge may not comprise a cutting member slot; however, such a staple cartridge may comprise a designated portion configured to be incised by a cutting member in lieu of a staple cartridge slot. In various embodiments, the inner staple rows can be arranged within the staple cartridge such that they are equally, or at least substantially equally, spaced from the cutting member slot. Similarly, the outer staple rows can be arranged within the staple cartridge such that they are equally, or at least substantially equally, spaced from the cutting member slot. In various embodiments, a staple cartridge can comprise more than or less than four rows of staples stored within a staple cartridge. In at least one embodiment, a staple cartridge can comprise six rows of staples. In at least one such embodiment, the staple cartridge can comprise three rows of staples on a first side of a cutting member slot and three rows of staples on a second side of the cutting member slot. In certain embodiments, a staple cartridge may comprise an odd number of staple rows. For example, a staple cartridge may comprise two rows of staples on a first side of a cutting member slot and three rows of staples on a second side of the cutting member slot. In various embodiments, the staple rows can comprise staples having the same, or at least substantially the same, unformed staple height. In certain other embodiments, one or more of the staple rows can comprise staples having a different unformed staple height than the other staples. In at least one such embodiment, the staples on a first side of a cutting member slot may have a first unformed height and the staples on a second side of a cutting member slot may have a second unformed height which is different than the first height, for example.

In various embodiments, as described above, a staple cartridge can comprise a cartridge body including a plurality of staple cavities defined therein. The cartridge body can comprise a deck and a top deck surface wherein each staple cavity can define an opening in the deck surface. As also described above, a staple can be positioned within each staple cavity such that the staples are stored within the cartridge body until they are ejected therefrom. Prior to being ejected from the cartridge body, in various embodiments, the staples can be contained with the cartridge body such that the staples do not protrude above the deck surface. As the staples are positioned below the deck surface, in such embodiments, the possibility of the staples becoming damaged and/or prematurely contacting the targeted tissue can be reduced. In various circumstances, the staples can be moved between an unfired position in which they do not protrude from the cartridge body and a fired position in which they have emerged from the cartridge body and can contact an anvil positioned opposite the staple cartridge. In various embodiments, the anvil, and/or the forming pockets defined within the anvil, can be positioned a predetermined distance above the deck surface such that, as the staples are being deployed from the cartridge body, the staples are deformed to a predetermined formed height. In some circumstances, the thickness of the tissue captured between the anvil and the staple cartridge may vary and, as a result, thicker tissue may be captured within certain staples while thinner tissue may be captured within certain other staples. In either event, the clamping pressure, or force, applied to the tissue by the staples may vary from staple to staple or vary between a staple on one end of a staple row and a staple on the other end of the staple row, for example. In certain circumstances, the gap between the anvil and the staple cartridge deck can be controlled such that the staples apply a certain minimum clamping pressure within each staple. In some such circumstances, however, significant variation of the clamping pressure within different staples may still exist. Surgical stapling instruments are disclosed in U.S. Pat. No. 7,380,696, which issued on Jun. 3, 2008, the entire disclosure of which is incorporated by reference herein. An illustrative multi-stroke handle for the surgical stapling and severing instrument is described in greater detail in the co-pending and co-owned U.S. patent application entitled SURGICAL STAPLING INSTRUMENT INCORPORATING A MULTISTROKE FIRING POSITION INDICATOR AND RETRACTION MECHANISM, Ser. No. 10/674,026, now U.S. Pat. No. 7,364,061, the disclosure of which is hereby incorporated by reference in its entirety. Other applications consistent with the present invention may incorporate a single firing stroke, such as described in co-pending and commonly owned U.S. patent application SURGICAL STAPLING INSTRUMENT HAVING SEPARATE DISTINCT CLOSING AND FIRING SYSTEMS, Ser. No. 10/441,632, now U.S. Pat. No. 7,000,818, the disclosure of which is hereby incorporated by reference in its entirety.

In various embodiments described herein, a staple cartridge can comprise means for compensating for the thickness of the tissue captured within the staples deployed from the staple cartridge. In various embodiments, referring to FIG. 14, a staple cartridge, such as staple cartridge 10000, for example, can include a rigid first portion, such as support portion 10010, for example, and a compressible second portion, such as tissue thickness compensator 10020, for example. In at least one embodiment, referring primarily to FIG. 16, the support portion 10010 can comprise a cartridge body, a top deck surface 10011, and a plurality of staple cavities 10012 wherein, similar to the above, each staple cavity 10012 can define an opening in the deck surface 10011. A staple 10030, for example, can be removably positioned in each staple cavity 10012. In at least one such embodiment, each staple 10030 can comprise a base 10031 and one or more legs 10032 extending from the base 10031. Prior to the staples 10030 being deployed, as also described in greater detail below, the bases 10031 of the staples 10030 can be supported by staple drivers positioned within the support portion 10010 and, concurrently, the legs 10032 of the staples 10030 can be at least partially contained within the staple cavities 10012. In various embodiments, the staples 10030 can be deployed between an unfired position and a fired position such that the legs 10032 move through the tissue thickness compensator 10020, penetrate through a top surface of the tissue thickness compensator 10020, penetrate the tissue T, and contact an anvil positioned opposite the staple cartridge 10000. As the legs 10032 are deformed against the anvil, the legs 10032 of each staple 10030 can capture a portion of the tissue thickness compensator 10020 and a portion of the tissue T within each staple 10030 and apply a compressive force to the tissue. Further to the above, the legs 10032 of each staple 10030 can be deformed downwardly toward the base 10031 of the staple to form a staple entrapment area 10039 in which the tissue T and the tissue thickness compensator 10020 can be captured. In various circumstances, the staple entrapment area 10039 can be defined between the inner surfaces of the deformed legs 10032 and the inner surface of the base 10031. The size of the entrapment area for a staple can depend on several factors such as the length of the legs, the diameter of the legs, the width of the base, and/or the extent in which the legs are deformed, for example.

Figure 49:
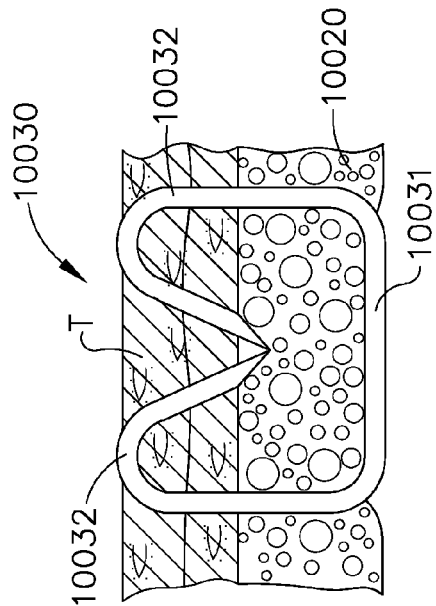
FIG. 49 is a diagram illustrating tissue and a tissue thickness compensator captured within a staple.
Figure 48:
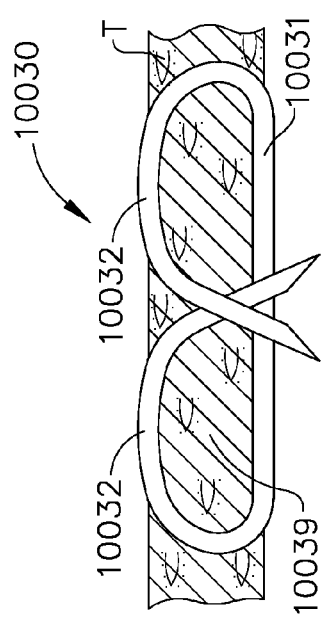
FIG. 48 is a diagram illustrating tissue captured within a staple.
Figure 50:
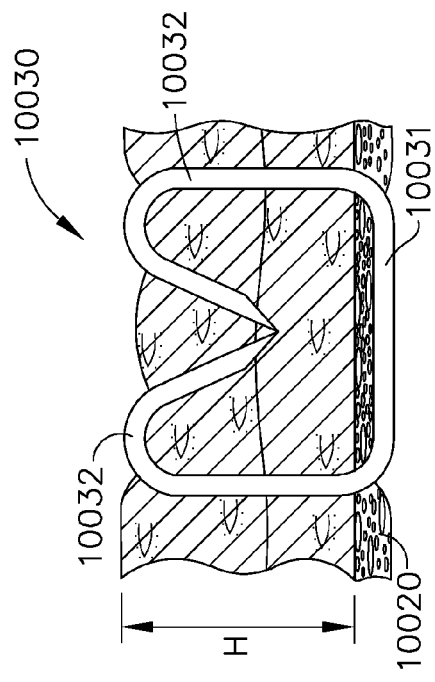
FIG. 50 is a diagram illustrating tissue captured within a staple.

In previous embodiments, a surgeon was often required to select the appropriate staples having the appropriate staple height for the tissue being stapled. For example, a surgeon could select tall staples for use with thick tissue and short staples for use with thin tissue. In some circumstances, however, the tissue being stapled did not have a consistent thickness and, thus, some staples were unable to achieve the desired fired configuration. For example, FIG. 48 illustrates a tall staple used in thin tissue. Referring now to FIG. 49, when a tissue thickness compensator, such as tissue thickness compensator 10020, for example, is used with thin tissue, for example, the larger staple may be formed to a desired fired configuration.

Figure 43:
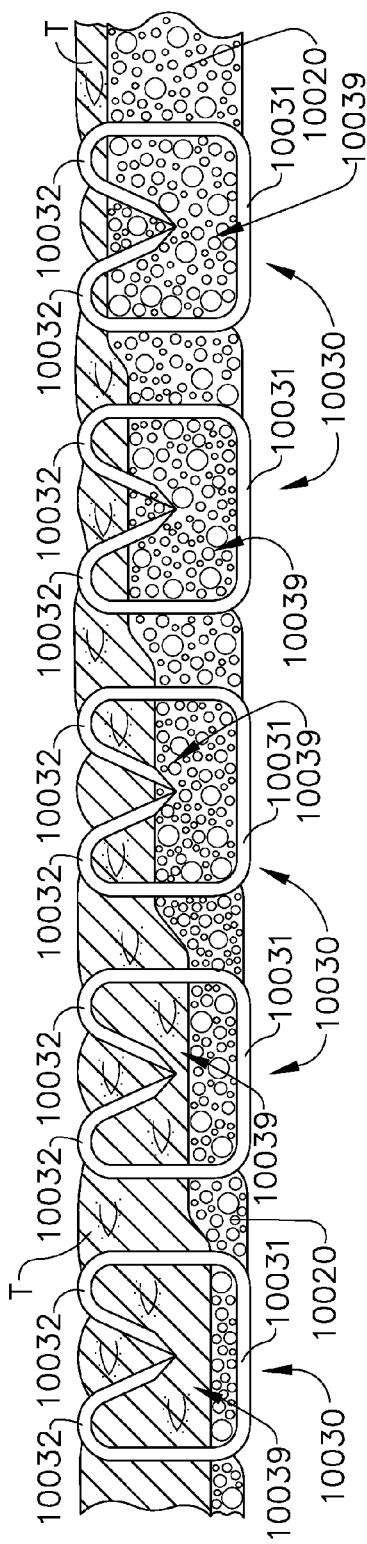
FIG. 43 is a diagram illustrating a tissue thickness compensator which is compensating for different tissue thickness captured within different staples.
Figure 44:
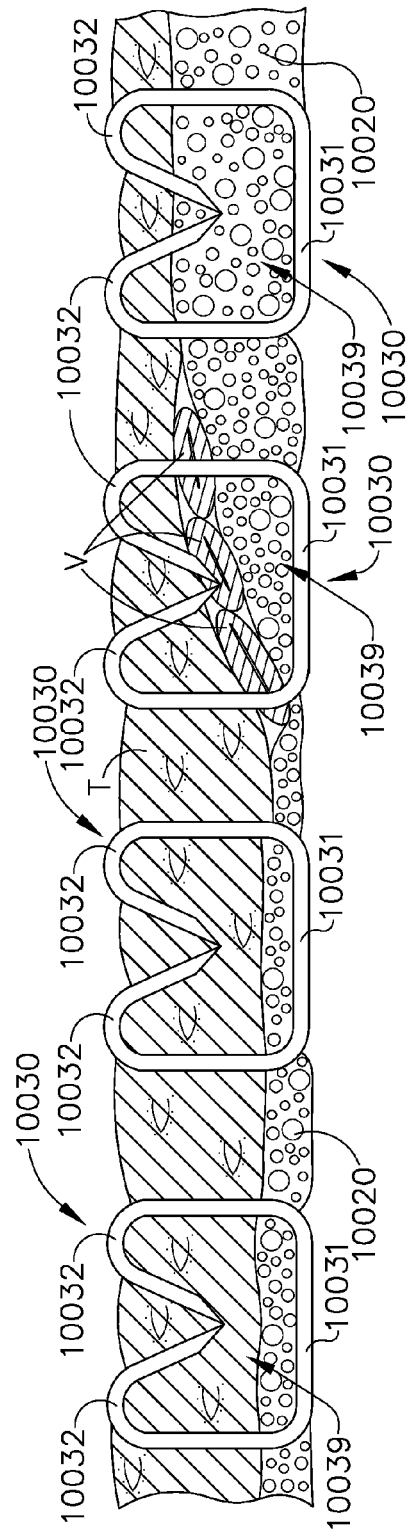
FIG. 44 is a diagram illustrating a tissue thickness compensator applying a compressive pressure to one or more vessels that have been transected by a staple line.
Figure 47:
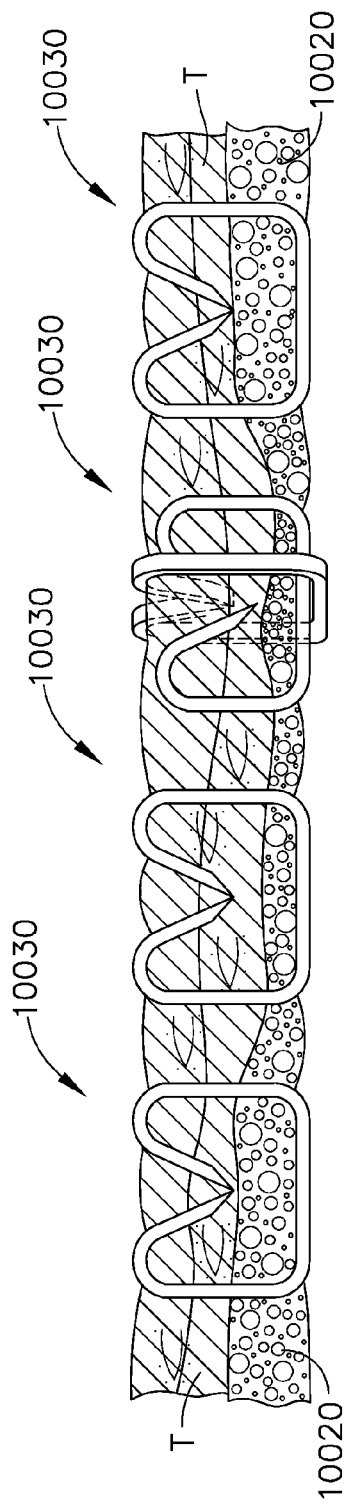
FIG. 47 is a diagram illustrating a tissue thickness compensator positioned in a region of tissue in which multiple staples lines have intersected.

Owing to the compressibility of the tissue thickness compensator, the tissue thickness compensator can compensate for the thickness of the tissue captured within each staple. More particularly, referring now to FIGS. 43 and 44, a tissue thickness compensator, such as tissue thickness compensator 10020, for example, can consume larger and/or smaller portions of the staple entrapment area 10039 of each staple 10030 depending on the thickness and/or type of tissue contained within the staple entrapment area 10039. For example, if thinner tissue T is captured within a staple 10030, the tissue thickness compensator 10020 can consume a larger portion of the staple entrapment area 10039 as compared to circumstances where thicker tissue T is captured within the staple 10030. Correspondingly, if thicker tissue T is captured within a staple 10030, the tissue thickness compensator 10020 can consume a smaller portion of the staple entrapment area 10039 as compared to the circumstances where thinner tissue T is captured within the staple 10030. In this way, the tissue thickness compensator can compensate for thinner tissue and/or thicker tissue and assure that a compressive pressure is applied to the tissue irrespective, or at least substantially irrespective, of the tissue thickness captured within the staples. In addition to the above, the tissue thickness compensator 10020 can compensate for different types, or compressibilities, of tissues captured within different staples 10030. Referring now to FIG. 44, the tissue thickness compensator 10020 can apply a compressive force to vascular tissue T which can include vessels V and, as a result, restrict the flow of blood through the less compressible vessels V while still applying a desired compressive pressure to the surrounding tissue T. In various circumstances, further to the above, the tissue thickness compensator 10020 can also compensate for malformed staples. Referring to FIG. 45, the malformation of various staples 10030 can result in larger staple entrapment areas 10039 being defined within such staples. Owing to the resiliency of the tissue thickness compensator 10020, referring now to FIG. 46, the tissue thickness compensator 10020 positioned within malformed staples 10030 may still apply a sufficient compressive pressure to the tissue T even though the staple entrapment areas 10039 defined within such malformed staples 10030 may be enlarged. In various circumstances, the tissue thickness compensator 10020 located intermediate adjacent staples 10030 can be biased against the tissue T by properly-formed staples 10030 surrounding a malformed staple 10030 and, as a result, apply a compressive pressure to the tissue surrounding and/or captured within the malformed staple 10030, for example. In various circumstances, a tissue thickness compensator can compensate for different tissue densities which can arise due to calcifications, fibrous areas, and/or tissue that has been previously stapled or treated, for example.

Figure 52:
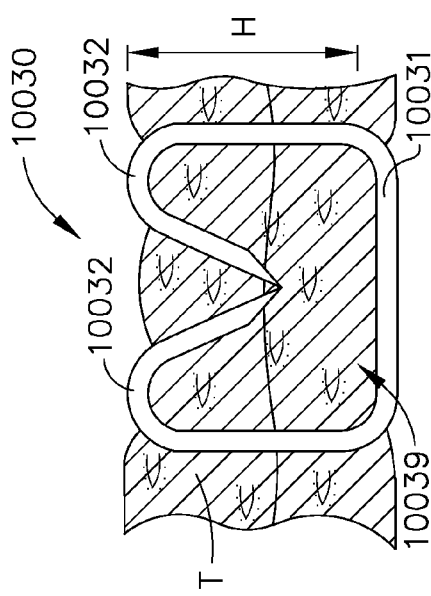
FIG. 52 is a diagram illustrating thin tissue and a tissue thickness compensator captured within a staple.
Figure 51:
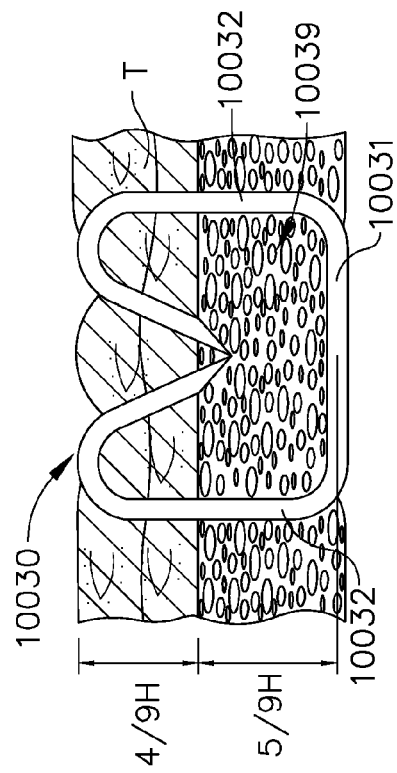
FIG. 51 is a diagram illustrating thick tissue and a tissue thickness compensator captured within a staple.
Figure 53:
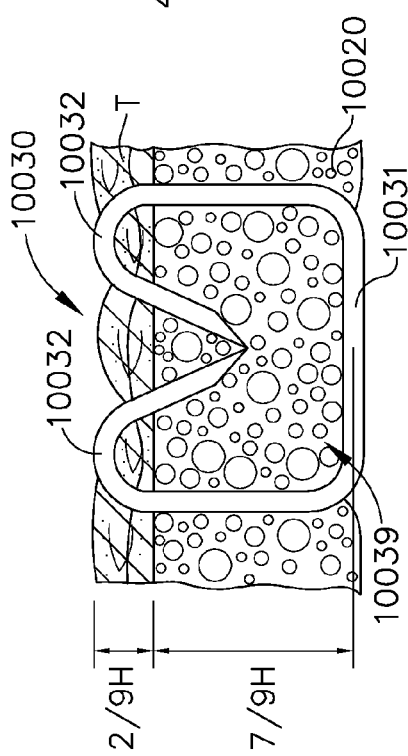
FIG. 53 is a diagram illustrating tissue having an intermediate thickness and a tissue thickness compensator captured within a staple.

In various embodiments, a fixed, or unchangeable, tissue gap can be defined between the support portion and the anvil and, as a result, the staples may be deformed to a predetermined height regardless of the thickness of the tissue captured within the staples. When a tissue thickness compensator is used with these embodiments, the tissue thickness compensator can adapt to the tissue captured between the anvil and the support portion staple cartridge and, owing to the resiliency of the tissue thickness compensator, the tissue thickness compensator can apply an additional compressive pressure to the tissue. Referring now to FIGS. 50-55, a staple 10030 has been formed to a predefined height H. With regard to FIG. 50, a tissue thickness compensator has not been utilized and the tissue T consumes the entirety of the staple entrapment area 10039. With regard to FIG. 57, a portion of a tissue thickness compensator 10020 has been captured within the staple 10030, compressed the tissue T, and consumed at least a portion of the staple entrapment area 10039. Referring now to FIG. 52, thin tissue T has been captured within the staple 10030. In this embodiment, the compressed tissue T has a height of approximately $\frac{2}{8}H$ and the compressed tissue thickness compensator 10020 has a height of approximately $\frac{7}{8}H$, for example. Referring now to FIG. 53, tissue T having an intermediate thickness has been captured within the staple 10030. In this embodiment, the compressed tissue T has a height of approximately $\frac{4}{8}H$ and the compressed tissue thickness compensator 10020 has a height of approximately $\frac{5}{8}H$, for example. Referring now to FIG. 54, tissue T having an intermediate thickness has been captured within the staple 10030. In this embodiment, the compressed tissue T has a height of approximately $\frac{2}{3}H$ and the compressed tissue thickness compensator 10020 has a height of approximately $\frac{1}{3}H$, for example. Referring now to FIG. 53, thick tissue T has been captured within the staple 10030. In this embodiment, the compressed tissue T has a height of approximately $\frac{8}{9}H$ and the compressed tissue thickness compensator 10020 has a height of approximately $\frac{1}{9}H$, for example. In various circumstances, the tissue thickness compensator can comprise a compressed height which comprises approximately 10% of the staple entrapment height, approximately 20% of the staple entrapment height, approximately 30% of the staple entrapment height, approximately 40% of the staple entrapment height, approximately 50% of the staple entrapment height, approximately 60% of the staple entrapment height, approximately 70% of the staple entrapment height, approximately 80% of the staple entrapment height, and/or approximately 90% of the staple entrapment height, for example.

In various embodiments, the staples 10030 can comprise any suitable unformed height. In certain embodiments, the staples 10030 can comprise an unformed height between approximately 2 mm and approximately 4.8 mm, for example. The staples 10030 can comprise an unformed height of approximately 2.0 mm, approximately 2.5 mm, approximately 3.0 mm, approximately 3.4 mm, approximately 3.5 mm, approximately 3.8 mm, approximately 4.0 mm, approximately 4.1 mm, and/or approximately 4.8 mm, for example. In various embodiments, the height H to which the staples can be deformed can be dictated by the distance between the deck surface 10011 of the support portion 10010 and the opposing anvil. In at least one embodiment, the distance between the deck surface 10011 and the tissue-contacting surface of the anvil can be approximately 0.097", for example. The height H can also be dictated by the depth of the forming pockets defined within the anvil. In at least one embodiment, the forming pockets can have a depth measured from the tissue-contacting surface, for example. In various embodiments, as described in greater detail below, the staple cartridge 10000 can further comprise staple drivers which can lift the staples 10030 toward the anvil and, in at least one embodiment, lift, or "overdrive", the staples above the deck surface 10011. In such embodiments, the height H to which the staples 10030 are formed can also be dictated by the distance in which the staples 10030 are overdriven. In at least one such embodiment, the staples 10030 can be overdriven by approximately 0.028", for example, and can result in the staples 10030 being formed to a height of approximately 0.189", for example. In various embodiments, the staples 10030 can be formed to a height of approximately 0.8 mm, approximately 1.0 mm, approximately 1.5 mm, approximately 1.8 mm, approximately 2.0 mm, and/or approximately 2.25 mm, for example. In certain embodiments, the staples can be formed to a height between approximately 2.25 mm and approximately 3.0 mm, for example. Further to the above, the height of the staple entrapment area of a staple can be determined by the formed height of the staple and the width, or diameter, of the wire comprising the staple. In various embodiments, the height of the staple entrapment area 10039 of a staple 10030 can comprise the formed height H of the staple less two diameter widths of the wire. In certain embodiments, the staple wire can comprise a diameter of approximately 0.0089", for example. In various embodiments, the staple wire can comprise a diameter between approximately 0.0069" and approximately 0.0119", for example. In at least one exemplary embodiment, the formed height H of a staple 10030 can be approximately 0.189" and the staple wire diameter can be approximately 0.0089" resulting in a staple entrapment height of approximately 0.171", for example.

In various embodiments, further to the above, the tissue thickness compensator can comprise an uncompressed, or pre-deployed, height and can be configured to deform to one of a plurality of compressed heights. In certain embodiments, the tissue thickness compensator can comprise an uncompressed height of approximately 0.125", for example. In various embodiments, the tissue thickness compensator can comprise an uncompressed height of greater than or equal to approximately 0.080", for example. In at least one embodiment, the tissue thickness compensator can comprise an uncompressed, or pre-deployed, height which is greater than the unfired height of the staples. In at least one embodiment, the uncompressed, or pre-deployed, height of the tissue thickness compensator can be approximately 10% taller, approximately 20% taller, approximately 30% taller, approximately 40% taller, approximately 50% taller, approximately 60% taller, approximately 70% taller, approximately 80% taller, approximately 90% taller, and/or approximately 100% taller than the unfired height of the staples, for example. In at least one embodiment, the uncompressed, or pre-deployed, height of the tissue thickness compensator can be up to approximately 100% taller than the unfired height of the staples, for example. In certain embodiments, the uncompressed, or pre-deployed, height of the tissue thickness compensator can be over 100% taller than the unfired height of the staples, for example. In at least one embodiment, the tissue thickness compensator can comprise an uncompressed height which is equal to the unfired height of the staples. In at least one embodiment, the tissue thickness compensator can comprise an uncompressed height which is less than the unfired height of the staples. In at least one embodiment, the uncompressed, or pre-deployed, height of the thickness compensator can be approximately 10% shorter, approximately 20% shorter, approximately 30% shorter, approximately 40% shorter, approximately 50% shorter, approximately 60% shorter, approximately 70% shorter, approximately 80% shorter, and/or approximately 90% shorter than the unfired height of the staples, for example. In various embodiments, the compressible second portion can comprise an uncompressed height which is taller than an uncompressed height of the tissue T being stapled. In certain embodiments, the tissue thickness compensator can comprise an uncompressed height which is equal to an uncompressed height of the tissue T being stapled. In various embodiments, the tissue thickness compensator can comprise an uncompressed height which is shorter than an uncompressed height of the tissue T being stapled.

As described above, a tissue thickness compensator can be compressed within a plurality of formed staples regardless of whether thick tissue or thin tissue is captured within the staples. In at least one exemplary embodiment, the staples within a staple line, or row, can be deformed such that the staple entrapment area of each staple comprises a height of approximately 2.0 mm, for example, wherein the tissue T and the tissue thickness compensator can be compressed within this height. In certain circumstances, the tissue T can comprise a compressed height of approximately 1.75 mm within the staple entrapment area while the tissue thickness compensator can comprise a compressed height of approximately 0.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 1.25 mm within the staple entrapment area while the tissue thickness compensator can comprise a compressed height of approximately 0.75 mm within the staple entrapment area, thereby totaling the approximately 2.0 mm staple entrapment area height, for example. In certain circumstances, the tissue T can comprise a compressed height of approximately 1.0 mm within the staple entrapment area while the tissue thickness compensator can comprise a compressed height of approximately 1.0 mm within the staple entrapment area, thereby totaling the approximately 2.0 mm staple entrapment area height, for example. In certain circumstances, the tissue T can comprise a compressed height of approximately 0.75 mm within the staple entrapment area while the tissue thickness compensator can comprise a compressed height of approximately 1.25 mm within the staple entrapment area, thereby totaling the approximately 2.0 mm staple entrapment area height, for example. In certain circumstances, the tissue T can comprise a compressed height of approximately 1.50 mm within the staple entrapment area while the tissue thickness compensator can comprise a compressed height of approximately 0.50 mm within the staple entrapment area, thereby totaling the approximately 2.0 mm staple entrapment area height, for example. In certain circumstances, the tissue T can comprise a compressed height of approximately 0.25 mm within the staple entrapment area while the tissue thickness compensator can comprise a compressed height of approximately 1.75 mm within the staple entrapment area, thereby totaling the approximately 2.0 mm staple entrapment area height, for example.

In various embodiments, further to the above, the tissue thickness compensator can comprise an uncompressed height which is less than the fired height of the staples. In certain embodiments, the tissue thickness compensator can comprise an uncompressed height which is equal to the fired height of the staples. In certain other embodiments, the tissue thickness compensator can comprise an uncompressed height which is taller than the fired height of the staples. In at least one such embodiment, the uncompressed height of a tissue thickness compensator can comprise a thickness which is approximately 110% of the formed staple height, approximately 120% of the formed staple height, approximately 130% of the formed staple height, approximately 140% of the formed staple height, approximately 150% of the formed staple height, approximately 160% of the formed staple height, approximately 170% of the formed staple height, approximately 180% of the formed staple height, approximately 190% of the formed staple height, and/or approximately 200% of the formed staple height, for example. In certain embodiments, the tissue thickness compensator can comprise an uncompressed height which is more than twice the fired height of the staples. In various embodiments, the tissue thickness compensator can comprise a compressed height which is from approximately 85% to approximately 150% of the formed staple height, for example. In various embodiments, as described above, the tissue thickness compensator can be compressed between an uncompressed thickness and a compressed thickness. In certain embodiments, the compressed thickness of a tissue thickness compensator can be approximately 10% of its uncompressed thickness, approximately 20% of its uncompressed thickness, approximately 30% of its uncompressed thickness, approximately 40% of its uncompressed thickness, approximately 50% of its uncompressed thickness, approximately 60% of its uncompressed thickness, approximately 70% of its uncompressed thickness, approximately 80% of its uncompressed thickness, and/or approximately 90% of its uncompressed thickness, for example. In various embodiments, the uncompressed thickness of the tissue thickness compensator can be approximately two times, approximately ten times, approximately fifty times, and/or approximately one hundred times thicker than its compressed thickness, for example. In at least one embodiment, the compressed thickness of the tissue thickness compensator can be between approximately 60% and approximately 99% of its uncompressed thickness. In at least one embodiment, the uncompressed thickness of the tissue thickness compensator can be at least 50% thicker than its compressed thickness. In at least one embodiment, the uncompressed thickness of the tissue thickness compensator can be up to one hundred times thicker than its compressed thickness. In various embodiments, the compressible second portion can be elastic, or at least partially elastic, and can bias the tissue T against the deformed legs of the staples. In at least one such embodiment, the compressible second portion can resiliently expand between the tissue T and the base of the staple in order to push the tissue T against the legs of the staple. In certain embodiments, discussed in further detail below, the tissue thickness compensator can be positioned intermediate the tissue T and the deformed staple legs. In various circumstances, as a result of the above, the tissue thickness compensator can be configured to consume any gaps within the staple entrapment area.

In various embodiments, the tissue thickness compensator may comprise materials characterized by one or more of the following properties: biocompatible, bioabsorable, bioresorbable, biodurable, biodegradable, compressible, fluid absorbable, swellable, self-expandable, bioactive, medicament, pharmaceutically active, anti-adhesion, haemostatic, antibiotic, anti-microbial, anti-viral, nutritional, adhesive, permeable, hydrophilic and/or hydrophobic, for example. In various embodiments, a surgical instrument comprising an anvil and a staple cartridge may comprise a tissue thickness compensator associated with the anvil and/or staple cartridge comprising at least one of a haemostatic agent, such as fibrin and thrombin, an antibiotic, such as doxycpl, and medicament, such as matrix metalloproteinases (MMPs).

In various embodiments, the tissue thickness compensator may comprise synthetic and/or non-synthetic materials. The tissue thickness compensator may comprise a polymeric composition comprising one or more synthetic polymers and/or one or more non-synthetic polymers. The synthetic polymer may comprise a synthetic absorbable polymer and/or a synthetic non-absorbable polymer. In various embodiments, the polymeric composition may comprise a biocompatible foam, for example. The biocompatible foam may comprise a porous, open cell foam and/or a porous, closed cell foam, for example. The biocompatible foam may have a uniform pore morphology or may have a gradient pore morphology (i.e. small pores gradually increasing in size to large pores across the thickness of the foam in one direction). In various embodiments, the polymeric composition may comprise one or more of a porous scaffold, a porous matrix, a gel matrix, a hydrogel matrix, a solution matrix, a filamentous matrix, a tubular matrix, a composite matrix, a membranous matrix, a biostable polymer, and a biodegradable polymer, and combinations thereof. For example, the tissue thickness compensator may comprise a foam reinforced by a filamentous matrix or may comprise a foam having an additional hydrogel layer that expands in the presence of bodily fluids to further provide the compression on the tissue. In various embodiments, a tissue thickness compensator could also be comprised of a coating on a material and/or a second or third layer that expands in the presence of bodily fluids to further provide the compression on the tissue. Such a layer could be a hydrogel that could be a synthetic and/or naturally derived material and could be either biodurable and/or biodegradable, for example. In various embodiments, the tissue thickness compensator may comprise a microgel or a nanogel. The hydrogel may comprise carbohydrate-derived microgels and/or nanogels. In certain embodiments, a tissue thickness compensator may be reinforced with fibrous non-woven materials or fibrous mesh type elements, for example, that can provide additional flexibility, stiffness, and/or strength. In various embodiments, a tissue thickness compensator that has a porous morphology which exhibits a gradient structure such as, for example, small pores on one surface and larger pores on the other surface. Such morphology could be more optimal for tissue in-growth or haemostatic behavior. Further, the gradient could be also compositional with a varying bio-absorption profile. A short term absorption profile may be preferred to address hemostasis while a long term absorption profile may address better tissue healing without leakages.

Examples of non-synthetic materials include, but are not limited to, lyophilized polysaccharide, glycoprotein, bovine pericardium, collagen, gelatin, fibrin, fibrinogen, elastin, proteoglycan, keratin, albumin, hydroxyethyl cellulose, cellulose, oxidized cellulose, oxidized regenerated cellulose (ORC), hydroxypropyl cellulose, carboxyethyl cellulose, carboxymethylcellulose, chitan, chitosan, casein, alginate, and combinations thereof.

Examples of synthetic absorbable materials include, but are not limited to, poly(lactic acid) (PLA), poly(L-lactic acid) (PLLA), polycaprolactone (PCL), polyglycolic acid (PGA), poly(trimethylene carbonate) (TMC), polyethylene terephthalate (PET), polyhydroxyalkanoate (PHA), a copolymer of glycolide and ε-caprolactone (PGCL), a copolymer of glycolide and -trimethylene carbonate, poly(glycerol sebacate) (PGS), poly(dioxanone) (PDS), polyesters, poly (orthoesters), polyoxaesters, polyetheresters, polycarbonates, polyamide esters, polyanhydrides, polysaccharides, poly(ester-amides), tyrosine-based polyarylates, polyamines, tyrosine-based polyiminocarbonates, tyrosine-based polycarbonates, poly(D,L-lactide-urethane), poly(hydroxybutyrate), poly(B-hydroxybutyrate), poly(E-caprolactone), polyethyleneglycol (PEG), poly[bis (carboxylatophenoxy)phosphazene]poly(amino acids), pseudo-poly(amino acids), absorbable polyurethanes, poly (phosphazine), polyphosphazenes, polyalkyleneoxides, polyacrylamides, polyhydroxyethylmethylacrylate, polyvinylpyrrolidone, polyvinyl alcohols, poly(caprolactone), polyacrylic acid, polyacetate, polypropylene, aliphatic polyesters, glycerols, copoly(ether-esters), polyalkylene oxalates, polyamides, poly(iminocarbonates), polyalkylene oxalates, and combinations thereof. In various embodiments, the polyester is may be selected from the group consisting of polylactides, polyglycolides, trimethylene carbonates, polydioxanones, polycaprolactones, polybutesters, and combinations thereof.

In various embodiments, the synthetic absorbable polymer may comprise one or more of 90/10 poly(glycolide-L-lactide) copolymer, commercially available from Ethicon, Inc. under the trade designation VICRYL (polyglactic 910), polyglycolide, commercially available from American Cyanamid Co. under the trade designation DEXON, polydioxanone, commercially available from Ethicon, Inc. under the trade designation PDS, poly(glycolide-trimethylene carbonate) random block copolymer, commercially available from American Cyanamid Co. under the trade designation MAXON, 75/25 poly(glycolide-ε-caprolactone-poliglecaprolactone 25) copolymer, commercially available from Ethicon under the trade designation MONOCRYL, for example.

Examples of synthetic non-absorbable materials include, but are not limited to, polyurethane, polypropylene (PP), polyethylene (PE), polycarbonate, polyamides, such as nylon, polyvinylchloride (PVC), polymethylmetacrylate (PMMA), polystyrene (PS), polyester, polyetheretherketone (PEEK), polytetrafluoroethylene (PTFE), polytrifluorochloroethylene (PTFCE), polyvinylfluoride (PVF), fluorinated ethylene propylene (FEP), polyacetal, polysulfone, silicons, and combinations thereof. The synthetic non-absorbable polymers may include, but are not limited to, foamed elastomers and porous elastomers, such as, for example, silicone, polyisoprene, and rubber. In various embodiments, the synthetic polymers may comprise expanded polytetrafluoroethylene (ePTFE), commercially available from W. L. Gore & Associates, Inc. under the trade designation GORE-TEX Soft Tissue Patch and co-polyetherester urethane foam commercially available from Polyganics under the trade designation NASOPORE.

In various embodiments, the polymeric composition may comprise from approximately 50% to approximately 90% by weight of the polymeric composition of PLLA and approximately 50% to approximately 10% by weight of the polymeric composition of PCL, for example. In at least one embodiment, the polymeric composition may comprise approximately 70% by weight of PLLA and approximately 30% by weight of PCL, for example. In various embodiments, the polymeric composition may comprise from approximately 55% to approximately 85% by weight of the polymeric composition of PGA and 15% to 45% by weight of the polymeric composition of PCL, for example. In at least one embodiment, the polymeric composition may comprise approximately 65% by weight of PGA and approximately 35% by weight of PCL, for example. In various embodiments, the polymeric composition may comprise from approximately 90% to approximately 95% by weight of the polymeric composition of PGA and approximately 5% to approximately 10% by weight of the polymeric composition of PLA, for example.

In various embodiments, the synthetic absorbable polymer may comprise a bioabsorbable, biocompatible elastomeric copolymer. Suitable bioabsorbable, biocompatible elastomeric copolymers include but are not limited to copolymers of ε-caprolactone and glycolide (preferably having a mole ratio of ε-caprolactone to glycolide of from about 30:70 to about 70:30, preferably 35:65 to about 65:35, and more preferably 45:55 to 35:65); elastomeric copolymers of ε-caprolactone and lactide, including L-lactide, D-lactide blends thereof or lactic acid copolymers (preferably having a mole ratio of ε-caprolactone to lactide of from about 35:65 to about 65:35 and more preferably 45:55 to 30:70) elastomeric copolymers of p-dioxanone (1,4-dioxan-2-one) and lactide including L-lactide, D-lactide and lactic acid (preferably having a mole ratio of p-dioxanone to lactide of from about 40:60 to about 60:40); elastomeric copolymers of ε-caprolactone and p-dioxanone (preferably having a mole ratio of ε-caprolactone to p-dioxanone of from about 30:70 to about 70:30); elastomeric copolymers of p-dioxanone and trimethylene carbonate (preferably having a mole ratio of p-dioxanone to trimethylene carbonate of from about 30:70 to about 70:30); elastomeric copolymers of trimethylene carbonate and glycolide (preferably having a mole ratio of trimethylene carbonate to glycolide of from about 30:70 to about 70:30); elastomeric copolymer of trimethylene carbonate and lactide including L-lactide, D-lactide, blends thereof or lactic acid copolymers (preferably having a mole ratio of trimethylene carbonate to lactide of from about 30:70 to about 70:30) and blends thereof. In one embodiment, the elastomeric copolymer is a copolymer of glycolide and ε-caprolactone. In another embodiment, the elastomeric copolymer is a copolymer of lactide and ε-caprolactone.

The disclosures of U.S. Pat. No. 5,468,253, entitled ELASTOMERIC MEDICAL DEVICE, which issued on Nov. 21, 1995, and U.S. Pat. No. 6,325,810, entitled FOAM BUTTRESS FOR STAPLING APPARATUS, which issued on Dec. 4, 2001, are hereby incorporated by reference in their respective entireties.

In various embodiments, the tissue thickness compensator may comprise an emulsifier. Examples of emulsifiers may include, but are not limited to, water-soluble polymers, such as, polyvinyl alcohol (PVA), polyvinyl pyrrolidone (PVP), polyethylene glycol (PEG), polypropylene glycol (PPG), PLURONICS, TWEENS, polysaccharides and combinations thereof.

In various embodiments, the tissue thickness compensator may comprise a surfactant. Examples of surfactants may include, but are not limited to, polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and poly-oxamers.

In various embodiments, the polymeric composition may comprise a pharmaceutically active agent. The polymeric composition may release a therapeutically effective amount of the pharmaceutically active agent. In various embodiments, the pharmaceutically active agent may be released as the polymeric composition is desorbed/absorbed. In various embodiments, the pharmaceutically active agent may be released into fluid, such as, for example, blood, passing over or through the polymeric composition. Examples of pharmaceutically active agents may include, but are not limited to, haemostatic agents and drugs, such as, for example, fibrin, thrombin, and oxidized regenerated cellulose (ORC); anti-inflammatory drugs, such as, for example, diclofenac, aspirin, naproxen, sulindac, and hydrocortisone; antibiotic and antimicrobial drug or agents, such as, for example, triclosan, ionic silver, ampicillin, gentamicin, polymyxin B, chloramphenicol; and anticancer agents, such as, for example, cisplatin, mitomycin, adriamycin.

In various embodiments, the polymeric composition may comprise a haemostatic material. The tissue thickness compensator may comprise haemostatic materials comprising poly(lactic acid), poly(glycolic acid), poly(hydroxybutyrate), poly(caprolactone), poly(dioxanone), polyalkyleneoxides, copoly(ether-esters), collagen, gelatin, thrombin, fibrin, fibrinogen, fibronectin, elastin, albumin, hemoglobin, ovalbumin, polysaccharides, hyaluronic acid, chondroitin sulfate, hydroxyethyl starch, hydroxyethyl cellulose, cellulose, oxidized cellulose, hydroxypropyl cellulose, carboxyethyl cellulose, carboxymethyl cellulose, chitan, chitosan, agarose, maltose, maltodextrin, alginate, clotting factors, methacrylate, polyurethanes, cyanoacrylates, platelet agonists, vasoconstrictors, alum, calcium, RGD peptides, proteins, protamine sulfate, $\epsilon$-amino caproic acid, ferric sulfate, ferric subsulfates, ferric chloride, zinc, zinc chloride, aluminum chloride, aluminum sulfates, aluminum acetates, permanganates, tannins, bone wax, polyethylene glycols, fucans and combinations thereof. The tissue thickness compensator may be characterized by haemostatic properties.

The polymeric composition of a tissue thickness compensator may be characterized by percent porosity, pore size, and/or hardness, for example. In various embodiments, the polymeric composition may have a percent porosity from approximately 30% by volume to approximately 99% by volume, for example. In certain embodiments, the polymeric composition may have a percent porosity from approximately 60% by volume to approximately 98% by volume, for example. In various embodiments, the polymeric composition may have a percent porosity from approximately 85% by volume to approximately 97% by volume, for example. In at least one embodiment, the polymeric composition may comprise approximately 70% by weight of PLLA and approximately 30% by weight of PCL, for example, and can comprise approximately 90% porosity by volume, for example. In at least one such embodiment, as a result, the polymeric composition would comprise approximately 10% copolymer by volume. In at least one embodiment, the polymeric composition may comprise approximately 65% by weight of PGA and approximately 35% by weight of PCL, for example, and can have a percent porosity from approximately 93% by volume to approximately 95% by volume, for example. In various embodiments, the polymeric composition may comprise greater than 85% porosity by volume. The polymeric composition may have a pore size from approximately 5 micrometers to approximately 2000 micrometers, for example. In various embodiments, the polymeric composition may have a pore size between approximately 10 micrometers to approximately 100 micrometers, for example. In at least one such embodiment, the polymeric composition can comprise a copolymer of PGA and PCL, for example. In certain embodiments, the polymeric composition may have a pore size between approximately 100 micrometers to approximately 1000 micrometers, for example. In at least one such embodiment, the polymeric composition can comprise a copolymer of PLLA and PCL, for example.

According to certain aspects, the hardness of a polymeric composition may be expressed in terms of the Shore Hardness, which can defined as the resistance to permanent indentation of a material as determined with a durometer, such as a Shore Durometer. In order to assess the durometer value for a given material, a pressure is applied to the material with a durometer indenter foot in accordance with ASTM procedure D2240-00, entitled, "Standard Test Method for Rubber Property-Durometer Hardness", the entirety of which is incorporated herein by reference. The durometer indenter foot may be applied to the material for a sufficient period of time, such as 15 seconds, for example, wherein a reading is then taken from the appropriate scale. Depending on the type of scale being used, a reading of 0 can be obtained when the indenter foot completely penetrates the material, and a reading of 100 can be obtained when no penetration into the material occurs. This reading is dimensionless. In various embodiments, the durometer may be determined in accordance with any suitable scale, such as Type A and/or Type OO scales, for example, in accordance with ASTM D2240-00. In various embodiments, the polymeric composition of a tissue thickness compensator may have a Shore A hardness value from approximately 4 A to approximately 16 A, for example, which is approximately 45 OO to approximately 65 OO on the Shore OO range. In at least one such embodiment, the polymeric composition can comprise a PLLA/PCL copolymer or a PGA/PCL copolymer, for example. In various embodiments, the polymeric composition of a tissue thickness compensator may have a Shore A Hardness value of less than 15 A. In various embodiments, the polymeric composition of a tissue thickness compensator may have a Shore A Hardness value of less than 10 A. In various embodiments, the polymeric composition of a tissue thickness compensator may have a Shore A Hardness value of less than 5 A. In certain embodiments, the polymeric material may have a Shore OO composition value from approximately 35 OO to approximately 75 OO, for example.

In various embodiments, the polymeric composition may have at least two of the above-identified properties. In various embodiments, the polymeric composition may have at least three of the above-identified properties. The polymeric composition may have a porosity from 85% to 97% by volume, a pore size from 5 micrometers to 2000 micrometers, and a Shore A hardness value from 4 A to 16 A and Shore OO hardness value from 45 OO to 65 OO, for example. In at least one embodiment, the polymeric composition may comprise 70% by weight of the polymeric composition of PLLA and 30% by weight of the polymeric composition of PCL having a porosity of 90% by volume, a pore size from 100 micrometers to 1000 micrometers, and a Shore A hardness value from 4 A to 16 A and Shore OO hardness value from 45 OO to 65 OO, for example. In at least one embodiment, the polymeric composition may comprise 65% by weight of the polymeric composition of PGA and 35% by weight of the polymeric composition of PCL having a porosity from 93% to 95% by volume, a pore size from 10 micrometers to 100 micrometers, and a Shore A hardness value from 4 A to 16 A and Shore OO hardness value from 45 OO to 65 OO, for example.

In various embodiments, the tissue thickness compensator may comprise a material that expands. As discussed above, the tissue thickness compensator may comprise a compressed material that expands when uncompressed or deployed, for example. In various embodiments, the tissue thickness compensator may comprise a self-expanding material formed in situ. In various embodiments, the tissue thickness compensator may comprise at least one precursor selected to spontaneously crosslink when contacted with at least one of other precursor(s), water, and/or bodily fluids. In various embodiments, a first precursor may contact one or more other precursors to form an expandable and/or swellable tissue thickness compensator. In various embodiments, the tissue thickness compensator may comprise a fluid-swellable composition, such as a water-swellable composition, for example. In various embodiments, the tissue thickness compensator may comprise a gel comprising water.

In various embodiments, the tissue thickness compensator may comprise a biodegradable foam having an encapsulation comprising dry hydrogel particles or granules embedded therein. Without wishing to be bound to any particular theory, the encapsulations in the foam may be formed by contacting an aqueous solution of a hydrogel precursor and an organic solution of biocompatible materials to form the foam. In various embodiments, the aqueous solution and organic solution may form micelles. The aqueous solution and organic solution may be dried to encapsulate dry hydrogel particles or granules within the foam. For example, a hydrogel precursor, such as a hydrophilic polymer, may be dissolved in water to form a dispersion of micelles. The aqueous solution may contact an organic solution of dioxane comprising poly(glycolic acid) and polycaprolactone. The aqueous and organic solutions may be lyophilized to form a biodegradable foam having dry hydrogel particles or granules dispersed therein. Without wishing to be bound to any particular theory, it is believed that the micelles form the encapsulation having the dry hydrogel particles or granules dispersed within the foam structure. In certain embodiments, the encapsulation may be ruptured, and the dry hydrogel particles or granules may contact a fluid, such as a bodily fluid, and expand.

In various embodiments, as described above, the tissue thickness compensator may comprise an initial thickness and an expanded thickness. In certain embodiments, the initial thickness of a tissue thickness compensator can be approximately 0.001% of its expanded thickness, approximately 0.01% of its expanded thickness, approximately 0.1% of its expanded thickness, approximately 1% of its expanded thickness, approximately 10% of its expanded thickness, approximately 20% of its expanded thickness, approximately 30% of its expanded thickness, approximately 40% of its expanded thickness, approximately 50% of its expanded thickness, approximately 60% of its expanded thickness, approximately 70% of its expanded thickness, approximately 80% of its expanded thickness, and/or approximately 90% of its expanded thickness, for example. In various embodiments, the expanded thickness of the tissue thickness compensator can be approximately two times, approximately five times, approximately ten times, approximately fifty times, approximately one hundred times, approximately two hundred times, approximately three hundred times, approximately four hundred times, approximately five hundred times, approximately six hundred times, approximately seven hundred times, approximately eight hundred times, approximately nine hundred times, and/or approximately one thousand times thicker than its initial thickness, for example. In various embodiments, the initial thickness of the tissue thickness compensator can be up to 1% its expanded thickness, up to 5% its expanded thickness, up to 10% its expanded thickness, and up to 50% its expanded thickness. In various embodiments, the expanded thickness of the tissue thickness compensator can be at least 50% thicker than its initial thickness, at least 100% thicker than its initial thickness, at least 300% thicker than its initial thickness, and at least 500% thicker than its initial thickness. As described above, in various circumstances, as a result of the above, the tissue thickness compensator can be configured to consume any gaps within the staple entrapment area.

As discussed above, in various embodiments, the tissue thickness compensator may comprise a hydrogel. In various embodiments, the hydrogel may comprise homopolymer hydrogels, copolymer hydrogels, multipolymer hydrogels, interpenetrating polymer hydrogels, and combinations thereof. In various embodiments, the hydrogel may comprise microgels, nanogels, and combinations thereof. The hydrogel may generally comprise a hydrophilic polymer network capable of absorbing and/or retaining fluids. In various embodiments, the hydrogel may comprise a non-crosslinked hydrogel, a crosslinked hydrogel, and combinations thereof. The hydrogel may comprise chemical crosslinks, physical crosslinks, hydrophobic segments and/or water insoluble segments. The hydrogel may be chemically crosslinked by polymerization, small-molecule crosslinking, and/or polymer-polymer crosslinking. The hydrogel may be physically crosslinked by ionic interactions, hydrophobic interactions, hydrogen bonding interactions, sterocomplexation, and/or supramolecular chemistry. The hydrogel may be substantially insoluble due to the crosslinks, hydrophobic segments and/or water insoluble segments, but be expandable and/or swellable due to absorbing and/or retaining fluids. In certain embodiments, the precursor may crosslink with endogenous materials and/or tissues.

In various embodiments, the hydrogel may comprise an environmentally sensitive hydrogel (ESH). The ESH may comprise materials having fluid-swelling properties that relate to environmental conditions. The environmental conditions may include, but are not limited to, the physical conditions, biological conditions, and/or chemical conditions at the surgical site. In various embodiments, the hydrogel may swell or shrink in response to temperature, pH, electric fields, ionic strength, enzymatic and/or chemical reactions, electrical and/or magnetic stimuli, and other physiological and environmental variables, for example. In various embodiments, the ESH may comprise multifunctional acrylates, hydroxyethylmethacrylate (HEMA), elastomeric acrylates, and related monomers.

In various embodiments, the tissue thickness compensator comprising a hydrogel may comprise at least one of the non-synthetic materials and synthetic materials described above. The hydrogel may comprise a synthetic hydrogel and/or a non-synthetic hydrogel. In various embodiments, the tissue thickness compensator may comprise a plurality of layers. The plurality of the layers may comprise porous layers and/or non-porous layers. For example, the tissue thickness compensator may comprise a non-porous layer and a porous layer. In another example, the tissue thickness compensator may comprise a porous layer intermediate a first non-porous layer and a second non-porous layer. In another example, the tissue thickness compensator may comprise a non-porous layer intermediate a first porous layer and a second porous layer. The non-porous layers and porous layers may be positioned in any order relative to the surfaces of the staple cartridge and/or anvil.

Examples of the non-synthetic material may include, but are not limited to, albumin, alginate, carbohydrate, casein, cellulose, chitin, chitosan, collagen, blood, dextran, elastin, fibrin, fibrinogen, gelatin, heparin, hyaluronic acid, keratin, protein, serum, and starch. The cellulose may comprise hydroxyethyl cellulose, oxidized cellulose, oxidized regenerated cellulose (ORC), hydroxypropyl cellulose, carboxyethyl cellulose, carboxymethylcellulose, and combinations thereof. The collagen may comprise bovine pericardium. The carbohydrate may comprise a polysaccharide, such as lyophilized polysaccharide. The protein may comprise glycoprotein, proteoglycan, and combinations thereof.

Examples of the synthetic material may include, but are not limited to, poly(lactic acid), poly(glycolic acid), poly(hydroxybutyrate), poly(phosphazine), polyesters, polyethylene glycols, polyethylene oxide, polyethylene oxide-co-polypropylene oxide, co-polyethylene oxide, polyalkyleneoxides, polyacrylamides, polyhydroxyethylmethylacrylate, poly(vinylpyrrolidone), polyvinyl alcohols, poly(caprolactone), poly(dioxanone), polyacrylic acid, polyacetate, polypropylene, aliphatic polyesters, glycerols, poly(amino acids), copoly(ether-esters), polyalkylene oxalates, polyamides, poly(iminocarbonates), polyoxaesters, polyorthoesters, polyphosphazenes and combinations thereof. In certain embodiments, the above non-synthetic materials may be synthetically prepared, e.g., synthetic hyaluronic acid, utilizing conventional methods.

In various embodiments, the hydrogel may be made from one or more hydrogel precursors. The precursor may comprise a monomer and/or a macromer. The hydrogel precursor may comprise an electrophile functional group and/or a nucleophile electrophile functional group. In general, electrophiles may react with nucleophiles to form a bond. The term "functional group" as used herein refers to electrophilic or nucleophilic groups capable of reacting with each other to form a bond. Examples of electrophilic functional groups may include, but are not limited to, N-hydroxysuccinimides ("NHS"), sulfosuccinimides, carbonyldiimidazole, sulfonyl chloride, aryl halides, sulfosuccinimidyl esters, N-hydroxysuccinimidyl esters, succinimidyl esters such as succinimidyl succinates and/or succinimidyl propionates, isocyanates, thiocyanates, carbodiimides, benzotriazole carbonates, epoxides, aldehydes, maleimides, imidoesters, combinations thereof, and the like. In at least one embodiment, the electrophilic functional group may comprise a succinimidyl ester. Examples of nucleophile functional groups may include, but are not limited to, $-NH_2$, $-SH$, $-OH$, $-PH_2$, and $-CO-NH-NH_2$.

In various embodiments, the hydrogel may be formed from a single precursor or multiple precursors. In certain embodiments, the hydrogel may be formed from a first precursor and a second precursor. The first hydrogel precursor and second hydrogel precursor may form a hydrogel in situ and/or in vivo upon contact. The hydrogel precursor may generally refer to a polymer, functional group, macromolecule, small molecule, and/or crosslinker that can take part in a reaction to form a hydrogel. The precursor may comprise a homogeneous solution, heterogeneous, or phase separated solution in a suitable solvent, such as water or a buffer, for example. The buffer may have a pH from about 8 to about 12, such as, about 8.2 to about 9, for example. Examples of buffers may include, but are not limited to borate buffers. In certain embodiments, the precursor(s) may be in an emulsion. In various embodiments, a first precursor may react with a second precursor to form a hydrogel. In various embodiments, the first precursor may spontaneously crosslink when contacted with the second precursor. In various embodiments, a first set of electrophilic functional groups on a first precursor may react with a second set of nucleophilic functional groups on a second precursor. When the precursors are mixed in an environment that permits reaction (e.g., as relating to pH, temperature, and/or solvent), the functional groups may react with each other to form covalent bonds. The precursors may become crosslinked when at least some of the precursors react with more than one other precursor.

In various embodiments, the tissue thickness compensator may comprise at least one monomer selected from the group consisting of 3-sulfopropyl acrylate potassium salt ("KSPA"), sodium acrylate ("NaA"), N-(tris(hydroxylmethyl)methyl)acrylamide ("tris acryl"), and 2-acrylamido-2-methyl-1-propane sulfonic acid (AMPS). The tissue thickness compensator may comprise a copolymer comprising two or more monomers selected from the group consisting of KSPA, NaA, tris acryl, AMPS. The tissue thickness compensator may comprise homopolymers derived from KSPA, NaA, trisacryl and AMPS. The tissue thickness compensator may comprise hydrophilicity modifying monomers copolymerizable therewith. The hydrophilicity modifying monomers may comprise methylmethacrylate, butylacrylate, cyclohexylacrylate, styrene, styrene sulphonic acid.

In various embodiments, the tissue thickness compensator may comprise a crosslinker. The crosslinker may comprise a low molecular weight di- or polyvinylic crosslinking agent, such as ethylenglycol diacrylate or dimethacrylate, di-, tri- or tetraethylen-glycol diacrylate or dimethacrylate, allyl(meth)acrylate, a $C_2$-$C_8$-alkylene diacrylate or dimethacrylate, divinyl ether, divinyl sulfone, di- and trivinylbenzene, trimethylolpropane triacrylate or trimethacrylate, pentaerythritol tetraacrylate or tetramethacrylate, bisphenol A diacrylate or dimethacrylate, methylene bisacrylamide or bismethacrylamide, ethylene bisacrylamide or ethylene bismethacrylamide, triallyl phthalate or diallyl phthalate. In at least one embodiment, the crosslinker may comprise N,N'-methylenebisacrylamide ("MBAA").

In various embodiments, the tissue thickness compensator may comprise at least one of acrylate and/or methacrylate functional hydrogels, biocompatible photoinitiator, alkylcyanoacrylates, isocyanate functional macromers, optionally comprising amine functional macromers, succinimidyl ester functional macromers, optionally comprising amine and/or sulfhydryl functional macromers, epoxy functional macromers, optionally comprising amine functional macromers, mixtures of proteins and/or polypeptides and aldehyde crosslinkers, Genipin, and water-soluble carbodiimides, anionic polysaccharides and polyvalent cations.

In various embodiments, the tissue thickness compensator may comprise unsaturated organic acid monomers, acrylic substituted alcohols, and/or acrylamides. In various embodiments, the tissue thickness compensator may comprise methacrylic acids, acrylic acids, glycerolacrylate, glycerolmethacrylate, 2-hydroxyethylmethacrylate, 2-hydroxyethylacrylate, 2-(dimethylaminoethyl)methacrylate, N-vinyl pyrrolidone, methacrylamide, and/or N,N-dimethylacrylamide poly(methacrylic acid).

In various embodiments, the tissue thickness compensator may comprise a reinforcement material. In various embodiments, the reinforcement material may comprise at least one of the non-synthetic materials and synthetic materials described above. In various embodiments, the reinforcement material may comprise collagen, gelatin, fibrin, fibrinogen, elastin, keratin, albumin, hydroxyethyl cellulose, cellulose, oxidized cellulose, hydroxypropyl cellulose, carboxyethyl cellulose, carboxymethylcellulose, chitan, chitosan, alginate, poly(lactic acid), poly(glycolic acid), poly(hydroxybutyrate), poly(phosphazine), polyesters, polyethylene glycols, polyalkyleneoxides, polyacrylamides, polyhydroxyethylmethylacrylate, polyvinylpyrrolidone, polyvinyl alcohols, poly(caprolactone), poly(dioxanone), polyacrylic acid, polyacetate, polycaprolactone, polypropylene, aliphatic polyesters, glycerols, poly(amino acids), copoly(ether-esters), polyalkylene oxalates, polyamides, poly(iminocarbonates), polyalkylene oxalates, polyoxaesters, polyorthoesters, polyphosphazenes and combinations thereof.

In various embodiments, the tissue thickness compensator may comprise a layer comprising the reinforcement material. In certain embodiments, a porous layer and/or a non-porous layer of a tissue thickness compensator may comprise the reinforcement material. For example, the porous layer may comprise the reinforcement material and the non-porous layer may not comprise the reinforcement material. In various embodiments, the reinforcement layer may comprise an inner layer intermediate a first non-porous layer and a second non-porous layer. In certain embodiments, the reinforcement layer may comprise an outer layer of the tissue thickness compensator. In certain embodiments, the reinforcement layer may comprise an exterior surface of the tissue thickness compensator.

In various embodiments, the reinforcement material may comprise meshes, monofilaments, multifilament braids, fibers, mats, felts, particles, and/or powders. In certain embodiments, the reinforcement material may be incorporated into a layer of the tissue thickness compensator. The reinforcement material may be incorporated into at least one of a non-porous layer and a porous layer. A mesh comprising the reinforcement material may be formed using conventional techniques, such as, for example, knitting, weaving, tatting, and/or knipling. In various embodiments, a plurality of reinforcement materials may be oriented in a random direction and/or a common direction. In certain embodiments, the common direction may be one of parallel to the staple line and perpendicular to the staple line, for example. For example, the monofilaments and/or multifilament braids may be oriented in a random direction and/or a common direction. The monofilaments and multifilament braids may be associated with the non-porous layer and/or the porous layer. In various embodiments, the tissue thickness compensator may comprise a plurality of reinforcement fibers oriented in a random direction within a non-porous layer. In various embodiments, the tissue thickness compensator may comprise a plurality of reinforcement fibers oriented in a common direction within a non-porous layer.

The fibers may form a non-woven material, such as, for example, a mat and a felt. The fibers may have any suitable length, such as, for example from 0.1 mm to 100 mm and 0.4 mm to 50 mm. The reinforcement material may be ground to a powder. The powder may have a particle size from 10 micrometers to 1 cm, for example. The powder may be incorporated into the tissue thickness compensator.

In various embodiments, the tissue thickness compensator may be formed in situ. In various embodiments, the hydrogel may be formed in situ. The tissue thickness compensator may be formed in situ by covalent, ionic, and/or hydrophobic bonds. Physical (non-covalent) crosslinks may result from complexation, hydrogen bonding, desolvation, Van der Waals interactions, ionic bonding, and combinations thereof. Chemical (covalent) crosslinking may be accomplished by any of a number of mechanisms, including: free radical polymerization, condensation polymerization, anionic or cationic polymerization, step growth polymerization, electrophile-nucleophile reactions, and combinations thereof.

In various embodiments, in situ formation of the tissue thickness compensator may comprise reacting two or more precursors that are physically separated until contacted in situ and/or react to an environmental condition to react with each other to form the hydrogel. In situ polymerizable polymers may be prepared from precursor(s) that can be reacted to form a polymer at the surgical site. The tissue thickness compensator may be formed by crosslinking reactions of the precursor(s) in situ. In certain embodiments, the precursor may comprise an initiator capable of initiating a polymerization reaction for the formation of the in situ tissue thickness compensator. The tissue thickness compensator may comprise a precursor that can be activated at the time of application to create, in various embodiments, a crosslinked hydrogel. In situ formation of the tissue thickness compensator may comprise activating at least one precursor to form bonds to form the tissue thickness compensator. In various embodiments, activation may be achieved by changes in the physical conditions, biological conditions, and/or chemical conditions at the surgical site, including, but not limited to temperature, pH, electric fields, ionic strength, enzymatic and/or chemical reactions, electrical and/or magnetic stimuli, and other physiological and environmental variables. In various embodiments, the precursors may be contacted outside the body and introduced to the surgical site.

In various embodiments, the tissue thickness compensator may comprise one or more encapsulations, or cells, which can be configured to store at least one component therein. In certain embodiments, the encapsulation may be configured to store a hydrogel precursor therein. In certain embodiments, the encapsulation may be configured to store two components therein, for example. In certain embodiments, the encapsulation may be configured to store a first hydrogel precursor and a second hydrogel precursor therein. In certain embodiments, a first encapsulation may be configured to store a first hydrogel precursor therein and a second encapsulation may be configured to store a second hydrogel precursor therein. As described above, the encapsulations can be aligned, or at least substantially aligned, with the staple legs to puncture and/or otherwise rupture the encapsulations when the staple legs contact the encapsulation. In certain embodiments, the encapsulations may be compressed, crushed, collapsed, and/or otherwise ruptured when the staples are deployed. After the encapsulations have been ruptured, the component(s) stored therein can flow out of the encapsulation. The component stored therein may contact other components, layers of the tissue thickness compensator, and/or the tissue. In various embodiments, the other components may be flowing from the same or different encapsulations, provided in the layers of the tissue thickness compensator, and/or provided to the surgical site by the clinician. As a result of the above, the component(s) stored within the encapsulations can provide expansion and/or swelling of the tissue thickness compensator.

In various embodiments, the tissue thickness compensator may comprise a layer comprising the encapsulations. In various embodiments, the encapsulation may comprise a void, a pocket, a dome, a tube, and combinations thereof associated with the layer. In certain embodiments, the encapsulations may comprise voids in the layer. In at least one embodiment, the layer can comprise two layers that can be attached to one another wherein the encapsulations can be defined between the two layers. In certain embodiments, the encapsulations may comprise domes on the surface of the layer. For example, at least a portion of the encapsulations can be positioned within domes extending upwardly from the layer. In certain embodiments, the encapsulations may comprise pockets formed within the layer. In certain embodiments, a first portion of the encapsulations may comprise a dome and a second portion of the encapsulations may comprise a pocket. In certain embodiments, the encapsulations may comprise a tube embedded within the layer. In certain embodiments, the tube may comprise the non-synthetic materials and/or synthetic materials described herein, such as PLA. In at least one embodiment, the tissue thickness compensator may comprise a bioabsorable foam, such as ORC, comprising PLA tubes embedded therein, and the tube may encapsulate a hydrogel, for example. In certain embodiments, the encapsulations may comprise discrete cells that are unconnected to each other. In certain embodiments, one or more of the encapsulations can be in fluid communication with each other via one or more passageways, conduits, and/or channels, for example, extending through the layer.

The rate of release of a component from the encapsulation may be controlled by the thickness of the tissue thickness compensator, the composition of tissue thickness compensator, the size of the component, the hydrophilicity of the component, and/or the physical and/or chemical interactions among the component, the composition of the tissue thickness compensator, and/or the surgical instrument, for example. In various embodiments, the layer can comprise one or more thin sections or weakened portions, such as partial perforations, for example, which can facilitate the incision of the layer and the rupture of the encapsulations. In various embodiments, the partial perforations may not completely extend through a layer while, in certain embodiments, perforations may completely extend through the layer.

In various embodiments, an anvil may comprise a tissue thickness compensator comprising an encapsulated component comprising at least one microsphere particle. In certain embodiments, the tissue thickness compensator may comprise an encapsulation comprising a first encapsulated component and a second encapsulated component. In certain embodiments, the tissue thickness compensator may comprise an encapsulation comprising a first microsphere particle and a second microsphere particle.

In various embodiments, the tissue thickness compensator may be suitable for use with a surgical instrument. As described above the tissue thickness compensator may be associated with the staple cartridge and/or the anvil. The tissue thickness compensator may be configured into any shape, size and/or dimension suitable to fit the staple cartridge and/or anvil. As described herein, the tissue thickness compensator may be releasably attached to the staple cartridge and/or anvil. The tissue thickness compensator may be attached to the staple cartridge and/or anvil in any mechanical and/or chemical manner capable of retaining the tissue thickness compensator in contact with the staple cartridge and/or anvil prior to and during the stapling process. The tissue thickness compensator may be removed or released from the staple cartridge and/or anvil after the staple penetrates the tissue thickness compensator. The tissue thickness compensator may be removed or released from the staple cartridge and/or anvil as the staple cartridge and/or anvil is moved away from the tissue thickness compensator.

Figure 14:
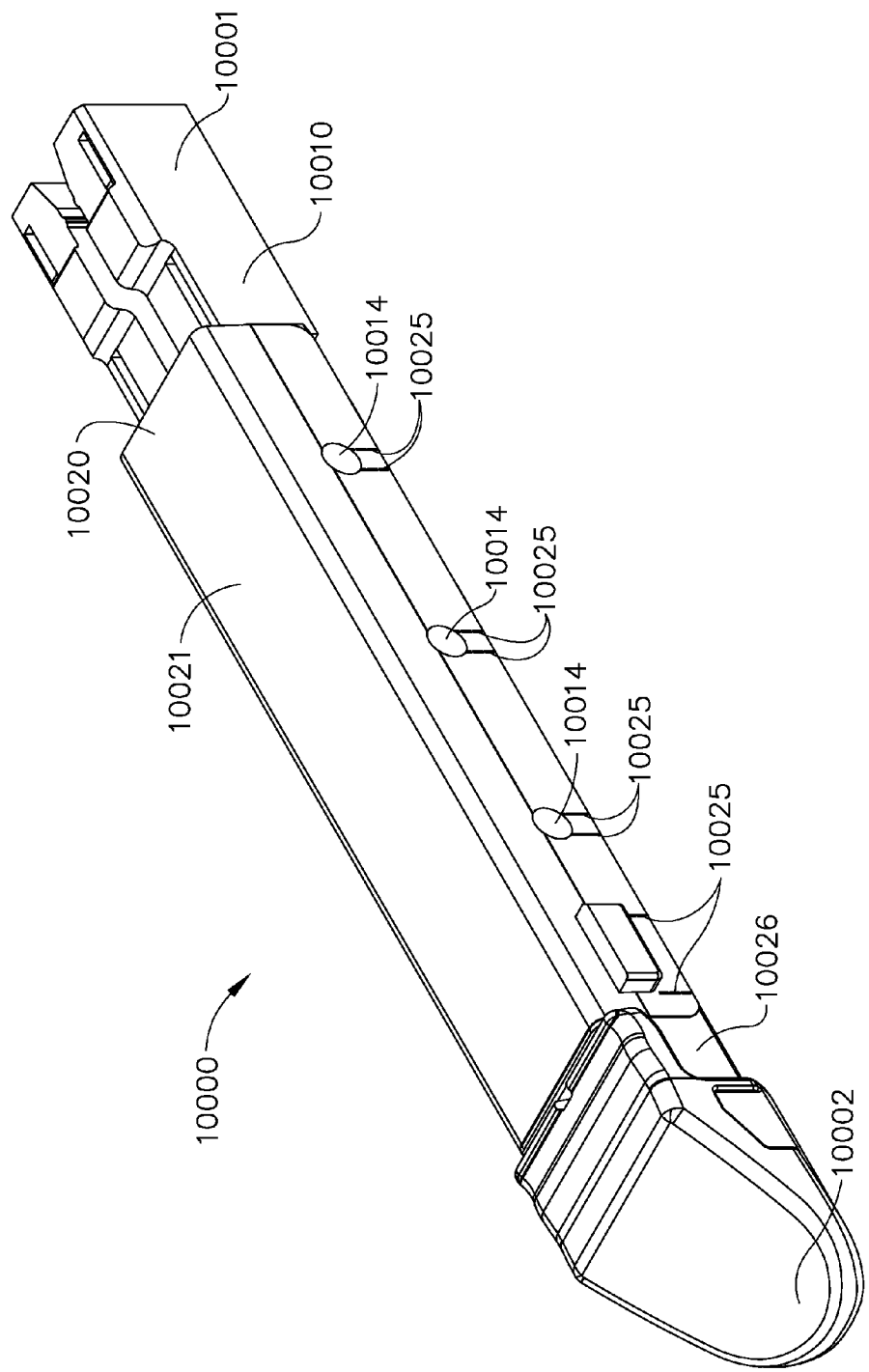
FIG. 14 is a perspective view of a staple cartridge comprising a rigid support portion and a compressible tissue thickness compensator for use with a surgical stapling instrument in accordance with at least one embodiment of the invention.
Figure 16:
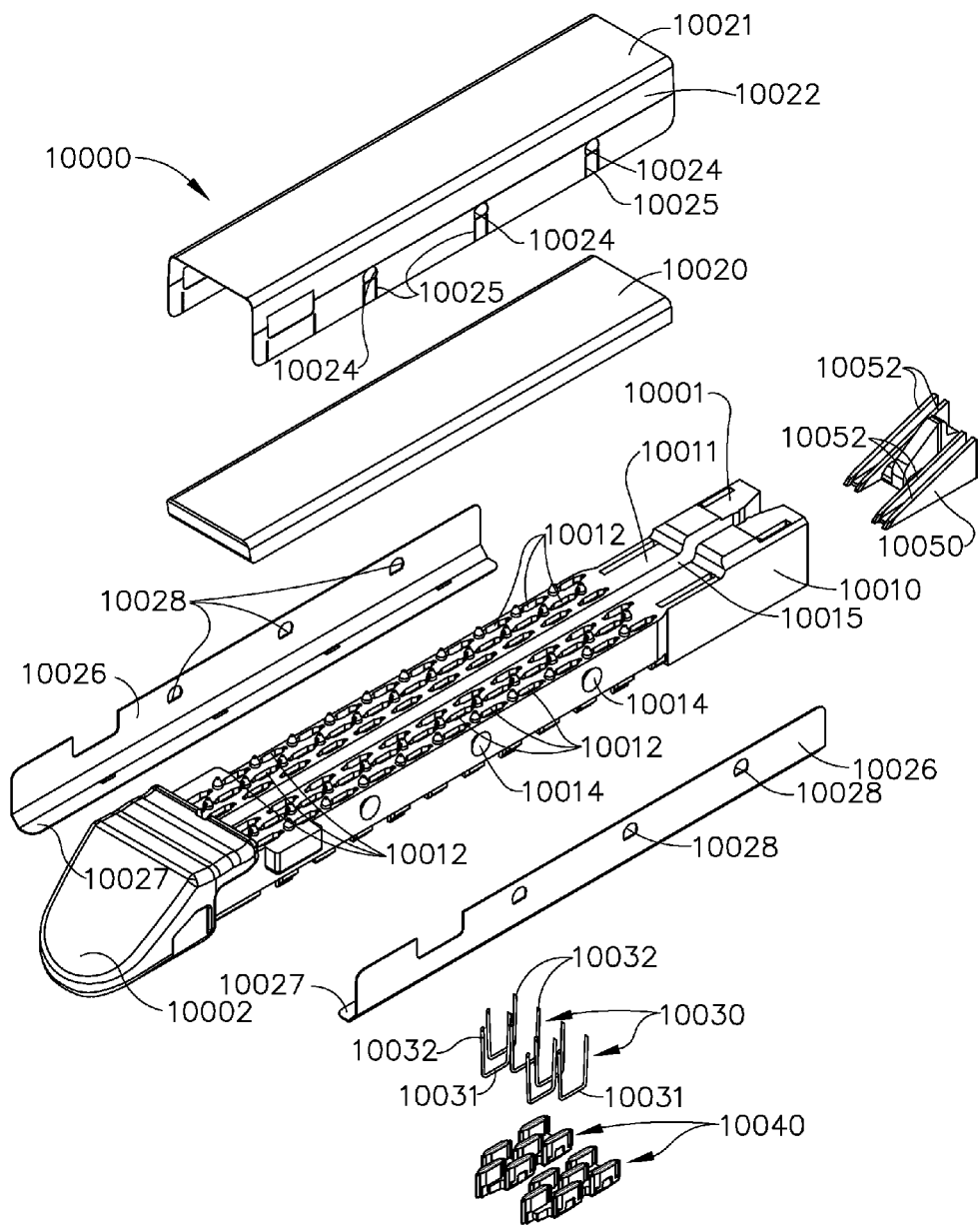
FIG. 16 is a fully exploded view of the staple cartridge of FIG. 14.
Figure 17:
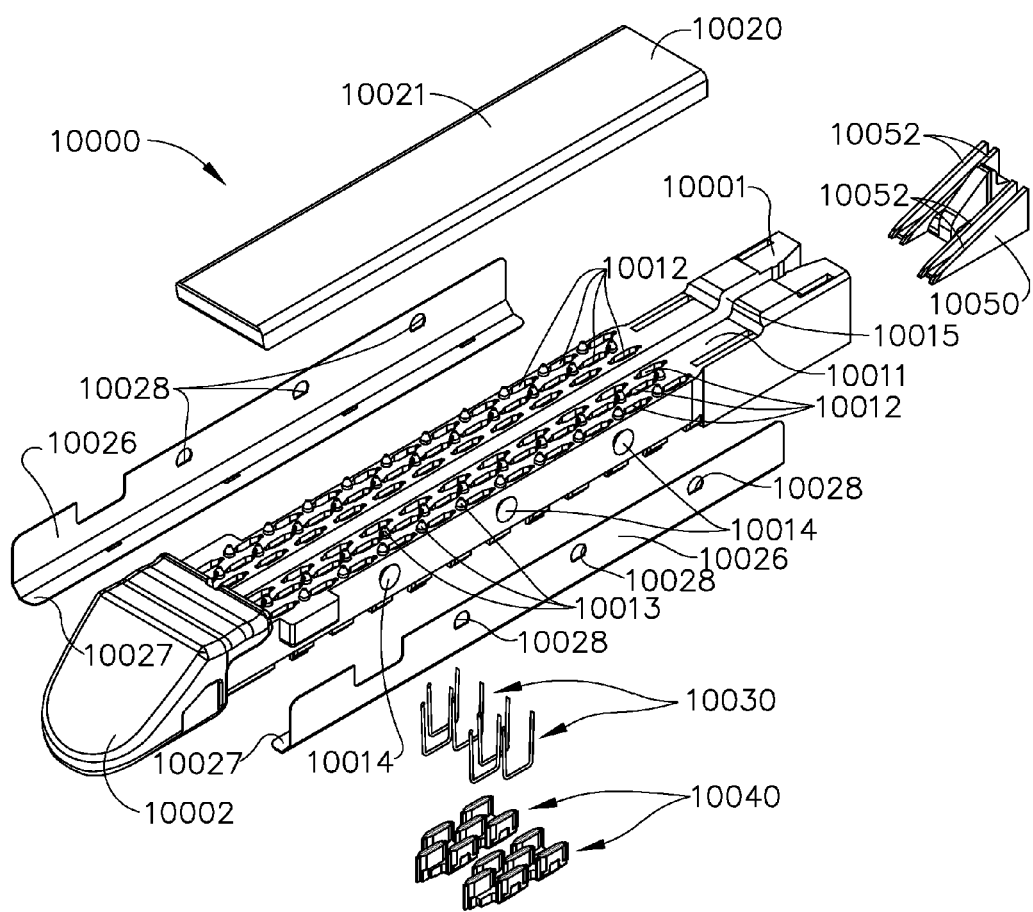
FIG. 17 is another exploded view of the staple cartridge of FIG. 14 without a warp covering the tissue thickness compensator.
Figure 18:
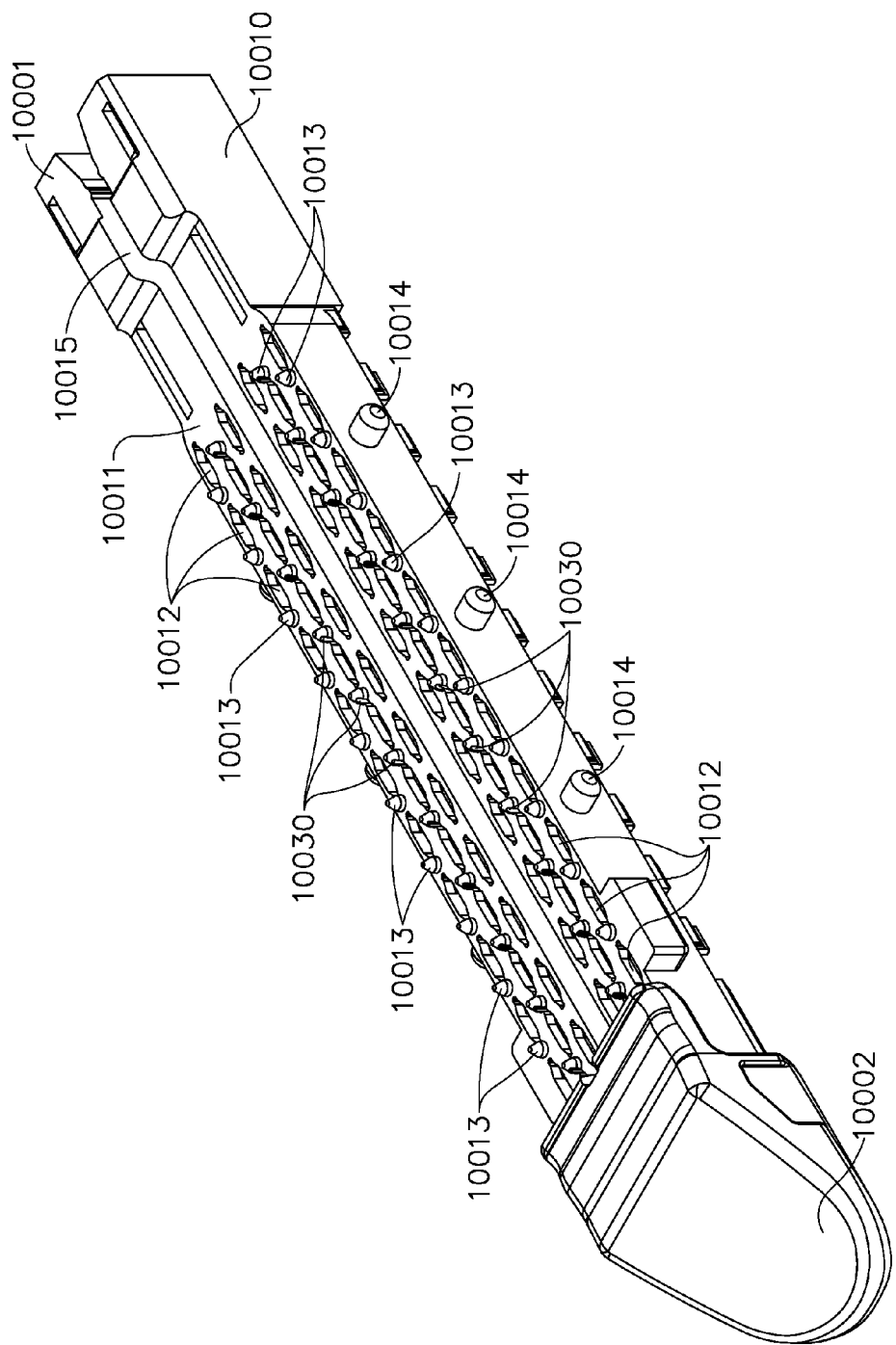
FIG. 18 is a perspective view of a cartridge body, or support portion, of the staple cartridge of FIG. 14.
Figure 19:
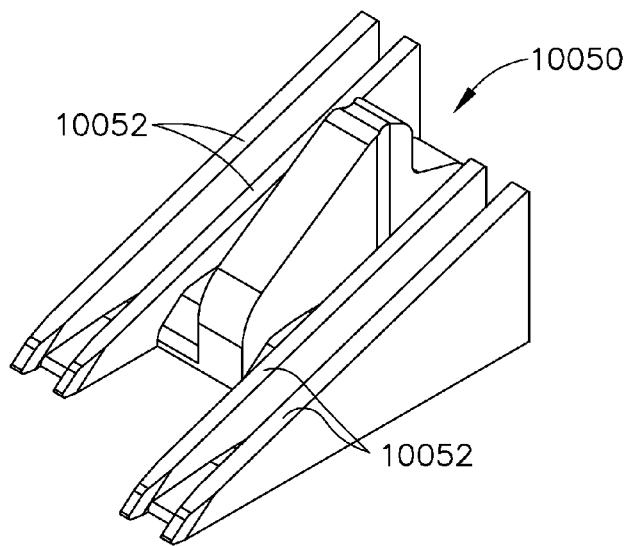
FIG. 19 is a top perspective view of a sled movable within the staple cartridge of FIG. 14 to deploy staples from the staple cartridge.
Figure 20:
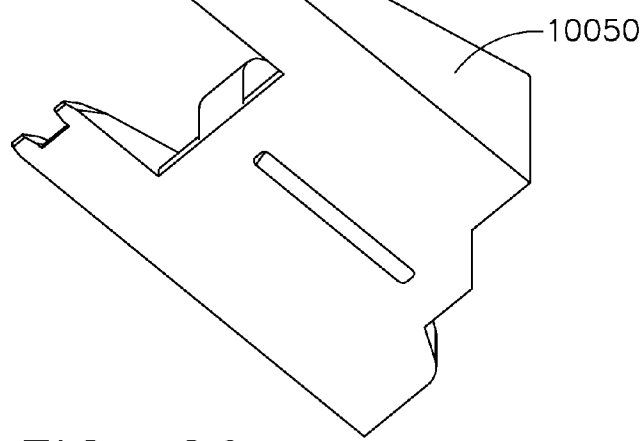
FIG. 20 is a bottom perspective view of the sled of FIG. 19.
Figure 21:
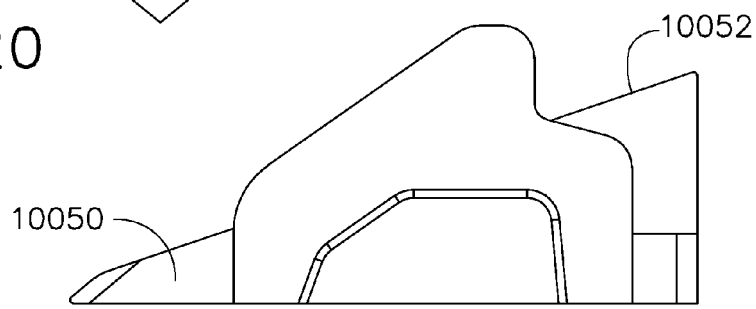
FIG. 21 is an elevational view of the sled of FIG. 19.
Figure 22:
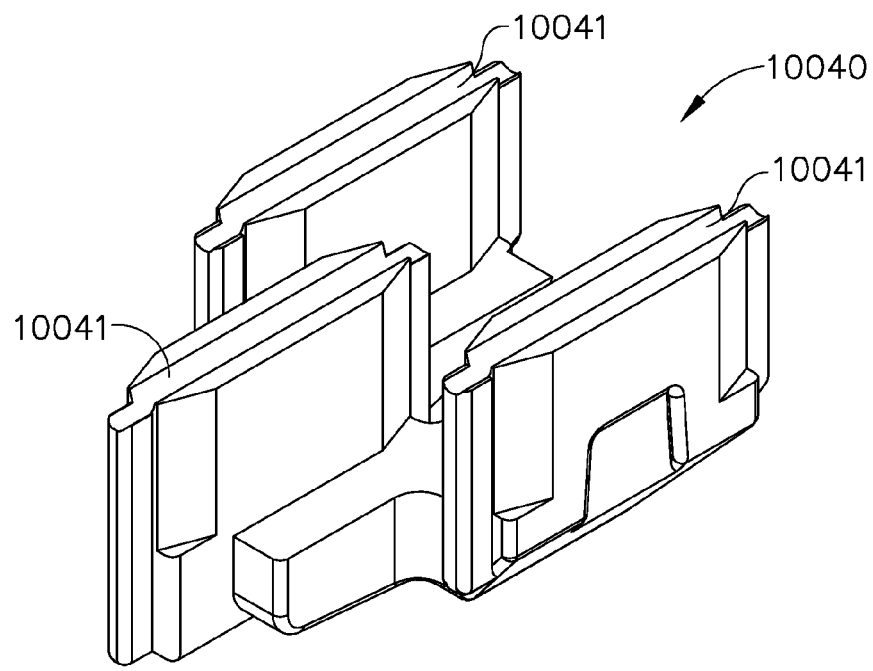
FIG. 22 is a top perspective view of a driver configured to support one or more staples and to be lifted upwardly by the sled of FIG. 19 to eject the staples from the staple cartridge.
Figure 23:
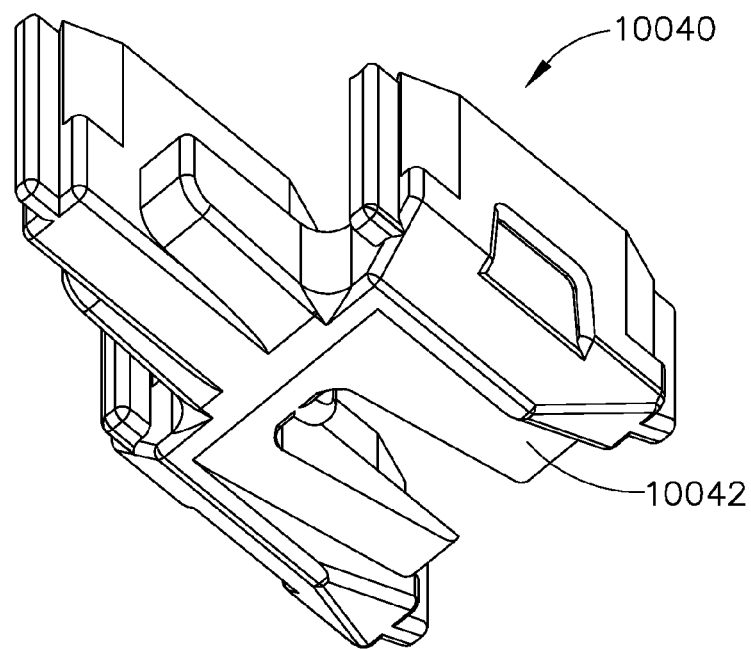
FIG. 23 is a bottom perspective view of the driver of FIG. 22.

In various embodiments, referring now to FIG. 14, a staple cartridge, such as staple cartridge 10000, for example, can comprise a support portion 10010 and a compressible tissue thickness compensator 10020. Referring now to FIGS. 16-18, the support portion 10010 can comprise a deck surface 10011 and a plurality of staple cavities 10012 defined within the support portion 10010. Each staple cavity 10012 can be sized and configured to removably store a staple, such as a staple 10030, for example, therein. The staple cartridge 10000 can further comprise a plurality of staple drivers 10040 which can each be configured to support one or more staples 10030 within the staple cavities 10012 when the staples 10030 and the staple drivers 10040 are in their unfired positions. In at least one such embodiment, referring primarily to FIGS. 22 and 23, each staple driver 10040 can comprise one or more cradles, or troughs, 10041, for example, which can be configured to support the staples and limit relative movement between the staples 10030 and the staple drivers 10040. In various embodiments, referring again to FIG. 16, the staple cartridge 10000 can further comprise a staple-firing sled 10050 which can be moved from a proximal end 10001 to a distal end 10002 of the staple cartridge in order to sequentially lift the staple drivers 10040 and the staples 10030 from their unfired positions toward an anvil positioned opposite the staple cartridge 10000. In certain embodiments, referring primarily to FIGS. 16 and 18, each staple 10030 can comprise a base 10031 and one or more legs 10032 extending from the base 10031 wherein each staple can be at least one of substantially U-shaped and substantially V-shaped, for example. In at least one embodiment, the staples 10030 can be configured such that the tips of the staple legs 10032 are recessed with respect to the deck surface 10011 of the support portion 10010 when the staples 10030 are in their unfired positions. In at least one embodiment, the staples 10030 can be configured such that the tips of the staple legs 10032 are flush with respect to the deck surface 10011 of the support portion 10010 when the staples 10030 are in their unfired positions. In at least one embodiment, the staples 10030 can be configured such that the tips of the staple legs 10032, or at least some portion of the staple legs 10032, extend above the deck surface 10011 of the support portion 10010 when the staples 10030 are in their unfired positions. In such embodiments, the staple legs 10032 can extend into and can be embedded within the tissue thickness compensator 10020 when the staples 10030 are in their unfired positions. In at least one such embodiment, the staple legs 10032 can extend above the deck surface 10011 by approximately 0.075", for example. In various embodiments, the staple legs 10032 can extend above the deck surface 10011 by a distance between approximately 0.025" and approximately 0.125", for example. In certain embodiments, further to the above, the tissue thickness compensator 10020 can comprise an uncompressed thickness between approximately 0.08" and approximately 0.125", for example.

Figure 25:
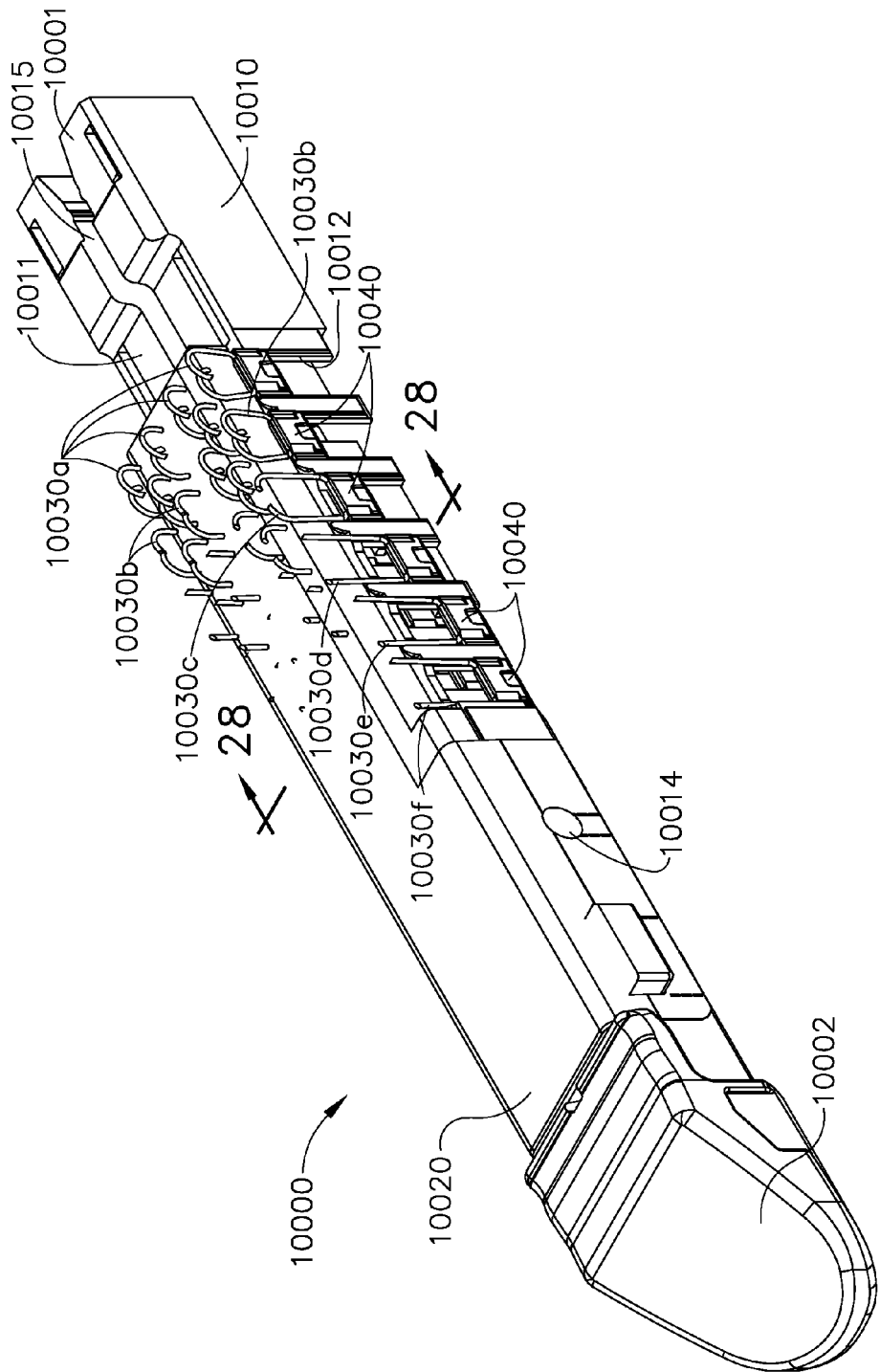
FIG. 25 is a partial cut away view of a staple cartridge comprising a rigid support portion and a compressible tissue thickness compensator illustrated with staples being moved from an unfired position to a fired position during a first sequence.
Figure 28:
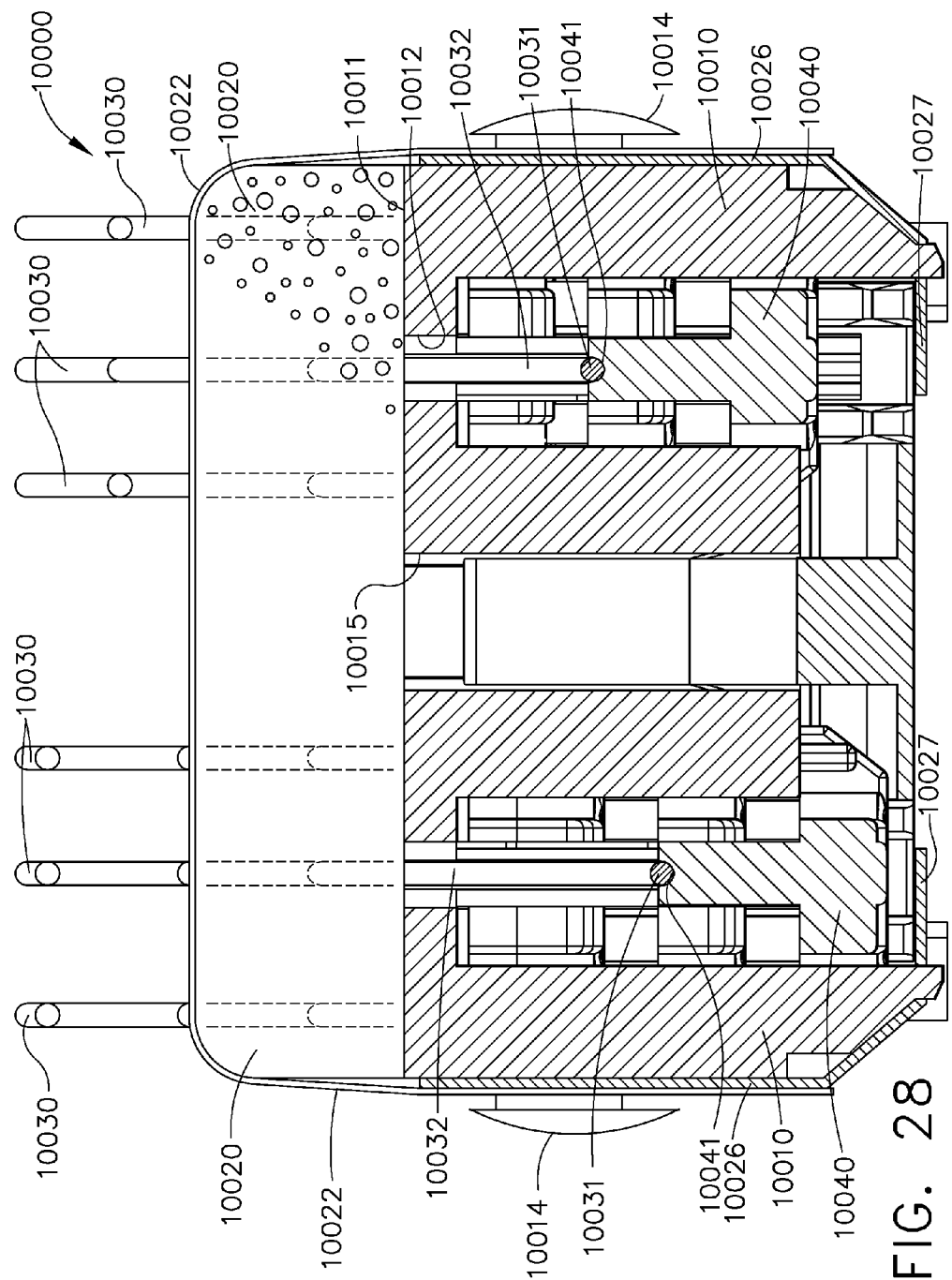
FIG. 28 is a cross-sectional end view of the staple cartridge of FIG. 25.

In use, further to the above and referring primarily to FIG. 31, an anvil, such as anvil, 10060, for example, can be moved into a closed position opposite the staple cartridge 10000. As described in greater detail below, the anvil 10060 can position tissue against the tissue thickness compensator 10020 and, in various embodiments, compress the tissue thickness compensator 10020 against the deck surface 10011 of the support portion 10010, for example. Once the anvil 10060 has been suitably positioned, the staples 10030 can be deployed, as also illustrated in FIG. 31. In various embodiments, as mentioned above, the staple-firing sled 10050 can be moved from the proximal end 10001 of the staple cartridge 10000 toward the distal end 10002, as illustrated in FIG. 32. As the sled 10050 is advanced, the sled 10050 can contact the staple drivers 10040 and lift the staple drivers 10040 upwardly within the staple cavities 10012. In at least one embodiment, the sled 10050 and the staple drivers 10040 can each comprise one or more ramps, or inclined surfaces, which can co-operate to move the staple drivers 10040 upwardly from their unfired positions. In at least one such embodiment, referring to FIGS. 19-23, each staple driver 10040 can comprise at least one inclined surface 10042 and the sled 10050 can comprise one or more inclined surfaces 10052 which can be configured such that the inclined surfaces 10052 can slide under the inclined surface 10042 as the sled 10050 is advanced distally within the staple cartridge. As the staple drivers 10040 are lifted upwardly within their respective staple cavities 10012, the staple drivers 10040 can lift the staples 10030 upwardly such that the staples 10030 can emerge from their staple cavities 10012 through openings in the staple deck 10011. During an exemplary firing sequence, referring primarily to FIGS. 25-27, the sled 10050 can first contact staple 10030a and begin to lift the staple 10030a upwardly. As the sled 10050 is advanced further distally, the sled 10050 can begin to lift staples 10030b, 10030c, 10030d, 10030e, and 10030f, and any other subsequent staples, in a sequential order. As illustrated in FIG. 27, the sled 10050 can drive the staples 10030 upwardly such that the legs 10032 of the staples contact the opposing anvil, are deformed to a desired shape, and ejected therefrom the support portion 10010. In various circumstances, the sled 10030 can move several staples upwardly at the same time as part of a firing sequence. With regard to the firing sequence illustrated in FIG. 27, the staples 10030a and 10030b have been moved into their fully fired positions and ejected from the support portion 10010, the staples 10030c and 10030d are in the process of being fired and are at least partially contained within the support portion 10010, and the staples 10030e and 10030f are still in their unfired positions.

Figure 33:
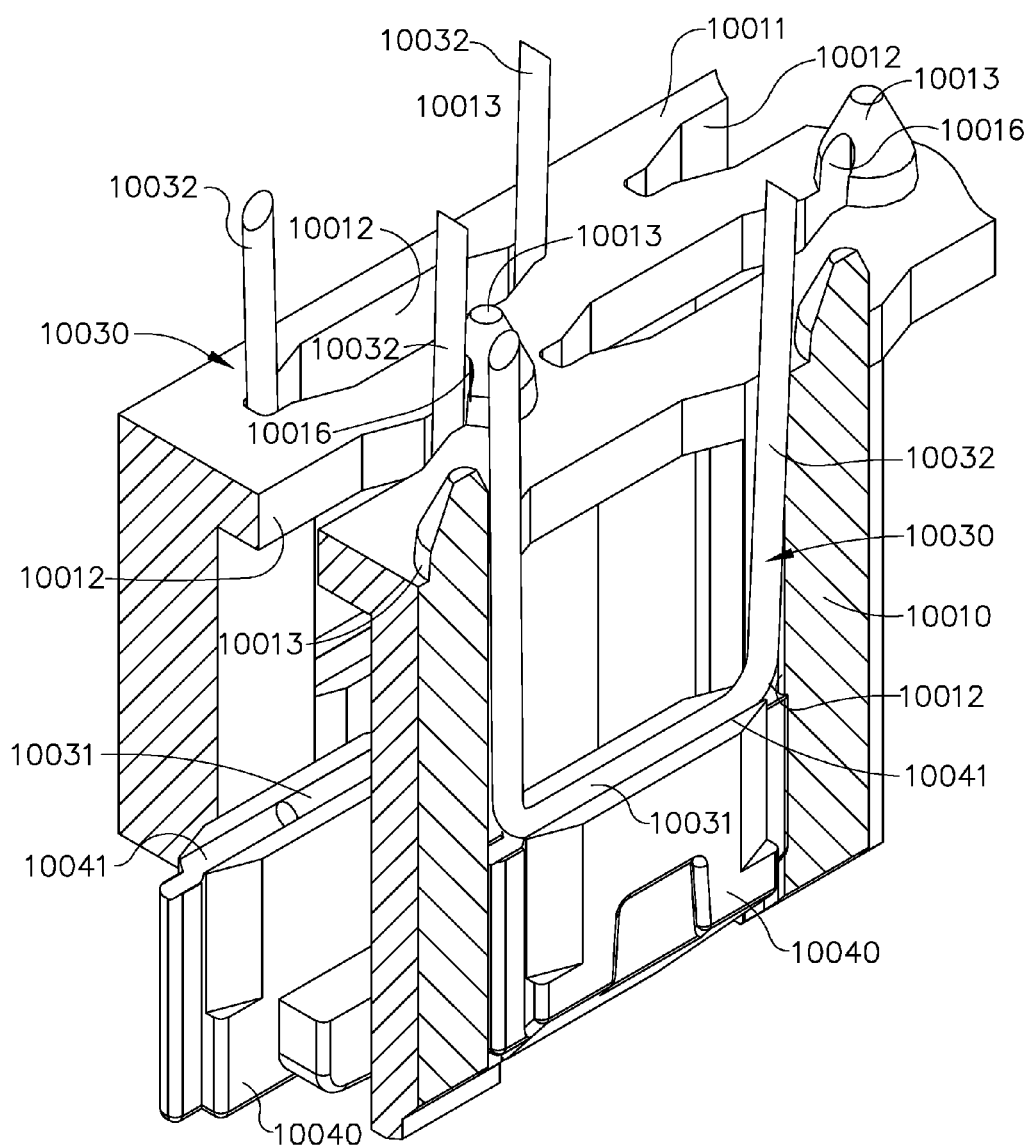
FIG. 33 is a partial detail view of the staple cartridge of FIG. 31 illustrating the staples in an unfired position.
Figure 34:
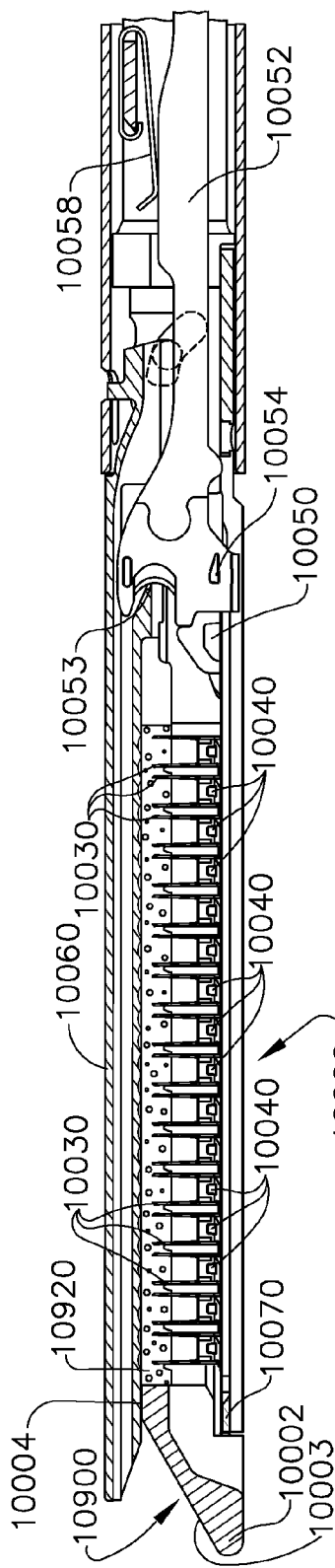
FIG. 34 is a cross-sectional elevational view of a staple cartridge comprising a rigid support portion and a compressible tissue thickness compensator illustrating the staples in an unfired position.
Figure 35:
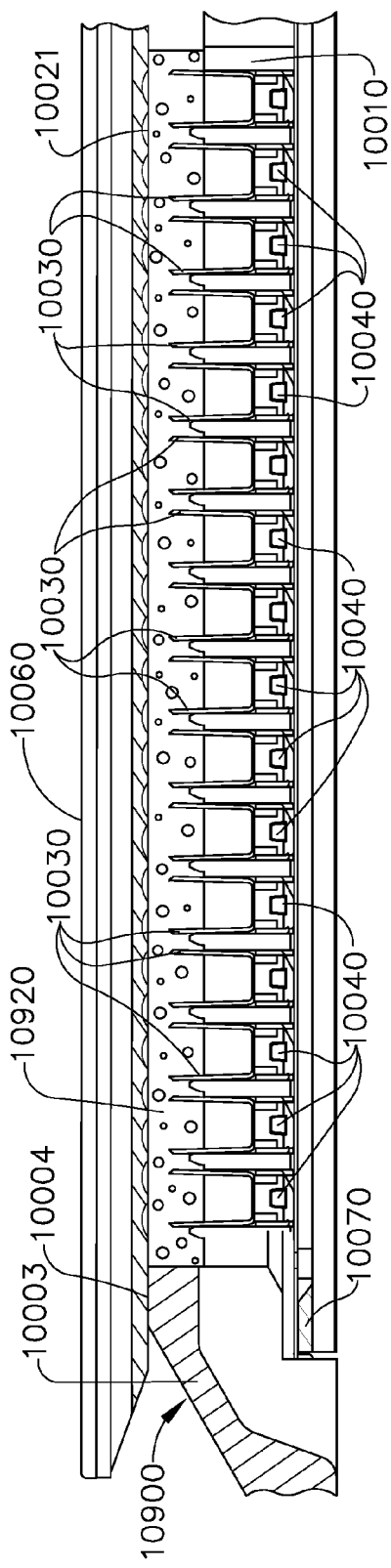
FIG. 35 is a detail view of the staple cartridge of FIG. 34.
Figure 36:
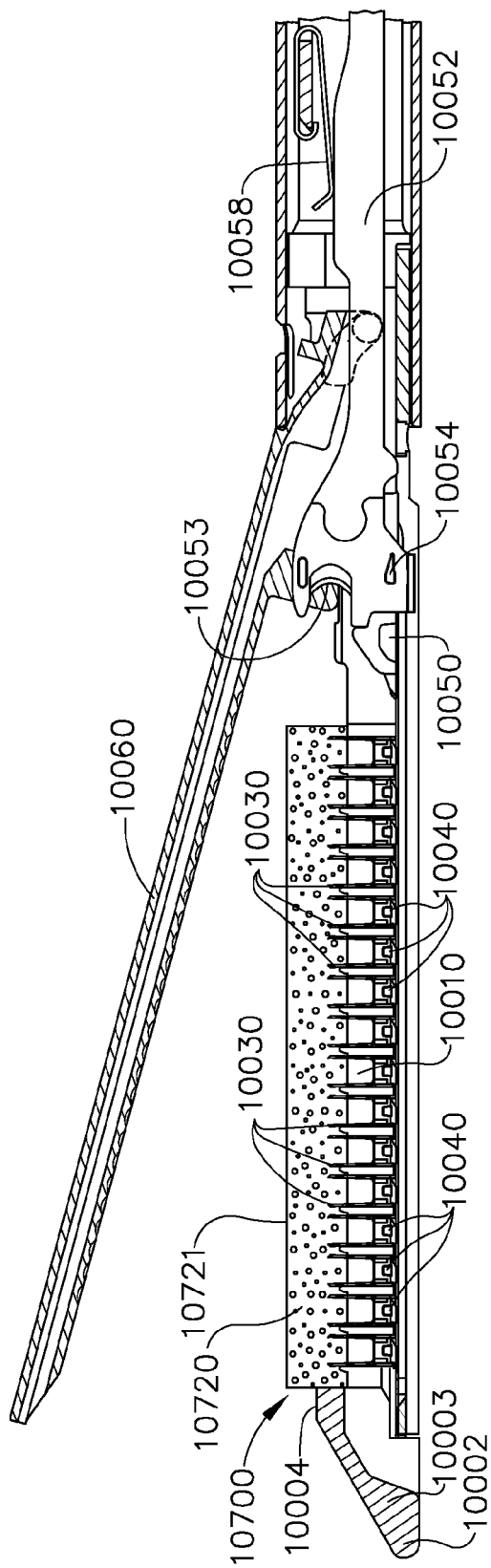
FIG. 36 is an elevational view of an anvil in an open position and a staple cartridge comprising a rigid support portion and a compressible tissue thickness compensator illustrating the staples in an unfired position.
Figure 37:
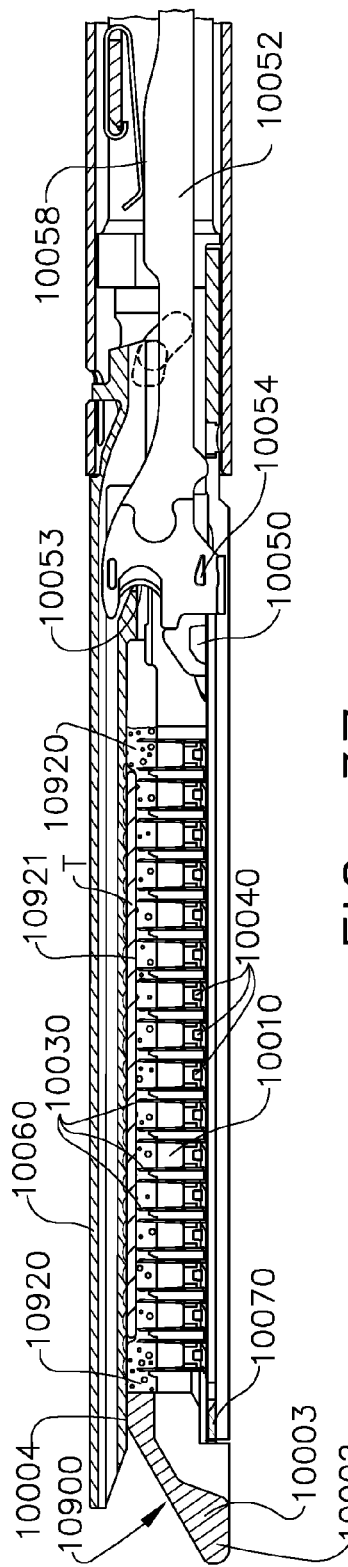
FIG. 37 is an elevational view of an anvil in a closed position and a staple cartridge comprising a rigid support portion and a compressible tissue thickness compensator illustrating the staples in an unfired position and tissue captured between the anvil and the tissue thickness compensator.
Figure 38:
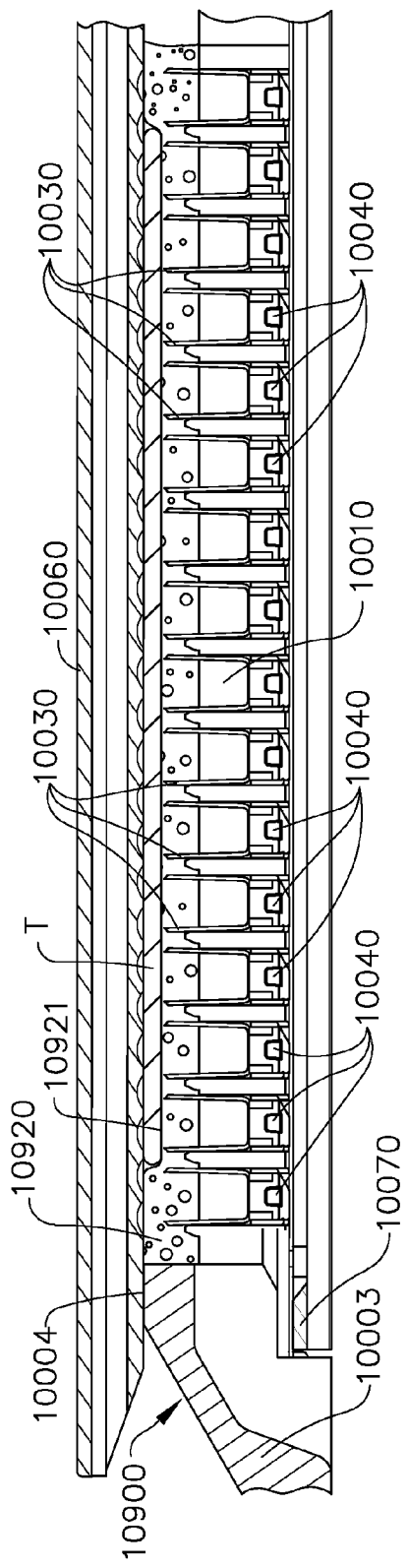
FIG. 38 is a detail view of the anvil and staple cartridge of FIG. 37.

As discussed above, and referring to FIG. 33, the staple legs 10032 of the staples 10030 can extend above the deck surface 10011 of the support portion 10010 when the staples 10030 are in their unfired positions. With further regard to this firing sequence illustrated in FIG. 27, the staples 10030e and 10030f are illustrated in their unfired position and their staple legs 10032 extend above the deck surface 10011 and into the tissue thickness compensator 10020. In various embodiments, the tips of the staple legs 10032, or any other portion of the staple legs 10032, may not protrude through a top tissue-contacting surface 10021 of the tissue thickness compensator 10020 when the staples 10030 are in their unfired positions. As the staples 10030 are moved from their unfired positions to their fired positions, as illustrated in FIG. 27, the tips of the staple legs can protrude through the tissue-contacting surface 10032. In various embodiments, the tips of the staple legs 10032 can comprise sharp tips which can incise and penetrate the tissue thickness compensator 10020. In certain embodiments, the tissue thickness compensator 10020 can comprise a plurality of apertures which can be configured to receive the staple legs 10032 and allow the staple legs 10032 to slide relative to the tissue thickness compensator 10020. In certain embodiments, the support portion 10010 can further comprise a plurality of guides 10013 extending from the deck surface 10011. The guides 10013 can be positioned adjacent to the staple cavity openings in the deck surface 10011 such that the staple legs 10032 can be at least partially supported by the guides 10013. In certain embodiments, a guide 10013 can be positioned at a proximal end and/or a distal end of a staple cavity opening. In various embodiments, a first guide 10013 can be positioned at a first end of each staple cavity opening and a second guide 10013 can be positioned at a second end of each staple cavity opening such that each first guide 10013 can support a first staple leg 10032 of a staple 10030 and each second guide 10013 can support a second staple leg 10032 of the staple. In at least one embodiment, referring to FIG. 33, each guide 10013 can comprise a groove or slot, such as groove 10016, for example, within which a staple leg 10032 can be slidably received. In various embodiments, each guide 10013 can comprise a cleat, protrusion, and/or spike that can extend from the deck surface 10011 and can extend into the tissue thickness compensator 10020. In at least one embodiment, as discussed in greater detail below, the cleats, protrusions, and/or spikes can reduce relative movement between the tissue thickness compensator 10020 and the support portion 10010. In certain embodiments, the tips of the staple legs 10032 may be positioned within the guides 10013 and may not extend above the top surfaces of the guides 10013 when the staples 10030 are in their unfired position. In at least such embodiment, the guides 10013 can define a guide height and the staples 10030 may not extend above this guide height when they are in their unfired position.

Figure 15:
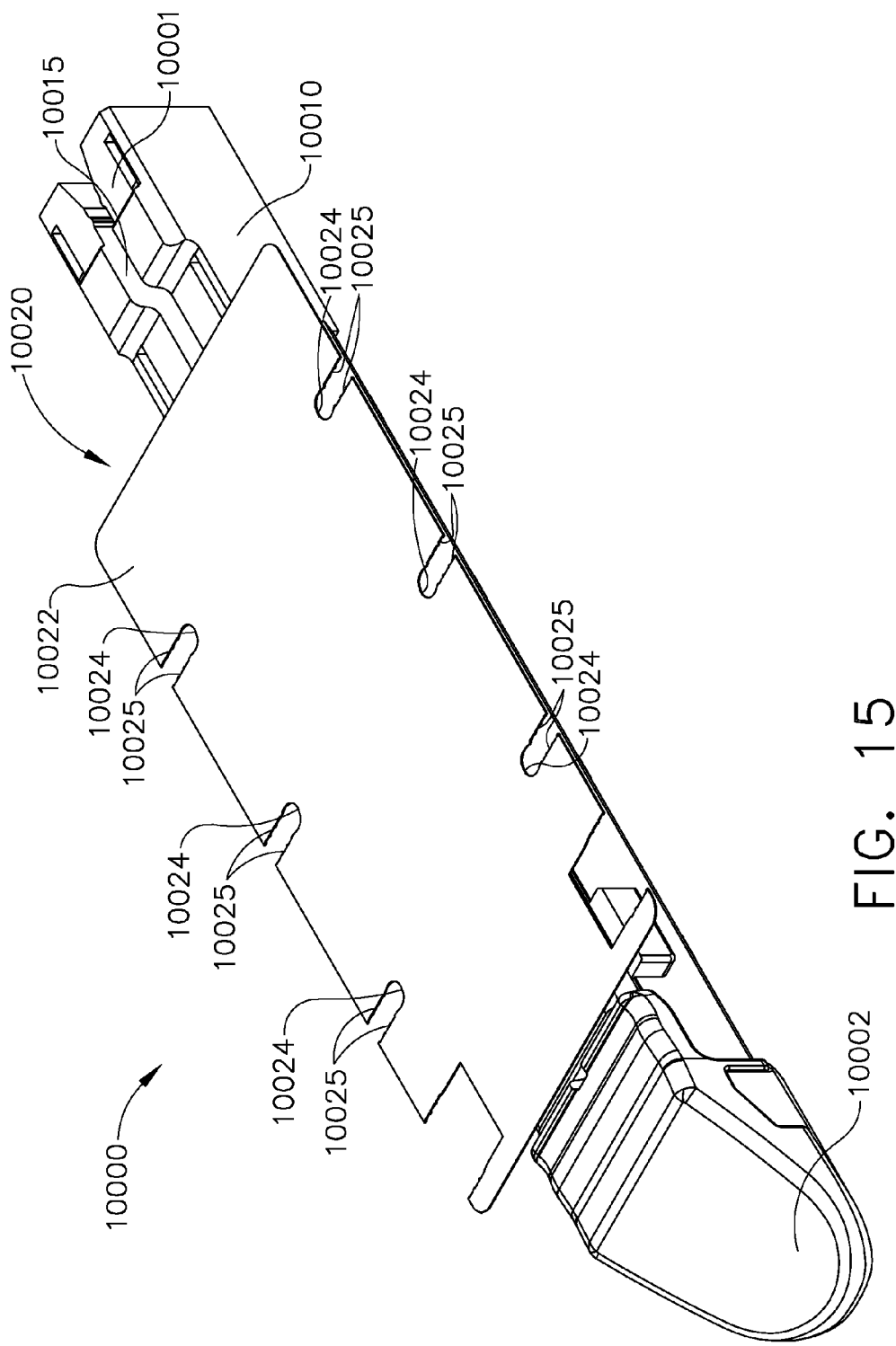
FIG. 15 is a partially exploded view of the staple cartridge of FIG. 14.
Figure 24:
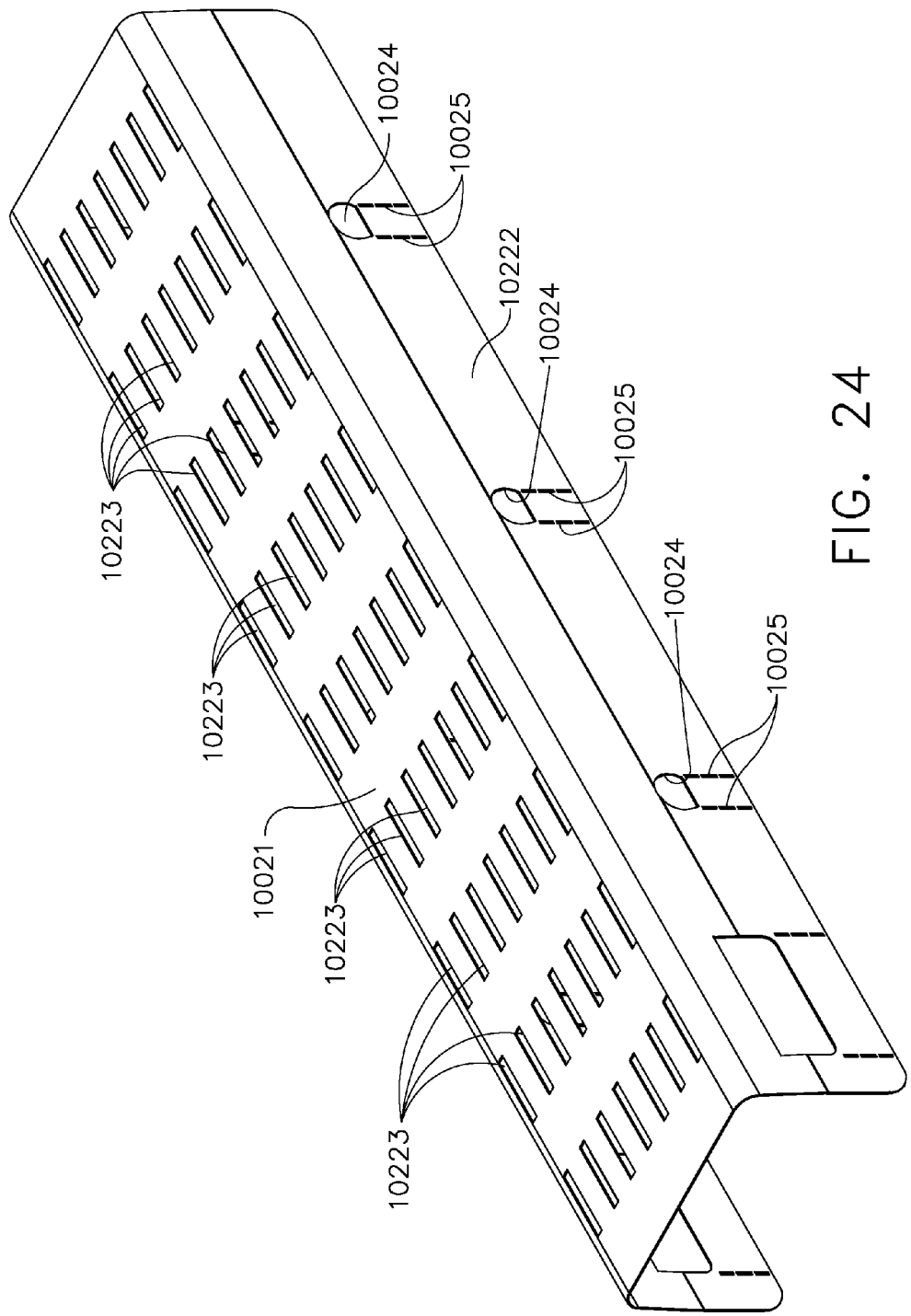
FIG. 24 is a wrap configured to at least partially surround a compressible tissue thickness compensator of a staple cartridge.

In various embodiments, a tissue thickness compensator, such as tissue thickness compensator 10020, for example, can be comprised of a single sheet of material. In at least one embodiment, a tissue thickness compensator can comprise a continuous sheet of material which can cover the entire top deck surface 10011 of the support portion 10010 or, alternatively, cover less than the entire deck surface 10011. In certain embodiments, the sheet of material can cover the staple cavity openings in the support portion 10010 while, in other embodiments, the sheet of material can comprise openings which can be aligned, or at least partially aligned, with the staple cavity openings. In various embodiments, a tissue thickness compensator can be comprised of multiple layers of material. In some embodiments, referring now to FIG. 15, a tissue thickness compensator can comprise a compressible core and a wrap surrounding the compressible core. In certain embodiments, a wrap 10022 can be configured to releasably hold the compressible core to the support portion 10010. In at least one such embodiment, the support portion 10010 can comprise one or more projections, such as projections 10014 (FIG. 18), for example, extending therefrom which can be received within one or more apertures and/or slots, such as apertures 10024, for example, defined in the wrap 10022. The projections 10014 and the apertures 10024 can be configured such that the projections 10014 can retain the wrap 10022 to the support portion 10010. In at least one embodiment, the ends of the projections 10014 can be deformed, such as by a heat-stake process, for example, in order to enlarge the ends of the projections 10014 and, as a result, limit the relative movement between the wrap 10022 and the support portion 10010. In at least one embodiment, the wrap 10022 can comprise one or more perforations 10025 which can facilitate the release of the wrap 10022 from the support portion 10010, as illustrated in FIG. 15. Referring now to FIG. 24, a tissue thickness compensator can comprise a wrap 10222 including a plurality of apertures 10223, wherein the apertures 10223 can be aligned, or at least partially aligned, with the staple cavity openings in the support portion 10010. In certain embodiments, the core of the tissue thickness compensator can also comprise apertures which are aligned, or at least partially aligned, with the apertures 10223 in the wrap 10222. In other embodiments, the core of the tissue thickness compensator can comprise a continuous body and can extend underneath the apertures 10223 such that the continuous body covers the staple cavity openings in the deck surface 10011.

In various embodiments, as described above, a tissue thickness compensator can comprise a wrap for releasably holding a compressible core to the support portion 10010. In at least one such embodiment, referring to FIG. 16, a staple cartridge can further comprise retainer clips 10026 which can be configured to inhibit the wrap, and the compressible core, from prematurely detaching from the support portion 10010. In various embodiments, each retainer clip 10026 can comprise apertures 10028 which can be configured to receive the projections 10014 extending from the support portion 10010 such that the retainer clips 10026 can be retained to the support portion 10010. In certain embodiments, the retainer clips 10026 can each comprise at least one pan portion 10027 which can extend underneath the support portion 10010 and can support and retain the staple drivers 10040 within the support portion 10010. In certain embodiments, as described above, a tissue thickness compensator can be removably attached to the support portion 10010 by the staples 10030. More particularly, as also described above, the legs of the staples 10030 can extend into the tissue thickness compensator 10020 when the staples 10030 are in their unfired position and, as a result, releasably hold the tissue thickness compensator 10020 to the support portion 10010. In at least one embodiment, the legs of the staples 10030 can be in contact with the sidewalls of their respective staple cavities 10012 wherein, owing to friction between the staple legs 10032 and the sidewalls, the staples 10030 and the tissue thickness compensator 10020 can be retained in position until the staples 10030 are deployed from the staple cartridge 10000. When the staples 10030 are deployed, the tissue thickness compensator 10020 can be captured within the staples 10030 and held against the stapled tissue T. When the anvil is thereafter moved into an open position to release the tissue T, the support portion 10010 can be moved away from the tissue thickness compensator 10020 which has been fastened to the tissue. In certain embodiments, an adhesive can be utilized to removably hold the tissue thickness compensator 10020 to the support portion 10010. In at least one embodiment, a two-part adhesive can be utilized wherein, in at least one embodiment, a first part of the adhesive can be placed on the deck surface 10011 and a second part of the adhesive can be placed on the tissue thickness compensator 10020 such that, when the tissue thickness compensator 10020 is placed against the deck surface 10011, the first part can contact the second part to active the adhesive and detachably bond the tissue thickness compensator 10020 to the support portion 10010. In various embodiments, any other suitable means could be used to detachably retain the tissue thickness compensator to the support portion of a staple cartridge.

Figure 59:
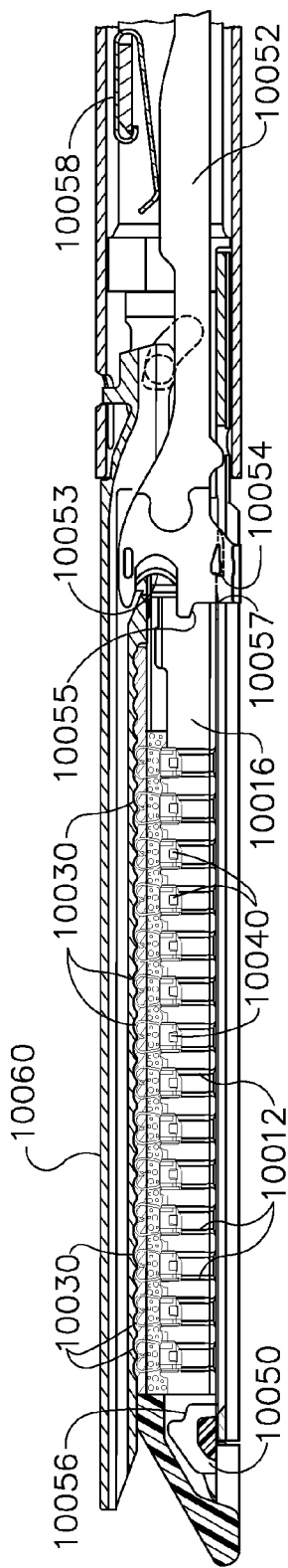
FIG. 59 is a cross-sectional view of the end effector of FIG. 56 illustrating the firing bar in a retracted position after being fired and the staple-firing sled left in its fully fired position.

In various embodiments, further to the above, the sled 10050 can be advanced from the proximal end 10001 to the distal end 10002 to fully deploy all of the staples 10030 contained within the staple cartridge 10000. In at least one embodiment, referring now to FIGS. 56-60, the sled 10050 can be advanced distally within a longitudinal cavity 10016 within the support portion 10010 by a firing member, or knife bar, 10052 of a surgical stapler. In use, the staple cartridge 10000 can be inserted into a staple cartridge channel in a jaw of the surgical stapler, such as staple cartridge channel 10070, for example, and the firing member 10052 can be advanced into contact with the sled 10050, as illustrated in FIG. 56. As the sled 10050 is advanced distally by the firing member 10052, the sled 10050 can contact the proximal-most staple driver, or drivers, 10040 and fire, or eject, the staples 10030 from the cartridge body 10010, as described above. As illustrated in FIG. 56, the firing member 10052 can further comprise a cutting edge 10053 which can be advanced distally through a knife slot in the support portion 10010 as the staples 10030 are being fired. In various embodiments, a corresponding knife slot can extend through the anvil positioned opposite the staple cartridge 10000 such that, in at least one embodiment, the cutting edge 10053 can extend between the anvil and the support portion 10010 and incise the tissue and the tissue thickness compensator positioned therebetween. In various circumstances, the sled 10050 can be advanced distally by the firing member 10052 until the sled 10050 reaches the distal end 10002 of the staple cartridge 10000, as illustrated in FIG. 58. At such point, the firing member 10052 can be retracted proximally. In some embodiments, the sled 10050 can be retracted proximally with the firing member 10052 but, in various embodiments, referring now to FIG. 59, the sled 10050 can be left behind in the distal end 10002 of the staple cartridge 10000 when the firing member 10052 is retracted. Once the firing member 10052 has been sufficiently retracted, the anvil can be re-opened, the tissue thickness compensator 10020 can be detached from the support portion 10010, and the remaining non-implanted portion of the expended staple cartridge 10000, including the support portion 10010, can be removed from the staple cartridge channel 10070.

Figure 60:
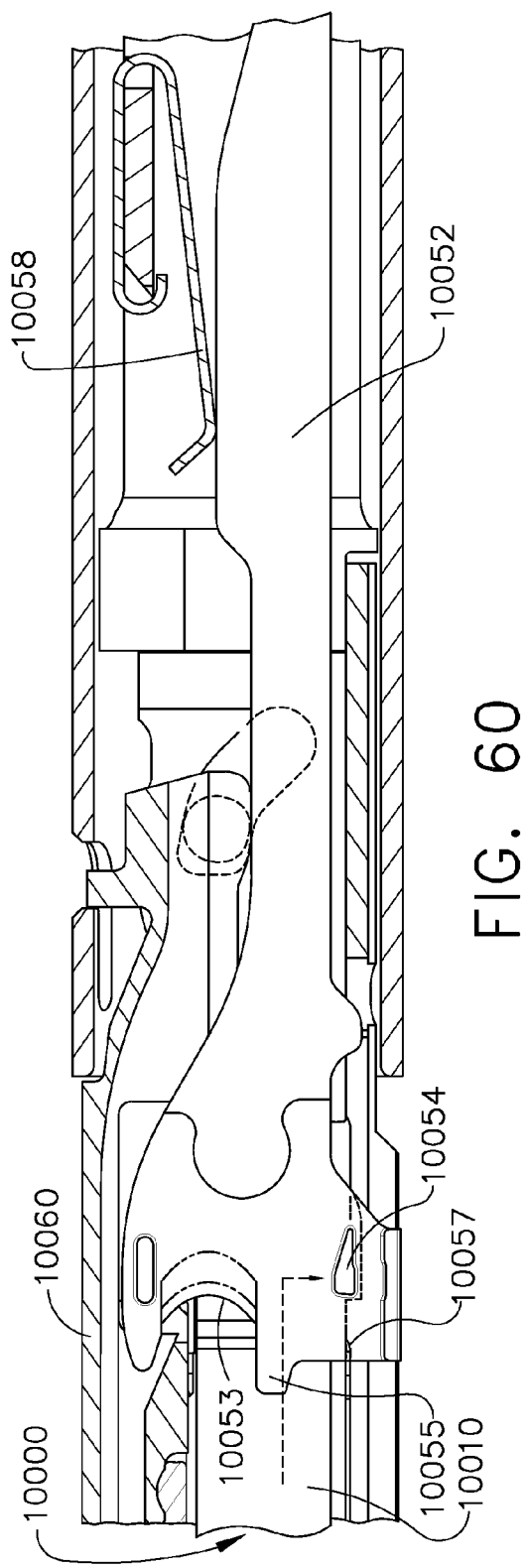
FIG. 60 is a detail view of the firing bar in the retracted position of FIG. 59.

After the expended staple cartridge 10000 has been removed from the staple cartridge channel, further to the above, a new staple cartridge 10000, or any other suitable staple cartridge, can be inserted into the staple cartridge channel 10070. In various embodiments, further to the above, the staple cartridge channel 10070, the firing member 10052, and/or the staple cartridge 10000 can comprise co-operating features which can prevent the firing member 10052 from being advanced distally a second, or subsequent, time without a new, or unfired, staple cartridge 10000 positioned in the staple cartridge channel 10070. More particularly, referring again to FIG. 56, as the firing member 10052 is advanced into contact with the sled 10050 and, when the sled 10050 is in its proximal unfired position, a support nose 10055 of the firing member 10052 can be positioned on and/or over a support ledge 10056 on the sled 10050 such that the firing member 10052 is held in a sufficient upward position to prevent a lock, or beam, 10054 extending from the firing member 10052 from dropping into a lock recess defined within the staple cartridge channel. As the lock 10054 will not drop into the lock recess, in such circumstances, the lock 10054 may not abut a distal sidewall 10057 of the lock recess as the firing member 10052 is advanced. As the firing member 10052 pushes the sled 10050 distally, the firing member 10052 can be supported in its upward firing position owing to the support nose 10055 resting on the support ledge 10056. When the firing member 10052 is retracted relative to the sled 10050, as discussed above and illustrated in FIG. 59, the firing member 10052 can drop downwardly from its upward position as the support nose 10055 is no longer resting on the support ledge 10056 of the sled 10050. In at least one such embodiment, the surgical staple can comprise a spring 10058, and/or any other suitable biasing element, which can be configured to bias the firing member 10052 into its downward position. Once the firing member 10052 has been completely retracted, as illustrated in FIG. 60, the firing member 10052 cannot be advanced distally through the spent staple cartridge 10000 once again. More particularly, the firing member 10052 can't be held in its upper position by the sled 10050 as the sled 10050, at this point in the operating sequence, has been left behind at the distal end 10002 of the staple cartridge 10000. Thus, as mentioned above, in the event that the firing member 10052 is advanced once again without replacing the staple cartridge, the lock beam 10054 will contact the sidewall 10057 of the lock recess which will prevent the firing member 10052 from being advanced distally into the staple cartridge 10000 once again. Stated another way, once the spent staple cartridge 10000 has been replaced with a new staple cartridge, the new staple cartridge will have a proximally-positioned sled 10050 which can hold the firing member 10052 in its upper position and allow the firing member 10052 to be advanced distally once again.

As described above, the sled 10050 can be configured to move the staple drivers 10040 between a first, unfired position and a second, fired position in order to eject staples 10030 from the support portion 10010. In various embodiments, the staple drivers 10040 can be contained within the staple cavities 10012 after the staples 10030 have been ejected from the support portion 10010. In certain embodiments, the support portion 10010 can comprise one or more retention features which can be configured to block the staple drivers 10040 from being ejected from, or falling out of, the staple cavities 10012. In various other embodiments, the sled 10050 can be configured to eject the staple drivers 10040 from the support portion 10010 with the staples 10030. In at least one such embodiment, the staple drivers 10040 can be comprised of a bioabsorbable and/or biocompatible material, such as Ultem, for example. In certain embodiments, the staple drivers can be attached to the staples 10030. In at least one such embodiment, a staple driver can be molded over and/or around the base of each staple 10030 such that the driver is integrally formed with the staple. U.S. patent application Ser. No. 11/541,123, entitled SURGICAL STAPLES HAVING COMPRESSIBLE OR CRUSHABLE MEMBERS FOR SECURING TISSUE THEREIN AND STAPLING INSTRUMENTS FOR DEPLOYING THE SAME, filed on Sep. 29, 2006, is hereby incorporated by reference in its entirety.

As described above, a surgical stapling instrument can comprise a staple cartridge channel configured to receive a staple cartridge, an anvil rotatably coupled to the staple cartridge channel, and a firing member comprising a knife edge which is movable relative to the anvil and the staple cartridge channel. In use, a staple cartridge can be positioned within the staple cartridge channel and, after the staple cartridge has been at least partially expended, the staple cartridge can be removed from the staple cartridge channel and replaced with a new staple cartridge. In some such embodiments, the staple cartridge channel, the anvil, and/or the firing member of the surgical stapling instrument may be re-used with the replacement staple cartridge. In certain other embodiments, a staple cartridge may comprise a part of a disposable loading unit assembly which can include a staple cartridge channel, an anvil, and/or a firing member, for example, which can be replaced along with the staple cartridge as part of replacing the disposable loading unit assembly. Certain disposable loading unit assemblies are disclosed in U.S. patent application Ser. No. 12/031,817, entitled END EFECTOR COUPLING ARRANGMENTS FOR A SURGICAL CUTTING AND STAPLING INSTRUMENT, which was filed on Feb. 15, 2008, the entire disclosure of which is incorporated by reference herein.

In various embodiments, the tissue thickness compensator may comprise an extrudable, a castable, and/or moldable composition comprising at least one of the synthetic and/or non-synthetic materials described herein. In various embodiments, the tissue thickness compensator may comprise a film or sheet comprising two or more layers. The tissue thickness compensator may be obtained using conventional methods, such as, for example, mixing, blending, compounding, spraying, wicking, solvent evaporating, dipping, brushing, vapor deposition, extruding, calendaring, casting, molding and the like. In extrusion, an opening may be in the form of a die comprising at least one opening to impart a shape to the emerging extrudate. In calendering, an opening may comprise a nip between two rolls. Conventional molding methods may include, but are not limited to, blow molding, injection molding, foam injection, compression molding, thermoforming, extrusion, foam extrusion, film blowing, calendaring, spinning, solvent welding, coating methods, such as dip coating and spin coating, solution casting and film casting, plastisol processing (including knife coating, roller coating and casting), and combinations thereof. In injection molding, an opening may comprise a nozzle and/or channels/runners and/or mold cavities and features. In compression molding, the composition may be positioned in a mold cavity, heated to a suitable temperature, and shaped by exposure to compression under relatively high pressure. In casting, the composition may comprise a liquid or slurry that may be poured or otherwise provided into, onto and/or around a mold or object to replicate features of the mold or object. After casting, the composition may be dried, cooled, and/or cured to form a solid.

In various embodiments, a method of manufacturing a tissue thickness compensator comprising at least one medicament stored and/or absorbed therein may generally comprise providing a tissue thickness compensator and contacting the tissue thickness compensator and the medicament to retain the medicament in the tissue thickness compensator. In at least one embodiment, a method of manufacturing a tissue thickness compensator comprising an antibacterial material may comprise providing a hydrogel, drying the hydrogel, swelling the hydrogel in an aqueous solution of silver nitrate, contacting the hydrogel and a solution of sodium chloride to form the tissue thickness compensator having antibacterial properties. The tissue thickness compensator may comprise silver dispersed therein.

Figure 116:
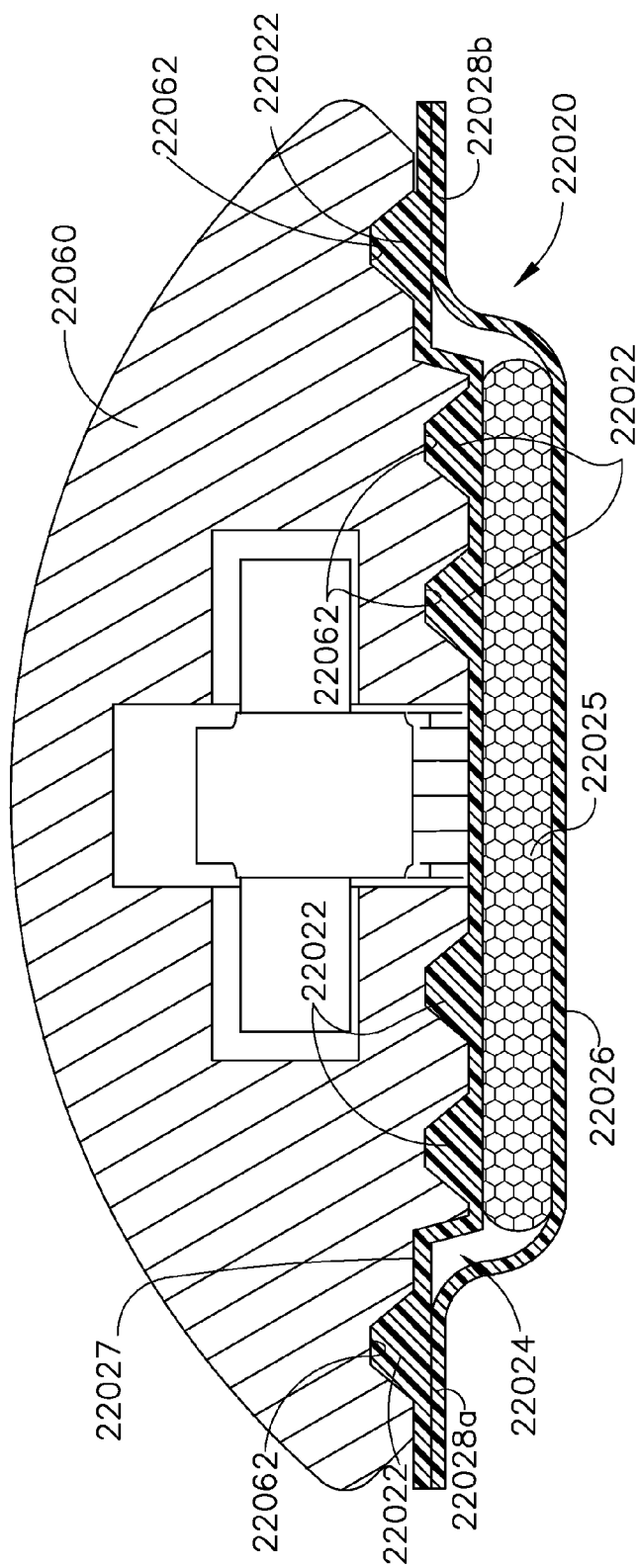

In various embodiments, referring now to FIG. 116, a tissue thickness compensator, such as tissue thickness compensator 22020, for example, can be attached to an anvil of a surgical stapling instrument, such as anvil 22060, for example. The tissue thickness compensator 22020 can include, in at least one embodiment, a cavity 22024 defined between a first film 22026 and a second film 22027, wherein at least portions of the first film 22026 are attached to the second film 22027. In at least one such embodiment, the first film 22026 can be attached to the second film 22027 along lateral seams 22028*a* and 22028*b*, for example. In various embodiments, the first film 22026 can be attached to the second film 22027 along a sealed perimeter in order to sealingly enclose the cavity 22024. In certain embodiments, the first film 22026 and the second film 22027 can be thermally welded along the lateral seams 22028*a*, 22028*b* and/or any other seams connecting the films 22026 and 22027, for example. Referring again to FIG. 116, the anvil 22060 can comprise a plurality of staple forming pockets 22062 which can each be configured to receive and deform the leg of staple wherein, in at least one embodiment, the second film 22027 can comprise projections 22022 which can extend into the forming pockets 22062. In certain embodiments, the projections 22022 can be sized and configured such that they fit snugly within the forming pockets 22062 and can retain the tissue thickness compensator 22020 to the anvil 22060. In the illustrated embodiment, the anvil 22060 can comprise six rows of forming pockets 22062 wherein the tissue thickness compensator 22020 can similarly comprise six rows of projections 22022 which are aligned with the forming pockets 22062, for example. Other embodiments comprising more than or less than six rows of forming pockets 22062 and/or projections 22022 could be utilized. In certain embodiments, one or more adhesives could be utilized to retain the tissue thickness compensator 22020 to the anvil 20060.

Figure 117:
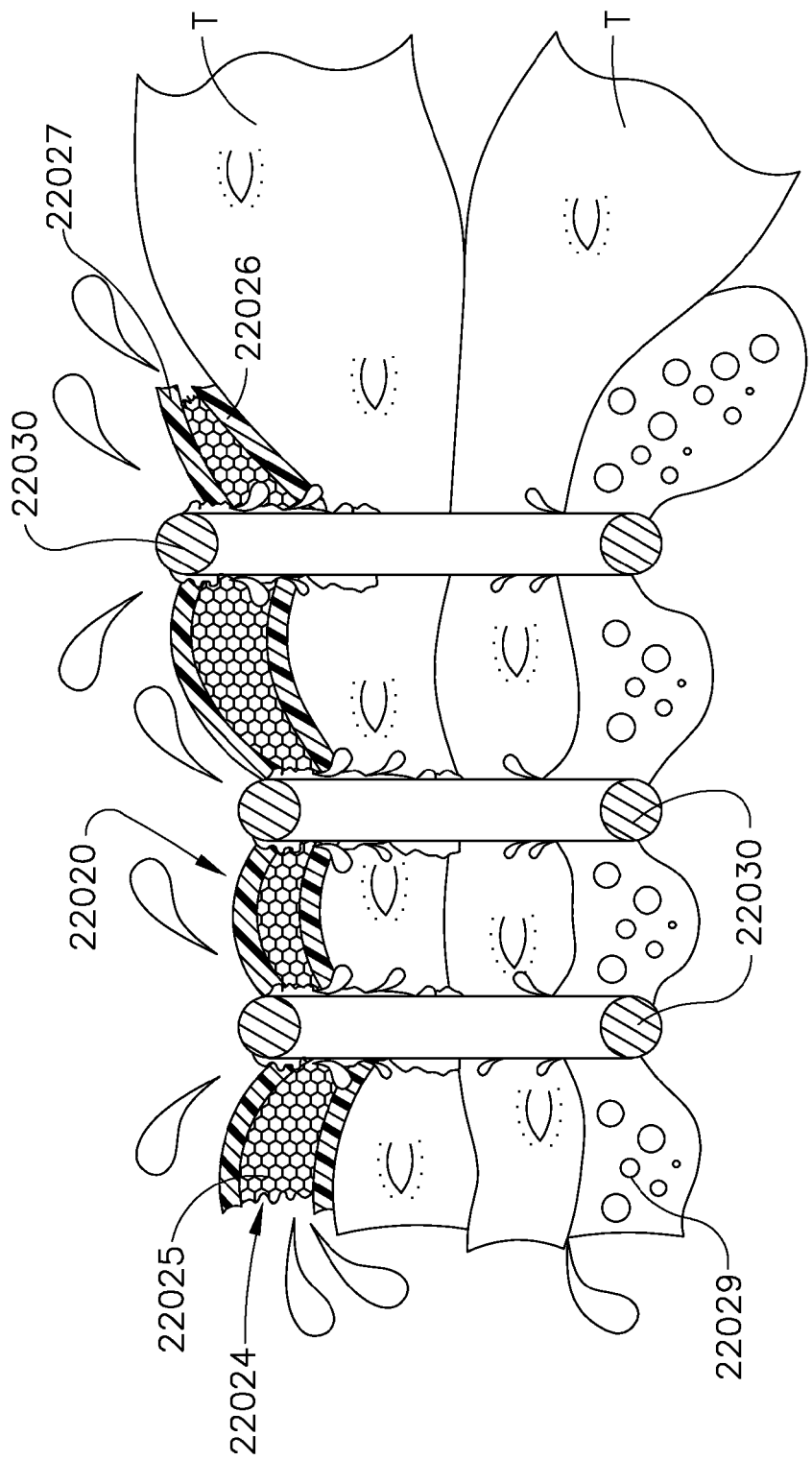

As discussed above, the tissue thickness compensator 22020 can comprise a cavity 22024 defined therein. In various embodiments, the cavity 22024 can extend longitudinally along the anvil 22060. Referring again to FIG. 116, the tissue thickness compensator 22020 can comprise a compressible material positioned within the cavity 22024. In at least one embodiment, referring now to FIG. 117, staples, such as staples 22030, for example, can be ejected from a staple cartridge such that the staples 22030 penetrate the tissue T and then penetrate the tissue thickness compensator 22020 before contacting the anvil 22060. As the legs of the staples 22030 are deformed by the anvil 22060, in various embodiments, the legs can be turned downwardly to repenetrate the tissue thickness compensator 22020 once again. In any event, once the staples 22030 have penetrated the tissue thickness compensator 22020, one or more fluids contained in the cavity 22024, for example, can flow or weep out of the tissue thickness compensator 22020 and onto the tissue T. In certain embodiments, the cavity 22024 can comprise one or more powders contained therein which can escape the cavity 22024 once the tissue thickness compensator 22020 has been at least partially ruptured by the staples 22030, for example. In various embodiments, a material 22025 positioned within the cavity 22024 can be compressed or squeezed within the staples 22030 when the staples 22030 are deformed into their fired configurations such that, in at least one embodiment, a fluid stored within the material 22025 can be expressed from the material 22025, for example. In various embodiments, referring again to FIG. 117, the staples 22030 can also be configured to capture a tissue thickness compensator, such as compensator 22029, for example, removably attached to the staple cartridge against the other side of the tissue T.

In various embodiments, further to the above, the material 22025 can comprise freeze-dried thrombin, freeze-dried fibrin, and/or small fiber non-woven oxidized regenerated cellulose, for example. In certain embodiments, the material 22025 can comprise a compressed powder wafer. In at least one embodiment, the sealed cavity 22024 can comprise an internal atmosphere having a pressure below that of the atmosphere surrounding the tissue thickness compensator 22020. In such an embodiment, the pressure difference between the atmosphere in the internal cavity 22024 and the atmosphere can cause the films 22027 and 22028 to be drawn inwardly. When the internal cavity 22024 is ruptured by the staples 22030, as described above, the vacuum within the internal cavity 22024 can equalize with the surrounding atmosphere and the material 22025 can escape the internal cavity 22024, as also described above. In such circumstances, the tissue thickness compensator 22020 can expand and apply a compressive force to the tissue T captured within the staples 20030. In embodiments in which the material 22025 is vacuum-packed within the tissue thickness compensator 22020, the material 22025 can expand after the internal cavity 22024 has been punctured. In certain embodiments, the films 22026, 22027 can be comprised of a bioabsorbable material and can be configured to dissolve once placed in the patient. In at least one such embodiment, each film 22026, 22027 can be comprised of a layer, or laminate, which is between approximately 0.25 mils and approximately 0.50 mils thick, for example. In any event, further to the above, the tissue thickness compensator 22020, including the material 22025, can be transected by a cutting element as the staples 22030 are fired from their staple cartridge.

Figure 118:
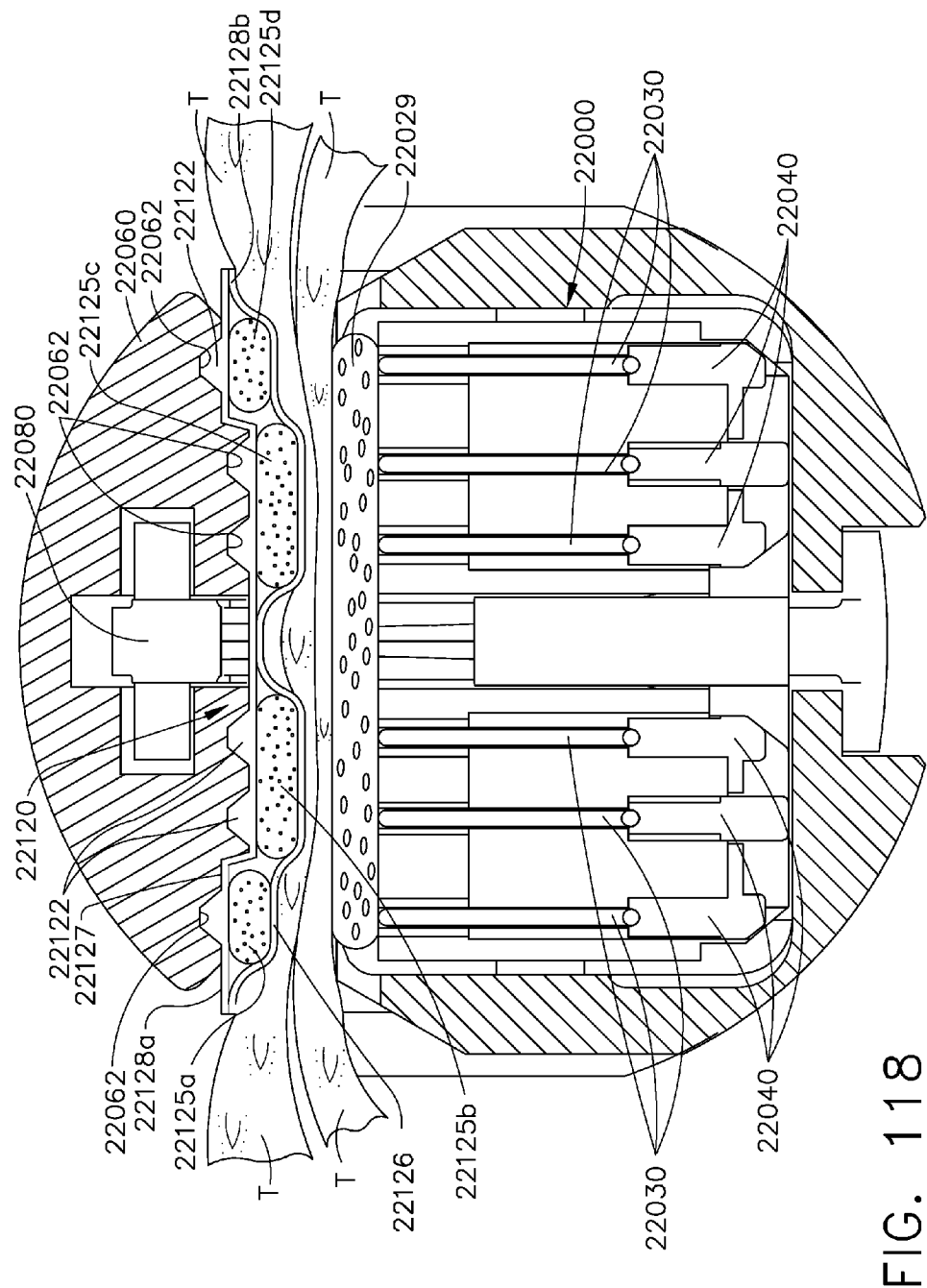
Figure 119:
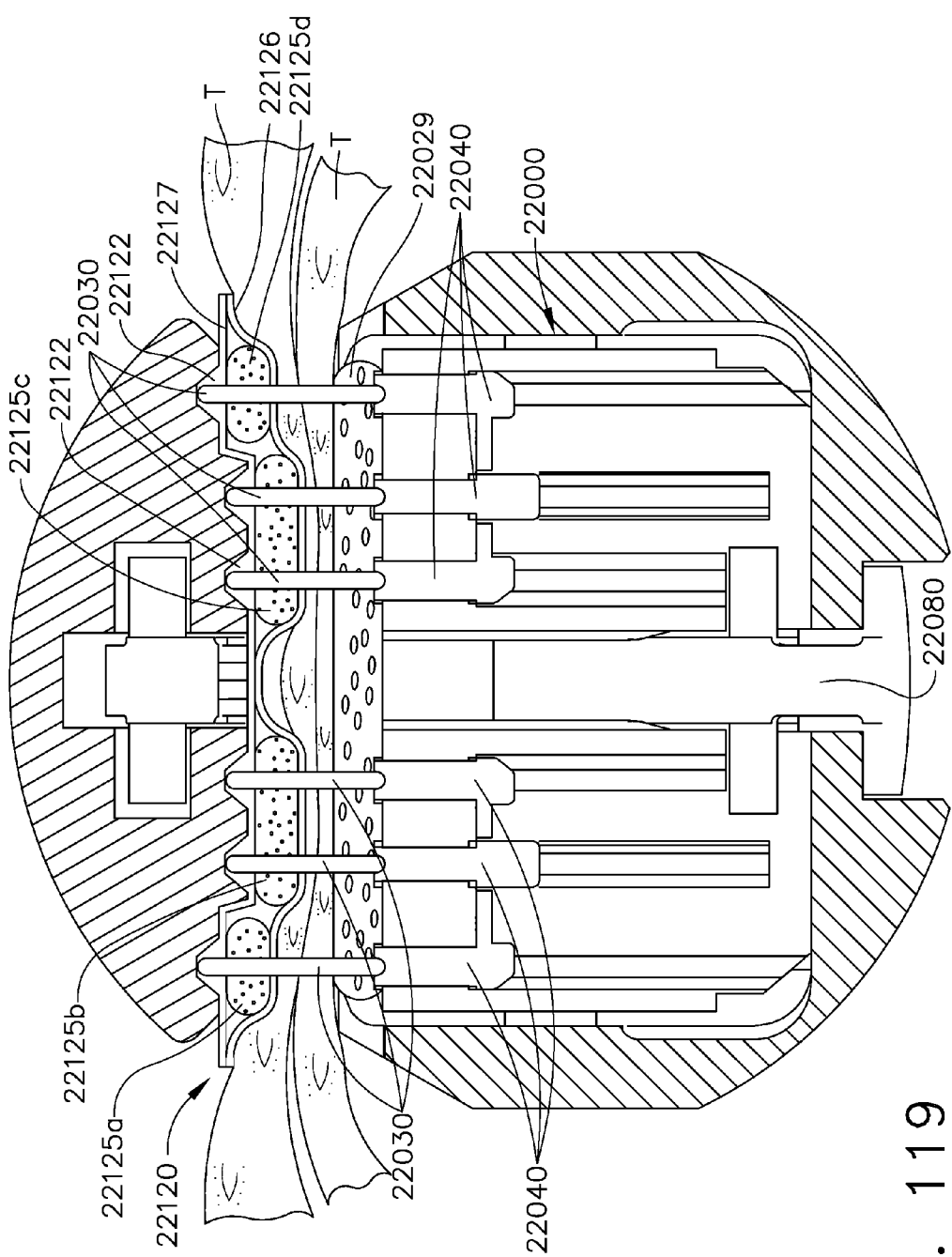

In certain embodiments, referring again to FIG. 116, the cavity 22024 and the material 22025 of the tissue thickness compensator 22020 can be positioned underneath the inner four rows of staple forming pockets 22062 while the seams 22028a, 22028b can be positioned underneath the outer rows of forming pockets 22062. In such embodiments, the staples in the outer rows of staples may not engage the material 22025 and, thus, they may not capture the material 22025 therein. Rather, such staples may only capture the films 22026 and 22027 along seams 22028a, 22028b. In various alternative embodiments, referring now to FIGS. 118 and 119, a tissue thickness compensator 22120 can comprise, similar to the above, a first film 22126, a second film 22127, and a plurality of materials 22125a-d captured between the first film 22126 and the second film 22127. In at least one such embodiment, referring primarily to FIG. 118, the first material 22125a can be aligned with an outer row of staples 22030 in staple cartridge 22000 and an outer row of staple cavities 22062 in anvil 22060, the second material 22125b and the third material 22125c can each be aligned with two inner rows of staples 22030 and staple cavities 22062, and the fourth material 22126d can be aligned with another outer row of staples 22030 and staple cavities 22062. In such an embodiment, referring now to FIG. 119, all of the staples 22030 can be arranged such that they can capture at least one of the materials 22125a-22125d therein. As illustrated in FIGS. 118 and 119, further to the above, the staples 22030 can be lifted upwardly between an unfired position and a fired position by staple drivers 22040 positioned within the staple cartridge 22000.

In various embodiments, referring again to FIGS. 118 and 119, the layers 22126 and 22127 can define one or more sealed cavities in which the materials 22125a-d can be positioned. In at least one embodiment, the layers 22126 and 22127 can be sealed together along a perimeter which can include lateral seams 22128a and 22128b, for example, utilizing any suitable process, such as thermal and/or laser welding, for example. In certain embodiments, each of the materials 22125a-22125d can be sealed within separate cavities while, in other embodiments, two or more of the materials 22125a-22125d can be sealed within the same cavity. In various embodiments, the materials 22125a-22125d can be comprised of the same material or materials while, in other embodiments, one or more of the materials 22125a-22125d can be comprised of different materials. In at least one embodiment, one or more of the materials 22125a-22125d can be comprised of sodium stearate and/or LAE, for example. In certain embodiments, the materials 22125a-22125d can comprise a lubricant. In such embodiments, the legs of the staples 22030 can be exposed to the lubricant when the staple legs penetrate the materials 22125a-22125d of the tissue thickness compensator 22120. After the legs pass through the tissue thickness compensator 22120, the legs can contact the anvil 22060 wherein the lubricant can reduce the coefficient of friction, and the friction forces, between the staple legs and the anvil 22060. In such circumstances, the force needed to fire the staples 22030 can be reduced. Owing to the position of the tissue thickness compensator 22120 against the anvil 22060, in at least one embodiment, the staple legs of the staples 22030 can contact the anvil 22060 directly after exiting the tissue thickness compensator 22120 thereby reducing the possibility that the lubricant may be wiped off the staple legs before they contact the anvil 22060. Similarly, the staple legs of the staples 22030 can contact the anvil 22060 directly after being exposed to one or medicaments in the tissue thickness compensator 22120 thereby reducing the possibility that medicaments may be wiped off the staple legs before they re-enter the tissue T. In some circumstances, the staple legs can re-enter the tissue thickness compensator 22120 as the staple legs are being deformed downwardly such that the staple legs can be re-exposed to the medicaments before re-entering the tissue T, for example. In various embodiments, similar to the above, the second film 22127 can comprise a plurality of projections 22122, for example, which can be snugly received within the staple cavities 22062 in order to retain the tissue thickness compensator 22120 to the anvil 22060, for example.

Figure 121:
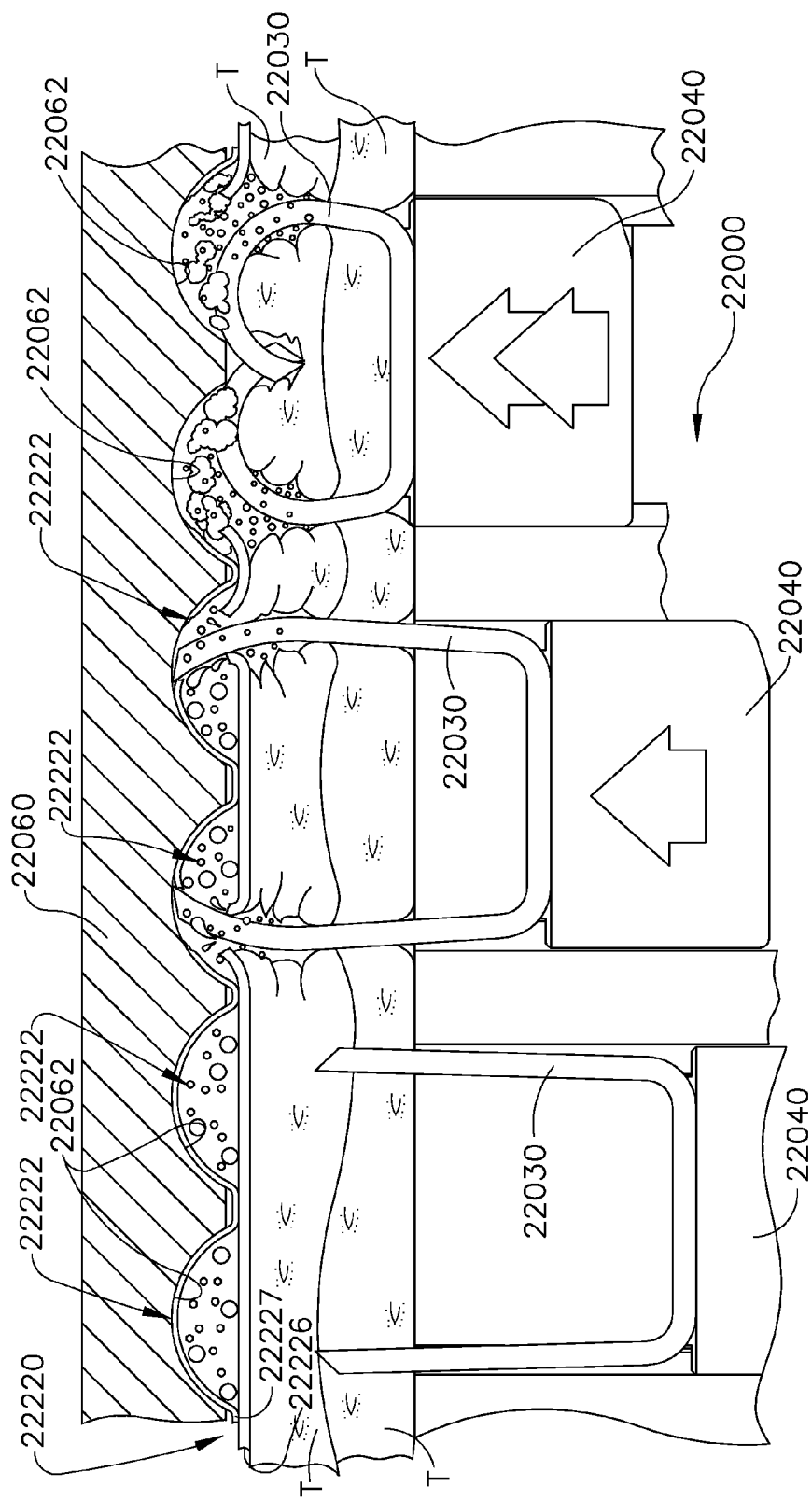

In various embodiments, referring now to FIGS. 120 and 121, an end effector of a surgical stapling instrument can comprise a tissue thickness compensator, such as compensator 22220, for example, which can comprise a plurality of cavities 22222 aligned with the staple forming pockets 22062 of the anvil 22060. In at least one embodiment, the compensator 22220 can be comprised of a first, or bottom, layer 22226 and a second, or top, layer 22227 wherein the first layer 22226 and/or the second layer 22227 can comprise a plurality of raised portions or partial bubbles which can define the cavities 22222. As illustrated in FIG. 120, the compensator 22220 can be attached to the anvil 22060 such that the cavities 22222 are aligned, or at least substantially aligned, with the staple forming pockets 22062 of the anvil 22060. In various embodiments, each cavity 22222 can include one or more medicaments contained therein, such as, for example, oxidized regenerated cellulose, calcium, and/or alginate. In use, in certain embodiments, each cavity 22222 can be in a sealed, unpunctuated state prior to being punctured by the staples 22030 ejected from the staple cartridge 22000, for example. After the legs of the staples 22030 have passed through the tissue T, referring now to FIG. 121, each staple leg can pierce and penetrate the first layer 22226 and enter into a cavity 22222 where the staple leg can then pass through one or more medicaments contained therein before piercing and penetrating the second layer 22227. Similar to the above, the legs of the staples 22030 can then contact the anvil 22060.

In various embodiments, the cavities 22222 can maintain the one or more medicaments stored therein in a dry or an at least substantially dry state before being ruptured. After a cavity 22222 has been ruptured, a fluid, such as blood, for example, can enter into the cavity 22222 and mix with the one or more medicaments. In at least one embodiment, the mixture of the fluid with a medicament can cause the medicament to expand within the cavity 22222 wherein, in at least one such embodiment, the medicament can comprise at least one hydrogel, for example. In certain embodiments, the medicament can comprise at least one haemostatic material, for example. In various embodiments, the first layer 22226 and/or the second layer 22227 can be comprised of a flexible material which can stretch to accommodate the expansion of the medicament. In at least one embodiment, the layers 22226, 22227 can be comprised of a CAP/GLY material, for example. In any event, the expansion of the medicament can apply a compressive force to the tissue T captured within and/or positioned around the staples 22030, for example. In various circumstances, the expansion of the medicament can cause the cavities 22222 to burst. In certain embodiments, a first group of cavities 22222 can comprise a first medicament therein while a second group of cavities 22222 can comprise a second medicament therein, for example. In at least one such embodiment, the first medicament can be configured to expand a first amount and/or at a first rate while the second medicament can be configured to expand a second amount and/or at a second rate, for example, wherein the first amount can be different than the second amount and/or the first rate can be different than the second rate. Further to the above, in various embodiments, one or more cavities 22222 can include two or more medicaments stored in each cavity wherein the medicaments can comprise a first medicament and a second medicament, for example. In certain embodiments, a cavity 22222 can maintain the first medicament and the second medicament in a dry, or an at least substantially dry, state before being ruptured. After the cavity 22222 has been ruptured, as described above, blood, for example, can enter into the cavity 22222 and mix with the first and second medicaments wherein, in at least one embodiment, the first and second medicaments can form a gel which expands.

Figure 122:
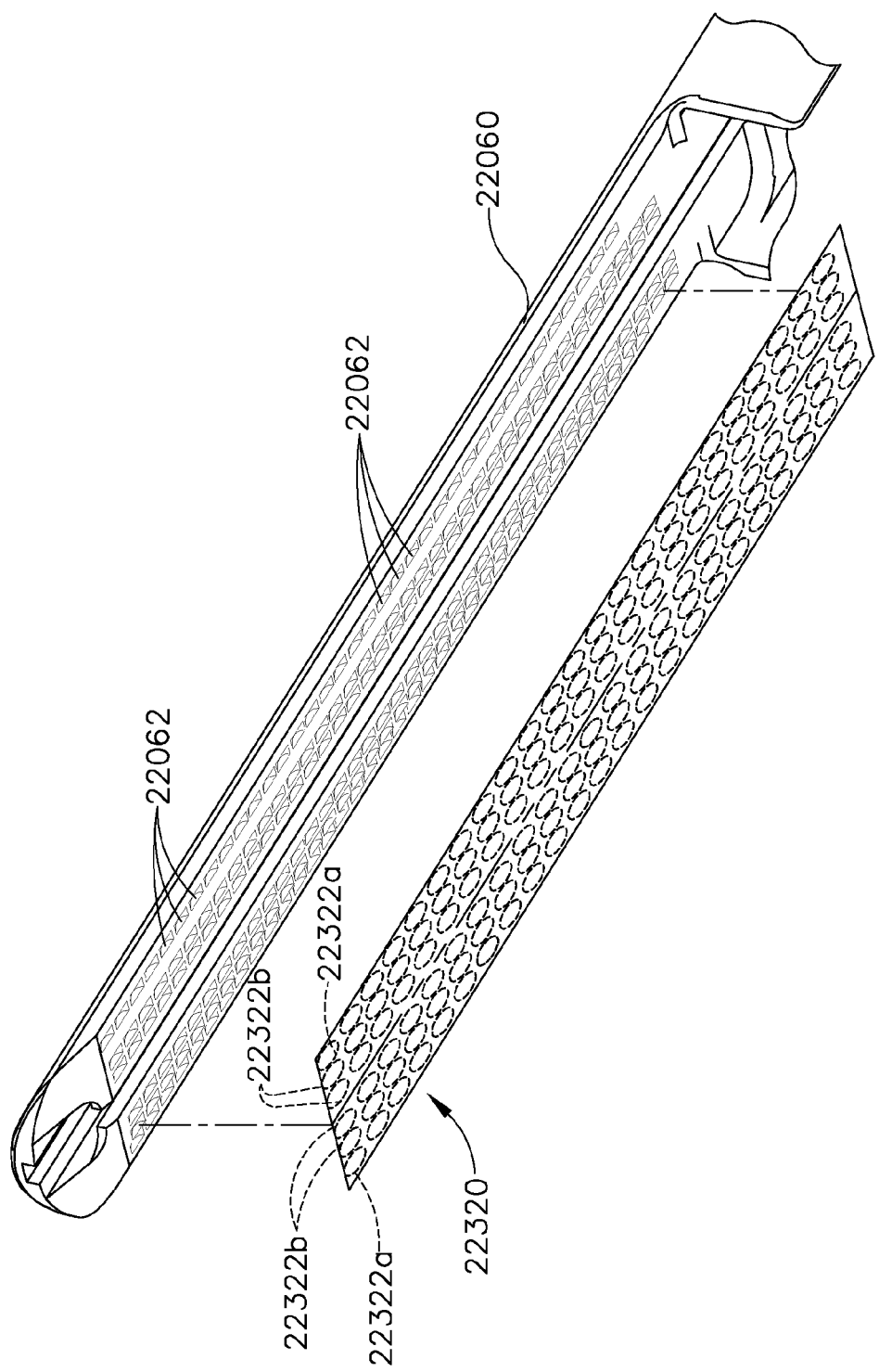

In various embodiments, referring now to FIGS. 122-124, a tissue thickness compensator, such as compensator 22320, for example, can comprise a plurality of first cavities 22322a and a plurality of second cavities 22322b which can be aligned with staple forming pockets 22062a and 22062b, respectively. In at least one embodiment, referring primarily to FIG. 123, the staple forming pockets 22062a and 22062b may be defined in separate stepped surfaces on the anvil 22060. More particularly, the forming pockets 22062a can be defined in first surfaces 22069a of anvil 22060 and the forming pockets 22062b can be defined in second surfaces 22069b wherein the first surfaces 22069a can be positioned offset, or higher, with respect to the second surfaces 22069b, for example. In various embodiments, the first cavities 22322a of the tissue thickness compensator 22320 can be larger than the second cavities 22322b wherein, in at least one such embodiment, the first cavities 22322a can extend higher than the second cavities 22322b. As a result of the above, the first cavities 22322a can extend upwardly into the first staple forming pockets 22062a while, concurrently, the second cavities 22322b can extend upwardly into the second staple forming pockets 22062b. In various embodiments, each of the first cavities 22322a can be configured to contain a larger quantity of a medicament than the second cavities 22322b, for example. In other embodiments, the first cavities 22322a and the second cavities 22322b can contain the same, or at least substantially the same, amount of medicament therein even though the cavities 22322a and 22322b may have different sizes.

In various embodiments, further to the above, the first cavities 22322a can be arranged in certain rows while the second cavities 22322b can be arranged in different rows. In certain embodiments, a tissue thickness compensator can comprise cavities aligned with each forming pocket while, in other embodiments, referring to FIG. 130, a tissue thickness compensator, such as compensator 22420, for example, may comprise cavities aligned with only some of the forming pockets. In various embodiments, referring again to FIG. 123, the compensator 22320 can be attached to the anvil 22060. In at least one embodiment, the cavities 22322*a* and/or the cavities 22322*b* can be configured such that fit snugly within staple forming pockets 22062*a* and/or 22062*b*, respectively. In certain embodiments, the compensator 22320 can be assembled to the anvil 22060 such that the second layer 22327 of the compensator 22320 is positioned against the second surfaces 22069*b* of the anvil 22060. In certain other embodiments, referring now to FIGS. 125 and 126, the compensator 22320 can be positioned adjacent to the anvil 22060 such that the compensator 22320 can abut the anvil 22060 when the anvil 22060 is displaced toward the staple cartridge 22000 to compress the tissue T therebetween. Once the staples 22030 have been fired from the staple cartridge 22000 and deformed by the anvil 22060, referring now to FIG. 127, the compensator 22320 can be trapped against the tissue T by the staples 22030 and the anvil 22060 can be moved away from the compensator 22320. In certain circumstances, referring now to FIG. 128, one or more of the staples 22030 may not be properly deformed by the anvil 22030. In such circumstances, referring now to FIG. 129, the cavities in the tissue thickness compensator which overlie the misfired or misformed staples may not be pierced when the staples are fired. In at least one such embodiment, the tissue thickness compensator may be comprised of a bioabsorbable material which can dissolve and subsequently release the medicament contained in the unpierced cavities.

In various embodiments, further to the above, the first cavities 22322*a* and/or the second cavities 22322*b* of the tissue thickness compensator 22320 can comprise a gas, such as air, carbon dioxide, and/or nitrogen, for example, sealed therein. In certain embodiments, the cavities 22322*a* and/or 22322*b* can comprise bubbles which can be popped when the staples 22030 are fired through the cavities 22322*a* and 22322*b* to release the gas contained therein. In at least one embodiment, such popping can provide an audio feedback to the surgeon that the cavities 22322*a* and 22322*b* are being ruptured. In some circumstances, however, some of the staples 22030 may be misfired, as described above, and the cavities 22322*a* and 22322*b* associated therewith may not be popped. In various circumstances, the surgeon can scan the stapled tissue for any unpopped bubbles, or cavities 22322*a* and 22322*b*, and determine whether any corrective action needs to be taken.

As discussed above, referring now to FIG. 131, a surgical stapling instrument can comprise a firing member, such as firing member 22080, for example, which can include a cutting member, or cutting edge, 22081 which can be advanced through the tissue T and one or more tissue thickness compensators as the firing member 22080 is advanced through the cartridge 22000 to deploy the staples 22030 therefrom. In various embodiments, referring primarily to FIG. 133, a compensator, such as compensator 22520, for example, can be attached to the anvil 22060 of the surgical stapling instrument wherein the anvil 22060 can include a knife slot 22061 sized and configured to receive at least a portion of the cutting member 22081. Similarly, the staple cartridge 22000 can comprise a knife slot 22011 which can also be sized and configured to receive at least a portion of the cutting member 22081. In various embodiments, referring again to FIG. 131, the compensator 22520 can comprise one or more cavities, such as cavities 22522, for example, positioned along a cutting line 22521 of the compensator 22520 wherein the cavities 22522 can be aligned with the knife slot 22061 defined in the anvil 22060. As the cutting member 22081 is progressed distally through the staple cartridge 22000 to deploy the staples 22030, the cutting member 22081 can incise the tissue T and the cavities 22522 of the compensator 22520. Similar to the above, referring primarily to FIG. 132, each cavity 22522 can define a sealed cavity 22524 which can contain one or more medicaments 22525 therein. In at least one embodiment, one or more of the cavities 22522 can be configured to contain a fluid which can be released when the cavities 22522 are at least partially incised by the cutting member 22081. In various circumstances, the cutting member 22081 can sequentially incise the cavities 22522 and, as a result, sequentially release the medicaments contained therein.

In various embodiments, referring primarily to FIG. 133, the compensator 22520 can comprise lateral projections, or wings, 22529 that extend along the sides thereof. In at least one embodiment, the projections 22529 can be secured to the anvil surfaces 22069*a* and/or anvil surfaces 22069*b* utilizing one or more adhesives, for example. In certain embodiments, the projections 22522 can be sized and configured to fit snugly within the knife slot 22061 of the anvil 22060 such that, in at least one such embodiment, the projections 22522 can retain the compensator 22520 to the anvil 22060. In various embodiments, the lateral projections 22529 can be sized and configured such that they extend over, or overlie, the staple forming pockets 22062*b* and/or the staple forming pockets 22062*a*. In certain other embodiments, referring now to FIGS. 134 and 135, a compensator 22620 can comprise lateral projections 22629 that do not extend over, or overlie, the staple forming pockets 22062*a* and 22062*b* of the anvil 22060 and/or any other staple forming pockets, for example. In at least one such embodiment, the compensator 22620 may not be captured within a staple 22030 ejected from the staple cartridge 22030. In any event, referring again to FIG. 131, the cutting member 22081 can transect the compensator 22520 as the compensator 22520 is being secured to the tissue T by the staples 22030. In such embodiments, the compensator 22520 can detach from the anvil 22060 and remain with the tissue T. Referring again to the compensator 22620 illustrated in FIGS. 134 and 135, the staples 22030 may not secure the compensator 22620 to the anvil 22060 and, in at least one embodiment, may remain attached to the anvil 22060 after the cutting member 22081 has transected the compensator 22620.

In various embodiment, referring now to FIGS. 136 and 137, an end effector of a surgical stapling instrument can comprise a tissue thickness compensator, such as compensator 22720, for example, which can be attached to, or can be configured to be attached to, an anvil, such as anvil 22760, among others. In at least one embodiment, similar to the above, the anvil 22760 can comprise a plurality of staple forming pockets 22762 and a longitudinal knife slot 22761 configured to receive a cutting member therein as the cutting member is advanced through the end effector. In certain embodiments, the compensator 22720 can comprise a first film layer 22726 and a second film layer 22727 which can be attached to one another to define a cavity 22724. In at least one such embodiment, the first film layer 22726 can be attached to the second film layer 22727 along a sealed outer perimeter 22728 wherein the sealed outer perimeter 22728 can contain at least one medicament 22725 in the cavity 22724, for example. As illustrated in FIG. 137, the cavity 22724 and the medicament 22725 can extend under all of the staple cavities 22762 and, in at least one embodiment, the sealed perimeter 22728 can be positioned laterally with respect to the outermost staple cavities 22762. In various embodiments, the compensator 22720 can further comprise a longitudinal rib 22721, for example, which can be configured to extend upwardly into the knife slot 22761. In at least one such embodiment, the rib 22721 can be sized and configured to fit snugly within the knife slot 22761 in order to secure the compensator 22720 to the anvil 22760. In certain embodiments, the rib 22721 can be configured to align or center the compensator 22720 with the anvil 22760. Similarly, referring to FIG. 138, a tissue thickness compensator 22820 can comprise a retention rib 22821 which can be positioned within the knife slot 22761, for example, in order to secure the compensator 22820 to the anvil 22760. Referring again to FIG. 137, as a cutting member is advanced through the knife slot 22761, in various circumstances, the cutting member can transect the rib 22721 and release the compensator 22720 from the anvil 22760. Such a cutting member is depicted in FIG. 138 as part of firing member 22080, for example.

In various embodiments, referring again to FIG. 138, the tissue thickness compensator 22820 can comprise a first layer 22826 and a second layer 22827 which can be configured and arranged to define a plurality of first packets 22824a and a plurality of second packets 22824b. In at least one embodiment, each of the first packets 22824a can be configured to contain a first medicament and each of the second packets 22824b can be configured to contain a second medicament, wherein the second medicament can be different than the first medicament. In various embodiments, the first packets 22824a and the second packets 22824b can be arranged in an alternating arrangement. In at least one such embodiment, the first packets 22824a and the second packets 22824b can extend laterally across the tissue thickness compensator 22820 such that a second packet 22824b is positioned intermediate two first packets 22824a and a first packet 22824a is positioned intermediate two second packets 22824b, for example. As the cutting member 22080 is progressed through the compensator 22820, as illustrated in FIG. 138, the cutting member 22080 can transect a first packet 22824a, followed by a second packet 22824b, followed by a first packet 22824a, followed by a second packet 22824b, and so forth. Correspondingly, in such embodiments, the cutting member 22080 can sequentially release the first medicament contained in a first packet 22824a and the second medicament contained in a second packet 22824b in an alternating arrangement, for example. In embodiments where the first packets 22824a and the second packets 22824b are positioned adjacent to one another, the first medicament can be configured to mix with the second medicament when they are released from their respective first packets 22824a and second packets 22824b. In at least one such embodiment, the advancement of the cutting member through the compensator 22820 can mix the first medicament with the second medicament.

In various embodiments, further to the above, the first medicament can comprise a first powder while the second medicament can comprise a second powder. In at least one embodiment, the first medicament and/or the second medicament can be comprised of a haemostatic material, oxidized regenerated cellulose, alginate, and/or calcium, for example. In certain embodiments, the first medicament and/or the second medicament can comprise a fluid. In at least one embodiment, one or more of the first packets 22824a and/or one or more of the second packets 22824b can comprise a lubricant which can reduce the force needed to advance the firing member 22080 through the compensator 22820 and/or the tissue T. In various embodiments, the first film layer 22826 and/or the second film layer 22827 can be comprised of a bioabsorbable material, such as PDS, for example. In certain embodiments, the first film layer 22826 and the second film layer 22827 can be attached to one another such that the first packets 22824a are sealed from the second packets 22824b prior to being incised by the firing member 22080. In certain embodiments, the first packets 22824a and/or the second packets 22825b can comprise a certain burst strength in order to withstand a certain burst pressure. More particularly, when an anvil, such as anvil 22760, for example, moves the compensator 22820 toward a staple cartridge positioned opposite the anvil 22760, the packets 22824a, 22824b can be positioned against the tissue positioned intermediate the packets 22824a, 22824b and the staple cartridge wherein the anvil 22760 can then be pushed, or clamped, downwardly toward the staple cartridge in order to compress the tissue positioned therebetween. In such circumstances, the packets 22824a, 22824b may be subjected to compressive pressures. In some circumstances, it may be desirable for the packets 22824a and/or packets 22824b to remain intact until they are incised by the cutting member 22080 and/or punctured by staples fired from the staple cartridge. In certain other circumstances, it may be desirable for the packets 22824a and/or the packets 22824b to burst from the compressive clamping load applied thereto.

As discussed above, the first packets 22824a and the second packets 22842b can extend laterally across the compensator 22820. In various embodiments, the first packets 22824a can extend along transverse axes 22823a while the second packets 22824b can extend along transverse axes 22823b, for example. In at least one embodiment, the first axes 22823a and/or the second axes 22823b can be perpendicular, or at least substantially perpendicular, to a longitudinal axis 22083 of the compensator 22820. In at least one such embodiment, the longitudinal axis 22083 can define the cutting path of the firing member 22080. In certain embodiments, the first axes 22823a and/or the second axes 22823b may not be perpendicular to the longitudinal axis 22083 and may be skew with respect to the longitudinal axis 22083. In various embodiments, as discussed above, the first packets 22824a and the second packets 22824b can be arranged in an alternating arrangement. In certain other embodiments, any other suitable arrangement of the first packets 22824a and the second packets 22824b may be utilized. For instance, a sequence of packets arranged in a tissue thickness compensator could include a first packet 22824a, a second packet 22824b, a second packet 22824b, and a first packet 22824a. In certain embodiments, a tissue thickness compensator can further comprise a plurality of third packets comprising a third medicament which is different than the first medicament and the second medicament. In at least one such embodiment, the first packets, the second packets, and the third packets can be arranged in an alternating arrangement. For instance, a sequence of packets arranged in a tissue thickness compensator could include a first packet, followed by a second packet, which is followed by a third packet, for example.

In various embodiments, referring again to FIG. 138, the first packets 22824a and/or the second packets 22824b of the tissue thickness compensator 22820 can define U-shaped, or at least substantially U-shaped, cross-sections, for example. In certain embodiments, referring now to FIG. 139, the packets 22924 of a tissue thickness compensator 22920 can define circular, or at least substantially circular, cross-sections, for example. In some embodiments, referring now to FIG. 140, the packets 23024 of a tissue thickness compensator 23020 can define oval and/or elliptical cross-sections, for example. In various embodiments, referring again to FIG. 138, the first cavities 22824a and the second cavities 22824b can comprise symmetrical, or at least nearly symmetrical, configurations which are defined in parallel, or at least substantially parallel, rows. In certain other embodiments, referring now to FIG. 141, a tissue thickness compensator, such as compensator 23120, for example, can comprise asymmetrical cavities 23122 defined therein which can have an irregular and/or non-repeating pattern, for example. In at least one such embodiment, each of the cavities 23122 can contain one or more different medicaments therein.

In various embodiments, referring now to FIG. 142, a tissue thickness compensator, such as tissue thickness compensator 23220, for example, can comprise a casing 23226 which defines a cavity 23224 therein and a material 23225 positioned within the cavity 23224. In certain embodiments, the casing 23226 can be comprised of a resorbable polymer, PDS, PGA, PLLA, Cap Gly, and/or PCL, for example, while the material 23225 could be comprised of a haemostatic agent, oxidized regenerated cellulose, Hercules, fibrin, and/or thrombin, for example, which can take any suitable form such as a powder, a fiber, and/or a gel, for example. In at least one embodiment, the casing 23226 can be manufactured utilizing an extrusion process. In such embodiments, the casing 23226 can comprise a constant, or an at least substantially constant, cross-section along the length thereof which can be created without having to weld a seam together. In at least one such embodiment, the cavity 23224 can be defined by a sidewall extending around the entire perimeter thereof without openings defined therein. In certain embodiments, the casing 23226 can be comprised of a mesh and/or a straw-like material having openings defined therein. In at least one embodiment, openings can be cut in the casing 23226 by a laser cutting process and/or a die cutting process, for example.

As part of manufacturing the material 23225, referring now to FIGS. 145-147, a yarn strand can be created utilizing fibers and/or a fibrous material, such as oxidized regenerated cellulose, for example. In certain embodiments, longer fibers 23325, depicted in FIG. 145, and shorter fibers 23425, depicted in FIG. 146, can be mixed together as illustrated in FIG. 147 to form the yarn strand of material 23225. In various embodiments, the yarn strand can be drawn and/or placed under tension in order to stretch the fibers contained therein in a longitudinal direction. In certain embodiments, referring now to FIG. 148, the yarn strand of material 23225 can be fluffed by graspers 23290 which can grasp and twist the material 23225 to increase the volume of the yarn strand. In at least one such embodiment, the graspers 23290 can fluff the material 23225 as the yarn strand is moving relative to the graspers 23290, for example. In some embodiments, referring again to FIG. 148, cutting members 23291 could be utilized to make small incisions and/or micro-cuts, for example, in the yarn strand of material 23225. Similar to the above, the cutting members 23291 can cut the material 23225 as the yarn strand is moving relative to the cutting members 23291. In certain embodiments, the yarn strand of material 23225 can be fluffed before the above-described incisions are made while, in other embodiments, the yarn strand of material 23225 could be incised before it is fluffed.

Once the yarn strand of material 23225 has been suitably prepared, the material 23225 can be positioned within the casing 23226. In at least one embodiment, referring now to FIG. 149, two or more casings 23226 could be formed together as part of an extrusion process, discussed above, wherein the casings 23226 can be connected together as part of a tube 23227. In various embodiments, the yarn strand of material 23225 can be positioned within, or drawn into, the cavity 23224 defined in the tube 23227. In at least one embodiment, the yarn strand of material 23225 can be positioned adjacent to and/or within a first open end 23221 of the cavity 23224 wherein a grasper 23292 can be inserted through a second open end 23222 of the cavity 23224. The grasper 23292 can then be pushed through the cavity 23224 until the jaws 23292a of the grasper 23292 pass through, and/or are positioned relative to, the first open end 23222 such that grasper jaws 23292a can be manipulated to grasp the yarn strand of material 23225. In certain embodiments, a grasper may comprise a hook member, for example, which can be configured to grasp the yarn strand of material 23225. In any event, once the grasper 23292 has sufficiently grasped the yarn strand of material 23225, the grasper 23292 can be drawn back into the cavity 23224 in order to pull the yarn strand of material 23225 into the cavity 23224. In various embodiments, the grasper 23292 can be configured to twist the yarn strand of material 23225 before, during, and/or after the yarn strand is pulled into the tube 23227.

Once the yarn strand of material 23225 has been suitably positioned within the tube 23227, the grasper 23292 can then be operated to release the yarn strand of material 23225. In various embodiments, the yarn strand can be released before the yarn strand has been pulled through the second open end 23222 of the tube 23227 while, in other embodiments, the yarn strand can be released after the yarn strand has been pulled through the second open end 23222, as illustrated in FIG. 150. In certain circumstances, the yarn strand can be pulled through the second open end 23222 such that, when the yarn strand is released, the yarn strand can shrink, or spring back, into the tube 23227 through the second open end 23222. In various circumstances, the yarn strand can be cut at a location adjacent to the first open end 23221 such that, similar to the above, the yarn strand can shrink, or spring back, into the tube 23227 through the first open end 23222. In various circumstances, further to the above, the grasper 23292 can apply a tension force to the yarn strand of material 23225 such that when the grasper 23292 releases the yarn strand and/or when the yarn strand is cut, the tension force within the yarn strand can be relieved thereby allowing the yarn strand to contract.

Once the yarn strand of material 23225 has been sufficiently positioned within the tube 23227, referring now to FIG. 151, the tube 23227 and the material 23225 can be cut into a plurality of segments, wherein each segment can be made into a tissue thickness compensator 23220, for example. In various embodiments, the cavity 23224 extending through the cover 23226 of each such segment can comprise an open end on opposite ends thereof. In at least one such embodiment, one or both of the open ends can be closed and/or sealed by a heat-staking, heat-welding, and/or laser welding process, for example. Referring to FIG. 152, a segment comprising a cover 23226 and a portion of the material 23225 therein can be positioned within a die configured to close and/or seal the open ends of the cover 23226. More particularly, in at least one embodiment, the die can comprise a base 23294 and a movable portion 23296, for example, wherein the segment can be positioned within a cavity 23295 defined in the base 23294. Once positioned, the movable portion 23296 can be moved downwardly to apply a force to the segment. In various embodiments, heat can be applied to the segment via the base 23294 and/or the movable portion 23296 wherein the heat and/or the force applied to the segment can distort the cover 23226. More specifically, in at least one embodiment, the movable portion 23296 can define a pocket 23297 which can be contoured to apply a clamping force to certain portions of the cover 23226, such as the open ends thereof, in order to close, flatten, and/or neck down such portions of the tissue thickness compensator 23220. For instance, the pocket 23297 can be configured to form the closed ends 23228 of the tissue thickness compensator 23220 and flatten the portion of the tissue thickness compensator 23220 positioned intermediate the closed ends 23228. After the tissue thickness compensator 23220 has been suitably formed, the movable portion 23296 can be moved to an open position and the tissue thickness compensator 23220 can be removed from the die. In various embodiments, the tissue thickness compensator 23220 can then be positioned in a cooling container wherein the compensator 23220 can be permitted to cool to room temperature and/or any other suitable temperature.

In certain alternative embodiments, further to the above, the tube 23227 can be positioned within a heat-forming die after the material 23225 has been positioned therein. After the tube 23227, and the material 23225 positioned therein, have been formed, the tube 23227 and the material 23225 can then be segmented into a plurality of tissue thickness compensators 23220, for example. In various embodiments, referring again to FIG. 142, the tissue thickness compensator 23220 can comprise lateral wings, or clips, 23229 which can be configured to be attached to the anvil 22060, for example. In at least one such embodiment, the lateral wings 23229 can be formed in the cover 23226 when the tissue thickness compensator 23220 is formed between the die portions 23294 and 23296, as described above. Referring now to FIG. 143, a tissue thickness compensator 23320 can comprise lateral wings 23329 extending from cover 23326. In certain embodiments, referring now to FIG. 144, a tissue thickness compensator 23420 can comprise a cover 23426 having one or more lateral flexible joints 23428, for example, which can permit the cover 23426 to flex and flatten when it is subjected to a compressive pressure in the heat-forming die described above. In various embodiments, as a result of the above, the tissue thickness compensator 23220 may not comprise lateral seams. In such embodiments, referring again to FIG. 142, the material 23225 may extend to the lateral edges of the anvil 22060, for example.

As described above, a yarn strand can be pulled through a tube and then cut to length to form one or more tissue thickness compensators. In various embodiments, further to the above, a yarn strand can be pulled or pushed through a tube utilizing a rigid strand of material. In at least one embodiment, a rigid strand of polymer material, such as PCL, for example, can be heated above its glass transition temperature and stretched into a deformed shape. In at least one such embodiment, the rigid strand can comprise an undeformed serpentine shape which, when stretched into its deformed shape, can comprise a straight, or at least substantially straight, shape, for example. Thereafter, the rigid strand can be cooled below the glass transition temperature of the material while the rigid strand is constrained so that the rigid strand can maintain its deformed shape. Once the rigid strand is in its deformed shape, in various embodiments, ORC fibers, for example, can be formed around the rigid strand. In certain embodiments, an ORC yarn strand, for example, can be wound around, flocked, and/or folded over the rigid strand. Alternatively, the rigid strand can be inserted into ORC fibers, for example. In certain embodiments, the rigid strand can comprise a sticky surface which can be rolled and/or dipped within the ORC fibers. In any event, the rigid strand and the ORC fibers can then be inserted into a tube, similar to the above, and reheated above the glass transition temperature of the rigid strand. In such circumstances, the rigid strand can be unconstrained, or at least substantially unconstrained, and can be permitted to return, or at least substantially return, to its original undeformed shape. In at least one such embodiment, the rigid strand can contract when returning to its original shape and retract the ORC fibers into the tube. In certain embodiments, the center of the tube can be clamped to hold the rigid strand and the ORC fibers in the center of the tube as the rigid tube contracts. Similar to the above, the ends of the tube can be sealed to enclose the rigid strand and the ORC fibers therein.

In various embodiments, referring now to FIG. 244, a tissue thickness compensator 33320 can comprise a shell 33326, a compressible core positioned within the shell 33326, and closed ends 33328 which can be configured to contain the compressible core within the shell 33326. In at least one embodiment, further to the above, the shell 33326 can be produced from a continuous extruding process and can comprise a continuous cross-sectional shape along the length thereof. In certain embodiments, referring now to FIGS. 245-247, a tissue thickness compensator 33420 can comprise a shell 33426, a cavity 33424 defined in the shell 33426, and a core 33425 positioned within the cavity 33424. In at least one such embodiment, the shell 33426 can comprise a film body formed from a continuous extruded shape and the core 33425 can comprise a fibrous medicament core, such as ORC, for example. In at least one embodiment, the shell 33426 can comprise one or more flexible legs 33423 which can be configured to extend into a knife slot 22063 defined in the anvil 22060 and releasably retain the tissue thickness compensator 33420 to the anvil 22060. In certain embodiments, referring now to FIGS. 248-250, a tissue thickness compensator 33520 can comprise a shell 33526, a cavity 33524 defined in the shell 33526, and a core 33425 positioned within the cavity 33524. In at least one such embodiment, the shell 33526 can comprise a film body formed from a continuous extruded shape and the core 33425 can comprise a fibrous medicament core, such as ORC, for example. In at least one embodiment, the shell 33526 can comprise one or more retention members 33528 which can be configured to extend around the outside surface of the anvil 22060 and releasably retain the tissue thickness compensator 33520 to the anvil 22060. In at least one such embodiment, referring primarily to FIG. 250, the shell 33526 can comprise movable portions 33527 and a gap 33523 defined between the movable portions 33527 wherein, after the tissue thickness compensator 33520 has detached from the anvil 22060, the movable portions 33527 can spring open to expose the core 33425 contained therein. In certain embodiments, referring now to FIGS. 251-252, a tissue thickness compensator 33620 can comprise a shell 33626, a cavity 33424 defined in the shell 33626, and a core 33425 positioned within the cavity 33424. In at least one such embodiment, the shell 33626 can comprise a film body formed from a continuous extruded shape and the core 33425 can comprise a fibrous medicament core, such as ORC, for example. In at least one embodiment, the shell 33626 can comprise a thin section 33623 which can be aligned with the knife slot 22063 defined in the anvil 22060 such that a cutting member passing through the tissue thickness compensator 33620 can pass through the thin section 33623 and reduce the force or energy needed to transect the tissue thickness compensator 33620. In certain embodiments, referring now to FIGS. 253-254, a tissue thickness compensator 33720 can comprise a shell 33726, a cavity 33424 defined in the shell

33726, and a core 33425 positioned within the cavity 33424. In at least one such embodiment, the shell 33726 can comprise a film body formed from a continuous extruded shape and the core 33425 can comprise a fibrous medicament core, such as ORC, for example. In at least one embodiment, the shell 33726 can comprise one or more retention members 33723 which can be configured to wrap around the outside surface of the anvil 22060 and releasably retain the tissue thickness compensator 33720 to the anvil 22060. In certain embodiments, referring now to FIGS. 255-256, a tissue thickness compensator 33820 can comprise a shell 33826, a cavity 33424 defined in the shell 33826, and a core 33425 positioned within the cavity 33424. In at least one such embodiment, the shell 33826 can comprise a film body formed from a continuous extruded shape and the core 33425 can comprise a fibrous medicament core, such as ORC, for example. In at least one embodiment, the shell 33826 can comprise a substantially rectangular cavity 33424 and a substantially flat tissue contacting surface 33829 as opposed to the arcuate cavity 33424 and tissue contacting surface depicted in FIG. 254, for example. In certain embodiments, referring now to FIGS. 257-258, a tissue thickness compensator 33920 can comprise a shell 33926, a plurality of cavities 33924 defined in the shell 33926, and a core 33925 positioned within each of the cavities 33924. In at least one such embodiment, the shell 33926 can comprise a film body formed from a continuous extruded shape and the cores 33925 can each comprise a fibrous medicament core, such as ORC, for example. In certain embodiments, the cores 33925 can be comprised of different materials. In at least one embodiment, the shell 33926 can comprise one or more retention members 33923 which can be configured to extend into the knife slot 22063 of the anvil 22060.

Referring now to FIG. 153, a tissue thickness compensator can be formed utilizing a folding process. In various embodiments, a material 23525, such as oxidized regenerated cellulose, for example, can be placed on a cover sheet 23526 which can be folded and then sealed in order to encapsulate the material 23525. In at least one such embodiment, the cover sheet 23526 can be comprised of cap gly, for example. In certain embodiments, a continuous process can be utilized in which the cover sheet 23526 can be passed under a hopper 23592 which is configured to dispense the material 23525 onto the cover sheet 23526. In at least one such embodiment, the cover sheet 23526 can be flattened between a roller 23591 and an anvil 23590 before the material 23525 is placed onto the cover sheet 23526. In certain embodiments, the material 23525 may be placed on one side, or half, of the cover sheet 23526 wherein the other side, or half, of the cover sheet 23526 can be folded, or flipped, over the material 23525. Before, during, and/or after the material 23525 has been placed on the cover sheet 23526, the cover sheet 23526 can be folded, or at least partially folded. In various embodiments, the anvil 23590, for example, can comprise a cam surface 23594 which can be configured to lift an edge or side of the longitudinally moving cover sheet 23526 and then fold the cover sheet 23526 in half, for example. In at least one embodiment, the cam surface 23594 can comprise a three-dimensional cam, or barrel cam, which progressively lifts and turns a portion of the cover sheet 23526 as the cover sheet 23526 passes by the cam surface 23594.

After the cover sheet 23526 has been folded over the material 23525, the folded cover sheet 23526 and the material 23525 positioned therein can pass through a die 23593 which can, in at least one embodiment, compress and/or compact the folded cover sheet 23526 and the material 23525 to form a tube 23527. In certain embodiments, the edges of the folded cover sheet 23526 can be sealed closed utilizing any suitable process such as thermal welding and/or laser welding, for example. In various embodiments, the tube 23527 can be further flattened by one or more rollers 23595, for example, before the sidewall of the tube 23527 has been sealed. In certain embodiments, the tube 23527 can be further flattened by one or more rollers after the sidewall of the tube 23527 has been sealed. In any event, the tube 23527 can be segmented into portions to create separate tissue thickness compensators. In various embodiments, the ends of the tissue thickness compensators can be sealed utilizing any suitable process such as thermal welding and/or laser welding, for example, while, in other embodiments, one or both of the ends of the tissue thickness compensator can remain in an open configuration, for example.

In various embodiments, referring now to FIG. 154, a compensator can be attached to an anvil, such as anvil 22060, for example, wherein the compensator can be configured to store at least one medicament therein. In at least one embodiment, a compensator 23620 can comprise a central body portion 23626 and lateral attachment portions 23628 which can be configured to be attached to the anvil 22060. In certain embodiments, the compensator 23620 can further comprise an array of capillary channels 23627 defined in a tissue contacting surface 23625 of the compensator 23620 wherein the capillary channels 23627 can be configured to store one or medicaments therein. In at least one such embodiment, the medicament can comprise a fluid which, owing to fluid tension forces, can be retained between the sidewalls of the capillary channels 23627. In various circumstances, the medicament can be applied to the compensator 23620 before the compensator 23620 is attached to the anvil 22060 while, in some circumstances, the medicament can be applied to the compensator 23620 after it has been attached to the anvil 22060, for example. In any event, the compensator 23620 can be configured to contact tissue positioned between the anvil 22060 and a staple cartridge positioned opposite the anvil 22060 wherein the medicament stored in the capillary channels 23627 can flow onto the tissue. In various circumstances, the medicament can flow within the capillary channels 23627.

In various embodiments, referring again to the compensator 23620 illustrated in FIG. 154, the array of capillary channels 23627 can be constructed and arranged in a cross-hatched pattern wherein a first quantity of channels 23627 can extend in a first direction and a second quantity of channels 23627 can extend in a second direction. In at least one embodiment, the first quantity of channels 23627 can intersect and can be in fluid communication with the second quantity of channels 23627. Referring now to FIG. 155, a compensator 23920 can comprise a body 23926 which includes an array of capillary channels 23927 defined in a tissue-contacting surface 23925. In various embodiments, the channels 23927 can be defined along linear paths while, in certain embodiments, the channels 23927 can be defined along non-linear paths. In at least one embodiment, a first quantity of channels 23927 can extend along axes 23923 while a second quantity of channels 23927 can extend along axes 23924, for example, wherein the axes 23923 can extend in different directions than the axes 23924. In various embodiments, the axes 23923 can be perpendicular, or at least substantially perpendicular, to the axes 23924 wherein, in at least one embodiment, the channels 23627 can define islands 23922 therebetween. In at least one such embodiment, the top surfaces of the islands 23922 can define the tissue contacting surface 23925 of the compensator 23920. In various embodiments, the compensator 23920 can comprise a longitudinal axis 23921 and the channels 23627 can extend in directions which are transverse or skew with respect to the longitudinal axis 23921. In certain embodiments, referring again to FIG. 154, a compensator 23720 can comprise a body 23726 and a plurality of capillary channels 23727 defined in the body 23726. In at least one embodiment, the compensator 23720 can further comprise a longitudinal channel 23721 which can be in fluid communication with the capillary channels 23727. In various embodiments, one or medicaments can be stored in the longitudinal channel 23721 wherein the medicaments can flow between the channel 23721 and the capillary channels 23727, for example. In at least one embodiment, the channel 23721 can define a longitudinal protrusion which can extend upwardly into a longitudinal knife slot 22061 defined in the anvil 22060.

As discussed above, referring again to FIG. 154, an array of capillary channels defined in a compensator can comprise a cross-hatched pattern. In various other embodiments, however, an array of capillary channels can comprise any suitable shape or configuration. For example, referring to compensator 23820 illustrated in FIG. 154, the channels 23827 defined in the body 23826 of the compensator 23820 can comprise parallel, diagonal channels which converge toward and/or diverge away from a central channel 23821, for example. Referring now to FIG. 158, an end effector of a surgical stapling instrument can include a staple cartridge 24000 including a tissue thickness compensator 24010 wherein, in at least one embodiment, the tissue thickness compensator 24010 can include at least one medicament, such as medicament 24001, for example, therein and/or thereon. Referring now to FIG. 159, a compensator 24020 attached to an anvil 24060, for example, can be moved into a closed position in order to place the compensator 24020 in contact with the tissue thickness compensator 24010. In such circumstances, the medicament 24001, for example, can be transferred from the tissue thickness compensator 24010 to the compensator 24020. In at least one embodiment, referring now to FIG. 160, the compensator 24020 can comprise a tissue contacting surface 24025 which can be brought into contact with the tissue thickness compensator 24010 wherein, in certain embodiments, the medicament 24001 can flow into capillary channels 24027 defined in the tissue contacting surface 24025. In certain embodiments, referring now to FIG. 157, the compensator 24020 can include at least one medicament, such as medicament 24002, for example, thereon and/or therein which can be transferred from the compensator 24020 to the tissue thickness compensator 24010.

In various embodiments, referring now to FIGS. 240 and 241, a tissue thickness compensator 33020 can comprise a plurality of channels and/or wells defined in the surface thereof. In at least one embodiment, the tissue thickness compensator 33020 can comprise a longitudinal channel 33026 that extends along a longitudinal axis defined through the tissue thickness compensator 33020. In at least one such embodiment, the end of the longitudinal channel 33026 can be in fluid communication with the perimeter of the tissue thickness compensator 33020. The tissue thickness compensator 33020 can further comprise a plurality of wells 33022 and, in addition, a plurality of diagonal channels 33024 which are in fluid communication with the wells 33022 and the longitudinal channel 33026. In certain embodiments, the tissue thickness compensator 33020 can further comprise a plurality of inlet-outlet channels 33027 which can be in fluid communication with the wells 33022 and the perimeter of the tissue thickness compensator 33020. In various embodiments, as a result of the above, fluids can flow into and/or out of the tissue thickness compensator 33020 before, during, and/or after it has been implanted against a patient's tissue. In certain embodiments, the pattern of channels 33024, 33026, and 33027 and the wells 33022 defined in the tissue-contacting surface 33025 of the tissue thickness compensator 33020 can define gripping edges which can be configured to contact the tissue and limit slipping between the tissue thickness compensator 33020 and the tissue. Referring now to the alternative embodiment illustrated in FIGS. 240A and 241A, a tissue thickness compensator 33120 can comprise a plurality of circular channels defined in the surface thereof. In various embodiments, the tissue thickness compensator 33120 can comprise concentric circular channels 33127 which comprise openings defined in the perimeter of the tissue thickness compensator 33120. Similar to the above, fluids can flow into and/or out of the tissue thickness compensator 33120 through the channels 33127. In at least one embodiment, the tissue thickness compensator 33120 can comprise concentric circular channels 33122 which may not include openings defined in the perimeter of the tissue thickness compensator 33120. Referring now to the alternative embodiment illustrated in FIGS. 242 and 243, a tissue thickness compensator 33220 can comprise a plurality of ridges 33227 extending therefrom which can be configured to grip tissue that is positioned against the tissue thickness compensator 33220. In at least one embodiment, the ridges 33227 can be straight while, in some embodiments, the ridges 33227 can comprise a curved contour, for example. Although the ridges and channels described above may be useful for tissue thickness compensators, in various embodiments, such ridges and channels could be utilized with any suitable bioabsorbable and/or biocompatible layer.

In various embodiments, a compensator can be comprised of a plurality of layers. In at least one embodiment, the compensator can comprise a first layer and a second layer attached to the first layer, for example. In certain embodiments, the first layer can comprise a tissue contacting surface and a plurality of capillary channels defined in the tissue contacting surface. In at least one embodiment, the first layer can also comprise capillary channels defined in a side which faces the second layer and faces opposite the tissue contacting surface. In certain embodiments, the second layer can comprise capillary channels defined therein. In at least one embodiment, wells can be defined between the first layer and the second layer of the compensator. In various embodiments, the capillary channels can be formed in the layers of the compensator utilizing any suitable process, such as during a molding process in which the layers are formed and/or during a heat-staking process, for example. In at least one embodiment, a heat-staking process can be utilized to attach the layers of the compensator to one another, for example. In at least one such embodiment, the layers can be comprised of a material which can become deformable when heat is applied thereto, such as CAP/GLY (36/64), for example. In any event, in various embodiments, the capillary channels defined in the tissue contacting surface of the compensator can define gripping surfaces therebetween which can improve the grip, or control, that can be applied to tissue positioned between the anvil and the staple cartridge of the surgical stapling instrument. Stated another way, the capillary channels defined in the tissue-contacting surface of a compensator can decrease the area in which the compensator can contact the tissue. In such circumstances, the smaller contact area can result in higher contact pressures between the compensator and the tissue for a given force. In various circumstances, the higher contact pressures can reduce slipping between the compensator and the tissue.

In various embodiments, one or medicaments can be positioned within the capillary channels and/or voids defined within and/or between the first layer and the second layer. In certain embodiments, the plurality of layers comprising a compensator can comprise a pack of therapeutic layers, or therapies. For instance, a first layer can be comprised of a first medicament and a second layer can be comprised of a second medicament, wherein the first medicament can be different than the second medicament. In at least one such embodiment, capillary channels defined in the first layer can store a third medicament and capillary channels defined in the second layer can store a fourth medicament, wherein the first, second, third, and/or fourth medicaments can be different, for example. In at least one embodiment, the first, second, third, and/or fourth medicaments can be different, for example. In various embodiments, referring now to FIG. 161, a compensator 24120 can comprise a plurality of layers, such as layers 24121-24125, for example. In at least one embodiment, the first layer 24121 and/or the fifth layer 24125 can comprise a flat sheet of material between which the second layer 24122, the third layer 24123, and/or the fourth layer 24124 can be sandwiched. In various embodiments, one or more of the layers 24121-24125 can comprise one or more channels 24127 defined therein. In at least one embodiment, the channels 24127 can extend from one end of the compensator 24120 to the other end and, in certain embodiments, the channels 24127 can extend between one side of the compensator 24120 to the other. In certain other embodiments, the channels 24127 can extend in any suitable direction between any suitable sides and/or ends of the compensator 24120. In various embodiments, referring now to FIGS. 164 and 165, a compensator 24820 can comprise two or more inner layers 24827 which can define lateral channels 24822, for example, which extend from one side of the compensator 24820 to the other. In certain embodiments, referring again to FIG. 161, the channels 24127 defined in one of the layers 24121-24125 can be aligned with the channels defined in a layer positioned adjacent thereto. In some embodiments, the channels 24127 defined in one of the layers 24121-24125 can face, or open toward, a flat surface on a layer positioned adjacent thereto. In various embodiments, referring again to FIG. 161, one or more of the layers 24121-24125 can comprise at least one well 24129 defined therein. In at least one embodiment, the wells 24129 can be in fluid communication with one or more of the channels 24127 defined in the layer. Similar to the above, the wells 24129 can comprise an opening which opens toward, or faces, an adjacent layer wherein the adjacent layer can cover the opening.

In various embodiments, further to the above, the channels 24127 and/or the wells 24129 can be configured to contain one or medicaments therein. In at least one embodiment, the channels 24127 can comprise one or more open ends which can permit a medicament to flow out of the channels 24127. Similarly, in at least one embodiment, the channels 24127 can include one or more openings which can be configured to permit a fluid, such as blood, for example, to flow into the channels 24127. In such embodiments, the fluid can flow into the compensator 24120, absorb at least a portion of a medicament and/or a layer 24121-24125, and then flow out of the compensator 24120. Referring again to FIGS. 164 and 165, the compensator 24820 can comprise apertures 24828 defined in outer layers 24826, for example.

In various embodiments, referring again to FIG. 161, the layers 24121-24125 can be comprised of any suitable material, such as a bioabsorbable polymer, PLA, and/or PGA, for example. In certain embodiments, all of the layers 24121-24125 can be comprised of the same material. In certain other embodiments, one or more of the layers 24121-24125 could be comprised of different materials. In various embodiments, one or more of the layers 24121-24125 can include through holes 24128 extending therethrough which can be configured to permit fluids, such as blood, for example, to flow into the channels 24127, wells 24126, and/or between two or more of the layers 24121-21135, for example. In certain embodiments, one or more of the layers 24121-24125 can be connected to each other utilizing a heat-welding and/or laser-welding process, for example. In such embodiments, the fluid, or fluids, flowing into the compensator 24120 can dissolve the welded portions of the layers 24121-24125 and permit the layers 24121-24125 to separate and/or delaminate. In certain embodiments, one or more of the layers 24121-24125 can be comprised of a material which dissolves at a faster rate and/or a slower rate than the material, or materials, comprising the other layers 24121-24125. In at least one such embodiment, the inner layers 24122-24124 of the compensator 24120 can be comprised of a material which dissolves at a faster rate than the material, or materials, which comprise the outer layers 24121 and 24125, for example. In such embodiments, the compensator 24120 can maintain a consistent, or at least substantially consistent, general shape while the interior of the compensator 24120 is dissolved away. In certain other embodiments, the outermost layers of a compensator can be comprised of a material which dissolves at a faster rate than the material, or materials, which comprise the innermost layers of the compensator, for example. In various embodiments, the layers can comprise sheets of material having a thickness between approximately 1 mil and approximately 4 mils, for example.

In various embodiments, referring now to FIGS. 162 and 163, a compensator, such as compensator 24220, for example, can comprise a support layer 24226 which can be configured to be attached to an anvil, such as anvil 22060, for example, and/or a staple cartridge. In certain embodiments, the compensator 24220 can further comprise a scaffold 24222 attached to the support layer 24226 wherein the scaffold 24222 can comprise a plurality of scaffold layers 24227. In at least one embodiment, the scaffold can comprise a three-dimensional structural matrix, for example. In various embodiments, each of the scaffold layers 24227 can be comprised of a plurality of fibers. In at least one embodiment, referring now to FIG. 166, each scaffold layer 24227 can be comprised of a fiber weave including a first plurality of fibers 24228 extending in a first direction and a second plurality of fibers 24229 extending in a second, or different, direction. In certain embodiments, each fiber weave can comprise a plurality of pockets, or cavities, 24223 wherein the layers 24227, the fibers 24228, 24229, and the cavities 24223 can define a matrix favorable to tissue and cellular ingrowth. In various embodiments, the fibers 24228, 24229, and/or any other suitable fibers, can be comprised of a bioabsorbable material. In at least one embodiment, the fibers can be comprised of a haemostatic agent, bound active agents such as those that are biologically and/or pharmacologically active, and/or support members, for example, which can be interweaved with one another. In any event, the material of the fibers can be selected to induce a desirable biologic response such as cellular migration into the scaffold 24222, ECM secretion, and/or the proliferation of structural support cells, for example.

In various embodiments, further to the above, the support layer 24226 can be configured to structurally support the scaffold 24222. In at least one embodiment, the scaffold 24222 can be attached to the support layer 24226 utilizing one or more bioabsorbable adhesives, for example. Similarly, in certain embodiments, the support layer 24226 can be attached to an anvil or a staple cartridge utilizing one or more biocompatible adhesives, for example. In various embodiments, the layers 24227 of the scaffold 24222 can be arranged, or stacked, in any suitable manner. In certain embodiments, each layer 24227 can comprise a pattern of fibers wherein the layers 24227 can be arranged in the scaffold 24222 such that the patterns of the layers 24227 are aligned with each other. In at least one embodiment, referring to FIG. 167, the layers 24227 can be stacked on one another such that the fibers 24228 in a first layer 24227 are aligned with the fibers 24228 in a second layer 24227. Likewise, the layers 24227 can be stacked on one another such that the fibers 24229 in the first layer 24227 are aligned with the fibers 24229 in the second layer 24227. In certain embodiments, referring now to FIG. 168, a scaffold 24422 can comprise a plurality of scaffold layers 24427 wherein the fibers 24429 in each scaffold layer 24427 are oriented in the same direction, such as a longitudinal direction, for example. In certain embodiments, referring now to FIG. 170, each scaffold layer 24227 can comprise a pattern of fibers wherein the layers 24227 can be arranged in a scaffold 24322 such that the patterns of the layers 24227 are not aligned with each other. In at least one embodiment, the layers 24227 can be stacked on one another such that the fibers 24228 in a first layer 24227 extend in a direction which is transverse to or oblique with the fibers 24228 in a second layer 24227. Likewise, the layers 24227 can be stacked on one another such that the fibers 24229 in the first layer 24227 extend in a direction which is transverse to or oblique with the fibers 24229 in the second layer 24227. In certain embodiments, referring now to FIG. 171, a scaffold 24522 can comprise a plurality of scaffold layers 24427 which are oriented such that the fibers 24229 in each scaffold layer 24427 are oriented in different directions, for example.

In various embodiments, further to the above, a first scaffold layer 24227 of a scaffold 24222, for example, can be comprised of a first material while a second scaffold layer 24227 of the scaffold 24222 can be comprised of a second, or different, material. In at least one embodiment, the first material can comprise a first medicament while the second material can comprise a second, or different, medicament, for example. In various embodiments, further to the above, a first scaffold layer 24227 of a scaffold 24222, for example, can comprise a first medicament absorbed into the fibers thereof while a second scaffold layer 24227 of the scaffold 24222 can comprise a second, or different, medicament absorbed into the fibers thereof, for example. In at least one embodiment, the first material can comprise a first medicament while the second material can comprise a second, or different, medicament, for example. In certain embodiments, a scaffold can comprise any suitable number of layers having any suitable density of fibers which are comprised of any suitable number of materials.

Tissue thickness compensators may be installed in a surgical device, such as a surgical cutting and stapling device, for example, utilizing a retainer. The retainer can include a gripping surface and enable a surgeon, nurse, technician, or other person to align one or more of the tissue thickness compensators with features of the surgical instrument, such as an anvil and/or a staple cartridge, for example. In various embodiments, the retainer may include features that align the one or more tissue thickness compensators by engaging a staple cartridge of the surgical instrument. In certain embodiments, the retainer may include features that align one or more tissue thickness compensators by engaging an anvil of a surgical instrument. In certain embodiments, a staple cartridge for the surgical instrument may be included with the retainer and engaging the retainer with the surgical instrument can install the staple cartridge in the surgical instrument and align one or more of the tissue thickness compensators. After the tissue thickness compensators have been aligned with and attached to the surgical instrument, the retainer may be detached from the tissue thickness compensators and then removed from the surgical instrument.

FIGS. 61-67 illustrate an embodiment of a retainer 19000 that may be used to attach a first tissue thickness compensator 19002 to an anvil 19040 and a second tissue thickness compensator 19004 to a staple cartridge 19050 of a surgical stapler, for example. A retainer assembly 19060 can be provided which includes the retainer 19000, the first tissue thickness compensator 19002, and the second tissue thickness compensator 19004. In use, generally, the retainer assembly 19060 may be inserted between the anvil 19040 and a channel configured to support the staple cartridge 19050. Thereafter, the anvil 19040 can be closed. By closing the anvil 19040, the anvil 19040 can push downwardly onto the first tissue thickness compensator 19002 such that the first tissue thickness compensator 19002 may be attached to the anvil 19040. In at least one embodiment, closing the anvil 19040 pushes downwardly on the retainer 19000 and seats the staple cartridge 19050 into the channel of the surgical instrument. When the anvil 19040 is reopened, the first tissue thickness compensator 19002 can detach from the retainer 19000 and when the retainer 19000 is subsequently removed from the surgical device, the retainer 19000 can detach from the second tissue thickness compensator 19004. The surgical device is then ready for use with the first tissue thickness compensator 19002 attached to the anvil 19040 and the second tissue thickness compensator 19004 attached to the staple cartridge 19050.

Figure 61:
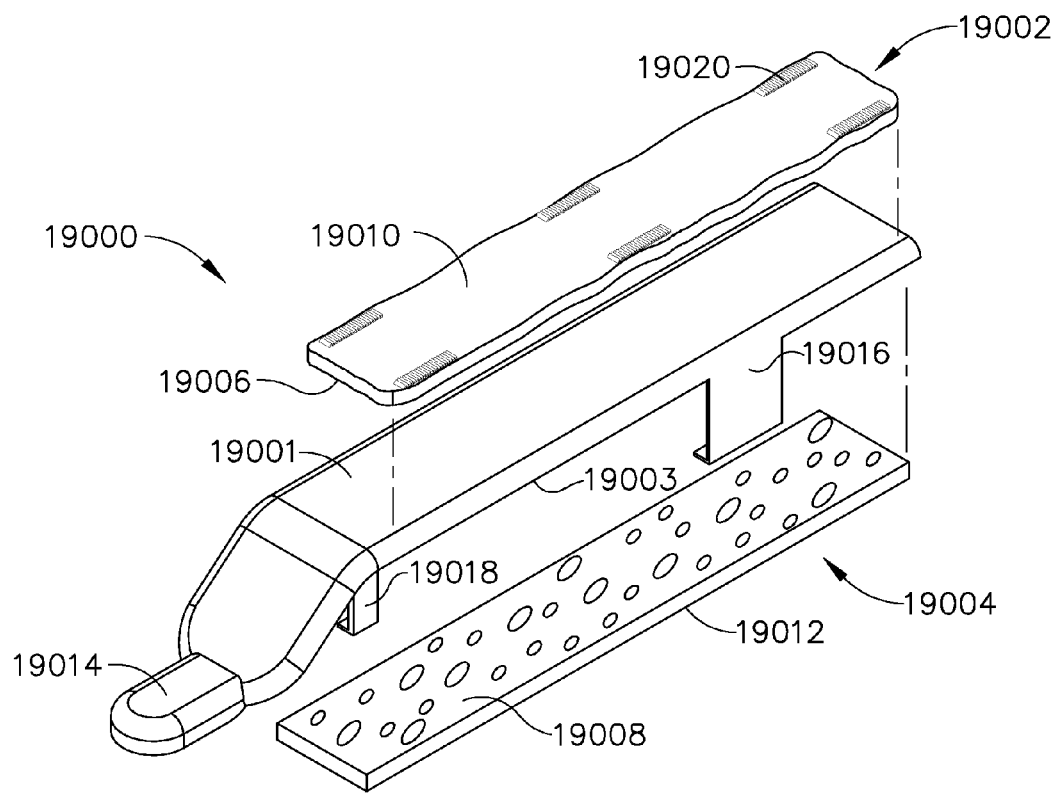
FIG. 61 is an exploded view of a retainer assembly including a retainer and two tissue thickness compensators in accordance with at least one embodiment.
Figure 62:
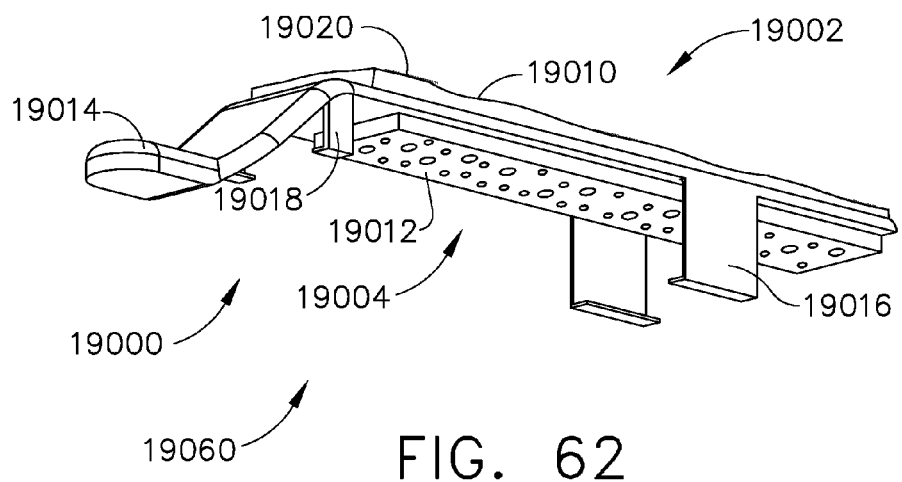
FIG. 62 is a perspective view of the retainer assembly shown in FIG. 61.
Figure 63:
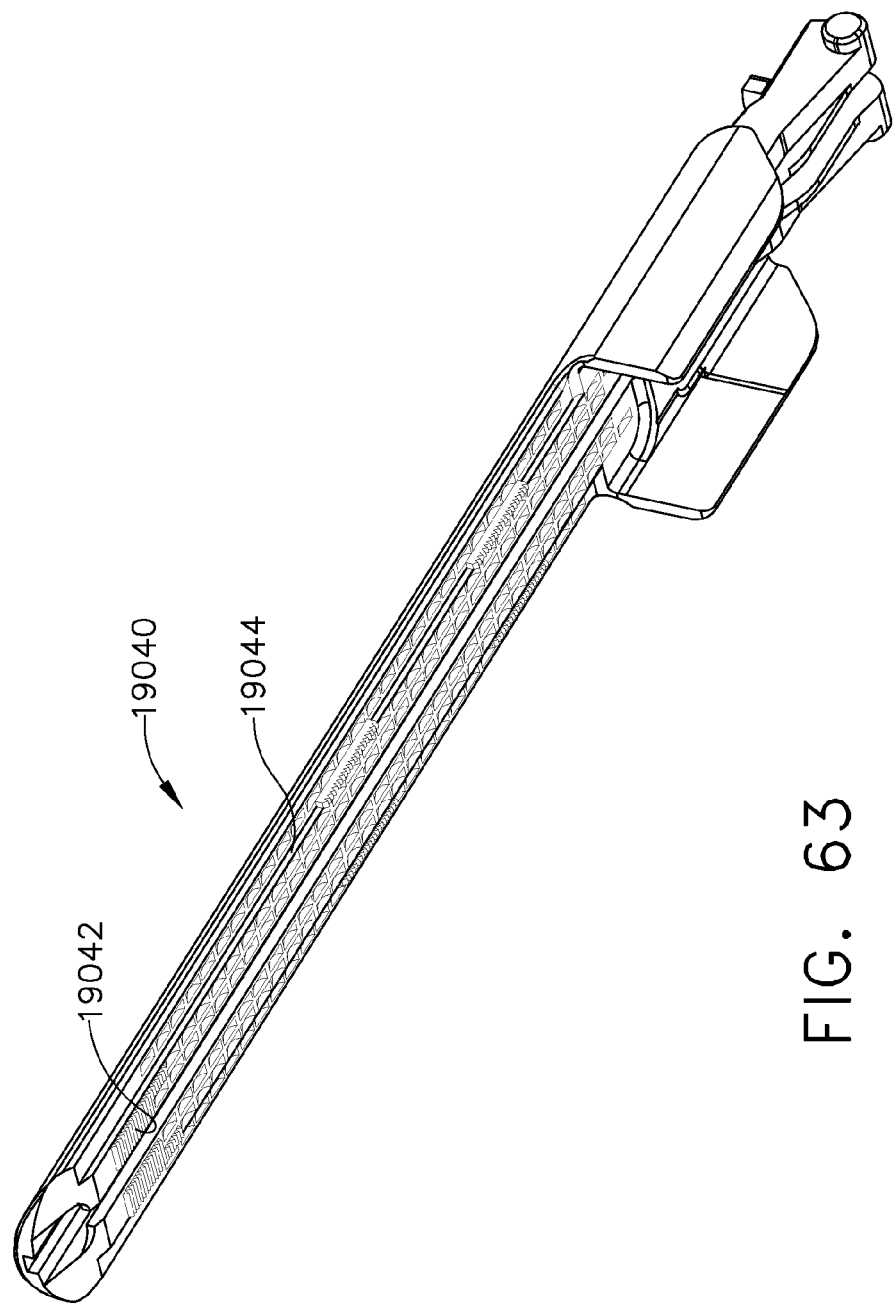
FIG. 63 is a perspective view of an anvil with which the retainer assembly of FIG. 61 may be used.

Referring to FIG. 61, the retainer 19000 may include a grip 19014 by which a person, such as a surgeon, nurse, or technician preparing surgical instruments may grasp the retainer 19000. The retainer 19000 may include a first surface 19001 on which a first tissue thickness compensator 19002 may be positioned and an opposing second surface 19003 on which a second tissue thickness compensator 19004 may be positioned. In various embodiments, one or more adhesives can be applied to the first surface 19001 and/or the second surface 19003 for attaching the first and second tissue thickness compensators 19002 and 19004 thereto. The retainer 19000 also may include clips that can engage a staple cartridge 19050 of the surgical device, for example. In at least one embodiment, referring to FIG. 64, the retainer 19000 may include distal clips 19108 configured to engage a recess 19056 at a distal end of the staple cartridge 19050 and/or proximal clips 19106 configured engage a ridge or edge 19054 on the staple cartridge 19050.

Referring to FIG. 61, in various embodiments, the first tissue thickness compensator 19002 may include a retainer-facing surface 19006 and an anvil-facing surface 19010. The retainer-facing surface 19006 can be attached to the first surface 19001 of the retainer 19000 by adhesives and/or engagement features, for example. The anvil-facing surface 19010 may include at least one adhesive thereon which can attach the first tissue thickness compensator 19002 to the anvil 19040 of the surgical device. For example, the adhesive can comprise an activatable adhesive that may adhere to a staple forming surface 19044 (FIG. 63) of the anvil 19040.

Referring to FIGS. 61 and 63-66, the anvil-facing surface 19010 of the first tissue thickness compensator may include engagement features 19020 that engage similar engagement features 19042 on the anvil 19040. Thus, in various embodiments, a first retention force can retain the first tissue thickness compensator 19002 to the retainer 19000 and a second retention force can retain the first tissue thickness compensator 19002 to the anvil 19040. In various embodiments, the second retention force can be greater than the first retention force such that the first tissue thickness compensator 19002 can remain attached to the anvil 19040 and separate from the retainer 19000 when the retainer 19000 is removed from the end effector.

Referring again to FIG. 61, the second tissue thickness compensator 19004 may include a retainer-facing surface 19008 and a staple-cartridge-facing surface 19012. The retainer-facing surface 19006 can be attached to the first surface 19001 of the retainer 19000 by one or more adhesives and/or engagement features. The staple-cartridge-facing surface 19012 may include an adhesive thereon which can attach the second tissue thickness compensator 19004 to the staple cartridge 19050 of the surgical device. For example, referring to FIG. 64, the adhesive may adhere the second tissue thickness compensator 19004 to a staple deck 19052 of the staple cartridge 19050. The staple-cartridge-facing surface 19012 also may include engagement features that engage co-operating engagement features on the staple cartridge 19050. Thus, in various embodiments, a first retention force can retain the second tissue thickness compensator 19004 to the retainer 19000 and a second retention force can retain the second tissue thickness compensator 19004 to the staple cartridge 19050. In various embodiments, the second retention force can be greater than the first retention force such that the second tissue thickness compensator 19004 can remain attached to the staple cartridge 19050 and separate from the retainer 19000 when the retainer 19000 is removed from the end effector.

Figure 64:
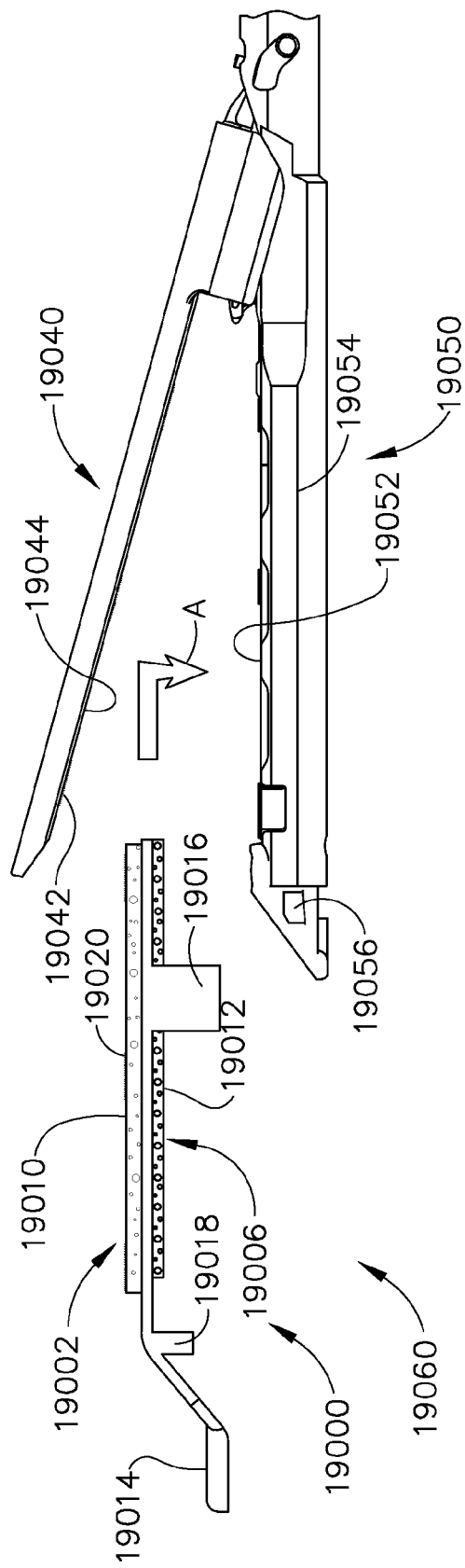
FIG. 64 is an illustration depicting the retainer assembly shown in FIG. 61 being inserted in an end effector of a surgical stapler which includes an anvil and a staple cartridge.

As shown in FIG. 64, the retainer assembly 19060 may be attached to a staple cartridge 19050 as indicated by arrow A. As described above, distal clips 19018 on the retainer 19000 may engage a recess 19056 in the staple cartridge and proximal clips 19016 on the retainer may engage the edge or ridge 19054 on the staple cartridge 19050. At such point, the retainer 19000 is attached to the staple cartridge 19050, as shown in FIG. 65, and the second tissue thickness compensator 19004 can be attached to the staple cartridge 19050. As shown in FIG. 66, closure of the anvil 19040 of the surgical device in the direction of arrow B may bring a surface 19044 of the anvil, such as a staple-forming surface and/or a tissue contacting surface, for example, into contact with the first tissue thickness compensator 19002. As described above, the anvil 19040 contacting the first tissue thickness compensator 19002 can cause the first tissue thickness compensator 19002 to become attached to the anvil 19040.

Figure 67:
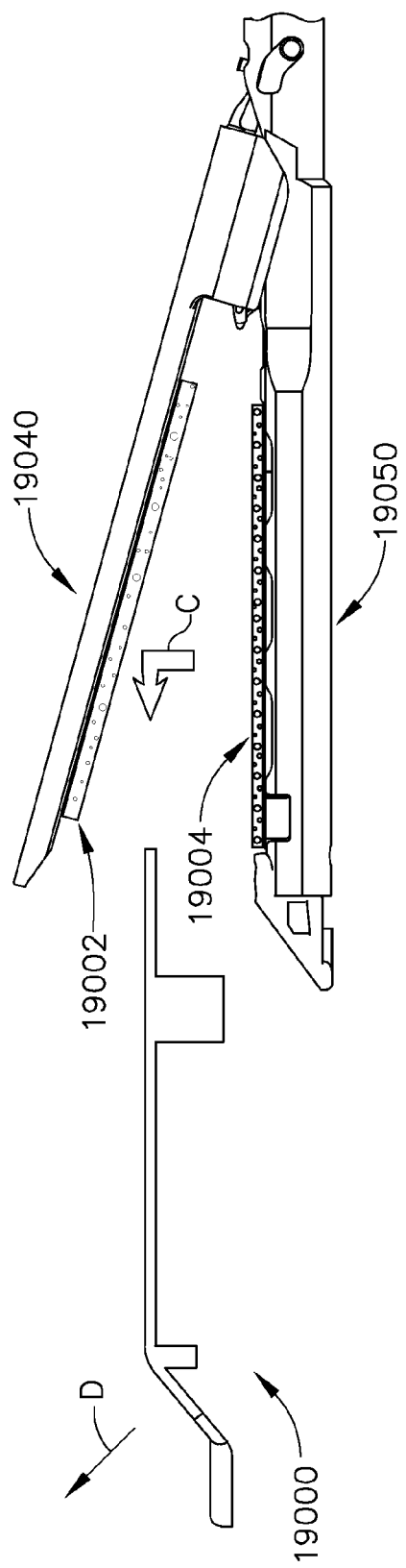
FIG. 67 is a side view of the retainer assembly of FIG. 61 being removed from the end effector of FIG. 64.

After the retainer assembly 19060 has been attached to the staple cartridge 19050 and the anvil 19040 has been closed, the first tissue thickness compensator 19002 can be attached to the anvil 19040 and the second tissue thickness compensator 19004 can be attached to the staple cartridge 19050. As described above, the retention force retaining the first tissue thickness compensator 19002 to the retainer 19000 can be less than the retention force holding the first tissue thickness compensator 19002 to the anvil 19040. Thus, when the anvil 19040 is reopened, the first tissue thickness compensator 19002 can detach from the retainer 19000 and remain with the anvil 19040, as shown in FIG. 67. As also described above, the retention force retaining the second tissue thickness compensator 19004 to the retainer 19000 can be less than the retention force holding the first tissue thickness compensator 19004 to the staple cartridge 19050. Thus, when the retainer 19000 is removed in the directions of arrows C and D in FIG. 67, the retainer 19000 can detach from the second tissue thickness compensator 19004. The surgical stapler shown in FIG. 67 includes the first tissue thickness compensator 19002 attached to the anvil 19040 and the second tissue thickness compensator 19004 attached to the staple cartridge 19050 and is ready for use.

FIGS. 390-396 show the retainer 19000 being used with a first tissue thickness compensator 19002 and a second tissue thickness compensator 19004. In various embodiments, the retainer 19000 may also be used with only one of the first tissue thickness compensator 19002 and the second tissue thickness compensator 19004. For example, the first tissue thickness compensator 19002 may be omitted.

Figure 68:
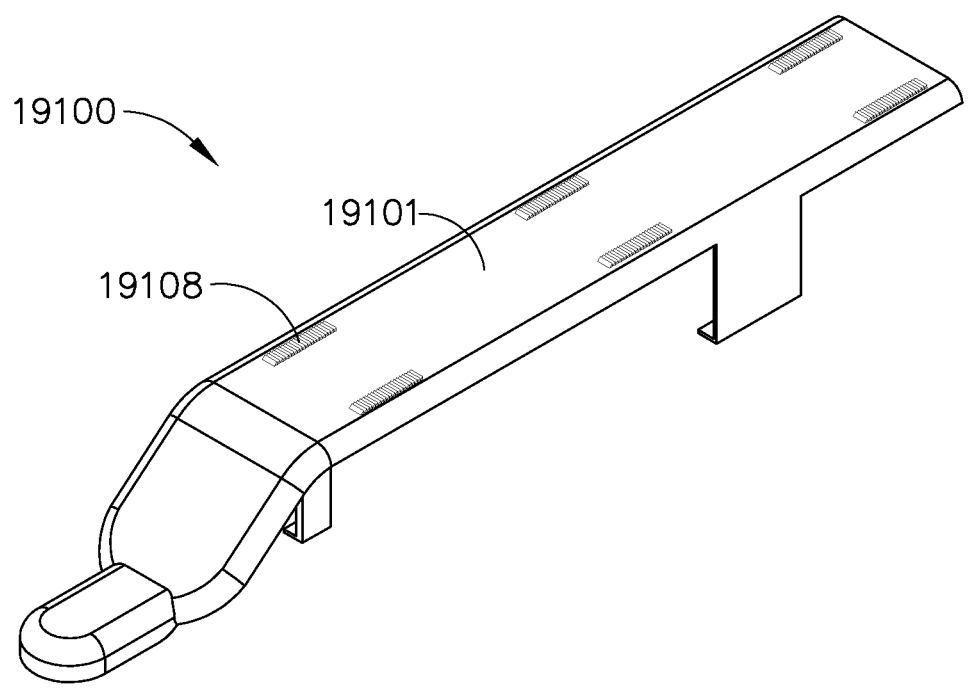
FIG. 68 is a perspective view of a retainer.
Figure 69:
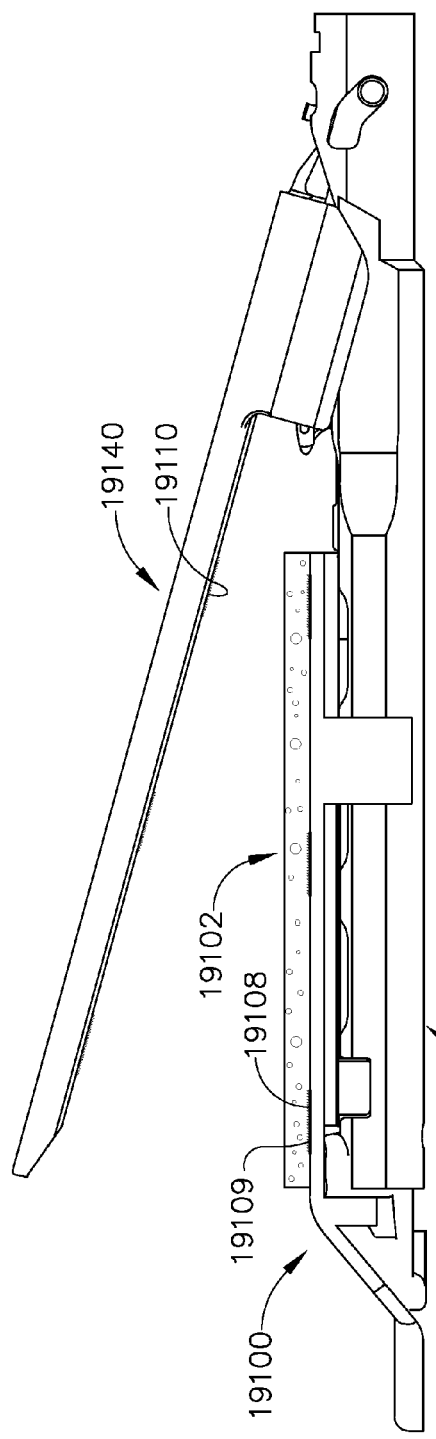
FIG. 69 is a side view of the retainer of FIG. 68 with tissue thickness compensators attached to bottom and top surfaces thereof illustrating one of the tissue thickness compensators engaged with a staple cartridge in a surgical stapler comprising an anvil.
Figure 70:
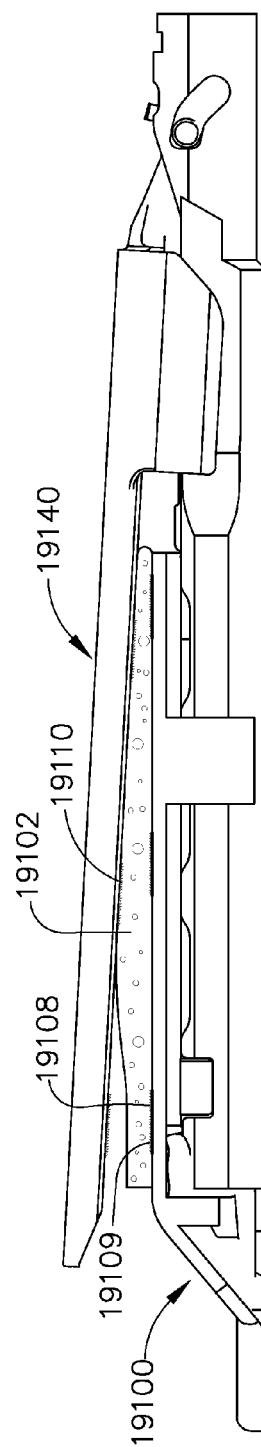
FIG. 70 is a side view illustrating the anvil of FIG. 69 in a closed position.

FIGS. 68-70 show an embodiment of a retainer 19100 that can include engagement features 19108 on a surface 19101. As shown in FIGS. 69 and 70, the engagement features 19108 on the retainer 19100 engage co-operating engagement features 19109 on a first tissue thickness compensator 19102.

Figure 71:
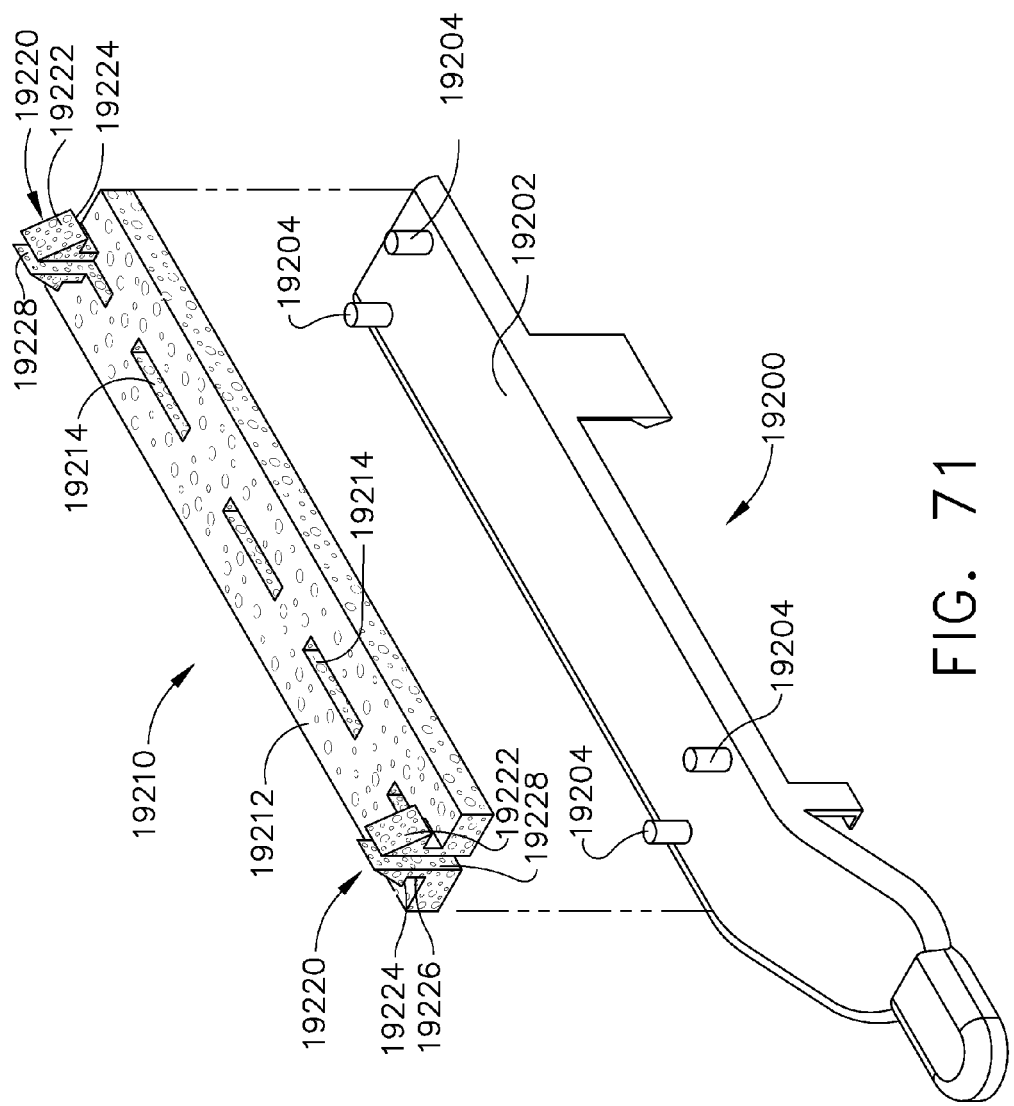
FIG. 71 is an exploded perspective view of a retainer and a tissue thickness compensator in accordance with at least one embodiment.
Figure 72:
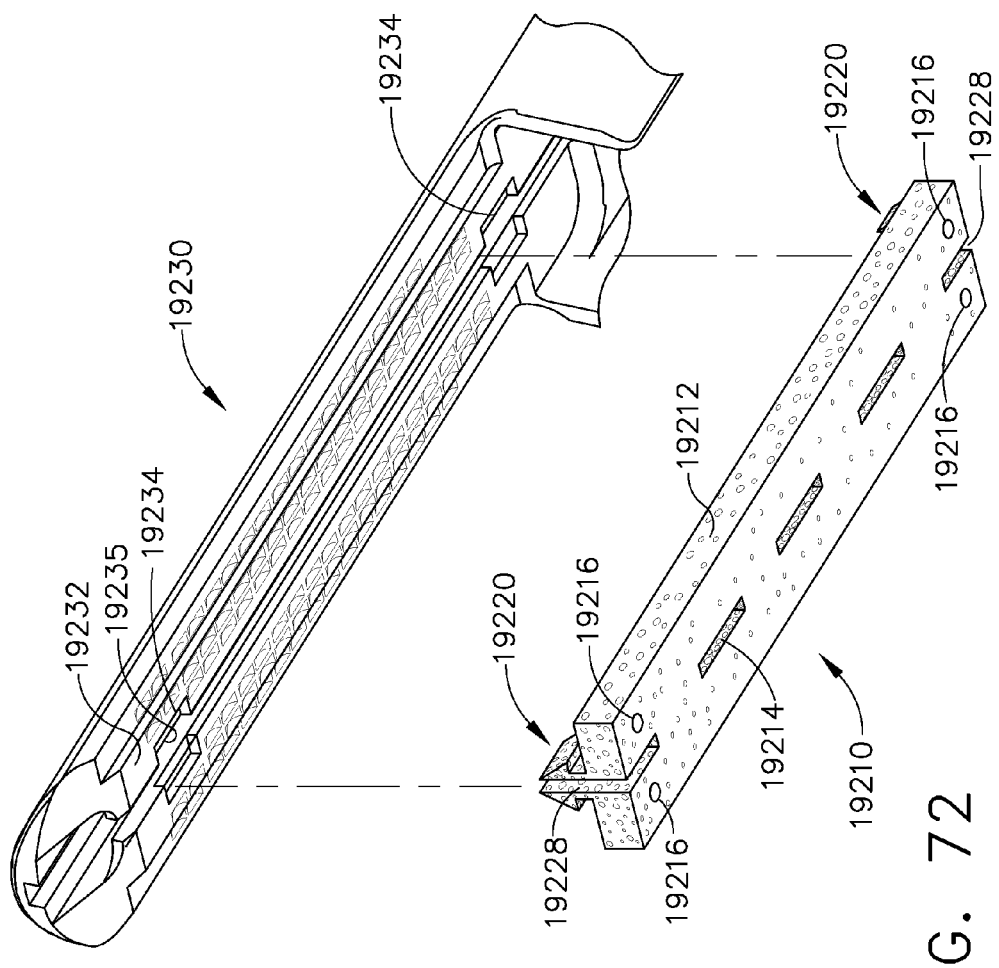
FIG. 72 is an exploded perspective view of the tissue thickness compensator of FIG. 71 and an anvil of a surgical stapler.
Figure 73:
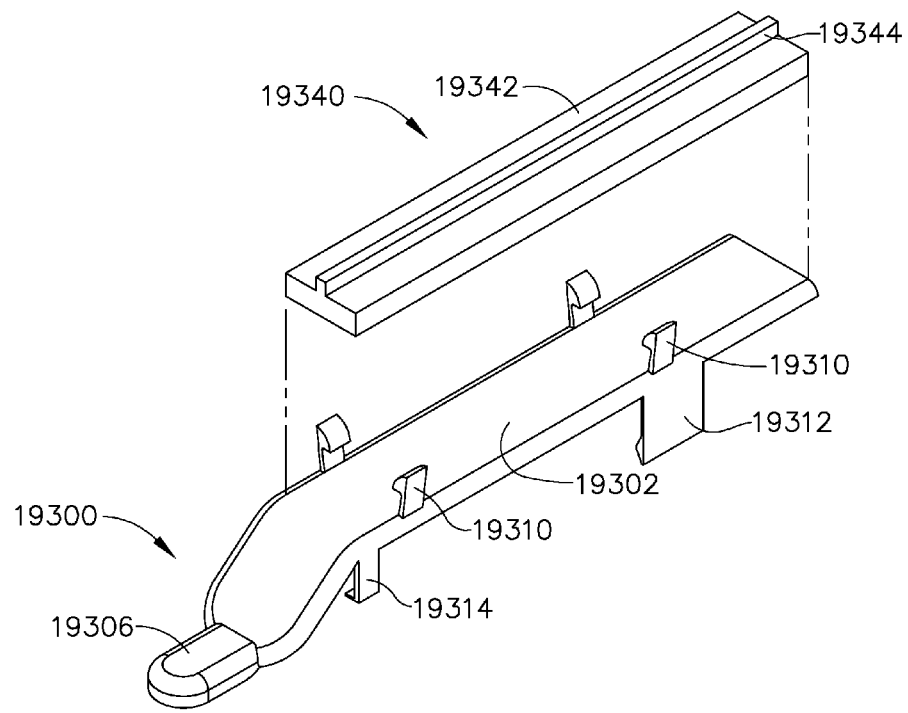
FIG. 73 is an exploded top perspective view of a retainer and a tissue thickness compensator in accordance with at least one embodiment.
Figure 74:
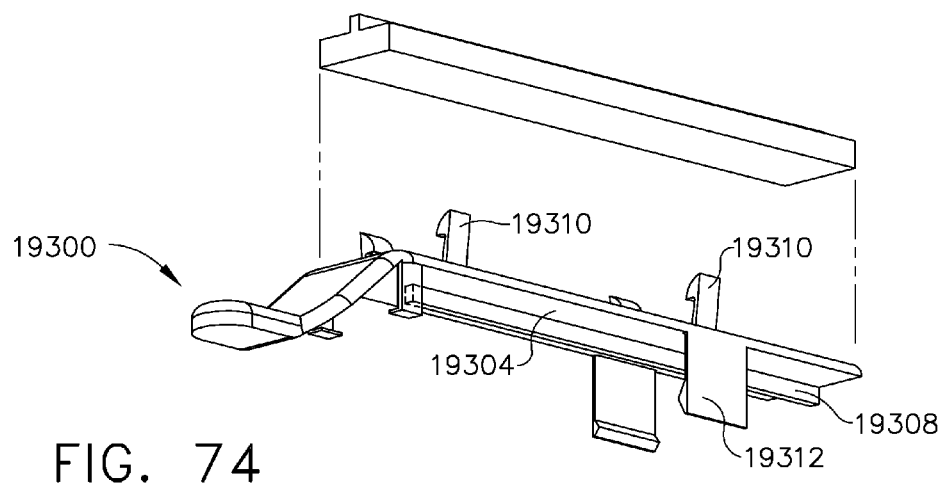
FIG. 74 is an exploded bottom perspective view of the retainer and tissue thickness compensator of FIG. 73.

FIGS. 71 and 72 show an embodiment of a retainer 19200 that may include a surface 19202 configured to align and attach a tissue thickness compensator 19210 to an anvil 19230. The retainer 19200 may include alignment pegs 19204 extending from the surface 19202. The retainer 19200 shown in FIGS. 71 and 72 includes four alignment pegs 19204, but more or fewer alignment pegs 19204 may be present. Referring to FIG. 72, the tissue thickness compensator 19210 can include a body 19212 that includes holes 19216 that can be located such that they that correspond to the locations of the alignment pegs 19204 extending from the retainer 19200. Each hole 19216 in the tissue thickness compensator 19210 fits over an alignment peg 19204, and owing to a close fit between the holes 19216 and the pegs 19204, the tissue thickness compensator 19210 can be aligned with the retainer 19200. In various embodiments, each hole 19216 may be slightly smaller than its corresponding peg 19204 such that each hole 19216 stretches when placed on its peg 19204. Such stretching can hold the holes 19216 on the pegs 19204. In certain embodiments, each hole 19216 may include an adhesive therein to create a releasable bond between the pegs 19204 and the tissue thickness compensator 19210.

The tissue thickness compensator 19220 may include tabs 19220 extending from a body 19212 of the tissue thickness compensator 19220 which can be configured to be received by slots 19234 in an anvil 19230. In various embodiments, the slots 19234 in the anvil 19230 may be located in a staple forming surface 19232, for example. After the retainer 19200 has been attached to a staple cartridge, similar to the embodiments described above, the anvil 19230 can be closed against the tissue thickness compensator 19210 on the retainer 19200. As the anvil 19230 is closed, referring to FIG. 72, the tabs 19220 on the tissue thickness compensator 19210 can engage the slots 19234, thereby attaching the tissue thickness compensator 19210 to the anvil 19230. Referring primarily to FIG. 71, each tab 19220 may include a tapered portion 19222 that guides the tab 19220 into the slots 19234 of the anvil 19230. The tapered portion 19222 can include sloped walls and may increase in cross-sectional area along the length thereof. A base portion 19226 of each tab 19220 may have a smaller cross-sectional area than the largest cross-sectional area of the tapered portion 19222. In various embodiments, the tapered portion 19222 may comprise a lock surface 19224 wherein, when a tab 19220 enters a slot 19234, the lock surface 19224 can catch on a lip 19235 in the slot 19234. As a result, the lock surface 19224 can hold the tab 19220 within the slot 19234 and thereby hold the tissue thickness compensator 19210 to the anvil 19230. Slots 19228 defined in the tissue thickness compensator 19210 and extending between the tabs 19220 can enable the tabs 19220 to flex inwardly and fit within the slots 19234. In various embodiments, the tabs 19220 being held with the slots 19234 can define a first retention force that retains the tissue thickness compensator 19210 to the anvil 19230 and the holes 19216 in the tissue thickness compensator 19210 being held on the pegs 19204 can define a second retention force. In various embodiments, the first retention force can be greater than the second retention force such that the tissue thickness compensator 19210 can remain attached to the anvil 19230 and separate from the retainer 19200 when the retainer 19200 is removed from the end effector.

The body 19212 of the tissue thickness compensator 19210 in FIGS. 71 and 72 also may define slots 19214 therewithin. The slots 19214 may be aligned along a longitudinal axis of the tissue thickness compensator 19210. For example, the slots 19214 may be arranged on a longitudinal axis such that the slots 19214 are aligned with a longitudinal path of a cutting blade of the surgical device when the tissue thickness compensator 19210 is attached to an anvil 19230. The slots 19214 may reduce the amount of energy required by the cutting blade to cut through the tissue thickness compensator 19210.

FIGS. 73-83 show an embodiment of a retainer 19300 that includes clips 19310 which are configured to retain a tissue thickness compensator 19340 on a first surface 19302 of the retainer 19300. When an anvil 19360 is closed on the retainer 19300, similar to the above, the anvil 19360 can push and displace the clips 19310 outwardly and, as a result, disengage the retainer 19300 from the tissue thickness compensator 19340. In various embodiments, the tissue thickness compensator 19340 can attach to the anvil 19360 when the anvil 19360 is pressed against the tissue thickness compensator 19340 and moved away from the retainer 19300 when the anvil 19360 is reopened.

The retainer 19300 may include staple cartridge mounting clips 19312 and 19314 which can be similar to those described above with respect to FIGS. 61-70. In addition to the first surface 19302 described above, the retainer 19300 also may include a second surface 19304 that may be configured to carry a second tissue thickness compensator. In various embodiments, the second surface 19304 may include an alignment feature, such as, for example, a raised ridge 19308. The raised ridge 19308 may engage a slot in a second tissue thickness compensator and/or a slot in a staple cartridge 19370, for example.

Figure 75:
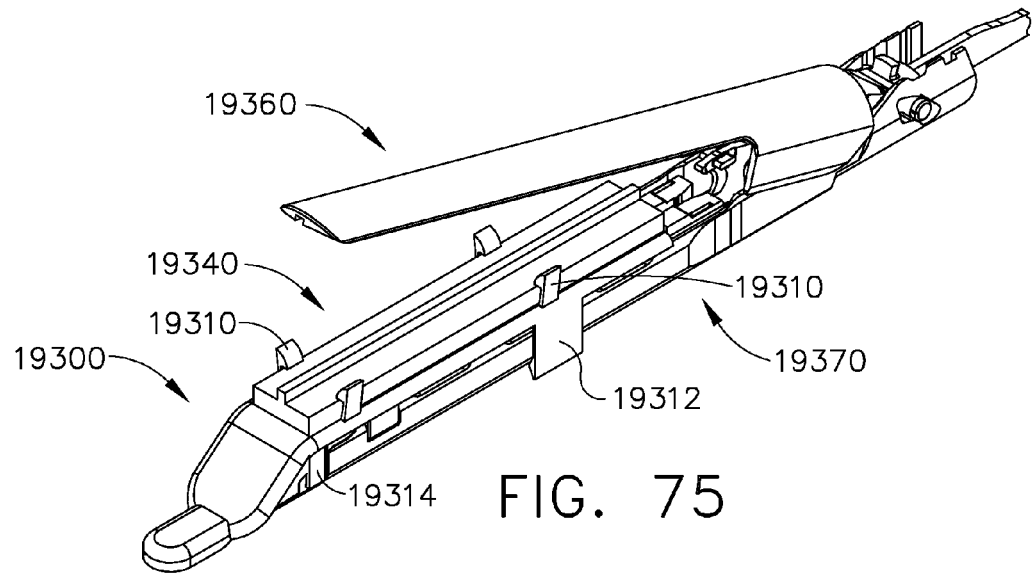
FIG. 75 is a top perspective view of the retainer and tissue thickness compensator of FIG. 73 engaged with a surgical stapler.
Figure 76:
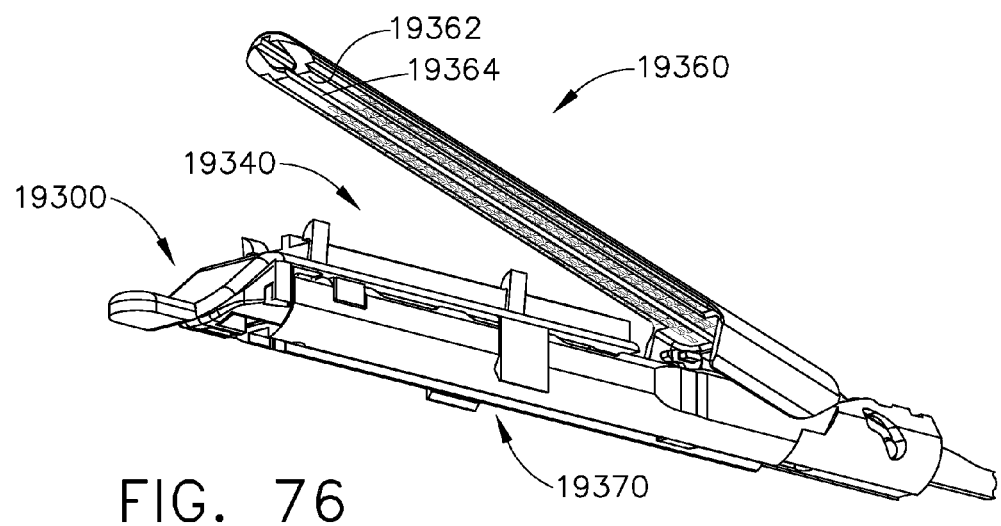
FIG. 76 is a bottom perspective view of the retainer and tissue thickness compensator of FIG. 73 engaged with the surgical stapler of FIG. 75.
Figure 77:
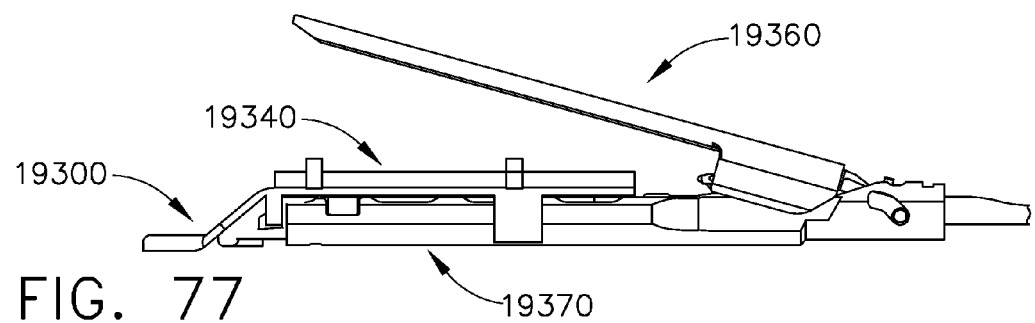
FIG. 77 is a side view of the retainer and tissue thickness compensator of FIG. 73 engaged with the surgical stapler of FIG. 75.
Figure 78:
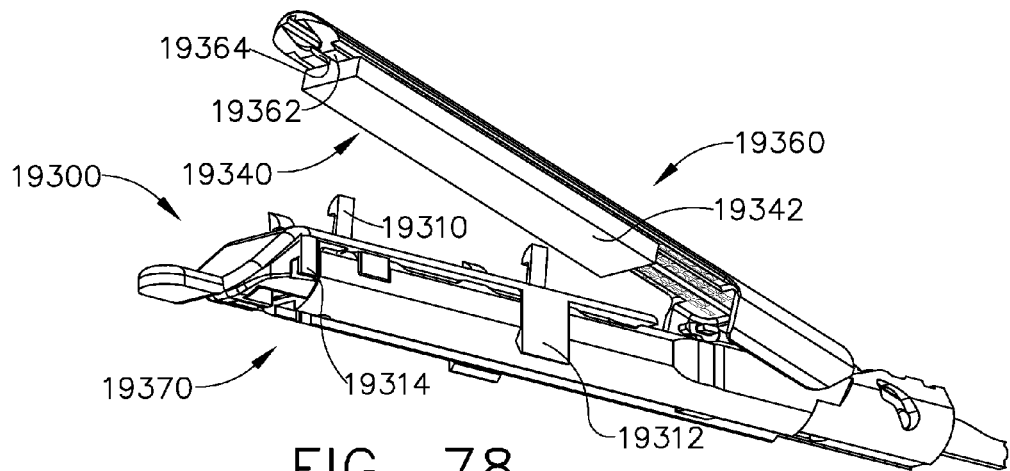
FIG. 78 is a bottom perspective view of the retainer and tissue thickness compensator of FIG. 73 illustrating the tissue thickness compensator attached to the anvil of the surgical stapler of FIG. 75.
Figure 79:
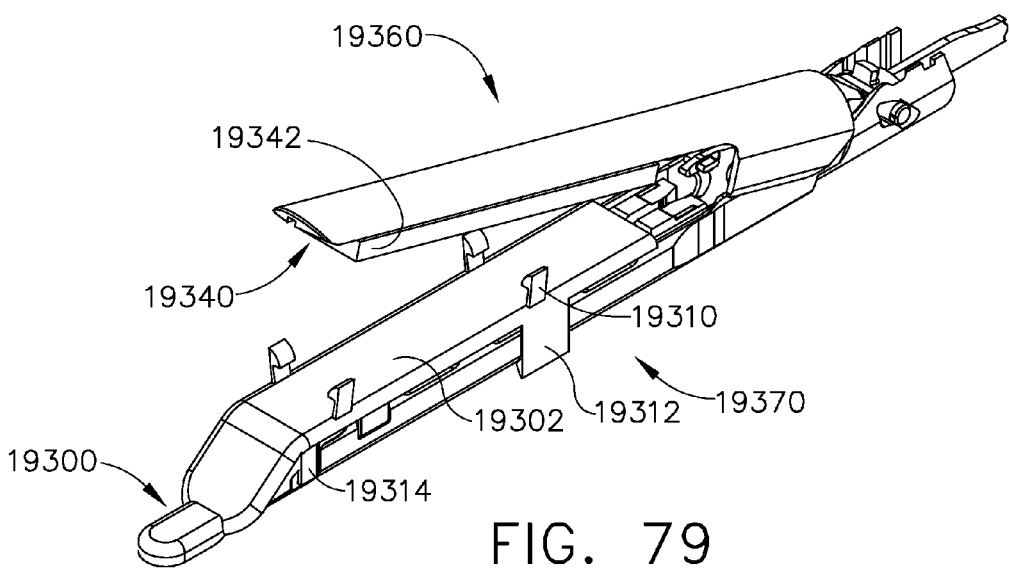
FIG. 79 is a top perspective view of the retainer and tissue thickness compensator of FIG. 73 illustrating the tissue thickness compensator attached to the anvil of FIG. 78.
Figure 80:
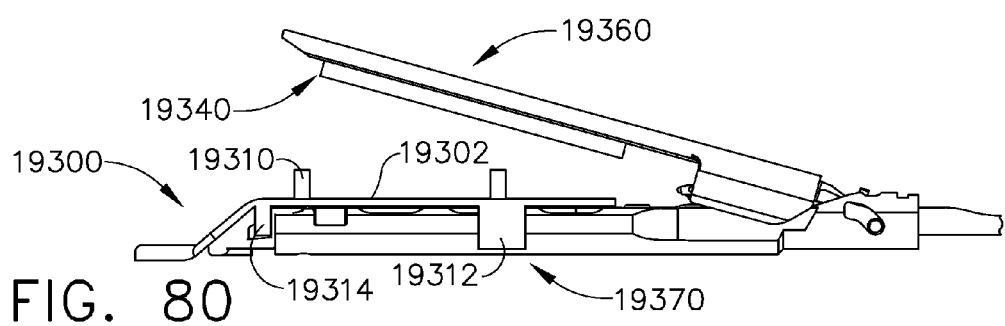
FIG. 80 is a side view of the tissue thickness compensator of FIG. 73 attached to the anvil of FIG. 78.
Figure 81:
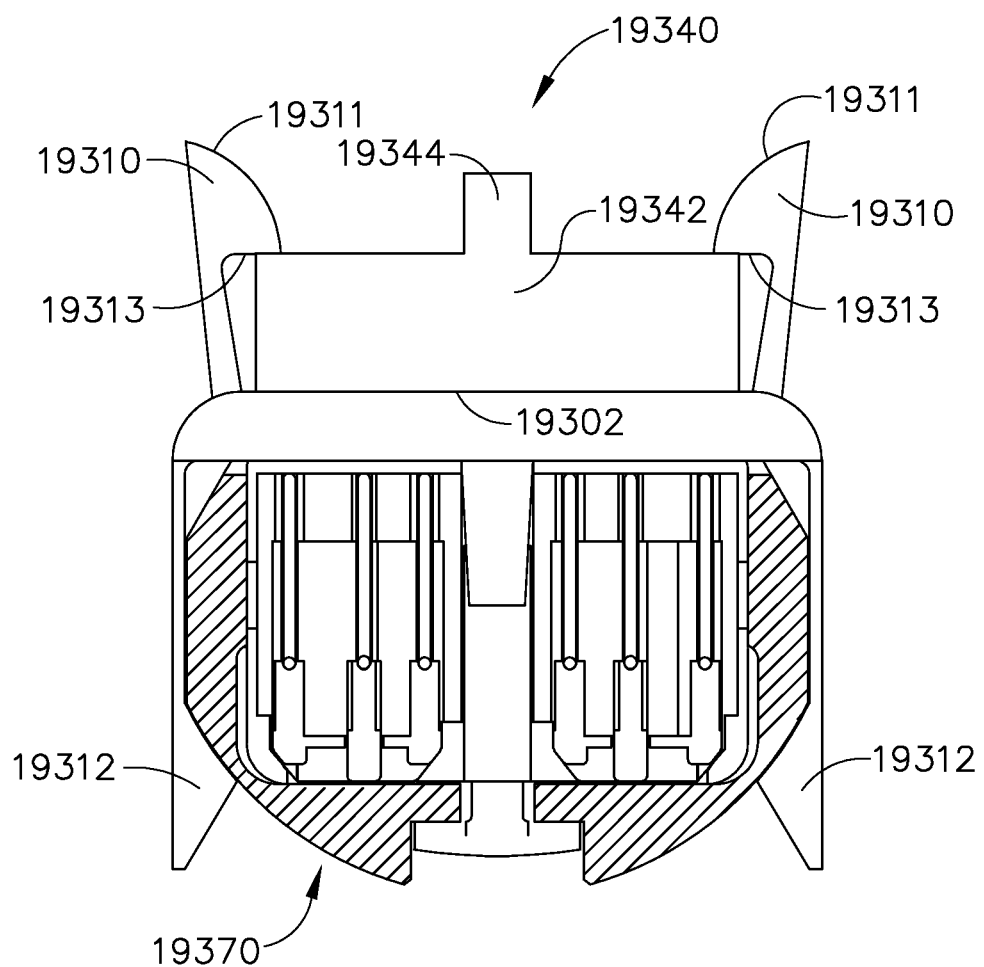
FIG. 81 is a cross-sectional view of the retainer and tissue thickness compensator of FIGS. 73 and 74 attached to a staple cartridge and channel of a surgical stapler.
Figure 82:
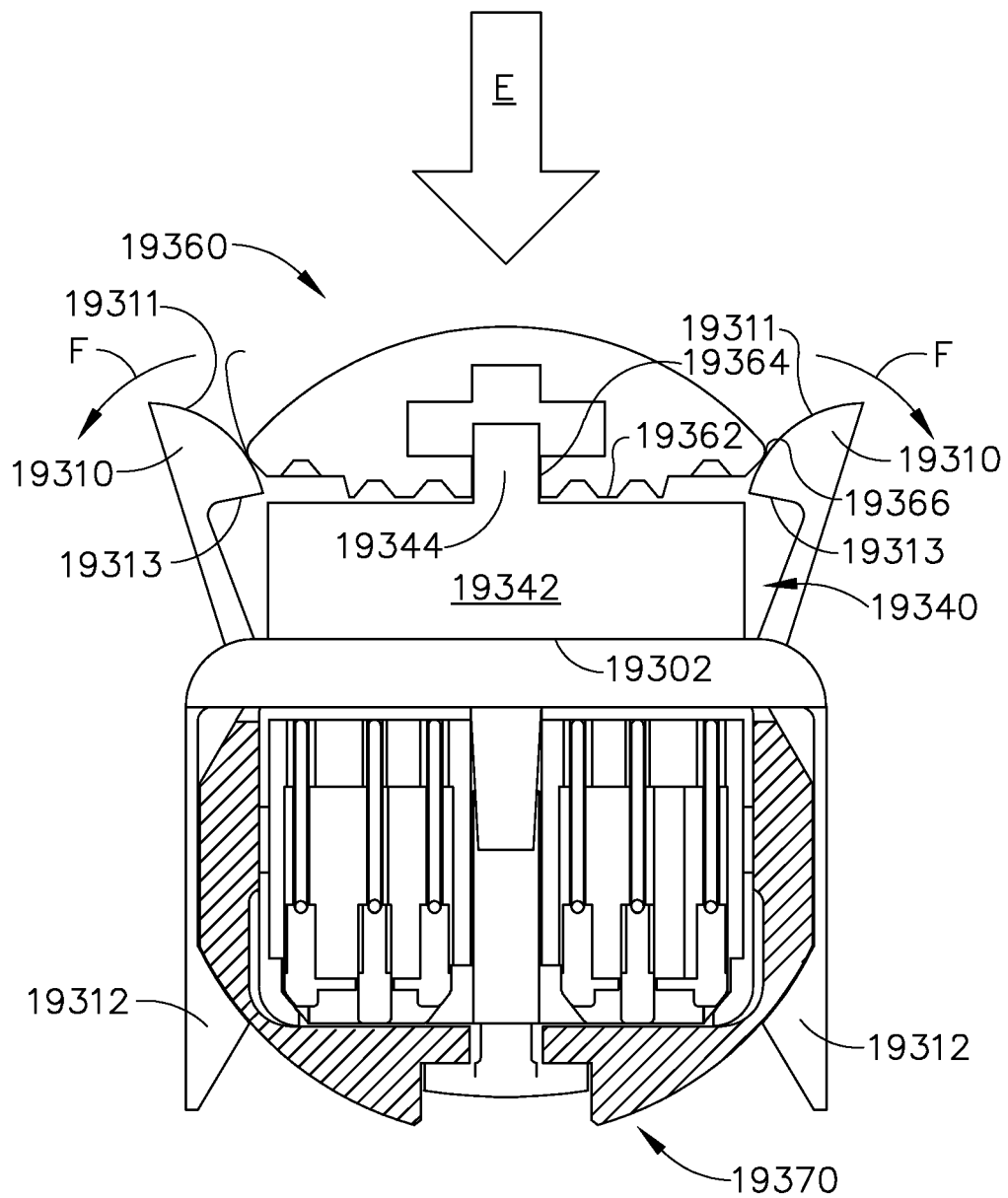
FIG. 82 is a cross-sectional view of the retainer and tissue thickness compensator of FIGS. 73 and 74 attached to the staple cartridge and channel of the surgical stapler of FIG. 81 illustrating an anvil of the surgical stapler engaged with the tissue thickness compensator.
Figure 83:
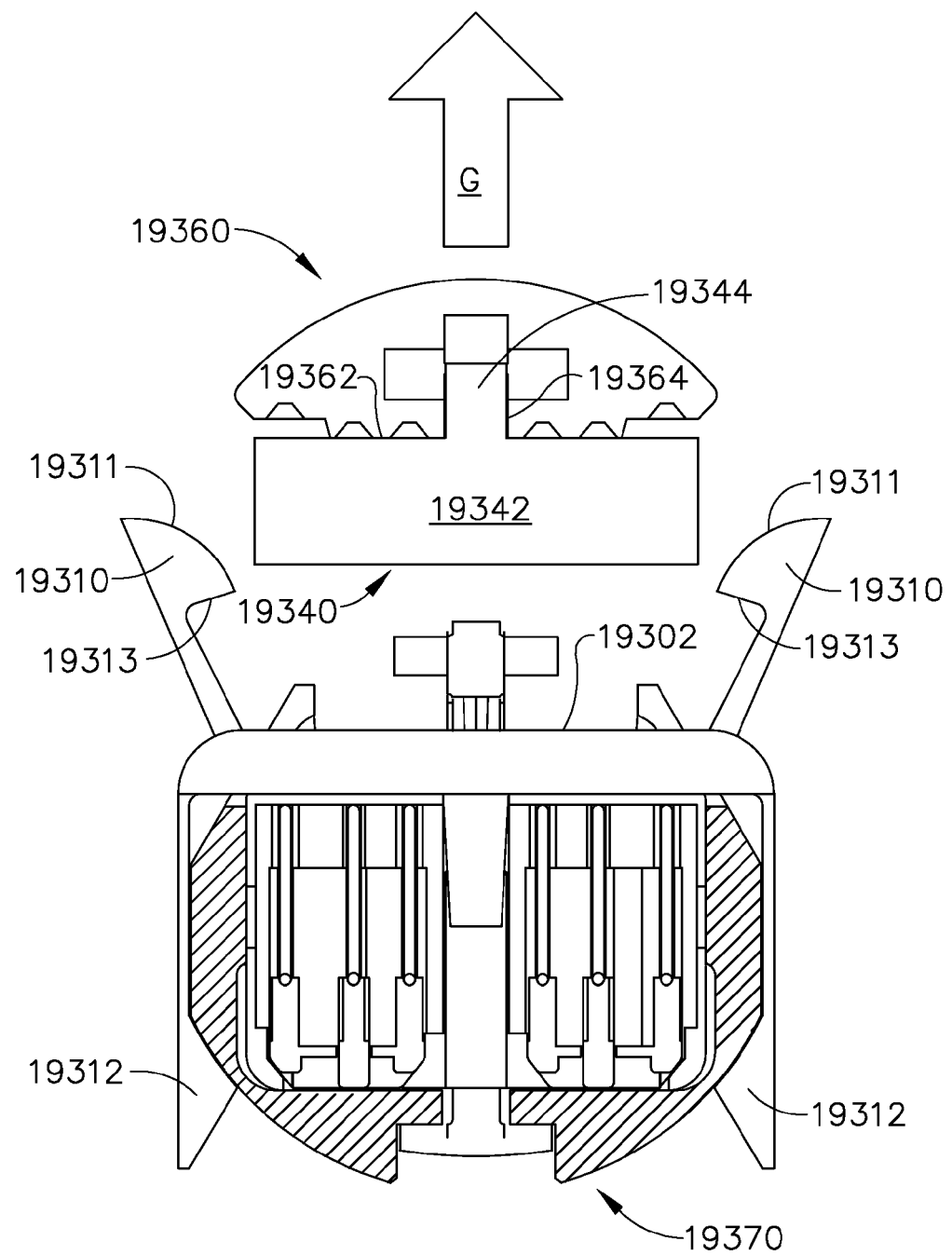
FIG. 83 is a cross-sectional view of the tissue thickness compensator of FIG. 73 attached to the anvil of the surgical stapler and being moved away from the retainer.

Referring to FIGS. 75-77, in use, the retainer 19300 may be attached to a staple cartridge 19370 by clips 19314 and 19312. The first tissue thickness compensator 19340 can be positioned on the first surface 19302 at the retainer 19300 and can be held in place by clips 19310. Referring primarily to FIGS. 81-83, each clip includes a flat 19313 that can clamp the first tissue thickness compensator 19340 against the first surface 19302 of the retainer 19300. Each clip 19310 can include an inward-facing tapered or curved surface 19311. As the anvil 19360 moves in the direction of arrow E, referring to FIG. 82, edges 19366 of the anvil 19360 can contact the inward-facing curved surfaces 19311 of the clips 19310. As the anvil 19360 continues to move in the direction of arrow E, interference between the edges 19366 of the anvil 19360 and the curved surfaces 19311 of the clips 19310 can push the clips 19310 outwardly in the direction of arrow F, as illustrated in FIG. 82. As the clips 19310 move in the direction of arrow F, the first tissue thickness compensator 19340 is freed from the flats 19313 of the clips 19310.

As the anvil 19360 continues to move in the direction of arrow E, it also contacts and attaches to the tissue thickness compensator 19340. For example, as the anvil 19360 moves in the direction of arrow E, an engagement feature, such as, for example, a raised ridge 19344, on the tissue thickness compensator 19340 engages a channel 19364 in the anvil 19360. The raised ridge 19344 may be configured to have an interference fit with the channel 19364 such that the tissue thickness compensator 19340 becomes attached to the anvil 19360. The tissue thickness compensator 19340 may include an adhesive that adheres to surfaces of the anvil 19360. In at least one embodiment, the raised ridge 19344 may include an adhesive that adheres to surfaces of the channel 19364. Likewise, surfaces of the body 19342 of the tissue thickness compensator 19340 may include an adhesive that adheres to a surface 19362 of the anvil 19360. After the tissue thickness compensator 19340 is attached to the anvil 19360, the tissue thickness compensator 19340 can lift from the retainer 19300 and remain with the anvil 19360 as the anvil 19360 returns to its open position by moving in the direction of arrow G, as illustrated in FIG. 83.

FIG. 84 shows a cross-sectional side view of an embodiment of a retainer 19400. A first tissue thickness compensator 19410 is positioned on a first side 19402 of the retainer 19400 and a second tissue thickness compensator 19420 is positioned on an opposing second side 19404 of the retainer 19400. The retainer 19400 defines one or more holes 19406 extending therethrough. The first tissue thickness compensator 19410 and the second tissue thickness compensator 19420 are connected through the holes by connectors 19430 which extend through the holes 19406. In various embodiments, the first tissue thickness compensator 19410, the second tissue thickness compensator 19420, and the connectors 19430 all may be formed of a unitary material. For example, the first tissue thickness compensator 19410, the second tissue thickness compensator 19420, and the connectors 19430 may be overmolded onto the retainer 19400. In various other embodiments, the connectors 19430 may be formed as part of one of the tissue thickness compensators, such as, for example, the first tissue thickness compensator 19410. The connectors 19430 may be passed through the holes 19406 and then attached to the remaining tissue thickness compensator, such as, for example, the second tissue thickness compensator 19420. The connectors 19430 may be attached to the second tissue thickness compensator 19420, for example, by using an adhesive or by using an interference fit between an end of the connector and a receiving port (not shown) in the second tissue thickness compensator 19420. In various embodiments, the connectors 19430 may be separate components that are placed into the holes 19406 and to which the first tissue thickness compensator 19410 and the second tissue thickness compensator 19410 may be attached, for example, by using adhesives or interference fits between ends of the connectors 19430 and receiving ports in the first tissue thickness compensator 19410 and the second tissue thickness compensator 19420.

Figure 89:
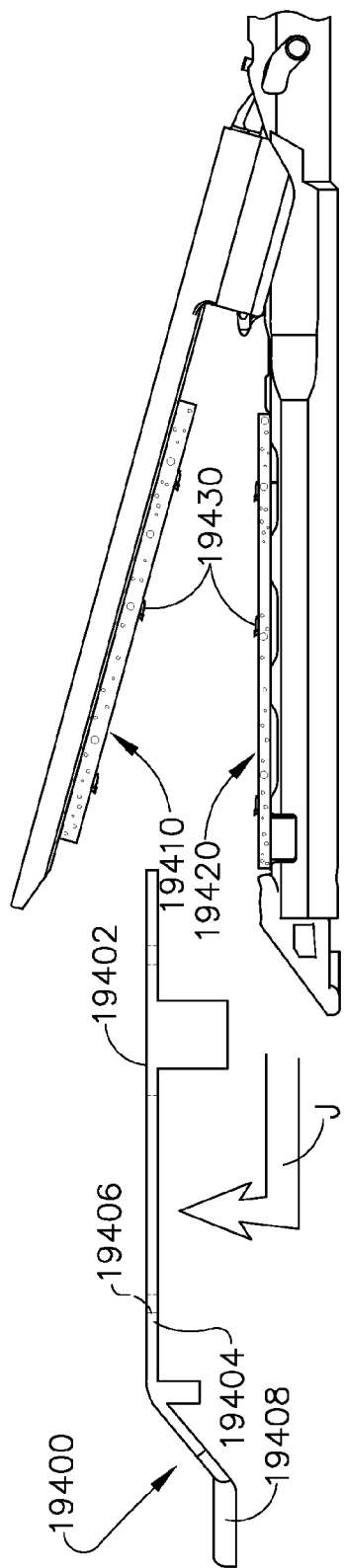
FIG. 89 is a side view of the retainer removed from the tissue thickness compensators of FIG. 84.
Figure 90:
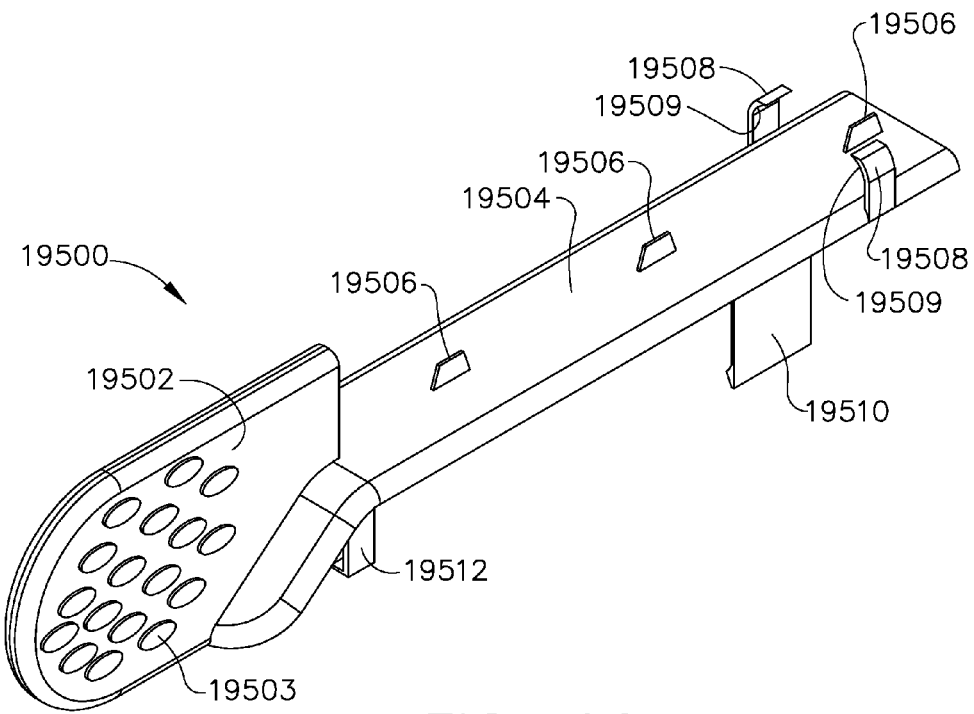
FIG. 90 is a perspective view of a retainer configured to engage an anvil of a surgical stapler in accordance with at least one embodiment.
Figure 91:
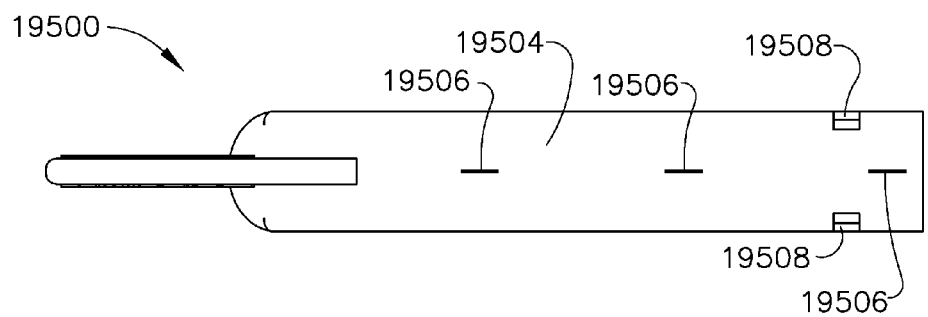
FIG. 91 is a top view of the retainer of FIG. 90.
Figure 92:
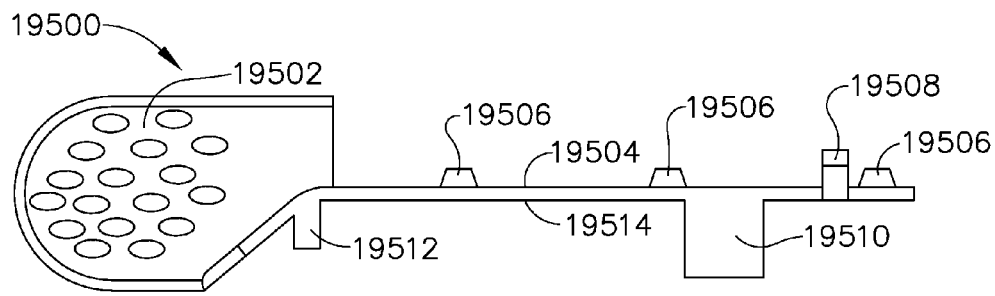
FIG. 92 is a side view of the retainer of FIG. 90.
Figure 93:
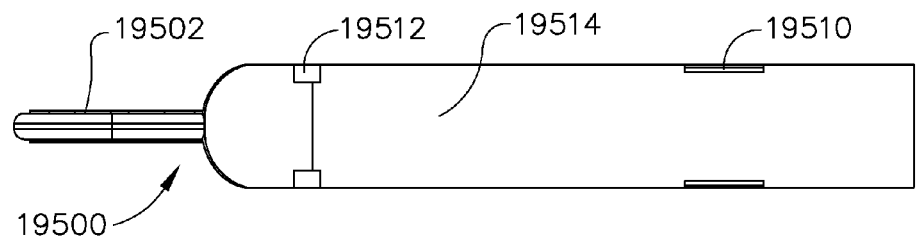
FIG. 93 is a bottom view of the retainer of FIG. 90.

After the retainer 19400 has been placed on a staple cartridge 19450, for example, an anvil 19440 of the surgical device can be moved in the direction of arrow H into a closed position. An adhesive and/or engagement features on a surface 19414 of the first tissue thickness compensator 19410 can attach the first tissue thickness compensator 19410 to the anvil 19440 when the anvil 19440 closes. Likewise, an adhesive and/or engagement features on a surface 19424 of the second tissue thickness compensator 19420 can attach the second tissue thickness compensator 19420 to the staple cartridge 19450. After the anvil 19440 is closed and the first and second tissue thickness compensators 19410 and 19420 are attached to the anvil 19440 and staple cartridge 19450, respectively, the retainer 19400 may be pulled in the direction of arrow I (FIG. 88) to remove the retainer 19400 from between the first tissue thickness compensator 19410 and the second tissue thickness compensator 19420 and to break the connectors 19430. As shown in FIG. 89, after the connectors 19430 are broken and the retainer 19400 has been removed, the anvil 19440 may be reopened, and the first tissue thickness compensator 19410 will be attached to the anvil 19440 and the second tissue thickness compensator 19420 will be attached to the staple cartridge 19450.

In various embodiments, a proximal portion 19407 of each hole 19406 in the retainer 19400 may include a cutting edge. When the retainer is pulled in the direction of arrow I (FIG. 88), a pulling force is transmitted through the proximal portion 19407 of the holes 19406 to break the connectors. A cutting edge at the proximal portion 19407 of each hole 19406 will concentrate the transmitted force on a relatively small area of each connector. As a result, the connectors will break more easily and a lower pulling force may be required to remove the retainer 19400 from between the first tissue thickness compensator 19410 and the second tissue thickness compensator 19420.

As described above, a retainer assembly can comprise a retainer positioned between a first tissue thickness compensator and a second tissue thickness compensator wherein, after the two tissue thickness compensators have been inserted into and attached to an end effector of a surgical instrument, the retainer can be pulled from between the tissue thickness compensators and removed from the end effector. In certain embodiments, the retainer can provide a barrier between the first and second tissue thickness compensators. Once the retainer is removed from between the first and second tissue thickness compensators, substances in and/or on the first tissue thickness compensator can react with substances in and/or on the second tissue thickness compensator, for example. In some embodiments, one or both of the tissue thickness compensators can include a film that can encase substances within the tissue thickness compensators. In certain embodiments, the films can be attached to the retainer wherein, when the retainer is pulled from between the tissue thickness compensators, as described above, the retainer can pull the films away from the tissue thickness compensators to expose the substances contained therein. At such point, the substances within each of the tissue thickness compensators can interact with each other.

FIGS. 90-100 illustrate an embodiment of a retainer that engages an anvil of a surgical device, such as, for example, a surgical stapler. The retainer may align a first tissue thickness compensator with the anvil and a second tissue thickness compensator with a staple cartridge. Closing the anvil causes the first tissue thickness compensator to attach to the anvil and the second tissue thickness compensator to attach to the staple cartridge. The retainer also may carry the staple cartridge with a tissue thickness compensator optionally disposed between the retainer and the staple cartridge. Closing the anvil causes the staple cartridge to attach to a channel of the surgical stapler and causes the first tissue thickness compensator to attach to the anvil.

FIGS. 90-93 show an embodiment of a retainer 19500. The retainer 19500 includes a grip 19502 by which a surgeon, nurse, technician, or other person may manipulate the retainer 19500. The grip 19502 may include a textured surface, such as raised portions 19503, for example, which may provide a better gripping surface. In various embodiments, the retainer 19500 can include a surface 19504 on which a tissue thickness compensator may be mounted. The surface 19504 may include one or more projections 19506 wherein the projections 19506 may engage recesses in the tissue thickness compensator and align the tissue thickness compensator relative to the surface 19504 of the retainer 19500. The recesses in the tissue thickness compensator may be slightly smaller than the projections 19506 such that, when engaged with the recesses, the projections 19506 can hold the tissue thickness compensator to the surface 19504. In various embodiments, the projections 19506 may pass through holes in the tissue thickness compensator and engage a slot, such as, for example, a cutting blade slot 19558 in anvil 19550 shown in FIG. 95, thereby aligning the tissue thickness compensator with the retainer 19500 and also providing additional alignment of the retainer 19500 with the anvil 19550. The tissue thickness compensator 19540 may include an adhesive and/or engagement features, described above, on a surface 19542 for attaching the tissue thickness compensator to an anvil 19550.

Figure 94:
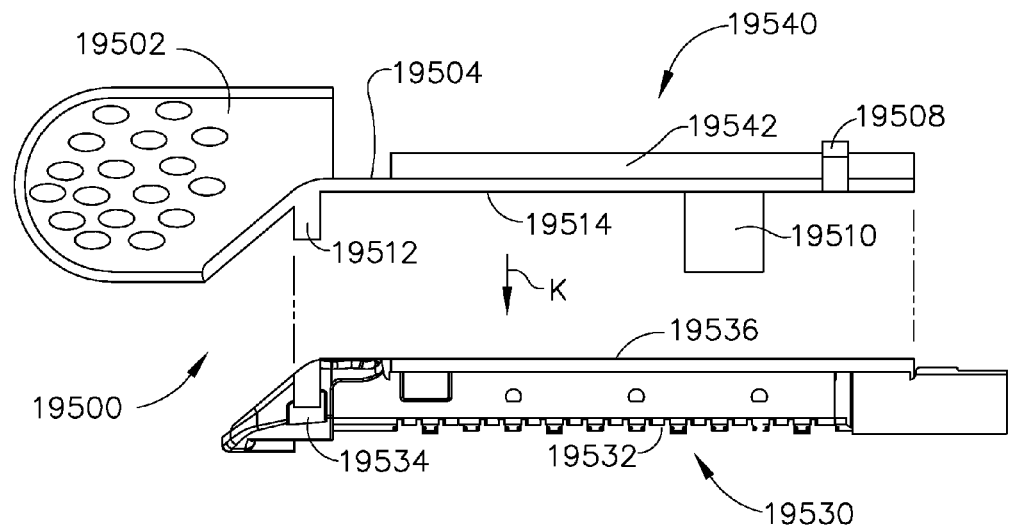
FIG. 94 illustrates a retainer assembly comprising the retainer of FIG. 90 and a tissue thickness compensator being attached to a staple cartridge for a surgical stapler.

As shown in FIG. 94, in various embodiments, a staple cartridge 19530 may be attached to the retainer 19500. The staple cartridge 19530 can be attached to the retainer 19500 by clips 19510 and 19512 extending from the retainer 19500. Clips 19512 on the retainer 19500 can engage a slot 19534 in the staple cartridge 19530. Clips 19510 of the retainer 19500 can surround the bottom 19532 of the staple cartridge 19532. In various embodiments, a second tissue thickness compensator may be attached to the staple cartridge 19530. In at least one embodiment, a second tissue thickness compensator may be attached to a staple deck 19536 of the staple cartridge 19530.

As shown in FIGS. 95 and 96, a retainer assembly 19590 comprising the retainer 19500, a tissue thickness compensator 19540, and a staple cartridge 19530, can slide onto the anvil 19550 of a surgical device, such as a surgical stapler, in the direction of arrow L. The guide tabs 19508 on the retainer 19500 can surround edges 19552 of the anvil 19550 and position the retainer assembly 19590 relative to the anvil 19550. After the retainer assembly 19590 is engaged on the anvil 19550, as shown in FIGS. 97 and 98, the anvil can be closed in the direction of arrow M. Closure of the anvil 19550 can position the staple cartridge 19530 in a channel 19560 of the surgical device. In at least one embodiment, closure of the anvil 19550 can cause the clips 19510 extending from the retainer 19500 to engage a ridge 19562 of the channel 19560 in order to securely position the staple cartridge 19530 in the channel 19560. When the anvil 19550 is reopened in the direction of arrow N, referring now to FIGS. 99 and 100, the tissue thickness compensator 19540 can remain attached to the anvil 19550 and separates from the retainer 19500. The retainer 19500 then can be removed from the surgical instrument in the direction of arrow O (FIGS. 99 and 100) leaving the staple cartridge 19530 in the channel 19560 of the surgical device and a tissue thickness compensator 19540 attached to the anvil 19550.

Figure 101:
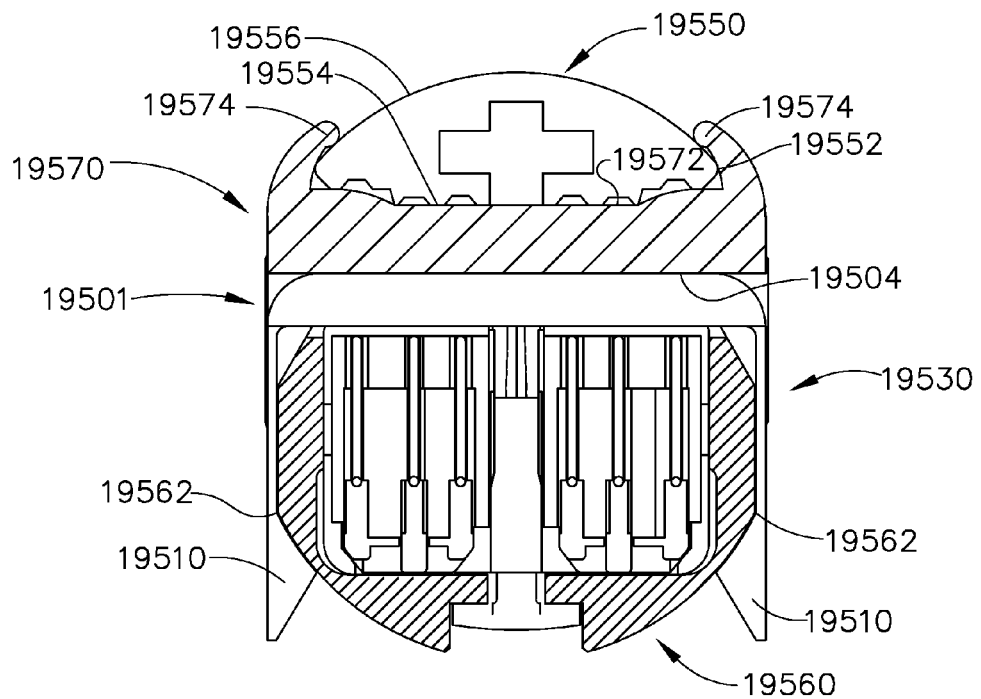
FIG. 101 is a cross-sectional view of a retainer including a tissue thickness compensator comprising protrusions or wings configured to engage an anvil of a surgical stapler.
Figure 102:
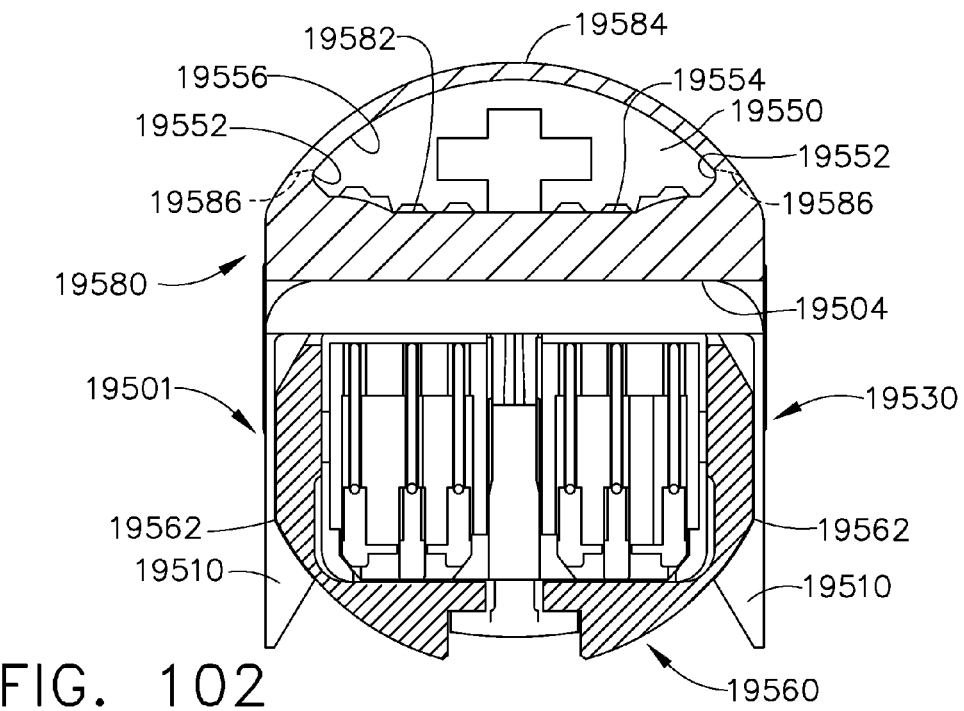
FIG. 102 is a cross-sectional view of a retainer including a tissue thickness compensator comprising a sock configured to engage an anvil of a surgical stapler.

FIGS. 101 and 102 show examples of two alternative embodiments of tissue thickness compensators 19570 and 19580, respectively. FIG. 101 is a cross-sectional view of a tissue thickness compensator 19570 attached to a retainer 19501 wherein the tissue thickness compensator 19570 can include protrusions 19574 which can contact edges 19552 of the anvil 19550 and partially surround an exterior surface 19556 of the anvil 19550. In various embodiments, the protrusions can grip the anvil 19550 and/or be attached to the anvil 19550 utilizing one or more adhesives. In order to release the tissue thickness compensator 19570 from the anvil 19550 after the compensator 19570 has been implanted against a patient's tissue, the protrusions 19574 can flex outwardly from the anvil 19550 thereby enabling the tissue thickness compensator 19570 to be pulled away from the anvil 19550. FIG. 102 is a cross-sectional view of a tissue thickness compensator 19580 attached to the retainer 19501 shown in FIG. 101. The tissue thickness compensator 19580 includes a sock 19584 that can surround the anvil 19550 to align the tissue thickness compensator 19580 with the anvil 19550 and/or to retain the tissue thickness compensator 19580 on the anvil 19550. In various embodiments, the sock 19584 can retain the tissue thickness compensator 19580 on the anvil 19550. In order to detach the sock 19584 from the anvil 19550, in various embodiments, the tissue thickness compensator 19580 can tear away from the sock 19584 at perforations 19586, for example. Thus, the sock 19584 can remain on the anvil 19550 while the remainder of the tissue thickness compensator 19580 can remain stapled to the patient tissue.

In certain embodiments, a tissue thickness compensator, such as tissue thickness compensator 19570, for example, can include an interior portion that comprises a biocompatible substance positioned therein. In various embodiments, the biocompatible substance can include an anti-inflammatory, a coagulant, and/or an antibiotic, for example. In various embodiments, a body, such as a wafer, for example can be inserted into the interior portion within the tissue thickness compensator. In at least one such embodiment, the wafer may be inserted through an open end of the tissue thickness compensator into a cavity defined therein. In certain embodiments, the wafer may be held within the cavity of the tissue thickness compensator by an interference fit. In certain embodiments, steps for assembling the wafer into the tissue thickness compensator can include a first step of heating the tissue thickness compensator such that the tissue thickness compensator expands. When the tissue thickness compensator expands, in various embodiments, the cavity defined therein can also expand. When the tissue thickness compensator is in an expanded state, according to a second step, the wafer may be inserted into the cavity. Then, as the tissue thickness compensator cools, according to a third step, the cavity can shrink onto the wafer and hold the wafer in place within the cavity.

Figure 103:
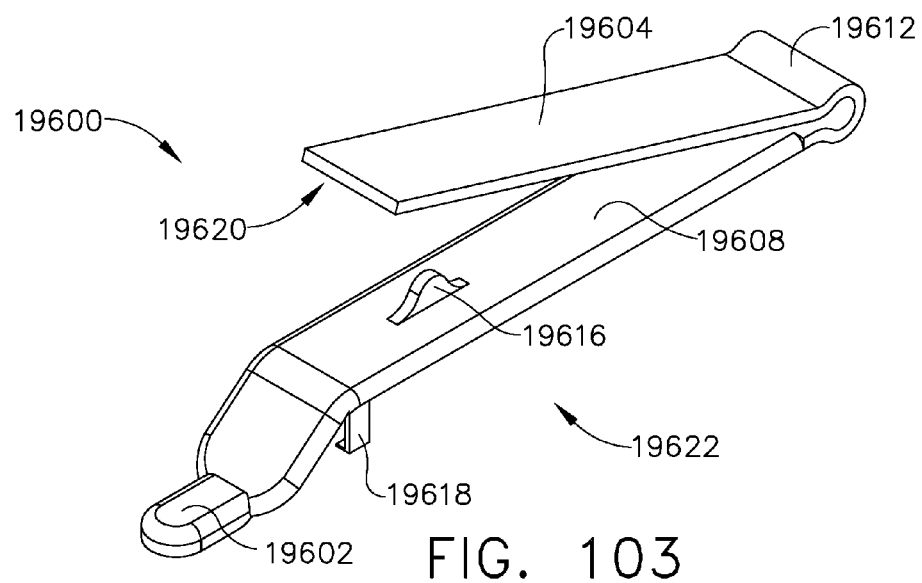
FIG. 103 is a perspective view of a retainer that includes two plates connected by a hinge according to at least one embodiment.
Figure 104:
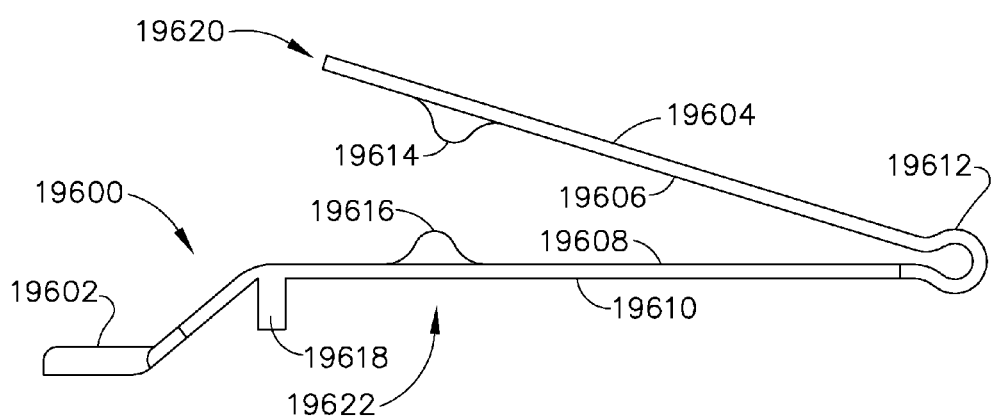
FIG. 104 is a side view of the retainer of FIG. 103.
Figure 107:
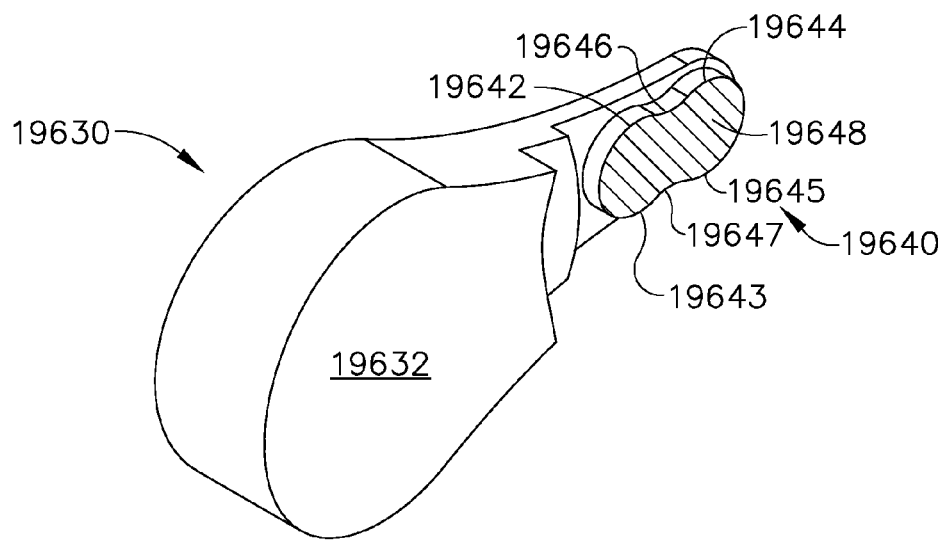
FIG. 107 is a rear perspective view of the insertion tool of FIG. 105 with a portion of the insertion tool removed for purposes of illustration.
Figure 108:
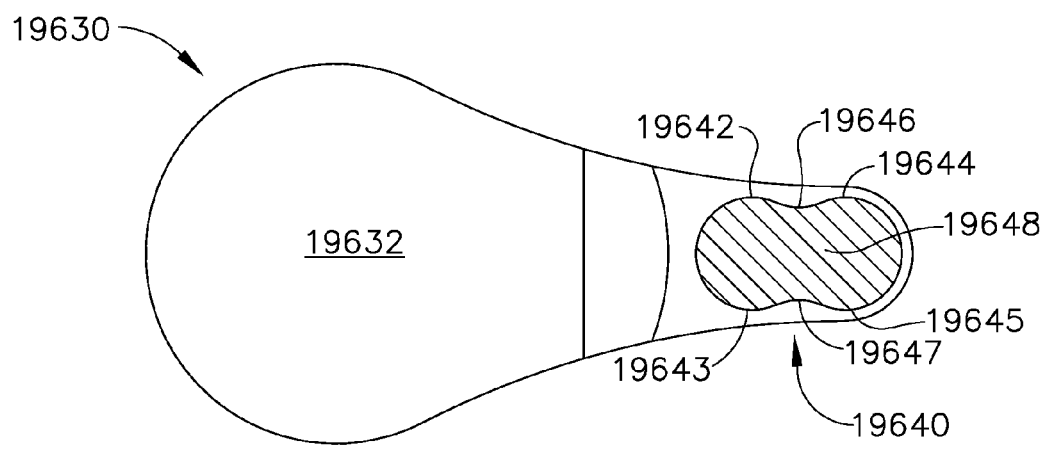
FIG. 108 is a side view of the insertion tool of FIG. 105 with a portion of the insertion tool removed for purposes of illustration.
Figure 109:
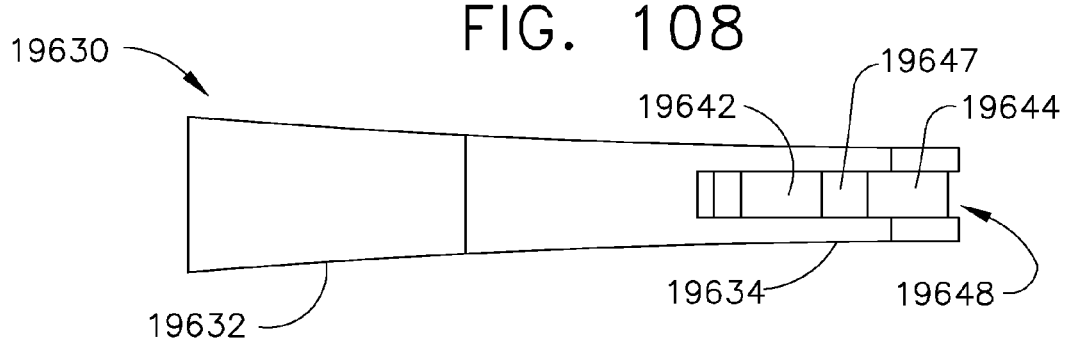
FIG. 109 is a top view of the insertion tool of FIG. 105.
Figure 110:
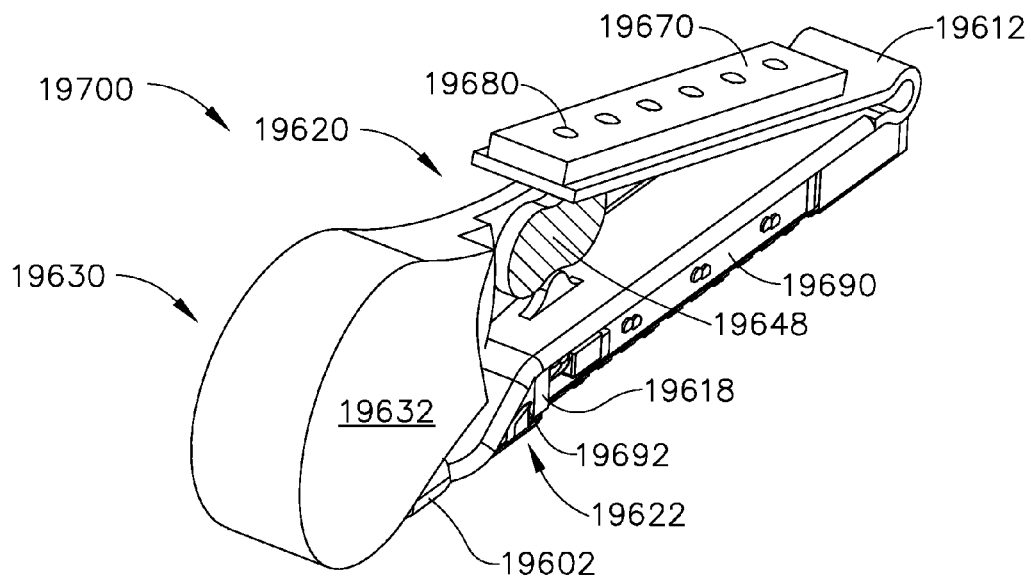
FIG. 110 is a perspective view of a retainer assembly comprising the retainer of FIG. 103, a tissue thickness compensator positioned on the retainer, a staple cartridge positioned on the retainer, and the insertion tool of FIG. 105 engaged with the retainer, wherein a portion of the insertion tool is removed for purposes of illustration.
Figure 111:
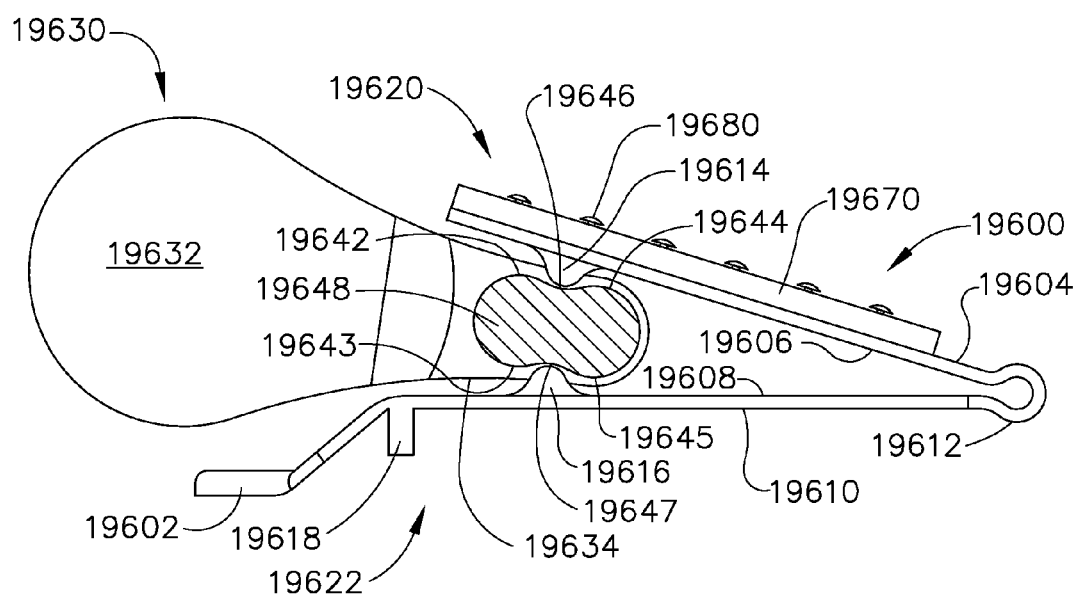
FIG. 111 is a side view of a retainer assembly comprising the retainer of FIG. 103, a tissue thickness compensator positioned on the retainer, and the insertion tool of FIG. 105 engaged with the retainer, wherein a portion of the insertion tool is removed for purposes of illustration.

FIGS. 103-115 illustrate an embodiment of a retainer comprising a separate insertion tool. The insertion tool can be used to insert an assembly into a surgical instrument, such as a surgical stapler, for example. The insertion tool can also press a staple cartridge and one or more tissue thickness compensators of the retainer assembly into position within the surgical instrument. Referring to FIGS. 103 and 104, a retainer 19600 may include a first plate 19620 and a second plate 19622. The first plate 19620 and the second plate 19622 may be connected by a hinge 19612. The hinge 19612 can position the first plate 19620 at an angle relative to the second plate 19622 and can also enable the first plate 19620 to rotate relative to the second plate 19622 about the hinge 19612.

In various embodiments, the first plate 19620 can include an outward-facing surface 19604 and an inward-facing surface 19606. Likewise, the second plate 19622 may include an outward-facing surface 19610 and an inward-facing surface 19608. In at least one embodiment, the inward-facing surface 19606 of the first plate 19620 may include a cam protrusion 19614. Similarly, the inward-facing surface 19608 of the second plate 19622 may include a cam protrusion 19616. Referring to FIGS. 110-115, outward-facing surface 19604 of the first plate may include a tissue thickness compensator positioned thereon. Outward-facing surface 19601 of the second plate 19622 may also include a tissue thickness compensator positioned thereon. The tissue thickness compensators may be attached to the outer surfaces 19604 and 19610 using adhesives, engagement features, and/or other suitable attachment means, for example. In various embodiments, the retainer 19600 can include clips 19618 extending from the second plate 19622 which can be configured to engage a staple cartridge 19690, as shown in FIGS. 110 and 112-115.

Referring now to FIGS. 105-109, an insertion tool 19630 can include a first end 19632 and a second end 19634. The first end 19632 can be large enough to be gripped by a surgeon, nurse, and/or technician, for example. In various embodiments, the second end 19634 defines a cavity 19640 wherein the cavity can include a cam 19648 positioned therein. A first side of the cam 19648 may include a first lobe 19642, a second lobe 19644, and a first anti-lobe 19646 positioned therebetween. A second side of the cam 19648 can include a third lobe 19643, a fourth lobe 19645, and a second anti-lobe 19647 positioned therebetween. In at least one such embodiment, the lobes and the anti-lobes can be arranged in a mirror-image manner. In other words, the first lobe 19642 may be arranged on the first side of the cam 19648 directly opposite the third lobe 19643 on the second side of the cam 19648. Likewise, the second lobe 19644 may be arranged on the first side of the cam 19648 directly opposite the fourth lobe 19645 on the second side of the cam 19648. Further, the first anti-lobe 19464 may be arranged on the first side of the cam 19648 directly opposite the second anti-lobe 19647 on the second side of the cam 19648.

Figure 112:
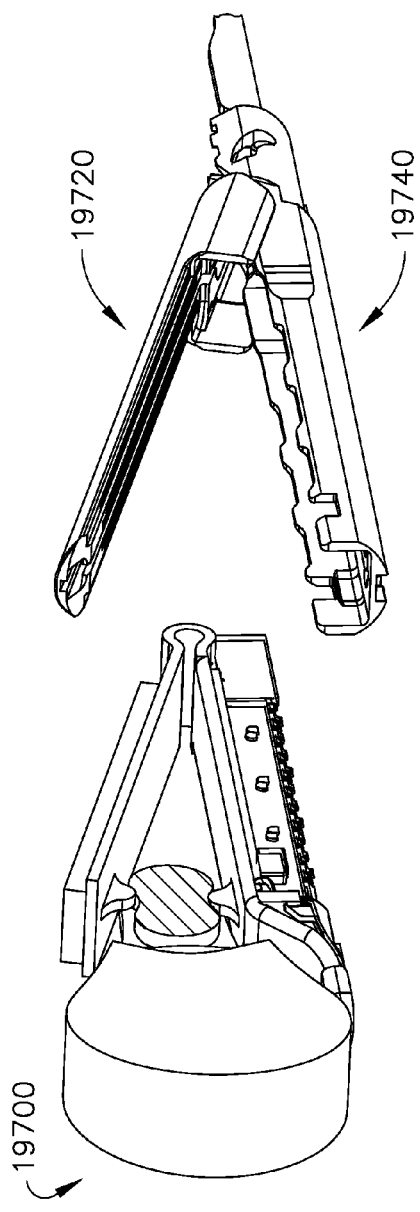
FIG. 112 illustrates the retainer assembly of FIG. 110 being inserted into a surgical instrument comprising an anvil and a staple cartridge channel, wherein a portion of the insertion tool is removed for the purposes of illustration.
Figure 113:
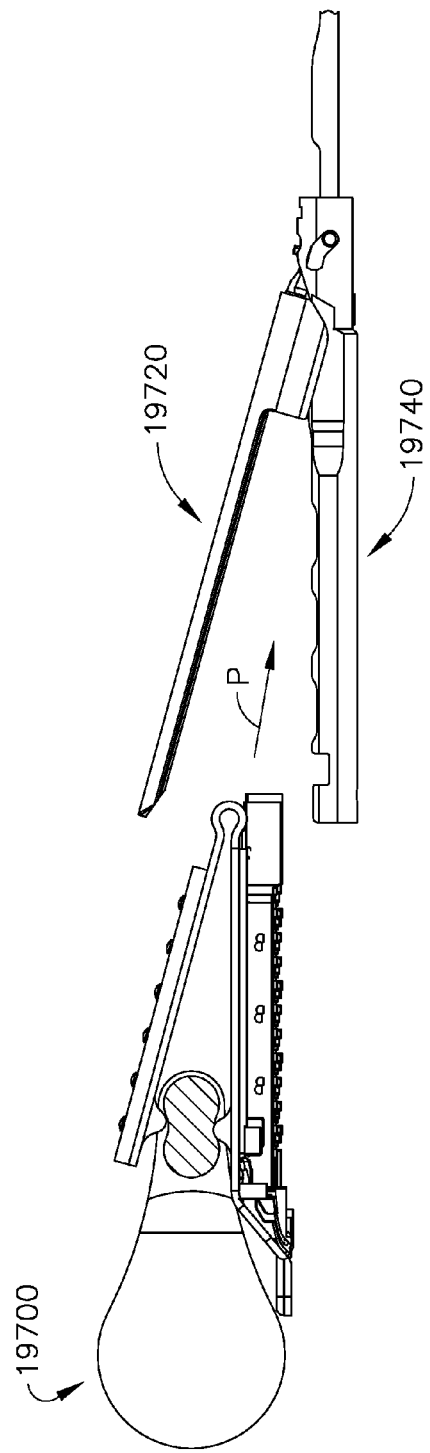

In use, the second end 19634 of the insertion tool 19630 is placed between the first plate 19620 and the second plate 19622 of the retainer 19600 such that the cam protrusion 19614 on the first plate 19620 is engaged with anti-lobe 19646 and cam protrusion 19616 on the second plate 19622 is engaged with anti-lobe 19647, for example. As shown in FIGS. 112 and 113, an insertion assembly 19700, which includes the retainer 19600, the insertion tool 19630, one or more tissue thickness compensators, and staple cartridge 19690 can be inserted into a surgical instrument. The surgical instrument, such as a surgical stapler, may include a channel 19740, which is configured to receive the staple cartridge 19690, and an anvil 19720. The insertion assembly 19700 can be inserted into the surgical instrument in the direction of arrow P (FIG. 113) to lock the staple cartridge 19690 into the channel 19740. In such a position, the cams 19614 and 19616 can be aligned with the anti-lobes 19646 and 19647, respectively.

After the staple cartridge 19690 is locked into the channel 19740, as shown in FIG. 114, the insertion tool 19600 can continue to be moved in the direction of arrow Q relative to the surgical instrument. Further movement of the insertion tool 19600 in the direction of arrow Q can align the first lobe 19642 with the first cam protrusion 19614 and the third lobe 19634 with the second cam protrusion 19616. Such an alignment can cause the retainer plates 19620 and 19622 to rotate away from each other about the hinge 19612 in the direction of arrow R (FIG. 114). In such circumstances, the retainer plate 19620 and the tissue thickness compensator 19670 can move toward the anvil 19720 and the retainer plate 19622 can move toward and contact the anvil 19720. In various embodiments, as a result of the above, the tissue thickness compensator 19670 can be seated on the anvil 19720. After the tissue thickness compensator 19670 is attached to the anvil 19720, the insertion tool 19630 may be retracted or moved in the direction of arrow S (shown in FIG. 115). Movement of the insertion tool 19630 in the direction of arrow S can causes the cam protrusions 19614 an 19616 to disengage from the first lobe 19642 and the third lobe 19643, respectively, and become re-aligned with the first anti-lobe 19646 and the second anti-lobe 19647, respectively. In various embodiments, the second lobe 19642 and the fourth lobe 19645 can abut the cam protrusions 19614 and 19616, respectively, and, in at least one embodiment, can prevent the insertion tool 19630 from completely separating from the retainer 19600. With the cam protrusions 19614 and 19616 realigned with the anti-lobes 19646 and 19647, the first plate 19620 can at least partially rotate toward the second plate 19622 about the hinge 19612 and away from the anvil 19720. The retainer 19600 can also be detached from the channel 19740, in various embodiments, and then removed in the direction of arrow S leaving the tissue thickness compensator 19670 attached to the anvil 19720, for example.

In the embodiments described herein, a retainer assembly can be utilized to install one or more tissue thickness compensators into an end effector of a surgical stapling instrument. In certain embodiments, a retainer assembly can install layers besides tissue thickness compensators into a surgical instrument. In at least one embodiment, the layers may include an absorbable material and/or a biocompatible material, for example.

Referring to FIG. 172, an end effector 12 can be configured to receive an end effector insert 25002. In various embodiments, the end effector 12 can comprise a lower jaw 25070 and an anvil 25060 that is configured to pivot relative to the lower jaw 25070. In some embodiments, the end effector insert 25002 can comprise a staple cartridge 25000 that is pivotably connected to an anvil insert 25004. The end effector 12 can be configured to receive the end effector insert 25002 such that the staple cartridge 25000 fits within a staple cartridge channel 25072 of the lower jaw 25070, for example, and the anvil insert 25004 contacts the anvil 25060, for example. In various embodiments, the lower jaw 25070 can comprise a plurality of securing members 25074 configured to secure the staple cartridge 25000 to the staple cartridge channel 25072. In some embodiments, the anvil insert 25004 can comprise at least one retaining protrusion configured to engage at least one retaining groove in the anvil 25060. The anvil insert 25004 can be configured to correspondingly pivot towards the staple cartridge 25000 when the anvil 25060 pivots towards the lower jaw 25070, as described in greater detail herein.

Referring still to FIG. 172, the end effector insert 25002 can further comprise a retainer 25010. In various embodiments, the retainer 25010 can securely engage at least one of the staple cartridge 25000 and the anvil insert 25004. In at least one embodiment, the retainer 25010 can comprise at least one securing clip 25012 that can clip, engage, snap, clamp, and/or hook the staple cartridge 25000. As illustrated in FIG. 172, the retainer 25010 can comprise two securing clips 25012 on each longitudinal side thereof, for example. In at least one such embodiment, the securing clips 25012 can be configured to clip onto a portion of the staple cartridge 25000, for example. In various embodiments, a tissue thickness compensator can be held in position relative to the end effector insert 25002 by the retainer 25010. For example, a tissue thickness compensator can be positioned between the retainer 25010 and the staple cartridge 25000.

In various embodiments, when an operator is inserting the end effector insert 25002 into the end effector 12, the retainer 25010 can provide a solid or substantially solid element for the operator to grasp. Furthermore, the retainer 25010 can prevent premature deformation of a tissue thickness compensator that is confined by the retainer 25010, for example. In various embodiments, the retainer 25010 can be removed from the end effector 12 prior to utilizing the end effector 12 to cut and/or fasten tissue. In other embodiments, the retainer 25010 can remain positioned in the end effector 12. For example, the retainer 25010 can be transected by the cutting element 25052 (FIG. 207) as staples are fired from staples cavities 25002 (FIG. 207) in the staple cartridge 25000. In various embodiments, the retainer 25010 can comprise a polymeric composition, such as a bioabsorbable, biocompatible elastomeric polymer, for example. The retainer 25010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the retainer 25010 can comprise at least one therapeutic agent such as a pharmaceutically active agent or medicament.

Referring to FIG. 173, an end effector 26012 can comprise an anvil 26060 and a lower jaw 26070. In various embodiments, a tissue compensator 26020 can be releasably secured to the anvil 26060, the lower jaw 26070, and/or both the anvil 26060 and the lower jaw 26070. For example, a first tissue compensator 26020 can be releasably secured to a staple cartridge 26000 in the lower jaw 26070 and a second tissue compensator 26022 can be releasably secured to the anvil 26060. In various embodiments, the first and second tissue compensators 26020, 26022 can be deformable and/or resilient, similar to at least one tissue thickness compensator described herein. For example, the first and second tissue compensators 26020, 26022 can comprise a polymeric composition, such as a bioabsorbable, biocompatible elastomeric polymer, for example. The first and second tissue compensators 26020, 26022 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the first and second tissue compensators 26020, 26022 can comprise at least one therapeutic agent such as a pharmaceutically active agent or medicament.

In some embodiments, the tissue compensator 26020, 26022 can comprise a firm or substantially firm tip 26024, 26026. For example, a first tip 26024 can be positioned at the distal end of the first tissue compensator 26020 and a second tip 26026 can be positioned at the distal end of the second tissue compensator 26022. In various embodiments, the tips 26024, 26026 may prevent or limit premature deformation of the tissue compensators 26020, 26022. For example, the tips 26024, 26026 can protect the tissue compensators 26020, 26022 when the tissue compensators 26020, 26022 are moved through a trocar and/or maneuvered around a patient's tissue, for example. Similarly, referring to FIG. 174, the end effector 12 can comprise a first tissue compensator 25020 releasably secured to the staple cartridge 25000 in the lower jaw 25070 and a second tissue compensator 25022 releasably secured to the anvil 25060. In various embodiments, a tip 25026 can be positioned at the distal end of the second tissue compensator 25022. The tip 25026 can be positioned adjacent to a deformable and/or resilient portion of the tissue compensator 25022. In some embodiments, the tip 25026 can extend over and/or around a portion of the tissue compensator 25022, such that the tip 25026 protects the distal end and an intermediate portion of the tissue compensator 25022.

Referring to FIGS. 175-202, a sleeve 27010 can be configured to engage the anvil 25060 of the end effector 12 of a surgical instrument, for example. In various embodiments, the sleeve 27010 can comprise a pronged portion 27040 (FIGS. 176-179), a nose 27080 (FIGS. 186-189) and a compensator 27120 (FIGS. 180-182). In some embodiments, the sleeve 27010 can be configured to release a compensator 27020 when a translating firing bar 25052 (FIG. 196) approaches the distal end of the end effector 12. In various embodiments, the compensator 27020 can be deformable and/or resilient, similar to at least one tissue thickness compensator described herein. For example, the compensator 27020 can comprise a polymeric composition, such as a bioabsorbable, biocompatible elastomeric polymer, for example. The compensator 27020 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the compensator 27020 can comprise at least one therapeutic agent such as a pharmaceutically active agent or medicament. Referring primarily to FIG. 175, the pronged portion 27040 can be positioned on and/or around an outer surface 25061 of the anvil 25060. In various embodiments, the nose 27080 of the sleeve 27010 can be positioned at and/or around a distal portion of the anvil 25060. In some embodiments, the compensator 27020 can be positioned on and/or around an inner surface of the anvil 25060.

Referring still to FIG. 175, the pronged portion 27040 can comprise at least one prong 27042a. In various embodiments, as illustrated in FIGS. 505-508, the pronged portion 27040 can comprise a first prong 27042a and a second prong 27042b. The prongs 27042a, 27042b can be symmetrical or substantially symmetrical, for example. In some embodiments, the first prong 27042a can be asymmetrical relative to the second prong 27042b. In various embodiments, the first and/or second prongs 27042a, 27042b can narrow at the distal end thereof. For example, each prong 27042a, 27042b can comprise a narrowed end 27048. Referring primarily to FIG. 178, the pronged portion 27040 can be contoured, for example. In various embodiments, referring again to FIG. 175, the contour of the pronged portion 27040 can match or substantially match a contour of the outer surface 25061 of the anvil 25060, for example. Referring primarily to FIGS. 178 and 179, the pronged portion 27040 can also comprise at least one catch 27044a extending from the first prong 27042a. In some embodiments, a first catch 27044a can be positioned on a first side of the pronged portion 27040 and a second catch 27044b can be positioned on a second side of the pronged portion 27040. In various embodiments, the catches 27044a, 27044b can be positioned at or near the proximal end of the pronged portion 27040, for example. In some embodiments, the catches 27044a, 27044b can be positioned at or near the distal end of the pronged portion 27040, such as along the first and/or second prongs 27042a, 27042b, for example. In various embodiments, the catches 27044a, 27044b can extend along a substantial length of the pronged portion 27040 and/or along a shorter length of the pronged portion 27040. In some embodiments, a plurality of catches 27044a, 27044b can be positioned along each longitudinal side of the pronged portion, for example. Referring primarily to FIG. 179, the first catch 27044a can comprise a first catch extension 27046a and/or the second catch 27044b can comprise a second catch extension 27046b. In various embodiments, the first catch extension 27046a can protrude from at least a portion of the catch 27044a and the second catch extension 27046b can protrude from at least a portion of the catch 27044b, for example. Further, the first catch extension 27046a and the second catch extension 27046b can each be configured to engage a gap 27128 (FIG. 181) in the compensator 27020, as described in greater detail herein.

Referring now to FIG. 201, the compensator 27020 for the sleeve 27010 can comprise a longitudinal protrusion 27024 and an edge 27026 on each longitudinal side of the compensator 27020. In various embodiments, the compensator 27020 can be positioned adjacent to an inner surface 25063 of the anvil 25060. Further, when the sleeve 27010 is positioned on the anvil 25060, the longitudinal protrusion 27024 can be substantially aligned with and/or positioned within a longitudinal slot 25062 in the anvil 25060. The edges 27026 of the compensator 27020 can at least partially wrap around the anvil 25060 towards the outer surface 25061 thereof. Referring primarily to FIGS. 180-181, a compensator 27120 for a sleeve 27110 can comprise a body 27122 having a longitudinal protrusion 27124 that extends along at least a portion of the body 27122. The longitudinal protrusion 27124 can define a longitudinal path along the midline of the body 27122, for example. In various embodiments, the longitudinal protrusion 27124 can be received by the longitudinal slot 25062 (FIG. 201) in the anvil 25060 when the sleeve 27110 is positioned on the anvil 25060. Referring primarily to FIG. 182, the longitudinal protrusion 27124 can comprise a rounded projection. For example, the cross-section of the longitudinal protrusion 27124 can form an arc and/or partial ring. In other embodiments, the longitudinal protrusion 27124 can comprise an angular and/or stepped projection. The compensator 27120 can further comprise an edge 27126, which can be straight, bent, fluted, wavy, and/or zigzagged, for example. In various embodiments, the edge 27126 can comprise gaps 27128 that can be configured to receive the catch extensions 27046a, 27046b (FIG. 179) when the assembled sleeve 27110 is positioned on the anvil 25060. The catch extensions 27046a, 27046b can fit through the gap 27128 to engage the anvil 25060 such that the catch extensions 27046a, 27046b help to secure the sleeve 27110 to the anvil 25060, for example.

Referring primarily to FIGS. 183-185, a compensator 27220 for a sleeve 27210 can comprise a body 27222 comprising a longitudinal protrusion 27224 extending along at least a portion of the body 27222. In various embodiments, similar to the above, the longitudinal protrusion 27224 can be received by the longitudinal slot 25062 (FIG. 202) in the anvil 25060 when the sleeve 27210 is positioned on the anvil 25060. Referring primarily to FIG. 185, the longitudinal protrusion 27224 can comprise an angular projection such that the cross-section of the protrusion 70224 forms a substantially rectangular shape. The compensator 27220 can further comprise an edge 27226, which can be straight, bent, fluted, wavy, and/or zigzagged, for example. In various embodiments, the edge 27226 can comprise gaps 27228 that can be configured to receive the catch extensions 27046a, 27046b (FIG. 179) when the assembled sleeve 27210 is positioned on the anvil 25060. The catch extensions 27046a, 27046b can fit through the gaps 27228 and engage the anvil 25060 such that the catch extensions 27046a, 27046b help to secure the sleeve 27210 to the anvil 25060, for example. In various embodiments, the compensator 27220 can further comprise a plurality of ribs 27229 that laterally traverse the body 27222 of the compensator 27220. The ribs 27229 can support the body 27222 of the compensator 27220 when the sleeve 27210 is positioned on the anvil 25060 and/or when the compensator 27220 contacts tissue.

Referring to FIGS. 386-390, the nose 27080 of the sleeve 27010 can comprise an alignment ridge 27082 that can be substantially aligned with the longitudinal slot 25062 (FIG. 201) in the anvil 25060. When the alignment ridge 27082 is aligned with the longitudinal slot 25062 and when the sleeve 27010 is positioned on the anvil 25060, the nose 27082 can at least partially surround a distal portion of the pronged portion 27040 of the sleeve 27010. For example, the narrowed end 27048 of each prong 27042a, 27042b can be positioned within the nose 27080 when the sleeve 27010 is positioned on the anvil 25060. As described in greater detail herein, the nose 27080 can flex the prongs 27042a, 27042b closer together and/or downward when the pronged portion 27042 is engaged with the nose 27080. Furthermore, as illustrated in FIG. 190, when the narrowed ends 27048 of the pronged portion 27040 are positioned within the nose 27080, the catches 27044a, 27044b on the pronged portion 27040 can engage the edges 27026 of the compensator 27020, for example. As a result of such engagement, the compensator 27010 can be secured to the anvil 25060.

Referring to FIGS. 191-195, when the nose 27080 is engaged with the pronged portion 27040 of the sleeve 27010, the compensator 27020 can be secured to the anvil 25060. The nose 27080 can remain engaged with the pronged portion 27040 as the firing bar 25050 translates along a portion of the longitudinal slot 25062 in the anvil 25060. Referring now to FIGS. 195-200, when the cutting element 25052 on the firing bar 25050, and/or any other suitable portion of the firing bar 25050, such as retaining flange 25054, for example, approaches the distal end of the anvil 25060, the firing bar 25050 can disengage the nose 27080 from the pronged portion 27040. The firing bar 25050 can, for example, contact the nose 27080 and push the nose 27080 off of the anvil 25060 such that the nose 27080 becomes disconnected from the pronged portion 27040 of the sleeve 27010. Referring now to FIG. 202, when the nose 27080 is disengaged with the pronged portion 27040, the first and second prongs 27042a, 27042b can be configured to flex away from the anvil 25060. For example, when the pronged portion 27070 is engaged with the nose 27080, the prongs 27042a, 27042b can be flexed closer together and/or downwards towards the anvil 25060 and held in such a position by the nose 27080. In various embodiments, the prongs 27042a, 27042b can be held under a spring load by the nose 27080 such that the prongs 27042a, 27042b seek to rebound to a neutral configuration once the nose 27080 is disengaged from the prongs 27042a, 27042b. In other embodiments, the prongs 27042a, 27042b can be sufficiently deformable such that the prongs 27042a, 27042b can be deformed or splayed outwardly by the firing bar 25050 once the nose 27080 is disengaged therefrom. When the prongs 27042a, 27042b move away from the anvil 25060, the catches 27044a, 27044b along a longitudinal side of each prong 27042a, 27042b can disengage the compensator 27020, which can allow the compensator 27020 to be released from the anvil 25060.

Referring to FIGS. 203-209, the end effector 12 of a surgical instrument, for example, can be configured to receive an end effector insert 28010. In various embodiments, the end effector insert 28010 can comprise a compensator body 28012 and at least one clip 28014a, 28014b. In various embodiments, the end effector insert 28010 can comprise a proximal clip 28014b at the proximal end of the compensator body 28012 and a distal clip 28014a at the distal end of the compensator body 28012, for example. Referring primarily to FIG. 206, the distal clip 28014a can be secured to the anvil 25060 of the end effector 12 at or near the distal end of the anvil 25060. For example, the distal clip 28014a can be substantially aligned with and/or partially positioned within the longitudinal slot 25062 of the anvil 25060. Referring primarily to FIG. 207, the proximal clip 28014b can be secured to a staple cartridge 25000 in the lower jaw 25070 of the end effector 12 (FIG. 208). The proximal clip 28014b can be secured to the staple cartridge 25000 at or near the proximal end of the staple cartridge 25000. For example, the proximal clip 28014b can be substantially aligned with and/or positioned within a longitudinal slot 25004 in the staple cartridge 25000.

Referring now to FIGS. 208 and 209, the end effector insert 28010 can be inserted into the end effector 12 of a surgical instrument. In various embodiments, at least a portion of the end effector insert 28010, such as the compensator body 28012, distal clips 28014a, and/or proximal clip 28014b, can be deformable and/or resilient, for example. When the end effector insert 28010 is inserted into the end effector 12, the distal and/or the proximal clips 28014a, 28014b can bend or flex. When the clips 28014a, 28014b are flexed, for example, the clips 28014a, 28014b can seek to return to their initial, undeformed configuration and can generate a corresponding springback or restoring force, for example. In various embodiments, when the end effector insert 28010 is positioned within the end effector 12, the end effector insert 28010 can apply a spring load to the end effector 12. In some embodiments, the end effector insert 28010 can be solid or substantially solid such that an operator can grasp the insert 28010 when the operator is inserting the end effector insert 28010 and staple cartridge 25000 into the end effector 12.

In some embodiments, the end effector insert 28010 can be removed from the end effector 12 prior to cutting and/or fastening operations of the end effector 12. In other embodiments, the end effector insert 28010 can remain positioned in the end effector 12 during cutting and/or firing operations. For example, the end effector insert 28010 can be transected by the cutting element 25052 as staples are fired from their staples cavities 25002 (FIG. 207) in the staple cartridge 25000. In various embodiments, the end effector insert 28010 can comprise a tissue thickness compensation material, similar to at least one of the tissue thickness compensators described herein. For example, the end effector insert 28010 can comprise a polymeric composition, such as a bioabsorbable, biocompatible elastomeric polymer, for example. The end effector insert 28010 can further comprise a bioabsorbable polymer, such as, for example, lyophilized polysaccharide, glycoprotein, elastin, proteoglycan, gelatin, collagen, and/or oxidized regenerated cellulose (ORC), for example. In some embodiments, the end effector insert 28010 can comprise at least one therapeutic agent such as a pharmaceutically active agent or medicament.

Referring to FIGS. 210-215, a tissue thickness compensator 29020 can be positioned in the end effector 12 of a surgical instrument. The tissue thickness compensator 29020 can be substantially similar to at least one of the tissue thickness compensators described herein. For example, the tissue thickness compensator 29020 can be sufficiently deformable and resilient such that deformation of the tissue thickness compensator 29020 generates a springback or restoring force. In various embodiments, referring primarily to FIG. 211, a static charge can attract the tissue thickness compensator 29020 to the anvil 25060 of the end effector 12 such that the static charge secures the tissue thickness compensator 29020 to the anvil 25060. In various embodiments, the static charge can be neutralized such that the anvil 25060 releases the tissue thickness compensator 29020. Additionally or alternatively, referring now to FIG. 212, the tissue thickness compensator 29020 can be secured to the anvil 25060 by at least one suction element 29022. For example, a plurality of micro-suction elements 29022 on a surface of the tissue thickness compensator 29020 can releasably secure the tissue thickness compensator 29020 to the anvil 25060. Additionally or alternatively, referring to FIG. 213, hook and loop fasteners 29024 can secure the tissue thickness compensator 29020 to the anvil 25060. For example, a surface of the tissue thickness compensator 29020 can comprise a plurality of hook fasteners 29024*a* and a surface of the anvil 25060 can comprise a plurality of loop fasteners 29024*b*, for example. The hook fasteners 29024*a* can engage the loop fasteners 29024*b* such that the tissue thickness compensator 29020 is releasably secured to the anvil 25060.

Additionally or alternatively, referring now to FIG. 214, the tissue thickness compensator 29020 can be secured to the anvil 25060 by a band 29026. In some embodiments, the band 29026 can comprise an elastomeric polymer and/or can be tied or knotted around the anvil 25060. When the band 29026 is removed from the anvil 25060, the tissue thickness compensator 29020 can be released from the anvil 25060. To facilitate removal of the band 29026, it can be stretched and/or cut, for example. In various embodiments, a plurality of bands 29026 can secure the tissue thickness compensator 29020 to the anvil 25060. Alternatively or additionally, referring now to FIG. 215, the tissue thickness compensator 29020 can be secured to the anvil 25060 by a sock 29028 positioned at the distal end of the tissue thickness compensator 29020. The sock 29028 can be configured to receive the distal end of the anvil 25060 therein, for example. In some embodiments, an alignment ledge 29029 on the tissue thickness compensator 29020 can be aligned with and/or positioned within the longitudinal slot 25062 in the anvil 25060. For example, the alignment ledge 29029 can slide within the longitudinal slot 25062 as the tissue thickness compensator 29020 is positioned on and/or removed from the anvil 25060.

Referring to FIGS. 216-218, a tissue thickness compensator 30020 can be positioned on the anvil 25060 of the end effector 12 of the surgical instrument. In various embodiments, the tissue thickness compensator 30020 can comprise a body 30022 and a pocket 30024. In at least one embodiment, a compensator material 30026 can be retained between the body 30022 and the pocket 30024, for example. In some embodiments, the compensator material 30026 can comprise a bioabsorbable polymer, such as, for example, lyophilized polysaccharide, glycoprotein, elastin, proteoglycan, gelatin, collagen, and/or oxidized regenerated cellulose (ORC), for example. Additionally or alternatively, the compensator material 30026 can comprise at least one therapeutic agent such as a pharmaceutically active agent or medicament. In various embodiments, the tissue thickness compensator 30020 can be deformable and/or resilient, similar to at least one tissue thickness compensator described herein. For example, the tissue thickness compensator 30020 can comprise a polymeric composition, such as a bioabsorbable, biocompatible elastomeric polymer, for example. The tissue thickness compensator 30020 can further comprise a bioabsorbable polymer, such as, for example, lyophilized polysaccharide, glycoprotein, elastin, proteoglycan, gelatin, collagen, and/or oxidized regenerated cellulose (ORC), for example.

Referring primarily to FIG. 217, the body 30022 of the tissue thickness compensator 30020 can comprise an alignment element 30028 that can be received within the longitudinal slot 25062 of the anvil 25060 when the tissue thickness compensator 30020 is secured to the anvil 25060. In some embodiments, the body 30022 can comprise a stepped thickness such that the geometry of the body 30022 substantially corresponds with the geometry of the anvil 25060. Further, in various embodiments, the body 30022 can comprise longitudinal flanges 30029. In at least one such embodiment, a longitudinal flange 30029 can extend along each longitudinal side of the body 30022 of the tissue thickness compensator 30020, for example. In various embodiments, the longitudinal flanges 30029 can at least partially wrap around the anvil 25060 to secure the tissue thickness compensator 30020 to the anvil 25060. Further, the longitudinal flanges 30029 can be sufficiently resilient such that the longitudinal flanges 30029 can flex to accommodate and/or engage the anvil 25060, for example. In various embodiments, the longitudinal flanges 30029 can exert a clamping force on the anvil 25060 when the flanges 30029 engage the anvil 25060. In some embodiments, the pocket 30024 can comprise an indentation 30025. When the tissue thickness compensator 30020 is secured to the anvil 25060, the indentation 30025 can be substantially aligned with the longitudinal slot 25062 in the anvil 25060, for example. In various embodiments, the tissue thickness compensator 30020 can be thinner at the indentation 30025 such that the translating cutting element 25052 (FIG. 207) severs the tissue thickness compensator 30020 where it is thinner.

Referring now to FIGS. 219 and 220, a tissue thickness compensator 30120 can comprise a body 30122 that is configured to retain compensation material 30026 therein. In various embodiments, the tissue thickness compensator 30120 can comprise an alignment element 30128, an indentation 30125, and/or longitudinal flanges 30129, similar to at least one of the embodiments described herein. In some embodiments, the tissue thickness compensator 30120 can also comprise a latch 30124 that can be moved between an open position and a closed position. When the latch 30124 is in the closed position, as illustrated in FIG. 219, the compensation material 30026 can be enclosed within the body 30122 of the tissue thickness compensator 30120 and, when the latch 30124 is in the open position, as illustrated in FIG. 220, the compensation material 30026 can escape from the body 30122. Similar to at least one of the tissue thickness compensators described herein, the tissue thickness compensator 30120 can be deformable and/or resilient. For example, the tissue thickness compensator 30120 can comprise a polymeric composition, such as a bioabsorbable, biocompatible elastomeric polymer, for example. The tissue thickness compensator 30120 can further comprise a bioabsorbable polymer, such as, for example, lyophilized polysaccharide, glycoprotein, elastin, proteoglycan, gelatin, collagen, and/or oxidized regenerated cellulose (ORC), for example. Owing to the resiliency of the tissue thickness compensator 30120, at least a portion of the body 30122 can be flexed to move the latch 30124 between the open position and the closed position. In at least one embodiment, the body 30122 of the tissue thickness compensator 30120 can remain attached to the anvil when the anvil is removed from the surgical site. In at least one such embodiment, the body 30122 can be configured to tear away from any staples that may have captured the body 30122 therein.

Referring to FIG. 221, a tissue thickness compensator 30220 can comprise a body 30222 and a pocket 30224. The compensator material 30026 can be retained between the body 30222 and the pocket 30224, for example. In various embodiments, the tissue thickness compensator 30220 can comprise an alignment element, an indentation, and/or longitudinal flanges 30229, similar to at least one of the embodiments described herein. Further, at least one longitudinal flange 30229 can comprise a groove, or slot, 30228, which can be configured to receive a tab 30225 extending from the pocket 30224 of the tissue thickness compensator 30220. In such an embodiment, engagement of the groove 30228 and the tab 30225 can connect the body 30222 and the pocket 30224. Further, in such an embodiment, the groove 30028 and tab 30025 connection can enclose and/or retain the compensation material 30026 within the tissue thickness compensator 30220. Referring now to FIG. 222, in various embodiments, a pocket 30324 of a tissue thickness compensator 30320 can comprise an anchor 30325 extending therefrom. Further, the tissue thickness compensator 30320 can comprise a body 30322 having an opening 30328. In various embodiments, the anchor 30325 can extend from the pocket 30324 to engage the opening 30328 in the body 30322. In such an arrangement, the pocket 30324 and the body 30222 can encase the compensation material 30026 therebetween. In at least one embodiment, the tissue thickness compensator 30320 can further comprise one or more flanges 30229 which can be mounted to the anvil in order to retain the body 30322 to the anvil.

Referring now to FIG. 223, a tissue thickness compensator 30420 can comprise a body 30422 and a pocket 30424. In various embodiments, the compensation material 30026 can be retained between the body 30422 and the pocket 30424 of the tissue thickness compensator 30420. In some embodiments, the body 30422 can comprise an orifice 30428 and the pocket 30424 can comprise an anchor 30425. The anchor 30425 can extend from the pocket 30424 and through the orifice 30428 of the body 30422, for example. In various embodiments, the anchor 30425 can engage the anvil 25060 when the tissue thickness compensator 30420 is secured to the anvil 25060, for example. The anchor 30525 can be sufficiently deformable and resilient such that the anchor 30425 flexes when it engages the anvil 25060. Further, in some embodiments, the flexed anchor 30425 can apply a clamping force to the anvil 25060 to secure or assist in securing the tissue thickness compensator 30420 to the anvil 25060. In other embodiments, an anchor may not extend completely through an orifice in the compensator body. Referring to FIG. 224, an anchor 30525 on a pocket 30524 of a tissue thickness compensator 30520 can engage an orifice 30528 in a body 30522 of the tissue thickness compensator 30520. In various embodiments, the anchor 30525 can engage the orifice 30528 to secure the pocket 30524 to the body 30522. For example, the orifice 30528 can comprise a necked portion that extends to a socket. The anchor 30525 can comprise securing edge, which can pass through the necked portion and engage the socket to secure the anchor 20525 within the orifice 30528. Similar to at least one of the embodiments described herein, the tissue thickness compensator 30520 can also comprise an alignment element, an indentation, and/or longitudinal flanges 30529, for example.

Referring to FIGS. 225-227, a tissue thickness compensator 31020 can be configured to engage an anvil 31060 of an end effector 31012 of a surgical instrument. In various embodiments, the tissue thickness compensator 31020 can comprise an outer film 31022, an inner film 31024 and a compensation material 31026 positioned therebetween. In various embodiments, the tissue thickness compensator 31020 can be deformable and/or resilient, similar to at least one of the tissue thickness compensators described herein. For example, the compensation material 31026 can comprise a polymeric composition, such as a bioabsorbable, biocompatible elastomeric polymer, for example. The tissue thickness compensator 31020 can further comprise a bioabsorbable polymer such as, for example, lyophilized polysaccharide, glycoprotein, elastin, proteoglycan, gelatin, collagen, and/or oxidized regenerated cellulose (ORC), for example. In some embodiments, the tissue thickness compensator 31020 can comprise at least one therapeutic agent such as a pharmaceutically active agent or medicament. In various embodiments, the compensation material 31206 of the tissue thickness compensator 31020 can comprise a therapeutic agent.

The inner film 31024 can be positioned adjacent to staple forming pockets 31066 in the anvil 31060, for example. Referring primarily to FIG. 225, the inner film 31024 can comprise a stepped geometry such that the geometry of the inner film 31024 substantially corresponds to the geometry of the anvil 31060. The inner film 31024 can further comprise an alignment ridge 31028, which can be substantially aligned with and/or parallel to a longitudinal slot 31062 in the anvil 31060, for example. As described in greater detail herein, the inner film 31024 can comprise an inner flange 31025 extending from each longitudinal side of the inner film 31024 and terminating in a catch 31027. The outer film 31022 can comprise a body 31021 and at least one outer flange 31023, for example. In various embodiments, an outer flange 31023 can extend from each longitudinal side of the body 31021, for example. In various embodiments, the outer flange 31023 can be secured to the inner flange 31025 such that the compensation material 31026 is retained between the outer film 31022 and the inner film 31024.

Referring primarily to FIG. 227, the anvil 31060 can comprise an outer surface 31061 and at least one groove 31064 along at least a portion of the outer surface 31061. In various embodiments, a catch 31027 on the inner flange 31025 of the inner film 31024 can be positioned within a groove 31064. Referring to FIG. 226, for example, the tissue thickness compensator 31020 can be slid around the anvil 31060. In various embodiments, the grooves 31064 on the anvil 31060 can extend to the distal end of the anvil 31060. In such embodiments, the catches 31027 of the tissue thickness compensator 31020 can slide into the grooves 31064 and along a length of the tissue thickness compensator 31020.

In various embodiments, referring now to FIGS. 228 and 229, a tissue thickness compensator 31120 can comprise a compensation material 31026 and at least one connector 31124. Each connector 31124 can extend around the compensation material 31026 and can terminate in a catch 31127 on opposite ends thereof. In various embodiments, the catches 31127 can be positioned within the grooves 31064 of the anvil 31060 to fasten the tissue thickness compensator 31120 to the anvil 31060. In various embodiments, the grooves 31164 on the anvil 31060 can extend to the distal end of the anvil 31060. In such embodiments, the catches 31127 of the connectors 31124 can slide into the grooves

31064. In other embodiments, the connectors 31224 can be resilient such that they can flex and snap around the anvil 31060. In use, the connectors 31224 can hold the compensation material 31026 in place until the compensation material 31026 detaches from the anvil 31060. In certain circumstances, the connectors 31224 can remain attached to the anvil 31060 and can be removed from the surgical site with the anvil. In certain other circumstances, the connectors 31224 can detach from the anvil 31060 and can be implanted with the compensation material 31026.

Referring to FIGS. 230-236, a tissue thickness compensator 32020 can comprise a body portion 32022, at least one longitudinal flange 32024, and at least one pocket 32026. In various embodiments, the tissue thickness compensator 31020 can be deformable and/or resilient, similar to at least one of the tissue thickness compensators described herein. For example, the compensation material 31026 can comprise a polymeric composition such as a bioabsorbable, biocompatible elastomeric polymer, for example. The tissue thickness compensator 31020 can further comprise a bioabsorbable polymer such as, for example, lyophilized polysaccharide, glycoprotein, elastin, proteoglycan, gelatin, collagen, and/or oxidized regenerated cellulose (ORC), for example. In various embodiments, the longitudinal flange 32024 can extend along each longitudinal side of the body portion 32022. Referring primarily to FIG. 233, the longitudinal flanges 32024 of the tissue thickness compensator 32020 can be configured to engage the anvil 25060. For example, the tissue thickness compensator 32020 can slide onto the anvil 25060 and the longitudinal flanges 32024 and can at least partially wrap around a portion of the anvil 25060. In such embodiments, the flanges 32024 can secure the tissue thickness compensator 32020 to the anvil 25060, for example. In various embodiments, when the tissue thickness compensator 32020 is secured to the anvil, the body portion 32022 of the tissue thickness compensator 32020 can overlap staple forming pockets 25066 on the inner surface of the anvil 25060.

Further to the above, in various embodiments, a plurality of pockets 32026 can laterally traverse the body portion 32022. Referring primarily to FIG. 234, the plurality of pockets 32026 can comprise at least one therapeutic agent such as a pharmaceutically active agent or medicament. In various embodiments, a plurality of first pockets 32026*a* can comprise a first therapeutic agent or combination thereof and a plurality of second pockets 32026*b* can comprise a second therapeutic agent or combination thereof. The first pockets 32026*a* and the second pockets 32026*b* can be alternatingly positioned along the body portion 32022, for example. Further, in various embodiments, when the first therapeutic agent is released from the first pocket 32026*a* and the second therapeutic agent is released from the second pocket 32026*b*, the first and second therapeutic agents can be configured to react with each other. Referring to FIG. 236, the pockets 32026 can release the therapeutic agent(s) retained therein when the cutting element 25052 on the firing bar 25050 translates along the longitudinal slot 25062 in the anvil 25060, for example.

In various embodiments, referring now to FIG. 237, an end effector of a surgical stapling instrument can comprise an anvil 32560 and a staple cartridge 32500 comprising a tissue thickness compensator 32520. Similar to the above, the staple cartridge 32500 can comprise a plurality of staples 32530 at least partially contained therein which can be ejected therefrom to capture the tissue thickness compensator 32520 therein. Also similar to the above, the staples 32530 can penetrate the tissue thickness compensator 32520 and contact staple forming pockets 32562 defined in the anvil 32560. In certain embodiments, referring now to FIG. 239, the anvil 32560 can further comprise a layer 32570 attached thereto which can be configured to retain a tissue thickness compensator 32580 to the anvil 32560. In at least one such embodiment, the layer 32570 can comprise a chargeable layer which can be configured to hold and/or generate an electrostatic charge and attract the tissue thickness compensator 32580 thereto. More specifically, in various embodiments, Van der Waals molecular forces, whether actively or passively actuated, for example, can hold the tissue thickness compensator 32580 to the layer 32570. In certain embodiments, the chargeable layer 32570 can be in electrical communication with a handle of the surgical stapling instrument which can comprise a control configured to selectively couple the chargeable layer 32570 with a power source and, as a result, allow an electrostatic charge to be selectively generated within the chargeable layer 32570. In at least one such embodiment, the chargeable layer 32570 can comprise conductive electrodes embedded within a polymer, for example. In any event, the statically-charged layer 32570 can attract oppositely-charged particles in the tissue thickness compensator 32580 and hold the tissue thickness compensator 32580 to the anvil. In certain embodiments, referring now to FIG. 238, the chargeable layer 32570 can comprise a grid, or lattice, of conductors 32571 which are in electrical communication with one another. In at least one such embodiment, the conductors can be positioned and arranged such that they surround the staple forming pockets 32562 defined in the anvil 32560. In such embodiments, staples 32530 can be ejected from the staple cartridge 32500 and then deformed by the anvil 32560 without capturing the conductors 32571 therein. In various circumstances, the chargeable layer 32570 can be uncoupled from the power source after the staples 32530 have been engaged with the tissue thickness compensator 32580 such that the electrostatic charge in the layer 32570 can dissipate. In certain other circumstances, the chargeable layer 32570 can be uncoupled from the power source prior to the staples 32530 being fired. In any event, as the electrostatic charge dissipates, the anvil 32560 can be re-opened and the layer 32570 can be moved away from the tissue thickness compensator 32580. In some embodiments, the electrostatic charge may need to dissipate completely before the layer 32570 can be detached from the tissue thickness compensator 32580 while, in other embodiments, the layer 32570 can be detached from the tissue thickness compensator 32580 before the electrostatic charge in the layer 32570 has completely dissipated. In certain embodiments, as a result of the above, the tissue thickness compensator 32580 can be attached to the anvil 32560 without the use of a chemical adhesive.

In various embodiments, further to the above, the layer 32570 can also provide feedback capability to the handle of the surgical stapling instrument. In at least one such embodiment, the layer 32570 can be pressure sensitive and can be configured to detect the clamping pressure being applied thereto by the anvil 32560, for example.

In various embodiments, further to the above, a tissue thickness compensator can be comprised of a biocompatible material. The biocompatible material, such as, a foam, may comprise tackifiers, surfactants, fillers, cross-linkers, pigments, dyes, antioxidants and other stabilizers and/or combinations thereof to provide desired properties to the material. In certain embodiments, a biocompatible foam may comprise a surfactant. The surfactant may be applied to the surface of the material and/or dispersed within the material.

Without wishing to be bound to any particular theory, the surfactant applied to the biocompatible material may reduce the surface tension of the fluids contacting the material. For example, the surfactant may reduce the surface tension of water contacting the material to accelerate the penetration of water into the material. In various embodiments, the water may act as a catalyst. The surfactant may increase the hydrophilicity of the material.

In various embodiments, the surfactant may comprise an anionic surfactant, a cationic surfactant, and/or a non-ionic surfactant. Examples surfactants include, but are not limited to polyacrylic acid, methalose, methyl cellulose, ethyl cellulose, propyl cellulose, hydroxy ethyl cellulose, carboxy methyl cellulose, polyoxyethylene cetyl ether, polyoxyethylene lauryl ether, polyoxyethylene octyl ether, polyoxyethylene octylphenyl ether, polyoxyethylene oleyl ether, polyoxyethylene sorbitan monolaurate, polyoxyethylene stearyl ether, polyoxyethylene nonylphenyl ether, dialkylphenoxy poly(ethyleneoxy) ethanol, and polyoxamers, and combinations thereof. In at least one embodiment, the surfactant may comprise a copolymer of polyethylene glycol and polypropylene glycol. In at least one embodiment, the surfactant may comprise a phospholipid surfactant. The phospholipid surfactant may provide antibacterial stabilizing properties and/or disperse other materials in the biocompatible material. In various embodiments, the tissue thickness compensator may comprise at least one medicament. The tissue thickness compensator may comprise one or more of the natural materials, non-synthetic materials, and/or synthetic materials described herein. In certain embodiments, the tissue thickness compensator may comprise a biocompatible foam comprising gelatin, collagen, hyaluronic acid, oxidized regenerated cellulose, polyglycolic acid, polycaprolactone, polylactic acid, polydioxanone, polyhydroxyalkanoate, poliglecaprone, and combinations thereof. In certain embodiments, the tissue thickness compensator may comprise a film comprising the at least one medicament. In certain embodiments, the tissue thickness compensator may comprise a biodegradable film comprising the at least one medicament. In certain embodiments, the medicament may comprise a liquid, gel, and/or powder. In various embodiments, the medicaments may comprise anticancer agents, such as, for example, cisplatin, mitomycin, and/or adriamycin.

In various embodiments, the tissue thickness compensator may comprise a biodegradable material to provide controlled elution or release of the at least one medicament as the biodegradable material degrades. In various embodiments, the biodegradable material may degrade may decompose, or loses structural integrity, when the biodegradable material contacts an activator, such as, for example an activator fluid. In various embodiments, the activator fluid may comprise saline or any other electrolyte solution, for example. The biodegradable material may contact the activator fluid by conventional techniques, including, but not limited to spraying, dipping, and/or brushing. In use, for example, a surgeon may dip an end effector and/or a staple cartridge comprising the tissue thickness compensator comprising the at least one medicament into an activator fluid comprising a salt solution, such as sodium chloride, calcium chloride, and/or potassium chloride. The tissue thickness compensator may release the medicament as the tissue thickness compensator degrades. In certain embodiments, the elution or release of the medicament from the tissue thickness compensator may be characterized by a rapid initial elution or release rate and a slower sustained elution or release rate.

In various embodiments, a tissue thickness compensator, for example, can be comprised of a biocompatible material which may comprise an oxidizing agent. In various embodiments, the oxidizing agent may be an organic peroxide and/or an inorganic peroxide. Examples of oxidizing agents may include, but are not limited to, hydrogen peroxide, urea peroxide, calcium peroxide, and magnesium peroxide, and sodium percarbonate. In various embodiments, the oxidizing agent may comprise peroxygen-based oxidizing agents and hypohalite-based oxidizing agents, such as, for example, hydrogen peroxide, hypochlorous acid, hypochlorites, hypocodites, and percarbonates. In various embodiments, the oxidizing agent may comprise alkali metal chlorites, hypochlorites and perborates, such as, for example, sodium chlorite, sodium hypochlorite and sodium perborate. In certain embodiments, the oxidizing agent may comprise vanadate. In certain embodiments, the oxidizing agent may comprise ascorbic acid. In certain embodiments, the oxidizing agent may comprise an active oxygen generator. In various embodiments, a tissue scaffold may comprise the biocompatible material comprising an oxidizing agent.

In various embodiments, the biocompatible material may comprise a liquid, gel, and/or powder. In certain embodiments, the oxidizing agent may comprise microparticles and/or nanoparticles, for example. For example, the oxidizing agent may be milled into microparticles and/or nanoparticles. In certain embodiments, the oxidizing agent may be incorporated into the biocompatible material by suspending the oxidizing agent in a polymer solution. In certain embodiments, the oxidizing agent may be incorporated into the biocompatible material during the lyophylization process. After lyophylization, the oxidizing agent may be attached to the cell walls of the biocompatible material to interact with the tissue upon contact. In various embodiments, the oxidizing agent may not be chemically bonded to the biocompatible material. In at least one embodiment, a percarbonate dry power may be embedded within a biocompatible foam to provide a prolonged biological effect by the slow release of oxygen. In at least one embodiment, a percarbonate dry power may be embedded within a polymeric fiber in a non-woven structure to provide a prolonged biological effect by the slow release of oxygen. In various embodiments, the biocompatible material may comprise an oxidizing agent and a medicament, such as, for example, doxycycline and ascorbic acid.

In various embodiments, the biocompatible material may comprise a rapid release oxidizing agent and/or a slower sustained release oxidizing agent. In certain embodiments, the elution or release of the oxidizing agent from the biocompatible material may be characterized by a rapid initial elution or release rate and a slower sustained elution or release rate. In various embodiments, the oxidizing agent may generate oxygen when the oxidizing agent contacts bodily fluid, such as, for example, water. Examples of bodily fluids may include, but are not limited to, blood, plasma, peritoneal fluid, cerebral spinal fluid, urine, lymph fluid, synovial fluid, vitreous fluid, saliva, gastrointestinal luminal contents, and/or bile. Without wishing to be bound to any particular theory, the oxidizing agent may reduce cell death, enhance tissue viability and/or maintain the mechanical strength of the tissue to tissue that may be damaged during cutting and/or stapling.

In various embodiments, the biocompatible material may comprise at least one microparticle and/or nanoparticle. The biocompatible material may comprise one or more of the natural materials, non-synthetic materials, and synthetic materials described herein. In various embodiments, the biocompatible material may comprise particles having a mean diameter of about 10 nm to about 100 nm and/or about 10 μm to about 100 μm, such as, for example, 45-50 nm and/or 45-50 μm. In various embodiments, the biocompatible material may comprise biocompatible foam comprising at least one microparticle and/or nanoparticle embedded therein. The microparticle and/or nanoparticle may not be chemically bonded to the biocompatible material. The microparticle and/or nanoparticle may provide controlled release of the medicament. In certain embodiments, the microparticle and/or nanoparticle may comprise at least one medicament. In certain embodiments, the microparticle and/or nanoparticle may comprise a hemostatic agent, an antimicrobial agent, and/or an oxidizing agent, for example. In certain embodiments, the tissue thickness compensator may comprise a biocompatible foam comprising an hemostatic agent comprising oxidized regenerated cellulose, an antimicrobial agent comprising doxycline and/or Gentamicin, and/or an oxidizing agent comprising a percarbant. In various embodiments, the microparticle and/or nanoparticle may provide controlled release of the medicament up to three days, for example.

In various embodiments, the microparticle and/or nanoparticle may be embedded in the biocompatible material during a manufacturing process. For example, a biocompatible polymer, such as, for example, a PGA/PCL, may contact a solvent, such as, for example, dioxane to form a mixture. The biocompatible polymer may be ground to form particles. Dry particles, with or without ORC particles, may be contacted with the mixture to form a suspension. The suspension may be lyophilized to form a biocompatible foam comprising PGA/PCL having dry particles and/or ORC particles embedded therein.

In various embodiments, the tissue thickness compensators or layers disclosed herein can be comprised of an absorbable polymer, for example. In certain embodiments, a tissue thickness compensator can be comprised of foam, film, fibrous woven, fibrous non-woven PGA, PGA/PCL (Poly(glycolic acid-co-caprolactone)), PLA/PCL (Poly(lactic acid-co-polycaprolactone)), PLLA/PCL, PGA/TMC (Poly(glycolic acid-co-trimethylene carbonate)), PDS, PEPBO or other absorbable polyurethane, polyester, polycarbonate, Polyorthoesters, Polyanhydrides, Polyesteramides, and/or Polyoxaesters, for example. In various embodiments, a tissue thickness compensator can be comprised of PGA/PLA (Poly(glycolic acid-co-lactic acid)) and/or PDS/PLA (Poly(p-dioxanone-co-lactic acid)), for example. In various embodiments, a tissue thickness compensator can be comprised of an organic material, for example. In certain embodiments, a tissue thickness compensator can be comprised of Carboxymethyl Cellulose, Sodium Alginate, Cross-linked Hyaluronic Acid, and/or Oxidized regenerated cellulose, for example. In various embodiments, a tissue thickness compensator can comprise a durometer in the 3-7 Shore A (30-50 Shore OO) ranges with a maximum stiffness of 15 Shore A (65 Shore OO), for example. In certain embodiments, a tissue thickness compensator can undergo 40% compression under 3 lbf load, 60% compression under 6 lbf load, and/or 80% compression under 20 lbf load, for example. In certain embodiments, one or more gasses, such as air, nitrogen, carbon dioxide, and/or oxygen, for example, can be bubbled through and/or contained within the tissue thickness compensator. In at least one embodiment, a tissue thickness compensator can comprise beads therein which comprise between approximately 50% and approximately 75% of the material stiffness comprising the tissue thickness compensator.

In various embodiments, a tissue thickness compensator can comprise hyaluronic acid, nutrients, fibrin, thrombin, platelet rich plasma, Sulfasalazine (Azulfidine®–5ASA+Sulfapyridine diazo bond))–prodrug–colonic bacterial (Azoreductase), Mesalamine (5ASA with different prodrug configurations for delayed release), Asacol® (5ASA+Eudragit-S coated–pH>7 (coating dissolution)), Pentasa® (5ASA+ethylcellulose coated–time/pH dependent slow release), Mesasal® (5ASA+Eudragit-L coated–pH>6), Olsalazine (5ASA+5ASA–colonic bacterial (Azoreductase)), Balsalazide (5ASA+4-Aminobenzoyl-B-alanine)–colonic bacterial (Azoreductase)), Granulated mesalamine, Lialda (delay and SR formulation of mesalamine), HMPL-004 (herbal mixture that may inhibit TNF-alpha, interleukin-1 beta, and nuclear-kappa B activation), CCX282-B (oral chemokine receptor antagonist that interferes with trafficking of T lymphocytes into the intestinal mucosa), Rifaximin (nonabsorbable broad-spectrum antibiotic), Infliximab, murine chymieric (monoclonal antibody directed against TNF-alpha-approved for reducing signs/symptoms and maintaining clinical remission in adult/pediatric patients with moderate/severe luminal and fistulizing Crohn's disease who have had inadequate response to conventional therapy), Adalimumab, Total Human IgG1 (anti-TNF-alpha monoclonal antibody—approved for reducing signs/symptoms of Crohn's disease, and for the induction and maintenance of clinical remission in adult patients with moderate/severe active Crohn's disease with inadequate response to conventional therapies, or who become intolerant to Infliximab), Certolizumab pegoll, humanized anti-TNF FAB' (monoclonal antibody fragment linked to polyethylene glycol—approved for reducing signs/symptoms of Crohn's disease and for the induction and maintenance of response in adult patients w/ moderate/severe disease with inadequate response to conventional therapies), Natalizumab, First non-TNF-alpha inhibitor (biologic compound approved for Crohn's disease), Humanized monoclonal IgG4 antibody (directed against alpha-4 integrin—FDA approved for inducing and maintaining clinical response and remission in patients with moderate/severe disease with evidence of inflammation and who have had inadequate response to or are unable to tolerate conventional Crohn's therapies and inhibitors of TNF-alpha), concomitant Immunomodulators potentially given with Infliximab, Azathioprine 6-Mercaptopurine (purine synthesis inhibitor—prodrug), Methotrexate (binds dihydrofolate reductase (DHFR) enzyme that participates in tetrahydrofolate synthesis, inhibits all purine synthesis), Allopurinol and Thioprine therapy, PPI, H2 for acid suppression to protect the healing line, C-Diff—Flagyl, Vancomycin (fecal translocation treatment; probiotics; repopulation of normal endoluminal flora), and/or Rifaximin (treatment of bacterial overgrowth (notably hepatic encephalopathy); not absorbed in GI tract with action on intraluminal bacteria), for example.

As described herein, a tissue thickness compensator can compensate for variations in the thickness of tissue that is captured within the staples ejected from a staple cartridge and/or contained within a staple line, for example. Stated another way, certain staples within a staple line can capture thick portions of the tissue while other staples within the staple line can capture thin portions of the tissue. In such circumstances, the tissue thickness compensator can assume different heights or thicknesses within the staples and apply a compressive force to the tissue captured within the staples regardless of whether the captured tissue is thick or thin. In various embodiments, a tissue thickness compensator can compensate for variations in the hardness of the tissue. For instance, certain staples within a staple line can capture highly compressible portions of the tissue while other staples within the staple line can capture portions of the tissue which are less compressible. In such circumstances, the tissue thickness compensator can be configured to assume a smaller height within the staples that have captured tissue having a lower compressibility, or higher hardness, and, correspondingly, a larger height within the staples that have captured tissue having a higher compressibility, or lower hardness, for example. In any event, a tissue thickness compensator, regardless of whether it compensates for variations in tissue thickness and/or variations in tissue hardness, for example, can be referred to as a 'tissue compensator' and/or as a 'compensator', for example.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A stapling assembly for use with a stapler, said stapling assembly comprising:
    an anvil comprising a plurality of forming surfaces;
    a fastener cartridge comprising a plurality of fasteners stored therein, wherein said fasteners are formable against said forming surfaces;
    a tissue thickness compensator attached to said anvil, wherein said tissue thickness compensator comprises:
        a body portion comprising a porous material; and
        a plurality of cavities defined in said body portion, wherein said cavities are aligned with said forming surfaces such that said fasteners are configured to at least one of puncture said cavities when said fasteners are ejected from said fastener cartridge or capture said cavities and compress said cavities within said tissue thickness compensator when said fasteners are ejected from said fastener cartridge and formed by said forming surfaces; and
    at least one medicament positioned within each said cavity prior to firing the stapler, wherein said medicament is different than said porous material,
    wherein said plurality of cavities comprises a plurality of bubbles,
    wherein said tissue thickness compensator comprises a first layer and a second layer, and wherein said bubbles are defined between said first layer and said second layer.

2. A stapling assembly for use with a stapler comprising an anvil, wherein the anvil includes a forming surface configured to deform a staple, said stapling assembly comprising:
    a releasing material configured to be at least partially captured by a plurality of staples, said releasing material comprising:
        a body portion comprising a porous material; and
        a cavity defined in said body portion, wherein said cavity is configured to be aligned with the forming surface of the anvil such that the staple is configured to puncture said cavity when the staple is ejected from a staple cartridge or capture said cavity and compress said cavity within said releasing material when the staple is ejected from the staple cartridge and formed by the forming surface;
    a medicament positioned within said cavity, wherein said medicament is different than said porous material; and
    an attachment portion configured to be attached to the anvil to attach said releasing material to the anvil,
    wherein said cavity is defined by a sidewall, wherein said releasing material comprises a first layer and a second layer, and wherein portions of said first layer are connected to said second layer to define said sidewall.

* * * * *